(12) United States Patent
Chokhawala et al.

(10) Patent No.: US 12,258,610 B2
(45) Date of Patent: Mar. 25, 2025

(54) PRODUCTION OF CHEMICALS FROM RENEWABLE SOURCES

(71) Applicant: ZYMOCHEM, INC., Alameda, CA (US)

(72) Inventors: Harshal Chokhawala, Castro Valley, CA (US); Jonathan Kuchenreuther, Alameda, CA (US); Jorge-Alonso Gutierrez, Alameda, CA (US); Yi-Shu Tai, Alameda, CA (US)

(73) Assignee: ZYMOCHEM, INC., San Leandro, CA (US)

(*) Notice: Subject to any disclaimer, the term of this patent is extended or adjusted under 35 U.S.C. 154(b) by 613 days.

(21) Appl. No.: 17/605,389

(22) PCT Filed: Apr. 25, 2020

(86) PCT No.: PCT/US2020/029981
§ 371 (c)(1),
(2) Date: Oct. 21, 2021

(87) PCT Pub. No.: WO2020/220001
PCT Pub. Date: Oct. 29, 2020

(65) Prior Publication Data
US 2022/0372528 A1   Nov. 24, 2022

Related U.S. Application Data

(60) Provisional application No. 62/868,824, filed on Jun. 28, 2019, provisional application No. 62/838,793, filed on Apr. 25, 2019.

(51) Int. Cl.
| | | |
|---|---|---|
| *C12N 1/20* | (2006.01) | |
| *C12N 15/52* | (2006.01) | |
| *C12N 15/70* | (2006.01) | |
| *C12P 7/40* | (2006.01) | |
| *C12P 7/62* | (2022.01) | |
| *C12P 7/625* | (2022.01) | |

(52) U.S. Cl.
CPC .......... *C12P 7/625* (2013.01); *C12N 1/20* (2013.01); *C12N 15/52* (2013.01); *C12N 15/70* (2013.01); *C12P 7/40* (2013.01); *C12P 7/62* (2013.01); *C12Y 106/05005* (2013.01); *C12Y 401/01004* (2013.01); *C12Y 401/02045* (2013.01); *C12Y 402/0103* (2013.01); *C12Y 402/01034* (2013.01); *C12N 2800/101* (2013.01)

(58) Field of Classification Search
CPC .... C12P 7/625; C12P 7/40; C12P 7/62; C12P 7/04; C12P 7/18; C12P 7/44; C12P 11/00; C12P 7/42; C12N 1/20; C12N 15/52; C12N 15/70; C12N 2800/101; C12N 9/0036; C12N 9/88; C12Y 106/05005; C12Y 401/01004; C12Y 401/02045; C12Y 402/0103; C12Y 402/01034; C12Y 401/02034

See application file for complete search history.

(56) References Cited

U.S. PATENT DOCUMENTS

| | | |
|---|---|---|
| 9,523,105 B2 | 12/2016 | Zanghellini |
| 11,692,208 B2 | 7/2023 | Chokhawala et al. |
| 2006/0252135 A1 | 11/2006 | Brazeau et al. |
| 2008/0020435 A1 | 1/2008 | Burke et al. |
| 2011/0177571 A1 | 7/2011 | Lee |
| 2011/0195466 A1 | 8/2011 | Burgard et al. |
| 2011/0236938 A1 | 9/2011 | Yoshikuni et al. |
| 2012/0282661 A1 | 11/2012 | Burk et al. |
| 2015/0147793 A1 | 5/2015 | Walther et al. |
| 2017/0044551 A1 | 2/2017 | Chokhawala |
| 2020/0255840 A1 | 8/2020 | Chokhawala |
| 2023/0109883 A1 | 4/2023 | Chokhawala et al. |

FOREIGN PATENT DOCUMENTS

| | | |
|---|---|---|
| CN | 102066551 A | 5/2011 |
| CN | 103180279 A | 6/2013 |
| CN | 103305450 A | 9/2013 |
| JP | 2012-525856 A | 10/2012 |
| JP | 2016-533162 A | 10/2016 |
| WO | WO-2009/151728 A2 | 12/2009 |
| WO | WO-2013/090837 A2 | 6/2013 |
| WO | WO-2015/042201 A2 | 3/2015 |

OTHER PUBLICATIONS

Bezborodnikov et al. (GenBank accession No. POA144, Feb. 15, 2017.*
Dixon et al. (GenBank accession No. P28304, Mar. 28, 2018.*
U.S. Appl. No. 17/307,850, filed May 4, 2021, Chokhawala.
Andrews, F. H. and McLeish, M. J., Substrate specificity in thiamin diphosphate-dependent decarboxylases, Bioorganic Chemistry, 43:26-36, (2012).
Baker, P. and Seah, S.Y.K., Rational design of stereoselectivity in the Class II Pyruvate Aldolase Bphl, Journal of the American Chemical Society, 134(1):507-513, (2012).
Baker, P., et. al., Probing the molecular basis of substrate specificity, stereospecificity, and catalysis in the class II pyruvate aldolase, Bphl, Biochemistr including biophysical chemistry and molecular biology, 50(17):3559-3569, (2011).
Branden et al., Introduction to Protein Structure, Garland Publishing Inc., 247 (1991).
Breitkreuz, K. E. et al., A Novel γ-Hydroxybutyrate Dehydrogenase, Identification and Expression of an *Arabidopsis* cDNA And Potential Role Under Oxygen Deficiency, The Journal of Biological Chemistry, 278(42):41552-41556, (2003).

(Continued)

*Primary Examiner* — Delia M Ramirez
(74) *Attorney, Agent, or Firm* — Choate, Hall & Stewart LLP; Xiadong Li; Alisha A. Contractor

(57) ABSTRACT

Among other things, the present disclosure provides biosynthesis polypeptides, methods, and non-naturally occurring microbial organisms for preparing various compounds such as 1,5-pentanediol, adipic acid, 1,6-hexanediol, 6-hydroxy hexanoic acid, and 2-keto carboxylic acids.

14 Claims, 3 Drawing Sheets

Specification includes a Sequence Listing.

(56) References Cited

OTHER PUBLICATIONS

Cheng, G., 1,6-Hexanediol Process Study, Thesis, 84 pages (Mar. 1, 2006). English Abstract on p. 3.
Cheriyan et al., Directed evolution of a pyruvate aldolase to recognize a long chain acyl substrate, Bioorganic & Medicinal Chemistry, 19:6447-6453 (2011).
De la Plaza, M. et al., Biochemical and molecular characterization of a-ketoisovalerate decarboxylase, an enzyme involved in the formation of aldehydes from amino acids by *Lactococcus lactis*, FEMS Microbiology Letters 238:367-374, (2004).
Eaton, R. W. and Chapman, P. J., Bacterial Metabolism of Naphthalene: Construction and Use of Recombinant Bacteria to Study Ring Cleavage of 1,2-Dihydroxynaphthalene and Subsequent Reactions, Journal of Bacteriology, 174(23):7542-7554, (1992).
Eaton, R. W., trans-o-Hydroxybenzylidenepyruvate Hydratase-Aldolase as a Biocatalyst, Applied and Environmental Microbiology, 66(6):2668-2672, (2000).
Ehrlich, K.C. et al, An Acid Phosphatase from *Aspergillus ficuum* Has Homology to *Penicillium chrysogenum* PhoA, Biochem. Biophys. Res. Commun., 204(1):63-68 (1994).
Ferrara, S. et al., Characterization of the aldol condensation activity of the trans-o-hydroxybenzylidenepyruvate hydratase-aldolase (tHBP-HA) cloned from Pseudomonas fluorescens N3, Biochimica et Biophysica Acta (BBA)—Proteins and Proteomics, 1814(5):622-629, (2011).
Gocke, D. et al., Comparative characterisation of thiamin diphosphate-dependent decarboxylases, Journal of Molecular Catalysis B: Enzymatic: 61(1-2):30-35, (2009).
Hara et al., Characterization of the 4-carboxy-4-hydroxy-2-oxoadipate aldolase gene and operon structure of the protocatechuate 4,5-cleavage pathway genes in Sphingomonas paucimobilis SYK-6, Journal of Bacteriology, 41-50 (2003).
International Search Report for PCT/US2014/056175, 4 pages (mailed Mar. 24, 2015).
International Search Report for PCT/US2020/029981 filed Apr. 25, 2020, 4 pages, (Sep. 24, 2020).
Iwabuchi, T. and Harayama, S., Biochemical and genetic characterization of trans-2'-carboxybenzalpyruvate Hydratase-Aldolase from a Phenanthrene-Degrading *Nocardioides* Strain, American Society for Microbiology, Journal of Bacteriology, 180(4):945-949, (1998).
Liu, X. et al., Two novel metal-independent long-chain alkyl alcohol dehydrogenases from *Geobacillus thermodenitrificans* NG80-2, Microbiology, 155(6):2078-2085, (2009).
Locus AAA62393.1, Aspergillus niger acid phosphatase protein, Accession L20566-1, 1 page (Feb. 23, 1995).
Mueller, L. S. et al., Sbi00515, a Protein of Unknown Function from *Streptomyces bingchenggensis*, Highlights the Functional Versatility of the Acetoacetate Decarboxylase Scaffold, Biochemistry, 54(25):3978-3988, (2015).
Petersen, D. J., et al., Molecular Cloning of an Alcohol (Butanol) Dehydrogenase Gene Cluster from *Clostridium acetobutylicum* ATCC 824, Journal of Bacteriology, 173(5):1831-1834, (1991).
Rea, et al., Crystal structure and functional assignment of YfaU, a metal ion dependent class II aldolase from *Escherichia coli* K12, American Chemical Society, 47(38):9955-9965, (2008).
Rodriguez, G. M. and Atsumi, S., Isobutyraldehyde production from *Escherichia coli* by removing aldehyde reductase activity, Microbial Cell Factories, 11:90:1-11, (2012), [http://www.microbialcellfactories.com/content/11/1/90].
Sadowski., M.I., and Jones, J.T., The sequence-structure relationship and protein function prediction, Current Opinion in Structural Biology, 19:357-362 (2009).
Saito, N. et al., Metabolite Profiling Reveals YihU as a Novel Hydroxybutyrate Dehydrogenase for Alternative Succinic Semialdehyde Metabolism in *Escherichia coli*, The Journal of Biological Chemistry, 284(24):16442-16451, (2009).
Seffernick et al., Melamine Deaminase and Atrazine Chlorohydrolase: 98 Percent Identical but Functionally Different, J. Bacteriol. 183(8):2405-2410 (2001).
Sello, G. and Gennaro, P. D., Aldol Reactions of the trans-o-Hydroxybenzylidenepyruvate Hydratase-Aldolase ((HBP-HA) from *Pseudomonas fluorescens* N3, Applied Biochemistry and Biotechnology, 170:1702-1712, (2013).
Siegert, P. et al., Exchanging the substrate specificities of pyruvate decarboxylase from *Zymomonas mobilis* and benzoylformate decarboxylase from Pseudomonas putida, Protein Engineering, Design & Selection, 18(7):345-357, (2005).
Sousa, S.,et. al., The ARO4 gene of Candida albicans encodes a tyrosine-sensitive DAHP synthase: evolution, functional conservation and phenotype of Aro3p-, Aro4p-deficient mutants, Microbiology148(Pt5):1291-1303 (2002).
Tani, A. et al., Thermostable NADP1-Dependent Medium-Chain Alcohol Dehydrogenase from *Acinetobacter* sp. Strain M-1: Purification and Characterization and Gene Expression in *Escherichia coli*, Applied and Environmental Microbiology, 66(12):5231-5235, (2000).
Wang, W. et al., Comparison of two metal-dependent pyruvate aldolases related by convergent evolution: substrate specificity, kinetic mechanism, and substrate channeling, Biochemistry, 49(17):3774-3782, (2010).
Witkowski et al., Conversion of a beta-ketoacyl synthase to a malonyl Decaboxylase by Replacement of the Active-Site Cysteine with Glutamine, Biochemistry, 38:11643-11650 (1999).
Wolff, R. A. and Kenealy, W. R., Purification and Characterization of the Oxygen-Sensitive 4-Hydroxybutanoate Dehydrogenase from *Clostridium kluyveri*, Protein Expression and Purification, 6(2):206-212, (1995).
Wolterink-Van Loo, S. et al., Improving low-temperature activity of Sulfolobus acidocaldarius 2-keto-3-deoxygluconate aldolase, Archaea, 2, 233-239 (2009).
Written Opinion for PCT/US2014/056175, 7 pages (mailed Mar. 24, 2015).
Written Opinion for PCT/US2020/029981 filed Apr. 25, 2020, 9 pages, (Sep. 24, 2020).
Anonymous, Hydratase-aldolase from Alcaligenes faecalis, 1 page, (2018).
Barbosa, J.A. et al., Active site modulation in the N-acetylneuraminate lyase sub-family as revealed by the structure of the inhibitor-complexed Haemophilus influenzae enzyme, J. Mol. Biol., 303(3):405-421 (2000).
Crits-Cristoph, A. et al., MAG: acetoacetate decarboxylase [Candidatus Rokubacteria bacterium], GenBank: PYN48855.1, 2 pages, (2018).
Fesko, K. and Gruber-Khadjawi, M., Biocatalytic methods for C—C bond formation, Chemcatchem, 5(6):1248-1272 (2013).
Hernandez, K. et al., Nucleophile Promiscuity of Natural and Engineered Aldolases, Chembiochem, 19(13):1353-1358 (2018).
Samland, A.K. and Sprenger, G.A., Microbial aldolases as C—C bonding enzymes—unknown treasures and new developments, Appl. Microbiol. Biotechnol., 71(3):253-264 (2006).
Tan, N.E. et al., Acetoacetate decarboxylase from *Pseudomonas* sp., GenBank: KPH00942.1, 1 page, (2015).

* cited by examiner

PRODUCTION OF CHEMICALS FROM RENEWABLE SOURCES

CROSS-REFERENCE TO RELATED APPLICATIONS

This application is a National Stage Entry of PCT/US2020/029981, filed Apr. 25, 2020, which claims priority to United States Provisional Application Nos. 62/838,793, filed Apr. 25, 2019, and 62/868,824, filed Jun. 28, 2019, the entirety of each of which is incorporated herein by reference.

SEQUENCE LISTING

The present application contains a Sequence Listing, which has been submitted electronically in ASCII format and is hereby incorporated by reference in its entirety. Said ASCII copy, created on Jun. 17, 2022, is named Sequence-Listing.txt and is 320,465 bytes in size.

TECHNICAL FIELD

This disclosure relates generally to compositions and methods of preparation of industrially useful chemicals.

BACKGROUND

Adipic acid (AA) is a widely used chemical with an estimated 2.3 million metric tons demand in 2012 (IHS Chemical, Process Economics Program Report: Bio-Based Adipic Acid (December 2012)). Along with hexamethylenediamine (HMDA), it is used in the production of nylon6,6, polyester resins, plasticizers, foods, and other materials. Thus, methods of preparing adipic acid in high yield using renewable sources are highly desirable.

1,5-Pentanediol is a major component of polyurethanes and polyesters (PDL). 1,6-Hexanediol (HDO), is a linear diol with terminal hydroxyl groups. It is used in polyesters for industrial coating applications, two-component polyurethane coatings for automotive applications. It is also used for production of macrodiols for example adipate esters and polycarbonate diols used in elastomers and polyurethane dispersions for parquet flooring and leather coatings.

6-Hydroxy hexanoic acid (6HH) can be cyclized to make ε-caprolactone which can then be aminated to make ε-caprolactam. ε-Caprolactam is used for the production of Nylon6, a widely used polymer in many different industries. ε-Caprolactone is polymerized to make polycaprolactone (PCL) a biodegradable polyester with applications for the production of specialty polyurethanes.

2-Keto carboxylic acids are useful intermediates for the preparation of a number of industrially relevant chemicals and pharmaceutical drugs. They are precursors for production of amino acids, as well as industrially useful α-hydroxy carboxylic acids.

SUMMARY

Among other things, the present disclosure encompasses the recognition that certain biosynthesis peptides, e.g., various enzymes, can be utilized to efficiently prepare various compounds, in many embodiments, from substrates that are structurally different from their natural and/or characterized substrates. In some embodiments, the present disclosure provides technologies (e.g., enzymes, nucleic acids, organisms, cultures, etc.) for preparing various compounds utilizing one or more such enzymes.

For example, in some embodiments, the present disclosure provides that aldol-dehydration product biosynthesis polypeptides, such as various hydratase-aldolases, can be effectively utilized to prepare a number of compounds from aliphatic aldehydes other than their typical aromatic aldehyde substrates. In some embodiments, the present disclosure provides a method comprising:

contacting pyruvate and an aliphatic aldehyde with an aldol-dehydration product biosynthesis polypeptide so that an aldol-dehydration product is produced, wherein:

the carbonyl group of the aliphatic aldehyde is not conjugated to a alkenyl, alkynyl, or aromatic group; and the aldol-dehydration product is a compound comprising an aldehyde or ketone group and a double bond conjugated with the aldehyde or ketone group.

In some embodiments, an aldehyde, e.g., an aliphatic aldehyde has the structure of formula A-1:

$$R^a\text{-}L^2\text{-}L^1\text{-}C(O)H, \qquad A\text{-}1$$

or a salt thereof, wherein:
$R^a$ is R" or —OR",
each of $L^1$ and $L^2$ is independently a covalent bond, or a bivalent, optionally substituted, linear or branched $C_{1-20}$ aliphatic or $C_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;
Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;
each R" is independently —R', —C(O)R', —CO$_2$R', or —SO$_2$R';
R' is hydrogen, or an optionally substituted group selected from $C_{1-10}$ aliphatic, $C_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:
two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

In some embodiments, $L^1$ is optionally substituted —CH$_2$—. In some embodiments, $L^1$ is optionally monosubstituted —CH$_2$—. In some embodiments, $L^1$ is —CH$_2$—.

In some embodiments, an aldol-dehydration product has the structure of formula P-2:

$$R^a\text{-}L^2\text{-}L^1\text{-}CH\text{=}CH\text{—}C(O)\text{—}C(O)OH, \qquad P\text{-}2$$

or a salt thereof, wherein each variable is independently as described herein.

As described herein, an aldol-dehydration product, e.g., a compound of formula P-2 or a salt thereof, can be further processed, in some embodiments, through one or more biosynthetic processes to provide various products, such as 1,5-pentanediol, HDO, 6HH, adipic acid, etc. (e.g., see FIGS. 2-5) and various products made therefrom, including various polymeric products made therefrom.

In some embodiments, as shown herein, an aldol-dehydration product, e.g., a compound of formula P-2 or a salt thereof may also be prepared from an aldol product, e.g., a compound of formula P-1:

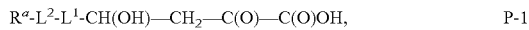

or a salt thereof, wherein each variable is independently as described herein.

In some embodiments, an aldol-dehydration product is manufactured by contacting an aldol product with a dehydration product biosynthesis polypeptide.

In some embodiments, an aldol product is manufactured by contacting suitable substrates with an aldol product biosynthesis polypeptide.

In some embodiments, the present disclosure demonstrates that various alkene reduction product biosynthesis polypeptides can be utilized to manufacture various compounds from their natural or non-natural substrates. In some embodiments, the present disclosure provides a method comprising:

contacting an alkene with an alkene reduction product biosynthesis polypeptide so that an alkene reduction product is produced, wherein:
the alkene comprises a double bond conjugated to a carbonyl group; and
a double bond conjugated to a carbonyl group in the alkene is reduced to a single bond to provide an alkene reduction product.

In some embodiments, an alkene is an aldol-dehydration product, e.g. one of formula P-2 or a salt thereof. In some embodiments, an alkene reduction product has the structure of formula P-3:

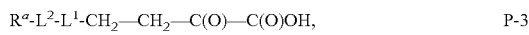

or a salt thereof, wherein each variable is independently as described herein.

Among other things, disclosed herein are enzymes, methods, and recombinant microorganisms for preparing 2-keto carboxylic acids, 1,5-pentanediol, adipic acid, 1,6-hexanediol, and 6-hydroxy hexanoic acid using renewable sources.

In one aspect, provided herein is a method for producing a 2-keto carboxylic acid of formula:

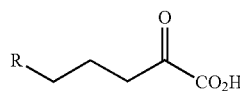

wherein R is H, CH$_3$, or CH$_2$OH;
the method comprising or consisting essentially of contacting pyruvate and

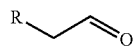

with a hydratase-aldolase and a quinone oxidoreductase in a culture or organisms comprising one or more non-naturally occurring microorganisms to produce the 2-keto carboxylic acid; wherein the hydratase-aldolase and the quinone oxidoreductase are expressed by the one or more non-naturally occurring microorganisms.

In another aspect, provided herein is a method for producing a 2-keto carboxylic acid of formula:

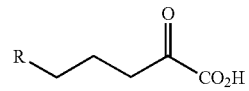

wherein R is H, CH$_3$, or CH$_2$OH;
the method comprising or consisting essentially of contacting pyruvate and

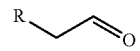

with a hydratase-aldolase and a quinone oxidoreductase in a culture or organisms comprising two or more non-naturally occurring microorganisms to produce the 2-keto carboxylic acid; wherein the hydratase-aldolase and the quinone oxidoreductase are expressed by the two or more non-naturally occurring microorganisms.

In another aspect, provided herein is a method for producing 1,5-pentanediol, the method comprising or consisting essentially of, contacting pyruvate and 3-hydroxy-propanal with a hydratase-aldolase and a quinone oxidoreductase to produce a 2-keto carboxylic acid of formula:

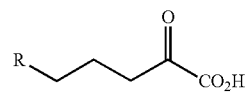

wherein R is CH$_2$OH;
contacting the 2-keto carboxylic acid with a 2-keto-acid-decarboxylase to produce a 5-hydroxy-pentanal; and
contacting the 5-hydroxy-pentanal with a primary alcohol dehydrogenase to produce the 1,5-pentanediol, wherein the method is performed in a culture comprising one or more non-naturally occurring microbial organisms.

In another aspect, provided herein is a method for producing 1,5-pentanediol, the method comprising or consisting essentially of, contacting pyruvate and 3-hydroxy-propanal with a hydratase-aldolase and a quinone oxidoreductase to produce a 2-keto carboxylic acid of formula:

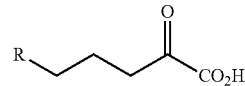

wherein R is CH$_2$OH;
contacting the 2-keto carboxylic acid with a 2-keto-acid-decarboxylase to produce a 5-hydroxy-pentanal; and
contacting the 5-hydroxy-pentanal with a primary alcohol dehydrogenase to produce the 1,5-pentanediol, wherein the method is performed in a culture comprising two or more non-naturally occurring microbial organisms.

In another aspect, provided herein is a method for producing 1,6-hexanediol, the method comprising
contacting pyruvate and 3-hydroxy-propanal with a hydratase-aldolase and a quinone oxidoreductase to produce a 2-keto carboxylic acid of formula:

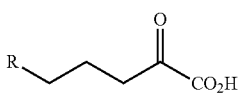

wherein R is CH$_2$OH;
  contacting the 2-keto carboxylic acid with a 6-hydroxy-2-oxohexanoate-2-reductase to produce 2,6-dihydroxy-hexanoate;
  contacting the 2,6-dihydroxy-hexanoate with a 2,6-dihydroxy-hexanoate CoA-transferase to produce 2,6-dihydroxy-hexanoyl-CoA;
  contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
  contacting the 6-hydroxy-2,3-dehydro-hexanoyl-CoA with a 2,3-dehydro-hexanoyl-CoA 2,3-reductase to produce 6-hydroxy-hexanoyl-CoA;
  contacting the 6-hydroxy-hexanoyl-CoA with a 6-hydroxyhexanoyl-CoA transferase to produce 6-hydroxy-hexanoate;
  contacting the 6-hydroxy-hexanoate with a 6-hydroxy-hexanoate 1-reductase to produce 6-hydroxy-hexanal; and
  contacting the 6-hydroxy-hexanal with a 6-hydroxyhexanal 1-reductase to produce the 1,6-hexanediol, wherein the method is performed in a culture comprising one or more non-naturally occurring microbial organisms.

In another aspect, provided herein is a method for producing 1,6-hexanediol, the method comprising
  contacting pyruvate and 3-hydroxy-propanal with a hydratase-aldolase and a quinone oxidoreductase to produce a 2-keto carboxylic acid of formula:

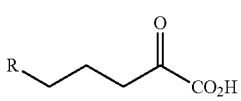

wherein R is CH$_2$OH;
  contacting the 2-keto carboxylic acid with a 6-hydroxy-2-oxohexanoate-2-reductase to produce 2,6-dihydroxy-hexanoate;
  contacting the 2,6-dihydroxy-hexanoate with a 2,6-dihydroxy-hexanoate CoA-transferase to produce 2,6-dihydroxy-hexanoyl-CoA;
  contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
  contacting the 6-hydroxy-2,3-dehydro-hexanoyl-CoA with a 2,3-dehydro-hexanoyl-CoA 2,3-reductase to produce 6-hydroxy-hexanoyl-CoA;
  contacting the 6-hydroxy-hexanoyl-CoA with a 6-hydroxyhexanoyl-CoA transferase to produce 6-hydroxy-hexanoate;
  contacting the 6-hydroxy-hexanoate with a 6-hydroxy-hexanoate 1-reductase to produce 6-hydroxy-hexanal; and
  contacting the 6-hydroxy-hexanal with a 6-hydroxyhexanal 1-reductase to produce the 1,6-hexanediol, wherein the method is performed in a culture comprising two or more non-naturally occurring microbial organisms.

In another aspect, provided herein is a method for producing 6-hydroxy-hexanoate, the method comprising
  contacting pyruvate and 3-hydroxy-propanal with a hydratase-aldolase and a quinone oxidoreductase to produce a 2-keto carboxylic acid of formula:

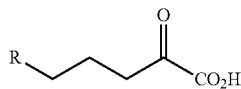

wherein R is CH$_2$OH;
  contacting the 2-keto carboxylic acid with a 6-hydroxy-2-oxohexanoate-2-reductase to produce 2,6-dihydroxy-hexanoate;
  contacting the 2,6-dihydroxy-hexanoate with a 2,6-dihydroxy-hexanoate CoA-transferase to produce 2,6-dihydroxy-hexanoyl-CoA;
  contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
  contacting the 6-hydroxy-2,3-dehydro-hexanoyl-CoA with a 2,3-dehydro-hexanoyl-CoA 2,3-reductase to produce 6-hydroxy-hexanoyl-CoA; and
  contacting the 6-hydroxy-hexanoyl-CoA with a 6-hydroxyhexanoyl-CoA transferase to produce the 6-hydroxy-hexanoate;
wherein the method is performed in a culture comprising one or more non-naturally occurring microbial organisms.

In another aspect, provided herein is a method for producing 6-hydroxy-hexanoate, the method comprising
  contacting pyruvate and 3-hydroxy-propanal with a hydratase-aldolase and a quinone oxidoreductase to produce a 2-keto carboxylic acid of formula:

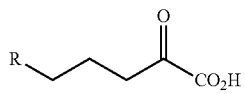

wherein R is CH$_2$OH;
  contacting the 2-keto carboxylic acid with a 6-hydroxy-2-oxohexanoate-2-reductase to produce 2,6-dihydroxy-hexanoate;
  contacting the 2,6-dihydroxy-hexanoate with a 2,6-dihydroxy-hexanoate CoA-transferase to produce 2,6-dihydroxy-hexanoyl-CoA;
  contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
  contacting the 6-hydroxy-2,3-dehydro-hexanoyl-CoA with a 2,3-dehydro-hexanoyl-CoA 2,3-reductase to produce 6-hydroxy-hexanoyl-CoA; and
  contacting the 6-hydroxy-hexanoyl-CoA with a 6-hydroxyhexanoyl-CoA transferase to produce the 6-hydroxy-hexanoate;
wherein the method is performed in a culture comprising two or more non-naturally occurring microbial organisms.

In another aspect, provided herein is a method for producing adipic acid, the method comprising
  contacting pyruvate and 3-hydroxy-propanal with a hydratase-aldolase and a quinone oxidoreductase to produce a 2-keto carboxylic acid of formula:

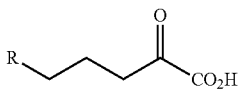

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA;
contacting the 6-hydroxy-hexanoyl-CoA with a 6-hydroxyhexanoyl-CoA transferase to produce 6-hydroxy-hexanoate;
contacting the 6-hydroxy-hexanoate with a 6-hydroxy-hexanoate dehydrogenase to produce 6-oxo-hexanoate; and
contacting the 6-oxo-hexanoate with a 6-oxo-hexanoate oxidase to produce the adipic acid,
wherein the method is performed in a culture comprising one or more non-naturally occurring microbial organisms.

In another aspect, provided herein is a method for producing adipic acid, the method comprising
contacting pyruvate and 3-hydroxy-propanal with a hydratase-aldolase and a quinone oxidoreductase to produce a 2-keto carboxylic acid of formula:

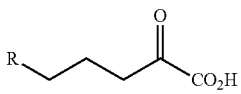

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA;
contacting the 6-hydroxy-hexanoyl-CoA with a 6-hydroxyhexanoyl-CoA transferase to produce 6-hydroxy-hexanoate;
contacting the 6-hydroxy-hexanoate with a 6-hydroxy-hexanoate dehydrogenase to produce 6-oxo-hexanoate; and
contacting the 6-oxo-hexanoate with a 6-oxo-hexanoate oxidase to produce the adipic acid,
wherein the method is performed in a culture comprising two or more non-naturally occurring microbial organisms.

In some embodiments, the hydratase-aldolase is an enzyme having an EC number 4.1.2.45, EC number 4.1.2.34 or EC number 4.1.1.4. In some embodiments, the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1.

In some embodiments, the hydratase-aldolase is an enzyme having an EC number 4.1.2.45, EC number 4.1.2.34 or EC number 4.1.1.4. In some embodiments, the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP_107818191, A0A023WZF9, PYN48855, A0A421PAQ6, WP_028217297, WP_034507049, KMK64081.1, WP_070028041.1, or KZL92449.1. In some embodiments, the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP_107818191, A0A023WZF9, PYN48855, A0A421PAQ6, WP_028217297, WP_034507049, KMK64081.1, WP_070028041.1, or KZL92449.1, or a portion (e.g., a domain, a set of amino acid residues (can be continuous or separated), etc.) thereof that promotes the formation of a aldol-dehydration product. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the hydratase-aldolase is an enzyme selected from Tables 1 and 5-8. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from Tables 1 and 5-8.

In some embodiments, the quinone oxidoreductase is an enzyme having an EC number 1.6.5. In some embodiments, the quinone oxidoreductase is an enzyme having an EC number 1.6.5.5. In some embodiments, the quinone oxidoreductase is an enzyme selected from the group of enzymes identified under GenBank, RefSeq, or Uniprot ID Nos. P28304, P40783, Q0K2I0, A0A1Z1SRY9, P43903, I7G8G0, or Q142L2, ALK19324.1, A0A1G9R408, G4Q8R5, ANA98723.1, K0EUQ3, A0A061CRS8, Q9A212, A0A1I6RWW2, WP_026197277.1, Q5NKZ3, WP_012333034.1, or WP_136898000.1. In some embodiments, the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under GenBank, RefSeq, or Uniprot ID Nos. P28304, P40783, Q0K2I0, A0A1Z1SRY9, P43903, I7G8G0, or Q142L2, ALK19324.1, A0A1G9R408, G4Q8R5, ANA98723.1, K0EUQ3, A0A061CRS8, Q9A212, A0A1I6RWW2, WP_026197277.1, Q5NKZ3, WP_012333034.1, or WP_136898000.1. In some embodiments, the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97. In some embodiments, the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

In some embodiments, the hydratase-aldolase and the quinone oxidoreductase are expressed by the one or more non-naturally occurring microbial organisms. In some embodiments, at least one of the hydratase-aldolase and the quinone oxidoreductase enzymes are expressed by one or more exogenous genes expressed by the one or more non-naturally occurring microorganisms. In some embodiments, the hydratase-aldolase is exogenously expressed by the one or more non-naturally occurring microorganisms. In some embodiments, the quinone oxidoreductase is exogenously expressed by the one or more non-naturally occurring microbial organisms. In some embodiments, the quinone oxidoreductase is overexpressed by the one or more non-naturally occurring microbial organisms. In some embodiments, the hydratase-aldolase is exogenously expressed by the one or more non-naturally occurring microbial organisms and the quinone oxidoreductase is overexpressed by the one or more non-naturally occurring microbial organisms.

In some embodiments, the hydratase-aldolase and the quinone oxidoreductase are expressed by the two or more non-naturally occurring microbial organisms. In some embodiments, at least one of the hydratase-aldolase and the quinone oxidoreductase enzymes are expressed by one or more exogenous genes expressed by the two or more non-naturally occurring microorganisms. In some embodiments, the hydratase-aldolase is exogenously expressed by the two or more non-naturally occurring microorganisms. In some embodiments, the quinone oxidoreductase is exogenously expressed by the two or more non-naturally occurring microbial organisms. In some embodiments, the quinone oxidoreductase is overexpressed by the one or more non-naturally occurring microbial organisms. In some embodiments, the hydratase-aldolase is exogenously expressed by the two or more non-naturally occurring microbial organisms and the quinone oxidoreductase is overexpressed by the two or more non-naturally occurring microbial organisms.

In some embodiments, one or more of the hydratase-aldolase and quinone oxidoreductase further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the method for producing a 2-keto carboxylic acid further comprises or consists essentially of separating the 2-keto carboxylic acid from the one or more non-naturally occurring microbial organisms or a culture comprising the one or more non-naturally occurring microbial organisms. In some embodiments, the method further comprises or consists essentially of separating the 2-keto carboxylic acid from the two or more non-naturally occurring microbial organisms or a culture comprising the two or more non-naturally occurring microbial organisms.

In some embodiments, the 2-keto-acid-decarboxylase is an enzyme selected from the group of enzymes identified under an EC number 4.1.1.1; EC number 4.1.1.2; EC number 4.1.1.3; EC number 4.1.1.4; EC number 4.1.1.5; EC number 4.1.1.6; EC number 4.1.1.7; EC number 4.1.1.11; EC number 4.1.1.12; EC number 4.1.1.15; EC number 4.1.1.16; EC number 4.1.1.17; EC number 4.1.1.18; EC number 4.1.1.19; EC number 4.1.1.20; EC number 4.1.1.34; EC number 4.1.1.35; EC number 4.1.1.40; EC number 4.1.1.54; EC number 4.1.1.56; EC number 4.1.1.71; EC number 4.1.1.72; EC number 4.1.1.73; EC number 4.1.1.74; EC number 4.1.1.75; or EC number 4.1.1.77. In some embodiments, the 2-keto-acid-decarboxylase is an enzyme selected from the group of enzymes identified under Uniprot ID No. Q6QBS4, A7M7D6, or P20906. In some embodiments, the 2-keto-acid-decarboxylase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under Uniprot ID No. Q6QBS4, A7M7D6, or P20906.

In some embodiments, the primary alcohol dehydrogenase is an enzyme having an EC number 1.1.1.61. In some embodiments, the primary alcohol dehydrogenase is an enzyme selected from the group of enzymes identified under Uniprot or GenBank ID Nos. NP_417279.1, NP_349892.1, NP_349891.1, BAB12273.1, L21902.1, Q94B07, AAB03015.1, NP_014032.1, NP_013892.1, NP_015019.1, NP_010996.2, ABX39192.1, XP_001210625.1, ABO67118, ABO68223, BAE77068.1, or CAA47743.1. In some embodiments, the primary alcohol dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under Uniprot or GenBank ID Nos. NP_417279.1, NP_349892.1, NP_349891.1, BAB12273.1, L21902.1, Q94B07, AAB03015.1, NP_014032.1, NP_013892.1, NP_015019.1, NP_010996.2, ABX39192.1, XP_001210625.1, ABO67118, ABO68223, BAE77068.1, or CAA47743.1. In some embodiments, the primary alcohol dehydrogenase is an enzyme comprising a sequence of SEQ ID NO:70, SEQ ID NO:71, SEQ ID NO:72, SEQ ID NO:73, or SEQ ID NO:74. In some embodiments, the primary alcohol dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:70, SEQ ID NO:71, SEQ ID NO:72, SEQ ID NO:73, or SEQ ID NO:74.

In some embodiments, the hydratase-aldolase is an enzyme identified under Uniprot ID No. A0A286PH18; the quinone oxidoreductase is an enzyme identified under Uniprot ID No. P28304; the 2-keto-acid-decarboxylase is an enzyme identified under Uniprot ID No. Q6QBS4; and the primary alcohol dehydrogenase is an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694. In some embodiments, the hydratase-aldolase is an enzyme comprising a sequence of SEQ ID NO:8; the quinone oxidoreductase is an enzyme comprising a sequence of SEQ ID NO:45; the 2-keto-acid-decarboxylase is an enzyme comprising a sequence of SEQ ID NO:83; and the primary alcohol dehydrogenase is an enzyme comprising a sequence of SEQ ID NO:70.

In some embodiments, the 2-keto-acid-decarboxylase and the primary alcohol dehydrogenase are expressed by the one or more non-naturally occurring microbial organisms. In some embodiments, the 2-keto-acid-decarboxylase and the primary alcohol dehydrogenase are exogenously expressed by the one or more non-naturally occurring microbial organisms.

In some embodiments, the 2-keto-acid-decarboxylase and the primary alcohol dehydrogenase are expressed by the two or more non-naturally occurring microbial organisms. In some embodiments, the 2-keto-acid-decarboxylase and the primary alcohol dehydrogenase are exogenously expressed by the two or more non-naturally occurring microbial organisms.

In some embodiments, one or more of the hydratase-aldolase, quinone oxidoreductase, 2-keto-acid-decarboxylase, and primary alcohol dehydrogenase further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the method for producing a 1,5-pentanediol further comprises or consists essentially of separating the 1,5-pentanediol from the one or more non-naturally occurring microbial organisms or a culture comprising the one or more non-naturally occurring microbial organisms. In some embodiments, the method further comprises or consists essentially of separating the 1,5-pentanediol from the two or more non-naturally occurring microbial organisms or a culture comprising the two or more non-naturally occurring microbial organisms.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are expressed by the one or more non-naturally occurring microbial organisms. In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are exogenously expressed by the one or more non-naturally occurring microbial organisms.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are expressed by the two or more non-naturally occurring microbial organisms. In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are exogenously expressed by the two or more non-naturally occurring microbial organisms.

In some embodiments, the 6-hydroxy-2-oxohexanoate-2-reductase is an enzyme selected from the group of enzymes identified under an EC number 1.1.99.6, EC number 1.1.1.169, EC number 1.1.1.215, EC number 1.1.1.28, or EC number 1.1.1.110; the 2,6-dihydroxy-hexanoate CoA-transferase is an enzyme selected from the group of enzymes identified under an EC number 2.8.3, EC number 2.8.3.1, or EC number 2.8.3.12; the 2,6-dihydroxy-hexanoyl-CoA 2-dehydratase is an enzyme having an EC number 4.2.1.167; the 2,3-dehydro-hexanoyl-CoA 2,3-reductase is an enzyme having an EC number 1.3.1.44; the 6-hydroxyhexanoyl-CoA transferase is an enzyme having an EC number 2.8.3, EC number 2.8.3.1, or EC number 2.8.3.12; the 6-hydroxyhexanoate 1-reductase is an enzyme having an EC number 1.2.99.6; and the 6-hydroxyhexanal 1-reductase is an enzyme having an EC number 1.1.1.

In some embodiments, the 6-hydroxy-2-oxohexanoate-2-reductase is an enzyme selected from the group of enzymes identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase is an enzyme selected from the group of enzymes identified under Uniprot ID No. T4VW93; the 2,6-dihydroxy-hexanoyl-CoA 2-dehydratase is an enzyme selected from the group of enzymes identified under Uniprot ID Nos. Q5U924, Q5U925, and Q5U923; the 2,3-dehydro-hexanoyl-CoA 2,3-reductase is an enzyme identified under Uniprot ID No. Q73Q47; the 6-hydroxyhexanoyl-CoA transferase is an enzyme identified under Uniprot ID No. T4VW93; the 6-hydroxyhexanoate 1-reductase is an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.1, WP_036338301.1, WP_007472106.1, or A0QWI7; and the 6-hydroxyhexanal 1-reductase is an enzyme identified under Uniprot or GenBank ID Nos. D6Z860, YP_001705436.1, ANO06407.1, AAR91681.1, AHH-98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.

In some embodiments, the 6-hydroxy-2-oxohexanoate-2-reductase is an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase is an enzyme comprising a sequence of SEQ ID NO:55, SEQ ID NO:56, SEQ ID NO:57, or SEQ ID NO:58; the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase is an enzyme comprising a sequence of SEQ ID NO:65; the 6-hydroxyhexanoyl-CoA transferase is an enzyme comprising a sequence of SEQ ID NO:55, SEQ ID NO:56, SEQ ID NO:57, or SEQ ID NO:58; the 6-hydroxyhexanoate 1-reductase is an enzyme comprising a sequence of SEQ ID NO:66, SEQ ID NO:67, or SEQ ID NO:68; and the 6-hydroxyhexanal 1-reductase is an enzyme comprising a sequence of SEQ ID NO:70.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:65; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58; the 6-hydroxyhexanoate 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:66, SEQ ID NO:67, or SEQ ID NO:68; and the 6-hydroxyhexanal 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:70.

In some embodiments, the 6-hydroxy-2-oxohexanoate-2-reductase is an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase is an enzyme identified under Uniprot ID Nos. T4VW93, A0A0C7GD16, A0A175L1W4, or A0A2X3BTQ9; the 2,6-dihydroxy-hexanoyl-CoA 2-dehydratase is an enzyme identified under Uniprot ID Nos. Q5U924, Q5U925, and Q5U923; or A0A2X3BK09, A0A2X3BU19, and A0A1V9IXA9; the 2,3-dehydro-hexanoyl-CoA 2,3-reductase is an enzyme identified under Uniprot ID No. Q73Q47; the 6-hydroxyhexanoyl-CoA transferase is an enzyme identified under Uniprot ID No. T4VW93, A0A0C7GD16, A0A175L1W4, or A0A2X3BTQ9; the 6-hydroxyhexanoate 1-reductase is an enzyme identified under Uniprot or GenBank ID Nos D6Z860, YP_001705436.1, ANO06407.1, AAR91681.1, AHH-98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.1, WP_036338301.1, WP_007472106.1, or A0QWI7; and the 6-hydroxyhexanal 1-reductase is an enzyme identified under Uniprot or GenBank ID Nos. D6Z860, YP_001705436.1, ANO06407.1, AAR91681.1, AHH-98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93, A0A0C7GD16, A0A175L1W4, or A0A2X3BTQ9; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q5U924, Q5U925, and Q5U923; or A0A2X3BK09, A0A2X3BU19, and A0A1V9IXA9; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q73Q47; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. T4VW93, A0A0C7GD16, A0A175L1W4, or A0A2X3BTQ9; the 6-hydroxyhexanoate 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.1, WP_036338301.1, WP_007472106.1, or A0QWI7; and the 6-hydroxyhexanal 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP001703694.

In some embodiments, one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the method for producing 1,6-hexanediol further comprises or consists essentially of separating the 1,6-hexanediol from the one or more non-naturally occurring microbial organisms or a culture comprising the one or more non-naturally occurring microbial organisms. In some embodiments, the method further comprises or consists essentially of separating the 1,6-hexanediol from the two or more non-naturally occurring microbial organisms or a culture comprising the two or more non-naturally occurring microbial organisms.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are expressed by the one or more non-naturally occurring microbial organisms. In some embodiments, 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are exogenously expressed by the one or more non-naturally occurring microbial organisms.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are expressed by the two or more non-naturally occurring microbial organisms. In some embodiments, 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are exogenously expressed by the two or more non-naturally occurring microbial organisms.

In some embodiments, the 6-hydroxy-2-oxohexanoate-2-reductase is an selected from the group of enzymes identified under an EC number 1.1.99.6, EC number 1.1.1.169, EC number 1.1.1.215, EC number 1.1.1.28, or EC number 1.1.1.110; the 2,6-dihydroxy-hexanoate CoA-transferase is an enzyme having an EC number 2.8.3, EC number 2.8.3.1, or EC number 2.8.3.12; the 2,6-dihydroxy-hexanoyl-CoA 2-dehydratase is an enzyme having an EC number 4.2.1.167; the 2,3-dehydro-hexanoyl-CoA 2,3-reductase is an enzyme having an EC number 1.3.1.44; and the 6-hydroxyhexanoyl-CoA transferase is an enzyme having an EC number 2.8.3, EC number 2.8.3.1, or EC number 2.8.3.12.

In some embodiments, the 6-hydroxy-2-oxohexanoate-2-reductase is an enzyme selected from the group of enzymes identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase is an enzyme identified under Uniprot ID Nos. T4VW93, A0A2X3BTQ9, A0A0C7GD16, or A0A175L1W4; the 2,6-dihydroxy-hexanoyl-CoA 2-dehydratase is an enzyme identified under Uniprot ID Nos. Q5U924, Q5U925, and Q5U923; or A0A2X3BK09, A0A2X3BU19, and A0A1V9IXA9; the 2,3-dehydro-hexanoyl-CoA 2,3-reductase is an enzyme identified under Uniprot ID No. Q73Q47; and the 6-hydroxyhexanoyl-CoA transferase is an enzyme identified under Uniprot ID Nos. T4VW93, A0A2X3BTQ9, A0A0C7GD16, or A0A175L1W4.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93, A0A2X3BTQ9, A0A0C7GD16, or A0A175L1W4; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q5U924, Q5U925, and Q5U923; or A0A2X3BK09, A0A2X3BU19, and A0A1V9IXA9; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q73Q47; and the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93, A0A2X3BTQ9, A0A0C7GD16, or A0A175L1W4.

In some embodiments, the 6-hydroxy-2-oxohexanoate-2-reductase is an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase is an enzyme comprising a sequence of SEQ ID NO:55, SEQ ID NO:56, SEQ ID NO:57, or SEQ ID NO:58; the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase is an enzyme comprising a sequence of SEQ ID NO:65; and the 6-hydroxyhexanoyl-CoA transferase is an enzyme comprising a sequence of SEQ ID NO:55, SEQ ID NO:56, SEQ ID NO:57, or SEQ ID NO:58.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:5, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:65; and the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58.

In some embodiments, one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the method for producing a 6-hydroxy-hexanoate further comprises or consists essentially of separating the 6-hydroxy-hexanoate from the one or more non-naturally occurring microbial organisms or a culture comprising the one or more non-naturally occurring microbial organisms. In some embodiments, the method further comprises or consists essentially of separating the 6-hydroxy-hexanoate from the two or more non-naturally occurring microbial organisms or a culture comprising the two or more non-naturally occurring microbial organisms.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are expressed by the one or more non-naturally occurring microbial organisms. In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are exogenously expressed by the one or more non-naturally occurring microbial organisms.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are expressed by the two or more non-naturally occurring microbial organisms. In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are exogenously expressed by the two or more non-naturally occurring microbial organisms.

In some embodiments, the 6-hydroxy-2-oxohexanoate-2-reductase is an selected from the group of enzymes identified under an EC number 1.1.99.6, EC number 1.1.1.169, EC number 1.1.1.215, EC number 1.1.1.28, or EC number 1.1.1.110; the 2,6-dihydroxy-hexanoate CoA-transferase is an enzyme having an EC number 2.8.3, EC number 2.8.3.1, or EC number 2.8.3.12; the 2,6-dihydroxy-hexanoyl-CoA 2-dehydratase is an enzyme having an EC number 4.2.1.167; the 2,3-dehydro-hexanoyl-CoA 2,3-reductase is an enzyme having an EC number 1.3.1.44; the 6-hydroxyhexanoyl-CoA transferase is an enzyme having an EC number 2.8.3, EC number 2.8.3.1, or EC number 2.8.3.12; the 6-hydroxyhexanoate dehydrogenase is an enzyme having an EC number 1.1.1.258; and the 6-oxo-hexanoate oxidase is an enzyme having an EC number 1.2.1.63.

In some embodiments, the 6-hydroxy-2-oxohexanoate-2-reductase is an enzyme selected from the group of enzymes identified under Uniprot or GenBank ID Nos. WP_003431407.1, BAL51292.1, Q5FTU6, AKC64094.1, WP_002876862.1, AGP69017.1, WP_003640741.1, AKC6409; the 2,6-dihydroxy-hexanoate CoA-transferase is an enzyme identified under Uniprot ID Nos. T4VW93 or A0A2X3BTQ9; the 2,6-dihydroxy-hexanoyl-CoA 2-dehydratase is an enzyme identified under Uniprot ID Nos. Q5U924, Q5U925, and Q5U923; or A0A2X3BK09, A0A2X3BU19, and A0A1V9IXA9; the 2,3-dehydro-hexanoyl-CoA 2,3-reductase is an enzyme identified under Uniprot ID No. Q73Q47; the 6-hydroxyhexanoyl-CoA transferase is an enzyme identified under Uniprot ID Nos. T4VW93 or A0A2X3BTQ9; the 6-hydroxyhexanoate dehydrogenase is an enzyme identified under Uniprot ID Nos. Q7WVD0 or Q84H78; and the 6-oxo-hexanoate oxidase is an enzyme identified under Uniprot ID No. Q9R2F4.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93 or A0A2X3BTQ9; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q5U924, Q5U925, and Q5U923; or A0A2X3BK09, A0A2X3BU19, and A0A1V9IXA9; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q73Q47; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93 or A0A2X3BTQ9; the 6-hydroxyhexanoate dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q7WVD0 or Q84H78; and the 6-oxo-hexanoate oxidase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q9R2F4.

In some embodiments, the 6-hydroxy-2-oxohexanoate-2-reductase is an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase is an enzyme comprising a sequence of SEQ ID NO:55 or SEQ ID NO:58; the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase is an enzyme comprising a sequence of SEQ ID NO:65; the 6-hydroxyhexanoyl-CoA transferase is an enzyme comprising a sequence of SEQ ID NO:55 or SEQ ID NO:58; the 6-hydroxyhexanoate dehydrogenase is an enzyme identified comprising a sequence of SEQ ID NO:71 or SEQ ID NO:72; and the 6-oxo-hexanoate oxidase is an enzyme comprising a sequence of SEQ ID NO:75.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55 or SEQ ID NO:58; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:65; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55 or SEQ ID NO:58; the 6-hydroxyhexanoate dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified comprising a sequence of SEQ ID NO:71 and SEQ ID NO:72; and the 6-oxo-hexanoate oxidase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:75.

In some embodiments, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, 6-hydroxyhexanoate dehydrogenase, and the 6-oxo-hexanoate oxidase are further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the method for producing a adipic acid further comprises or consists essentially of separating the adipic acid from the one or more non-naturally occurring microbial organisms or a culture comprising the one or more non-naturally occurring microbial organisms. In some embodiments, the method further comprises or consists essentially of separating the adipic acid from the two or more non-naturally occurring microbial organisms or a culture comprising the two or more non-naturally occurring microbial organisms.

In some embodiments, the pyruvate is produced from carbon sources is selected from glycerol, glucose, xylose, arabinose, galactose, mannose, fructose, sucrose, and starch, or a combination thereof. In some embodiments,

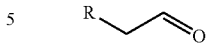

is 3-hydroxy-propanal. In some embodiments, the 3-hydroxy-propanal is produced by dehydration of glycerol by a glycerol dehydratase enzyme exogenously expressed by the one or more non-naturally occurring microbial organisms.

In another aspect, provided herein is a recombinant microbial organism comprising a first exogenous nucleic acid encoding an aldolase hydratase enzyme, wherein the recombinant microbial organism is further modified to express an increased amount of quinone oxidoreductase as compared to wild-type or the same microbial organism that is not modified, and optionally wherein the microbial organism is *Corynebacterium glutamicum*, a *clostridium* species, or *E. coli*. In some embodiments, the organism comprises a second exogenous nucleic acid encoding quinone oxidoreductase. In some embodiments, the first and/or second exogenous nucleic acid further comprises a regulatory element that drives expression of the second exogenous nucleic acid. Alternatively, the first and second nucleic are under the control of the same promoter regulatory element. In some embodiments, the regulatory element is selected from a promoter or an enhancer. In some embodiments, the aldolase hydratase enzyme has an EC number 4.1.2.45 or EC number 4.1.2.34 or EC number 4.1.1.4. In some embodiments, the aldolase hydratase enzyme is an enzyme selected from the group of enzymes identified under Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1. In some embodiments, the aldolase hydratase enzyme is an enzyme selected from the group of enzymes identified under Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP_107818191, A0A023WZF9, PYN48855, A0A421PAQ6, WP_028217297, WP_034507049, KMK64081.1, WP_070028041.1, or KZL92449.1. In some embodiments, the aldolase hydratase enzyme is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the first exogenous nucleic acid and the second exogenous nucleic acid are each contained in a vector, e.g., a plasmid or viral vector. In some embodiments, the first exogenous nucleic acid and the second exogenous nucleic acid are each contained in the same vector. In some embodiments, the first exogenous nucleic acid and the second exogenous nucleic acid are each contained in their own separate vectors. In some embodiments, the vector is a plasmid. In some embodiments, a quinone oxidoreductase is an enzyme having an EC number 1.6.5. In some embodiments, a quinone oxidoreductase is an enzyme having an EC number 1.6.5.5. In some embodiments, the quinone oxidoreductase is an enzyme selected from the group of enzymes identified under GenBank, RefSeq, or Uniprot ID Nos. P28304, P40783, Q0K2I0, A0A1Z1SRY9, P43903, 17G8G0, or Q142L2, ALK19324.1, A0A1G9R408, G4Q8R5, ANA98723.1, K0EUQ3, A0A061CRS8, Q9A212, A0A1I6RWW2, WP_026197277.1, Q5NKZ3, WP_012333034.1, or WP_136898000.1. In some embodiments, the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97. In some embodiments, the recombinant microbial organism is capable of producing a 2-keto carboxylic acid of formula:

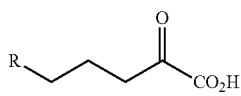

wherein R is H, CH$_3$, or CH$_2$OH. In some embodiments, the recombinant microbial organism is capable of producing 1,5-pentanediol, 1,6-hexanediol, adipic acid, or 6-hydroxy hexanoate. In some embodiments, the recombinant microbial organism is genetically modified to improve production of pyruvate from a carbon source. In some embodiments, the carbon source is selected from glycerol, glucose, xylose, arabinose, galactose, mannose, fructose, sucrose, and starch, or a combination thereof.

In another aspect, provided herein is a culture comprising the recombinant microbial organisms disclosed herein.

In another aspect, provided herein is a population of recombinant microbial organisms as disclosed herein. In some embodiments, the population is substantially homogenous.

In another aspect, provided herein is a culture comprising the populations disclosed herein.

In another aspect, provided herein is a method of producing 1,5-pentanediol, 1,6-hexanediol, adipic acid, or 6-hydroxy hexanoate, comprising culturing the population or recombinant microorganisms as disclosed herein under suitable conditions that promote expression of the exogenous nucleic acids as disclosed herein. In one aspect, the exogenous nucleic acids are overexpressed as compared to a wild-type or unmodified counterpart microbial organism. In some embodiments, the method further comprises isolating the 1,5-pentanediol, 1,6-hexanediol, adipic acid, or 6-hydroxy hexanoate from the culture or the microbial organisms.

DETAILED DESCRIPTION

Definitions

Figure 1:
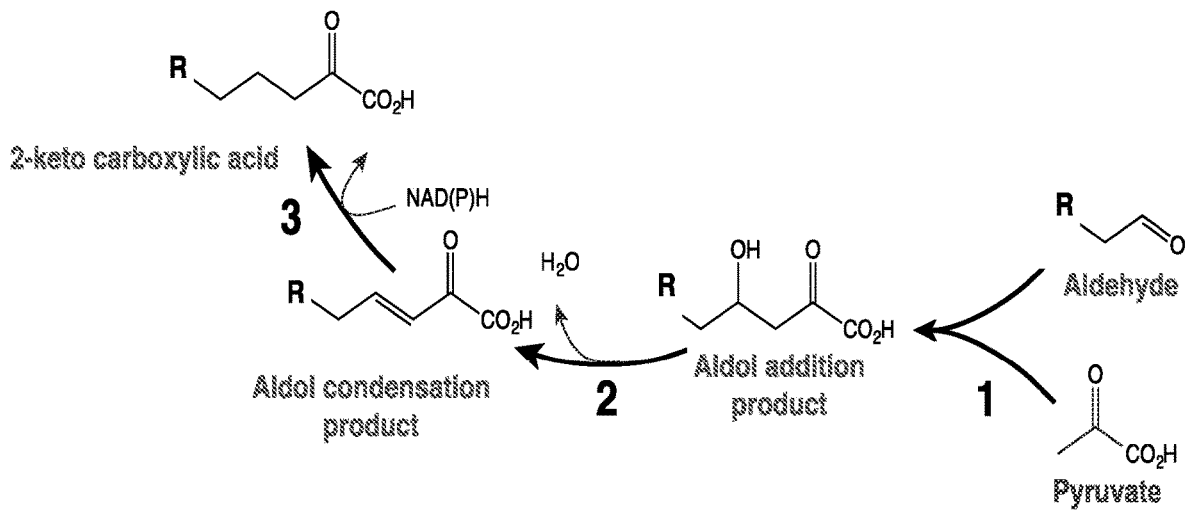
FIG. 1 shows a two-enzyme biosynthetic pathway for production of 2-keto carboxylic acids from pyruvate and aldehydes as an example. An aldol-dehydration product (e.g., an aldol condensation product described herein) can be generated from a process catalyzed by a single enzyme (e.g., an aldol-dehydration product biosynthesis polypeptide such as a hydratase-aldolase (in some embodiments, referred as Ads-Hyd) through, without the intention to be limited by theory, step 1 and 2 as depicted. As those skilled in the art will appreciate, the double bond in the illustrated aldol condensation product may exist as E or Z. In many embodiments, step 3 as illustrated can catalyzed by an oxidoreductase, e.g., one belonging to EC 1.6.5 (e.g., EC 1.6.5.5) that utilizes NADH and/or NADPH for reduction of quinones. As described herein, various aldehydes may be utilized. For example, in the illustrated aldehydes in some embodiments, R is H, CH$_3$, CH$_2$CH$_3$, OH, CH$_2$OH, or CH$_2$CH$_2$OH.

As used herein, certain terms may have the following defined meanings. As used herein, the singular form "a," "an" and "the" include singular and plural references unless the context clearly indicates otherwise.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Aspects defined by each of these transition terms are within the scope of the present disclosure. Accordingly, it is intended that the methods and compositions can include additional steps and components (comprising) or alternatively including steps and compositions of no significance (consisting essentially of) or alternatively, intending only the stated method steps or compositions (consisting of).

As used therein, the term "aldol-dehydration product biosynthesis polypeptide" refers to a polypeptide that is involved in the synthesis of an aldol-dehydration product as described herein. In some embodiments, an aldol-dehydration product biosynthesis polypeptide may be or comprise an aldolase polypeptide, a hydratase, a hydratase-aldolase polypeptide (e.g., a hydratase-aldolase) as described herein. In some embodiments, an aldol-dehydration product biosynthesis polypeptide may be or comprise a hydratase-aldolase polypeptide (e.g., a hydratase-aldolase) as described herein. In some embodiments, an aldol-dehydration product biosynthesis polypeptide has an amino acid sequence that is found in nature, for example in a microbe (e.g., in a reference aldol-dehydration biosynthesis polypeptide found in nature). Alternatively or additionally, in some embodiments, an aldol-dehydration biosynthesis polypeptide shares a characteristic sequence element and/or an overall percent identity with an appropriate reference aldol-dehydration biosynthesis polypeptide (e.g., as is found in nature and/or is presented herein (e.g., in one or more of relevant Tables (e.g., Tables 1 and 5-8))) or a portion thereof (e.g., a portion (e.g., a domain (e.g., a relevant catalytic domain) and/or a set of amino acid residues (which can be continuous or separated)) that promotes a relevant reaction).

As used herein, an "aldol-dehydration product" refers to a compound comprising an aldehyde or ketone group and a double bond conjugated with the aldehyde or ketone group. In some embodiments, an aldol-dehydration product is a compound of formula P-2 or a salt thereof.

As used herein, the term "aldol product" refers to a compound which comprises an aldehyde or ketone group and a hydroxyl group attached to a beta-carbon of an aldehyde or ketone carbonyl group. In some embodiments, an aldol product is a product of an aldol reaction. In some embodiments, an aldol product has a structure formula P-1 or a salt thereof.

As used herein, the term "aldol product biosynthesis polypeptide" refers to a polypeptide that is involved in the synthesis of an aldol product as described herein. In some embodiments, an aldol product biosynthesis polypeptide may be or comprise an aldolase polypeptide, a hydratase-aldolase polypeptide (e.g., a hydratase-aldolase) as described herein. In some embodiments, an aldol product biosynthesis polypeptide is or comprises a aldolase polypeptide as described herein. In some embodiments, an aldol product biosynthesis polypeptide has an amino acid sequence that is found in nature, for example in a microbe (e.g., in a reference aldol biosynthesis polypeptide found in nature). Alternatively or additionally, in some embodiments, an aldol biosynthesis polypeptide shares a characteristic sequence element and/or an overall percent identity with an appropriate reference aldol biosynthesis polypeptide (e.g., as is found in nature and/or is presented herein (e.g., in one or more of relevant Tables)) or a portion thereof (e.g., a portion (e.g., a domain (e.g., a relevant catalytic domain) and/or a set of amino acid residues (which can be continuous or separated)) that promotes a relevant reaction).

As used herein, the term "alkene reduction product biosynthesis polypeptide" refers to a polypeptide that is involved in the conversion of a double bond into a single bond as described herein (and forming an alkene reduction product). In some embodiments, an alkene reduction product biosynthesis polypeptide may be or comprise quinone oxidoreductase as described herein. In some embodiments, an alkene reduction product biosynthesis polypeptide has an amino acid sequence that is found in nature, for example in a microbe (e.g., in a reference alkene reduction biosynthesis polypeptide found in nature). Alternatively or additionally, in some embodiments, an aldol biosynthesis polypeptide shares a characteristic sequence element and/or an overall percent identity with an appropriate reference aldol biosynthesis polypeptide (e.g., as is found in nature and/or is presented herein (e.g., in one or more of relevant Tables)) or a portion thereof (e.g., a portion (e.g., a domain (e.g., a relevant catalytic domain) and/or a set of amino acid residues (which can be continuous or separated)) that promotes a relevant reaction).

As used herein, the term "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation (but not aromatic), or combinations thereof. In some embodiments, aliphatic groups contain 1-50 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-C20 for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "aryl", used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but is not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

As used herein, the term "cycloaliphatic," "carbocycle," "carbocyclyl," "carbocyclic radical," and "carbocyclic ring," are used interchangeably, and refer to saturated or partially unsaturated, but non-aromatic, cyclic aliphatic monocyclic, bicyclic, or polycyclic ring systems, as described herein, having, unless otherwise specified, from 3 to 30 ring members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, a cycloaliphatic group has 3-6 carbons. In some embodiments, a cycloaliphatic group is saturated and is cycloalkyl. The term "cycloaliphatic" may also include aliphatic rings that are fused to one or more aromatic or nonaromatic rings, such as decahydronaphthyl or tetrahydronaphthyl. In some embodiments, a cycloaliphatic group is bicyclic. In some embodiments, a cycloaliphatic group is tricyclic. In some embodiments, a cycloaliphatic group is polycyclic. In some embodiments, "cycloaliphatic" refers to $C_3$-$C_6$ monocyclic hydrocarbon, or $C_8$-$C_{10}$ bicyclic or polycyclic hydrocarbon, that is completely saturated or that contains one or more units of unsaturation, but which is not aromatic, that has a single point of attachment to the rest of the molecule, or a $C_9$-$C_{16}$ polycyclic hydrocarbon that is completely saturated or that contains one or more units of unsaturation, but which is not aromatic, that has a single point of attachment to the rest of the molecule.

As used herein, the term "heteroaliphatic" is given its ordinary meaning in the art and refers to aliphatic groups as described herein in which one or more carbon atoms are independently replaced with one or more heteroatoms (e.g., oxygen, nitrogen, sulfur, silicon, phosphorus, and the like). In some embodiments, one or more units selected from C, CH, $CH_2$, and $CH_3$ are independently replaced by one or more heteroatoms (including oxidized and/or substituted forms thereof). In some embodiments, a heteroaliphatic group is heteroalkyl. In some embodiments, a heteroaliphatic group is heteroalkenyl.

As used herein, the term "heteroalkyl" is given its ordinary meaning in the art and refers to alkyl groups as described herein in which one or more carbon atoms are independently replaced with one or more heteroatoms (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

As used herein, the terms "heteroaryl" and "heteroar-", used alone or as part of a larger moiety, e.g., "heteroaralkyl," or "heteroaralkoxy," refer to monocyclic, bicyclic or polycyclic ring systems having a total of five to thirty ring members, wherein at least one ring in the system is aromatic and at least one aromatic ring atom is a heteroatom. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

As used herein, the term "heteroatom" refers to an atom that is not carbon or hydrogen. In some embodiments, a heteroatom is boron, oxygen, sulfur, nitrogen, phosphorus, or silicon (including oxidized forms of nitrogen, sulfur, phosphorus, or silicon; charged forms of nitrogen (e.g., quaternized forms, forms as in iminium groups, etc.), phosphorus, sulfur, oxygen; etc.). In some embodiments, a heteroatom is oxygen, sulfur or nitrogen.

As used herein, the terms "heterocycle," "heterocyclyl," "heterocyclic radical," and "heterocyclic ring", as used herein, are used interchangeably and refer to a monocyclic, bicyclic or polycyclic ring moiety (e.g., 3-30 membered) that is saturated or partially unsaturated and has one or more heteroatom ring atoms. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Optionally Substituted: As described herein, chemical entities, e.g., various compounds, of the disclosure may contain optionally substituted and/or substituted moieties. In general, the term "substituted" means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. In some embodiments, an optionally substituted group is substituted. In some embodiments, an optionally substituted group is unsubstituted. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. Certain substituents are described below.

Suitable monovalent substituents on a substitutable atom, e.g., a suitable carbon atom, are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH═CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR$^\circ$, —SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —Si(R$^\circ$)$_3$; —OSi(R$^\circ$)$_3$; —B(R$^\circ$)$_2$; —OB(R$^\circ$)$_2$; —OB(OR$^\circ$)$_2$; —P(R$^\circ$)$_2$; —P(OR$^\circ$)$_2$; —P(R$^\circ$)(OR$^\circ$; —OP(R$^\circ$)$_2$; —OP(OR$^\circ$)$_2$; —OP(R$^\circ$)(OR$^\circ$; —P(O)(R$^\circ$)$_2$; —P(O)(OR$^\circ$)$_2$; —OP(O)(R$^\circ$)$_2$; —OP(O)(OR$^\circ$)$_2$; —OP(O)(OR$^\circ$)(SR$^\circ$; —SP(O)(R$^\circ$)$_2$; —SP(O)(OR$^\circ$)$_2$; —N(R$^\circ$)P(O)(R$^\circ$)$_2$; —N(R$^\circ$)P(O)(OR$^\circ$)$_2$; —P(R$^\circ$)$_2$[B(R$^\circ$)$_3$]; —P(OR$^\circ$)$_2$[B(R$^\circ$)$_3$]; —OP(R$^\circ$)$_2$[B(R$^\circ$)$_3$]; —OP(OR$^\circ$)$_2$[B(R$^\circ$)$_3$]; —(C$_{1-4}$ straight or branched alkylene)O—N(R$^\circ$)$_2$; or —(C$_{1-4}$ straight or branched)alkylene)C(O)O—N(R$^\circ$$_2$, wherein each R$^\circ$ may be substituted as defined herein and is independently hydrogen, C$_{1-20}$ aliphatic, C$_{1-20}$ heteroaliphatic having 1-5 heteroatoms independently selected from nitrogen, oxygen, sulfur, silicon and phosphorus, —CH$_2$—(C$_{6-14}$ aryl), —O(CH$_2$)$_{0-1}$(C$_{6-14}$ aryl), —CH$_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of R$^\circ$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$ SR$^\bullet$, —(CH$_2$)$_{0-2}$ SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, and a 5-6-membered saturated, partially unsaturated, or aryl ring having 0-4 heteroatoms independently selected from nitrogen, oxygen, and sulfur. Suitable divalent substituents on a saturated carbon atom of R$^\circ$ include ═O and ═S.

Suitable divalent substituents, e.g., on a suitable carbon atom, are independently the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, and an unsubstituted 5-6-membered saturated, partially unsaturated, and aryl ring having 0-4 heteroatoms independently selected from nitrogen, oxygen, and sulfur.

Suitable substituents on the aliphatic group of R* are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

In some embodiments, suitable substituents on a substitutable nitrogen are independently —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of $R^†$ are independently halogen, —$R^■$, -(halo$R^■$), —OH, —$OR^■$, —$O(haloR^■)$, —CN, —C(O)OH, —$C(O)OR^■$, —$NH_2$, —$NH^■$, —$NR^■_2$, or —$NO_2$, wherein each $R^■$ is unsubstituted or where preceded by "halo" is substituted only with one or more halogens, and is independently $C_1$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

"Wild-type" defines the cell, composition, tissue or other biological material as it exists in nature.

In some embodiments, the 3-hydroxy-propanal and pyruvate are prepared from one or more of glycerol, C5 sugars, C6 sugars, phosphor-glycerates, other carbon sources, intermediates of the glycolysis pathway, and combinations thereof. In some embodiments, the C5 sugars comprise or alternatively consists essentially of, or yet further consists of, one or more of xylose, xylulose, ribulose, arabinose, lyxose, and ribose, and the C6 sugars comprise or alternatively consist essentially of, or yet further consist of, allose, altrose, glucose, mannose, gulose, idose, talose, fructose, psicose, sorbose, and tagatose. In some embodiments, the other carbon source is a feedstock suitable as a carbon source for a microorganism wherein the feedstock comprises or alternatively consists essentially of, or yet further consists of, one or more of amino acids, lipids, corn stover, *miscanthus*, municipal waste, energy cane, sugar cane, bagasse, starch stream, dextrose stream, formate, methanol, and combinations thereof.

As used herein, the term "C5 sugar" refers to a sugar molecule containing 5 carbons.

As used herein, the term "C6 sugar" refers to a sugar molecule containing 6 carbons.

In some embodiments, the term "aldol addition" refers to a chemical reaction in which a pyruvate molecule forms a corresponding enol or an enolate ion or a Schiff's base or an enamine that reacts with the aldehyde functional group of the CN aldehyde to produce a $C_{N+3}$ 4-hydroxy-2-keto-carboxylic acid intermediate. In some embodiments, the CN aldehyde is 3-hydroxy-propanal and the $C_{N+3}$ 4-hydroxy-2-keto-carboxylic acid intermediate is 4,6-dihydroxy-2-keto-hexanoic acid.

In some embodiments, the term "aldol condensation" refers to a chemical reaction in which a pyruvate molecule forms a corresponding enol or an enolate ion or a Schiff's base or an enamine that reacts with the aldehyde functional group of the CN aldehyde to produce a $C_{N+3}$ 3,4-dehydro-2-keto-carboxylic acid. In some embodiments, the $C_N$ aldehyde is 3-hydroxy-propanal and the $C_{N+3}$ 3,4-dehydro-2-keto-carboxylic acid is 6-hydroxy-3,4-dehydro-2-keto-hexanoic acid.

As used herein, the term "solution" refers to a liquid composition that contains a solvent and a solute, such as a starting material used in the methods described herein. In some embodiments, the solvent is water. In some embodiments, the solvent is an organic solvent.

As used herein, the term "enzymatic step" or "enzymatic reaction" refers to a molecular reaction catalyzed by an enzyme that is selected to facilitate the desired enzymatic reaction. Enzymes are large biological molecules and highly selective catalysts. Most enzymes are proteins, but some catalytic RNA molecules have been identified.

Throughout the application, enzymatic steps may be denoted as "step 1", "step 2" and so on so forth and the enzyme specifically catalyzing these steps is denoted as "1", "2" and so on so forth, respectively. Such an enzyme is also referred to as a "reaction specific enzyme".

As used herein, the term "CoA" or "coenzyme A" is intended to mean an organic cofactor or prosthetic group (nonprotein portion of an enzyme) whose presence is required for the activity of many enzymes to form an active enzyme system.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

As used herein, the term "non-naturally occurring" or "non-natural" when used in reference to a microbial organism or microorganism of the present disclosure is intended to mean that the microbial organism has at least one genetic alteration not normally found in a naturally occurring strain of the referenced species, including wild-type strains of the referenced species. Genetic alterations include, for example, but are not limited to, modifications introducing expressible nucleic acids encoding polypeptides, other nucleic acid additions, nucleic acid deletions and/or other functional disruption of the microbial organism's genetic material. Such modifications include, for example, but are not limited to, coding regions and functional fragments thereof, for heterologous, homologous or both heterologous and homologous polypeptides for the referenced species. Additional modifications include, for example, but are not limited to, non-coding regulatory regions in which the modifications alter expression of a gene or operon.

As is used herein "exogenous" is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to an enzymatic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is originally or naturally present in the wild-type host. Similarly, the term when used in reference to expression of an encoding nucleic acid refers to expression of an encoding nucleic acid contained within the wild-type microorganism.

The term "heterologous" refers to a molecule or activity derived from a source other than the referenced species whereas "homologous" when used in this context refers to a molecule or activity derived from the host microbial organism. Accordingly, exogenous expression of an encoding nucleic acid can utilize either or both a heterologous or homologous encoding nucleic acid.

It is understood that when more than one exogenous nucleic acid is included in a microbial organism, that the more than one exogenous nucleic acids refers to the referenced encoding nucleic acid or enzymatic activity, as discussed above. It is further understood, as disclosed herein, that more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein, a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or enzymatic activities refers to the number of encoding nucleic acids or the number of enzymatic activities, not the number of separate nucleic acids introduced into the host organism.

In some embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

Those skilled in the art will understand that the genetic alterations are described with reference to a suitable host organism such as *E. coli* and their corresponding metabolic reactions or a suitable source organism for desired genetic material such as genes for a desired biosynthetic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

Sources of encoding nucleic acids the pathway enzymes can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Pseudomonas knackmussii, Pseudomonas putida, Pseudomonas fluorescens, Klebsiella pneumoniae, Serratia proteamaculans, Streptomyces* sp. 2065, *Pseudomonas aeruginosa, Ralstonia eutropha, Clostridium acetobutylicum, Euglena gracilis, Treponema denticola, Clostridium kluyveri, Homo sapiens, Rattus norvegicus, Acinetobacter* sp. ADP1, *Streptomyces coelicolor, Eubacterium barkeri, Peptostreptococcus asaccharolyticus, Clostridium botulinum, Clostridium tyrobutyricum, Clostridium thermoaceticum (Moorella thermoaceticum), Acinetobacter calcoaceticus, Mus musculus, Sus scrofa, Flavobacterium* sp, *Arthrobacter aurescens, Penicillium chrysogenum, Aspergillus niger, Aspergillus nidulans, Bacillus subtilis, Saccharomyces cerevisiae, Zymomonas mobilis, Mannheimia succiniciproducens, Clostridium ljungdahlii, Clostridium carboxydivorans, Geobacillus stearothermophilus, Agrobacterium tumefaciens, Achromobacter denitrificans, Arabidopsis thaliana, Haemophilus influenzae, Acidaminococcus fermentans, Clostridium* sp. M62/1, *Fusobacterium nucleatum*, as well as other exemplary species disclosed herein or available as source organisms for corresponding genes (see Examples). However, with the complete genome sequence available for now more than 400 microorganism genomes and a variety of yeast, fungi, plant, and mammalian genomes, the identification of genes encoding the requisite pathway enzymes, for one or more genes in related or distant species, including for example, homologues, orthologs, paralogs and nonorthologous gene displacements of known genes, and the interchange of genetic alterations between organisms is routine and well known in the art.

Ortholog refers to genes in different species that evolved from a common ancestral gene by speciation. Normally, orthologs retain the same function in the course of evolution. Identification of orthologs is critical for reliable prediction of gene function in newly sequenced genomes.

Paralog refers to genes related by duplication within a genome. While orthologs generally retain the same function in the course of evolution, paralogs can evolve new functions, even if these are related to the original one.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

As used herein, the terms "microorganism" or "microbial organism" or "microbes" are used interchangeably and refer to a living biological and isolated prokaryotic or eukaryotic cell that can be transformed or transfected via insertion of an exogenous or recombinant nucleic acid, such as DNA or RNA. Any suitable prokaryotic or eukaryotic microorganism may be used in the present disclosure so long as it remains viable after being transformed with a sequence of nucleic acids. A suitable microorganism of the present disclosure is one capable of expressing one or more nucleic acid constructs encoding one or more recombinant proteins that can catalyze at least one step in the methods. Microorganism can be selected from group of bacteria, yeast, fungi, mold, and archaea. These are commercially available.

As used herein, "fungal" refers to any eukaryotic organism categorized within the kingdom of Fungi. Phyla within the kingdom of Fungi include Ascomycota, Basidiomycota, Blastocladiomycota, Chytridiomycota, Glomeromycota, Microsporidia, and Neocallimastigomycota. As used herein, "yeast" refers to fungi growing in single-celled forms (for example, by budding), whereas "mold" refers to fungi growing in filaments made of multicellular hyphae or mycelia (McGinnis, M. R. and Tyring, S. K. "Introduction to Mycology." Medical Microbiology. 4$^{th}$ ed. Galveston: Univ. of TX Medical Branch at Galveston, 1996).

In some embodiments, the microorganisms are yeast cells. In some embodiments, the yeast cell is from a *Candida, Hansenula, Issatchenkia, Kluyveromyces, Pichia, Saccharomyces, Schizosaccharomyces*, or *Yarrowia* species.

In some embodiments, the microorganisms are mold cells. In some embodiments, the mold host cell is from a *Neurospora, Trichoderma, Aspergillus, Fusarium*, or *Chrysosporium* species.

In some embodiments, the microorganism is an archaea. In some embodiments, a suitable archaea is from an *Archaeoglobus, Aeropyrum, Halobacterium, Pyrobaculum, Pyrococcus, Sulfolobus, Methanococcus, Methanosphaera, Methanopyrus, Methanobrevibacter, Methanocaldococcus*, or *Methanosarcina* species.

The term "bacteria" refers to any microorganism within the domain or kingdom of prokaryotic organisms. Phyla within the domain or kingdom of bacteria include Acidobacteria, Actinobacteria, *Actinobacillus, Agrobacterium*, Anaerobiospirrulum, Aquificae, Armatimonadetes, Bacteroidetes, *Burkholderia*, Caldiserica, Chlamydiae, Chlorobi, *Chlorella*, Chloroflexi, Chrysiogenetes, *Citrobacter, Clostridium*, Cyanobacteria, Deferribacteres, *Deinococcusthermus*, Dictyoglomi, *Enterobacter*, Elusimicrobia, Fibrobacteres, Firmicutes, Fusobacteria, *Geobacillus, Gemmatimonadetes, Gluconobacter, Halanaerobium, Klebsiella, Kluyvera, Lactobacillus*, Lentisphaerae, *Methylobacterium, Nitrospira*, Pasteurellaceae, *Paenibacillus*, Planctomycetes, *Propionibacterium, Pseudomonas*, Proteobacteria, *Ralstonia*, Schizochytrium, Spirochaetes, *Streptomyces*, Synergistetes, Tenericutes, *Thermoanaerobacterium*, Thermodesulfobacteria, Thermotogae, Verrucomicrobia, *Zobellella*, and *Zymomonas*. In some embodiments, the bacterial microorganisms are *E. coli* cells. In some embodiments, the bacterial microorganisms are *Bacillus* sp. cells. Examples of *Bacillus* species include without limitation *Bacillus subtilis, Bacillus megaterium, Bacillus cereus, Bacillus thuringiensis, Bacillus mycoides*, and *Bacillus licheniformis*.

A carboxylic acid compound prepared by the methods of the present disclosure can form a salt with a counter ion including, but not limited to, a metal ion, e.g., an alkali metal ion, such as sodium, potassium, an alkaline earth ion, such as calcium, magnesium, or an aluminum ion; or coordinates with an organic base such as tetraalkylammonium, ethanolamine, diethanolamine, triethanolamine, trimethylamine, N-methylglucamine, and the like. The acid can form a salt with a counter ion or organic base present in the reaction conditions or can be converted to a salt by reacting with an inorganic or organic base.

Any carboxylic acid containing compound herein is referred to as either an acid or a salt, which has been used interchangeably throughout to refer to the compound in any of its neutral or ionized forms, including any salt forms thereof. It is understood by those skilled understand that the specific form will depend on the pH.

A solvate of a compound is a solid-form of the compound that crystallizes with less than one, one or more than one molecules of solvent inside in the crystal lattice. A few examples of solvents that can be used to create solvates, such as pharmaceutically acceptable solvates, include, but are not limited to, water, $C_1$-$C_6$ alcohols (such as methanol, ethanol, isopropanol, butanol, and can be optionally substituted) in general, tetrahydrofuran, acetone, ethylene glycol, propylene glycol, acetic acid, formic acid, and solvent mixtures thereof. Other such biocompatible solvents which may aid in making a pharmaceutically acceptable solvate are well known in the art. Additionally, various organic and inorganic acids and bases can be added to create a desired solvate. Such acids and bases are known in the art. When the solvent is water, the solvate can be referred to as a hydrate. In some embodiments, one molecule of a compound can form a solvate with from 0.1 to 5 molecules of a solvent, such as 0.5 molecules of a solvent (hemisolvate, such as hemihydrate), one molecule of a solvent (monosolvate, such as monohydrate) and 2 molecules of a solvent (disolvate, such as dihydrate).

When referring to a compound for which several isomers exist (e.g., cis and trans isomer, and R and S isomer, or a combination thereof), the compound in principle includes all possible enantiomers, diastereomers and cis/trans isomers of that compound that may be used in the method of the present disclosure.

For each species, any cell belonging to that species is considered a suitable microorganism of the present disclosure. A host cell of any species may exist as it was isolated from nature, or it may contain any number of genetic modifications (e.g., genetic mutations, deletions, or recombinant polynucleotides).

The term "recombinant nucleic acid" or "recombinant polynucleotide" as used herein refers to a polymer of nucleic acids where at least one of the following is true: (a) the sequence of nucleic acids is foreign to (i.e., not naturally found in) a given microorganism; (b) the sequence may be naturally found in a given microorganism, but in an unnatural (e.g., greater than expected) amount; or (c) the sequence of nucleic acids contains two or more subsequences that are not found in the same relationship to each other in nature. For example, regarding instance (c), a recombinant nucleic acid sequence will have two or more sequences from unrelated genes arranged to make a new functional nucleic acid.

In some embodiments, recombinant polypeptides or proteins or enzymes of the present disclosure may be encoded by genetic material as part of one or more expression vectors. An expression vector contains one or more polypeptide-encoding nucleic acids, and it may further contain any desired elements that control the expression of the nucleic acid(s), as well as any elements that enable the replication and maintenance of the expression vector inside a given host cell. All of the recombinant nucleic acids may be present on a single expression vector, or they may be encoded by multiple expression vectors.

An expression vector or vectors can be constructed to include one or more pathway-encoding nucleic acids as exemplified herein operably linked to expression control sequences functional in the host organism. Expression vectors applicable for use in the microbial host organisms provided include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, CA) and Promega Biotech (Madison, WI). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Exogenous nucleic acid sequences involved in a pathway for synthesis of desired compounds described herein can be introduced stably or transiently into a host cell using techniques well known in the art including, but not limited to, conjugation, electroporation, chemical transformation, transduction, transfection, and ultrasound transformation. For exogenous expression in E. coli or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in E. coli (Hoffmeister et al., J. Biol. Chem. 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. It is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". As used herein, "about" will mean up to plus or minus 10%. It also is to be understood, although not always explicitly stated, that the reagents described herein are merely exemplary and that equivalents of such are known in the art.

"Operatively linked" refers to a juxtaposition wherein the elements are in an arrangement allowing them to function.

The term "culturing" refers to the in vitro propagation of cells or organisms on or in media (culture) of various kinds. It is understood that the descendants of a cell grown in culture may not be completely identical (i.e., morphologically, genetically, or phenotypically) to the parent cell.

A "gene" refers to a polynucleotide containing at least one open reading frame (ORF) that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art.

The term "express" refers to the production of a gene product. The term overexpression refers to the production of the mRNA transcribed from the gene or the protein product encoded by the gene that is more than that of a normal or control cell, for example 0.5 times, 1.0 times, 1.5 times, or alternatively, 2 times, or alternatively, at least 2.5 times, or alternatively, at least 3.0 times, or alternatively, at least 3.5 times, or alternatively, at least 4.0 times, or alternatively, at least 5 times, or alternatively 10 times higher than the expression level detected in a control sample or wild-type cell.

As used herein, "homology" refers to sequence similarity between a reference sequence and at least a fragment of a second sequence. Homologs may be identified by any method known in the art, preferably, by using the BLAST tool to compare a reference sequence to a single second sequence or fragment of a sequence or to a database of sequences. As described below, BLAST will compare sequences based upon percent identity and similarity.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 29% identity, optionally 30%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200, or more amino acids) in length.

Methods of alignment of sequences for comparison are well-known in the art. For example, the determination of percent sequence identity between any two sequences can be accomplished using a mathematical algorithm. Non-limiting examples of such mathematical algorithms are the algorithm of Myers and Miller, *CABIOS* 4:11 17 (1988); the local homology algorithm of Smith et al., *Adv. Appl. Math.* 2:482 (1981); the homology alignment algorithm of Needleman and Wunsch, *J. Mol. Biol.* 48:443 453 (1970); the search-for-similarity-method of Pearson and Lipman, *Proc. Natl. Acad. Sci.* 85:2444 2448 (1988); the algorithm Karlin and Altschul *Proc. Natl. Acad. Sci. USA* 90:5873 5877 (1993).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window," as used herein, includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981), by the homology alignment algorithm of Needleman and Wunsch, *J Mol Biol* 48(3):443-453 (1970), by the search for similarity method of Pearson and Lipman, *Proc Natl Acad Sci USA* 85(8):2444-2448 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection [see, e.g., Brent et al., (2003) Current Protocols in Molecular Biology, John Wiley & Sons, Inc. (Ringbou Ed)].

Two examples of algorithms that are suitable for determining percent sequence identity and sequence similarity are the BLAST and BLAST 2.0 algorithms, which are described in Altschul et al., Nucleic Acids Res 25(17):3389-3402 (1997) and Altschul et al., J Mol Biol 215(3)-403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4, and a comparison of both strands. For amino acid sequences, the BLASTP program uses as defaults a wordlength of 3, and expectation (E) of 10, and the BLOSUM62 scoring matrix (see Henikoff and Henikoff, Proc Natl Acad Sci USA 89(22):10915-10919 (1992)) alignments (B) of 50, expectation (E) of 10, M=5, N=-4, and a comparison of both strands.

The BLAST algorithm also performs a statistical analysis of the similarity between two sequences (see, e.g., Karlin and Altschul, Proc Natl Acad Sci USA 90(12):5873-5877 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Other than percentage of sequence identity noted above, another indication that two nucleic acid sequences or polypeptides are substantially identical is that the polypeptide encoded by the first nucleic acid is immunologically cross-reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions. Yet another indication that two nucleic acid sequences are substantially identical is that the same primers can be used to amplify the sequence.

The phrase "functionally equivalent protein" refers to protein or polynucleotide which hybridizes to the exemplified polynucleotide under stringent conditions and which exhibit similar or enhanced biological activity in vivo, e.g., over 120%, or alternatively over 110%, or alternatively over 100%, or alternatively, over 90% or alternatively over 85% or alternatively over 80%, as compared to the standard or control biological activity. Additional embodiments within the scope of the present disclosure are identified by having more than 80%, or alternatively, more than 85%, or alternatively, more than 90%, or alternatively, more than 95%, or alternatively more than 97%, or alternatively, more than 98 or 99% sequence homology. Percentage homology can be determined by sequence comparison programs such as BLAST run under appropriate conditions. In some embodiments, the program is run under default parameters. In some embodiments, reference to a certain enzyme or protein includes its functionally equivalent enzyme or protein.

A population of cells intends a collection of more than one cell that is identical (clonal) or non-identical in phenotype and/or genotype. A substantially homogenous population of cells is a population having at least 70%, or alternatively at least 75%, or alternatively at least 80%, or alternatively at least 85%, or alternatively at least 90%, or alternatively at least 95%, or alternatively at least 98% identical phenotype, as measured by pre-selected markers.

When an enzyme is mentioned with reference to an enzyme class (EC), the enzyme class is a class wherein the enzyme is classified or may be on classified on the basis of the enzyme nomenclature provided by the Nomenclature Committee of the International Union of Biochemistry and Molecular Biology. Other suitable enzymes that have not yet been classified in a specific class but may be classified as such are also included.

Non-Naturally Occurring Microbial Organisms

The non-naturally occurring microbial organisms provided herein are constructed using methods well known in the art as exemplified herein to exogenously express at least one nucleic acid encoding an enzyme or protein used in a biosynthetic pathway described herein in sufficient amounts to produce compounds such as 2-keto pentanoic acid, 2-keto hexanoic acid, 6-hydroxy-2-keto-hexanoic acid, 1,5-pentanediol, adipic acid, 1, 6-hexanediol, or 6-hydroxy hexanoic acid.

Successful engineering of a microbial host capable of producing the desired product described herein involves identifying the appropriate set of enzymes with sufficient activity and specificity for catalyzing various steps in the pathway, for example those described in the Examples herein and in literature. The individual enzyme or protein activities from the exogenous DNA sequences can also be assayed using methods well known in the art. In addition, these enzymes can be engineered using modern protein engineering approaches (Protein Engineering Handbook; Lutz S., & Bornscheuer U. T. Wiley-VCH Verlag GmbH & Co. KGaA: 2008; Vol. 1 & 2) such as directed evolution, rational mutagenesis, computational design (Zanghellini, A et al, 2008) or a combination thereof, for achieving the desired substrate specificity, controlling the stereoselectivity to synthesize enantiopure or racemic products, stabilizing the enzyme to withstand harsh industrial process conditions by improving half-life, thermostability, inhibitor/product tolerance and improving enzyme expression and solubility in the desired microbial production host of choice. Once the desired enzymes that can catalyze each step of the pathway are characterized, the genes encoding these enzymes will be cloned in the microorganism of choice, fermentation conditions will be optimized and product formation will be monitored following fermentation. After the enzymes are identified, the genes corresponding to one or more of the enzymes are cloned into a microbial host. In some embodiments, the genes encoding each enzyme of a particular pathway described herein are cloned into a microbial host.

Methods to introduce recombinant/exogenous nucleic acids/proteins into a microorganism, and vectors suitable for this purpose, are well known in the art. For example, various techniques are illustrated in Current Protocols in Molecular Biology, Ausubel et al., eds. (Wiley & Sons, New York, 1988, and quarterly updates). Methods for transferring expression vectors into microbial host cells are well known in the art. Specific methods and vectors may differ depending upon the species of the desired microbial host. For example, bacterial host cells may be transformed by heat shock, calcium chloride treatment, electroporation, liposomes, or phage infection. Yeast host cells may be transformed by lithium acetate treatment (may further include carrier DNA and PEG treatment) or electroporation. These methods are included for illustrative purposes and are in no way intended to be limiting or comprehensive. Routine experimentation through means well known in the art may be used to determine whether a particular expression vector or transformation method is suited for a given microbial host. Furthermore, reagents and vectors suitable for many different microbial hosts are commercially available and well known in the art.

Methods for construction, expression or overexpression of enzymes and testing the expression levels in non-naturally occurring microbial hosts are well known in art (Protein Expression Technologies: Current Status and Future Trends, Baneyx F. eds. Horizon Bioscience, 2004, Norfolk, UK; and Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, MD (1999)).

Methods for carrying out fermentation of microorganisms are well known in art. For example, various techniques are illustrated in Biochemical Engineering, Clark et al., eds. (CRC press, 1997, $2^{nd}$ edition). Specific methods for fermenting may differ depending upon the species of the desired microbial host. Typically, the microorganism is grown in appropriate media along with the carbon source in a batch or a continuous fermentation mode. The use of agents known to modulate catabolite repression or enzyme activity can be used to enhance adipic acid or glutaric acid production. Suitable pH for fermentation is between 3-10. Fermentation can be performed under aerobic, anaerobic, or anoxic conditions based on the requirements of the microorganism. Fermentations can be performed in a batch, fed-batch or continuous manner. Fermentations can also be conducted in two phases, if desired. For example, the first phase can be aerobic to allow for high growth and therefore high productivity, followed by an anaerobic phase of high caprolactone yields.

The carbon source can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the present disclosure include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the present disclosure for the production of desired compound.

The reactions described herein can be monitored and the starting materials, the products or intermediates in the fermentation media can be identified by analyzing the media using high pressure liquid chromatography (HPLC) analysis, GC-MS (Gas Chromatography-Mass Spectroscopy) and LC-MS (Liquid Chromatography-Mass Spectroscopy) or other suitable analytical methods using routine procedures well known in the art.

Any of the non-naturally occurring microbial organisms described herein can be cultured to produce and/or secrete the products of the present disclosure.

Compounds prepared by the methods described herein can be isolated by methods generally known in the art for isolation of an organic compound prepared by biosynthesis or fermentation. For example, the compounds can be isolated from solution by crystallization, salt formation, pervaporation, reactive extraction, extraction (liquid-liquid and two-phase), adsorption, ion exchange, dialysis, distillation, gas stripping, and membrane based separations (Roffler et al., *Trends Biotechnolgy.* 2: 129-136 (1984)). 1,5-Pentanediol can be isolated from solution using distillation, extraction (liquid-liquid and two-phase), pervaporation, and membrane based separations (Roffler et al., *Trends Biotechnolgy.* 2: 129-136 (1984)).

As described herein, one exemplary growth condition for achieving biosynthesis of desired product includes anaerobic culture or fermentation conditions. In certain embodiments, the non-naturally occurring microbial organisms of the present disclosure can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also include growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of products. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production in commercial quantities.

The term "pathway enzyme expressed in a sufficient amount" implies that the enzyme is expressed in an amount that is sufficient to allow detection of the desired pathway product.

In another aspect, provided herein is a recombinant microbial organism comprising a first exogenous nucleic acid encoding an aldolase hydratase enzyme, wherein the recombinant microbial organism is further modified to express an increased amount of quinone oxidoreductase as compared to wild-type or the same microbial organism that is not modified, and optionally wherein the microbial organism is *Corynebacterium glutamicum*, a *clostridium* species, or *E. coli*.

In some embodiments, the organism comprises a second exogenous nucleic acid encoding quinone oxidoreductase. In some embodiments, the first exogenous nucleic acid and/or the second exogenous nucleic acid further comprises a regulatory element that drives expression of the second exogenous nucleic acid. In some embodiments, the first exogenous nucleic acid and the second exogenous nucleic acid further comprises a regulatory element that drives expression of the second exogenous nucleic acid. In some embodiments, the first exogenous nucleic acid or the second exogenous nucleic acid further comprises a regulatory element that drives expression of the second exogenous nucleic acid. In some embodiments, the first exogenous nucleic acid further comprises a regulatory element that drives expression of the second exogenous nucleic acid. In some embodiments, the second exogenous nucleic acid further comprises a regulatory element that drives expression of the second exogenous nucleic acid. In some embodiments, the regulatory element is selected from a promoter or an enhancer. In some embodiments, the regulatory element is a promoter. In some embodiments, the regulatory element is an enhancer.

In some embodiments, the aldolase hydratase enzyme has an EC number 4.1.2.45, EC number 4.1.2.34 or EC number 4.1.1.4. In some embodiments, the aldolase hydratase enzyme is an enzyme selected from the group of enzymes identified under Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1. In some embodiments, the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP_107818191, A0A023WZF9, PYN48855, A0A421PAQ6, WP_028217297, WP_034507049, KMK64081.1, WP_070028041.1, or KZL92449.1. In some embodiments, the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP_107818191, A0A023WZF9, PYN48855, A0A421PAQ6, WP_028217297, WP_034507049, KMK64081.1, WP_070028041.1, or KZL92449.1, or a portion (e.g., a domain, a set of amino acid residues (can be continuous or separated), etc.) thereof that promotes the formation of a aldol-dehydration product. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the hydratase-aldolase is an enzyme selected from Tables 1, 5, 6, 7, and 8. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from Tables 1, 5, 6, 7, and 8.

In some embodiments, the hydratase-aldolase further comprises one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the first exogenous nucleic acid and the second exogenous nucleic acid are each contained in a vector. In some embodiments, the first exogenous nucleic acid and the second exogenous nucleic acid are each contained in the same vector. In some embodiments, the first exogenous nucleic acid and the second exogenous nucleic acid are each contained in their own separate vectors. In some embodiments, the vector is a plasmid. In some embodiments, the vector is a viral vector.

In some embodiments, the quinone oxidoreductase is an enzyme having an EC number 1.6.5. In some embodiments, the quinone oxidoreductase is an enzyme having an EC number 1.6.5.5. In some embodiments, the quinone oxidoreductase is an enzyme selected from the group of enzymes identified under GenBank, RefSeq, or Uniprot ID Nos. P28304, P40783, Q0K2I0, A0A1Z1SRY9, P43903, I7G8G0, or Q142L2, ALK19324.1, A0A1G9R408, G4Q8R5, ANA98723.1, K0EUQ3, A0A061CRS8, Q9A212, A0A1I6RWW2, WP_026197277.1, Q5NKZ3, WP_012333034.1, or WP_136898000.1. In some embodiments, the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

In some embodiments, the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under under GenBank, RefSeq, or Uniprot ID Nos. P28304, P40783, Q0K2I0, A0A1Z1SRY9, P43903, I7G8G0, or Q142L2, ALK19324.1, A0A1G9R408, G4Q8R5, ANA98723.1, K0EUQ3, A0A061CRS8, Q9A212, A0A1I6RWW2, WP_026197277.1, Q5NKZ3, WP_012333034.1, or WP_136898000.1. In some embodiments, the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

In some embodiments, the quinone oxidoreductase further comprises one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the recombinant microbial organism is capable of producing a 2-keto carboxylic acid of formula:

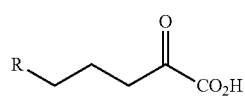

wherein R is H, CH$_3$, or CH$_2$OH.

In some embodiments, the recombinant microbial organism is capable of producing 1,5-pentanediol, 1,6-hexanediol, adipic acid, or 6-hydroxy hexanoate.

In some embodiments, the recombinant microbial organism is genetically modified to improve production of pyruvate from a carbon source. In some embodiments, the carbon source is selected from glycerol, glucose, xylose, arabinose, galactose, mannose, fructose, sucrose, and starch, or a combination thereof.

In another aspect, provided herein is a population of recombinant microbial organisms disclosed herein. In some embodiments, the population is substantially homogenous. In some embodiments, substantially homogenous refers to at least 90%, 91%, 92%, 93%, 94%, 95%, 96%, 97%, 98%, or 99%, or more, homogenous.

In another aspect, provided herein is a method of producing 1,5-pentanediol, 1,6-hexanediol, adipic acid, or 6-hydroxy hexanoate, comprising culturing the population disclosed herein under suitable conditions. In some embodiments, the method further comprises isolating the 1,5-pentanediol, 1,6-hexanediol, adipic acid, or 6-hydroxy hexanoate from the culture or the microbial organisms.

Detailed Description of Certain Embodiments

Among other things, the present disclosure encompasses the recognition that certain polypeptides, e.g., various aldol-dehydration product biosynthesis polypeptides which are or comprise hydratase-aldolase polypeptides, can be utilized to effectively produce various compounds. In some embodiments, the present disclosure demonstrates that various aldehydes, e.g., various aliphatic aldehydes described herein, which are structurally different from natural and/or known aldehyde substrates of such polypeptides, can be utilized for effective manufacturing of many products using aldol-dehydration product biosynthesis polypeptide described herein. Among other things, the present disclosure demonstrates that production of various aldol-dehydration products can be catalyzed by a single aldol-dehydration product biosynthesis polypeptide (e.g., various hydratase-aldolase polypeptides as described herein).

In some embodiments, the present disclosure provides a method comprising:

contacting pyruvate and an aldehyde with an aldol-dehydration product biosynthesis polypeptide so that an aldol-dehydration product is produced, wherein:

the aldol-dehydration product is a compound comprising an aldehyde or ketone group and a double bond conjugated with the aldehyde or ketone group.

In some embodiments, an aldehyde is an aliphatic aldehyde. In some embodiments, a —CHO group of an aldehyde is not conjugated, e.g., to a double bond, a triple bond or an aromatic group.

In some embodiments, the present disclosure provides a method comprising:

contacting pyruvate and an aliphatic aldehyde with an aldol-dehydration product biosynthesis polypeptide so that an aldol-dehydration product is produced, wherein:

the carbonyl group of the aliphatic aldehyde is not conjugated to a alkenyl, alkynyl, or aromatic group; and the aldol-dehydration product is a compound comprising an aldehyde or ketone group and a double bond conjugated with the aldehyde or ketone group.

In some embodiments, an aldol-dehydration product biosynthesis polypeptide is or comprises a hydratase-aldolase polypeptide, e.g., those exemplified herein. In some embodiments, provided methods comprise contacting pyruvate and an aliphatic aldehyde with a hydratase-aldolase to produce an aldol-dehydration product.

In some embodiments, an aldol-dehydration product biosynthesis polypeptide comprises an aldolase polypeptide. In some embodiments, an aldol-dehydration product biosynthesis polypeptide comprises a hydratase polypeptide. In some embodiments, an aldol-dehydration product biosynthesis polypeptide comprises a hydratase-aldolase polypeptide. In some embodiments, an aldol-dehydration product biosynthesis polypeptide is a hydratase-aldolase polypeptide. In some embodiments, a hydratase-aldolase polypeptide is or comprises a hydratase-aldolase as described herein, e.g., an enzyme having an EC number 4.1.2.45 or EC number 4.1.2.34, or EC 4.1.1.4, or is selected from Tables 1 and 5-8.

In some embodiments, an aldol-dehydration product biosynthesis polypeptide is within an organism, e.g., a microbe. In some embodiments, an organism expresses an engineered aldol-dehydration product biosynthesis polypeptide. In some embodiments, an organism expresses an increased level and/or activity of aldol-dehydration product biosynthesis polypeptide. In some embodiments, an organism provides an increased rate and/or yield for producing an aldol-dehydration product. In some embodiments, an organism provides an increased substrate utilization for producing an aldol-dehydration product.

In some embodiments, conversion of pyruvate and an aliphatic aldehyde into an aldol-dehydration product is catalyzed by an aldol-dehydration product biosynthesis polypeptide.

In some embodiments, an aldol-dehydration product can be provided through alternative pathways. In some embodiments, an aldol-dehydration product is produced from an aldol product.

In some embodiments, the present disclosure provides a method comprising:

contacting pyruvate and an aldehyde with an aldol product biosynthesis polypeptide so that an aldol product is produced, wherein:

the aldol-dehydration product is a compound comprising an aldehyde or ketone group and a double bond conjugated with the aldehyde or ketone group.

In some embodiments, an aldehyde is an aliphatic aldehyde. In some embodiments, a —CHO group of an aldehyde is not conjugated to a double bond, triple bond or an aromatic group.

In some embodiments, the present disclosure provides a method comprising:

contacting pyruvate and an aliphatic aldehyde with an aldol product biosynthesis polypeptide so that an aldol product is produced, wherein:

the carbonyl group of the aliphatic aldehyde is not conjugated to a alkenyl, alkynyl, or aromatic group; and the aldol product is a compound comprising an aldehyde or ketone group and a hydroxyl group attached to a beta-carbon of an aldehyde or ketone carbonyl group.

Various methods of the present disclosure comprise utilization of biosynthesis polypeptides. In some embodiments, a biosynthesis polypeptide, when used together with a particular product, e.g., an aldol product biosynthesis polypeptide, a reduction product biosynthesis polypeptide, etc., refers to a polypeptide that is involved in the synthesis of the particular product. In some embodiments, a biosynthesis polypeptide when used together with a particular product is or comprises an enzyme that catalyzes formation of the particular product. In some embodiments, a biosynthesis polypeptide has an amino acid sequence that is found in nature, for example in a microbe (e.g., in a reference biosynthesis polypeptide for a particular product found in nature). Alternatively or additionally, in some embodiments, a biosynthesis polypeptide shares a characteristic sequence element and/or an overall percent identity with an appropriate reference biosynthesis polypeptide (e.g., as is found in nature and/or is presented herein (e.g., in one or more of relevant Tables) or a portion thereof (e.g., a portion (e.g., a domain (e.g., a relevant catalytic domain) and/or a set of amino acid residues (which can be continuous or separated)) that promotes a relevant reaction).

In some embodiments, an aldol product biosynthesis polypeptide is or comprises an aldolase polypeptide. Those skilled in the art reading the present disclosure appreciate that various aldolase polypeptides can be utilized in accordance with the present disclosure. In some embodiments, an aldolase polypeptide is or comprises an aldolase described in US20170044551, the aldolases of which are incorporated herein by reference.

In some embodiments, an aldol product biosynthesis polypeptide is or comprises an aldolase-hydratase as described herein.

In some embodiments, an aldol product biosynthesis polypeptide is in an organism such as a microbe. In some embodiments, organisms are engineered to express an engineered or exogenous aldol product biosynthesis polypeptides, often at higher protein levels and/or activity levels. In some embodiments, conversion of pyruvate and an aliphatic aldehyde into an aldol product is catalyzed by an aldol product biosynthesis polypeptide. In some embodiments, a method is performed in a culture, e.g., a bacteria culture. As for other biosynthesis polypeptides, aldol product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, an aldol product is converted into an aldol-dehydration product, either catalyzed by an enzyme, through biosynthesis, or through traditional organic synthesis without enzymatic catalysis. In some embodiments, a conversion comprises contacting an aldol product with a dehydration product biosynthesis polypeptide so that an aldol-dehydration product is produced. In some embodiments, a dehydration product biosynthesis polypeptide is or comprises a hydratase. In some embodiments, a dehydration product biosynthesis polypeptide is or comprises a dehydratase. In some embodiments, a hydratase or dehydratase is described in US20170044551, the hydratases and dehydratases of which are incorporated herein by reference. As for other biosynthesis polypeptides, dehydration product biosynthesis polypeptides may be in organisms such as bacteria, may be engineered, and/or may be expressed at increased at increased protein and/or activity levels, and their products may be generated at increased rates and/or yields and/or substrates utilization.

As appreciated by those skilled in the art, aldol-dehydration products can be utilized to manufacture various products, e.g., 1,5-pentanediol, 1,6-hexanediol, 6HH, adipic acid, etc. which can be utilized to manufacture a wide range of products, such as polymers, resins, coating products, etc. In some embodiments, utilization of aldol-dehydration products comprises one or more chemical conversions, each of which may be independently catalyzed by a polypeptide (e.g., an enzyme described herein), optionally in an organism, or performed through traditional chemical processes without utilization of enzymes. As appreciated by those skilled in the art, one or more or all steps can be performed in one or more organisms, each of which may independently perform one or more reactions using substrate(s) generated within itself or from outside of the organism, and/or one or more cultures which independently comprises one or more types of organisms (each of which may independently perform one or more reactions using substrate(s) generated within itself or from a culture (e.g., a feed compound, a compound generated by another organism, etc.)). In some embodiments, one or more or all biosynthesis polypeptides are independently in one organism, e.g., an bacterium optionally engineered. In some embodiments, one or more of a set of biosynthesis polypeptides for producing a product is expressed in one organism, e.g., an bacterium optionally engineered, and one or more of the other biosynthesis polypeptides in the set is expressed in one or more other organisms, e.g., bacteria optionally engineered. In some embodiments, an organism, e.g., a bacterium is engineered to contain one or more exogenous nucleic acids that encode one or more or all of the biosynthesis polypeptides. In some embodiments, manufacturing of a product comprises multiple steps of reactions which are performed in a single culture comprising one or more bacteria each independently comprises one or more or all, and together comprise all, required biosynthesis polypeptides. In some embodiments, manufacturing of a product comprises multiple steps of reactions which are performed in two or more cultures each independently comprising one or more bacteria each independently comprises one or more or all, and together comprise all, required biosynthesis polypeptides.

For example, in some embodiments, double bonds in aldol-dehydration products are converted to single bonds.

In some embodiments, the present disclosure provides a method comprising:
  contacting an alkene with an alkene reduction product biosynthesis polypeptide so that an alkene reduction product is produced, wherein:
  the alkene comprises a double bond conjugated to a carbonyl group; and
  a double bond conjugated to a carbonyl group in the alkene is reduced to a single bond to provide an alkene reduction product.

In some embodiments, an alkene is an aldol-dehydration product.

In some embodiments, an alkene reduction product biosynthesis polypeptide is or comprises an enzyme that catalyze reduction of aldol-dehydration product, e.g., 2-oxo-3-enoic acids, as described herein. In some embodiments, such an enzyme is a quinone oxidoreductase as described herein. In some embodiments, such an enzyme belongs to EC 1.6.5. In some embodiments, such an enzyme belongs to EC 1.6.5.5. In some embodiments, such an enzyme is selected from Table 9.

In some embodiments, alkene reduction product biosynthesis polypeptide is within an organism, e.g., a microbe. In some embodiments, an organism expresses an engineered alkene reduction product biosynthesis polypeptide. In some embodiments, an organism expresses an increased level and/or activity of alkene reduction product biosynthesis polypeptide. In some embodiments, an organism provides an increased rate and/or yield for producing an alkene reduction product. In some embodiments, an organism provides an increased substrate utilization for producing an alkene reduction product.

In some embodiments, an alkene reduction product biosynthesis polypeptide is or comprises an enzyme that encoded and/or expressed by an organism endogenously without engineering.

Those skilled in the art reading the present disclosure appreciate that various aldehydes may be utilized in accordance with the present disclosure. In some embodiments, an aldehyde is a natural or known substrate of a biosynthesis polypeptide, e.g., aldol-dehydration product biosynthesis polypeptide which is or comprises a hydratase-aldolase. In some embodiments, an aldehyde is not a natural or known substrate. For example, among other things, the present disclosure demonstrates that aliphatic aldehydes can be utilized for product manufacturing using hydratase-aldolases whose natural or known substrates are aromatic or conjugated aldehydes.

In some embodiments, an aldehyde is an aliphatic aldehyde. In some embodiments, an aldehyde has one or two alpha-hydrogen. In some embodiments, an aldehyde has the structure of formula A-1:

$$R^a\text{-}L^2\text{-}L^1\text{-}C(O)H, \qquad \text{A-1}$$

or a salt thereof, wherein:
  $R^a$ is R" or —OR",
  each of $L^1$ and $L^2$ is independently a covalent bond, or a bivalent, optionally substituted, linear or branched $C_{1\text{-}20}$ aliphatic or $C_{1\text{-}20}$ heteroaliphatic, wherein one or more methylene units are optionally and independently replaced by —C≡C—, 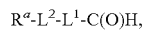, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;
  Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;
  each R" is independently —R', —C(O)R', —CO$_2$R', or —SO$_2$R';
  R' is hydrogen, or an optionally substituted group selected from $C_{1\text{-}10}$ aliphatic, $C_{1\text{-}10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:
  two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

In some embodiments, an aldol product has the structure of formula P-1:

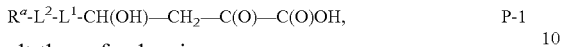

R$^a$-L$^2$-L$^1$-CH(OH)—CH$_2$—C(O)—C(O)OH,      P-1 or a salt thereof, wherein:
R$^a$ is R" or —OR",
each of L$^1$ and L$^2$ is independently a covalent bond, or a bivalent, optionally substituted, linear or branched C$_{1-20}$ aliphatic or C$_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;
Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;
each R" is independently —R', —C(O)R', —CO$_2$R', or —SO$_2$R';
R' is hydrogen, or an optionally substituted group selected from C$_{1-10}$ aliphatic, C$_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:
two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

In some embodiments, an aldol-dehydration product has the structure of formula P-2:

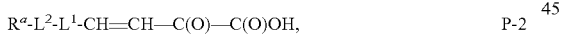

R$^a$-L$^2$-L$^1$-CH=CH—C(O)—C(O)OH,      P-2 or a salt thereof, wherein:
R$^a$ is R" or —OR",
each of L$^1$ and L$^2$ is independently a covalent bond, or a bivalent, optionally substituted, linear or branched C$_{1-20}$ aliphatic or C$_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;
Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;
each R" is independently —R', —C(O)R', —CO$_2$R', or —SO$_2$R';
R' is hydrogen, or an optionally substituted group selected from C$_{1-10}$ aliphatic, C$_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:
two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

In some embodiments, —CH=CH— in formula P-2 is in E configuration. In some embodiments, —CH=CH— in formula P-2 is in Z configuration.

In some embodiments, an alkene reduction product has the structure of formula P-3:

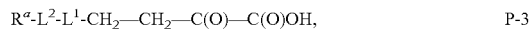

R$^a$-L$^2$-L$^1$-CH$_2$—CH$_2$—C(O)—C(O)OH,      P-3 or a salt thereof, wherein:
R$^a$ is R" or —OR",
each of L$^1$ and L$^2$ is independently a covalent bond, or a bivalent, optionally substituted, linear or branched C$_{1-20}$ aliphatic or C$_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;
Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;
each R" is independently —R', —C(O)R', —CO$_2$R', or —SO$_2$R';
R' is hydrogen, or an optionally substituted group selected from C$_{1-10}$ aliphatic, C$_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:
two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

In some embodiments, R$^a$ is R". In some embodiments, R$^a$ is —OR".

In some embodiments, R" is R'. In some embodiments, R" is —C(O)R'. In some embodiments, R" is —CO$_2$R'. In some embodiments, R" is —SO$_2$R'.

In some embodiments, R' is hydrogen. In some embodiments, R' is not hydrogen.

In some embodiments, R$^a$ is R'. In some embodiments, R$^a$ is —OR'. In some embodiments, R$^a$ is —H. In some embodiments, R$^a$ is —OH.

In some embodiments, L$^1$ is a covalent bond. In some embodiments, L$^1$ is not a covalent bond.

In some embodiments, L$^1$ is optionally substituted C$_{1-6}$ alkylene. In some embodiments, L$^1$ is optionally substituted linear C$_{1-6}$ alkylene. In some embodiments, L$^1$ is optionally substituted —CH$_2$—. In some embodiments, L$^1$ is optionally substituted —CH$_2$CH$_2$—. In some embodiments, L$^1$ is optionally substituted —CH$_2$CH$_2$CH$_2$—. In some embodiments, L$^1$ is optionally substituted —CH$_2$CH$_2$CH$_2$CH$_2$—. In some embodiments, L$^1$ is optionally substituted —CH$_2$CH$_2$CH$_2$CH$_2$CH$_2$—. In some embodiments, L$^1$ is optionally substituted —CH$_2$CH$_2$CH$_2$CH$_2$CH$_2$CH$_2$—. In some embodiments, —CH$_2$— bonded to —C(O)H is unsubstituted. In some embodiments, —CH$_2$— bonded to —C(O)H is monosubstituted. In some embodiments, L$^1$ is substituted. In some embodiments, L$^1$ is unsubstituted. In some embodiments, L$^1$ is —CH$_2$—. In some embodiments, L$^1$ is —CH$_2$CH$_2$—. In some embodiments, L$^1$ is —CH$_2$CH$_2$CH$_2$—. In some embodiments, L$^1$ is —CH$_2$CH$_2$CH$_2$CH$_2$—. In some embodiments, L$^1$ is —CH$_2$CH$_2$CH$_2$CH$_2$CH$_2$—. In some embodiments, L$^1$ is —CH$_2$CH$_2$CH$_2$CH$_2$CH$_2$CH$_2$—.

In some embodiments, L$^2$ is a covalent bond. In some embodiments, L$^2$ is not a covalent bond.

In some embodiments, L$^2$ is optionally substituted C$_{1-6}$ alkylene. In some embodiments, L$^2$ is optionally substituted linear C$_{1-6}$ alkylene. In some embodiments, L$^2$ is optionally substituted —CH$_2$—. In some embodiments, L$^2$ is optionally substituted —CH$_2$CH$_2$—. In some embodiments, L$^2$ is optionally substituted —CH$_2$CH$_2$CH$_2$—. In some embodiments, L$^2$ is optionally substituted —CH$_2$CH$_2$CH$_2$CH$_2$—. In some embodiments, L$^2$ is optionally substituted —CH$_2$CH$_2$CH$_2$CH$_2$CH$_2$—. In some embodiments, L$^2$ is optionally substituted —CH$_2$CH$_2$CH$_2$CH$_2$CH$_2$CH$_2$—. In some embodiments, —CH$_2$— bonded to —C(O)H is unsubstituted. In some embodiments, —CH$_2$— bonded to —C(O)H is monosubstituted. In some embodiments, L$^2$ is substituted. In some embodiments, L$^2$ is unsubstituted. In some embodiments, L$^2$ is —CH$_2$—. In some embodiments, L$^2$ is —CH$_2$CH$_2$—. In some embodiments, L$^2$ is —CH$_2$CH$_2$CH$_2$—. In some embodiments, L$^2$ is —CH$_2$CH$_2$CH$_2$CH$_2$—. In some embodiments, L$^2$ is —CH$_2$CH$_2$CH$_2$CH$_2$CH$_2$—. In some embodiments, L$^2$ is —CH$_2$CH$_2$CH$_2$CH$_2$CH$_2$CH$_2$—.

In some embodiments, at least one of L$^1$ and L$^2$ is not a covalent bond.

In some embodiments, an aldehyde is CH$_3$CHO. In some embodiments, an aldehyde is CH$_3$CH$_2$CHO. In some embodiments, an aldehyde is CH$_3$CH$_2$CH$_2$CHO. In some embodiments, an aldehyde is CH$_2$OHCHO. In some embodiments, an aldehyde is CH$_2$OHCH$_2$CHO. In some embodiments, an aldehyde is CH$_2$OHCH$_2$CH$_2$CHO.

In some embodiments, an aldol product is CH$_3$CH(OH)CH$_2$C(O)COOH. In some embodiments, an aldol product is CH$_3$CH$_2$CH(OH)CH$_2$C(O)COOH. In some embodiments, an aldol product is CH$_3$CH$_2$CH$_2$CH(OH)CH$_2$C(O)COOH. In some embodiments, an aldol product is CH$_2$OHCH(OH)CH$_2$C(O)COOH. In some embodiments, an aldol product is CH$_2$OHCH$_2$CH(OH)CH$_2$C(O)COOH. In some embodiments, an aldol product is CH$_2$OHCH$_2$CH$_2$CH(OH)CH$_2$C(O)COOH.

In some embodiments, an aldol-dehydration product is CH$_3$CH=CHC(O)COOH. In some embodiments, an aldol-dehydration product is CH$_3$CH$_2$CH=CHC(O)COOH. In some embodiments, an aldol-dehydration product is CH$_3$CH$_2$CH$_2$CH=CHC(O)COOH. In some embodiments, an aldol-dehydration product is CH$_2$OHCH=CHC(O)COOH. In some embodiments, an aldol-dehydration product is CH$_2$OHCH$_2$CH=CHC(O)COOH. In some embodiments, an aldol-dehydration product is CH$_2$OH CH$_2$CH$_2$CH=CHC(O)COOH.

In some embodiments, an alkene reduction product is CH$_3$CH$_2$CH$_2$C(O)COOH. In some embodiments, an alkene reduction product is CH$_3$CH$_2$CH$_2$CH$_2$C(O)COOH. In some embodiments, an alkene reduction product is CH$_3$CH$_2$CH$_2$CH$_2$CH$_2$C(O)COOH. In some embodiments, an alkene reduction product is CH$_2$OHCH$_2$CH$_2$C(O)COOH. In some embodiments, an alkene reduction product is CH$_2$OHCH$_2$CH$_2$CH$_2$C(O)COOH. In some embodiments, an alkene reduction product is CH$_2$OHCH$_2$CH$_2$CH$_2$CH$_2$C(O)COOH.

In some embodiments, an alkene reduction product is converted into a carbonyl reduction product, either catalyzed by an enzyme, through biosynthesis, or through traditional organic synthesis without enzymatic catalysis. In some embodiments, an alkene reduction product comprises a carbonyl group, and the carbonyl group is converted to —CH(OH)—. In some embodiments, a method comprises contacting an alkene reduction product with a carbonyl reduction product biosynthesis polypeptide so that a carbonyl reduction product is produced, wherein:

the alkene reduction product comprises a carbonyl group; and a carbonyl group of the alkene reduction product is converted to —CH(OH)—.

In some embodiments, a carbonyl reduction product biosynthesis polypeptide is or comprises a reductase. In some embodiments, a carbonyl reduction product biosynthesis polypeptide is or comprises a keto reductase as described herein. In some embodiments, a carbonyl reduction product biosynthesis polypeptide is or comprises a 2-keto acid-2-reductase as described herein. In some embodiments, such an enzyme is a 6-hydroxy-2-oxohexanoate-2-reductase as described herein. In some embodiments, such an enzyme is described in US20170044551, the enzymes of which are incorporated herein by reference.

In some embodiments, conversion of an alkene reduction product into a carbonyl reduction product is catalyzed by a carbonyl reduction product biosynthesis polypeptide.

As for many other biosynthesis polypeptides, carbonyl reduction product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a carbonyl reduction product has the structure of formula P-4:

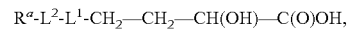

$$R^a\text{-}L^2\text{-}L^1\text{-}CH_2\text{—}CH_2\text{—}CH(OH)\text{—}C(O)OH, \quad \text{P-4}$$

or a salt thereof, wherein each variable is independently as described herein.

In some embodiments, a carbonyl reduction product is CH$_3$CH$_2$CH$_2$CH(OH)COOH. In some embodiments, a carbonyl reduction product is CH$_3$CH$_2$CH$_2$CH$_2$CH(OH)COOH. In some embodiments, a carbonyl reduction product is CH$_3$CH$_2$CH$_2$CH$_2$CH$_2$CH(OH)COOH. In some embodiments, a carbonyl reduction product is CH$_2$OHCH$_2$CH$_2$CH(OH)COOH. In some embodiments, a carbonyl reduction product is CH$_2$OHCH$_2$CH$_2$CH$_2$CH(OH)COOH. In some embodiments, a carbonyl reduction product is CH$_2$OHCH$_2$CH$_2$CH$_2$CH$_2$CH(OH)COOH.

In some embodiments, a carbonyl reduction product is converted into a CoA transfer product, either catalyzed by an enzyme, through biosynthesis, or through traditional organic synthesis without enzymatic catalysis. In some embodiments, a CoA transfer product is a compound of formula P-5:

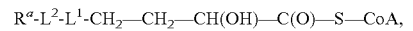

$$R^a\text{-}L^2\text{-}L^1\text{-}CH_2\text{—}CH_2\text{—}CH(OH)\text{—}C(O)\text{—}S\text{—}CoA, \quad \text{P-5}$$

or a salt thereof, wherein each variable is independently as described herein.

In some embodiments, such a conversion is catalyzed by a CoA (CoA=Coenzyme A) transfer product biosynthesis polypeptide. In some embodiments, a CoA transfer product biosynthesis polypeptide is or comprises a CoA transferase as described herein, e.g., 2,6-dihydroxy-hexanoate CoA-transferase. In some embodiments, a CoA transferase is one described in US20170044551, the CoA transferases of which are incorporated herein by reference. In some embodiments, such a conversion is catalyzed by a CoA transfer product biosynthesis polypeptide.

As for many other biosynthesis polypeptides, CoA transfer product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a CoA transfer product is CH₃CH₂CH₂CH(OH)C(O)S-CoA. In some embodiments, a CoA transfer product is CH₃CH₂CH₂CH₂CH(OH)C(O)S-COA. In some embodiments, a CoA transfer product is CH₃CH₂CH₂CH₂CH₂CH(OH)C(O)S-COA. In some embodiments, a CoA transfer product is CH₂OHCH₂CH₂CH(OH)C(O)S-COA. In some embodiments, a CoA transfer product is CH₂OHCH₂CH₂CH₂CH(OH)C(O)S-COA. In some embodiments, a CoA transfer product is CH₂OHCH₂CH₂CH₂CH₂CH(OH)C(O)S-COA.

In some embodiments, a CoA transfer product is converted into a dehydration product, either catalyzed by an enzyme, through biosynthesis, or through traditional organic synthesis without enzymatic catalysis. In some embodiments, a dehydration product is a compound of formula P-6:

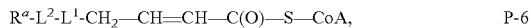

$$R^a\text{-}L^2\text{-}L^1\text{-}CH_2\text{—}CH\text{=}CH\text{—}C(O)\text{—}S\text{—}CoA, \qquad \text{P-6}$$

or a salt thereof, wherein each variable is independently as described herein.

In some embodiments, such a conversion is catalyzed by a dehydration product biosynthesis polypeptide. In some embodiments, a dehydration product biosynthesis polypeptide is or comprises a dehydratase as described herein. In some embodiments, a dehydratase is or comprises a 2,6-dihydroxy-hexanoyl-CoA 2-dehydratase as described herein. In some embodiments, a dehydratase is described in US20170044551, the dehydratases of which is incorporated by reference.

In some embodiments, such a conversion is catalyzed by a dehydration product biosynthesis polypeptide.

As for many other biosynthesis polypeptides, dehydration product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a dehydration product is CH₃CH₂CH=CHC(O)S-CoA. In some embodiments, a dehydration product is CH₃CH₂CH₂CH=CHC(O)S-COA. In some embodiments, a dehydration product is CH₃CH₂CH₂CH₂CH=CHC(O)S-COA. In some embodiments, a dehydration product is CH₂OHCH₂CH=CHC(O)S-COA. In some embodiments, a dehydration product is CH₂OHCH₂CH₂CH=CHC(O)S-COA. In some embodiments, a dehydration product is CH₂OHCH₂CH₂CH₂CH=CHC(O)S-COA.

In some embodiments, a dehydration product, e.g. a compound of formula P-6 or a salt thereof, is converted into a reduction product, either catalyzed by an enzyme, through biosynthesis, or through traditional organic synthesis without enzymatic catalysis. In some embodiments, a reduction product is a compound of formula P-7:

$$R^a\text{-}L^2\text{-}L^1\text{-}CH_2\text{—}CH_2\text{—}CH_2\text{—}C(O)\text{—}S\text{—}CoA, \qquad \text{P-7}$$

or a salt thereof, wherein each variable is independently as described herein.

In some embodiments, such a conversion is catalyzed by a reduction product biosynthesis polypeptide. In some embodiments, a reduction product biosynthesis polypeptide is or comprises a 2,3-enoyl-CoA reductase, 2,3-dehydro-carboxyl CoA 2'3-reductase, e.g., 2,3-dehydro-hexanoyl-CoA 2,3-reductase as described herein. In some embodiments, a suitable reductase is described in US20170044551, the reductases of which are incorporated herein by reference. In some embodiments, such a conversion is catalyzed by a reduction product biosynthesis polypeptide.

As for many other biosynthesis polypeptides, reduction product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a reduction product is CH₃CH₂CH₂CH₂C(O)S-CoA. In some embodiments, a reduction product is CH₃CH₂CH₂CH₂CH₂C(O)S-COA. In some embodiments, a reduction product is CH₃CH₂CH₂CH₂CH₂CH₂C(O)S-COA. In some embodiments, a reduction product is CH₂OHCH₂CH₂CH₂C(O)S-COA. In some embodiments, a reduction product is CH₂OHCH₂CH₂CH₂CH₂C(O)S-COA. In some embodiments, a reduction product is CH₂OHCH₂CH₂CH₂CH₂CH₂C(O)S-COA.

In some embodiments, a reduction product, e.g. a compound of formula P-7 or a salt thereof, is converted into a CoA transfer product, either catalyzed by an enzyme, through biosynthesis, or through traditional organic synthesis without enzymatic catalysis. In some embodiments, a CoA transfer product is a compound of formula P-8:

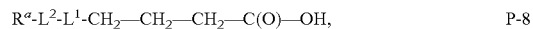

$$R^a\text{-}L^2\text{-}L^1\text{-}CH_2\text{—}CH_2\text{—}CH_2\text{—}C(O)\text{—}OH, \qquad \text{P-8}$$

or a salt thereof, wherein each variable is independently as described herein.

In some embodiments, such a conversion is catalyzed by a CoA transfer product biosynthesis polypeptide. In some embodiments, a CoA transfer product biosynthesis polypeptide is or comprises a CoA transferase as described herein, e.g., a 6-hydroxyhexanoyl-CoA transferase as described herein. In some embodiments, a CoA transferase is described in US20170044551, the CoA transferases of which are incorporated herein by reference. In some embodiments, such a conversion is catalyzed by a CoA transfer product biosynthesis polypeptide.

As for many other biosynthesis polypeptides, CoA transfer product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a CoA transfer product is CH₃CH₂CH₂CH₂C(O)OH. In some embodiments, a CoA transfer product is CH₃CH₂CH₂CH₂CH₂C(O)OH. In some embodiments, a CoA transfer product is CH₃CH₂CH₂CH₂CH₂CH₂C(O)OH. In some embodiments, a CoA transfer product is CH₂OHCH₂CH₂CH₂C(O)OH. In some embodiments, a CoA transfer product is CH₂OHCH₂CH₂CH₂CH₂C(O)OH. In some embodiments, a CoA transfer product is CH₂OHCH₂CH₂CH₂CH₂CH₂C(O)OH.

In some embodiments, a CoA transfer product, e.g. a compound of formula P-8 or a salt thereof wherein $R^a$ is —OH, is converted into an oxidation product, either catalyzed by an enzyme, through biosynthesis, or through traditional organic synthesis without enzymatic catalysis. In some embodiments, an oxidation product is a compound of formula P-9:

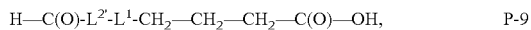
$$H—C(O)-L^{2'}-L^1-CH_2—CH_2—CH_2—C(O)—OH, \quad P-9$$

or a salt thereof, wherein $L^{2'}$ is a covalent bond, or a bivalent, optionally substituted, linear or branched $C_{1-19}$ aliphatic or $C_{1-19}$ heteroaliphatic, wherein one or more methylene units are optionally and independently replaced by —C≡C—, —C(R")₂—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)₂—, —S(O)₂N(R")—, —C(O)S—, or —C(O)O—, and each other variable is independently as described herein.

In some embodiments, $L^{2'}$ is a covalent bond. In some embodiments, $L^{2'}$ is not a covalent bond. In some embodiments, at least one of $L^1$ and $L^{2'}$ is not a covalent bond.

In some embodiments, $L^{2'}$ is optionally substituted $C_{1-6}$ alkylene. In some embodiments, $L^{2'}$ is optionally substituted linear $C_{1-6}$ alkylene. In some embodiments, $L^{2'}$ is optionally substituted —CH₂—. In some embodiments, $L^{2'}$ is optionally substituted —CH₂CH₂—. In some embodiments, $L^{2'}$ is optionally substituted —CH₂CH₂CH₂—. In some embodiments, $L^{2'}$ is optionally substituted —CH₂CH₂CH₂CH₂—. In some embodiments, $L^{2'}$ is optionally substituted —CH₂CH₂CH₂CH₂CH₂—. In some embodiments, $L^{2'}$ is optionally substituted —CH₂CH₂CH₂CH₂CH₂CH₂—. In some embodiments, —CH₂— bonded to —C(O)H is unsubstituted. In some embodiments, —CH₂— bonded to —C(O)H is monosubstituted. In some embodiments, $L^{2'}$ is substituted. In some embodiments, $L^{2'}$ is unsubstituted. In some embodiments, $L^{2'}$ is —CH₂—. In some embodiments, $L^{2'}$ is —CH₂CH₂—. In some embodiments, $L^{2'}$ is —CH₂CH₂CH₂—. In some embodiments, $L^{2'}$ is —CH₂CH₂CH₂CH₂—. In some embodiments, $L^{2'}$ is —CH₂CH₂CH₂CH₂CH₂—. In some embodiments, $L^{2'}$ is —CH₂CH₂CH₂CH₂CH₂CH₂—.

In some embodiments, such a conversion is catalyzed by an oxidation product biosynthesis polypeptide. In some embodiments, an oxidation product biosynthesis polypeptide is or comprises an alcohol dehydrogenase, e.g., a primary alcohol dehydrogenase such as 6-hydroxyhexanoate dehydrogenase, as described herein. In some embodiments, an alcohol dehydrogenase is described in US20170044551, the alcohol dehydrogenases of which are incorporated herein by reference. In some embodiments, such a conversion is catalyzed by an oxidation product biosynthesis polypeptide.

As for many other biosynthesis polypeptides, oxidation product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, an oxidation product is HC(O)CH₂CH₂CH₂C(O)OH. In some embodiments, an oxidation product is HC(O)CH₂CH₂CH₂CH₂C(O)OH. In some embodiments, an oxidation product is HC(O)CH₂CH₂CH₂CH₂CH₂C(O)OH.

In some embodiments, an oxidation product, e.g. a compound of formula P-9 or a salt thereof, is converted into an aldehyde oxidation product, either catalyzed by an enzyme, through biosynthesis, or through traditional organic synthesis without enzymatic catalysis. In some embodiments, an oxidation product is a compound of formula P-10:

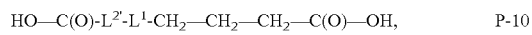
$$HO—C(O)-L^{2'}-L^1-CH_2—CH_2—CH_2—C(O)—OH, \quad P-10$$

or a salt thereof, wherein each other variable is independently as described herein.

In some embodiments, such a conversion is catalyzed by an aldehyde oxidation product biosynthesis polypeptide. In some embodiments, an aldehyde oxidation product biosynthesis polypeptide is or comprises an aldehyde dehydrogenase, e.g., a 6-hydroxyhexanoate dehydrogenase, as described herein. In some embodiments, an aldehyde dehydrogenase is described in US20170044551, the aldehyde dehydrogenases of which are incorporated herein by reference. In some embodiments, such a conversion is catalyzed by an aldehyde oxidation product biosynthesis polypeptide.

As for many other biosynthesis polypeptides, aldehyde oxidation product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, an aldehyde oxidation product is HOC(O)CH₂CH₂CH₂C(O)OH. In some embodiments, an oxidation product is HOC(O)CH₂CH₂CH₂CH₂C(O)OH. In some embodiments, an oxidation product is HOC(O)CH₂CH₂CH₂CH₂CH₂C(O)OH.

In some embodiments, a CoA transfer product, e.g. a compound of formula P-8 or a salt thereof, is converted into a carboxyl reduction product, either catalyzed by an enzyme, through biosynthesis, or through traditional organic synthesis without enzymatic catalysis. In some embodiments, a carboxyl reduction product is a compound of formula P-9':

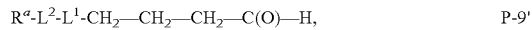
$$R^a\text{-}L^2\text{-}L^1\text{-}CH_2—CH_2—CH_2—C(O)—H, \quad P-9'$$

or a salt thereof, wherein each variable is independently as described herein.

In some embodiments, such a conversion is catalyzed by a carboxyl reduction product biosynthesis polypeptide. In some embodiments, a carboxyl reduction product biosynthesis polypeptide is or comprises a carboxylic acid reductase or aldehyde dehydrogenase as described herein. In some embodiments, a carboxyl reduction product biosynthesis polypeptide is or comprises a 6-hydroxyhexanoate 1-reductase. In some embodiments, a carboxyl reduction product biosynthesis polypeptide is or comprises a carboxylic acid reductase or aldehyde dehydrogenase described in US20170044551, the carboxylic acid reductases or aldehyde dehydrogenases of which are incorporated herein by reference. In some embodiments, such a conversion is catalyzed by a carboxyl reduction product biosynthesis polypeptide.

As for many other biosynthesis polypeptides, carboxyl reduction product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a carboxyl reduction product is CH₃CH₂CH₂CH₂C(O)H. In some embodiments, a carboxyl reduction product is CH₃CH₂CH₂CH₂CH₂C(O)H. In some embodiments, a carboxyl reduction product is CH₃CH₂CH₂CH₂CH₂CH₂C(O)H. In some embodiments, a carboxyl reduction product is CH₂OHCH₂CH₂CH₂C(O)H. In some embodiments, a carboxyl reduction product is CH₂OHCH₂CH₂CH₂CH₂C(O)H. In some embodiments, a carboxyl reduction product is CH$_2$OHCH$_2$CH$_2$CH$_2$CH$_2$C(O)H.

In some embodiments, a carboxyl reduction product, e.g. a compound of formula P-9' or a salt thereof, is converted into an aldehyde reduction product, either catalyzed by an enzyme, through biosynthesis, or through traditional organic synthesis without enzymatic catalysis. In some embodiments, an aldehyde reduction product is a compound of formula P-10':

$$R^\alpha\text{-L}^2\text{-L}^1\text{-CH}_2\text{---CH}_2\text{---CH}_2\text{---CH}_2\text{---OH,} \qquad \text{P-10'}$$

or a salt thereof, wherein each variable is independently as described herein.

In some embodiments, such a conversion is catalyzed by an aldehyde reduction product biosynthesis polypeptide. In some embodiments, an aldehyde reduction product biosynthesis polypeptide is or comprises an aldehyde reductase or an alcohol (e.g., primary alcohol) dehydrogenase as described herein. In some embodiments, an aldehyde reductase or an alcohol (e.g., primary alcohol) dehydrogenase is described in US20170044551, the reductases and dehydrogenases of which are incorporated herein by reference. In some embodiments, such a conversion is catalyzed by an aldehyde reduction product biosynthesis polypeptide.

As for many other biosynthesis polypeptides, aldehyde reduction product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, an aldehyde reduction product is CH$_3$CH$_2$CH$_2$CH$_2$CH$_2$OH. In some embodiments, an aldehyde reduction product is CH$_3$CH$_2$CH$_2$CH$_2$CH$_2$CH$_2$OH. In some embodiments, an aldehyde reduction product is CH$_3$CH$_2$CH$_2$CH$_2$CH$_2$CH$_2$CH$_2$OH. In some embodiments, an aldehyde reduction product is CH$_2$OHCH$_2$CH$_2$CH$_2$CH$_2$OH. In some embodiments, an aldehyde reduction product is CH$_2$OHCH$_2$CH$_2$CH$_2$CH$_2$CH$_2$OH. In some embodiments, an aldehyde reduction product is CH$_2$OHCH$_2$CH$_2$CH$_2$CH$_2$CH$_2$CH$_2$OH.

In some embodiments, an alkene reduction product, e.g. a compound of formula P-3 or a salt thereof, is converted into a decarboxylation product, either catalyzed by an enzyme, through biosynthesis, or through traditional organic synthesis without enzymatic catalysis. In some embodiments, a decarboxylation product is a compound of formula P-4':

$$R^\alpha\text{-L}^2\text{-L}^1\text{-CH}_2\text{---CH}_2\text{---C(O)---H,} \qquad \text{P-4'}$$

or a salt thereof, wherein each variable is independently as described herein.

In some embodiments, such a conversion is catalyzed by a decarboxylation product biosynthesis polypeptide. In some embodiments, a decarboxylation product biosynthesis polypeptide is or comprises a decarboxylase as described herein. In some embodiments, a decarboxylase is a 2-keto-acid decarboxylase as described herein. In some embodiments, a decarboxylase is described in US20170044551, the decarboxylases of which are incorporated herein by reference. In some embodiments, such a conversion is catalyzed by a decarboxylation product biosynthesis polypeptide.

As for many other biosynthesis polypeptides, decarboxylation product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, a decarboxylation product is CH$_3$CH$_2$CH$_2$CHO. In some embodiments, a decarboxylation product is CH$_3$CH$_2$CH$_2$CH$_2$CHO. In some embodiments, a decarboxylation product is CH$_3$CH$_2$CH$_2$CH$_2$CH$_2$CHO. In some embodiments, a decarboxylation product is CH$_2$OHCH$_2$CH$_2$CHO. In some embodiments, a decarboxylation product is CH$_2$OHCH$_2$CH$_2$CH$_2$CHO. In some embodiments, a decarboxylation product is CH$_2$OHCH$_2$CH$_2$CH$_2$CH$_2$CHO.

In some embodiments, a decarboxylation product, e.g. a compound of formula P-4' or a salt thereof, is converted into an aldehyde reduction product, either catalyzed by an enzyme, through biosynthesis, or through traditional organic synthesis without enzymatic catalysis. In some embodiments, an aldehyde reduction product is a compound of formula P-5':

$$R^\alpha\text{-L}^2\text{-L}^1\text{-CH}_2\text{---CH}_2\text{---CH}_2\text{---OH,} \qquad \text{P-5'}$$

or a salt thereof, wherein each variable is independently as described herein.

In some embodiments, such a conversion is catalyzed by an aldehyde reduction product biosynthesis polypeptide. In some embodiments, an aldehyde reduction product biosynthesis polypeptide is or comprises a primary alcohol dehydrogenase as described herein. In some embodiments, a primary alcohol dehydrogenase is described in US20170044551, the primary alcohol dehydrogenase of which are incorporated herein by reference. In some embodiments, such a conversion is catalyzed by an aldehyde reduction product biosynthesis polypeptide.

As for many other biosynthesis polypeptides, aldehyde reduction product biosynthesis polypeptides may be in organisms such as bacteria, may be engineered, and/or may be expressed at increased at increased protein and/or activity levels, and their products may be generated at increased rates and/or yields and/or substrates utilization.

In some embodiments, an aldehyde reduction product is CH$_3$CH$_2$CH$_2$CH$_2$OH. In some embodiments, an aldehyde reduction product is CH$_3$CH$_2$CH$_2$CH$_2$CH$_2$OH. In some embodiments, an aldehyde reduction product is CH$_3$CH$_2$CH$_2$CH$_2$CH$_2$CH$_2$OH. In some embodiments, an aldehyde reduction product is CH$_2$OHCH$_2$CH$_2$CH$_2$OH. In some embodiments, an aldehyde reduction product is CH$_2$OHCH$_2$CH$_2$CH$_2$CH$_2$OH. In some embodiments, an aldehyde reduction product is CH$_2$OHCH$_2$CH$_2$CH$_2$CH$_2$CH$_2$OH.

In some embodiments, the present disclosure provides nucleic acids encoding one or more biosynthesis polypeptides. In some embodiments, such nucleic acids comprise unnatural sequences. In some embodiments, such nucleic acids are optimized for expression in production organisms, e.g., bacteria.

As demonstrated herein, various technologies are available for assess activities of polypeptides for biosynthesis activities. For example, various technologies for assessing activities of aldol-dehydration product biosynthesis polypeptides (e.g., hydratase-aldolases) or alkene reduction product biosynthesis polypeptides (e.g., enzymes for reducing aldol-dehydration products) are described in the Examples.

In some embodiments, various biosynthesis polypeptides, e.g., an aldol-dehydration product biosynthesis polypeptide, are in organisms, in many embodiments, microorganisms such as bacteria, fungi, etc. In some embodiments, they are expressed from one or more recombinant nucleic acids. In some embodiments, various transformations are performed biosynthetically, e.g., in organisms such as bacteria. In some embodiments, organisms (e.g., microbes such as bacteria) are engineered to contain exogenous nucleic acids that encode biosynthetic polypeptides, e.g., aldol-dehydration product biosynthesis polypeptides such as hydratase-aldolases.

In some embodiments, organism, e.g., those engineered for producing aldol-dehydration products, express modulated levels, typically increased levels and/or activities of aldol-dehydration product biosynthesis polypeptides such as hydratase-aldolase polypeptides.

In some embodiments, organisms comprise engineered nucleic acids and/or express engineered biosynthesis polypeptides, e.g., aldol-dehydration product biosynthesis polypeptides (e.g., various hydratase-aldolases). In some embodiments, an engineered nucleic acid comprises one or more sequence difference compared to a reference nucleic acid. In some embodiments, a reference nucleic acid is a corresponding nucleic acid in an organism to which an engineered nucleic acid is introduced. In some embodiments, a reference nucleic acid is a natural nucleic acid. In some embodiments, an engineered nucleic acid encodes the same polypeptide or a characteristic element thereof as a reference nucleic acid, e.g., a natural nucleic acid. In some embodiments, an engineered nucleic acid encodes a polypeptide or a characteristic element thereof which is different than that encoded by as a reference nucleic acid. In some embodiments, an engineered polypeptide comprises one or more differences compared to a reference polypeptide (e.g., encoded by a reference nucleic acid, found in nature, etc.). In some embodiments, an engineered polypeptide comprises one or more different amino acid residues compared to a reference polypeptide. In some embodiments, an engineered polypeptide is a polypeptide which is absent from an organism to which it is introduced. In some embodiments, an engineered polypeptide is homologous to a reference polypeptide, e.g., sharing 10%, 15%, 20%, 25%, 30%, 35%, 40%, 45%, 50%, 55%, 60%, 65%, 70%, 75%, 80%, 85%, 90%, 95%, 96%, 97%, 95%, 99% or more homology with a reference polypeptide or a characteristic element thereof. In some embodiments, a characteristic element is a domain which catalyzes a relevant reaction. In some embodiments, a characteristic element is a set of amino acid residues. In some embodiments, a characteristic element is a set of amino acid residues that form contact with substrates, products, co-factors, etc. and/or promotes a relevant reaction. As appreciated by those skilled in the art, residues in a set of amino acid residues can be next to each other in sequence, or can be separated. In some embodiments, two or more amino acid residues in a set may be spatially close to each other, e.g., in a catalytic pocket.

In some embodiments, for biosynthetic productions, organisms may express high levels and/or activities of one or more biosynthetic polypeptides. In some embodiments, an organism provides an increased rate and/or yield for producing a desired product.

As described herein, in some embodiments, the present disclosure provides high product yields. In some embodiments, a yield, e.g., of a one or multiple step process involving one or more biosynthesis polypeptides, is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. In some embodiments, provided technologies provide high utilization of a substrate, e.g., pyruvate, for a desired product. In some embodiments, the utilization percentage for a desired product is at least about 5%, 10%, 15%, 20%, 25%, 30%, 35%, 40%, 45%, 50%, 55%, 60%, 65%, 70%, 75%, 80%, 85%, 90%, or 95%.

Those skilled in the art appreciate that various compounds of the present disclosure, e.g., compounds of formula P-1, P-2, P-3, P-4, P-4', P-5, P-5', P-6, P-7, P-8, P-9, P-9', P-10, or P-10', or salts thereof, are useful as materials for production of various compounds, materials and products. For example, adipic acid can be used to produce nylon 6,6, polyester polyols, polyester resins, plasticizers, foods, and other materials. 1,5-Pentanediol can be used to manufacture various polyurethanes, polyester polyols, and polyesters. 1,6-Hexanediol (HDO) can be used to manufacture various polyesters, some of which are useful for industrial coating applications. HDO can also be utilized to produce polyurethane, which among other things can be used as coatings for automotive applications. In some embodiments, HDO is used for production of macrodiols, for example, adipate esters and polycarbonate diols used in, e.g., elastomers and polyurethane dispersions (e.g., for parquet flooring and leather coatings). Through traditional chemical or through biosynthesis processes or combinations thereof, 6-hydroxy hexanoic acid can be cyclized to make ε-caprolactone which can then be aminated to make ε-caprolactam. Through traditional chemical or through biosynthesis processes or combinations thereof, 6-hydroxy hexanoic acid can be aminated to make 6-amino hexanoic acid which can then be cyclized to make ε-caprolactam. ε-Caprolactam, among other things, can be used for the production of Nylon6, a widely used polymer in many different industries. ε-Caprolactone can be polymerized to make polycaprolactone (PCL) a biodegradable polyester with various applications including for the production of specialty polyurethanes. Various 2-ketocarboxylic acids are useful for various industrial relevant chemicals and pharmaceuticals. In some embodiments, such chemicals and pharmaceuticals, or intermediates thereof, are amino acids or α-hydroxy carboxylic acids. In some embodiments, compounds of the present disclosure are utilized to manufacture polyesters, polyester polyols, polyurethane, nylon (e.g., from adipic acid), polycarbonate diols (e.g., from HDO or 1,5-pentanediol, etc.), diacrylate esters (e.g., from HDO or 1,5-pentanediol, etc.), diglycidyl ethers (e.g., from HDO or 1,5-pentanediol, etc.), etc.

In some embodiments, the present disclosure provides preparations of provided processes, e.g., preparations of compounds of formula P-1, P-2, P-3, P-4, P-4', P-5, P-5', P-6, P-7, P-8, P-9, P-9', P-10, or P-10', or salts thereof, and various compounds, materials, products, etc., prepared from such compounds.

Provided technologies provide a number of advantages. Among other things, provided processes utilize one or more biosynthesis polypeptides and/or materials from renewable sources, which can improve efficiency and/or reduce pollution. In some embodiments, preparations of the present disclosure (e.g., of compounds of formula P-1, P-2, P-3, P-4, P-4', P-5, P-5', P-6, P-7, P-8, P-9, P-9', P-10, or P-10', or salts thereof, and various compounds, materials, products, etc., prepared from such compounds) comprise enriched levels of one or more isotopes, e.g., $^{14}C$, compared to those prepared from fossil carbon sources. In some embodiments, preparations using fossil carbon sources have a $^{14}C$ level of 0 or virtually 0. Technologies for assessing isotopic ratios and/or levels of various atoms in compounds, compositions, preparations products, etc., are well known to those skilled in the art and can be utilized in accordance with the present disclosure. For example, in some embodiments, isotopic enrichment can be readily assessed by mass spectrometry using techniques such as accelerated mass spectrometry (AMS) and/or Stable Isotope Ratio Mass Spectrometry (SIRMS), and/or by Site-Specific Natural Isotopic Fractionation by Nuclear Magnetic Resonance (SNIF-NMR).

As appreciated by those skilled in the art, provided methods can be performed in vitro in a system comprising one or more biosynthesis polypeptides. In many embodiments, provided technologies are performed using organisms, e.g., microorganisms such as bacteria, that express one or more biosynthesis polypeptides. In some embodiments, the present disclosure provides organisms, e.g., bacteria, that express one or more biosynthesis polypeptides as described herein. In some embodiments, such organisms are engineered. In some embodiments, such organisms are engineered and/or cultured to express increased levels of proteins and/or activities of one or more biosynthesis polypeptides. In some embodiments, such organisms are engineered and/or cultured to utilize carbon sources to more efficiently produce desired products.

In some embodiments, the present disclosure provides an organism that produces an aldol product of an aliphatic aldehyde, the microbe comprising increased expression or activity of an aldol product biosynthesis polypeptide. In some embodiments, an organism is engineered. In some embodiments, an organism is a bacterium.

In some embodiments, the present disclosure provides an organism that produces an aldol-dehydration product of an aldehyde, the microbe comprising increased expression or activity of an aldol product biosynthesis polypeptide, an aldol-dehydration product biosynthesis polypeptide, a dehydration product biosynthesis polypeptide, and combinations thereof. In some embodiments, the present disclosure provides an organism that produces an aldol-dehydration product of an aldehyde, the microbe comprises increased expression or activity of an aldol-dehydration product biosynthesis polypeptide. In some embodiments, an organism is engineered. In some embodiments, an organism is a bacterium. In some embodiments, an aldehyde is an aliphatic aldehyde.

In some embodiments, the present disclosure provides an organism that produces an alkene reduction product, the microbe comprising increased expression or activity of an alkene reduction product biosynthesis polypeptide. In some embodiments, the present disclosure provides an organism that produces an alkene reduction product from pyruvate and an aldehyde, the microbe comprising increased expression or activity of an alkene reduction product biosynthesis polypeptide. In some embodiments, an organism is engineered. In some embodiments, an organism is a bacterium.

In some embodiments, the present disclosure provides cultures of organisms as described herein. In some embodiments, the present disclosure provides cultures of bacteria. In some embodiments, a culture comprises one or more products of one or more biosynthesis polypeptides, e.g., one or more compounds of formula P-1, P-2, P-3, P-4, P-4', P-5, P-5', P-6, P-7, P-8, P-9, P-9', P-10, or P-10', or salts thereof.

As appreciated by those skilled in the art, pyruvate may be provided as pyruvic acid or a salt thereof.

In one aspect, provided herein is a method for preparing a compound of Formula I:

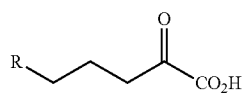

wherein R is CH$_2$OH, CH$_3$ or H,
or a salt thereof, or a solvate of the compound or the salt, wherein the method comprises enzymatic steps.

In some embodiments, the method comprises, or alternatively consists essentially of, or yet further consists of, combining or incubating a C$_N$ aldehyde of formula

wherein R is CH$_2$OH, CH$_3$ or H, and a pyruvate in a solution under conditions that (a) convert the C$_N$ aldehyde and the pyruvate to a C$_{N+3}$ 3,4-dehydro-2-keto-carboxylic acid intermediate through an aldol condensation reaction catalyzed by a hydratase-aldolase having an EC number 4.1.2.45 or EC number 4.1.2.34 or EC number 4.1.1.4 (referred herein as Ads-Hyd); and then (b) convert the C$_{N+3}$ 3,4-dehydro-2-keto-carboxylic acid to C$_{N+3}$ 2-keto-carboxylic acid (i.e., the compound of Formula I), or salt thereof, or a solvate of the compound or the salt, using a oxidoreductase having an EC number 1.6.5. (e.g., EC number 1.6.5.5.).

In some embodiments, the method comprises, or alternatively consists essentially of, or yet further consists of, combining or incubating a C$_N$ aldehyde of formula

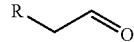

wherein R is CH$_2$OH, CH$_3$ or H, and a pyruvate in a solution under conditions that (a) convert the C$_N$ aldehyde and the pyruvate first to a C$_{N+3}$ 4-hydroxy-2-keto-carboxylic acid intermediate through an aldol addition reaction catalyzed by a hydratase-aldolase having an EC number 4.1.2.45 or EC number 4.1.2.34 or EC number 4.1.1.4 (referred herein as Ads-Hyd); then (b) convert 4-hydroxy-2-keto-carboxylic acid to C$_{N+3}$ 3,4-dehydro-2-keto-carboxylic acid using the hydratase-aldolase; and then (c) convert the C$_{N+3}$ 3,4-dehydro-2-keto-carboxylic acid to C$_{N+3}$ 2-keto-carboxylic acid (i.e., the compound of Formula I), or salt thereof, or a solvate of the compound or the salt, using a oxidoreductase having an EC number 1.6.5. (e.g., EC number 1.6.5.5.)

In another aspect, provided herein is a method for preparing a compound selected from 1,5-pentanediol, adipic acid, 1,6-hexanediol, and 6-hydroxy hexanoic acid, said method comprising, or alternatively consisting essentially of, or yet further consisting of: a) converting a 3-hydroxypropanal and a pyruvate to a 6-hydroxy-2-keto carboxylic acid intermediate using a combination of a hydratase-aldolase having an EC number 4.1.2.45 or EC number 4.1.2.34 or EC number 4.1.1.4 and a oxidoreductase having an EC number 1.6.5 (e.g., EC number 1.6.5.5); and b) converting the 6-hydroxy-2-keto carboxylic acid intermediate to the compound through enzymatic steps.

In some embodiments, the hydratase-aldolase is a trans-o-hydroxybenzylidenepyruvate hydratase-aldolase having an EC number 4.1.2.45. In some embodiments, the hydratase-aldolase is a trans-2'-carboxybenzalpyruvate hydratase-aldolase having an EC number 4.1.2.34. In some embodiments, the hydratase-aldolase is a Acetoacetate decarboxylase having an EC number 4.1.1.4.

In some embodiments, a microorganism is used as a host for the preparation of a compound of Formula I, or a compound selected from 1,5-pentanediol, adipic acid, 1,6-hexanediol, and 6-hydroxy hexanoic acid, or a salt thereof, or a solvate of the compound or the salt. As used herein, a "host" refers to a cell or microorganism that can produce one or more enzymes capable of catalyzing a reaction either inside (by, e.g., uptaking the starting material(s) and optionally secreting the product(s)) or outside (by, e.g., secreting the enzyme) the cell or microorganism.

In some embodiments, the method further comprises or alternatively consists essentially of, or yet further consists of, isolating the compound selected from 1,5-pentanediol, adipic acid, 1,6-hexanediol, and 6-hydroxy hexanoic acid or a salt thereof, or a solvate of the compound or the salt from the solution, culture, and/or the host cell.

In some embodiments, the conditions of the methods disclosed herein comprise or alternatively consist essentially of, or yet further consist of, incubating or contacting the components at a temperature from about 10 to about 200° C., or alternatively at least (all temperatures provided in degrees Celsius) 10, 15, 20, 25, 28, 29, 30, 31, 32, 33, 34, 35, 37, 37, 38, 39, 40, 45, 50, 60, 70, 80, 90, 100, 110, 120, 130, 140, 150, 160, 170, 180 or 190° C., or not higher than 190, 180, 170, 160, 150, 140, 130, 120, 110, 100, 90, 80, 70, 60, 50, 40, 39, 38, 37, 36, 35, 34, 33, 32, 31, 30, 29, 28, or 25° C. with the lower temperature limit being 10° C. In some embodiments, the conditions or alternatively consists essentially of, or yet further consists of, the pH of the incubation solution is from about 2 to about 12. In some embodiments, the pH is at least 2, or 3, 4, 5, 5.5, 6, 6.5, 7, 7.5, 8, or 9 up to about 12. In some embodiments, the pH is not higher than 12, 11, 10, 9, 8, 7.5, 7, 6.5, 6, 5.5, or 4 with the lower pH limit being no lower than 2.

In some embodiments, the conditions comprise or alternatively consist essentially of, or yet further consist of, a molar concentration of pyruvate and $C_N$ aldehyde are present at a concentration from about 0.1 µM to about 5 M. In some embodiments, the concentration is at least about 0.1, 0.5, 1, 10, 100, 500 µM or 1 M. In some embodiments, the concentration is not higher than about 4 M, 3 M, 2 M, 1 M, 500 µM, 200 µM, 100 µM, or 10 µM. The concentration of pyruvate and $C_N$ can be independently the same or different and will vary with the other conditions of the incubation.

In some embodiments, the conditions comprise the presence of a non-natural microorganism that produces one or more enzymes selected from the group consisting of a class I/II pyruvate dependent aldolase, hydratase-aldolase, dehydratase, quinone oxidoreductase, enoyl-CoA reductase, primary alcohol dehydrogenase, keto-acid decarboxylase, coenzyme A transferase, and carboxylic acid reductase. Each of these enzymes is a reaction specific enzyme.

In some embodiments, the microorganism or host is genetically engineered to overexpress the enzymes or to express enzymes in an amount greater than the wild-type counterpart. Methods to determine the expression level of an enzyme or expression product are known in the art, e.g., by PCR.

In some embodiments, the $C_N$ aldehyde is 3-hydroxy-propanal.

In some embodiments, the method further comprises or alternatively consists essentially of, or yet further consists of, preparing the 3-hydroxy-propanal and pyruvate from glycerol, C5 sugars, C6 sugars, phospho-glycerates, other carbon sources, intermediates of the glycolysis pathway, intermediates of propanoate metabolism, or combinations thereof.

In some embodiments, the 3-hydroxy-propanal is obtained through dehydration of glycerol.

In some embodiments, the C5 sugar comprises or alternatively consists essentially of, or yet further consists of, one or more of xylose, xylulose, ribulose, arabinose, lyxose, and ribose.

In some embodiments, the C6 sugar comprises or alternatively consists essentially of, or yet further consists of, one or more of allose, altrose, glucose, mannose, gulose, idose, talose, galactose, fructose, psicose, sorbose, and tagatose.

In some embodiments, the other carbon source is a feedstock suitable as a carbon source for a microorganism, wherein the feedstock comprises or alternatively consists essentially of, or yet further consists of, amino acids, lipids, corn stover, *miscanthus*, municipal waste, energy cane, sugar cane, bagasse, starch stream, dextrose stream, methanol, formate, or combinations thereof.

In some embodiments, a microorganism is used as a host for the preparation of 1,5-pentanediol, adipic acid, 1,6-hexanediol, or 6-hydroxy hexanoic acid.

In some embodiments, the microorganism has the ability to convert C5 sugars, C6 sugars, glycerol, other carbon sources, or a combination thereof to pyruvate.

In some embodiments, the microorganism is engineered for enhanced sugar uptake, e.g., C5 sugar uptake, simultaneous C6/C5 sugar uptake, simultaneous C6 sugar/glycerol uptake, simultaneous C5 sugar/glycerol uptake, or combinations thereof.

In another aspect, provided herein is a method for producing a 2-keto carboxylic acid of formula:

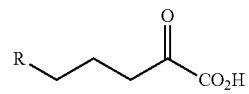

wherein R is H, CH₃, or CH₂OH;
the method comprising, consisting essentially of, or consisting of contacting pyruvate and

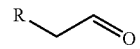

with a hydratase-aldolase and a quinone oxidoreductase in a culture comprising one or more non-naturally occurring microbial organisms to produce the 2-keto carboxylic acid; wherein the hydratase-aldolase and the quinone oxidoreductase are expressed by the one or more non-naturally occurring microbial organisms.

In another aspect, provided herein is a method for producing a 2-keto carboxylic acid of formula:

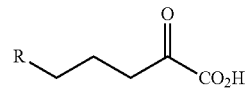

wherein R is H, CH₃, or CH₂OH;
the method comprising, consisting essentially of, or consisting of contacting pyruvate and

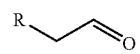

with a hydratase-aldolase and a quinone oxidoreductase in a culture comprising one or more non-naturally occurring microbial organisms to produce the 2-keto carboxylic acid; wherein the hydratase-aldolase and the quinone oxidoreductase are expressed by the one or more non-naturally occurring microbial organisms, and the method is performed in the presence of the one or more non-naturally occurring microbial organisms.

In another aspect, provided herein is a method for producing a 2-keto carboxylic acid of formula:

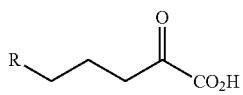

wherein R is H, CH$_3$, or CH$_2$OH;
the method comprising, consisting essentially of, or consisting of contacting pyruvate and

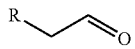

with a trans-o-hydroxybenzylidenepyruvate hydratase-aldolase and a quinone oxidoreductase in a culture comprising one or more non-naturally occurring microbial organisms to produce the 2-keto carboxylic acid; wherein the trans-o-hydroxybenzylidenepyruvate hydratase-aldolase and the quinone oxidoreductase are expressed by the one or more non-naturally occurring microbial organisms, and the method is performed in the presence of the one or more non-naturally occurring microbial organisms.

In another aspect, provided herein is a method for producing a 2-keto carboxylic acid of formula:

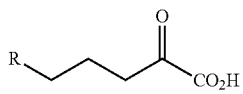

wherein R is H, CH$_3$, or CH$_2$OH;
the method comprising, consisting essentially of, or consisting of contacting pyruvate and

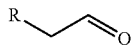

with a hydratase-aldolase and a quinone oxidoreductase in a culture comprising one or more non-naturally occurring microbial organisms to produce the 2-keto carboxylic acid; wherein the hydratase-aldolase and the quinone oxidoreductase are expressed by the one or more non-naturally occurring microbial organisms; and wherein the pyruvate and

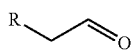

undergo an aldol condensation reaction solely catalyzed by the hydratase-aldolase to produce a 2-oxo-3-enoic acid, and the 2-oxo-3-enoic acid undergoes a reduction solely catalyzed by the quinone oxidoreductase to produce the 2-keto carboxylic acid.

In another aspect, provided herein is a method for producing a 2-keto carboxylic acid of formula:

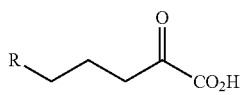

wherein R is H, CH$_3$, or CH$_2$OH;
the method comprising, consisting essentially of, or consisting of contacting pyruvate and

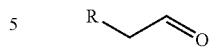

with a hydratase-aldolase and a quinone oxidoreductase in a culture comprising one or more non-naturally occurring microbial organisms to produce the 2-keto carboxylic acid; wherein the hydratase-aldolase and the quinone oxidoreductase are expressed by the one or more non-naturally occurring microbial organisms, and the method is performed in the presence of the one or more non-naturally occurring microbial organisms; and wherein the pyruvate and

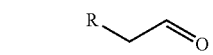

undergo an aldol condensation reaction solely catalyzed by the hydratase-aldolase to produce a 2-oxo-3-enoic acid, and the 2-oxo-3-enoic acid undergoes a reduction solely catalyzed by the quinone oxidoreductase to produce the 2-keto carboxylic acid.

In another aspect, provided herein is a method for producing a 2-keto carboxylic acid of formula:

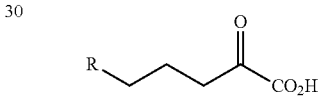

wherein R is H, CH$_3$, or CH$_2$OH;
the method comprising, consisting essentially of, or consisting of contacting pyruvate and

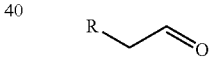

with a hydratase-aldolase and a quinone oxidoreductase in a culture comprising two or more non-naturally occurring microbial organisms to produce the 2-keto carboxylic acid; wherein the hydratase-aldolase and the quinone oxidoreductase are expressed by the two or more non-naturally occurring microbial organisms.

In another aspect, provided herein is a method for producing a 2-keto carboxylic acid of formula:

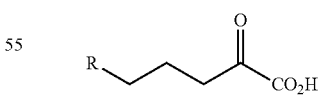

wherein R is H, CH$_3$, or CH$_2$OH;
the method comprising, consisting essentially of, or consisting of contacting pyruvate and

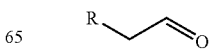

with a hydratase-aldolase and a quinone oxidoreductase in a culture comprising two or more non-naturally occurring microbial organisms to produce the 2-keto carboxylic acid; wherein the hydratase-aldolase and the quinone oxidoreductase are expressed by the two or more non-naturally occurring microbial organisms, and the method is performed in the presence of the two or more non-naturally occurring microbial organisms.

In another aspect, provided herein is a method for producing a 2-keto carboxylic acid of formula:

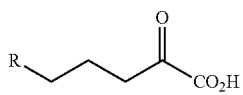

wherein R is H, CH$_3$, or CH$_2$OH;
the method comprising, consisting essentially of, or consisting of contacting pyruvate and

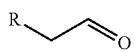

with a trans-o-hydroxybenzylidenepyruvate hydratase-aldolase and a quinone oxidoreductase in a culture comprising two or more non-naturally occurring microbial organisms to produce the 2-keto carboxylic acid; wherein the trans-o-hydroxybenzylidenepyruvate hydratase-aldolase and the quinone oxidoreductase are expressed by the two or more non-naturally occurring microbial organisms, and the method is performed in the presence of the two or more non-naturally occurring microbial organisms.

In another aspect, provided herein is a method for producing a 2-keto carboxylic acid of formula:

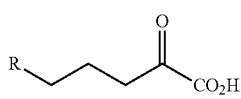

wherein R is H, CH$_3$, or CH$_2$OH;
the method comprising, consisting essentially of, or consisting of contacting pyruvate and

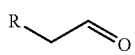

with a hydratase-aldolase and a quinone oxidoreductase in a culture comprising two or more non-naturally occurring microbial organisms to produce the 2-keto carboxylic acid; wherein the hydratase-aldolase and the quinone oxidoreductase are expressed by the two or more non-naturally occurring microbial organisms; and wherein the pyruvate and

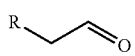

undergo an aldol condensation reaction solely catalyzed by the hydratase-aldolase to produce a 2-oxo-3-enoic acid, and the 2-oxo-3-enoic acid undergoes a reduction solely catalyzed by the quinone oxidoreductase to produce the 2-keto carboxylic acid.

In another aspect, provided herein is a method for producing a 2-keto carboxylic acid of formula:

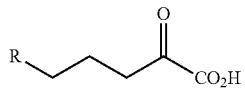

wherein R is H, CH$_3$, or CH$_2$OH;
the method comprising, consisting essentially of, or consisting of contacting pyruvate and

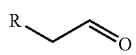

with a hydratase-aldolase and a quinone oxidoreductase in a culture comprising two or more non-naturally occurring microbial organisms to produce the 2-keto carboxylic acid; wherein the hydratase-aldolase and the quinone oxidoreductase are expressed by the two or more non-naturally occurring microbial organisms, and the method is performed in the presence of the two or more non-naturally occurring microbial organisms; and wherein the pyruvate and

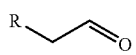

undergo an aldol condensation reaction solely catalyzed by the hydratase-aldolase to produce a 2-oxo-3-enoic acid, and the 2-oxo-3-enoic acid undergoes a reduction solely catalyzed by the quinone oxidoreductase to produce the 2-keto carboxylic acid.

In some embodiments, the

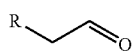

is 3-hydroxy-propanal. In some embodiments, the 3-hydroxy-propanal is produced by dehydration of glycerol by a glycerol dehydratase enzyme exogenously expressed by the one or more non-naturally occurring microbial organisms.

In some embodiments, the method for producing the 2-keto carboxylic acid further comprises separating the 2-keto carboxylic acid from the one or more non-naturally occurring microbial organisms or a culture comprising the one or more non-naturally occurring microbial organisms.

In another aspect, provided herein is a method for producing 1,5-pentanediol, the method comprising
  contacting pyruvate and 3-hydroxy-propanal with a hydratase-aldolase and a quinone oxidoreductase to produce a 2-keto carboxylic acid of formula:

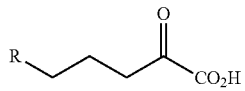

wherein R is CH$_2$OH;
  contacting the 2-keto carboxylic acid with a 2-keto-acid-decarboxylase to produce a 5-hydroxy-pentanal; and
  contacting the 5-hydroxy-pentanal with a primary alcohol dehydrogenase to produce the 1,5-pentanediol, wherein the method is performed in a culture comprising one or more non-naturally occurring microbial organisms.

In another aspect, provided herein is a method for producing 1,5-pentanediol, the method comprising
contacting pyruvate and 3-hydroxy-propanal with a hydratase-aldolase and a quinone oxidoreductase to produce a 2-keto carboxylic acid of formula:

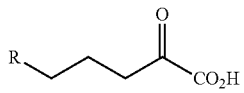

wherein R is CH$_2$OH;
contacting the 2-keto carboxylic acid with a 2-keto-acid-decarboxylase to produce a 5-hydroxy-pentanal; and
contacting the 5-hydroxy-pentanal with a primary alcohol dehydrogenase to produce the 1,5-pentanediol, wherein the method is performed in a culture comprising two or more non-naturally occurring microbial organisms.

In another aspect, provided herein is a method for producing 1,6-hexanediol, the method comprising
contacting pyruvate and 3-hydroxy-propanal with a hydratase-aldolase and a quinone oxidoreductase to produce a 2-keto carboxylic acid of formula:

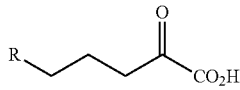

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA;
contacting the 6-hydroxy-hexanoyl-CoA with a 6-hydroxyhexanoyl-CoA transferase to produce 6-hydroxy-hexanoate;
contacting the 6-hydroxy-hexanoate with a 6-hydroxy-hexanoate 1-reductase to produce 6-hydroxy-hexanal; and
contacting the 6-hydroxy-hexanal with a 6-hydroxyhexanal 1-reductase to produce the 1,6-hexanediol, wherein the method is performed in a culture comprising one or more non-naturally occurring microbial organisms.

In another aspect, provided herein is a method for producing 1,6-hexanediol, the method comprising
contacting pyruvate and 3-hydroxy-propanal with a hydratase-aldolase and a quinone oxidoreductase to produce a 2-keto carboxylic acid of formula:

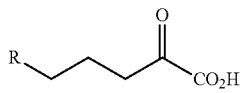

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA;
contacting the 6-hydroxy-hexanoyl-CoA with a 6-hydroxyhexanoyl-CoA transferase to produce 6-hydroxy-hexanoate;
contacting the 6-hydroxy-hexanoate with a 6-hydroxy-hexanoate 1-reductase to produce 6-hydroxy-hexanal; and
contacting the 6-hydroxy-hexanal with a 6-hydroxyhexanal 1-reductase to produce the 1,6-hexanediol, wherein the method is performed in a culture comprising two or more non-naturally occurring microbial organisms.

In another aspect, provided herein is a method for producing 6-hydroxy-hexanoate, the method comprising
contacting pyruvate and 3-hydroxy-propanal with a hydratase-aldolase and a quinone oxidoreductase to produce a 2-keto carboxylic acid of formula:

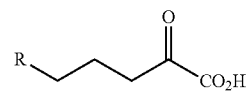

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA; and
contacting the 6-hydroxy-hexanoyl-CoA with a 6-hydroxyhexanoyl-CoA transferase to produce the 6-hydroxy-hexanoate;
wherein the method is performed in a culture comprising one or more non-naturally occurring microbial organisms.

In another aspect, provided herein is a method for producing 6-hydroxy-hexanoate, the method comprising
contacting pyruvate and 3-hydroxy-propanal with a hydratase-aldolase and a quinone oxidoreductase to produce a 2-keto carboxylic acid of formula:

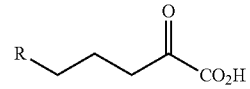

wherein R is CH$_2$OH;

contacting the 2-keto carboxylic acid with a 6-hydroxy-2-oxohexanoate-2-reductase to produce 2,6-dihydroxy-hexanoate;

contacting the 2,6-dihydroxy-hexanoate with a 2,6-dihydroxy-hexanoate CoA-transferase to produce 2,6-dihydroxy-hexanoyl-CoA;

contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;

contacting the 6-hydroxy-2,3-dehydro-hexanoyl-CoA with a 2,3-dehydro-hexanoyl-CoA 2,3-reductase to produce 6-hydroxy-hexanoyl-CoA; and contacting the 6-hydroxy-hexanoyl-CoA with a 6-hydroxyhexanoyl-CoA transferase to produce the 6-hydroxy-hexanoate;

wherein the method is performed in a culture comprising two or more non-naturally occurring microbial organisms.

In another aspect, provided herein is a method for producing adipic acid (AA), the method comprising contacting pyruvate and 3-hydroxy-propanal with a hydratase-aldolase and a quinone oxidoreductase to produce a 2-keto carboxylic acid of formula:

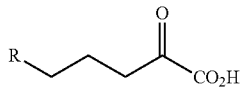

wherein R is CH$_2$OH;

contacting the 2-keto carboxylic acid with a 6-hydroxy-2-oxohexanoate-2-reductase to produce 2,6-dihydroxy-hexanoate;

contacting the 2,6-dihydroxy-hexanoate with a 2,6-dihydroxy-hexanoate CoA-transferase to produce 2,6-dihydroxy-hexanoyl-CoA;

contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;

contacting the 6-hydroxy-2,3-dehydro-hexanoyl-CoA with a 2,3-dehydro-hexanoyl-CoA 2,3-reductase to produce 6-hydroxy-hexanoyl-CoA;

contacting the 6-hydroxy-hexanoyl-CoA with a 6-hydroxyhexanoyl-CoA transferase to produce 6-hydroxy-hexanoate;

contacting the 6-hydroxy-hexanoate with a 6-hydroxy-hexanoate dehydrogenase to produce 6-oxo-hexanoate; and contacting the 6-oxo-hexanoate with a 6-oxo-hexanoate oxidase to produce the adipic acid, wherein the method is performed in a culture comprising one or more non-naturally occurring microbial organisms.

In another aspect, provided herein is a method for producing adipic acid (AA), the method comprising contacting pyruvate and 3-hydroxy-propanal with a hydratase-aldolase and a quinone oxidoreductase to produce a 2-keto carboxylic acid of formula:

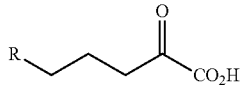

wherein R is CH$_2$OH;

contacting the 2-keto carboxylic acid with a 6-hydroxy-2-oxohexanoate-2-reductase to produce 2,6-dihydroxy-hexanoate;

contacting the 2,6-dihydroxy-hexanoate with a 2,6-dihydroxy-hexanoate CoA-transferase to produce 2,6-dihydroxy-hexanoyl-CoA;

contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;

contacting the 6-hydroxy-2,3-dehydro-hexanoyl-CoA with a 2,3-dehydro-hexanoyl-CoA 2,3-reductase to produce 6-hydroxy-hexanoyl-CoA;

contacting the 6-hydroxy-hexanoyl-CoA with a 6-hydroxyhexanoyl-CoA transferase to produce 6-hydroxy-hexanoate;

contacting the 6-hydroxy-hexanoate with a 6-hydroxy-hexanoate dehydrogenase to produce 6-oxo-hexanoate; and contacting the 6-oxo-hexanoate with a 6-oxo-hexanoate oxidase to produce the adipic acid, wherein the method is performed in a culture comprising two or more non-naturally occurring microbial organisms.

In some embodiments, the hydratase-aldolase is an enzyme having an EC number 4.1.2.45 or EC number 4.1.2.34 or EC number 4.1.1.4. In some embodiments, the hydratase-aldolase is an enzyme having an EC number 4.1.2.45. In some embodiments, the hydratase-aldolase is a trans-o-hydroxybenzylidenepyruvate hydratase-aldolase having an EC number 4.1.2.45. In some embodiments, the hydratase-aldolase is an enzyme having an EC number 4.1.2.34. In some embodiments, the hydratase-aldolase is an enzyme having an EC number 4.1.1.4.

In some embodiments, the hydratase-aldolase is an enzyme selected from the group of enzymes identified under Genbank or RefSeq or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1. In some embodiments, the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP_107818191, A0A023WZF9, PYN48855, A0A421PAQ6, WP_028217297, WP_034507049, KMK64081.1, WP_070028041.1, or KZL92449.1. In some embodiments, the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under Genbank or RefSeq or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, A0A370X7D8, WP_028222253, F2J6L6, A0A0N0L9F6, A0A1G9YWG7, A0A2U1BT09, A0A244DHE8, WP_107818191, A0A023WZF9, PYN48855, A0A421PAQ6, WP_028217297, WP_034507049, KMK64081.1, WP_070028041.1, or KZL92449.1. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

In some embodiments, the hydratase-aldolase is an enzyme selected from Tables 1, 5, 6, 7, and 8. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from Tables 1, 5, 6, 7, and 8.

In some embodiments, the hydratase-aldolase further comprises one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the quinone oxidoreductase is an enzyme having an EC number 1.6.5. In some embodiments, the quinone oxidoreductase is an enzyme having an EC number 1.6.5.5. In some embodiments, the quinone oxidoreductase is an enzyme selected from the group of enzymes identified under Under GenBank, RefSeq, or Uniprot ID Nos. P28304, P40783, Q0K2I0, A0A1Z1SRY9, P43903, I7G8G0, or Q142L2, ALK19324.1, A0A1G9R408, G4Q8R5, ANA98723.1, K0EUQ3, A0A061CRS8, Q9A212, A0A1I6RWW2, WP_026197277.1, Q5NKZ3, WP_012333034.1, or WP_136898000.1. In some embodiments, the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

In some embodiments, the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under Under GenBank, RefSeq, or Uniprot ID Nos. P28304, P40783, Q0K2I0, A0A1Z1SRY9, P43903, I7G8G0, or Q142L2, ALK19324.1, A0A1G9R408, G4Q8R5, ANA98723.1, K0EUQ3, A0A061CRS8, Q9A212, A0A1I6RWW2, WP_026197277.1, Q5NKZ3, WP_012333034.1, or WP_136898000.1. In some embodiments, the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

In some embodiments, the quinone oxidoreductase further comprises one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, at least one of the hydratase-aldolase and the quinone oxidoreductase is exogenously expressed by the one or more non-naturally occurring microbial organisms. In some embodiments, at least one of the hydratase-aldolase and the quinone oxidoreductase is exogenously expressed by the two or more non-naturally occurring microbial organisms.

In some embodiments, at least one of the hydratase-aldolase and the quinone oxidoreductase enzymes are expressed by one or more exogenous genes expressed by the one or more non-naturally occurring microorganisms. In some embodiments, at least one of the hydratase-aldolase and the quinone oxidoreductase enzymes are expressed by one or more exogenous genes expressed by the two or more non-naturally occurring microorganisms. In some embodiments, at least one of the hydratase-aldolase and the quinone oxidoreductase enzymes are expressed by two or more exogenous genes expressed by the one or more non-naturally occurring microorganisms. In some embodiments, at least one of the hydratase-aldolase and the quinone oxidoreductase enzymes are expressed by two or more exogenous genes expressed by the two or more non-naturally occurring microorganisms. One or more exogenous genes includes 1, 2, 3, 4, 5, 6, 7, 8, 9, 10, 11, 12, 13, 14, 15, 16, 17, 18, 19, or 20, or more, exogenous genes. Two or more exogenous genes includes 2, 3, 4, 5, 6, 7, 8, 9, 10, 11, 12, 13, 14, 15, 16, 17, 18, 19, or 20, or more, exogenous genes.

In some embodiments, the hydratase-aldolase is exogenously expressed by the one or more non-naturally occurring microbial organisms. In some embodiments, the hydratase-aldolase is exogenously expressed by the two or more non-naturally occurring microbial organisms.

In some embodiments, the quinone oxidoreductase is exogenously expressed by the one or more non-naturally occurring microbial organisms. In some embodiments, the quinone oxidoreductase is overexpressed by the one or more non-naturally occurring microbial organisms. In some embodiments, the quinone oxidoreductase is exogenously expressed by the two or more non-naturally occurring microbial organisms. In some embodiments, the quinone oxidoreductase is overexpressed by the two or more non-naturally occurring microbial organisms.

In some embodiments, the hydratase-aldolase is exogenously expressed by the one or more non-naturally occurring microbial organisms and the quinone oxidoreductase is overexpressed by the one or more non-naturally occurring microbial organisms. In some embodiments, the hydratase-aldolase is exogenously expressed by the two or more non-naturally occurring microbial organisms and the quinone oxidoreductase is overexpressed by the two or more non-naturally occurring microbial organisms.

In some embodiments, the 2-keto-acid-decarboxylase and the primary alcohol dehydrogenase are expressed by the one or more non-naturally occurring microbial organisms. In some embodiments, the 2-keto-acid-decarboxylase and the primary alcohol dehydrogenase are exogenously expressed by the one or more non-naturally occurring microbial organisms.

In some embodiments, the 2-keto-acid-decarboxylase is an enzyme selected from the group of enzymes identified under EC number 4.1.1.1; EC number 4.1.1.2; EC number 4.1.1.3; EC number 4.1.1.4; EC number 4.1.1.5; EC number 4.1.1.6; EC number 4.1.1.7; EC number 4.1.1.11; EC number 4.1.1.12; EC number 4.1.1.15; EC number 4.1.1.16; EC number 4.1.1.17; EC number 4.1.1.18; EC number 4.1.1.19; EC number 4.1.1.20; EC number 4.1.1.34; EC number 4.1.1.35; EC number 4.1.1.40; EC number 4.1.1.54; EC number 4.1.1.56; EC number 4.1.1.71; EC number 4.1.1.72; EC number 4.1.1.73; EC number 4.1.1.74; EC number 4.1.1.75; or EC number 4.1.1.77. In some embodiments, the 2-keto-acid-decarboxylase is an enzyme selected from the group of enzymes identified under Uniprot ID No. Q6QBS4, A7M7D6, or P20906. In some embodiments, the 2-keto-acid-decarboxylase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under Uniprot ID Nos. Q6QBS4, A7M7D6, or P20906.

In some embodiments, the 2-keto-acid-decarboxylase further comprises one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the primary alcohol dehydrogenase is an enzyme having an EC number 1.1.1.61. In some embodiments, the primary alcohol dehydrogenase is an enzyme selected from the group of enzymes identified under Uniprot or GenBank ID Nos. NP_417279.1, NP_349892.1, NP_349891.1, BAB12273.1, L21902.1, Q94B07, AAB03015.1, NP_014032.1, NP_013892.1, NP_015019.1, NP_010996.2, ABX39192.1, XP_001210625.1, ABO67118, ABO68223, BAE77068.1, or CAA47743.1. In some embodiments, the primary alcohol dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme selected from the group of enzymes identified under Uniprot or GenBank ID Nos. NP_417279.1, NP_349892.1, NP_349891.1, BAB12273.1, L21902.1, Q94B07, AAB03015.1, NP_014032.1, NP_013892.1, NP_015019.1, NP_010996.2, ABX39192.1, XP_001210625.1, ABO67118, ABO68223, BAE77068.1, or CAA47743.1. In some embodiments, the primary alcohol dehydrogenase is an enzyme comprising a sequence of SEQ ID NO:70, SEQ ID NO:71, SEQ ID NO:72, SEQ ID NO:73, or SEQ ID NO:74. In some embodiments, the primary alcohol dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:70, SEQ ID NO:71, SEQ ID NO:72, SEQ ID NO:73, or SEQ ID NO:74.

In some embodiments, the primary alcohol dehydrogenase further comprises one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the hydratase-aldolase is an enzyme identified under Uniprot ID No. A0A286PH18; the quinone oxidoreductase is an enzyme identified under Uniprot ID No. P28304; the 2-keto-acid-decarboxylase is an enzyme identified under Uniprot ID No. Q6QBS4; and the primary alcohol dehydrogenase is an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694. In some embodiments, the hydratase-aldolase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. A0A286PH18; the quinone oxidoreductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. P28304; the 2-keto-acid-decarboxylase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q6QBS4; and the primary alcohol dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.

In some embodiments, the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxy-hexanoyl-CoA transferase, the 6-hydroxyhexanoate 1-reductase, and the 6-hydroxyhexanal 1-reductase are expressed by the one or more non-naturally occurring microbial organisms.

In some embodiments, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are exogenously expressed by the one or more non-naturally occurring microbial organisms.

In some embodiments, the 6-hydroxy-2-oxohexanoate-2-reductase is an selected from the group of enzymes identified under an EC number 1.1.99.6, EC number 1.1.1.169, EC number 1.1.1.215, EC number 1.1.1.28, or EC number 1.1.1.110; the 2,6-dihydroxy-hexanoate CoA-transferase is an enzyme having an EC number 2.8.3, EC number 2.8.3.1, or EC number 2.8.3.12; the 2,6-dihydroxy-hexanoyl-CoA 2-dehydratase is an enzyme having an EC number 4.2.1.167; the 2,3-dehydro-hexanoyl-CoA 2,3-reductase is an enzyme having an EC number 1.3.1.44; the 6-hydroxyhexanoyl-CoA transferase is an enzyme having an EC number 2.8.3, EC number 2.8.3.1, or EC number 2.8.3.12; the 6-hydroxy-hexanoate 1-reductase is an enzyme having an EC number 1.2.99.6; and the 6-hydroxyhexanal 1-reductase is an enzyme having an EC number 1.1.1.

In some embodiments, the 6-hydroxy-2-oxohexanoate-2-reductase is an enzyme selected from the group of enzymes identified under Uniprot or GenBank ID Nos. WP_003431407.1, BAL51292.1, Q5FTU6, AKC64094.1, WP_002876862.1, AGP69017.1, WP_003640741.1, AKC6409; the 2,6-dihydroxy-hexanoate CoA-transferase is an enzyme identified under Uniprot ID No. T4VW93; the 2,6-dihydroxy-hexanoyl-CoA 2-dehydratase is an enzyme identified under Uniprot ID Nos. Q5U924, Q5U925, and Q5U923; the 2,3-dehydro-hexanoyl-CoA 2,3-reductase is an enzyme identified under Uniprot ID No. Q73Q47; the 6-hydroxyhexanoyl-CoA transferase is an enzyme identified under Uniprot ID No. T4VW93; the 6-hydroxyhexanoate 1-reductase is an enzyme identified under Uniprot or GenBank ID Nos. D6Z860, YP_001705436.1, ANO06407.1, AAR91681.1, AHH-98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.1, WP_036338301.1, WP_007472106.1, or A0QWI7; and the 6-hydroxyhexanal 1-reductase is an enzyme identified under Uniprot or GenBank ID Nos. D6Z860, YP_001705436.1, ANO06407.1, AAR91681.1, AHH-98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.

In some embodiments, the 6-hydroxy-2-oxohexanoate-2-reductase is an enzyme selected from the group of enzymes identified under Uniprot or GenBank ID Nos. WP_003431407.1, BAL51292.1, Q5FTU6, AKC64094.1, WP_002876862.1, AGP69017.1, WP_003640741.1, AKC6409; the 2,6-dihydroxy-hexanoate CoA-transferase is an enzyme identified under Uniprot ID Nos. T4VW93, A0A0C7GD16, A0A175L1W4, or 0A2X3BTQ9; the 2,6-dihydroxy-hexanoyl-CoA 2-dehydratase is an enzyme identified under Uniprot ID Nos. Q5U924, Q5U925, and Q5U923; or A0A2X3BK09, A0A2X3BU19, and A0A1V9IXA9; the 2,3-dehydro-hexanoyl-CoA 2,3-reductase is an enzyme identified under Uniprot ID No. Q73Q47; the 6-hydroxyhexanoyl-CoA transferase is an enzyme identified under Uniprot ID No. T4VW93, A0A0C7GD16, A0A175L1W4, or A0A2X3BTQ9; the 6-hydroxyhexanoate 1-reductase is an enzyme identified under Uniprot or GenBank ID Nos. D6Z860, YP_001705436.1, ANO06407.1, AAR91681.1, AHH-98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.1, WP_036338301.1, WP_007472106.1, or A0QWI7; and the 6-hydroxyhexanal 1-reductase is an enzyme identified under Uniprot or GenBank ID Nos. D6Z860, YP_001705436.1, ANO06407.1, AAR91681.1, AHH-98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93, A0A0C7GD16, A0A175L1W4, or 0A2X3BTQ9; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q5U924, Q5U925, and Q5U923; or A0A2X3BK09, A0A2X3BU19, and A0A1V9IXA9; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q73Q47; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. T4VW93, A0A0C7GD16, A0A175L1W4, or A0A2X3BTQ9; the 6-hydroxyhexanoate 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. D6Z860, YP_001705436.1, ANO06407.1, AAR91681.1, AHH-98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP_001703694.1, WP_036338301.1, WP_007472106.1, or A0QWI7; and the 6-hydroxyhexanal 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. D6Z860, YP_001705436.1, ANO06407.1, AAR91681.1, AHH98121.1, ANB00612.1, ANO04655.1, A0R484, AFP42026.1, GAJ86510.1, YP_001704097.1, ANA99315.1, GAJ83027.1, ANA98925.1, ANA98924.1, ANO04656.1, YP001703694.

In some embodiments, the 6-hydroxy-2-oxohexanoate-2-reductase is an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase is an enzyme comprising a sequence of SEQ ID NO:55, SEQ ID NO:56, SEQ ID NO:57, or SEQ ID NO:58; the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase is an enzyme comprising a sequence of SEQ ID NO:65; the 6-hydroxyhexanoyl-CoA transferase is an enzyme comprising a sequence of SEQ ID NO:55, SEQ ID NO:56, SEQ ID NO:57, or SEQ ID NO:58; the 6-hydroxyhexanoate 1-reductase is an enzyme comprising a sequence of SEQ ID NO:66, SEQ ID NO:67, or SEQ ID NO:68; and the 6-hydroxyhexanal 1-reductase is an enzyme comprising a sequence of SEQ ID NO:70.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:65; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58; the 6-hydroxyhexanoate 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:66, SEQ ID NO:67, or SEQ ID NO:68; and the 6-hydroxyhexanal 1-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:70.

In some embodiments, one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

In some embodiments, the 6-hydroxy-2-oxohexanoate-2-reductase is an selected from the group of enzymes identified under an EC number 1.1.99.6, EC number 1.1.1.169, EC number 1.1.1.215, EC number 1.1.1.28, or EC number 1.1.1.110; the 2,6-dihydroxy-hexanoate CoA-transferase is an enzyme having an EC number 2.8.3, EC number 2.8.3.1, or EC number 2.8.3.12; the 2,6-dihydroxy-hexanoyl-CoA 2-dehydratase is an enzyme having an EC number 4.2.1.167; the 2,3-dehydro-hexanoyl-CoA 2,3-reductase is an enzyme having an EC number 1.3.1.44; and the 6-hydroxyhexanoyl-CoA transferase is an enzyme having an EC number 2.8.3, EC number 2.8.3.1, or EC number 2.8.3.12.

In some embodiments, the 6-hydroxy-2-oxohexanoate-2-reductase is an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase is an enzyme identified under Uniprot ID Nos. T4VW93, A0A2X3BTQ9, A0A0C7GD16, or A0A175L1W4; the 2,6-dihydroxy-hexanoyl-CoA 2-dehydratase is an enzyme identified under Uniprot ID Nos. Q5U924, Q5U925, and Q5U923; or A0A2X3BK09, A0A2X3BU19, and A0A1V9IXA9; the 2,3-dehydro-hexanoyl-CoA 2,3-reductase is an enzyme identified under Uniprot ID No. Q73Q47; and the 6-hydroxyhexanoyl-CoA transferase is an enzyme identified under Uniprot ID Nos. T4VW93, A0A2X3BTQ9, A0A0C7GD16, or A0A175L1W4.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot or GenBank ID Nos. WP_003431407.1, BAL51292.1, Q5FTU6, AKC64094.1, WP_002876862.1, AGP69017.1, WP_003640741.1, AKC64095.1, and AKC64094.1; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93, A0A2X3BTQ9, A0A0C7GD16, or A0A175L1W4; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q5U924, Q5U925, and Q5U923; or A0A2X3BK09, A0A2X3BU19, and A0A1V9IXA9; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q73Q47; and the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93, A0A2X3BTQ9, A0A0C7GD16, or A0A175L1W4.

In some embodiments, the 6-hydroxy-2-oxohexanoate-2-reductase is an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase is an enzyme comprising a sequence of SEQ ID NO:55, SEQ ID NO:56, SEQ ID NO:57, or SEQ ID NO:58; the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase is an enzyme comprising a sequence of SEQ ID NO:65; and the 6-hydroxyhexanoyl-CoA transferase is an enzyme comprising a sequence of SEQ ID NO:55, SEQ ID NO:56, SEQ ID NO:57, or SEQ ID NO:58.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:65; and the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55, SEQ ID NO:56, SEQ ID NO:57, or SEQ ID NO:58.

In some embodiments, the 6-hydroxy-2-oxohexanoate-2-reductase is an selected from the group of enzymes identified under an EC number 1.1.99.6, EC number 1.1.1.169, EC number 1.1.1.215, EC number 1.1.1.28, or EC number 1.1.1.110; the 2,6-dihydroxy-hexanoate CoA-transferase is an enzyme having an EC number 2.8.3, EC number 2.8.3.1, or EC number 2.8.3.12; the 2,6-dihydroxy-hexanoyl-CoA 2-dehydratase is an enzyme having an EC number 4.2.1.167; the 2,3-dehydro-hexanoyl-CoA 2,3-reductase is an enzyme having an EC number 1.3.1.44; the 6-hydroxyhexanoyl-CoA transferase is an enzyme having an EC number 2.8.3, EC number 2.8.3.1, or EC number 2.8.3.12; the 6-hydroxyhexanoate dehydrogenase is an enzyme having an EC number 1.1.1.258; and the 6-oxo-hexanoate oxidase is an enzyme having an EC number 1.2.1.63.

In some embodiments, the 6-hydroxy-2-oxohexanoate-2-reductase is an enzyme identified under Uniprot ID No. Q5FTU6; the 2,6-dihydroxy-hexanoate CoA-transferase is an enzyme identified under Uniprot ID Nos. T4VW93 or A0A2X3BTQ9; the 2,6-dihydroxy-hexanoyl-CoA 2-dehydratase is an enzyme identified under Uniprot ID Nos. Q5U924, Q5U925, and Q5U923; or A0A2X3BK09, A0A2X3BU19, and A0A1V9IXA9; the 2,3-dehydrohexanoyl-CoA 2,3-reductase is an enzyme identified under Uniprot ID No. Q73Q47; the 6-hydroxyhexanoyl-CoA transferase is an enzyme identified under Uniprot ID Nos. T4VW93 or A0A2X3BTQ9; the 6-hydroxyhexanoate dehydrogenase is an enzyme identified under Uniprot ID Nos. Q7WVD0 or Q84H78; and the 6-oxo-hexanoate oxidase is an enzyme identified under Uniprot ID No. Q9R2F4.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q5FTU6; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93 or A0A2X3BTQ9; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q5U924, Q5U925, and Q5U923; or A0A2X3BK09, A0A2X3BU19, and A0A1V9IXA9; the 2,3-dehydrohexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q73Q47; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. T4VW93 or A0A2X3BTQ9; the 6-hydroxyhexanoate dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID Nos. Q7WVD0 or Q84H78; and the 6-oxo-hexanoate oxidase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified under Uniprot ID No. Q9R2F4.

In some embodiments, the 6-hydroxy-2-oxohexanoate-2-reductase is an enzyme comprising a sequence of SEQ ID NO:53; the 2,6-dihydroxy-hexanoate CoA-transferase is an enzyme comprising a sequence of SEQ ID NO:55 or SEQ ID NO:58; the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase is an enzyme comprising a sequence of SEQ ID NO:65; the 6-hydroxyhexanoyl-CoA transferase is an enzyme comprising a sequence of SEQ ID NO:55 or SEQ ID NO:58; the 6-hydroxyhexanoate dehydrogenase is an enzyme identified comprising a sequence of SEQ ID NO:71 or SEQ ID NO:72; and the 6-oxo-hexanoate oxidase is an enzyme comprising a sequence of SEQ ID NO:75.

In some embodiments, the 6-hydroxy-2-oxohexanoate-2-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:53; the 2,6-dihydroxy-hexanoate CoA-transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55 or SEQ ID NO:58; the 2,6-dihydroxy-hexanoyl-CoA 2-dehydratase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:59, SEQ ID NO:61, and SEQ ID NO:63; or SEQ ID NO:60, SEQ ID NO:62, and SEQ ID NO:64; the 2,3-dehydro-hexanoyl-CoA 2,3-reductase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:65; the 6-hydroxyhexanoyl-CoA transferase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:55 or SEQ ID NO:58; the 6-hydroxyhexanoate dehydrogenase has at least 10%, 15%, 20%, 25%, 30%, 35%, 40%, 45%, 50%, 55%, 60%, 65%, 70%, 75%, 80%, 85%, 90%, or 95% identity, or more, to an enzyme identified comprising a sequence of SEQ ID NO:71 and SEQ ID NO:72; and the 6-oxo-hexanoate oxidase has at least 10%, 15%, 20%, 25%, 30%, 35%, 40%, 45%, 50%, 55%, 60%, 65%, 70%, 75%, 80%, 85%, 90%, or 95% identity, or more, to an enzyme comprising a sequence of SEQ ID NO:75.

In some embodiments, one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, 6-hydroxyhexanoate dehydrogenase, and the 6-oxo-hexanoate oxidase further comprise one or more protein tags. In some embodiments, the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag In some embodiments, the pyruvate is produced from carbon sources selected from glycerol, glucose, xylose, arabinose, galactose, mannose, fructose, sucrose, and starch, or a combination of thereof.

In some embodiments, the 3-hydroxy-propanal is produced by dehydration of glycerol by a glycerol dehydratase enzyme exogenously expressed by the one or more non-naturally occurring microbial organisms.

The one or more non-naturally occurring microbial organisms include 1, 2, 3, 4, 5, 6, 7, 8, 9, 10, 11, 12, 13, 14, 15, 16, 17, 18, 19, or 20, or more non-naturally occurring microbial organisms. The two or more non-naturally occurring microbial organisms include 2, 3, 4, 5, 6, 7, 8, 9, 10, 11, 12, 13, 14, 15, 16, 17, 18, 19, or 20, or more non-naturally occurring microbial organisms. In some embodiments, the method disclosed herein is performed in the presence of one non-naturally occurring microbial organism. In some embodiments, the method disclosed herein is performed in the presence of two non-naturally occurring microbial organisms. In some embodiments, the method disclosed herein is performed in the presence of three non-naturally occurring microbial organisms. In some embodiments, the method disclosed herein is performed in the presence of four non-naturally occurring microbial organisms. In some embodiments, the method disclosed herein is performed in the presence of five non-naturally occurring microbial organisms.

Throughout this application various publications have been referenced. The disclosure of these publications in their entireties, including GenBank accession number(s) or Uniprot ID number(s) or RefSeq ID numbers in these publications, are hereby incorporated by reference in this application in order to more fully describe the state of the art to which this present disclosure pertains.

In some embodiments, the present disclosure provides the following Embodiments as examples:

1. A method for producing a 2-keto carboxylic acid of formula:

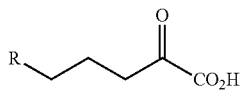

wherein R is H, CH$_3$, or CH$_2$OH;
the method comprising contacting pyruvate and

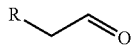

with a hydratase-aldolase and a quinone oxidoreductase in a culture comprising one or more non-naturally occurring microbial organisms to produce the 2-keto carboxylic acid; wherein the hydratase-aldolase and the quinone oxidoreductase are expressed by the one or more non-naturally occurring microbial organisms.

2. The method of Embodiment 1, wherein at least one of the hydratase-aldolase and the quinone oxidoreductase is exogenously expressed by the one or more non-naturally occurring microbial organisms.

3. The method of Embodiment 1, wherein the hydratase-aldolase is exogenously expressed by the one or more non-naturally occurring microbial organisms.

4. The method of Embodiment 1, wherein the quinone oxidoreductase is exogenously expressed by the one or more non-naturally occurring microbial organisms.

5. The method of Embodiment 1, wherein the quinone oxidoreductase is overexpressed by the one or more non-naturally occurring microbial organisms.

6. The method of Embodiment 1, wherein the hydratase-aldolase is exogenously expressed by the one or more non-naturally occurring microbial organisms and the quinone oxidoreductase is overexpressed by the one or more non-naturally occurring microbial organisms.

7. The method of any one of Embodiments 1-6, wherein

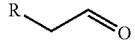

is 3-hydroxy-propanal.

8. The method of Embodiment 7, wherein the 3-hydroxy-propanal is produced by dehydration of glycerol by a glycerol dehydratase enzyme exogenously expressed by the one or more non-naturally occurring microbial organisms.

9. The method of any one of Embodiments 1-8, further comprising separating the 2-keto carboxylic acid from the one or more non-naturally occurring microbial organisms or a culture comprising the one or more non-naturally occurring microbial organisms.

10. A method for producing a 2-keto carboxylic acid of formula:

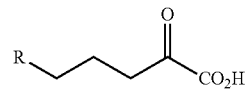

wherein R is H, CH$_3$, or CH$_2$OH;
the method comprising contacting pyruvate and

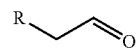

with a hydratase-aldolase and a quinone oxidoreductase in a culture comprising two or more non-naturally occurring microbial organisms to produce the 2-keto carboxylic acid; wherein the hydratase-aldolase and the quinone oxidoreductase are expressed by the two or more non-naturally occurring microbial organisms.

11. The method of Embodiment 10, wherein at least one of the hydratase-aldolase and the quinone oxidoreductase is exogenously expressed by the two or more non-naturally occurring microbial organisms.

12. The method of Embodiment 10, wherein the hydratase-aldolase is exogenously expressed by the two or more non-naturally occurring microbial organisms.

13. The method of Embodiment 10, wherein the quinone oxidoreductase is exogenously expressed by the two or more non-naturally occurring microbial organisms.

14. The method of Embodiment 10, wherein the quinone oxidoreductase is overexpressed by the two or more non-naturally occurring microbial organisms.

15. The method of Embodiment 10, wherein the hydratase-aldolase is exogenously expressed by the two or more non-naturally occurring microbial organisms and the quinone oxidoreductase is overexpressed by the two or more non-naturally occurring microbial organisms.

16. The method of any one of Embodiments 10-15, wherein

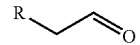

is 3-hydroxy-propanal.

17. The method of Embodiment 16, wherein the 3-hydroxy-propanal is produced by dehydration of glycerol by a glycerol dehydratase enzyme exogenously expressed by the two or more non-naturally occurring microbial organisms.

18. The method of any one of Embodiments 10-17, further comprising separating the 2-keto carboxylic acid from the two or more non-naturally occurring microbial organisms or a culture comprising the two or more non-naturally occurring microbial organisms.

19. The method of any one of Embodiments 1-18, wherein the hydratase-aldolase is an enzyme having an EC number 4.1.2.45 or EC number 4.1.2.34 or EC number 4.1.1.4.

20. The method of any one of Embodiments 1-18, wherein the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1.

21. The method of any one of Embodiments 1-18, wherein the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

22. The method of any one of Embodiments 1-18, wherein the hydratase-aldolase has at least 50% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

23. The method of any one of Embodiments 1-18, wherein the hydratase-aldolase has at least 70% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

24. The method of any one of Embodiments 1-18, wherein the hydratase-aldolase has at least 90% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

25. The method of any one of Embodiments 1-18, wherein the hydratase-aldolase is an enzyme selected from Tables 1, 5-8.

26. The method of any one of Embodiments 1-25, wherein the quinone oxidoreductase is an enzyme having an EC number 1.6.5 (e.g., EC 1.6.5.5).

27. The method of any one of Embodiments 1-25, wherein the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

28. The method of any one of Embodiments 1-25, wherein the quinone oxidoreductase has at least 50% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

29. The method of any one of Embodiments 1-25, wherein the quinone oxidoreductase has at least 70% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

30. The method of any one of Embodiments 1-25, wherein the quinone oxidoreductase has at least 90% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

31. The method of any one of Embodiments 1-30, wherein one or more of the hydratase-aldolase and quinone oxidoreductase further comprise one or more protein tags.

32. The method of Embodiment 31, wherein the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

33. The method of any one of Embodiments 1-32, wherein the pyruvate is produced from carbon sources selected from glycerol, glucose, xylose, arabinose, galactose, mannose, fructose, sucrose, and starch, or a combination of thereof.

34. The method of any one of Embodiments 1-11, wherein R is CH$_2$OH.

35. A method for producing 1,5-pentanediol, the method comprising
contacting pyruvate and 3-hydroxy-propanal with a hydratase-aldolase and a quinone oxidoreductase to produce a 2-keto carboxylic acid of formula:

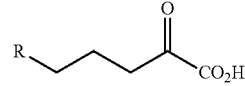

wherein R is CH$_2$OH;
contacting the 2-keto carboxylic acid with a 2-keto-acid-decarboxylase to produce a 5-hydroxy-pentanal; and
contacting the 5-hydroxy-pentanal with a primary alcohol dehydrogenase to produce the 1,5-pentanediol, wherein the method is performed in a culture comprising one or more non-naturally occurring microbial organisms.

36. The method of Embodiment 35, wherein the hydratase-aldolase and the quinone oxidoreductase are expressed by the one or more non-naturally occurring microbial organisms.

37. The method of Embodiment 35, wherein at least one of the hydratase-aldolase and the quinone oxidoreductase is exogenously expressed by the one or more non-naturally occurring microbial organisms.

38. The method of Embodiment 35, wherein the hydratase-aldolase is exogenously expressed by the one or more non-naturally occurring microbial organisms.

39. The method of Embodiment 35, wherein the quinone oxidoreductase is exogenously expressed by the one or more non-naturally occurring microbial organisms.

40. The method of Embodiment 35, wherein the quinone oxidoreductase is overexpressed by the one or more non-naturally occurring microbial organisms.

41. The method of any one of Embodiments 35-40, wherein the 2-keto-acid-decarboxylase and the primary alcohol dehydrogenase are expressed by the one or more non-naturally occurring microbial organisms.

42. The method of any one of Embodiments 35-40, wherein the 2-keto-acid-decarboxylase and the primary alcohol dehydrogenase are exogenously expressed by the one or more non-naturally occurring microbial organisms.

43. The method of any one of Embodiments 35-40, wherein one or more of the 2-keto-acid-decarboxylase and the primary alcohol dehydrogenase are overexpressed by the one or more non-naturally occurring microbial organisms.

44. The method of any one of Embodiments 35-43, further comprising separating the 1,5-pentanediol from the one or more non-naturally occurring microbial organisms or a culture comprising the one or more non-naturally occurring microbial organisms.

45. A method for producing 1,5-pentanediol, the method comprising
contacting pyruvate and 3-hydroxy-propanal with a hydratase-aldolase and a quinone oxidoreductase to produce a 2-keto carboxylic acid of formula:

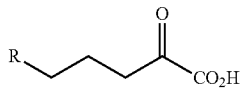

wherein R is CH$_2$OH;
contacting the 2-keto carboxylic acid with a 2-keto-acid-decarboxylase to produce a 5-hydroxy-pentanal; and
contacting the 5-hydroxy-pentanal with a primary alcohol dehydrogenase to produce the 1,5-pentanediol, wherein the method is performed in a culture comprising two or more non-naturally occurring microbial organisms.

46. The method of Embodiment 45, wherein the hydratase-aldolase and the quinone oxidoreductase are expressed by the two or more non-naturally occurring microbial organisms.

47. The method of Embodiment 45, wherein at least one of the hydratase-aldolase and the quinone oxidoreductase is exogenously expressed by the two or more non-naturally occurring microbial organisms.

48. The method of Embodiment 45, wherein the hydratase-aldolase is exogenously expressed by the two or more non-naturally occurring microbial organisms.

49. The method of Embodiment 45, wherein the quinone oxidoreductase is exogenously expressed by the two or more non-naturally occurring microbial organisms.

50. The method of Embodiment 45, wherein the quinone oxidoreductase is overexpressed by the two or more non-naturally occurring microbial organisms.

51. The method of any one of Embodiments 45-50, wherein the 2-keto-acid-decarboxylase and the primary alcohol dehydrogenase are expressed by the two or more non-naturally occurring microbial organisms.

52. The method of any one of Embodiments 45-50, wherein the 2-keto-acid-decarboxylase and the primary alcohol dehydrogenase are exogenously expressed by the two or more non-naturally occurring microbial organisms.

53. The method of any one of Embodiments 45-50, wherein one or more of the 2-keto-acid-decarboxylase and the primary alcohol dehydrogenase are overexpressed by the two or more non-naturally occurring microbial organisms.

54. The method of any one of Embodiments 45-53, further comprising separating the 1,5-pentanediol from the two or more non-naturally occurring microbial organisms or a culture comprising the two or more non-naturally occurring microbial organisms.

55. The method of any one of Embodiments 35-54, wherein the hydratase-aldolase is an enzyme having an EC number 4.1.2.45 or EC number 4.1.2.34 or EC number 4.1.1.4.

56. The method of any one of Embodiments 35-54, wherein the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1.

57. The method of any one of Embodiments 35-54, wherein the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

58. The method of any one of Embodiments 35-54, wherein the hydratase-aldolase has at least 50% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

59. The method of any one of Embodiments 35-54, wherein the hydratase-aldolase has at least 70% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, 60. The method of any one of Embodiments 35-54, wherein the hydratase-aldolase has at least 90% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

61. The method of any one of Embodiments 35-54, wherein the hydratase-aldolase is an enzyme selected from Tables 1, 5-8.

62. The method of any one of Embodiments 35-61, wherein the quinone oxidoreductase is an enzyme having an EC number 1.6.5 (e.g., EC 1.6.5.5).

63. The method of any one of Embodiments 35-61, wherein the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

64. The method of any one of Embodiments 35-61, wherein the quinone oxidoreductase has at least 50% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

65. The method of any one of Embodiments 35-61, wherein the quinone oxidoreductase has at least 70% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

66. The method of any one of Embodiments 35-61, wherein the quinone oxidoreductase has at least 90% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

67. The method of any one of Embodiments 35-66, wherein the 2-keto-acid-decarboxylase is an enzyme having an EC number 4.1.1.1; EC number 4.1.1.2; EC number 4.1.1.3; EC number 4.1.1.4; EC number 4.1.1.5; EC number 4.1.1.6; EC number 4.1.1.7; EC number 4.1.1.11; EC number 4.1.1.12; EC number 4.1.1.15; EC number 4.1.1.16; EC number 4.1.1.17; EC number 4.1.1.18; EC number 4.1.1.19; EC number 4.1.1.20; EC number 4.1.1.34; EC number 4.1.1.35; EC number 4.1.1.40; EC number 4.1.1.54; EC number 4.1.1.56; EC number 4.1.1.71; EC number 4.1.1.72; EC number 4.1.1.73; EC number 4.1.1.74; EC number 4.1.1.75; or EC number 4.1.1.77.

68. The method of any one of Embodiments 35-66, wherein the 2-keto-acid-decarboxylase is an enzyme selected from the group of enzymes identified under Uniprot ID Nos. Q6QBS4, A7M7D6, or P20906.

69. The method of any one of Embodiments 35-66, wherein the 2-keto-acid-decarboxylase has at least 50% identity to an enzyme selected from the group of enzymes identified under Uniprot ID Nos. Q6QBS4, A7M7D6, or P20906.

70. The method of any one of Embodiments 35-66, wherein the 2-keto-acid-decarboxylase has at least 70% identity to an enzyme selected from the group of enzymes identified under Uniprot ID Nos. Q6QBS4, A7M7D6, or P20906.

71. The method of any one of Embodiments 35-66, wherein the 2-keto-acid-decarboxylase has at least 90% identity to an enzyme selected from the group of enzymes identified under Uniprot ID Nos. Q6QBS4, A7M7D6, or P20906.

72. The method of any one of Embodiments 35-71, wherein the primary alcohol dehydrogenase is an enzyme having an EC number 1.1.1.61.

73. The method of any one of Embodiments 35-71, wherein the primary alcohol dehydrogenase is an enzyme selected from the group of enzymes identified under Uniprot or GenBank ID Nos. NP_417279.1, NP_349892.1, NP_349891.1, BAB12273.1, L21902.1, Q94B07, AAB03015.1, NP_014032.1, NP_013892.1, NP_015019.1, NP_010996.2, ABX39192.1, XP_001210625.1, ABO67118, ABO68223, BAE77068.1, or CAA47743.1.

74. The method of any one of Embodiments 35-71, wherein the primary alcohol dehydrogenase is an enzyme comprising a sequence of SEQ ID NO:70, SEQ ID NO:71, SEQ ID NO:72, SEQ ID NO:73, or SEQ ID NO:74.

75. The method of any one of Embodiments 35-71, wherein the primary alcohol dehydrogenase has at least 50% identity to an enzyme comprising a sequence of SEQ ID NO:70, SEQ ID NO:71, SEQ ID NO:72, SEQ ID NO:73, or SEQ ID NO:74.

76. The method of any one of Embodiments 35-71, wherein the primary alcohol dehydrogenase has at least 70% identity to an enzyme comprising a sequence of SEQ ID NO:70, SEQ ID NO:71, SEQ ID NO:72, SEQ ID NO:73, or SEQ ID NO:74.

77. The method of any one of Embodiments 35-71, wherein the primary alcohol dehydrogenase has at least 90% identity to an enzyme comprising a sequence of SEQ ID NO:70, SEQ ID NO:71, SEQ ID NO:72, SEQ ID NO:73, or SEQ ID NO:74.

78. The method of any one of Embodiments 35-54, wherein
the hydratase-aldolase is an enzyme comprising a sequence of SEQ ID NO:8;
the quinone oxidoreductase is an enzyme comprising a sequence of SEQ ID NO:45;
the 2-keto-acid-decarboxylase is an enzyme comprising a sequence of SEQ ID NO:83; and
the primary alcohol dehydrogenase is an enzyme comprising a sequence of SEQ ID NO:70.

79. The method of any one of Embodiments 35-78, wherein one or more of the hydratase-aldolase, quinone oxidoreductase, 2-keto-acid-decarboxylase, and primary alcohol dehydrogenase further comprise one or more protein tags.

80. The method of Embodiment 79, wherein the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

81. The method of any one of Embodiments 35-80, wherein the pyruvate is produced from carbon sources selected from glycerol, glucose, xylose, arabinose, galactose, mannose, fructose, sucrose, and starch, or a combination thereof 82. The method of any one of Embodiments 35-81, wherein the 3-hydroxy-propanal is produced by dehydration of glycerol by a glycerol dehydratase enzyme exogenously expressed by the one or more non-naturally occurring microbial organisms.

83. A method for producing 1,6-hexanediol, the method comprising
   contacting pyruvate and 3-hydroxy-propanal with a hydratase-aldolase and a quinone oxidoreductase to produce a 2-keto carboxylic acid of formula:

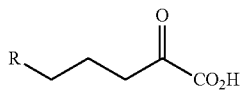

wherein R is CH$_2$OH;
   contacting the 2-keto carboxylic acid with a 6-hydroxy-2-oxohexanoate-2-reductase to produce 2,6-dihydroxy-hexanoate;
   contacting the 2,6-dihydroxy-hexanoate with a 2,6-dihydroxy-hexanoate CoA-transferase to produce 2,6-dihydroxy-hexanoyl-CoA;
   contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
   contacting the 6-hydroxy-2,3-dehydro-hexanoyl-CoA with a 2,3-dehydro-hexanoyl-CoA 2,3-reductase to produce 6-hydroxy-hexanoyl-CoA;
   contacting the 6-hydroxy-hexanoyl-CoA with a 6-hydroxyhexanoyl-CoA transferase to produce 6-hydroxy-hexanoate;
   contacting the 6-hydroxy-hexanoate with a 6-hydroxy-hexanoate 1-reductase to produce 6-hydroxy-hexanal; and
   contacting the 6-hydroxy-hexanal with a 6-hydroxyhexanal 1-reductase to produce the 1,6-hexanediol, wherein the method is performed in a culture comprising one or more non-naturally occurring microbial organisms.

84. The method of Embodiment 83, wherein the hydratase-aldolase and the quinone oxidoreductase are expressed by the one or more non-naturally occurring microbial organisms.

85. The method of Embodiment 83, wherein at least one of the hydratase-aldolase and the quinone oxidoreductase is exogenously expressed by the one or more non-naturally occurring microbial organisms.

86. The method of Embodiment 83, wherein the hydratase-aldolase is exogenously expressed by the one or more non-naturally occurring microbial organisms.

87. The method of Embodiment 83, wherein the quinone oxidoreductase is exogenously expressed by the one or more non-naturally occurring microbial organisms.

88. The method of Embodiment 83, wherein the quinone oxidoreductase is overexpressed by the one or more non-naturally occurring microbial organisms.

89. The method of any one of Embodiments 83-88, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are expressed by the one or more non-naturally occurring microbial organisms.

90. The method of any one of Embodiments 83-88, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are exogenously expressed by the one or more non-naturally occurring microbial organisms.

91. The method of any one of Embodiments 83-88, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are overexpressed by the one or more non-naturally occurring microbial organisms.

92. The method of any one of Embodiments 83-91, further comprising separating the 1,6-hexanediol from the one or more non-naturally occurring microbial organisms or a culture comprising the one or more non-naturally occurring microbial organisms.

93. A method for producing 1,6-hexanediol, the method comprising
   contacting pyruvate and 3-hydroxy-propanal with a hydratase-aldolase and a quinone oxidoreductase to produce a 2-keto carboxylic acid of formula:

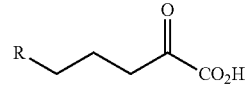

wherein R is CH$_2$OH;
   contacting the 2-keto carboxylic acid with a 6-hydroxy-2-oxohexanoate-2-reductase to produce 2,6-dihydroxy-hexanoate;
   contacting the 2,6-dihydroxy-hexanoate with a 2,6-dihydroxy-hexanoate CoA-transferase to produce 2,6-dihydroxy-hexanoyl-CoA;
   contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
   contacting the 6-hydroxy-2,3-dehydro-hexanoyl-CoA with a 2,3-dehydro-hexanoyl-CoA 2,3-reductase to produce 6-hydroxy-hexanoyl-CoA;
   contacting the 6-hydroxy-hexanoyl-CoA with a 6-hydroxyhexanoyl-CoA transferase to produce 6-hydroxy-hexanoate;
   contacting the 6-hydroxy-hexanoate with a 6-hydroxy-hexanoate 1-reductase to produce 6-hydroxy-hexanal; and
   contacting the 6-hydroxy-hexanal with a 6-hydroxyhexanal 1-reductase to produce the 1,6-hexanediol, wherein the method is performed in a culture comprising two or more non-naturally occurring microbial organisms.

94. The method of Embodiment 93, wherein the hydratase-aldolase and the quinone oxidoreductase are expressed by the two or more non-naturally occurring microbial organisms.

95. The method of Embodiment 93, wherein at least one of the hydratase-aldolase and the quinone oxidoreductase is exogenously expressed by the two or more non-naturally occurring microbial organisms.

96. The method of Embodiment 93, wherein the hydratase-aldolase is exogenously expressed by the two or more non-naturally occurring microbial organisms.

97. The method of Embodiment 93, wherein the quinone oxidoreductase is exogenously expressed by the two or more non-naturally occurring microbial organisms.

98. The method of Embodiment 93, wherein the quinone oxidoreductase is overexpressed by the two or more non-naturally occurring microbial organisms.

99. The method of any one of Embodiments 93-98, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are expressed by the two or more non-naturally occurring microbial organisms.

100. The method of any one of Embodiments 93-98, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate 1-reductase, and the 6-hydroxyhexanal 1-reductase are exogenously expressed by the two or more non-naturally occurring microbial organisms.

101. The method of any one of Embodiments 93-98, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxy-hexanoyl-CoA transferase, the 6-hydroxyhexanoate 1-reductase, and the 6-hydroxyhexanal 1-reductase are overexpressed by the two or more non-naturally occurring microbial organisms.

102. The method of any one of Embodiments 93-101, further comprising separating the 1,6-hexanediol from the two or more non-naturally occurring microbial organisms or a culture comprising the two or more non-naturally occurring microbial organisms.

103. The method of any one of Embodiments 83-102, wherein the hydratase-aldolase is an enzyme having an EC number 4.1.2.45 or EC number 4.1.2.34 or EC number 4.1.1.4.

104. The method of any one of Embodiments 83-102, wherein the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1.

105. The method of any one of Embodiments 83-102, wherein the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

106. The method of any one of Embodiments 83-102, wherein the hydratase-aldolase has at least 50% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

107. The method of any one of Embodiments 83-102, wherein the hydratase-aldolase has at least 70% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

108. The method of any one of Embodiments 83-102, wherein the hydratase-aldolase has at least 90% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

109. The method of any one of Embodiments 83-102, wherein the hydratase-aldolase is an enzyme selected from Tables 1 and 5-8.

110. The method of any one of Embodiments 83-109, wherein the quinone oxidoreductase is an enzyme having an EC number 1.6.5 (e.g., EC 1.6.5.5).

111. The method of any one of Embodiments 83-109, wherein the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

112. The method of any one of Embodiments 83-109, wherein the quinone oxidoreductase has at least 50% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

113. The method of any one of Embodiments 83-109, wherein the quinone oxidoreductase has at least 70% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

114. The method of any one of Embodiments 83-109, wherein the quinone oxidoreductase has at least 90% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

115. The method of any one of Embodiments 83-102, wherein
the 6-hydroxy-2-oxohexanoate-2-reductase is an enzyme having an EC number 1.1.99.6, EC number 1.1.1.169, EC number 1.1.1.215, EC number 1.1.1.28, or EC number 1.1.1.110;
the 2,6-dihydroxy-hexanoate CoA-transferase is an enzyme having an EC number 2.8.3, EC number 2.8.3.1, or EC number 2.8.3.12;
the 2,6-dihydroxy-hexanoyl-CoA 2-dehydratase is an enzyme having an EC number 4.2.1.167;
the 2,3-dehydro-hexanoyl-CoA 2,3-reductase is an enzyme having an EC number 1.3.1.44;
the 6-hydroxyhexanoyl-CoA transferase is an enzyme having an EC number 2.8.3, EC number 2.8.3.1, or EC number 2.8.3.12;
the 6-hydroxyhexanoate 1-reductase is an enzyme having an EC number 1.2.99.6; and
the 6-hydroxyhexanal 1-reductase is an enzyme having an EC number 1.1.1.

116. The method of any one of Embodiments 83-102, wherein
the 6-hydroxy-2-oxohexanoate-2-reductase is an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase is an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase is an enzyme comprising a sequence of SEQ ID NO:65;
the 6-hydroxyhexanoyl-CoA transferase is an enzyme comprising a sequence of SEQ ID NO:55, SEQ ID NO:56, SEQ ID NO:57, or SEQ ID NO:58;
the 6-hydroxyhexanoate 1-reductase is an enzyme comprising a sequence of SEQ ID NO:66, SEQ ID NO:67, or SEQ ID NO:68; and
the 6-hydroxyhexanal 1-reductase is an enzyme comprising a sequence of SEQ ID NO:70.

117. The method of any one of Embodiments 83-102, wherein
the 6-hydroxy-2-oxohexanoate-2-reductase has at least 50% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 50% identity to an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase has at least 50% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 50% identity to an enzyme comprising a sequence of SEQ ID NO:65;
the 6-hydroxyhexanoyl-CoA transferase has at least 50% identity to an enzyme comprising a sequence of SEQ ID NO:55, SEQ ID NO:56, SEQ ID NO:57, or SEQ ID NO:58;
the 6-hydroxyhexanoate 1-reductase has at least 50% identity to an enzyme comprising a sequence of SEQ ID NO:66, SEQ ID NO:67, or SEQ ID NO:68; and
the 6-hydroxyhexanal 1-reductase has at least 50% identity to an enzyme comprising a sequence of SEQ ID NO:70.

118. The method of any one of Embodiments 83-102, wherein
the 6-hydroxy-2-oxohexanoate-2-reductase has at least 70% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 70% identity to an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase has at least 70% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 70% identity to an enzyme comprising a sequence of SEQ ID NO:65;
the 6-hydroxyhexanoyl-CoA transferase has at least 70% identity to an enzyme comprising a sequence of SEQ ID NO:55, SEQ ID NO:56, SEQ ID NO:57, or SEQ ID NO:58;
the 6-hydroxyhexanoate 1-reductase has at least 70% identity to an enzyme comprising a sequence of SEQ ID NO:66, SEQ ID NO:67, or SEQ ID NO:68; and
the 6-hydroxyhexanal 1-reductase has at least 70% identity to an enzyme comprising a sequence of SEQ ID NO:70.

119. The method of any one of Embodiments 83-102, wherein
the 6-hydroxy-2-oxohexanoate-2-reductase has at least 90% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 90% identity to an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase has at least 90% identity to an enzyme comprising a sequence of SEQ ID NO:59, SEQ ID NO:61, and SEQ ID NO:63; or SEQ ID NO:60, SEQ ID NO:62, and SEQ ID NO:64;

the 2,3-dehydro-hexanoyl-CoA 2,3-reductase has at least 90% identity to an comprising a sequence of SEQ ID NO:65;
the 6-hydroxyhexanoyl-CoA transferase has at least 90% identity to an enzyme comprising a sequence of SEQ ID NO:55, SEQ ID NO:56, SEQ ID NO:57, or SEQ ID NO:58;
the 6-hydroxyhexanoate 1-reductase has at least 90% identity to an enzyme comprising a sequence of SEQ ID NO:66, SEQ ID NO:67, or SEQ ID NO:68; and
the 6-hydroxyhexanal 1-reductase has at least 90% identity to an enzyme comprising a sequence of SEQ ID NO:70.

120. The method of any one of Embodiments 83-119, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxy-hexanoyl-CoA transferase, the 6-hydroxyhexanoate 1-reductase, and the 6-hydroxyhexanal 1-reductase further comprise one or more protein tags.

121. The method of Embodiment 120, wherein the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

122. The method of any one of Embodiments 83-121, wherein the pyruvate is produced from carbon sources is selected from glycerol, glucose, xylose, arabinose, galactose, mannose, fructose, sucrose, and starch, or a combination thereof.

123. The method of any one of Embodiments 83-122, wherein the 3-hydroxy-propanal is produced by dehydration of glycerol by a glycerol dehydratase enzyme exogenously expressed by the one or more non-naturally occurring microbial organisms.

124. A method for producing 6-hydroxy-hexanoate, the method comprising
contacting pyruvate and 3-hydroxy-propanal with a hydratase-aldolase and a quinone oxidoreductase to produce a 2-keto carboxylic acid of formula:

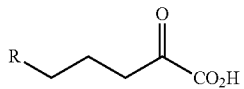

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA; and
contacting the 6-hydroxy-hexanoyl-CoA with a 6-hydroxyhexanoyl-CoA transferase to produce the 6-hydroxy-hexanoate;
wherein the method is performed in a culture comprising one or more non-naturally occurring microbial organisms.

125. The method of Embodiment 124, wherein the hydratase-aldolase and the quinone oxidoreductase are expressed by the one or more non-naturally occurring microbial organisms.

126. The method of Embodiment 124, wherein at least one of the hydratase-aldolase and the quinone oxidoreductase is exogenously expressed by the one or more non-naturally occurring microbial organisms.

127. The method of Embodiment 124, wherein the hydratase-aldolase is exogenously expressed by the one or more non-naturally occurring microbial organisms.

128. The method of Embodiment 124, wherein the quinone oxidoreductase is exogenously expressed by the one or more non-naturally occurring microbial organisms.

129. The method of Embodiment 124, wherein the quinone oxidoreductase is overexpressed by the one or more non-naturally occurring microbial organisms.

130. The method of any one of Embodiments 124-129, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are expressed by the one or more non-naturally occurring microbial organisms.

131. The method of any one of Embodiments 124-129, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are exogenously expressed by the one or more non-naturally occurring microbial organisms.

132. The method of any one of Embodiments 124-129, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxy-hexanoyl-CoA transferase are overexpressed by the one or more non-naturally occurring microbial organisms.

133. The method of any one of Embodiments 124-132, further comprising separating the 6-hydroxy-hexanoate from the one or more non-naturally occurring microbial organisms or a culture comprising the one or more non-naturally occurring microbial organisms.

134. A method for producing 6-hydroxy-hexanoate, the method comprising
contacting pyruvate and 3-hydroxy-propanal with a hydratase-aldolase and a quinone oxidoreductase to produce a 2-keto carboxylic acid of formula:

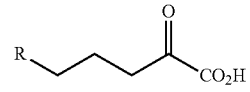

wherein R is CH$_2$OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;

contacting the 6-hydroxy-2,3-dehydro-hexanoyl-CoA with a 2,3-dehydro-hexanoyl-CoA 2,3-reductase to produce 6-hydroxy-hexanoyl-CoA; and contacting the 6-hydroxy-hexanoyl-CoA with a 6-hydroxyhexanoyl-CoA transferase to produce the 6-hydroxy-hexanoate;

wherein the method is performed in a culture comprising two or more non-naturally occurring microbial organisms.

135. The method of Embodiment 134, wherein the hydratase-aldolase and the quinone oxidoreductase are expressed by the two or more non-naturally occurring microbial organisms.

136. The method of Embodiment 134, wherein at least one of the hydratase-aldolase and the quinone oxidoreductase is exogenously expressed by the two or more non-naturally occurring microbial organisms.

137. The method of Embodiment 134, wherein the hydratase-aldolase is exogenously expressed by the two or more non-naturally occurring microbial organisms.

138. The method of Embodiment 134, wherein the quinone oxidoreductase is exogenously expressed by the two or more non-naturally occurring microbial organisms.

139. The method of Embodiment 134, wherein the quinone oxidoreductase is overexpressed by the two or more non-naturally occurring microbial organisms.

140. The method of any one of Embodiments 134-139, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are expressed by the two or more non-naturally occurring microbial organisms.

141. The method of any one of Embodiments 134-139, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are exogenously expressed by the two or more non-naturally occurring microbial organisms.

142. The method of any one of Embodiments 134-139, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase are overexpressed by the two or more non-naturally occurring microbial organisms.

143. The method of any one of Embodiments 134-142, further comprising separating the 6-hydroxy-hexanoate from the two or more non-naturally occurring microbial organisms or a culture comprising the two or more non-naturally occurring microbial organisms.

115. The method of any one of Embodiments 83-102, wherein the 6-hydroxy-2-oxohexanoate-2-reductase is an enzyme having an EC number 1.1.99.6, EC number 1.1.1.169, EC number 1.1.1.215, EC number 1.1.1.28, or EC number 1.1.1.110;

the 2,6-dihydroxy-hexanoate CoA-transferase is an enzyme having an EC number 2.8.3, EC number 2.8.3.1, or EC number 2.8.3.12;

the 2,6-dihydroxy-hexanoyl-CoA 2-dehydratase is an enzyme having an EC number 4.2.1.167;

the 2,3-dehydro-hexanoyl-CoA 2,3-reductase is an enzyme having an EC number 1.3.1.44;

the 6-hydroxyhexanoyl-CoA transferase is an enzyme having an EC number 2.8.3, EC number 2.8.3.1, or EC number 2.8.3.12;

the 6-hydroxyhexanoate 1-reductase is an enzyme having an EC number 1.2.99.6; and the 6-hydroxyhexanal 1-reductase is an enzyme having an EC number 1.1.1.

116. The method of any one of Embodiments 83-102, wherein the 6-hydroxy-2-oxohexanoate-2-reductase is an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;

the 2,6-dihydroxy-hexanoate CoA-transferase is an enzyme comprising a sequence of SEQ ID NO:55, SEQ ID NO:56, SEQ ID NO:57, or SEQ ID NO:58;

the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64;

the 2,3-dehydro-hexanoyl-CoA 2,3-reductase is an enzyme comprising a sequence of SEQ ID NO:65; the 6-hydroxyhexanoyl-CoA transferase is an enzyme comprising a sequence of SEQ ID NO:55, SEQ ID NO:56, SEQ ID NO:57, or SEQ ID NO:58;

the 6-hydroxyhexanoate 1-reductase is an enzyme comprising a sequence of SEQ ID NO:66, SEQ ID NO:67, or SEQ ID NO:68; and the 6-hydroxyhexanal 1-reductase is an enzyme comprising a sequence of SEQ ID NO:70.

117. The method of any one of Embodiments 83-102, wherein the 6-hydroxy-2-oxohexanoate-2-reductase has at least 50% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;

the 2,6-dihydroxy-hexanoate CoA-transferase has at least 50% identity to an enzyme comprising a sequence of SEQ ID NO:55, SEQ ID NO:56, SEQ ID NO:57, or SEQ ID NO:58;

the 2,6-dihydroxy-hexanoyl-CoA 2-dehydratase has at least 50% identity to an enzyme comprising a sequence of SEQ ID NO:59, SEQ ID NO:61, and SEQ ID NO:63; or SEQ ID NO:60, SEQ ID NO:62, and SEQ ID NO:64;

the 2,3-dehydro-hexanoyl-CoA 2,3-reductase has at least 50% identity to an enzyme comprising a sequence of SEQ ID NO:65;

the 6-hydroxyhexanoyl-CoA transferase has at least 50% identity to an enzyme comprising a sequence of SEQ ID NO:55, SEQ ID NO:56, SEQ ID NO:57, or SEQ ID NO:58;

the 6-hydroxyhexanoate 1-reductase has at least 50% identity to an enzyme comprising a sequence of SEQ ID NO:66, SEQ ID NO:67, or SEQ ID NO:68; and the 6-hydroxyhexanal 1-reductase has at least 50% identity to an enzyme comprising a sequence of SEQ ID NO:70.

118. The method of any one of Embodiments 83-102, wherein the 6-hydroxy-2-oxohexanoate-2-reductase has at least 70% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;

the 2,6-dihydroxy-hexanoate CoA-transferase has at least 70% identity to an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase has at least 70% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 70% identity to an enzyme comprising a sequence of SEQ ID NO:65;
the 6-hydroxyhexanoyl-CoA transferase has at least 70% identity to an enzyme comprising a sequence of SEQ ID NO:55, SEQ ID NO:56, SEQ ID NO:57, or SEQ ID NO:58;
the 6-hydroxyhexanoate 1-reductase has at least 70% identity to an enzyme comprising a sequence of SEQ ID NO:66, SEQ ID NO:67, or SEQ ID NO:68; and
the 6-hydroxyhexanal 1-reductase has at least 70% identity to an enzyme comprising a sequence of SEQ ID NO:70.

119. The method of any one of Embodiments 83-102, wherein
the 6-hydroxy-2-oxohexanoate-2-reductase has at least 90% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 90% identity to an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase has at least 90% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 90% identity to an comprising a sequence of SEQ ID NO:65;
the 6-hydroxyhexanoyl-CoA transferase has at least 90% identity to an enzyme comprising a sequence of SEQ ID NO:55, SEQ ID NO:56, SEQ ID NO:57, or SEQ ID NO:58;
the 6-hydroxyhexanoate 1-reductase has at least 90% identity to an enzyme comprising a sequence of SEQ ID NO:66, SEQ ID NO:67, or SEQ ID NO:68; and
the 6-hydroxyhexanal 1-reductase has at least 90% identity to an enzyme comprising a sequence of SEQ ID NO:70.

156. The method of any one of Embodiments 124-143, wherein
the 6-hydroxy-2-oxohexanoate-2-reductase is an enzyme having an EC number 1.1.99.6, EC number 1.1.1.169, EC number 1.1.1.215, EC number 1.1.1.28, or EC number 1.1.1.110;
the 2,6-dihydroxy-hexanoate CoA-transferase is an enzyme having an EC number 2.8.3, EC number 2.8.3.1, or EC number 2.8.3.12;
the 2,6-dihydroxy-hexanoyl-CoA 2-dehydratase is an enzyme having an EC number 4.2.1.167;
the 2,3-dehydro-hexanoyl-CoA 2,3-reductase is an enzyme having an EC number 1.3.1.44; and
the 6-hydroxyhexanoyl-CoA transferase is an enzyme having an EC number 2.8.3, EC number 2.8.3.1, or EC number 2.8.3.12.

157. The method of any one of Embodiments 124-143, wherein
the 6-hydroxy-2-oxohexanoate-2-reductase is an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase is an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase is an enzyme comprising a sequence of SEQ ID NO:65; and
the 6-hydroxyhexanoyl-CoA transferase is an enzyme comprising a sequence of SEQ ID NO:55, SEQ ID NO:56, SEQ ID NO:57, or SEQ ID NO:58.

158. The method of any one of Embodiments 124-143, wherein
the 6-hydroxy-2-oxohexanoate-2-reductase has at least 50% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 50% identity to an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase has at least 50% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 50% identity to an enzyme comprising a sequence of SEQ ID NO:65; and
the 6-hydroxyhexanoyl-CoA transferase has at least 50% identity to an enzyme comprising a sequence of SEQ ID NO:55, SEQ ID NO:56, SEQ ID NO:57, or SEQ ID NO:58.

159. The method of any one of Embodiments 124-143, wherein
the 6-hydroxy-2-oxohexanoate-2-reductase has at least 70% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 70% identity to an enzyme comprising a sequence of SEQ ID NO:55, SEQ ID NO:56, SEQ ID NO:57, or SEQ ID NO:58;
the 2,6-dihydroxy-hexanoyl-CoA 2-dehydratase has at least 70% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 70% identity to an comprising a sequence of SEQ ID NO:65; and
the 6-hydroxyhexanoyl-CoA transferase has at least 70% identity to an enzyme comprising a sequence of SEQ ID NO:55, SEQ ID NO:56, SEQ ID NO:57, or SEQ ID NO:58.

160. The method of any one of Embodiments 124-143, wherein the 6-hydroxy-2-oxohexanoate-2-reductase has at least 90% identity to an enzyme comprising a sequence of SEQ ID NO:53, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;

the 2,6-dihydroxy-hexanoate CoA-transferase has at least 90% identity to an enzyme comprising a sequence of SEQ ID NO:55, SEQ ID NO:56, SEQ ID NO:57, or SEQ ID NO:58;

the 2,6-dihydroxy-hexanoyl-CoA 2-dehydratase has at least 90% identity to an enzyme comprising a sequence of SEQ ID NO:59, SEQ ID NO:61, and SEQ ID NO:63; or SEQ ID NO:60, SEQ ID NO:62, and SEQ ID NO:64;

the 2,3-dehydro-hexanoyl-CoA 2,3-reductase has at least 90% identity to an enzyme comprising a sequence of SEQ ID NO:65; and the 6-hydroxyhexanoyl-CoA transferase has at least 90% identity to an enzyme comprising a sequence of SEQ ID NO:55, SEQ ID NO:56, SEQ ID NO:57, or SEQ ID NO:58.

161. The method of any one of Embodiments 124-160, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, and the 6-hydroxyhexanoyl-CoA transferase further comprise one or more protein tags.

162. The method of Embodiment 161, wherein the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

163. The method of any one of Embodiments 124-162, wherein the pyruvate is produced from carbon sources is selected from glycerol, glucose, xylose, arabinose, galactose, mannose, fructose, sucrose, and starch, or a combination thereof.

164. The method of any one of Embodiments 124-163, wherein the 3-hydroxy-propanal is produced by dehydration of glycerol by a glycerol dehydratase enzyme exogenously expressed by the one or more non-naturally occurring microbial organisms.

165. A method for producing adipic acid, the method comprising contacting pyruvate and 3-hydroxy-propanal with a hydratase-aldolase and a quinone oxidoreductase to produce a 2-keto carboxylic acid of formula:

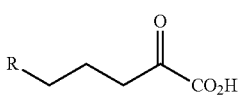

wherein R is CH$_2$OH;

contacting the 2-keto carboxylic acid with a 6-hydroxy-2-oxohexanoate-2-reductase to produce 2,6-dihydroxy-hexanoate;

contacting the 2,6-dihydroxy-hexanoate with a 2,6-dihydroxy-hexanoate CoA-transferase to produce 2,6-dihydroxy-hexanoyl-CoA;

contacting the 2,6-dihydroxy-hexanoyl-CoA with a 2,6-dihydroxy-hexanoyl-CoA 2-dehydratase to produce 6-hydroxy-2,3-dehydro-hexanoyl-CoA;

contacting the 6-hydroxy-2,3-dehydro-hexanoyl-CoA with a 2,3-dehydro-hexanoyl-CoA 2,3-reductase to produce 6-hydroxy-hexanoyl-CoA;

contacting the 6-hydroxy-hexanoyl-CoA with a 6-hydroxyhexanoyl-CoA transferase to produce 6-hydroxy-hexanoate;

contacting the 6-hydroxy-hexanoate with a 6-hydroxy-hexanoate dehydrogenase to produce 6-oxo-hexanoate; and contacting the 6-oxo-hexanoate with a 6-oxo-hexanoate oxidase to produce the adipic acid, wherein the method is performed in a culture comprising one or more non-naturally occurring microbial organisms.

166. The method of Embodiment 165, wherein the hydratase-aldolase and the quinone oxidoreductase are expressed by the one or more non-naturally occurring microbial organisms.

167. The method of Embodiment 165, wherein at least one of the hydratase-aldolase and the quinone oxidoreductase is exogenously expressed by the one or more non-naturally occurring microbial organisms.

168. The method of Embodiment 165, wherein the hydratase-aldolase is exogenously expressed by the one or more non-naturally occurring microbial organisms.

169. The method of Embodiment 165, wherein the quinone oxidoreductase is exogenously expressed by the one or more non-naturally occurring microbial organisms.

170. The method of Embodiment 165, wherein the quinone oxidoreductase is overexpressed by the one or more non-naturally occurring microbial organisms.

171. The method of any one of Embodiments 165-170, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are expressed by the one or more non-naturally occurring microbial organisms.

172. The method of any one of Embodiments 165-170, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are exogenously expressed by the one or more non-naturally occurring microbial organisms.

173. The method of any one of Embodiments 165-170, wherein one or more of 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are overexpressed by the one or more non-naturally occurring microbial organisms.

174. The method of any one of Embodiments 165-173, further comprising separating the adipic acid from the one or more non-naturally occurring microbial organisms or a culture comprising the one or more non-naturally occurring microbial organisms.

175. A method for producing adipic acid, the method comprising contacting pyruvate and 3-hydroxy-propanal with a hydratase-aldolase and a quinone oxidoreductase to produce a 2-keto carboxylic acid of formula:

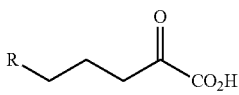

wherein R is CH₂OH;
contacting the 2-keto carboxylic acid with a 6-hydroxy-2-oxohexanoate-2-reductase to produce 2,6-dihydroxy-hexanoate;
contacting the 2,6-dihydroxy-hexanoate with a 2,6-dihydroxy-hexanoate CoA-transferase to produce 2,6-dihydroxy-hexanoyl-CoA;
contacting the 2,6-dihydroxy-hexanoyl-CoA with a the 2,6-dihydroxy-hexanoyl-CoA 2-dehydratase to produce 6-hydroxy-2,3-dehydro-hexanoyl-CoA;
contacting the 6-hydroxy-2,3-dehydro-hexanoyl-CoA with a 2,3-dehydro-hexanoyl-CoA 2,3-reductase to produce 6-hydroxy-hexanoyl-CoA;
contacting the 6-hydroxy-hexanoyl-CoA with a 6-hydroxyhexanoyl-CoA transferase to produce 6-hydroxy-hexanoate;
contacting the 6-hydroxy-hexanoate with a 6-hydroxy-hexanoate dehydrogenase to produce 6-oxo-hexanoate; and
contacting the 6-oxo-hexanoate with a 6-oxo-hexanoate oxidase to produce the adipic acid, wherein the method is performed in a culture comprising two or more non-naturally occurring microbial organisms.

176. The method of Embodiment 175, wherein the hydratase-aldolase and the quinone oxidoreductase are expressed by the two or more non-naturally occurring microbial organisms.

177. The method of Embodiment 175, wherein at least one of the hydratase-aldolase and the quinone oxidoreductase is exogenously expressed by the two or more non-naturally occurring microbial organisms.

178. The method of Embodiment 175, wherein the hydratase-aldolase is exogenously expressed by the two or more non-naturally occurring microbial organisms.

179. The method of Embodiment 175, wherein the quinone oxidoreductase is exogenously expressed by the two or more non-naturally occurring microbial organisms.

180. The method of Embodiment 175, wherein the quinone oxidoreductase is overexpressed by the two or more non-naturally occurring microbial organisms.

181. The method of any one of Embodiments 175-180, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are expressed by the two or more non-naturally occurring microbial organisms.

182. The method of any one of Embodiments 175-180, wherein the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxyhexanoyl-CoA transferase, the 6-hydroxyhexanoate dehydrogenase, and the 6-oxo-hexanoate oxidase are exogenously expressed by the two or more non-naturally occurring microbial organisms.

183. The method of any one of Embodiments 175-180, wherein one or more of 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxy-hexanoyl-CoA transferase, the 6-hydroxyhexanoate dehydrogenase, and the 6-oxo-hexanoate oxidase are overexpressed by the two or more non-naturally occurring microbial organisms.

184. The method of any one of Embodiments 175-183, further comprising separating the adipic acid from the two or more non-naturally occurring microbial organisms or a culture comprising the two or more non-naturally occurring microbial organisms.

185. The method of any one of Embodiments 165-184, wherein the hydratase-aldolase is an enzyme having an EC number 4.1.2.45 or EC number 4.1.2.34 or EC number 4.1.1.4.

186. The method of any one of Embodiments 165-184, wherein the hydratase-aldolase is an enzyme selected from the group of enzymes identified under GenBank, RefSeq, or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1.

187. The method of any one of Embodiments 165-184, wherein the hydratase-aldolase is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

188. The method of any one of Embodiments 165-184, wherein the hydratase-aldolase has at least 50% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

189. The method of any one of Embodiments 165-184, wherein the hydratase-aldolase has at least 70% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

190. The method of any one of Embodiments 165-184, wherein the hydratase-aldolase has at least 90% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

191. The method of any one of Embodiments 165-184, wherein the hydratase-aldolase is an enzyme selected from Tables 1 and 5-8.

192. The method of any one of Embodiments 165-191, wherein the quinone oxidoreductase is an enzyme having an EC number 1.6.5 (e.g., EC 1.6.5.5).

193. The method of any one of Embodiments 165-191, wherein the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

194. The method of any one of Embodiments 165-191, wherein the quinone oxidoreductase has at least 50% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

195. The method of any one of Embodiments 165-191, wherein the quinone oxidoreductase has at least 70% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

196. The method of any one of Embodiments 165-191, wherein the quinone oxidoreductase has at least 90% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

197. The method of any one of Embodiments 165-184, wherein
the 6-hydroxy-2-oxohexanoate-2-reductase is an enzyme having an EC number 1.1.99.6, EC number 1.1.1.169, EC number 1.1.1.215, EC number 1.1.1.28, or EC number 1.1.1.110;
the 2,6-dihydroxy-hexanoate CoA-transferase is an enzyme having an EC number 2.8.3, EC number 2.8.3.1, or EC number 2.8.3.12;
the 2,6-dihydroxy-hexanoyl-CoA 2-dehydratase is an enzyme having an EC number 4.2.1.167;
the 2,3-dehydro-hexanoyl-CoA 2,3-reductase is an enzyme having an EC number 1.3.1.44;
the 6-hydroxyhexanoyl-CoA transferase is an enzyme having an EC number 2.8.3, EC number 2.8.3.1, or EC number 2.8.3.12;
the 6-hydroxyhexanoate dehydrogenase is an enzyme having an EC number 1.1.1.258; and
the 6-oxo-hexanoate oxidase is an enzyme having an EC number 1.2.1.63.

198. The method of any one of Embodiments 165-184, wherein
the 6-hydroxy-2-oxohexanoate-2-reductase is an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase is an enzyme comprising a sequence of SEQ ID NO:55 or SEQ ID NO:58;
the 2,6-dihydroxy-hexanoyl-CoA 2-dehydratase is an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase is an enzyme comprising a sequence of SEQ ID NO:65; the 6-hydroxyhexanoyl-CoA transferase is an enzyme comprising a sequence of SEQ ID NO:55 or SEQ ID NO:58;
the 6-hydroxyhexanoate dehydrogenase is an enzyme identified comprising a sequence of SEQ ID NO:71 or SEQ ID NO:72; and
the 6-oxo-hexanoate oxidase is an enzyme comprising a sequence of SEQ ID NO:75.

199. The method of any one of Embodiments 165-184, wherein
the 6-hydroxy-2-oxohexanoate-2-reductase has at least 50% identity to an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 50% identity to an enzyme comprising a sequence of SEQ ID NO:55 or SEQ ID NO:58;
the 2,6-dihydroxy-hexanoyl-CoA 2-dehydratase has at least 50% identity to an enzyme comprising a sequence of SEQ ID NO:59, SEQ ID NO:61, and SEQ ID NO:63; or SEQ ID NO:60, SEQ ID NO:62, and SEQ ID NO:64;
the 2,3-dehydro-hexanoyl-CoA 2,3-reductase has at least 50% identity to an enzyme comprising a sequence of SEQ ID NO:65;
the 6-hydroxyhexanoyl-CoA transferase has at least 50% identity to an enzyme comprising a sequence of SEQ ID NO:55 or SEQ ID NO:58;
the 6-hydroxyhexanoate dehydrogenase has at least 50% identity to an enzyme comprising a sequence of SEQ ID NO:71 or SEQ ID NO:72; and
the 6-oxo-hexanoate oxidase has at least 50% identity to an enzyme comprising a sequence of SEQ ID NO:75.

200. The method of any one of Embodiments 165-184, wherein
the 6-hydroxy-2-oxohexanoate-2-reductase has at least 70% identity to an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;
the 2,6-dihydroxy-hexanoate CoA-transferase has at least 70% identity to an enzyme comprising a sequence of SEQ ID NO:55 or SEQ ID NO:58;
the 2,6-dihydroxy-hexanoyl-CoA 2-dehydratase has at least 70% identity to an enzyme comprising a sequence of SEQ ID NO:59, SEQ ID NO:61, and SEQ ID NO:63; or SEQ ID NO:60, SEQ ID NO:62, and SEQ ID NO:64;

the 2,3-dehydro-hexanoyl-CoA 2,3-reductase has at least 70% identity to an comprising a sequence of SEQ ID NO:65;

the 6-hydroxyhexanoyl-CoA transferase has at least 70% identity to an enzyme comprising a sequence of SEQ ID NO:55 or SEQ ID NO:58;

the 6-hydroxyhexanoate dehydrogenase has at least 70% identity to an enzyme comprising a sequence of SEQ ID NO:71 or SEQ ID NO:72; and the 6-oxo-hexanoate oxidase has at least 70% identity to an enzyme comprising a sequence of SEQ ID NO:75.

201. The method of any one of Embodiments 165-184, wherein the 6-hydroxy-2-oxohexanoate-2-reductase has at least 90% identity to an enzyme comprising a sequence of SEQ ID NO:53, SEQ ID NO:54, SEQ ID NO:98, SEQ ID NO:99, SEQ ID NO:100, SEQ ID NO:101, SEQ ID NO:102, SEQ ID NO:103, SEQ ID NO:104, or SEQ ID NO:105;

the 2,6-dihydroxy-hexanoate CoA-transferase has at least 90% identity to an enzyme comprising a sequence of SEQ ID NO:55 or SEQ ID NO:58;

the 2,6-dihydroxy-hexanoyl-CoA 2-dehydratase has at least 90% identity to an enzyme comprising a sequence of SEQ ID NO:59, SEQ ID NO:61, and SEQ ID NO:63; or SEQ ID NO:60, SEQ ID NO:62, and SEQ ID NO:64;

the 2,3-dehydro-hexanoyl-CoA 2,3-reductase has at least 90% identity to an comprising a sequence of SEQ ID NO:65;

the 6-hydroxyhexanoyl-CoA transferase has at least 90% identity to an enzyme comprising a sequence of SEQ ID NO:55 or SEQ ID NO:58;

the 6-hydroxyhexanoate dehydrogenase has at least 90% identity to an enzyme comprising a sequence of SEQ ID NO:71 or SEQ ID NO:72; and the 6-oxo-hexanoate oxidase has at least 90% identity to an enzyme comprising a sequence of SEQ ID NO:75.

202. The method of any one of Embodiments 165-201, wherein one or more of the 6-hydroxy-2-oxohexanoate-2-reductase, the 2,6-dihydroxy-hexanoate CoA-transferase, the 2,6-dihydroxy-hexanoyl-CoA 2-dehydratase, the 2,3-dehydro-hexanoyl-CoA 2,3-reductase, the 6-hydroxy-hexanoyl-CoA transferase, 6-hydroxyhexanoate dehydrogenase, and the 6-oxo-hexanoate oxidase are further comprise one or more protein tags.

203. The method of Embodiment 202, wherein the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

204. The method of any one of Embodiments 165-203, wherein the pyruvate is produced from carbon sources is selected from glycerol, glucose, xylose, arabinose, galactose, mannose, fructose, sucrose, and starch, or a combination thereof 205. The method of any one of Embodiments 165-204, wherein the 3-hydroxy-propanal is produced by dehydration of glycerol by a glycerol dehydratase enzyme exogenously expressed by the one or more non-naturally occurring microbial organisms.

206. A recombinant microbial organism comprising a first exogenous nucleic acid encoding an aldolase hydratase enzyme, wherein the recombinant microbial organism is further modified to express an increased amount of quinone oxidoreductase as compared to wild-type or the same microbial organism that is not modified, and optionally wherein the microbial organism is *Corynebacterium glutamicum*, a *clostridium* species, or *E. coli*.

207. The recombinant microorganism of Embodiment 206, wherein the organism comprises a second exogenous nucleic acid encoding quinone oxidoreductase.

208. The recombinant microorganism of Embodiment 207, wherein the first and/or second exogenous nucleic acid further comprises a regulatory element that drives expression of the second exogenous nucleic acid.

209. The recombinant microorganism of Embodiment 208, wherein the regulatory element is selected from a promoter or an enhancer.

210. The recombinant microbial organism of any one of Embodiments 206-209, wherein the aldolase hydratase enzyme has an EC number 4.1.2.45 or EC number 4.1.2.34 or EC number 4.1.1.4.

211. The recombinant microbial organism of any one of Embodiments 206-209, wherein the aldolase hydratase enzyme is an enzyme selected from the group of enzymes identified under Genbank or RefSeq or Uniprot ID Nos. D7C0E5, P0A144, Q79EM8, A0A0N0AHI8, A0A0N1FRY3, M3DYR1, W7SU48, A0A286PH18, Q9X9Q6, Q9WXH7, A4XDS1, F2J6N9, A0A063BFL5, Q9ZHH6, A0A0C1K853, WP_034398482, PYK12191, WP_115478033, WP_028222253, WP_013654807, WP_059403060, WP_092508530, WP_116642627, WP_009770659, WP_107818191, WP_003292061, PYN48855, WP_122212965, WP_028217297, WP_034507049, KMK64081.1, WP_070028041.1, or KZL92449.1.

212. The recombinant microbial organism of any one of Embodiments 206-209, wherein the aldolase hydratase enzyme is an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

213. The recombinant microbial organism of any one of Embodiments 206-209, wherein the aldolase hydratase enzyme has at least 50% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

214. The recombinant microbial organism of any one of Embodiments 206-209, wherein the aldolase hydratase enzyme has at least 70% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

215. The recombinant microbial organism of any one of Embodiments 206-209, wherein the aldolase hydratase enzyme has at least 90% identity to an enzyme comprising a sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:84, SEQ ID NO:85, or SEQ ID NO:86.

216. The recombinant microbial organism of any one of Embodiments 206-209, wherein the aldolase hydratase enzyme is an enzyme selected from Tables 1, 5-8.

217. The recombinant microbial organism of any one of Embodiments 206-216, wherein the first exogenous nucleic acid and the second exogenous nucleic acid are each contained in a vector.

218. The recombinant microbial organism of Embodiment 217, wherein the first exogenous nucleic acid and the second exogenous nucleic acid are each contained in the same vector.

219. The recombinant microbial organism of Embodiment 218, wherein the first exogenous nucleic acid and the second exogenous nucleic acid are each contained in their own separate vectors.

220. The recombinant microbial organism of any one of Embodiments 217-219, wherein the vector is a plasmid.

221. The recombinant microbial organism of any one of Embodiments 206-220, wherein the quinone oxidoreductase is an enzyme having an EC number 1.6.5 (e.g., EC 1.6.5.5).

222. The recombinant microbial organism of any one of Embodiments 206-220, wherein the quinone oxidoreductase is an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

223. The recombinant microbial organism of any one of Embodiments 206-220, wherein the quinone oxidoreductase has at least 50% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

224. The recombinant microbial organism of any one of Embodiments 206-220, wherein the quinone oxidoreductase has at least 70% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

225. The recombinant microbial organism of any one of Embodiments 206-220, wherein the quinone oxidoreductase has at least 90% identity to an enzyme comprising a sequence of SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, or SEQ ID NO:97.

226. The recombinant microbial organism of any one of Embodiments 206-220, wherein one or more of the hydratase-aldolase enzyme and quinone oxidoreductase further comprise one or more protein tags.

227. The recombinant microbial organism of Embodiment 226, wherein the protein tags are selected from polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag.

228. The recombinant microbial organism of any one of Embodiments 206-227, wherein the recombinant microbial organism is capable of producing a 2-keto carboxylic acid of formula:

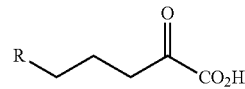

wherein R is H, CH$_3$, or CH$_2$OH.

229. The recombinant microbial organism of any one of Embodiments 206-228, wherein the recombinant microbial organism is capable of producing 1,5-pentanediol, 1,6-hexanediol, adipic acid, or 6-hydroxy hexanoate.

230. The recombinant microbial organism of any one of Embodiments 206-229, wherein the recombinant microbial organism is genetically modified to improve production of pyruvate from a carbon source.

231. The recombinant microbial organism of Embodiment 230, wherein the carbon source is selected from glycerol, glucose, xylose, arabinose, galactose, mannose, fructose, sucrose, and starch, or a combination thereof.

232. A population of recombinant microbial organisms of any one of Embodiments 206-231.

233. The population of Embodiment 232, which is substantially homogenous.

234. A method of producing 1,5-pentanediol, 1,6-hexanediol, adipic acid, or 6-hydroxy hexanoate, comprising culturing the population of Embodiment 232 or Embodiment 233 under suitable conditions.

235. The method of Embodiment 234, further comprising isolating the 1,5-pentanediol, 1,6-hexanediol, adipic acid, or 6-hydroxy hexanoate from the culture or the microbial organisms.

236. A culture comprising the recombinant microbial organisms of any one of Embodiments 206-231.

237. A culture comprising the populations of Embodiment 232 or Embodiment 233.

238. A method comprising:
  contacting pyruvate and an aldehyde with an aldol product biosynthesis polypeptide so that an aldol product is produced, wherein:
  the aldol product is a compound comprising an aldehyde or ketone group and a hydroxyl group attached to a beta-carbon of an aldehyde or ketone carbonyl group.

239. The method of Embodiment 238, wherein a —CHO group of the aldehyde is not conjugated to a double bond, a triple bond or an aromatic group.

240. A method comprising:
  contacting pyruvate and an aliphatic aldehyde with an aldol product biosynthesis polypeptide so that an aldol product is produced, wherein:
  the carbonyl group of the aliphatic aldehyde is not conjugated to a alkenyl, alkynyl, or aromatic group; and
  the aldol product is a compound comprising an aldehyde or ketone group and a hydroxyl group attached to a beta-carbon of an aldehyde or ketone carbonyl group.

241. The method of any one of Embodiments 238-240, wherein the aldol product biosynthesis polypeptide is or comprises an aldolase.

242. The method of any one of Embodiments 238-241, wherein the aldol product biosynthesis polypeptide is in a microbe.

243. The method of Embodiment 242, wherein the microbe is engineered to contain an exogenous nucleic acid that encodes an aldol product biosynthesis polypeptide.

244. The method of Embodiment any one of Embodiments 242-243, wherein the microbe expresses a modulated level of an aldol product biosynthesis polypeptide.

245. The method of Embodiment any one of Embodiments 242-244, wherein the microbe expresses an engineered aldol product biosynthesis polypeptide.

246. The method of any one of Embodiments 238-245, wherein conversion of pyruvate and an aliphatic aldehyde into an aldol product is catalyzed by an aldol product biosynthesis polypeptide.

247. The method of any one of Embodiments 238-246, wherein the method is performed in a culture.

248. The method of any one of Embodiments 238-247, comprising converting an aldol product into an aldol-dehydration product, wherein the aldol-dehydration product is a compound comprising an aldehyde or ketone group and a double bond conjugated with the aldehyde or ketone group.

249. The method of Embodiment 248, wherein the converting comprises contacting an aldol product with a dehydration product biosynthesis polypeptide so that an aldol-dehydration product is produced.

250. The method of any one of Embodiments 248-249, wherein the dehydration product biosynthesis polypeptide is in a microbe.

251. The method of Embodiment 250, wherein the microbe is engineered to contain an exogenous nucleic acid that encodes a dehydration product biosynthesis polypeptide.

252. The method of Embodiment any one of Embodiments 250-251, wherein the microbe expresses a modulated level of a dehydration product biosynthesis polypeptide.

253. The method of Embodiment any one of Embodiments 250-252, wherein the microbe expresses an engineered dehydration product biosynthesis polypeptide.

254. The method of any one of Embodiments 248-253, wherein conversion of an aldol product into an aldol-dehydration product is catalyzed by a dehydration product biosynthesis polypeptide.

255. The method of any one of Embodiments 248-254, wherein the method is performed in a culture.

256. The method of Embodiment 249, wherein a dehydration product biosynthesis polypeptide is a dehydratase.

257. A method comprising:
  contacting pyruvate and an aldehyde with an aldol-dehydration product biosynthesis polypeptide so that an aldol-dehydration product is produced, wherein:
  the aldol-dehydration product is a compound comprising an aldehyde or ketone group and a double bond conjugated with the aldehyde or ketone group.

258. The method of Embodiment 257, wherein a —CHO group of the aldehyde is not conjugated to a double bond, a triple bond or an aromatic group.

259. A method comprising:
  contacting pyruvate and an aliphatic aldehyde with an aldol-dehydration product biosynthesis polypeptide so that an aldol-dehydration product is produced, wherein:
  the carbonyl group of the aliphatic aldehyde is not conjugated to a alkenyl, alkynyl, or aromatic group; and
  the aldol-dehydration product is a compound comprising an aldehyde or ketone group and a double bond conjugated with the aldehyde or ketone group.

260. The method of any one of Embodiments 257-259, wherein the aldol-dehydration product biosynthesis polypeptide is or comprises a hydratase-aldolase.

261. The method of Embodiment 260, wherein contacting pyruvate and an aliphatic aldehyde with a hydratase-aldolase produces an aldol-dehydration product.

262. The method of any one of Embodiments 257-259, wherein the aldol-dehydration product biosynthesis polypeptide is or comprises an enzyme having an EC number 4.1.2.45 or EC number 4.1.2.34, or EC 4.1.1.4, or is selected from Tables 1 and 5-8.

263. The method of any one of Embodiments 257-259, wherein the aldol-dehydration product biosynthesis polypeptide is or comprises a polypeptide which shares 10%, 15%, 20%, 25%, 30%, 35%, 40%, 45%, 50%, 55%, 60%, 65%, 70%, 75%, 80%, 85%, 90%, 95%, 96%, 97%, 95%, 99% or more homology with an enzyme of Embodiment 262.

264. The method of any one of Embodiments 257-259, wherein the aldol-dehydration product biosynthesis polypeptide is or comprises an aldolase.

265. The method of any one of Embodiments 257-264, wherein the aldol-dehydration product biosynthesis polypeptide is in a microbe.

266. The method of Embodiment 265, wherein the microbe is engineered to contain an exogenous nucleic acid that encodes an aldol-dehydration product biosynthesis polypeptide.

267. The method of Embodiment any one of Embodiments 265-266, wherein the microbe expresses a modulated level of an aldol-dehydration product biosynthesis polypeptide.

268. The method of Embodiment any one of Embodiments 265-267, wherein the microbe expresses an engineered aldol-dehydration product biosynthesis polypeptide.

269. The method of any one of Embodiments 257-268, wherein conversion of pyruvate and an aliphatic aldehyde into an aldol-dehydration product is catalyzed by an aldol-dehydration product biosynthesis polypeptide.

270. The method of any one of Embodiments 257-269, wherein the method is performed in a culture.

271. A method comprising:
  contacting an alkene with an alkene reduction product biosynthesis polypeptide so that an alkene reduction product is produced, wherein:
  the alkene comprises a double bond conjugated to a carbonyl group; and
  a double bond conjugated to a carbonyl group in the alkene is reduced to a single bond to provide an alkene reduction product.

272. The method of Embodiment 271, wherein the alkene is an aldol-dehydration product of any one of Embodiments 257-270.

273. The method of any one of Embodiments 271-272, wherein an alkene reduction product biosynthesis polypeptide is or comprises an enzyme that catalyzes reduction of a 2-oxo-3-enoic acid or a salt thereof.

274. The method of any one of Embodiments 271-272, wherein an alkene reduction product biosynthesis polypeptide is or comprises an enzyme that belongs to EC 1.6.5.

275. The method of any one of Embodiments 271-272, wherein an alkene reduction product biosynthesis polypeptide is or comprises an enzyme that belongs to EC 1.6.5.5 or is selected from Table 9.

276. The method of any one of Embodiments 271-272, wherein the alkene reduction product biosynthesis polypeptide is or comprises a polypeptide which shares 10%, 15%, 20%, 25%, 30%, 35%, 40%, 45%, 50%, 55%, 60%, 65%, 70%, 75%, 80%, 85%, 90%, 95%, 96%, 97%, 95%, 99% or more homology with an enzyme of any one of Embodiments 274-275.

277. The method of any one of Embodiments 271-276, wherein an alkene reduction product biosynthesis polypeptide is in a microbe.

278. The method of Embodiment 277, wherein the microbe is engineered to contain an exogenous nucleic acid that encodes an alkene reduction product biosynthesis polypeptide.

279. The method of Embodiment any one of Embodiments 277-278, wherein the microbe expresses a modulated level of an alkene reduction product biosynthesis polypeptide.

280. The method of Embodiment any one of Embodiments 277-279, wherein the microbe expresses an engineered alkene reduction product biosynthesis polypeptide.

281. The method of any one of Embodiments 271-280, wherein conversion of an alkene into an alkene reduction product is catalyzed by an alkene reduction product biosynthesis polypeptide.

282. The method of any one of Embodiments 271-281, wherein the method is performed in a culture.

283. The method of any one of Embodiments 238-270, comprising a method of any one of Embodiments 271-282.

284. The method of any one of Embodiments 238-283, wherein the aldehyde has the structure of formula A-1 thereof:

$$R^a\text{-}L^2\text{-}O\text{—}C(O)H, \qquad \text{A-1}$$

or a salt thereof, wherein:

$R^a$ is R" or —OR", each of $L^1$ and $L^2$ is independently a covalent bond, or a bivalent, optionally substituted, linear or branched $C_{1-20}$ aliphatic or $C_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)$_5$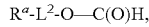—, or —C(O)O—;

Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;

each R" is independently —R', —C(O)R', —CO$_2$R', or —SO$_2$R';

R' is hydrogen, or an optionally substituted group selected from $C_{1-10}$ aliphatic, $C_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:

two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

285. The method of any one of Embodiments 238-256 and 284, wherein the aldol product has the structure of formula P-1:

$$R^a\text{-}L^2\text{-}L^1\text{-}CH(OH)\text{—}CH_2\text{—}C(O)\text{—}C(O)OH, \qquad \text{P-1}$$

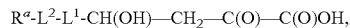

or a salt thereof, wherein:

$R^a$ is R" or —OR", each of $L^1$ and $L^2$ is independently a covalent bond, or a bivalent, optionally substituted, linear or branched $C_{1-20}$ aliphatic or $C_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;

Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;

each R" is independently —R', —C(O)R', —CO$_2$R', or —SO$_2$R';

R' is hydrogen, or an optionally substituted group selected from $C_{1-10}$ aliphatic, $C_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:

two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

286. The method of any one of Embodiments 257-285, wherein the aldol-dehydration product has the structure of formula P-2:

$$R^a\text{-}L^2\text{-}O\text{—}CH\text{=}CH\text{—}C(O)\text{—}C(O)OH, \qquad \text{P-2}$$

or a salt thereof, wherein:

$R^a$ is R" or —OR", each of $L^1$ and $L^2$ is independently a covalent bond, or a bivalent, optionally substituted, linear or branched $C_{1-20}$ aliphatic or $C_{1-20}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)$_2$—, —S(O)$_2$N(R")—, —C(O)S—, or —C(O)O—;

Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;

each R" is independently —R', —C(O)R', —CO₂R', or —SO₂R';

R' is hydrogen, or an optionally substituted group selected from $C_{1-10}$ aliphatic, $C_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:

two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

287. The method of Embodiment 286, wherein the —CH=CH— is in E configuration.

288. The method of Embodiment 286, wherein the —CH=CH— is in Z configuration.

289. The method of any one of Embodiments 271-288, wherein the alkene reduction product has the structure of formula P-3:

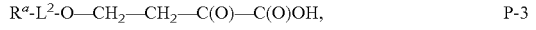

R$^a$-L²-O—CH₂—CH₂—C(O)—C(O)OH,   P-3 or a salt thereof, wherein:

R$^a$ is R" or —OR", each of L¹ and L² is independently a covalent bond, or a bivalent, optionally substituted, linear or branched $C_{1-20}$ aliphatic or $C_{1-20}$ heteroaliphatic, wherein one or more methylene units are optionally and independently replaced by —C≡C—, —C(R")₂—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)₂—, —S(O)₂N(R")—, —C(O)S—, or —C(O)O—;

Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;

each R" is independently —R', —C(O)R', —CO₂R', or —SO₂R';

R' is hydrogen, or an optionally substituted group selected from $C_{1-10}$ aliphatic, $C_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:

two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

290. The method of any one of Embodiments 238-284, comprising converting an alkene reduction product into a compound of formula P-10:

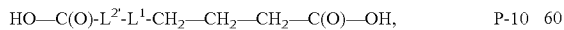

HO—C(O)-L²-L¹-CH₂—CH₂—CH₂—C(O)—OH,   P-10 or a salt thereof.

291. The method of any one of Embodiments 238-284, comprising converting an alkene reduction product into a compound of formula P-10':

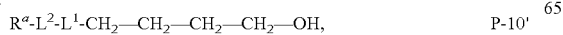

R$^a$-L²-L¹-CH₂—CH₂—CH₂—CH₂—OH,   P-10' or a salt thereof.

292. The method of any one of Embodiments 238-291, comprising converting an alkene reduction product into a carbonyl reduction product, wherein:

the alkene reduction product comprises a carbonyl group; and a carbonyl group of the alkene reduction product is converted to —CH(OH)—.

293. The method of any one of Embodiments 238-291, comprising contacting an alkene reduction product with a carbonyl reduction product biosynthesis polypeptide so that a carbonyl reduction product is produced, wherein:

the alkene reduction product comprises a carbonyl group; and a carbonyl group of the alkene reduction product is converted to —CH(OH)—.

294. The method of Embodiment 293, wherein the carbonyl reduction product biosynthesis polypeptide is or comprises a keto reductase or a 2-keto acid-2-reductase.

295. The method of any one of Embodiments 293-294, wherein the carbonyl reduction product biosynthesis polypeptide is in a microbe.

296. The method of Embodiment 295, wherein the microbe is engineered to contain an exogenous nucleic acid that encodes a carbonyl reduction product biosynthesis polypeptide.

297. The method of Embodiment any one of Embodiments 295-296, wherein the microbe expresses a modulated level of a carbonyl reduction product biosynthesis polypeptide.

298. The method of Embodiment any one of Embodiments 295-297, wherein the microbe expresses an engineered carbonyl reduction product biosynthesis polypeptide.

299. The method of any one of Embodiments 290-298, wherein conversion of an alkene reduction product into a carbonyl reduction product is catalyzed by a carbonyl reduction product biosynthesis polypeptide.

300. The method of any one of Embodiments 290-299, wherein the method is performed in a culture.

301. The method of any one of Embodiments 290-300, wherein a carbonyl reduction product has the structure of formula P-4:

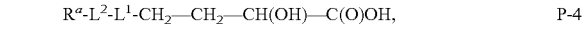

R$^a$-L²-L¹-CH₂—CH₂—CH(OH)—C(O)OH,   P-4 or a salt thereof, wherein:

R$^a$ is R" or —OR", each of L¹ and L² is independently a covalent bond, or a bivalent, optionally substituted, linear or branched $C_{1-20}$ aliphatic or $C_{1-20}$ heteroaliphatic, wherein one or more methylene units are optionally and independently replaced by —C≡C—, —C(R")₂—, -Cy-, —O—, —S—, —S—S—, —N(R")—, —C(O)—, —C(S)—, —C(NR")—, —C(O)N(R")—, —N(R")C(O)N(R")—, —N(R")C(O)O—, —S(O)—, —S(O)₂—, —S(O)₂N(R")—, —C(O)S—, or —C(O)O—;

Cy- is a bivalent, optionally substituted 3-20 membered monocyclic, bicyclic or polycyclic ring, wherein each monocyclic ring is independently an optionally substituted, saturated, partially saturated or aromatic 3-20 membered ring having 0-5 heteroatoms;

each R" is independently —R', —C(O)R', —CO₂R', or —SO₂R';

R' is hydrogen, or an optionally substituted group selected from $C_{1-10}$ aliphatic, $C_{1-10}$ heteroaliphatic having 1-5 heteroatoms, a 6-10 membered aryl ring, a 5-10 membered heteroaryl ring having 1-5 heteroatoms, and a 3-10 membered heterocyclic ring having 1-5 heteroatoms, or:

two or more R' groups are taken together with their intervening atoms to form an optionally substituted 3-20 membered monocyclic, bicyclic or polycyclic ring having, in addition to the intervening atoms, 0-5 heteroatoms, wherein each monocyclic ring is independently an optionally substituted, saturated, partially saturated or aromatic 3-20 membered ring having 0-5 heteroatoms.

302. The method of any one of Embodiments 238-301, comprising converting a compound of formula P-4 or a salt thereof into a compound of formula P-5:

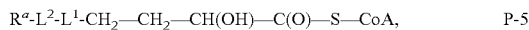
$$R^a\text{-}L^2\text{-}L^1\text{-}CH_2\text{—}CH_2\text{—}CH(OH)\text{—}C(O)\text{—}S\text{—}CoA, \quad \text{P-5}$$

or a salt thereof.

303. The method of Embodiment 302, wherein the conversion comprises contacting a compound of formula P-4 or a salt thereof with a CoA transfer product biosynthesis polypeptide.

304. The method of any one of Embodiments 238-303, comprising converting a compound of formula P-5 or a salt thereof into a compound of formula P-6:

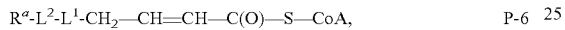
$$R^a\text{-}L^2\text{-}L^1\text{-}CH_2\text{—}CH\!=\!CH\text{—}C(O)\text{—}S\text{—}CoA, \quad \text{P-6}$$

or a salt thereof.

305. The method of Embodiment 304, wherein the conversion comprises contacting a compound of formula P-5 or a salt thereof with a dehydration product biosynthesis polypeptide.

306. The method of any one of Embodiments 238-305, comprising converting a compound of formula P-6 or a salt thereof into a compound of formula P-7:

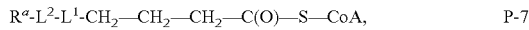
$$R^a\text{-}L^2\text{-}L^1\text{-}CH_2\text{—}CH_2\text{—}CH_2\text{—}C(O)\text{—}S\text{—}CoA, \quad \text{P-7}$$

or a salt thereof.

307. The method of Embodiment 306, wherein the conversion comprises contacting a compound of formula P-6 or a salt thereof with a reduction product biosynthesis polypeptide which is or comprises 2,3-enoyl-CoA reductase.

308. The method of any one of Embodiments 238-307, comprising converting a compound of formula P-7 or a salt thereof into a compound of formula P-8:

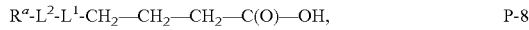
$$R^a\text{-}L^2\text{-}L^1\text{-}CH_2\text{—}CH_2\text{—}CH_2\text{—}C(O)\text{—}OH, \quad \text{P-8}$$

or a salt thereof.

309. The method of Embodiment 308, wherein the conversion comprises contacting a compound of formula P-7 or a salt thereof with a CoA transfer product biosynthesis polypeptide.

310. The method of any one of Embodiments 238-309, comprising converting a compound of formula P-8, wherein $L^2$ is —$CH_2$-$L^{2'}$-, or a salt thereof into a compound of formula P-9:

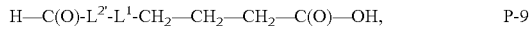
$$H\text{—}C(O)\text{-}L^{2'}\text{-}L^1\text{-}CH_2\text{—}CH_2\text{—}CH_2\text{—}C(O)\text{—}OH, \quad \text{P-9}$$

or a salt thereof, wherein:

$L^{2'}$ is a covalent bond, or a bivalent, optionally substituted, linear or branched $C_{1-19}$ aliphatic or $C_{1-19}$ heteroaliphatic, wherein one or more methylene units are optionally and independently replaced by —C≡C—, —C(R")$_2$—, -Cy-, —O—, —S—, —S—S—, —N(R")—, —C(O)—, —C(S)—, —C(NR")—, —C(O)N(R")—, —N(R")C(O)N (R")—, —N(R")C(O)O—, —S(O)—, —S(O)$_2$—, —S(O)$_2$N(R")—, —C(O)S—, or —C(O)O—.

311. The method of Embodiment 310, wherein the conversion comprises contacting a compound of formula P-8 or a salt thereof with an oxidation product biosynthesis polypeptide which is or comprises an alcohol dehydrogenase.

312. The method of any one of Embodiments 238-311, comprising converting a compound of formula P-9 or a salt thereof into a compound of formula P-10:

$$HO\text{—}C(O)\text{-}L^{2'}\text{-}L^1\text{-}CH_2\text{—}CH_2\text{—}CH_2\text{—}C(O)\text{—}OH, \quad \text{P-10}$$

or a salt thereof.

313. The method of Embodiment 312, wherein the conversion comprises contacting a compound of formula P-9 or a salt thereof with an aldehyde oxidation product biosynthesis polypeptide.

314. The method of any one of Embodiments 238-312, comprising converting a compound of formula P-8 or a salt thereof into a compound of formula P-9':

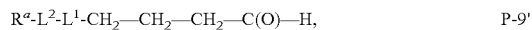
$$R^a\text{-}L^2\text{-}L^1\text{-}CH_2\text{—}CH_2\text{—}CH_2\text{—}C(O)\text{—}H, \quad \text{P-9'}$$

or a salt thereof.

315. The method of Embodiment 314, comprising contacting a compound of formula P-8 or a salt thereof with a carboxyl reduction product biosynthesis polypeptide.

316. The method of any one of Embodiments 238-315, comprising converting a compound of formula P-9' or a salt thereof into a compound of formula P-10':

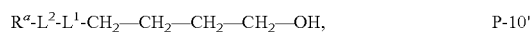
$$R^a\text{-}L^2\text{-}L^1\text{-}CH_2\text{—}CH_2\text{—}CH_2\text{—}CH_2\text{—}OH, \quad \text{P-10'}$$

or a salt thereof.

317. The method of Embodiment 316, comprising contacting a compound of formula P-9' or a salt thereof with an aldehyde reduction product biosynthesis polypeptide which is or comprises an aldehyde reductase or a primary alcohol dehydrogenase.

318. The method of any one of Embodiments 238-290, comprising converting a compound of formula P-3 or a salt thereof into a compound of formula P-5':

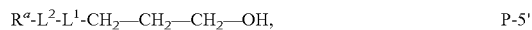
$$R^a\text{-}L^2\text{-}L^1\text{-}CH_2\text{—}CH_2\text{—}CH_2\text{—}OH, \quad \text{P-5'}$$

or a salt thereof.

319. The method of any one of Embodiments 238-290 or 318, comprising converting a compound of formula P-3 or a salt thereof into a compound of formula P-4':

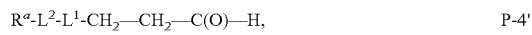
$$R^a\text{-}L^2\text{-}L^1\text{-}CH_2\text{—}CH_2\text{—}C(O)\text{—}H, \quad \text{P-4'}$$

or a salt thereof.

320. The method of Embodiment 319, comprising contacting a compound of formula P-3 or a salt thereof with a decarboxylation product biosynthesis polypeptide.

321. The method of any one of Embodiments 238-290, comprising converting a compound of formula P-4' or a salt thereof into a compound of formula P-5':

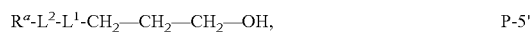
$$R^a\text{-}L^2\text{-}L^1\text{-}CH_2\text{—}CH_2\text{—}CH_2\text{—}OH, \quad \text{P-5'}$$

or a salt thereof.

322. The method of Embodiment 321, comprising contacting a compound of formula P-4' or a salt thereof with an aldehyde reduction product biosynthesis polypeptide.

323. The method of any one of Embodiments 301-322, wherein one or more or each converting independently comprises contacting a compound with a suitable biosynthesis polypeptide.

324. The method of Embodiment 323, wherein one or more or all biosynthesis polypeptides are independently in a microbe.

325. The method of Embodiment 324, wherein the microbe is engineered to contain one or more exogenous nucleic acids that encode one or more or all of the biosynthesis polypeptides.

326. The method of Embodiment any one of Embodiments 324-325, wherein the microbe expresses a modulated level of one or more or all of the biosynthesis polypeptides.

327. The method of Embodiment any one of Embodiments 324-326, wherein one or more or all of the biosynthesis polypeptides are independently engineered.

328. The method of any one of Embodiments 324-326, wherein a suitable biosynthesis polypeptide catalyzes a corresponding conversion.

329. The method of any one of Embodiments 285-328, wherein W is —H.

330. The method of any one of Embodiments 285-328, wherein W is —OH.

331. The method of any one of Embodiments 285-330, wherein $L^1$ is optionally substituted $C_{1-6}$ alkylene.

332. The method of any one of Embodiments 285-330, wherein $L^1$ is unsubstituted $C_{1-6}$ alkylene.

333. The method of any one of Embodiments 331-332, wherein the alkylene is —$CH_2$—.

334. The method of any one of Embodiments 331-332, wherein the alkylene is —$CH_2CH_2$—.

335. The method of any one of Embodiments 331-332, wherein the alkylene is —$CH_2CH_2CH_2$—.

336. The method of any one of Embodiments 285-330, wherein $L^1$ is a covalent bond.

337. The method of any one of Embodiments 285-336, wherein $L^2$ is a covalent bond.

338. The method of any one of Embodiments 285-336, wherein $L^2$ is optionally substituted $C_{1-6}$ alkylene.

339. The method of any one of Embodiments 285-336, wherein $L^2$ is unsubstituted $C_{1-6}$ alkylene.

340. The method of any one of Embodiments 338-339, wherein the alkylene is —$CH_2$—.

341. The method of any one of Embodiments 338-339, wherein the alkylene is —$CH_2CH_2$—.

342. The method of any one of Embodiments 338-339, wherein the alkylene is —$CH_2CH_2CH_2$—.

343. The method of Embodiment 284, wherein the aliphatic aldehyde is HO—$CH_2$—$CH_2$—CHO.

344. The method of Embodiment 285 or 343, wherein the aldol product is HO—$CH_2$—$CH_2$—CH(OH)—$CH_2$—C(O)—COOH or a salt thereof.

345. The method of any one of Embodiments 286 and 343-344, wherein the aldol-dehydration product is HO—$CH_2$—$CH_2$—CH=CH—C(O)—COOH or a salt thereof.

346. The method of any one of Embodiments 289 and 343-345, wherein the alkene reduction product is HO—$CH_2$—$CH_2$—$CH_2$—$CH_2$—C(O)—COOH or a salt thereof.

347. The method of any one of Embodiments 301 and 343-346, wherein the carbonyl reduction product is HO—$CH_2$—$CH_2$—$CH_2$—$CH_2$—CH(OH)—COOH or a salt thereof.

348. The method of any one of Embodiments 302 and 343-347, wherein a compound of formula P-5 or a salt thereof is HO—$CH_2$—$CH_2$—$CH_2$—$CH_2$—CH(OH)—CO—S—CoA or a salt thereof.

349. The method of any one of Embodiments 303 and 343-348, wherein a compound of formula P-6 or a salt thereof is HO—$CH_2$—$CH_2$—$CH_2$—CH=CH—CO—S—CoA or a salt thereof.

350. The method of any one of Embodiments 305 and 343-349, wherein a compound of formula P-7 or a salt thereof is HO—$CH_2$—$CH_2$—$CH_2$—$CH_2$—$CH_2$—CO—S-CoA or a salt thereof.

351. The method of any one of Embodiments 308 and 343-350, wherein a compound of formula P-8 or a salt thereof is HO—$CH_2$—$CH_2$—$CH_2$—$CH_2$—$CH_2$—CO—OH or a salt thereof.

352. The method of any one of Embodiments 310 and 343-351, wherein a compound of formula P-9 or a salt thereof is H—C(O)—$CH_2$—$CH_2$—$CH_2$—$CH_2$—CO—OH or a salt thereof.

353. The method of any one of Embodiments 312 and 343-352, wherein a compound of formula P-10 or a salt thereof is HO—CO—$CH_2$—$CH_2$—$CH_2$—$CH_2$—CO—OH or a salt thereof.

354. The method of any one of Embodiments 310 and 343-351, wherein a compound of formula P-9' or a salt thereof is HO—$CH_2$—$CH_2$—$CH_2$—$CH_2$—$CH_2$—C(O)—H or a salt thereof.

355. The method of any one of Embodiments 312 and 343-351 and 354, wherein a compound of formula P-10' or a salt thereof is HO—$CH_2$—$CH_2$—$CH_2$—$CH_2$—$CH_2$—$CH_2$—OH or a salt thereof.

356. The method of any one of Embodiments 317 and 343-346, wherein a compound of formula P-4' or a salt thereof is HO—$CH_2$—$CH_2$—$CH_2$—$CH_2$—C(O)—H or a salt thereof.

357. The method of any one of Embodiments 317 and 343-346 and 356, wherein a compound of formula P-5' or a salt thereof is HO—$CH_2$—$CH_2$—$CH_2$—$CH_2$—$CH_2$—OH or a salt thereof.

358. The method of any one of Embodiments 238-357, wherein a microbe comprises two or more biosynthesis polypeptides in the contacting steps.

359. The method of any one of Embodiments 238-358, comprising performing one or more contacting and/or conversion steps in one type of microbe, and one or more other contacting and/or conversion steps in another type of microbe.

360. The method of any one of Embodiments 238-359, comprising performing one or more contacting and/or conversion steps in one culture, and one or more other contacting and/or conversion steps in another culture.

361. The method of any one of Embodiments 238-359, comprising performing the contacting and/or conversion steps in a single culture.

362. The method of any one of Embodiments 238-361, wherein a microbe comprises all biosynthesis polypeptides recited in the contacting steps.

363. The method of Embodiment 362, comprising performing the contacting and/or conversion steps in a single culture.

364. The method of any one of the preceding Embodiments, wherein the product is produced at about or at least about 0.1, 0.2, 0.3, 0.4, 0.5, 0.6, 0.7, 0.8, 0.9, 1, 2, 3, 4, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L of culture.

365. The method of any one of the preceding Embodiments, wherein pyruvate utilization for a desired product is about or is at least about 5%, 10%, 15%, 20%, 25%, 30%, 35%, 40%, 45%, 50%, 55%, 60%, 65%, 70%, 75%, 80%, 85%, 90%, or 95%.

366. A preparation prepared by a method of any one of the preceding Embodiments.

367. A preparation of a compound of formula P-1, P-2, P-3, P-4, P-4', P-5, P-5', P-6, P-7, P-8, P-9, P-9', P-10, or P-10', or salt thereof, or a preparation prepared by a method of any one of the preceding Embodiments, which preparation is enriched for $^{14}C$ isotope relative to that observed in a reference preparation of the compound, which reference preparation is prepared using fossil carbon source.

368. A preparation of a polyester, a polyester polyol, a polyurethane, nylon 6, nylon 6,6, a polycarbonate diol, diacrylate ester, or diglycidyl ether, which preparation is manufactured using a preparation prepared by a method of any one of the preceding claims.

369. The preparation of Embodiment 368, wherein the preparation is enriched for $^{14}C$ isotope relative to that observed in a reference preparation of the compound, which reference preparation is prepared using fossil carbon source.

370. An nucleic acid encoding one or more biosynthesis polypeptides of any one of the preceding Embodiments.

371. The nucleic acid of Embodiment 370, wherein the nucleic acid differs from a natural nucleic acid which encodes the same biosynthesis polypeptide.

372. The nucleic acid of Embodiment 370 or 371, wherein the nucleic acid is optimized for expression in a microorganism.

373. An engineered microbe that produces an aldol product of an aliphatic aldehyde, the microbe comprising increased expression or activity of an aldol product biosynthesis polypeptide, wherein:
the carbonyl group of the aliphatic aldehyde is not conjugated to a alkenyl, alkynyl, or aromatic group;
the aldol product is a compound comprising an aldehyde or ketone group and a hydroxyl group attached to a beta-carbon of an aldehyde or ketone carbonyl group.

374. The microbe of Embodiment 373, wherein the aliphatic aldehyde is described in any one of Embodiments 238-363.

375. The microbe of Embodiment 373, wherein the aldol product is described in any one of Embodiments 238-363.

376. An engineered microbe that produces an aldol-dehydration product of an aliphatic aldehyde, the microbe comprising increased expression or activity of an aldol product biosynthesis polypeptide, an aldol-dehydration product biosynthesis polypeptide, a dehydration product biosynthesis polypeptide, or any combination thereof, wherein:
the carbonyl group of the aliphatic aldehyde is not conjugated to a alkenyl, alkynyl, or aromatic group; and
the aldol-dehydration product is a compound comprising an aldehyde or ketone group and a double bond conjugated with the aldehyde or ketone group.

377. The microbe of Embodiment 376, wherein the aliphatic aldehyde is described in any one of Embodiments 238-363.

378. The microbe of Embodiment 376, wherein the aldol-dehydration product is described in any one of Embodiments 238-363.

379. An engineered microbe that produces an alkene reduction product, the microbe comprising increased expression or activity of an alkene reduction product biosynthesis polypeptide, wherein:
the alkene comprises a double bond conjugated to a carbonyl group; and
a double bond conjugated to a carbonyl group in the alkene is reduced to a single bond to provide an alkene reduction product.

380. The microbe of Embodiment 379, wherein the alkene is described in any one of Embodiments 271-363.

381. The microbe of Embodiment 379, wherein the alkene reduction product is described in any one of Embodiments 238-363.

382. The microbe of any one of Embodiments 373-381, further comprising increased expression or activity of a biosynthesis polypeptide of any one of Embodiments 271-363.

383. A culture, comprising a microbe of any one of Embodiments 238-382, and one or more compounds independently of formulae P-1 to P-10, P-9', P-10', P-4' or P-5', or a salt thereof.

384. The culture of Embodiment 383, wherein one or more compounds are independently of higher levels compared to a reference culture of comparable microbes without the increased expression or activity of a biosynthesis polypeptide(s).

385. The culture of any one of Embodiments 383-384, wherein each of the compounds of formulae P-1 to P-10, P-9', P-10', P-4' or P-5', or a salt thereof is independently as described in any one of Embodiments 238-363.

386. A method, preparation, compound, organism, microorganism, culture or product as described herein.

EXAMPLES

The following examples are set forth below to illustrate the methods and results according to the disclosed subject matter. These examples are not intended to be inclusive of all aspects of the subject matter disclosed herein, but rather to illustrate certain representative methods and results. These examples are not intended to exclude equivalents and variations of the subject matter described herein which are apparent to one skilled in the art. Throughout the examples, sequences of enzymes or proteins are identified by their Uniprot ID or by their GenBank Accession Numbers (referred to as GenBank ID or GenBank Accession No.) or by their RefSeq ID. In case of Uniprot ID, the sequences are denoted by the primary (citable) accession number. RefSeq protein record represents non-redundant protein sequences within the NCBI database. Non-redundant protein records represent one exact sequence that has been observed once or many times in different strains or species.

Example 1: Enzymes that Catalyze Aldol-Dehydration Product Biosynthesis Using Aliphatic Aldehydes It has not previously been demonstrated that trans-o-hydroxybenzylidenepyruvate hydratase-aldolases (EC 4.1.2.45)[1-5] or 4-(2-carboxyphenyl)-2-oxobut-3-enoate aldolases (E.C. 4.1.2.34; also referred to as trans-2'-carboxybenzalpyruvate hydratase-aldolases)[6], referred cumulatively herein as hydratase-aldolases or Ads-Hyd, possess any aldol addition or aldol condensation activity on aliphatic aldehydes,[1-6] especially those without any unsaturation next to the aldehyde group.[5] Instead, the aldol condensation activity of these enzymes has previously been limited to substrates wherein the newly formed unsaturation can be stabilized via conjugation to unsaturation present within the aldehyde substrate.[1-5] Examples of such aldehyde substrates include aromatic conjugated aldehydes such as benzaldehyde or alkenals (i.e., aliphatic aldehydes with double bonds between C2 and C3). It has been unexpectedly discovered that these hydratase-aldolases are capable of utilizing a number of aliphatic aldehydes, e.g., linear aldehydes of different carbon lengths and different functionalities as substrates and are able to provide aldol-dehydration products, without the intention to be limited by any theory, through carrying out both aldol addition and aldol condensation reactions with pyruvate as the donor (nucleophile) to give the corresponding 4-hydroxy-2-keto-carboxylic acids and 3,4-dehydro-2-keto-carboxylic acids respectively as products. Results for representative trans-o-hydroxybenzylidenepyruvate hydratase-aldolases (e.g., entries Ads-Hyd 2 & 9 in Table 1) and trans-2'-carboxybenzalpyruvate hydratase-aldolases (e.g., entry Ads-Hyd 3 in Table 1) are summarized in Table 1 for aldol-dehydration activity (both aldol addition and aldol condensation), wherein pyruvate is used as donor and acetaldehyde, propionaldehyde, and 3-hydroxy-propanal are used as acceptor aldehydes.

TABLE 1

Provided technologies are active toward various aldehydes.

| Ads-Hyd ID | Uniprot ID or Genbank or RefSeq ID | EC Number | % Identitiy to following Ads-Hyd sequences | | | Activity on Different substrates | | |
|---|---|---|---|---|---|---|---|---|
| | | | A0A286PH18 | P0A144 | Q79EM8 | Acetaldehyde | Propanal | 3-hydroxy-propanal |
| Ads-Hyd 1 | D7C0E5 | UA | 93.6 | ND | ND | + | + | + |
| Ads-Hyd 2 | P0A144 | 4.1.2.45 | ND | 100 | 38.3 | + | + | + |
| Ads-Hyd 3 | Q79EM8 | 4.1.2.34 | ND | 38.3 | 100 | + | + | NA |
| Ads-Hyd 4 | A0A0N0AHI8 | UA | 59.2 | ND | ND | NT | NT | + |
| Ads-Hyd 5 | A0A0N1FRY3 | UA | 93.6 | ND | ND | NT | NT | + |
| Ads-Hyd 6 | M3DYR1 | UA | 59 | ND | ND | NT | + | + |
| Ads-Hyd 7 | W7SU48 | UA | 63 | ND | ND | NT | NT | + |
| Ads-Hyd 8 | A0A286PH18 | UA | 100 | 13.7 | 17 | NT | + | + |
| Ads-Hyd 9 | Q9X9Q6 | 4.1.2.45 | ND | 57 | 36.3 | NT | NT | + |
| Ads-Hyd 10 | Q9WXH7 | UA | ND | 55.6 | 36 | NT | + | + |
| Ads-Hyd 11 | A4XDS1 | UA | ND | 56 | 36.5 | NT | NT | + |
| Ads-Hyd 12 | F2J6N9 | UA | ND | 60.1 | 40.2 | NT | NT | + |
| Ads-Hyd 13 | A0A063BFL5 | UA | ND | 63.2 | 34.7 | NT | NT | + |
| Ads-Hyd 14 | Q9ZHH6 | UA | ND | 73.1 | 38.6 | NT | NT | + |
| Ads-Hyd 15 | A0A0C1K853 | UA | ND | 75.2 | 38.6 | NT | NT | + |
| Ads-Hyd 62 | WP_034398482 | UA | ND | 81.7 | 36.8 | NT | NT | + |
| Ads-Hyd 87 | PYK12191 | UA | 50.4 | ND | ND | NT | NT | + |
| Ads-Hyd 96 | A0A370X7D8 | UA | 55.8 | ND | ND | NT | NT | + |
| Ads-Hyd 104 | WP_028222253 | UA | 56.1 | ND | ND | NT | NT | + |
| Ads-Hyd 65 | F2J6L6 | UA | ND | 59.8 | 39.8 | NT | NT | + |
| Ads-Hyd 89 | A0A0N0L9F6 | UA | 54 | ND | ND | NT | NT | + |
| Ads-Hyd 97 | A0A1G9YWG7 | UA | 56.6 | ND | ND | NT | NT | + |
| Ads-Hyd 68 | A0A2U1BT09 | UA | ND | 50.7 | 34.8 | NT | NT | + |
| Ads-Hyd 108 | A0A244DHE8 | UA | 57.4 | ND | ND | NT | NT | + |
| Ads-Hyd 29 | WP_107818191 | UA | ND | 58.3 | 39.8 | NT | NT | + |
| Ads-Hyd 69 | A0A023WZF9 | UA | ND | 91.3 | 37.1 | NT | NT | + |
| Ads-Hyd 93 | PYN48855 | UA | 49.3 | ND | ND | NT | NT | + |
| Ads-Hyd 98 | A0A421PAQ6 | UA | 58.3 | ND | ND | NT | NT | NA |
| Ads-Hyd 99 | WP_028217297 | UA | 56.7 | ND | ND | NT | NT | + |
| Ads-Hyd 100 | WP_034507049 | UA | 56 | ND | ND | NT | NT | NA |
| Ads-Hyd 110 | KMK64081.1 | 4.1.2.45 | ND | 56 | 36 | + | + | + |
| Ads-Hyd 111 | WP_070028041.1 | 4.1.2.45 | ND | 35 | 35 | NT | NT | + |
| Ads-Hyd 112 | KZL92449.1 | 4.1.1.4 | 40 | ND | ND | NT | NT | + |

NT = Not tested;
NA = Not active;
+ = active;
UA = EC number is unassigned;
ND = Actual value is not determined as sequence identity is too blow (~<25%)

Aldol addition and aldol condensation activity on aliphatic unconjugated aldehydes of different carbon lengths and functionalities by a subset of enzymes from Table 1 is summarized in Table 2, further demonstrating the versatility of unconjugated aldehyde substrates suitable for this reaction.

TABLE 2

Provided technologies are active toward various aldehydes.

| Enzyme ID | Aldol Addition | | | | | | Aldol Condensation | | | | | |
|---|---|---|---|---|---|---|---|---|---|---|---|---|
| | A | B | C | D | E | F | A | B | C | D | E | F |
| Ads-Hyd 1 | Yes | Yes | NT | NT | Yes | NT | Yes | Yes | NT | NT | Yes | NT |
| Ads-Hyd 2 | Yes | Yes | NT | Yes | Yes | NT | Yes | Yes | NT | Yes | Yes | NT |
| Ads-Hyd 108 | Yes | Yes | NT | NT | Yes | NT | Yes | Yes | NT | NT | Yes | NT |
| Ads-Hyd 3 | Yes | Yes | Yes | Yes | Yes | Yes | Yes | Yes | Yes | Yes | Yes | Yes |
| Ads-Hyd 8 | Yes | Yes | Yes | Yes | Yes | Yes | Yes | Yes | Yes | Yes | Yes | Yes |
| Ads-Hyd 89 | Yes | Yes | NT | Yes | Yes | Yes | Yes | Yes | NT | Yes | Yes | Yes |
| Ads-Hyd 110 | Yes | Yes | Yes | Yes | Yes | Yes | Yes | Yes | Yes | Yes | Yes | Yes |
| Ads-Hyd 112 | NT | NT | NT | Yes | Yes | NT | NT | NT | NT | Yes | Yes | NT |
| HpaI | Yes | Yes | Yes | Yes | Yes | Yes | No | No | No | No | No | No |

NT = Not tested;
A = acetaldehyde;
B = propionaldehyde;
C = butyraldehyde;
D = 2-hydroxy acetaldehyde;
E = 3'-hydroxy-propanal;
F = 4-hydroxy butyraldehyde Among other things, the technologies provide high efficiency, e.g., in terms of product production rate, yield and/or utilization of substrates, e.g., pyruvate. In some embodiments, a biosynthesis polypeptide is about 50%, 100%, or 1.5, 2, 3, 4, 5, 6, 7, 8, 9, 10, 20, 50, 100 fold or more active, as measured by production of comparable products under suitable conditions, compared to a relevant reference biosynthesis polypeptide. In some embodiments, the present disclosure provides highly efficient utilization of a substrate, e.g., pyruvate. In some embodiments, utilization of a substrate, e.g., pyruvate, is about or at least about 5%, 10%, 15%, 20%, 25%, 30%, 35%, 40%, 45%, 50%, 55%, 60%, 65%, 70%, 75%, 80%, 85%, 90%, or 95%. In some embodiments, desired product concentration in a culture is about or is at least about 0.1, 0.2, 0.3, 0.4, 0.5, 0.6, 0.7, 0.8, 0.9, 1, 2, 3, 4, 5, 6, 7, 8, 9, or 10 g/L after a period of production time (e.g., 90 min). In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. For example, Table 3 demonstrates dramatically improved efficiency of provided technologies compared to aldolases known previously to catalyze corresponding reactions: a representative trans-o-hydroxybenzylidenepyruvate hydratase-aldolase in Table 3 outperforms (e.g., >5 times activity) the other aldolases in terms of aldol addition activity on the tested substrates. Among other things, Table 4 demonstrated that Ads-Hyd enzymes can provide improved product yields as well as highly efficient utilization of substrate pyruvate compared to the comparative aldolases. This is particularly notable since pyruvate is a central metabolite and may be consumed by other reactions within a microorganism. As demonstrated herein, provided technologies comprising aldol-dehydration product biosynthesis polypeptides can effectively minimize pyruvate consumption in vivo by undesirable reactions, which is crucial to improve desired product yield in vivo.

TABLE 4

Provided technologies can provide high yields and highly efficient substrate utilization.

| Enzyme Name | Enzyme ID | Product Formation (g/L) After 90 mins | | | % Pyruvate Used For Production | | |
|---|---|---|---|---|---|---|---|
| | | A | B | C | A | B | C |
| Sb Ads-Hyd | Ads-Hyd 1 | >3 | >3 | + | 25 | 57 | NT |
| G12 Ads-Hyd | Ads-Hyd 108 | NT | NT | + | + | NT | Not applicable |
| Aldolase | HpaI | 0.2 | 0.7 | + | 1 | 4 | Not applicable |

NT = Not tested;
+ = activity confirmed but not quantified;
A = acetaldehyde;
B = propionaldehyde;
C = 3'-hydroxy-propanal Although a few hydratase-aldolases have been categorized as belonging to EC 4.1.2.45 or EC 4.1.2.34 (see Table 5), most enzyme sequences reported in Table 1 and sequences identified by homology searches (using BLAST; see Tables 6-8) have not been assigned an EC number. Additionally, these enzymes have also been annonated in literature or databases (e.g., Uniprot) as acetoacetate decarboxylase or dihydrodipicolinate synthetase or simply as aldolases due to the similarity with these other classes of enzymes. For example, Ads-Hyd 8 enzyme is not annotated as a hydratase-aldolase and is annotated to be an acetoacetate decarboxylase (see Uniprot page for this sequence), when it functions as a hydratase-aldolase (see Table 1). Similarly, Ads-Hyd 11-13 enzymes have been annotated as dihydrodipicolinate synthetase, but they function as a hydratase-aldolase (see Table 1). It is expected that many hydratase-aldolase enzyme sequences are or will be annotated or inferred in public databases as belonging to acetoacetate decarboxylase or dihydrodipicolinate synthetase or aldolases and are not categorized to either belonging to EC 4.1.2.45 or EC 4.1.2.34. Thus, to identify hydratase-aldolase enzyme sequences, homology-based searches to hydratase-aldolase sequences were conducted, and the resultant

TABLE 3

Provided technologies can provide high activity.

| Enzyme Type | Enzyme ID | Uniprot ID | Activity on Different substrates | | |
|---|---|---|---|---|---|
| | | | Acetaldehyde | Propionaldehyde | 3-hydroxy-propanal |
| aldolase | yagE | P75682 | 25000 | NT | NT |
| aldolase | nanA | P0A6L4 | 25000 | NT | NT |
| aldolase | garL | P23522 | 15000 | NT | NT |
| aldolase | eda | P0A955 | 5000 | NT | NT |
| aldolase | dgoA | Q6BF16 | 25000 | NT | NT |
| aldolase | Av-Ads | M9YI86 | NT | 20000 | NT |
| aldolase | Cg-Ads | Q8NMD2 | NT | 45000 | NT |
| aldolase | Cj-Ads | A0A1J6QD42 | NT | 5000 | NT |
| aldolase | Mt-Ads | Q8RBI5 | NT | 5000 | NT |
| aldolase | Ps-Ads | A3LZU9 | NT | 25000 | NT |
| aldolase | Sa-Ads | Q4JC35 | NT | 30000 | NT |
| hydratase-aldolase | Ads-Hyd 1 | D7C0E5 | 270000 | 405000 | NT |
| aldolase | Ss-Ads | O54288 | NT | 25000 | NT |
| aldolase | St-Ads | F9VPG1 | NT | 25000 | NT |
| aldolase | HpaI | Q47098 | 15000 | 25000 | NT |

NT = Not tested. For activity determination, pyruvate (20 g/L) was incubated with either acetaldehyde (40 g/L) or propionaldehyde (40 g/L) for 12 hr aerobically.

enzymes were subsequently validated regarding their activity using methods described herein. An exemplary, homology-based search using (a) one sequence belonging to EC 4.1.2.34 (Ads-Hyd 3; results in Table 8); (b) one sequence belonging to an unassigned enzyme with extremely low homology to enzymes belonging to EC 4.1.2.34 and EC 4.1.2.45 (Ads-Hyd 8; results in Table 6) and (c) one sequence belonging to an unassigned enzyme show moderate homology to enzymes belonging to EC 4.1.2.34 and EC 4.1.2.45 (Ads-Hyd 10; results in Table 7) revealed >500 enzymes, some of which are listed in the tables below, and many of which upon testing were confirmed to be active for aldol addition and condensation (data in Table 1). For example, 13 sequences identified in Table 6 (see underlined sequences in Table 6 with data for those sequence in Table 1), and 11 sequences identified in Table 7 (see underlined sequences in Table 7 with data for those sequence in Table 1) were confirmed to be functional Ads-Hyd enzymes. Among other things, the present disclosure demonstrated that Ads-Hyd 112, which is classified as belonging to E.C 4.1.1.4 and annotated as an acetetoacetate decarboxylase, was also found to catalyze aldol addition and aldol condensation reactions with a number of different aldehydes (Table 2). In some embodiments, enzymes annotated as acetoacetate decarboxylases as well as those belonging to E.C 4.1.1.4 are useful for catalyzing aldol condensation and addition reactions as well. Enzymes with identities ranging from as low as 35% (Ads-Hyd 68 in Table 1), 38% (Ads-Hyd 3 in Table 1) and 49% (Ads-Hyd 93 in Table 1) to Ads-Hyd 3 belonging to EC 4.1.2.34, Ads-Hyd 2 belonging to EC 4.1.2.45, and Ads-Hyd 8 enzymes respectively, were confirmed to have hydratase-aldolase activity.

TABLE 5

Certain biosynthesis polypeptides.

| Uniprot ID | Genbank ID | EC Number | Protein names |
| --- | --- | --- | --- |
| Q9X9Q6 | AAD45417.1 | 4.1.2.45 | Trans-O-hydroxybenzylidenepyruvate hydratase-aldolase (2'-hydroxybenzalpyruvate aldolase) |
| P0A144 | AAB62713.1 | 4.1.2.45 | Trans-O-hydroxybenzylidenepyruvate hydratase-aldolase (2'-hydroxybenzalpyruvate aldolase) |
| P0A142 | BAA12246.1 | 4.1.2.45 | Trans-O-hydroxybenzylidenepyruvate hydratase-aldolase (2'-hydroxybenzalpyruvate aldolase) |
| Q79EM8 | BAA23263.1 | 4.1.2.34 | Trans-2'-carboxybenzalpyruvate hydratase-aldolase |
| Q51947 | AAA66357.1 | 4.1.2.45 | Trans-O-hydroxybenzylidenepyruvate hydratase-aldolase (2'-hydroxybenzalpyruvate aldolase) |
| P0A143 | AAA16132.1 | 4.1.2.45 | Trans-O-hydroxybenzylidenepyruvate hydratase-aldolase (2'-hydroxybenzalpyruvate aldolase) |
| A0A0J5Q5D8 | KMK64081.1 | 4.1.2.45 | Dihydrodipicolinate synthase/N-acetylneuraminate lyase |
| A0A1Y5PJE4 | SBS78822.1 | 4.1.2.34 | Trans-2'-carboxybenzalpyruvate hydratase-aldolase |
| A0A2H5YJ14 | GBD13407.1 | 4.1.2.34 | Trans-2'-carboxybenzalpyruvate hydratase-aldolase |
| A0A1V6C3X5 | OQB71622.1 | 4.1.2.45 | Trans-O-hydroxybenzylidenepyruvate hydratase-aldolase (2'-hydroxybenzalpyruvate aldolase) |
| A0A2H5YYR5 | GBD18589.1 | 4.1.2.45 | Trans-O-hydroxybenzylidenepyruvate hydratase-aldolase (2'-hydroxybenzalpyruvate aldolase) |
| A0A2H5VLK1 | GBC77546.1 | 4.1.2.45 | Trans-O-hydroxybenzylidenepyruvate hydratase-aldolase (2'-hydroxybenzalpyruvate aldolase) |
| A0A1K2FZU3 | SFY52690.1 | 4.1.2.45 | Trans-O-hydroxybenzylidenepyruvate hydratase-aldolase (2'-hydroxybenzalpyruvate aldolase) |
| A0A2H5W1Y6 | GBC82821.1 | 4.1.2.45 | Trans-O-hydroxybenzylidenepyruvate hydratase-aldolase (2'-hydroxybenzalpyruvate aldolase) |

TABLE 6

Certain biosynthesis polypeptides - enzymes that show homology to Ads-Hyd 8.

| Genbank ID (Enzyme ID if verified) | Protein names |
| --- | --- |
| KZL92449.1 (Ads-Hyd 112) | Acetoacetate decarboxylase (EC 4.1.1.4) |
| AOS64057.1 | Acetoacetate decarboxylase (ADC) (EC 4.1.1.4) |
| GBC87126.1 | Acetoacetate decarboxylase (EC 4.1.1.4) |
| AKL97316.1 | Acetoacetate decarboxylase (EC 4.1.1.4) |
| PZG 10242.1 | Acetoacetate decarboxylase |
| AEB44722.1 | Acetoacetate decarboxylase |
| ABG04000.1 | Acetoacetate decarboxylase |

TABLE 6-continued

Certain biosynthesis polypeptides - enzymes that show homology to Ads-Hyd 8.

| Genbank ID (Enzyme ID if verified) | Protein names |
|---|---|
| KPH00942.1 (Ads-Hyd 89) | Acetoacetate decarboxylase |
| EMF26762.1 (Ads-Hyd 6) | Acetoacetate decarboxylase |
| PVY06388.1 | Acetoacetate decarboxylase |
| AOJ06649.1 | Acetoacetate decarboxylase |
| KOX08160.1 (Ads-Hyd 4) | Acetoacetate decarboxylase |
| OPG13060.1 | Enduracididine biosynthesis enzyme MppR |
| SDQ34954.1 | Acetoacetate decarboxylase |
| OIJ66442.1 | Acetoacetate decarboxylase |
| GCE00545.1 | Acetoacetate decarboxylase |
| ACK51122.1 | Acetoacetate decarboxylase |
| PJJ78777.1 | Acetoacetate decarboxylase |
| GAU76561.1 | Acetoacetate decarboxylase |
| SEM36970.1 | Acetoacetate decarboxylase |
| REK87553.1 | Enduracididine biosynthesis enzyme MppR |
| KPI02092.1 (Ads-Hyd 5) | Acetoacetate decarboxylase |
| KPC94750.1 | Acetoacetate decarboxylase (Fragment) |
| AEF90707.1 | Acetoacetate decarboxylase |
| OPC78676.1 | Acetoacetate decarboxylase |
| OPY57828.1 | Acetoacetate decarboxylase |
| KUL75432.1 | Acetoacetate decarboxylase |
| OEV06324.1 | Acetoacetate decarboxylase |
| PVX87320.1 | Acetoacetate decarboxylase |
| PIG16285.1 | Acetoacetate decarboxylase |
| POR47715.1 | Acetoacetate decarboxylase |
| SFH06339.1 | Acetoacetate decarboxylase |
| KUM42217.1 | Acetoacetate decarboxylase |
| PZT77592.1 | Acetoacetate decarboxylase |
| KYC38950.1 | Acetoacetate decarboxylase |
| RKS77249.1 | Acetoacetate decarboxylase |
| OIJ92678.1 | Acetoacetate decarboxylase |
| BAU27837.1 | Acetoacetate decarboxylase |
| QAV71426.1 | Acetoacetate decarboxylase |
| PQZ48703.1 | Uncharacterized protein |
| EXU61971.1 | Acetoacetate decarboxylase |
| SHN38127.1 | Acetoacetate decarboxylase |
| KGT73177.1 | Acetoacetate decarboxylase |
| SIO29145.1 | Acetoacetate decarboxylase |
| KGT73210.1 | Acetoacetate decarboxylase |
| SIO27946.1 | Acetoacetate decarboxylase |
| OSJ25700.1 | Acetoacetate decarboxylase |
| RMD31380.1 | Acetoacetate decarboxylase |
| SIO53681.1 | Acetoacetate decarboxylase |
| RFU48568.1 | Acetoacetate decarboxylase |
| OSJ25816.1 | Acetoacetate decarboxylase |
| HCV33217.1 | Acetoacetate decarboxylase |
| KPD20047.1 | Acetoacetate decarboxylase |
| OFW57075.1 | Uncharacterized protein |
| HCW00147.1 | Acetoacetate decarboxylase |
| EIM94241.1 | Acetoacetate decarboxylase |
| OYV58956.1 | Acetoacetate decarboxylase |
| REK15702.1 | Acetoacetate decarboxylase |
| MBV14559.1 | Acetoacetate decarboxylase |
| HAN36693.1 | Acetoacetate decarboxylase |
| HAP74745.1 | Acetoacetate decarboxylase |
| PYR38950.1 | Acetoacetate decarboxylase (Fragment) |
| PYR49219.1 | Acetoacetate decarboxylase |
| PTB41031.1 | Uncharacterized protein |
| EHK39542.1 | Uncharacterized protein |
| SYX90497.1 | Acetoacetate decarboxylase |
| RKN45560.1 | Acetoacetate decarboxylase |
| KJC40693.1 | Uncharacterized protein |
| RKR91249.1 | Acetoacetate decarboxylase |
| EJL77881.1 | Acetoacetate decarboxylase |
| PIG41119.1 | Acetoacetate decarboxylase |
| KJC40569.1 | Acetoacetate decarboxylase |
| KGF80061.1 | Acetoacetate decarboxylase |
| SON57276.1 | Acetoacetate decarboxylase (ADC) |
| KYO55945.1 | Acetoacetate decarboxylase |
| RFC69939.1 | Acetoacetate decarboxylase |
| RPE56489.1 | Acetoacetate decarboxylase |
| SFQ35591.1 | Acetoacetate decarboxylase |
| SCD72996.1 | Acetoacetate decarboxylase |
| RQO46864.1 | Acetoacetate decarboxylase |
| RLK57997.1 | Enduracididine biosynthesis enzyme MppR |
| ACZ90180.1 | Acetoacetate decarboxylase |
| GCD42233.1 | Uncharacterized protein |

TABLE 6-continued

Certain biosynthesis polypeptides - enzymes that show homology to Ads-Hyd 8.

| Genbank ID (Enzyme ID if verified) | Protein names |
|---|---|
| PIF96550.1 | Enduracididine biosynthesis enzyme MppR |
| PBC93106.1 | Acetoacetate decarboxylase |
| SIO44972.1 | Acetoacetate decarboxylase |
| OYD73530.1 | Acetoacetate decarboxylase |
| SEC28728.1 | Enduracididine biosynthesis enzyme MppR |
| RFC78087.1 | Acetoacetate decarboxylase |
| PWC35104.1 | Acetoacetate decarboxylase |
| AWL33917.1 | Enduracididine biosynthesis enzyme MppR |
| SED37560.1 | Acetoacetate decarboxylase |
| KOG37070.1 | Acetoacetate decarboxylase |
| SDJ19059.1 | Enduracididine biosynthesis enzyme MppR |
| PHX81843.1 | Acetoacetate decarboxylase |
| MBJ31847.1 | Acetoacetate decarboxylase |
| RPJ15459.1 | Acetoacetate decarboxylase |
| ABD65946.1 | Enduracididine biosynthesis enzyme MppR |
| RSM78635.1 | Acetoacetate decarboxylase |
| RSM86524.1 | Acetoacetate decarboxylase |
| AUG07753.1 | Acetoacetate decarboxylase |
| SHG60447.1 | Acetoacetate decarboxylase |
| SMC73048.1 | Acetoacetate decarboxylase |
| PKR44685.1 | Enduracididine biosynthesis enzyme MppR |
| AUC95510.1 | Acetoacetate decarboxylase |
| SUZ73052.1 | Uncharacterized protein (Fragment) |
| SNS52433.1 | Acetoacetate decarboxylase (ADC) |
| MMZ55024.1 | Acetoacetate decarboxylase |
| MNQ33472.1 | Acetoacetate decarboxylase |
| KJC46837.1 | Acetoacetate decarboxylase |
| SDL38666.1 | Acetoacetate decarboxylase |
| ONI74756.1 | Acetoacetate decarboxylase |
| SOD30619.1 | Acetoacetate decarboxylase |
| KJC46838.1 | Acetoacetate decarboxylase |
| RUL62263.1 | Acetoacetate decarboxylase |
| RMI93268.1 (Ads-Hyd 98) | Acetoacetate decarboxylase |
| RKR21285.1 | Acetoacetate decarboxylase |
| SDK87733.1 | Acetoacetate decarboxylase |
| PZS29802.1 | Acetoacetate decarboxylase |
| AAU34211.1 | Uncharacterized protein |
| CNE94443.1 | Acetoacetate decarboxylase |
| CDR14781.1 | Acetoacetate decarboxylase |
| OGI63453.1 | Acetoacetate decarboxylase |
| SDW59396.1 | Enduracididine biosynthesis enzyme MppR |
| MBE40108.1 | Acetoacetate decarboxylase |
| RPI20925.1 | Acetoacetate decarboxylase |
| AVZ77933.1 | Acetoacetate decarboxylase |
| CRK83612.1 | Acetoacetate decarboxylase |
| AOP51678.1 | Enduracididine biosynthesis enzyme MppR |
| KJC56449.1 | Uncharacterized protein |
| POX38729.1 | Acetoacetate decarboxylase |
| RDS84232.1 (Ads-Hyd 96) | Acetoacetate decarboxylase |
| ABK52869.1 | Acetoacetate decarboxylase |
| ERI08645.1 | Putative acetoacetate decarboxylase |
| SED02700.1 | Acetoacetate decarboxylase |
| SED57674.1 | Acetoacetate decarboxylase |
| AJQ29697.1 | Acetoacetate decarboxylase |
| AUS77184.1 | Enduracididine biosynthesis enzyme MppR |
| OEV05744.1 | Enduracididine biosynthesis enzyme MppR |
| SHJ82744.1 | Acetoacetate decarboxylase (ADC) |
| PDQ21702.1 | Acetoacetate decarboxylase |
| MBF06178.1 | Acetoacetate decarboxylase |
| SDI62088.1 | Acetoacetate decarboxylase |
| SES42580.1 | Enduracididine biosynthesis enzyme MppR |
| OAN53209.1 | Acetoacetate decarboxylase |
| CUU19651.1 | Acetoacetate decarboxylase CDS |
| PIG70517.1 | Acetoacetate decarboxylase |
| GAT80125.1 | Acetoacetate decarboxylase |
| RMI45923.1 | Acetoacetate decarboxylase |
| RFS83293.1 | Acetoacetate decarboxylase |
| RUL90134.1 | Enduracididine biosynthesis enzyme MppR |
| CEH29276.1 | Putative acetoacetate decarboxylase |
| KJC56043.1 | Acetoacetate decarboxylase |
| KJC56044.1 | Acetoacetate decarboxylase |
| AWE54161.1 | Acetoacetate decarboxylase |
| ADI03636.1 (Ads-Hyd 1) | Acetoacetate decarboxylase |
| GAT84669.1 | Acetoacetate decarboxylase |
| RUQ72183.1 | Acetoacetate decarboxylase |
| RSN12399.1 | Acetoacetate decarboxylase |

TABLE 6-continued

Certain biosynthesis polypeptides - enzymes that show homology to Ads-Hyd 8.

| Genbank ID (Enzyme ID if verified) | Protein names |
|---|---|
| RKD49684.1 | Acetoacetate decarboxylase |
| RKR34606.1 | Acetoacetate decarboxylase |
| PIG06713.1 | Acetoacetate decarboxylase |
| ROQ34846.1 | Enduracididine biosynthesis enzyme MppR |
| KXU84461.1 | Acetoacetate decarboxylase |
| OUL77098.1 (Ads-Hyd 108) | Acetoacetate decarboxylase |
| PYK12191.1 (Ads-Hyd 87) | Acetoacetate decarboxylase |
| RUL72479.1 | Acetoacetate decarboxylase |
| PWK86305.1 | Enduracididine biosynthesis enzyme MppR |
| GCD34260.1 | Uncharacterized protein |
| SOE90358.1 | Acetoacetate decarboxylase |
| SDG84621.1 | Enduracididine biosynthesis enzyme MppR |
| EWM12399.1 (Ads-Hyd 7) | Acetoacetate decarboxylase |
| SDG23054.1 | Acetoacetate decarboxylase |
| AFK55453.1 | Uncharacterized protein |
| AUT62680.1 | Acetoacetate decarboxylase |
| RPE37958.1 | Acetoacetate decarboxylase |
| EWM12653.1 | Acetoacetate decarboxylase |
| RSN04866.1 | Enduracididine biosynthesis enzyme MppR |
| KQV82686.1 | Acetoacetate decarboxylase |
| RKF38182.1 | Acetoacetate decarboxylase |
| REE27044.1 | Acetoacetate decarboxylase |
| PJN40277.1 | Enduracididine biosynthesis enzyme MppR |
| SDN12921.1 | Acetoacetate decarboxylase |
| PYG36199.1 | Acetoacetate decarboxylase |
| RKQ65112.1 | Acetoacetate decarboxylase |
| SDN12891.1 (Ads-Hyd 97) | Acetoacetate decarboxylase |
| EIW19392.1 | Acetoacetate decarboxylase |
| RSN99590.1 | Acetoacetate decarboxylase |
| PON28167.1 | Uncharacterized protein |
| PNP43262.1 | Uncharacterized protein |
| PON20078.1 | Uncharacterized protein |
| AEM85455.1 | Acetoacetate decarboxylase |
| AOT70611.1 | Acetoacetate decarboxylase |
| OPF83246.1 | Acetoacetate decarboxylase |
| PYN48855.1 (Ads-Hyd 93) | Acetoacetate decarboxylase |
| SFH92960.1 | Acetoacetate decarboxylase |
| SME92731.1 | Acetoacetate decarboxylase |
| RKQ67404.1 | Acetoacetate decarboxylase |
| RAK24761.1 | Acetoacetate decarboxylase |
| ALV48823.1 | Acetoacetate decarboxylase |
| SHG57166.1 | Acetoacetate decarboxylase |
| SHI09865.1 | Acetoacetate decarboxylase |
| RLV76922.1 | Acetoacetate decarboxylase |
| SHG57190.1 | Acetoacetate decarboxylase |
| KXU84652.1 | Acetoacetate decarboxylase |
| SIO27627.1 | Acetoacetate decarboxylase |
| AXQ55553.1 | Enduracididine biosynthesis enzyme MppR |
| AOJ04944.1 | Acetoacetate decarboxylase |
| ARH95437.1 | Enduracididine biosynthesis enzyme MppR |
| REH48625.1 | Acetoacetate decarboxylase |
| RLJ42250.1 | Acetoacetate decarboxylase |
| SHN71285.1 | Acetoacetate decarboxylase |
| SHN71288.1 | Acetoacetate decarboxylase |
| SHI09851.1 | Acetoacetate decarboxylase |
| SHN71296.1 | Acetoacetate decarboxylase |
| SIO27636.1 | Acetoacetate decarboxylase |
| REH35177.1 | Acetoacetate decarboxylase |
| SOE93021.1 | Acetoacetate decarboxylase |
| ALO91482.1 | Acetoacetate decarboxylase |
| AKJ70148.1 | Acetoacetate decarboxylase |
| EJL71335.1 | Acetoacetate decarboxylase |
| KMS76577.1 | Acetoacetate decarboxylase |
| SAL51447.1 | Acetoacetate decarboxylase |
| MBA77131.1 | Acetoacetate decarboxylase |
| MAM76769.1 | Acetoacetate decarboxylase |
| AXL50798.1 | Acetoacetate decarboxylase |
| SOE99541.1 | Acetoacetate decarboxylase |
| PIF38354.1 | Acetoacetate decarboxylase |
| GAX58847.1 | Acetoacetate decarboxylase |
| SFN30008.1 | Acetoacetate decarboxylase |
| KUL58863.1 | Enduracididine biosynthesis enzyme MppR |
| KOG74850.1 | Acetoacetate decarboxylase |
| AEY87061.1 | Acetoacetate decarboxylase |
| RDS66140.1 | Acetoacetate decarboxylase |
| ONI72521.1 | Acetoacetate decarboxylase |

TABLE 6-continued

Certain biosynthesis polypeptides - enzymes that show homology to Ads-Hyd 8.

| Genbank ID (Enzyme ID if verified) | Protein names |
| --- | --- |
| AHH95455.1 | Carboxy-lyase |
| SOE19480.1 | Acetoacetate decarboxylase (ADC) |
| ROO80377.1 | Acetoacetate decarboxylase |
| SAL27032.1 | Acetoacetate decarboxylase |
| HAM27991.1 | Acetoacetate decarboxylase |
| KDN75868.1 | Acetoacetate decarboxylase |
| AEW99245.1 | Uncharacterized protein |
| AAR35773.1 | Acetoacetate decarboxylase family protein |
| PMR61960.1 | Acetoacetate decarboxylase |
| OXL32653.1 | Acetoacetate decarboxylase |
| KUN27737.1 | Acetoacetate decarboxylase |
| EPR75769.1 | Acetoacetate decarboxylase |
| SFT90048.1 | Acetoacetate decarboxylase |
| RFU39638.1 | Acetoacetate decarboxylase |
| SMG22616.1 | Acetoacetate decarboxylase |

TABLE 7

Certain biosynthesis polypeptides - enzymes that show homology to Ads-Hyd 10.

| Genbank ID (Enzyme ID) | Protein names |
| --- | --- |
| SBS78822.1 | Trans-2'-carboxybenzalpyruvate hydratase-aldolase (EC 4.1.2.34) |
| GBD13407.1 | Trans-2'-carboxybenzalpyruvate hydratase-aldolase (EC 4.1.2.34) |
| BAA23263.1 (Ads-Hyd 3) | Trans-2'-carboxybenzalpyruvate hydratase-aldolase (EC 4.1.2.34) |
| AAD45417.1 (Ads-Hyd 9) | Trans-O-hydroxybenzylidenepyruvate hydratase-aldolase (EC 4.1.2.45) |
| AAA16132.1 | Trans-O-hydroxybenzylidenepyruvate hydratase-aldolase (EC 4.1.2.45) |
| BAA12246.1 | Trans-O-hydroxybenzylidenepyruvate hydratase-aldolase (EC 4.1.2.45) |
| AAB62713.1 (Ads-Hyd 2) | Trans-O-hydroxybenzylidenepyruvate hydratase-aldolase (EC 4.1.2.45) |
| AAA66357.1 | Trans-O-hydroxybenzylidenepyruvate hydratase-aldolase (EC 4.1.2.45) |
| KMK64081.1 | Dihydrodipicolinate synthase/N-acetylneuraminate lyase (EC 4.1.2.45) |
| GBD18589.1 | Trans-O-hydroxybenzylidenepyruvate hydratase-aldolase (EC 4.1.2.45) |
| GBC82821.1 | Trans-O-hydroxybenzylidenepyruvate hydratase-aldolase (EC 4.1.2.45) |
| ART89851.1 | 4-hydroxy-tetrahydrodipicolinate synthase (EC 4.3.3.7) |
| SJM52860.1 | 4-hydroxy-tetrahydrodipicolinate synthase (EC 4.3.3.7) |
| ART58441.1 | Aldolase |
| BAA76332.1 (Ads-Hyd 10) | Hydratase-aldolase |
| AEF88788.1 | Dihydrodipicolinate synthetase |
| ART51183.1 | Aldolase |
| KLU36881.1 | Aldolase |
| AKM12047.1 | Aldolase |
| CCA93880.1 | Dihydrodipicolinate synthetase |
| EZP70093.1 | Putative 2-hydroxy-benzylpyruvate aldolase |
| EHJ58034.1 | Putative 2-hydroxy-benzylpyruvate aldolase |
| ART40746.1 | L352 |
| ATW03328.1 | Aldolase |
| CCA92467.1 | Dihydrodipicolinate synthetase |
| ABM79813.1 | Aldolase (Hydratase-aldolase) |
| BAC65452.1 | Putative 2-hydroxy-benzylpyruvate aldolase |
| GAM16817.1 | Hydratase-aldolase |
| PBN41471.1 | Trans-o-hydroxybenzylidenepyruvate hydratase-aldolase |
| OWQ92810.1 | Aldolase |
| SHN54758.1 | Dihydrodipicolinate synthase/N-acetylneuraminate lyase |
| KDA01194.1 | Dihydrodipicolinate synthetase |
| KJS38380.1 | Aldolase |
| AKQ42951.1 | 1,2-dihydroxybenzylpyruvate aldolase |
| PNU02635.1 | Aldolase |
| EJU12841.1 | 1,2-dihydroxybenzylpyruvate aldolase |
| OAP30848.1 | Aldolase |
| ETI62764.1 | Aldolase |
| KKW89821.1 | Aldolase |
| PNQ03402.1 | Aldolase |
| AGZ63484.1 | NahE |
| PKB13561.1 | Dihydrodipicolinate synthase/N-acetylneuraminate lyase |
| PEQ10932.1 | Aldolase |
| AYO76044.1 | Aldolase |
| ABP64082.1 (Ads-Hyd 11) | Dihydrodipicolinate synthetase |
| KHS42353.1 | Dihydrodipicolinate synthetase |
| AAD03976.1 | 1,2-dihydroxybenzylpyruvate aldolase |
| KTE40403.1 | Aldolase |
| KTE22766.1 | Aldolase |
| RJG53082.1 | Aldolase |

TABLE 7-continued

Certain biosynthesis polypeptides - enzymes that show homology to Ads-Hyd 10.

| Genbank ID (Enzyme ID) | Protein names |
|---|---|
| PQM29276.1 | Aldolase |
| KTE33221.1 | Aldolase |
| KGB52059.1 | Putative 2-hydroxy-benzylpyruvate aldolase |
| ART37867.1 | F474 |
| ODU68266.1 | Aldolase (Fragment) |
| PXV63448.1 | Trans-o-hydroxybenzylidenepyruvate hydratase-aldolase |
| AJP47897.1 | Aldolase |
| ADZ72499.1 (Ads-Hyd 65) | Dihydrodipicolinate synthetase |
| AER08042.1 | Hydratase-aldolase |
| EIF28466.1 | Dihydrodipicolinate synthase/N-acetylneuraminate lyase |
| ALE55172.1 | Aldolase |
| OWJ56339.1 | Aldolase |
| PJJ06708.1 | Trans-o-hydroxybenzylidenepyruvate hydratase-aldolase |
| AKM10279.1 | Aldolase |
| ART40122.1 | K159 |
| ART38154.1 | F222 |
| PWJ76345.1 | Trans-o-hydroxybenzylidenepyruvate hydratase-aldolase |
| PTQ67744.1 | Trans-o-hydroxybenzylidenepyruvate hydratase-aldolase |
| KGB81035.1 | Aldolase |
| PTQ65074.1 | Trans-o-hydroxybenzylidenepyruvate hydratase-aldolase |
| ADZ72522.1 (Ads-Hyd 12) | Dihydrodipicolinate synthetase |
| ALG93322.1 | Aldolase |
| KEP68746.1 | Aldolase |
| AMM86059.1 | Aldolase |
| MAM12073.1 | Aldolase |
| EIT71336.1 | Dihydrodipicolinate synthetase |
| AEF05081.1 | Dihydrodipicolinate synthetase |
| PAL23311.1 | Aldolase |
| PWJ76353.1 | Trans-o-hydroxybenzylidenepyruvate hydratase-aldolase |
| RVT39492.1 | Aldolase |
| SEP74235.1 | Trans-o-hydroxybenzylidenepyruvate hydratase-aldolase |
| BAA20397.1 | Hydratase-aldolase |
| AAL07266.1 | 2-hydroxybenzalpyruvate aldolase |
| ETI60157.1 | Aldolase |
| ART36295.1 | C905 |
| BAF34962.1 | Trans-o-hydrobenzylidenepyruvate hydratase aldolase |
| BAF34972.1 | Trans-o-hydrobenzylidenepyruvate hydratase aldolase |
| AAP44192.1 | 1,2-dihydroxybenzyl pyruvate aldolase |
| EXF90974.1 | Aldolase |
| OPK08859.1 | Trans-o-hydroxybenzylidenepyruvate hydratase-aldolase |
| APV43293.1 | Aldolase (Trans-o-hydroxybenzylidenepyruvate hydratase-aldolase) |
| AAO64280.1 | Trans-o-hydroxybenzylidenepyruvate hydratase-aldolase |
| ALC77286.1 | Trans-O-hydroxybenzylidenepyruvate hydratase-aldolase |
| ACQ63497.1 | Trans-o-hydroxybenzylidenepyruvate hydratase-aldolase |
| ASW04047.1 | Aldolase |
| KKC26031.1 | Aldolase |
| AEV45882.1 | Trans-o-hydroxybenzylidenepyruvate hydratase-aldolase NahE |
| BAE92162.1 | Trans-o-hydroxybenzylidenepyruvate hydratase-aldolase NahE |
| BAF30942.1 | Trans-ohydrobenzylidenepyruvate hydratase aldolase |
| APP18116.1 | Trans-o-hydroxybenzylidenepyruvate hydratase-aldolase |
| AEV41420.1 | Trans-o-hydroxybenzylidenepyruvate hydratase-aldolase |
| AAD02141.1 | 1, 2-dihydroxybenzylpyruvate aldolase |
| OCX93212.1 | Aldolase |
| EPL61966.1 | Trans-o-hydroxybenzylidenepyruvate hydratase-aldolase |
| AFM32586.1 | Trans-o-hydroxybenzylidenepyruvate hydratase-aldolase |
| AAD12616.1 | Trans-o-hydroxybenzylidenepyruvate hydratase-aldolase |
| MAS13884.1 | Aldolase |
| EWC41257.1 | Aldolase |
| AHY45199.1 (Ads-Hyd 69) | Aldolase |
| AJE45 066.1 | Dihydrodipicolinate synthetase |
| VBB16389.1 | Aldolase |
| AAZ93394.1 | Dihydrodipicolinate synthetase (Trans-o-hydroxybenzylidenepyruvate hydratase-aldolase) |
| SAL31848.1 | Dihydrodipicolinate synthetase family protein |
| ALE55136.1 | Aldolase |
| OWJ56143.1 | Aldolase |
| AAD09869.1 (Ads-hyd 14) | Hydratase/aldolase PhnE |
| ACT53260.1 | Hydratase/aldolase |
| ANI13636.1 | Aldolase |
| EZQ14085.1 | Aldolase |
| PRF53899.1 | Aldolase |
| EHJ59545.1 | Hydratase-aldolase |
| ODU66836.1 | Aldolase |
| AZI70977.1 | 1,2-dihydroxybenzylpyruvate aldolase (Trans-o-hydroxybenzylidenepyruvate hydratase-aldolase) |

TABLE 7-continued

Certain biosynthesis polypeptides - enzymes that show homology to Ads-Hyd 10.

| Genbank ID (Enzyme ID) | Protein names |
|---|---|
| KIC79255.1 (Ads-Hyd 15) | Aldolase |
| AMK37583.1 | Trans-o-hydroxybenzylidenepyruvate hydratase-aldolase |
| KGH10186.1 | Aldolase |
| PHR55511.1 | Aldolase |
| RAK18497.1 | Trans-o-hydroxybenzylidenepyruvate hydratase-aldolase |
| EHJ59565.1 | 2-hydroxybenzalpyruvate aldolase |
| PVY51792.1 (Ads-Hyd 68) | Dihydrodipicolinate synthase/N-acetylneuraminate lyase |
| KDB08187.1 (Ads-Hyd 13) | Dihydrodipicolinate synthetase |
| APP18130.1 | Hydratase-aldolase |
| EHJ59532.1 | Hydratase/aldolase |
| EIE49938.1 | Trans-o-hydroxybenzylidenepyruvate hydratase-aldolase NahE |
| KHK92942.1 | Aldolase |
| ART39436.1 | J508 |
| RSM40400.1 | Aldolase |
| HAC32985.1 | Aldolase |
| SED12223.1 | Dihydrodipicolinate synthase/N-acetylneuraminate lyase |
| ART36910.1 | D219 |
| HCO44328.1 | Aldolase |
| OUR88246.1 | Aldolase |
| ANX02865.1 | Aldolase |
| PCI67543.1 | Aldolase |
| SHJ43395.1 | Trans-o-hydroxybenzylidenepyruvate hydratase-aldolase |
| AGS39599.1 | Dihydrodipicolinate synthase/N-acetylneuraminate lyase |
| MBG95280.1 | Aldolase |
| AFT67194.1 | Dihydrodipicolinate synthetase |
| PHS71704.1 | Aldolase |
| HAI96648.1 | Aldolase |
| EHJ59569.1 | Dihydrodipicolinate synthetase |
| AIN43768.1 | Hydratase-aldolase (Fragment) |
| ART35398.1 | A220 |
| SDM13008.1 | Trans-o-hydroxybenzylidenepyruvate hydratase-aldolase |
| SDG98718.1 | Trans-o-hydroxybenzylidenepyruvate hydratase-aldolase |
| EKX84573.1 | Trans-o-hydroxybenzylidenepyruvate hydratase-aldolase NahE |
| RTL66015.1 | Aldolase |
| KPK20478.1 | Uncharacterized protein |
| SEH64089.1 | Dihydrodipicolinate synthase/N-acetylneuraminate lyase |
| ART37041.1 | D408 |
| PYC47978.1 | Aldolase |
| OUS22376.1 | Uncharacterized protein |
| ANX03747.1 | Uncharacterized protein |
| KDE97295.1 | Aldolase |
| OPX10770.1 | Uncharacterized protein |
| ODQ85801.1 | Aldolase |
| ORB11495.1 | Aldolase |
| ORA58811.1 | Aldolase |
| ABL90862.1 | Dihydrodipicolinate synthetase |
| ADT96876.1 | Dihydrodipicolinate synthase/N-acetylneuraminate lyase |
| ABM11316.1 | Dihydrodipicolinate synthetase |
| BBA72532.1 | Dihydrodipicolinate synthetase |
| GAT12856.1 | Dihydrodipicolinate synthetase |
| ARV80195.1 | Aldolase (Dihydrodipicolinate synthase/N-acetylneuraminate lyase) |
| ABP43078.1 | Dihydrodipicolinate synthetase |
| AKK27886.1 | Aldolase |
| SEH58270.1 | 4-(2-carboxyphenyl)-2-oxobut-3-enoate aldolase |
| APE19406.1 | Aldolase |
| AAT51742.1 | PhdJ |
| BBA72542.1 | Dihydrodipicolinate synthetase |
| BBA72825.1 | Dihydrodipicolinate synthetase |
| AEV73682.1 | Dihydrodipicolinate synthase/N-acetylneuraminate lyase |
| ORB61988.1 | Aldolase |
| RDH74327.1 | Aldolase |
| ACN38282.1 | Trans-2'-carboxybenzalpyruvate hydratase-aldolase |
| KLU36867.1 | Aldolase |
| OUS03890.1 | Uncharacterized protein |
| ORW27057.1 | Uncharacterized protein |
| OAR05193.1 | 4-hydroxy-tetrahydrodipicolinate synthase (Aldolase) |
| CQD18686.1 | Dihydrodipicolinate synthetase |
| ORB04914.1 | Uncharacterized protein |
| AJP48436.1 | Uncharacterized protein |
| ACM06757.1 | Aldolase |
| HCO44883.1 | Aldolase |
| ANX04975.1 | Uncharacterized protein |
| SPM40709.1 | Dihydrodipicolinate synthase/N-acetylneuraminate lyase |
| SPM34880.1 | Dihydrodipicolinate synthase/N-acetylneuraminate lyase |
| OLT42115.1 | Aldolase |

TABLE 7-continued

Certain biosynthesis polypeptides - enzymes that show homology to Ads-Hyd 10.

| Genbank ID (Enzyme ID) | Protein names |
| --- | --- |
| HAC33263.1 | Aldolase |
| RFU95674.1 | Dihydrodipicolinate synthetase |
| OGQ80071.1 | Uncharacterized protein |
| SFB53516.1 | Dihydrodipicolinate synthase/N-acetylneuraminate lyase |
| PVY51809.1 | Dihydrodipicolinate synthase/N-acetylneuraminate lyase |
| PVY51803.1 | Dihydrodipicolinate synthase/N-acetylneuraminate lyase |
| ORB07056.1 | Aldolase |
| PVY51800.1 | Dihydrodipicolinate synthase/N-acetylneuraminate lyase |
| RIA44335.1 | Dihydrodipicolinate synthase/N-acetylneuraminate lyase |
| EHJ59573.1 | Uncharacterized protein |
| PVY51825.1 | Dihydrodipicolinate synthase/N-acetylneuraminate lyase |
| AIJ21944.1 | Putative aldolase |
| ORB38363.1 | Aldolase |
| AWK75959.1 | Aldolase |
| EID78824.1 | Putative aldolase NarC |
| ACV96860.1 | Putative aldolase |
| HAC33092.1 | Aldolase |
| AKM10259.1 | Uncharacterized protein |
| ART40134.1 | K171 |
| ELB89137.1 | Putative aldolase NarC |
| BAH47216.1 | Putative aldolase NarC |
| AAR05117.1 | Putative aldolase |
| EKT84398.1 | Putative aldolase NarC |
| KDE09923.1 | Aldolase |
| BAE53379.1 | Aldolase |
| AAR05109.1 | Putative aldolase |
| AQW45620.1 | Putative aldolase |
| API60260.1 | Uncharacterized protein |
| RLA50226.1 | Aldolase |
| OUZ12202.1 | Aldolase |
| RLV57233.1 | Aldolase |
| BAA94711.1 | Hydratase-aldolase |
| AFC42746.1 | Dihydrodipicolinate synthetase |
| ASW94610.1 | Aldolase |
| ORW23722.1 | Aldolase |
| ORB75698.1 | Aldolase |
| AAG53397.1 | 1,2-dihydroxybenzylpyruvate aldolase 2 (Fragment) |
| CRL08851.1 | 2-carboxybenzalpyruvate hydratase aldolase |
| OSC27070.1 | Aldolase |
| RKO19521.1 | Aldolase |
| ADX75098.1 | Dihydrodipicolinate synthase/N-acetylneuraminate lyase |
| RTL66022.1 | Dihydrodipicolinate synthetase |
| AAG53396.1 | 1,2-dihydroxybenzylpyruvate aldolase 1 (Fragment) |
| ADK82461.1 | Dihydrodipicolinate synthetase |
| OLT33718.1 | Aldolase |
| ADX73348.1 | Dihydrodipicolinate synthase/N-acetylneuraminate lyase |
| PSQ18743.1 | Aldolase |
| APA86915.1 | Aldolase |
| RAW15463.1 | Aldolase |
| AYY15006.1 | Aldolase |
| SEH58300.1 | Hydratase-aldolase |
| ORB22843.1 | Aldolase |

TABLE 8

Certain biosynthesis polypeptides - enzymes that show homology to Ads-Hyd 3.

| Genbank ID | Protein names |
| --- | --- |
| WP_013601270.1 | aldolase [*Pseudarthrobacter phenanthrenivorans*] |
| WP_013602982.1 | aldolase [*Pseudarthrobacter phenanthrenivorans*] |
| WP_127127049.1 | aldolase [*Georgenia* sp. SYP-B2076] |
| WP_075839590.1 | aldolase [*Rhodococcus* sp. CUA-806] |
| WP_086725852.1 | aldolase [*Streptomyces carpinensis*] |
| WP_137144035.1 | aldolase [*Mycolicibacterium* sp. CR10] |
| WP_047330709.1 | aldolase [*Mycobacterium* sp. EPa45] |
| WP_011559036.1 | MULTISPECIES: aldolase [Mycobacteriaceae] |
| WP_036349078.1 | aldolase [*Mycolicibacterium aromaticivorans*] |
| RTL66015.1 | aldolase [Pseudonocardiaceae bacterium] |
| WP_087139803.1 | aldolase [*Mycobacterium chimaera*] |
| WP_011777788.1 | aldolase [*Mycolicibacterium vanbaalenii*] |
| WP_011891552.1 | aldolase [*Mycolicibacterium gilvum*] |

TABLE 8-continued

Certain biosynthesis polypeptides - enzymes that show homology to Ads-Hyd 3.

| Genbank ID | Protein names |
| --- | --- |
| WP_069416983.1 | aldolase [*Mycolicibacterium flavescens*] |
| WP_083043896.1 | aldolase [*Mycolicibacterium elephantis*] |
| WP_083410401.1 | aldolase [*Mycolicibacterium rutilum*] |
| BBA72542.1 | dihydrodipicolinate synthetase [*Mycobacterium* sp. PO1] |
| WP_042910008.1 | MULTISPECIES: aldolase [*Mycobacterium avium* complex (MAC)] |
| WP_067396827.1 | aldolase [*Mycolicibacterium novocastrense*] |
| WP_083128714.1 | aldolase [*Mycolicibacterium tusciae*] |
| AAT51742.1 | PhdJ [*Mycolicibacterium vanbaalenii* PYR-1] |
| WP_114740710.1 | aldolase [*Mycolicibacterium moriokaense*] |
| WP_071950246.1 | aldolase [*Mycobacterium* sp. WY10] |
| GAT12856.1 | dihydrodipicolinate synthetase [*Mycolicibacterium novocastrense*] |
| WP_094286221.1 | aldolase [*Mycobacterium lehmannii*] |
| BBA72532.1 | dihydrodipicolinate synthetase [*Mycobacterium* sp. PO1] |
| WP_041303477.1 | aldolase [*Mycolicibacterium rhodesiae*] |
| AEV73682.1 | dihydrodipicolinate synthase/N-acetylneuraminate lyase [*Mycolicibacterium rhodesiae* NBB3] |
| 6DAQ_A | Chain A, PhdJ [*Mycolicibacterium vanbaalenii*] |
| WP_099039075.1 | aldolase [*Mycobacterium* sp. CECT 8778] |
| ACN38282.1 | trans-2'-carboxybenzalpyruvate hydratase-aldolase [*Mycobacterium* sp. CH1] |
| CRL08851.1 | 2-carboxybenzalpyruvate hydratase aldolase [*Mycobacterium* sp. 6PY1] |
| WP_096699239.1 | aldolase [*Polaromonas* sp. AER18D-145] |
| WP_047824912.1 | MULTISPECIES: aldolase [Massilia] |
| KPK20478.1 | hypothetical protein AMJ67_01080 [*Betaproteobacteria* bacterium SG8_41] |
| WP_027197771.1 | aldolase [*Paraburkholderia sprentiae*] |
| SDR61564.1 | Dihydrodipicolinate synthase/N-acetylneuraminate lyase [*Paraburkholderia tuberum*] |
| WP_090812328.1 | aldolase [*Paraburkholderia tuberum*] |
| WP_077079464.1 | MULTISPECIES: aldolase [*Mycobacterium*] |
| WP_090422646.1 | aldolase [*Mycobacterium europaeum*] |
| WP_062895341.1 | aldolase [*Mycobacterium avium*] |
| WP_011856608.1 | MULTISPECIES: aldolase [Mycobacteriaceae] |
| WP_123787007.1 | aldolase [*Achromobacter denitrificans*] |
| WP_083173134.1 | aldolase [*Mycobacterium paraseoulense*] |
| WP_071394168.1 | hypothetical protein [*Bacillus tuaregi*] |
| WP_083094487.1 | aldolase [*Mycobacterium mantenii*] |
| ETZ38018.1 | trans-2'-carboxybenzalpyruvate hydratase-aldolase [*Mycobacterium intracellulare* MIN_061107_1834] |
| WP_009953931.1 | MULTISPECIES: aldolase [*Mycobacterium*] |
| WP_085290658.1 | aldolase [*Mycolicibacterium vulneris*] |
| RLA50226.1 | aldolase [Gammaproteobacteria bacterium] |
| WP_107764147.1 | dihydrodipicolinate synthetase [*Coprothermobacter proteolyticus*] |
| WP_007179239.1 | aldolase [*Burkholderia* sp. Ch1-1] |
| WP_067464354.1 | aldolase [*Actinomadura macra*] |
| WP_083829069.1 | aldolase [*Delftia* sp. Cs1-4] |
| AEF88778.1 | dihydrodipicolinate synthetase [*Delftia* sp. Cs1-4] |
| WP_086911711.1 | aldolase [*Acidovorax carolinensis*] |
| WP_036562639.1 | aldolase [*Oceanicola* sp. MCTG156(1a)] |
| TAD90455.1 | aldolase [Alphaproteobacteria bacterium] |
| WP_047824930.1 | MULTISPECIES: aldolase [Massilia] |
| WP_018963718.1 | hypothetical protein [*Coprothermobacter platensis*] |
| OGB50545.1 | aldolase [*Burkholderiales* bacterium RIFOXYD12_FULL_59_19] |
| GBD13407.1 | Trans-2'-carboxybenzalpyruvate hydratase-aldolase [bacterium HR24] |
| WP_066198397.1 | aldolase [*Hydrogenibacillus schlegelii*] |
| WP_007298126.1 | MULTISPECIES: aldolase [*Rhodococcus*] |
| WP_051423516.1 | hypothetical protein [*Arthrobacter* sp. MA-N2] |
| WP_117329621.1 | dihydrodipicolinate synthetase [*Sphaerochaeta halotolerans*] |
| WP_128644286.1 | dihydrodipicolinate synthetase [*Rhodococcus opacus*] |
| WP_087561951.1 | MULTISPECIES: dihydrodipicolinate synthetase [*Rhodococcus*] |
| WP_012642744.1 | aldolase [*Thermomicrobium roseum*] |
| WP_017681823.1 | MULTISPECIES: aldolase [*Rhodococcus*] |
| WP_124259333.1 | aldolase [*Rhodococcus ruber*] |
| TAN29949.1 | hypothetical protein EPN30_01545 [*Actinobacteria* bacterium] |
| WP_005570095.1 | MULTISPECIES: aldolase [*Rhodococcus*] |
| WP_005253631.1 | aldolase [*Rhodococcus opacus*] |
| WP_079931448.1 | hypothetical protein [*Gordonia* sp. i37] |
| AAR05109.1 | putative aldolase [*Rhodococcus* sp. P400] |
| OUS22376.1 | hypothetical protein A9Q95_05145 [Rhodobacterales bacterium 59_46_T64] |
| WP_013602975.1 | aldolase [*Pseudarthrobacter phenanthrenivorans*] |
| GBD18589.1 | Trans-O-hydroxybenzylidenepyruvate hydratase-aldolase [bacterium HR27] |
| WP_110795628.1 | aldolase [Rhodobacteraceae bacterium FSX-11] |
| WP_013255920.1 | dihydrodipicolinate synthetase [*Sediminispirochaeta smaragdinae*] |
| WP_075849231.1 | aldolase [*Saccharomonospora* sp. CUA-673] |
| WP_020501058.1 | aldolase [*Sciscionella marina*] |
| OUS03890.1 | hypothetical protein A9Q96_17015 [Rhodobacterales bacterium 52_120_T64] |
| WP_091675950.1 | MULTISPECIES: aldolase [*Amycolatopsis*] |
| WP_038532000.1 | aldolase [*Amycolatopsis methanolica*] |

TABLE 8-continued

Certain biosynthesis polypeptides - enzymes that show homology to Ads-Hyd 3.

| Genbank ID | Protein names |
|---|---|
| WP_087059681.1 | aldolase [Actinomycetales bacterium JB111] |
| WP_092817818.1 | hypothetical protein [Halopenitus malekzadehii] |
| WP_065123170.1 | aldolase [Mycobacterium asiaticum] |
| WP_107447362.1 | aldolase [Streptomyces sp. P3] |
| WP_067937422.1 | aldolase [Mycobacterium sp. E2479] |
| WP_027943869.1 | aldolase [Amycolatopsis taiwanensis] |
| WP_078947647.1 | aldolase [Streptomyces griseus] |
| WP_121792642.1 | aldolase [Aeromicrobium sp. 9W16Y-2] |
| WP_010204520.1 | aldolase [Salinibacterium sp. PAMC 21357] |
| AMK37583.1 | trans-o-hydroxybenzylidenepyruvate hydratase-aldolase [Pseudomonas sp. C5pp] |
| WP_087622569.1 | aldolase [Aeromicrobium sp. PE09-221] |
| WP_032395674.1 | MULTISPECIES: aldolase [Rhodococcus] |
| WP_039615401.1 | MULTISPECIES: aldolase [Pseudomonas] |

Cloning, and expression: DNA encoding heterologous aldolase hydratase enzymes were codon-optimized for expression in E. coli and synthesized by a commercial DNA synthesis company. Using standard cloning methods, each gene was cloned downstream of the T7 RNA polymerase promoter and upstream of the T7 terminator sequence in pB11 backbone plasmid. Additionally, for experiments wherein the aldehyde selected was 3-hydroxy-propionaldehyde a glycerol dehydratase enzyme that is a B12-dependent enzyme (Lactococcus reuteri glycerol dehydratase that is comprised of five genes as follows: pduC [Uniprot ID No. A5VMB2]; pduD [Uniprot ID No. A5VMB1]; pduE [Uniprot ID No. A5VMB0]; pduG [Uniprot ID No. A5VMA9]; and pduH [Uniprot ID No. A5VMA8]) was also cloned on a second compatible plasmid to enable production of 3-hydroxy-propionaldehyde from glycerol using this enzyme. The plasmids were transformed in E. coli BL21*(DE3) ΔldhA. Starter cultures for each clone were grown overnight in tubes containing 5 mL 2×YT media with 1 g/L D-glucose and appropriate antibiotics. Cell cultures for expression were carried out in 2 mL growth medium in 96 well plates. Complex (2×YT) growth medium was used and supplemented with 2 g/L D-glucose, 0.5 g/L potassium phosphate buffer (pH 7.2), and 100 mg/L ferric ammonium citrate. Pre-induction growth was carried out for 2 hours under aerobic conditions and at 30° C. Recombinant protein expression was induced at an OD600 of 0.2-0.4 with 250 µM IPTG. Post-induction expression was carried out for 30-180 minutes at 30° C. and under aerobic conditions followed by 0-60 mins under anaerobic conditions.

Enzyme assay: Post expression, cells were harvested and re-suspended in 0.4 mL fresh medium (0D600~30) containing 15 g/L potassium phosphate buffer (pH 7.2) with substrates for the reaction. For activity determination, pyruvate (10-20 g/L) was incubated with 5-40 g/L aldehydes (e.g., acetaldehyde, propionaldehyde, butyraldehyde, 2-hydroxy-acetaldehyde, or 4-hydroxy-butyraldehyde) for 12 hr aerobically. For activity determination with 3-hydroxy-propanal, post expression cells were harvested and re-suspended in 0.4 mL fresh medium (0D600~30) containing 15 g/L potassium phosphate buffer (pH 7.2) with 10-20 g/L glucose, 5-10 g/L glycerol, and 10 g/L pyruvate for 15 hr under anaerobic conditions. The reaction mix was also supplemented with 10 µM vitamin B12 and 1 g/L glutathione. After incubation at room temperature, the cells were centrifuged, and the supernatant was filtered and analyzed via HPLC.

Analysis of product: Isocratic HPLC was primarily used to detect and quantify production of enzyme products, aldol addition products (4-hydroxy-2-keto-carboxylic acids), aldol condensation products (3,4-dehydro-2-keto-carboxylic acids). One method employed a Bio-Rad Aminex HPX-87 column, 0.7 mL/min of 0.05% formic acid (or 5 mM sulfuric acid) at 35° C. Detection was carried out using an RID (refractive index detector) and UV detector, the latter of which was used to measure signals at 210 and 260 nm. Additionally, aldol addition and aldol condensation products were also confirmed by LC-MS, by measuring the masses of the respective peaks identified previously via HPLC (data not included herein).

Example 2: Enzymes that Catalyze Reduction of Aldol-Dehydration Products

Figure 6:
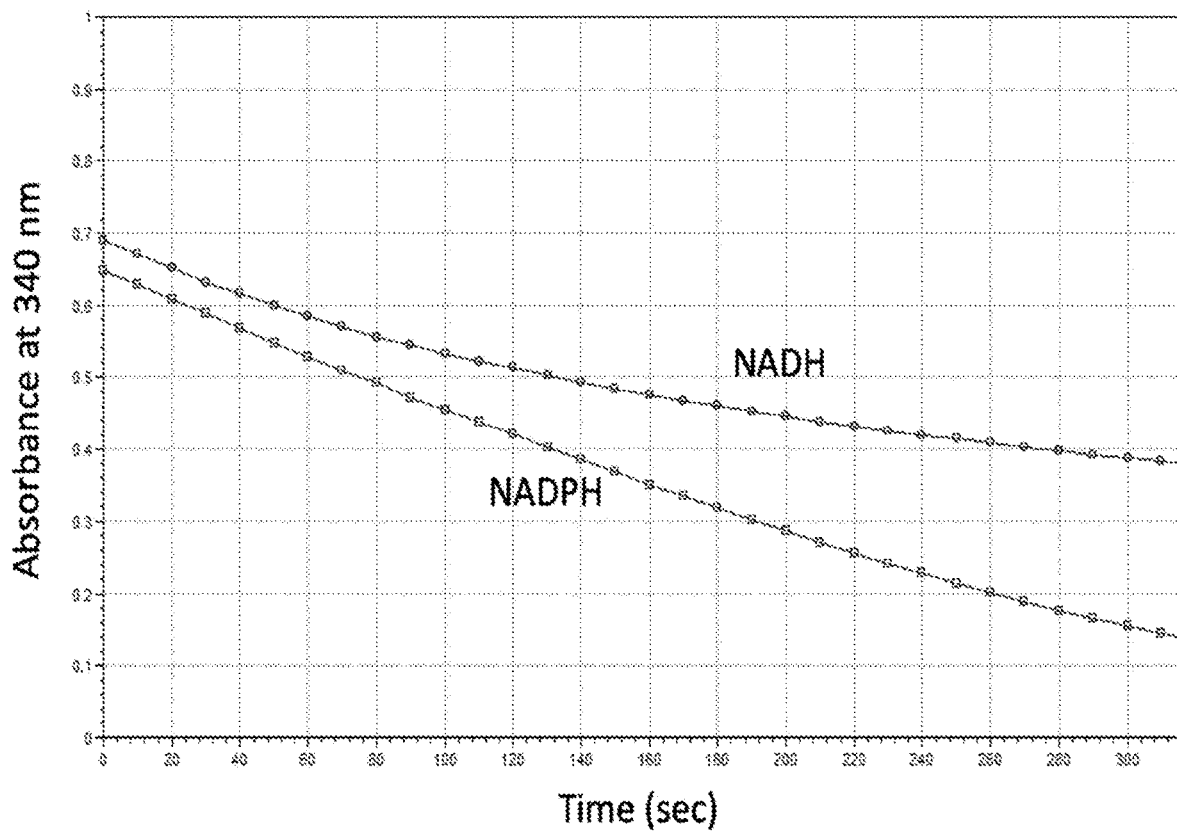
FIG. 6 shows the activity of the quinone oxidoreductase-1 (Qor-1) for reducing 6-hydroxy-3,4-dehydro-2-keto-hexenoate to 6-hydroxy-2-keto-hexenoate with cofactor NADH and NADPH.

As demonstrated herein, reduction of activated double bonds, i.e., double bonds next to a carbonyl or carboxylate group, can be catalyzed by enzymes. Aldol-dehydration products, e.g., 2-oxo-3-enoic acids, can be further reduced using enzymes, to give the corresponding 2-oxo-carboxylic acids. It was unexpectedly discovered that oxidoreductases belonging to EC 1.6.5 (e.g., EC 1.6.5.5) that utilize NADH and/or NADPH for reduction of quinones are capable of catalyzing this reaction. For example, when Ads-Hyd enzymes (see Example 1) were recombinantly expressed in E. coli BL21 or E. coli MG1655 strains for the production of 2-keto-carboxylic acids as described in Example 1, it was discovered that a portion of the Ads-Hyd enzyme product (i.e., 2-oxo-3-enoic acids) was converted to the corresponding 2-keto-carboxylic acid. This led to the possibility that some natively expressed enzyme or enzymes within these E. coli strains was responsible for carrying out the reduction of 2-oxo-3-enoic acids. A survey of known oxidoreductases that could conceivably carry out reduction of activated double bonds (i.e., EC 1.3.- and EC 1.6.-) within these strains was carried out. Seventeen such promising enzymes were identified within E. coli MG1655 and E. coli BL21 each. Knock-out strains for each of these enzymes in both of these hosts were prepared using known methods in the art. Subsequently each such knockout strain was tested for its ability to produce both of 2-oxo-3-enoic acid and its product of 2-keto-carboxylic acid using methods described above and using recombinantly expressed Ads-Hyd enzymes. This led to identification that knocking out the qorA gene or quinone oxidoreductase-1 led to production of 2-oxo-3-enoic acid and no 2-keto-carboxylic acid. This confirmed that the enzyme encoded by the qorA was likely responsible for natively carrying out this reaction. Subsequently, a N-terminal His6 tagged QorA enzyme ("His6" disclosed as SEQ ID NO: 106) was overexpressed and purified, and it was confirmed that it was indeed active for carrying out the desired reaction (FIG. 6). This unequivocally confirmed for the first time that quinone oxidoreductase enzyme from *E. coli* belonging to EC 1.6.5 (e.g., EC 1.6.5.5) is capable of functioning on substrates that are very different from their natural substrates, which are cyclic in structure. Furthermore, it was confirmed that this enzyme is able to utilize both NADH and NADPH as cofactors during the reaction (FIG. 6), which is very advantageous as it enables use of this enzyme under both aerobic and anaerobic conditions during bioproduction.

Various biosynthesis polypeptides belonging to EC 1.6.5 can be utilized in accordance with the present disclosure, e.g., as alkene reduction product biosynthesis polypeptides and/or for reduction of aldol-dehydration products. For example, a number of quinone oxidoreductases of EC 1.6.5.5 were assessed for their activities in accordance with the present disclosure, including eighteen enzymes (see Table 9) whose identities to *E. coli* Qor-1 enzyme ranged from 37-90%. All enzymes selected were confirmed to be active on at least one substrate (Table 9), further confirming the generality of this class of enzymes to carry out this reaction.

pB11 backbone plasmid. Additionally, for experiments wherein the aldehyde selected was 3-hydroxy-propionaldehyde a glycerol dehydratase enzyme that is a B12-dependent enzyme (*Lactococcus reuteri* glycerol dehydratase that is comprised of five genes as follows: pduC [Uniprot ID No. A5VMB2]; pduD [Uniprot ID No. A5VMB1]; pduE [Uniprot ID No. A5VMB0]; pduG [Uniprot ID No. A5VMA9]; and pduH [Uniprot ID No. A5VMA8]) was also cloned on a second compatible plasmid to enable production of 3-hydroxy-propionaldehyde from glycerol using this enzyme. The plasmids were transformed in *E. coli* BL21*(DE3) ΔldhA ΔqorA. Recombinant protein expression was carried out as described above in Example 1. For in vitro studies, the Qor-1 enzyme was induced at an OD600 of 0.2-0.4 with 250 μM IPTG. Post-induction expression was carried out for 180 minutes at 30° C. and under aerobic conditions. Post induction the enzyme was purified using Ni-NTA affinity chromatography using standard methods in art.

Enzyme assay: Same as Example 1 of in vivo activity measurement of the different quinone oxidoreductases. For in vitro activity measurement shown FIG. 6, the Qor-1 enzyme (0.3 mg/ml) was incubated with ~10 mM of 6-hydroxy-3,4-dehydro-2-oxohexanoate (synthesized in house), 0.5 mM of either NADH or NADPH in 100 mM pH 7 phosphate buffer.

TABLE 9

Certain useful biosynthesis polypeptides - reductase.

| | | | | Activity on Different substrates | | |
|---|---|---|---|---|---|---|
| Enzyme Name | Enzyme ID | % Identity to Qor-1 | Uniprot ID or Genbank ID | 3,4-dehydro-2-oxopentanoate | 3,4-dehydro-2-oxohexanoate | 6-hydroxy-3,4-dehydro-2-oxohexanoate |
| Ec QorA | Qor-1 | 100 | P28304 | + | + | + |
| Stm Qor | Qor-2 | 90 | P40783 | NT | NT | + |
| Reh Qor1 | Qor-3 | 43 | Q0K2I0 | NT | NT | + |
| Pvl Qor | Qor-4 | 67 | A0A1Z1SRY9 | NT | NT | + |
| Pae Qor | Qor-5 | 59 | P43903 | NT | NT | + |
| Msg Qor | Qor-6 | 44 | I7G8G0 | NT | NT | + |
| Bxb Qor | Qor-7 | 48 | Q142L2 | NT | NT | + |
| Bcep Qor | Qor-8 | 48 | ALK19324.1 | NT | NT | + |
| Aalbi Qor | Qor-9 | 42 | A0A1G9R408 | NT | NT | + |
| Ain Qor | Qor-10 | 29 | G4Q8R5 | NT | NT | + |
| Mche Qor | Qor-11 | 37 | ANA98723.1 | NT | NT | + |
| Nbr Qor | Qor-12 | 42 | K0EUQ3 | NT | NT | + |
| Pole Qor | Qor-13 | 60 | A0A061CRS8 | NT | NT | + |
| Ccr Qor | Qor-14 | 46 | Q9A212 | NT | NT | + |
| Sflav Qor | Qor-15 | 42 | A0A1I6RWW2 | NT | NT | + |
| Smari Qor | Qor-16 | 44 | WP_026197277.1 | NT | NT | + |
| Zmo Qor | Qor-17 | 37 | Q5NKZ3 | NT | NT | + |
| Met Qor | Qor-18 | 48 | WP_012333034.1 | NT | NT | + |
| Tri Qor | Qor-19 | 47 | WP_136898000.1 | NT | NT | + |

NT = Not tested;
NA = Not active;
+ = activity confirmed but not quantified

Other reduction product biosynthesis polypeptides, e.g., those belonging to various subclasses of EC 1.6.5 such as various quinone oxidoreductase enzymes belonging to EC 1.6.5.5 may also carry out this reaction.

Cloning and expression: DNA encoding heterologous aldolase hydratase (Ads-Hyd 1) and quinone oxidoreductase enzymes shown in Table 5 were codon-optimized for expression in *E. coli* and synthesized by a commercial DNA synthesis company. For in vitro activity measurements, and N-terminal His6 tag (SEQ ID NO: 106) was added onto Qor-1 enzyme. Using standard cloning methods, each gene was cloned downstream of the T7 RNA polymerase promoter and upstream of the T7 terminator sequence in single Analysis of product: Isocratic HPLC method described in Example 1 was used to detect and quantify production of enzyme product, i.e., 2-keto-carboxylic acids. For in vitro activity measurement, the decrease in absorbance at 340 nm was used to measure depletion of NADH or NADPH cofactor and thus Qor-1 activity.

Example 3: A Two-Enzyme System for the Production of 2-Keto-Carboxylic Acids from Pyruvate and Aliphatic Aldehydes The use of aldolase-hydratase enzyme(s) in combination with quinone oxidoreductase enzymes for the production of a range of 2-keto acids was examined. This combination enables the production of a range of 2-keto acids, which are precursors for the production of a number of industrially desirable products such as 1,5-pentanediol, 1,6-hexanediol, adipic acid, caprolactam, caprolactone, 6-hydroxy hexanoic acid, 6-amino caproic acid, amino acids, and many different fatty molecules. A number of different combinations of aldolase-hydratase enzymes and oxidoreductases were confirmed to be active for the production of different 2-keto acids (Table 10). As demonstrated herein, provided technologies can provide high products concentration, e.g., about or at least about 1, 2, 3, 4, 5, 6, 7, 8, 9, 10, 11, 12, 13, 14, 15, 16, 15, 17, 18, 20, 21, 22, 23, 24, 25, 30, 35, 40, 45, 50, 55, 60, 70, 80, 90, 100, 200, 300, 400, 500, 600, 700, 800, 900, 1000, 1200, 1500, 2000, 2500, 3000 mM.

TABLE 10

Provided technologies comprising multiple biosynthesis polypeptides generate desired products.

| Ads-Hyd ID | Reductase ID | Activity on Different substrates | | |
|---|---|---|---|---|
| | | mM of 2-keto pentanoic acid product | mM of 2-keto hexanoic acid product | mM of 6-hydroxy-2-keto hexanoic acid product |
| Ads-Hyd 1 | Qor-1 | + | + | 3.2 |
| Ads-Hyd 2 | Qor-1 | NT | NT | + |
| Ads-Hyd 3 | Qor-1 | NT | NT | NA |
| Ads-Hyd 4 | Qor-1 | NT | NT | 7.1 |
| Ads-Hyd 5 | Qor-1 | NT | NT | NA |
| Ads-Hyd 6 | Qor-1 | NT | NT | + |
| Ads-Hyd 7 | Qor-1 | NT | NT | + |
| Ads-Hyd 8 | Qor-1 | NT | NT | 5.8 |
| Ads-Hyd 9 | Qor-1 | NT | NT | + |
| Ads-Hyd 10 | Qor-1 | NT | NT | 12.3 |
| Ads-Hyd 11 | Qor-1 | NT | NT | + |
| Ads-Hyd 12 | Qor-1 | NT | NT | + |
| Ads-Hyd 13 | Qor-1 | NT | NT | + |
| Ads-Hyd 14 | Qor-1 | NT | NT | + |
| Ads-Hyd 15 | Qor-1 | NT | NT | + |
| Ads-Hyd 62 | Qor-1 | NT | NT | 20.0 |
| Ads-Hyd 87 | Qor-1 | NT | NT | 28.4 |
| Ads-Hyd 96 | Qor-1 | NT | NT | 28.3 |
| Ads-Hyd 104 | Qor-1 | NT | NT | 24.6 |
| Ads-Hyd 65 | Qor-1 | NT | NT | 18.9 |
| Ads-Hyd 89 | Qor-1 | NT | NT | 8.5 |
| Ads-Hyd 97 | Qor-1 | NT | NT | 26.1 |
| Ads-Hyd 68 | Qor-1 | NT | NT | 18.5 |
| Ads-Hyd 108 | Qor-1 | NT | NT | 33.8 |
| Ads-Hyd 29 | Qor-1 | NT | NT | 18.3 |
| Ads-Hyd 69 | Qor-1 | NT | NT | 8.9 |
| Ads-Hyd 93 | Qor-1 | NT | NT | 40.5 |
| Ads-Hyd 8 | Qor-1 | NT | NT | 5.8 |
| Ads-Hyd 8 | Qor-2 | NT | NT | + |
| Ads-Hyd 8 | Qor-3 | NT | NT | + |
| Ads-Hyd 8 | Qor-4 | NT | NT | + |
| Ads-Hyd 8 | Qor-5 | NT | NT | + |
| Ads-Hyd 8 | Qor-6 | NT | NT | + |
| Ads-Hyd 8 | Qor-7 | NT | NT | + |
| Ads-Hyd 8 | Qor-8 | NT | NT | + |
| Ads-Hyd 8 | Qor-9 | NT | NT | + |
| Ads-Hyd 8 | Qor-10 | NT | NT | + |
| Ads-Hyd 8 | Qor-11 | NT | NT | + |
| Ads-Hyd 8 | Qor-12 | NT | NT | + |
| Ads-Hyd 8 | Qor-13 | NT | NT | + |
| Ads-Hyd 8 | Qor-14 | NT | NT | + |
| Ads-Hyd 8 | Qor-15 | NT | NT | + |
| Ads-Hyd 8 | Qor-16 | NT | NT | + |
| Ads-Hyd 8 | Qor-17 | NT | NT | + |
| Ads-Hyd 8 | Qor-18 | NT | NT | + |
| Ads-Hyd 8 | Qor-19 | NT | NT | + |

NT = Not tested;
NA = Not active;
+ = activity confirmed but not quantified

Various biosynthesis polypeptides, particularly those belonging to EC 1.6.5, may be utilized for a reduction. For example, quinone oxidoreductases belonging to EC 1.6.5.5. are reported to be involved in electron carrier activity and are reported to be ubiquitous enzymes as they are reported to be present in, e.g., mammals, fungi, and bacteria (see entry for this EC class on Brenda.org). Although the native expression levels of these enzymes across various hosts are not known, it has been postulated previously that the expression level of this class of enzymes natively can be affected by the oxidative stress faced by the microbial host. It was discovered that E. coli (MG1655 and BL 21 strains) QorA gene (Qor-1) is natively expressed, especially under conditions described in Example 2. It was demonstrated that even native enzyme levels of Qor-1 in E. coli can be sufficient for production of 2-keto acids when Ads-Hyd enzymes (e.g., Ads-Hyd 8) are overexpressed in E. coli. For example, when Ads-Hyd 8 is overexpressed in E. coli BL 21*(DE3) ΔldhA, this resulted in the production of ~3 mM 6-hydroxy 2-keto hexanoate. However, overexpression of Qor-1 from plasmids in addition to Ads-Hyd 8, led to ~2× improved production (~5.8 mM 6-hydroxy 2-keto hexanoate). Based on this result, the in vitro kinetics data gathered in-house, and typical enzyme levels discovered in E. coli, it is estimated that in some embodiments, the native amounts of Qor-1 enzyme expressed under these conditions is <100 µM, and likely in the range of 0.1-100 µM.

Compared to a three-enzyme system, wherein aldol addition, dehydration, and subsequent reduction are carried out by three separate enzymes, provided technologies using two-enzyme systems provided significant improvement, for example: (1) only two enzymes need to be expressed rather than three enzymes—thus reducing catalysts required, and reducing cell resources for protein production when reaction are conducted in vivo, and (2) by having a single biosynthesis polypeptide carry out both the aldol addition and condensation reactions, reaction equilibrium is shifted towards the direction of production of desired products, which can be favorable to overall yields feasible through the process.

Cloning, and expression: DNA encoding heterologous aldolase hydratases and quinone oxidoreductase enzymes shown in Table 5 were codon-optimized for expression in E. coli and synthesized by a commercial DNA synthesis company. Using standard cloning methods, each gene was cloned downstream of the T7 RNA polymerase promoter and upstream of the T7 terminator sequence on two compatible plasmids. Additionally, for experiments wherein the aldehyde selected was 3-hydroxy-propionaldehyde, a glycerol dehydratase enzyme that is a B12-dependent enzyme (Lactococcus reuteri glycerol dehydratase that is comprised of five genes as follows: pduC [Uniprot ID No. A5VMB2]; pduD [Uniprot ID No. A5VMB1]; pduE [Uniprot ID No. A5VMB0]; pduG [Uniprot ID No. A5VMA9]; and pduH [Uniprot ID No. A5VMA8]) was also cloned on a third compatible plasmid to enable production of 3-hydroxy-propionaldehyde from glycerol using this enzyme. The plasmids were transformed in E. coli MG1655 (DE3) rne131 ΔldhA ΔadhE ΔfrdBC ΔpoxB ΔpflB ΔackA-pta ΔyqhD, ΔadhP, ΔeutG, ΔgldA, ΔyiaY, ΔfucO. Recombinant protein expression was carried out as described above in Example 1.

Enzyme assay: Same as Example 1.

Analysis of product: Isocratic HPLC method described in Example 1 was used to detect and quantify production of enzyme product, i.e., 2-keto-carboxylic acids.

Example 4: Biosynthetic Pathway for the Production of 1,5-Pentanediol

Figure 2:
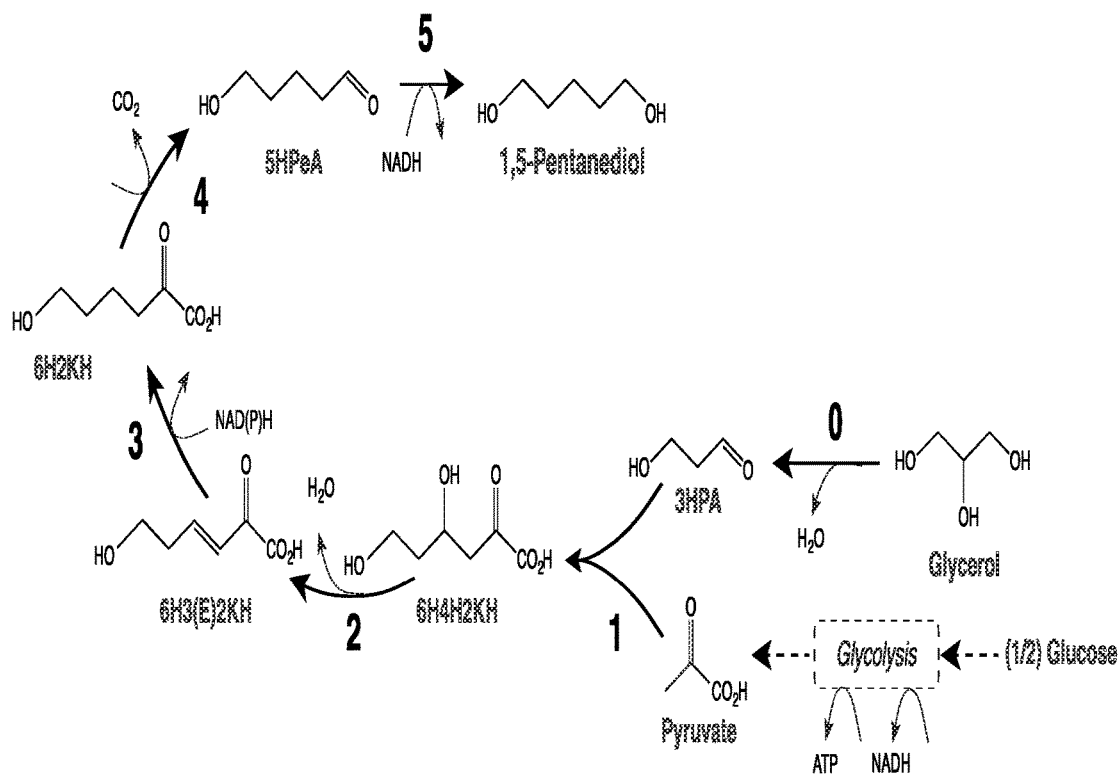
FIG. 2 shows a biosynthetic pathway for production of 1,5-pentanediol via 6-hydroxy-2-keto-hexanoate (6H2KH) intermediate. As used herein 3HPA refers to 3-hydroxy-propanal; 6H4H2KH refers to 4,6-dihydroxy-2-keto-hexanoate; 6H3(E)2KH refers to 6-hydroxy-3,4-dehydro-2-keto-hexenoate; and 5HPeA refers to 5-hydroxy pentanal. NADH is depicted as the cofactors for many reduction steps of the pathway for illustrative purposes. Either NADPH or NADH could be a cofactor.

This example describes a biosynthetic pathway for the production of 1,5-pentanediol from pyruvate and 3-hydroxy-propionaldehyde. As shown in FIG. 2, the biosynthetic pathway from pyruvate and 3-hydroxy-propionaldehyde includes five reactions. The first three reactions are described in Example 3, which involve converting pyruvate and 3-hydroxy-propionaldehyde to 6-hydroxy-2-keto-hexanoate. Described below are both known enzymes from the remaining two steps of the pathway. Notably, enzymes have been validated for all five reactions, which included demonstrating the complete pathway in vivo (see Example 5).

Steps 1-3: Conversion of pyruvate and 3-hydroxy-propionaldehyde to 6-hydroxy-2-oxo-hexanoate. See Example 3 for details.

Step 4: Conversion of 6-hydroxy-2-oxo-hexanoate to 5-hydroxy-pentanal. Exemplary enzymes are shown in Table 11. 2-Keto-acid decarboxylases (EC 4.1.1.7) catalyze the thiamine diphosphate (TPP) dependent decarboxylation of (CO 2-keto acids to give the corresponding ($C_{n-1}$) aldehydes. Enzymes that possess high-activity towards long-chain 2-oxo-acids with minimal or no activity on pyruvate are desired since cross-reactivity with pyruvate can dramatically affect yields of this pathway. Z. mobilis pyruvate decarboxylase (PDC) has been mutated (I472A/I476F) to significantly modify its active site for increased efficiency towards long-chain 2-oxo-acids along with a dramatic reduction (>2000 fold) in its activity towards pyruvate.[7] Z. mobilis PDC mutant I472A/I476F also shows excellent kinetic properties on 2-oxo-hexanoate which is structurally similar to desired substrate. Another promising enzyme candidate for catalyzing this step is L. lactis branched chain keto-acid decarboxylase KdcA (ketoacid decarboxylase), and P. putida benzoyl formate decarboxylase (BFD) mutant A460I.[8-10] The Pseudomonas putida BFD and L. lactis KdcA show >50 and 500-fold selectivity towards long-chain 2-oxo-acids compared to pyruvate for decarboxylation. In particular, L. lactis KdcA has specific activity towards 2-oxo-hexanoic acid and can tolerate substitutions on C3 and C4 positions. This enzyme was confirmed to be active for catalyzing the decarboxylation reaction (Table 14).

TABLE 11

Exemplary enzymes.

| Uniprot ID | Protein Name | Gene Name | Organism | E.C. Number |
|---|---|---|---|---|
| Q6QBS4 | Branched-chain alpha-ketoacid decarboxylase | kdcA | Lactococcus lactis | 4.1.1.72 |
| A7M7D6 | Pyruvate decarboxylase | pdc | Zymomonas mobilis | 4.1.1.1 |
| P20906 | benzoyl formate decarboxylase | mdlc | Pseudomonas putida | 4.1.1.7 |

Decarboxylases having other EC numbers are also suitable for carrying out this reaction. A representative list is shown in Table 12.

TABLE 12

Exemplary decarboxylases.

| E.C. Number | Name |
|---|---|
| 4.1.1.1 | Pyruvate decarboxylase |
| 4.1.1.2 | Oxalate decarboxylase |
| 4.1.1.3 | oxaloacetate decarboxylase |
| 4.1.1.4 | acetoacetate decarboxylase |
| 4.1.1.5 | acetolactate decarboxylase |
| 4.1.1.6 | aconitate decarboxylase |
| 4.1.1.7 | benzyl formate decarboxylase |
| 4.1.1.11 | aspartate-1-decarboxylase |
| 4.1.1.12 | aspartate-4-decarboxylase |
| 4.1.1.15 | glutamate decarboxylase |
| 4..1.1.16 | hydroxyglutamate decarboxylase |
| 4.1.1.17 | ornithine decaraboxylase |
| 4.1.1.18 | lysine decarboxylase |
| 4.1.1.19 | arginine decarboxylase |
| 4.1.1.20 | diaminopimelate decarboxylase |
| 4.1.1.34 | dehydro-L-gulonate decarboxylase |
| 4.1.1.35 | UDP-glucuronate decarboxylase |
| 4.1.1.40 | hydroxypyruvate decarboxylase |
| 4.1.1.54 | dihydroxyfumarate decarboxylase |
| 4.1.1.56 | 3-oxolaurate decarboxylase |
| 4.1.1.71 | 2-oxoglutarate decarboxylase |
| 4.1.1.72 | branched chain 2-oxo-acid decarboxylase |
| 4.1.1.73 | tartarate decarboxylase |
| 4.1.1.74 | indolepyruvate decarboxylase |
| 4.1.1.75 | 5-guanidino-2-oxopentanoate decarboxylase |
| 4.1.1.77 | 2-oxo-3-hexnedioate decarboxylase |

Step 5: Conversion of 5-hydroxy-pentaldehyde to 1,5-pentanediol. Primary alcohol dehydrogenases catalyze the NAD(P)H-dependent reduction of aldehydes to primary alcohols.

Many primary alcohol dehydrogenases are known in literature, and exemplary candidates to catalyze this step are described below and shown in Table 13 below. A number of E. coli alcohol-aldehyde dehydrogenases are known including AdhE, adhP, eutG, yiaY, yqhD, fucO, and yjgB.[11] Recently, 44 aldehyde reductases have been identified in E. coli. Butanol dehydrogenases[12] from C. acetobutylicum are of interest to catalyze these transformations. A number of S. cerevisiae alcohol dehydrogenases have been shown to reduce a range of different aldehydes including, ADH2-6. Of particular interest is ADHI-ADHII from two alkyl alcohol dehydrogenase (ADH) genes[13] from the long-chain alkane-degrading strain Geobacillus thermodenitrificans NG80-2. Other promiscuous ADH include AlrA which encodes a medium-chain alcohol dehydrogenase.[14] Also of interest are 4-hydroxy butyrate dehydrogenases (EC 1.1.1.61) that catalyze reduction of 4-oxo butyrate that have been found in A. thaliana[15], E. coli (yihu)[16], and as well as C. Eluyveri.[17] A. thaliana enzyme as well as A. terrus enzyme (ATEG in Table 13) can reduce glutarate semialdehyde (WO 20101068953A2, WO 20101068953A2). Although a number of alcohol dehydrogenase are of interest for carrying out this reaction, a specific enzyme of particular interest due to its high level of activity for reducing 5-hydroxy pentanal is alcohol dehydrogenase from Leifsonia sp. S749 (GenBank ID No. AB213459.1). This enzyme and four other alcohol dehydrogenases were validated (Table 14) to carry out this reaction.

TABLE 13

Exemplary dehydrogenases.

| Gene | GenBank ID or Uniprot ID | Name | Organism |
|---|---|---|---|
| fucO | NP_417279.1 | Alcohol Dehydrogenase | Escherichia coli |
| bdh I | NP_349892.1 | Alcohol Dehydrogenase | Clostridium acetobutylicum |
| bdh II | NP_349891.1 | Alcohol Dehydrogenase | Clostridium acetobutylicum |
| alrA | BAB12273.1 | Alcohol Dehydrogenase | Acinetobacter sp. strain |
| 4hbd | L21902.1 | 4-hydroxy butyrate dehydorgenase | Clostridium kluyveri |
| 4hbd | Q94B07 | 4-hydroxy butyrate dehydorgenase | Arabidopsis thaliana |
| yihu | AAB03015.1. | 4-hydroxy butyrate dehydorgenase | Escherichia coli |
| ADH2 | NP_014032.1 | Alcohol Dehydrogenase | Saccharomyces cerevisiae |
| ADH3 | NP_013892.1 | Alcohol Dehydrogenase | Saccharomyces cerevisiae |
| ADH4 | NP_015019.1 | Alcohol Dehydrogenase | Saccharomyces cerevisiae |
| ADH5 | NP_010996.2 | Alcohol Dehydrogenase | Saccharomyces cerevisiae |
| ADH6 | ABX39192.1 | Alcohol Dehydrogenase | Saccharomyces cerevisiae |
| ATEG | XP_001210625.1 | Alcohol Dehydrogenase | Aspergillus terreus |
| ADHI | ABO67118 | Alcohol Dehydrogenase | Geobacillus thermodenitrificans NG80-2 |
| ADHII | ABO68223 | Alcohol Dehydrogenase | Geobacillus thermodenitrificans NG80-2 |
| YqhD | BAE77068.1 | Alcohol Dehydrogenase | Escherichia coli |
| bdh CLJU_c23460 | D8GL45 | butanol dehydrogenase | Clostridium ljungdahlii |
| bdhA CA_C3299 | Q04944 | butanol dehydrogenase A | Clostridium acetobutylicum |
| chnD | Q84H78 | 6-hydroxyhexanoate dehydrogenase | Rhodococcus sp. Phi2 |
| chnD | Q7WVD0 | 6-hydroxyhexanoate dehydrogenase | Acinetobacter sp. NCIMB9871 |
| lsadh | AB213459.1 | Short chain alcohol dehydrogenase | Leifsonia sp. S749 |
| Adhe | CAA47743.1. | Alcohol Dehydrogenase | Escherichia coli |

Cloning, and expression: DNA encoding heterologous 2-keto acid decarboxylase and alcohol dehydrogenase enzymes shown in Table 14 below were codon-optimized for expression in E. coli and synthesized. Using standard cloning methods, each gene was cloned downstream of the T7 RNA polymerase promoter and upstream of the T7 terminator sequence on a single plasmid. The plasmid was transformed in E. coli MG1655 (DE3) rne131 ΔldhA ΔadhE ΔfrdBC. Recombinant protein expression was carried out as described above in Example 1.

TABLE 14

Production of 1,5-pentanediol.

| Example No: | Uniprot ID of Keto acid decarboxylase | Uniprot ID of primary alcohol dehydrogenase* | 1,5-pentanediol produced (g/L) |
|---|---|---|---|
| 4A | Q6QBS4 | D8GL45 | 0.6 |
| 4B | Q6QBS4 | Q04944 | 0.8 |
| 4C | Q6QBS4 | Q84H78 | 1.4 |
| 4D | Q6QBS4 | Q7WVD0 | 1.4 |
| 4E | Q6QBS4 | AB213459.1 | 1.4 |

*In this case, this enzyme also can be referred to as 5-hydroxy-pentanal 1-reductase.

Activity Assay: Observation of the production of 1,5-pentanediol from externally fed 6-hydroxy-2-keto-hexanoate indicated successful activity of the 2-keto acid decarboxylase and alcohol dehydrogenase enzymes. Thus post expression, cells were harvested and re-suspended in 0.4 mL fresh medium (0D600-30) containing 15 g/L potassium phosphate buffer (pH 7.2) with 6-hydroxy-2-keto-hexanoate (~5 g/L) and 10 g/L glucose, for 15 hr under anaerobic conditions. After incubation at room temperature, the cells were centrifuged, and the supernatant was filtered and analyzed via HPLC for the formation of 1,5-pentanediol from 6-hydroxy-2-keto-hexanoate.

HPLC analysis of 1,5-pentanediol production: Isocratic HPLC was used to detect and quantify 1,5-pentanediol. The method employed a Bio-Rad Aminex HPX-87 column, 0.7 mL/min of 0.05% formic acid (or 5 mM sulfuric acid) at 35° C. Detection was carried out using an RID (refractive index detector) and UV detector, the latter of which was used to measure signals at 210 and 260 nm. The HPLC results showed production of 1,5-pentanediol; results of certain preparations were presented in Table 14.

Example 5: Preparation and Use of Microbial Organism for Production of 1,5-Pentanediol from Different Carbon Sources Via 6-hydroxy-2-keto-hexanoate Intermediate In some embodiments, the present disclosure provides technologies for producing 1,5-pentanediol. In some embodiments, glycerol is utilized as a carbon source. In some embodiments, one or more, or all, biosynthesis steps are performed in one organism (e.g., bacterium) and culture. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L.

E. coli was used as an exemplary organism to engineer the production of 1,5-pentanediol from carbon sources such as glycerol and/or glucose via metabolic precursor pyruvate and 3-hydroxy-propionaldehyde that are derived from these carbon sources, using the metabolic pathway which is shown in FIG. 2, and which is also described in Example 4. To generate E. coli capable of making 1,5-pentanediol via this pathway from desired carbon sources (e.g. glycerol and/or glucose), the nucleic acid encoding each individual enzyme in the pathway and other enzymes necessary for 3-hydroxy-propionaldehyde production were either codon-optimized for *E. coli* and synthesized commercially or obtained via PCR amplification using *E. coli* genomic DNA. Genes were cloned into plasmids, which were transformed in *E. coli*. In vivo expression of all of the pathway enzymes resulted in production of 1,5-pentanediol.

Cloning of 1,5-pentanediol pathway genes: DNA encoding heterologous enzymes in the 1,5-pentanediol pathway were codon-optimized for expression in *E. coli* and synthesized by a commercial DNA synthesis company (e.g., Twist Biosciences). DNA encoding native enzymes in the 1,5-pentanediol pathway were amplified from *E. coli* genomic DNA via PCR. Using standard cloning methods, each gene was cloned downstream of the T7 RNA polymerase promoter and upstream of a terminator sequence. Compatible plasmids harboring expression cassettes for the genes contained one of the following combinations of a marker and replicon: (1) chloramphenicol maker+P15A replicon, (2) ampicillin marker+ColE1 replicon, and (3) kanamycin marker+COLA replicon. Examples of genes used include the following: Ads-Hyd 8 (Uniprot ID No. A0A286PH18), Qor-1 (Uniprot ID No. P28304), 6-hydroxy-2-oxo-hexanoate decarboxylase (Uniprot ID No. Q6QBS4), primary alcohol dehydrogenase also referred to as 5-hydroxy-pentanal 1-reductase (GenBank ID No. AB213459.1). Additionally, glycerol dehydratase enzyme that is vitamin B12-independent (e.g. *Clostridium butyricum* glycerol dehydratase that is comprised of two subunits as follows: DhaB1 [Uniprot ID No. Q8GEZ8]; DhaB2 [Uniprot ID No. Q8GEZ7]) or glycerol dehydratase enzyme that is a B12-dependent enzyme (*Lactococcus reuteri* glycerol dehydratase that is comprised of five genes as follows: pduC [Uniprot ID No. A5VMB2]; pduD [Uniprot ID No. A5VMB1]; pduE [Uniprot ID No. A5VMB0]; pduG [Uniprot ID No. A5VMA9]; and pduH [Uniprot ID No. A5VMA8]) was also cloned to enable production of 3-hydroxy-propionaldehyde—a 1,5-pentanediol pathway precursor that can be made from glycerol using this enzyme. All five genes encoding the *Lactococcus reuteri* glycerol dehydratase were cloned as a single gene operon.

Construction of strain(s) for the production of 1,5-pentanediol: The *E. coli* strain BL21* (DE3) ΔldhA was used as the background strain for testing of the 1,5-pentanediol pathway enzymes. Plasmids harboring the genes encoding the pathway enzymes were transformed using standard electroporation methods associated with transforming *E. coli*.

Production of 1,5-pentanediol: The following expression strains were obtained after sequentially transforming the following plasmids into *E. coli*.

Strain PeDO1: Plasmid 1 (COLA replicon, kanamycin marker): Gene 1 (Glycerol dehydratase—DhaB1), Gene 2 (Glycerol dehydratase—DhaB2), Gene 3 (Qor 1). Plasmid 2 (ColE1 replicon, ampicillin marker): Gene 1 (6-hydroxy-2-oxo-hexanoate decarboxylase), Gene 2 (Ads-Hyd 8). Plasmid 3 (P15A replicon, chloramphenicol marker): Gene 1 (5-hydroxy-pentanal 1-reductase).

Strain PeDO2: Plasmid 1 (COLA replicon, kanamycin marker): Gene 1 (Glycerol dehydratase—DhaB1), Gene 2 (Glycerol dehydratase—DhaB2), Gene 3 (Qor 1). Plasmid 2 (ColE1 replicon, ampicillin marker): Gene 1 (6-hydroxy-2-oxo-hexanoate decarboxylase), Gene 2 (Ads-Hyd 8).

Strain PeDO3: Plasmid 1 (COLA replicon, kanamycin marker): Gene 1 (Glycerol dehydratase—pduCDEGH). Plasmid 2 (ColE1 replicon, ampicillin marker): Gene 1 (6-hydroxy-2-oxo-hexanoate decarboxylase), Gene 2 (Ads-Hyd 8), Gene 3 (5-hydroxy-pentanal 1-reductase). Plasmid 3 (P15A replicon, chloramphenicol marker): Gene 1 (Qor 1).

Strain PeDO4: Plasmid 1 (COLA replicon, kanamycin marker): Gene 1 (Glycerol dehydratase—pduCDEGH). Plasmid 2 (ColE1 replicon, ampicillin marker): Gene 1 (6-hydroxy-2-oxo-hexanoate decarboxylase), Gene 2 (Ads-Hyd 8). Plasmid 3 (P15A replicon, chloramphenicol marker): Gene 1 (5-hydroxy-pentanal 1-reductase).

Culturing for Strain PeDO1 and PeDO2: Starter cultures were grown overnight in tubes containing 5 mL 2×YT media with 1 g/L D-glucose and appropriate antibiotics. Cell cultures for the expression and the 1,5-pentanediol pathway enzymes were carried out in 40 mL growth medium using 125 mL baffled flasks. Complex (2×YT) growth medium was used and supplemented with 2 g/L D-glucose, 0.5 g/L potassium phosphate buffer (pH 7.2), and 100 mg/L ferric ammonium citrate. Pre-induction growth was carried out for 2 hours under aerobic conditions and at 30° C. Recombinant protein expression was induced at an OD600 of 0.2-0.4 with 250 µM IPTG. Post-induction expression was carried out for 30 minutes at 30° C. and under aerobic conditions. Cell cultures were then transferred to 100 mL glass bottles, L-cysteine-HCl-monohydrate was added to the growth medium (1 g/L final concentration), and the bottles were sealed within an anaerobic glove box (Coy Laboratory). Cultures were then grown in the glass bottles for 2 hours at 30° C. and under anaerobic conditions. Afterwards, cells were harvested and re-suspended in 0.4 mL fresh medium (OD600~30) containing 8 g/L glucose, 4 g/L glycerol, and 15 g/L potassium phosphate buffer (pH 7.2). After incubation under anaerobic conditions for 24 hours and at room temperature, the cells were centrifuged, and the supernatant was filtered and analyzed via HPLC.

Culturing for Strain PeDO3 and PeDO4: Production medium contains following composition: 1×MOPS minimal medium, 5 g/L yeast extract, 10 g/L glycerol, 20 g/L glucose, and 10 uM of Cyanocobalamin (pH7.2). The 1×MOPS minimal medium is composed of 40 mM MOPS, 4 mM tricine, 0.01 mM FeSO$_4$, 9.5 mM NH$_4$Cl, 0.276 mM K2504, 0.5 µM CaCl$_2$, 0.525 mM MgCl$_2$, 50 mM NaCl, 2.92E$^{-7}$ mM (NH4)2MoO4, 4.0E$^{-5}$ mM H$_3$BO$_3$, 3.02E$^{-6}$ mM CoCl$_2$, 9.62E$^{-7}$ mM CuSO$_4$, 8.08E$^{-6}$ mM MnCl$_2$, 9.74E$^{-7}$ mM ZnSO4, and 1.32 mM K$_2$PO$_4$. Seed cultures were grown overnight in tubes containing 10 mL 2×YT media and appropriate antibiotics. Cell cultures for 1,5-pentanediol production were prepared using 10 mL production medium with appropriate antibiotics in 125 mL flask with a stopper, 1 mL of seed culture was inoculated and allow cell to grow at 37° C. for 2 hr before induction. After 2 hr, cell culture was induced with 0.1 mM IPTG and the culture was transferred to 26° C. to start the production. Samples were taken every 12 hr aerobically with final sample taken at 72 hr, and the supernatant was filtered and analyzed via HPLC.

HPLC analysis of 1,5-pentanediol production: Isocratic HPLC was used to detect and quantify 1,5-pentanediol. The method employed a Bio-Rad Aminex HPX-87 column, 0.7 mL/min of 0.05% formic acid (or 5 mM sulfuric acid) at 35° C. Detection was carried out using an RID (refractive index detector) and UV detector, the latter of which was used to measure signals at 210 and 260 nm. The HPLC results showed evidence 1,5-pentanediol production at a final titer of 800 mg/L (Strain PeDO1), 400 mg/L (PeDO2), 212 mg/L (PeDO3), and 41 mg/L (PeDO4).

Additional Working Examples for 1,5-Pentanediol Production

Based on the success of producing 1,5-pentanediol using the above-described strains, the use of alternative quinone oxidoreductases identified in Examples 2 & 3 for the production of 1,5-pentanediol was assessed. Briefly, the plasmid combination of Strain PeDO3 in the above-described example was used, wherein the plasmid 3 contained different Qor enzymes namely Qor-1 (Uniprot ID No. P28304), Qor-2 (Uniprot ID No. P40783), and Qor-5 (Uniprot ID No. P43903). The strain construction, production, and analytical methods were identical to those described above. Strain PeDO5 (containing Qor-1), Strain PeDO6 (containing Qor-2), and Strain PeDO6 (containing Qor-5) led to the production of ~2 g/L, 2.2 g/L and 2.4 g/L 1,5-pentanediol respectively under production conditions described above

Figure 3:
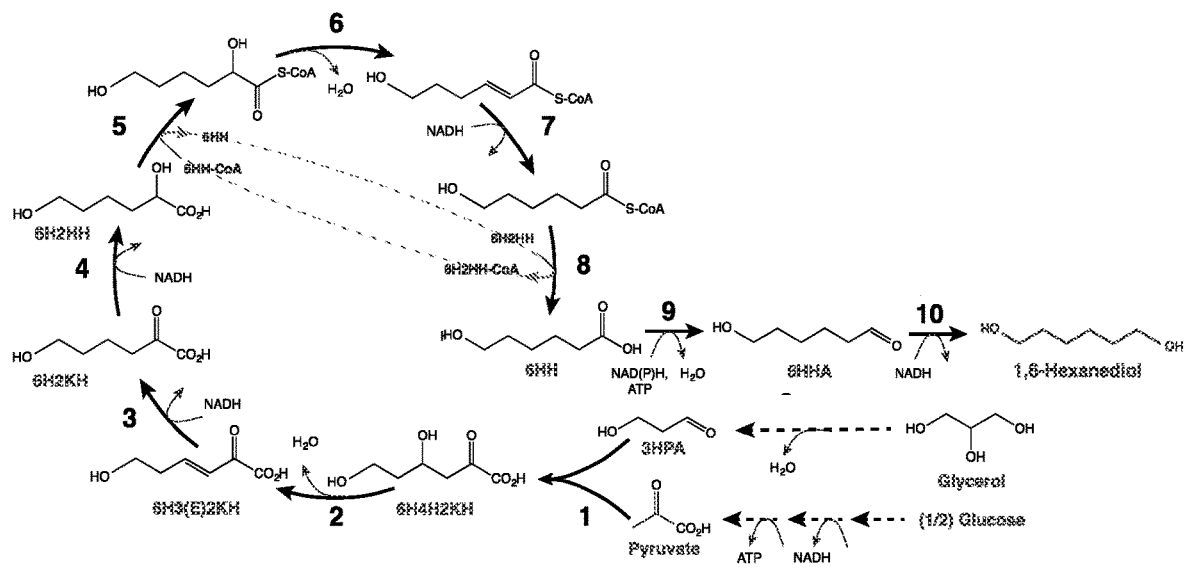
FIG. 3 shows a biosynthetic pathway for production of 1,6-hexanediol via 6-hydroxy-2-keto-hexanoate (6H2KH) intermediate. As used herein 3HPA refers to 3-hydroxy-propanal; 6H4H2KH refers to 4,6-dihydroxy-2-keto-hexanoate; 6H3(E)2KH refers to 6-hydroxy-3,4-dehydro-2-keto-hexenoate; 6H2HH refers to 2,6-dihydroxy-hexanoate; 6-HH-CoA refers to 6-hydroxy-hexanoyl-CoA; 6HH refers to 6-hydroxy hexanoate; 6H2-HH-CoA refers to 2,6-dihydroxy-hexanoyl-CoA; and 6-HHA refers to 6-hydroxy hexanal. Either NADPH or NADH could be a cofactor. Step 5 and 8 are catalyzed by a single CoA-transferase enzyme. 6HH-CoA is depicted as donor for Step 5 reaction and 6H2HH as the acceptor for illustrative purposes. Other CoA-esters or carboxylic acids can serve as donors and acceptors for this enzyme in vivo.

Example 6: Preparation and Use of Microbial Organism for Production of 1,6-Hexanediol from 6-hydroxy-hexanoate Intermediate In some embodiments, the present disclosure provides technologies for preparing 6HH and HDO. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of 1,6-hexanediol from 6-hydroxyhexanoate (6HH) intermediate is shown in FIG. 3. Shown below are examples incorporating the use of different enzymes for each step of this pathway to validate the production of 1,6-hexanediol from 6HH. Examples of genes and corresponding enzymes from which they are encoded that were used to carry out each step of the 1,6-hexanediol biosynthetic pathway from 6HH intermediate are shown in Table 15 below. Each enzyme therein may be substituted with homologous enzymes that belong to the same E.C. class.

TABLE 15

Production of HDO.

| ENTRY No: | Gene 1 Uniprot ID or Genbank ID | Gene 2 Uniprot ID or Genbank ID | Gene 3 Uniprot ID or Genbank ID |
|---|---|---|---|
| 1 | D6Z860 | P39135 | AB213459.1 |
| 2 | YP_001705436.1 | P39135 | AB213459.1 |
| 3 | ANO06407.1 | P39135 | AB213459.1 |
| 4 | AAR91681.1 | P39135 | AB213459.1 |
| 5 | AHH98121.1 | P39135 | AB213459.1 |
| 6 | ANB00612.1 | P39135 | AB213459.1 |
| 7 | ANO04655.1 | P39135 | AB213459.1 |
| 8 | A0R484 | P39135 | AB213459.1 |
| 9 | AFP42026.1 | P39135 | AB213459.1 |
| 10 | GAJ86510.1 | P39135 | AB213459.1 |
| 11 | YP_001704097.1 | P39135 | AB213459.1 |
| 12 | ANA99315.1 | P39135 | AB213459.1 |
| 13 | GAJ83027.1 | P39135 | AB213459.1 |
| 14 | ANA98925.1 | P39135 | AB213459.1 |
| 15 | ANA98924.1 | P39135 | AB213459.1 |
| 16 | ANO04656.1 | P39135 | AB213459.1 |
| 17 | YP_001703694.1 | P39135 | AB213459.1 |
| 18 | WP_036338301.1 | P39135 | AB213459.1 |
| 19 | WP_007472106.1 | P39135 | AB213459.1 |
| 20 | A0QWI7 | P39135 | AB213459.1 |

Reaction catalyzed by enzyme named 6-hydroxyhexanoate 1-reductase, which is coded by gene 1: 6-hydroxy-hexanoate->6-hydroxy-hexanal. Enzyme coded by gene 2: 6-hydroxyhexanoate 1-reductase activator. Reaction catalyzed by enzyme named 6-hydroxyhexanal 1-reductase, which is coded by gene 3: 6-hydroxy-hexanal->1,6-hexanediol (i) Preparation of Plasmids for HDO Production:

The HDO production pathway genes were cloned on a two plasmids shown below.

Synthetic genes were obtained from commercial vendors, and each gene was codon optimized for expression in *E. coli*. Each gene was cloned under its own T7 promoter and terminator using standard molecular biology methods. *Escherichia coli* was used as a target organism to engineer the 1,6-hexanediol production. The expression strains were obtained after co-transforming all two plasmids in electro competent *E. coli* MG1655 (DE3) Δrne131, ΔldhA.

Plasmid 1 (ColE1 replicon, ampicillin marker): Gene 1.
Plasmid 2 (COLA replicon, kanamycin marker): Gene 2, and Gene 3

(ii) Cell Culturing, Protein Expression, and HDO Production Analysis:

Starter cultures were grown overnight in tubes containing 10 mL LB media with appropriate antibiotics. Cell cultures for the expression and HDO production were carried out in 100 mL volume using glass bottles. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. Recombinant protein expression was induced at an OD600 of 0.2-0.4 with 250 μM IPTG. Post-induction expression was carried out at 30° C. under aerobic conditions for 60-90 minutes followed by 2-3 hours of anaerobic conditions. Afterwards, cells were harvested, concentrated, and re-suspended in 0.5 ml volume at OD600 of ~40 in fresh medium containing ~10 g/L glucose, 6-hydroxy-hexanoate (~5 g/L), and 15 g/L potassium phosphate buffer (pH 7.2). After incubation for 24 hours at room temperature, the cells were centrifuged, and supernatant was filtered and analyzed via HPLC.

(iii) HPLC analysis of HDO production: Isocratic HPLC was used to detect and quantify HDO. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of 0.1 to 2.5 g/L of 1,6-hexanediol for all examples in Table 15.

Example 7: Preparation and Use of Microbial Organism for Production of 1,6-Hexanediol from 6-hydroxy-2-keto-hexanoate Intermediate In some embodiments, the present disclosure provides technologies for preparing 6HH and HDO. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of 1,6-hexanediol from 6-hydroxy-2-keto-hexanoate intermediate is shown in FIG. 3. Shown below are examples incorporating the use of different enzymes for each step of this pathway to validate the production of 1,6-hexanediol via this pathway. Examples of genes and corresponding enzymes from which they are encoded that were used to carry out each step of the 1,6-hexanediol biosynthetic pathway from 6-hydroxy-2-keto-hexanoate intermediate are shown in Table 16 below. Each enzyme therein may be substituted with homologous enzymes that belong to the same E.C. class. Additionally, the example below highlights the confirmation of multiple enzymes for carrying out both the CoA-transfer reaction and the 2,6-dihidroxy-hexanoyl-CoA dehydration reaction.

(i) Preparation of Plasmids for HDO Production:

Starter cultures were grown overnight in tubes containing 10 mL LB media with appropriate antibiotics. Cell cultures for the expression and HDO production were carried out in 100 mL volume using glass bottles. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. Recombinant protein expression was induced at an OD600 of 0.2-0.4 with 250 µM IPTG. Post-induction expression was carried out at 30° C. under aerobic conditions for 60-90 minutes followed by 2-3 hours

TABLE 16

Biosynthesis polypeptides for HDO production.

| Reaction Catalyzed | Enzyme Name | Gene Number | Example 7A Uniprot ID or Genbank ID | Example 7B Uniprot ID or Genbank ID | Example 7C Uniprot ID or Genbank ID | Example 7D Uniprot ID or Genbank ID | Example 7E Uniprot ID or Genbank ID |
|---|---|---|---|---|---|---|---|
| 6-hydroxy-2-oxohexanoate- → 2,6-dihydroxy-hexanoate | 6-hydroxy-2-oxohexanoate 2-reductase | Gene 1 | Q5FTU6 | Q5FTU6 | Q5FTU6 | Q5FTU6 | Q5FTU6 |
| 2,6-dihydroxy-hexanoate → 2,6-dihydroxy-hexanoyl-CoA | 2,6-dihydroxy-hexanoate CoA-transferase | Gene 2 and Gene 3 | T4VW93* | T4VW93** | T4VW93 + A0A0C7GD16 | T4VW93 + A0A175L1W4 | T4VW93 + A0A2X3BTQ9 |
| 2,6-dihydroxy-hexanoyl-CoA → 6-hydroxy-2,3-dehydro-hexanoyl-CoA | 2,6-dihydroxy-hexanoyl-CoA 2-dehydratase - Subunit A | Gene 4 | Q5U924 | A0A2X3BK09 | A0A2X3BK09 | A0A2X3BK09 | A0A2X3BK09 |
| | 2,6-dihydroxy-hexanoyl-CoA 2-dehydratase - Subunit B | Gene 5 | Q5U925 | A0A2X3BU19 | A0A2X3BU19 | A0A2X3BU19 | A0A2X3BU19 |
| | 2,6-dihydroxy-hexanoyl-CoA 2-dehydratase - Subunit C | Gene 6 | Q5U923 | A0A1V9IXA9 | A0A1V9IXA9 | A0A1V9IXA9 | A0A1V9IXA9 |
| 6-hydroxy-2,3-dehydro-hexanoyl-CoA → 6-hydroxy-hexanoyl-CoA | 2,3-dehydro-hexanoyl-CoA 2,3-reductase | Gene 7 | Q73Q47 | Q73Q47 | Q73Q47 | Q73Q47 | Q73Q47 |
| 6-hydroxy-hexanoyl-CoA → 6-hydroxy-hexanoate | 6-hydroxyhexanoyl-CoA transferase | Gene 8 | Same as Gene 2 & Gene 3 | Same as Gene 2 & Gene 3 | Same as Gene 2 & Gene 4 | Same as Gene 2 & Gene 5 | Same as Gene 2 & Gene 6 |
| 6-hydroxy-hexanoate → 6-hydroxy-hexanal | 6-hydroxyhexanoate 1-reductase | Gene 9 | A0R484 | A0R484 | A0R484 | A0R484 | A0R484 |
| | 6-hydroxyhexanoate 1-reductase activator | Gene 10 | P39135 | P39135 | P39135 | P39135 | P39135 |
| 6-hydroxy-hexanal → 1,6-hexanediol | 6-hydroxyhexanal 1-reductase | Gene 11 | AB213459.1 | AB213459.1 | AB213459.1 | AB213459.1 | AB213459.1 |

*single copy of the same gene;
**dual copy of the same gene

The HDO production pathway genes were cloned on two separate compatible plasmids shown below. Each plasmid had a different origin of replication and antibiotic marker, as indicated. Synthetic genes were obtained from commercial vendors, and each gene was codon optimized for expression in *E. coli*. Each gene was cloned under its own T7 promoter and terminator using standard molecular biology methods. *Escherichia coli* was used as a target organism to engineer the 1,6-hexanediol production. The expression strains were obtained after co-transforming all three plasmids in electro competent *E. coli* BL21*(DE3) Δldh, ΔadhE, ΔfrdA.

Plasmid 1 (COLA replicon, kanamycin marker): Gene 10, Gene 9,
Plasmid 2 (ColE1 replicon, ampicillin marker): Gene 1, Gene 2, Gene 3, and Gene 4
Plasmid 3 (P15A replicon, chloramphenicol marker): Gene 5, Gene 6, Gene 7, Gene 8, and Gene 11.

(ii) Cell Culturing, Protein Expression, and HDO Production Analysis:

of anaerobic conditions. Afterwards, cells were harvested, concentrated, and re-suspended in 0.5 ml volume at OD600 of ~40 in fresh medium containing ~10 g/L glucose, 6-hydroxy-2-keto-hexanoate (~5 g/L), and 15 g/L potassium phosphate buffer (pH 7.2). After incubation for 24 hours at room temperature, the cells were centrifuged, and supernatant was filtered and analyzed via HPLC.

(iii) HPLC analysis of HDO production: Isocratic HPLC was used to detect and quantify HDO. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of 700 mg/L, 1.2 g/L, 1.1 g/L, 1.1 g/L, and 1 g/L of 1,6-hexanediol for Examples 7A-7E from Table 16, respectively.

Example 8: Preparation and Use of Microbial Organism for Production of 1,6-Hexanediol from Different Carbon Sources Via 6-hydroxy-2-keto-hexanoate Intermediate In some embodiments, the present disclosure provides technologies for preparing 6HH and HDO. In some embodiments, the present disclosure provides technologies for producing HDO using glycerol as a carbon source. In some embodiments, production is carried out in one organism. In some embodiments, production is carried out in two or more organisms each expressing a different set of biosynthesis polypeptides. In some embodiments, production is carried out in a single bacteria strain. In some embodiments, production is carried out in two or more bacteria strains, each independently carrying out one or more biosynthesis reactions. In some embodiments, a culture comprises two or more or all strains for HDO production. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of 1,6-hexanediol from pyruvate and 3-hydroxy-propanal through the 6-hydroxy-2-keto-hexanoate intermediate is shown in FIG. 3. Shown below are examples (8a and 8b) incorporating the use of aldolase-hydratase based two enzyme system for production of 1,6-hexanediol via this pathway. A glycerol dehydratase enzyme that is vitamin B12-independent or glycerol dehydratase enzyme that is a B12-dependent enzyme can be cloned to enable production of 3-hydroxy-propionaldehyde—a 1,6-hexanediol pathway precursor that can be made from glycerol using this enzyme. The B12-dependent glycerol dehydratase was used herein. Examples of genes and corresponding enzymes they encode that were used to carry out each step of the 1,6-hexanediol biosynthetic pathway as well as production of 3-hydroxy-propionaldehyde are shown in Table 17. It is important to note that each enzyme herein could be substituted with homologous enzymes that belong to the same E.C class.

TABLE 17

Biosynthesis of HDO.

| Reaction Catalyzed | Enzyme Name | Enzyme ID | Gene Number | Uniprot ID or Genbank ID |
|---|---|---|---|---|
| Pyruvate + 3-hydroxy propanal → 6-hydroxy-3,4-dehydro-2-oxohexanoate | Trans-o-hydroxybenzylidenepyruvate hydratase-aldolases | Ads-Hyd 8 | Gene 1 | A0A286PH18 |
| 6-hydroxy-3,4-dehydro-2-oxohexanoate → 6-hydroxy-2-oxohexanoate | Quinone oxidoreductase | Qor 1 | Gene 2 | P28304 |
| 6-hydroxy-2-oxohexanoate- → 2,6-dihydroxy-hexanoate | 6-hydroxy-2-oxohexanoate 2-reductase | | Gene 3 | Q5FTU6 |
| 2,6- dihydroxy-hexanoate → 2,6- dihydroxy-hexanoyl-CoA | 2,6-dihydroxy-hexanoate CoA-transferase | | Gene 4 | T4VW93 |
| 2,6-dihydroxy-hexanoyl-CoA → 6-hydroxy-2,3-dehydro-hexanoyl-CoA | 2,6-dihydroxy-hexanoyl-CoA 2-dehydratase - Subunit A | | Gene 5 | Q5U924 |
| | 2,6-dihydroxy-hexanoyl-CoA 2-dehydratase - Subunit B | | Gene 6 | Q5U925 |
| | 2,6-dihydroxy-hexanoyl-CoA 2-dehydratase - Subunit C | | Gene 7 | Q5U923 |
| 6-hydroxy-2,3-dehydro-hexanoyl-CoA → 6-hydroxy-hexanoyl-CoA | 2,3- dehydro-hexanoyl-CoA 2,3- reductase | | Gene 8 | Q73Q47 |
| 6-hydroxy-hexanoyl-CoA → 6-hydroxy-hexanoate | 6-hydroxyhexanoyl-CoA transferase | | Gene 4 | T4VW93 |
| 6-hydroxy-hexanoate → 6-hydroxy-hexanal | 6-hydroxyhexanoate 1-reductase | | Gene 9 | A0R484 |
| | 6-hydroxyhexanoate 1-reductase activator | | Gene 10 | P39135 |
| 6-hydroxy-hexanal → 1,6-hexanediol | 6-hydroxyhexanal 1-reductase | | Gene 11 | AB213459.1 |
| Glycerol dehyration | Glyerol dehydratase | | Gene 12 | Q8GEZ8 |
| | Glyerol dehydratase activator | | Gene 13 | Q8GEZ7 |

Example 8a: Production of 1,6-Hexanediol (HDO) in a Single E. coli Strain (i) Preparation of Plasmids for HDO Production The HDO production pathway genes were cloned on three separate compatible plasmids shown below. Each plasmid had a different origin of replication and antibiotic marker, as indicated. Synthetic genes were obtained from commercial vendors, and each gene was codon optimized for expression in E. coli. Each gene was cloned under its own T7 promoter and terminator using standard molecular biology methods. Escherichia coli was used as a target organism to engineer the 1,6-hexanediol production. The expression strains were obtained after co-transforming all three plasmids in electro competent E. coli BL21*(DE3) Δldh, ΔadhE, ΔfrdA.

Plasmid 1 (COLA replicon, kanamycin marker): Gene 12, Gene 13, Gene 2, Gene 10

Plasmid 2 (ColE1 replicon, ampicillin marker): Gene 3, Gene 4, Gene 1, and Gene 9

Plasmid 3 (P15A replicon, chloramphenicol marker): Gene 5, Gene 6, Gene 7, Gene 8, and Gene 11.

(ii) Cell Culturing, Protein Expression, and HDO Production Analysis:

Starter cultures were grown overnight in tubes containing 10 mL LB media with appropriate antibiotics. Cell cultures for the expression and HDO production were carried out in 100 mL volume using glass bottles. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. Recombinant protein expression was induced at an OD600 of 0.2-0.4 with 250 µM IPTG. Post-induction expression was carried out at 30° C. under aerobic conditions for 60-90 minutes followed by 2-3 hours of anaerobic conditions. Afterwards, cells were harvested, concentrated, and re-suspended in 0.5 ml volume at OD600 of ~40 in fresh medium containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and analyzed via HPLC.

(iii) HPLC analysis of HDO production: Isocratic HPLC was used to detect and quantify HDO. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of 25-100 mg/L of 1,6-hexanediol. To illustrate that alternate enzymes previously validated to carry out specific steps of the pathway can be used for HDO production using this methodology, an alternate HDO production strain wherein genes 5-7 were encoded by Uniport IDs A0A2X3BK09, A0A2X3BU19, and A0A1V9IXA9 respectively was constructed and evaluated using above methods. This production strain also led to production of >10 mg/L of of 1,6-hexanediol.

Example 8b: Production of 1,6-Hexanediol (HDO) in Two *E. coli* Strains (i) Preparation of Plasmids & Strains for HDO Production:

To minimize the number of HDO production pathway genes expressed from plasmids, *E. coli* expression strain was constructed wherein certain pathway genes were integrated in the genome. Specifically, HDO production strain BL21* (DE3) Δldh, ΔadhE, ΔfrdA containing HDO pathway genes (Gene 12, Gene 13) at the arsB location with expression of each gene controlled by its own T7 promoter. The remaining HDO production pathway genes were cloned on four separate plasmids shown below using techniques described in example above. Identity of Genes was as described in Example 8a. Two *E. coli* based expression strains were constructed. Expression strain 1 was obtained after co-transforming plasmids 1, and plasmid 2 in *E. coli*; and Expression strain 2 was obtained after co-transforming plasmid 3 and plasmid 4 in *E. coli*.

Plasmid 1 (ColE1 replicon, ampicillin marker): Gene 4, gene 3, and gene 1.

Plasmid 2 (P15A replicon, chloramphenicol marker): Gene 5, Gene 6, Gene 7, Gene 8, and Gene 2.

Plasmid 3 (RSF replicon, kanamycin marker): Gene 4, and gene 11.

Plasmid 4 (ColE1 replicon, ampicillin marker): Gene 9 and gene 10.

(ii) Cell Culturing, Protein Expression, and HDO Production Analysis:

Starter cultures were grown overnight in tubes containing 10 mL LB media with appropriate antibiotics for each expression strain separately. Cell cultures for the expression and HDO production were carried out in 100 mL volume using glass bottles for each expression strain separately. Complex growth medium was used and supplemented with 2 g/L D-glucose, 0.5 g/L potassium phosphate buffer (pH 7.2), and other substrates/nutrients important for enzyme expression. Pre-induction growth was carried out for—2 hours under aerobic conditions and at 30° C. for each expression strain separately. Recombinant protein expression was induced at an OD600 of 0.2-0.4 with 250 µM IPTG and was carried out separately for each expression strain. Post-induction expression was carried out at 30° C. under aerobic conditions for 30 minutes followed by 2-3 hours of anaerobic conditions for each expression strain separately. Afterwards, cells from both expression strains were mixed in equal amounts, after which they were harvested, concentrated, and re-suspended in 0.5 ml volume at OD600 of ~40 in fresh medium containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and analyzed via HPLC.

(iii) HPLC analysis of HDO production: Isocratic HPLC was used to detect and quantify HDO. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of 100-550 mg/L of 1,6-hexanediol.

Figure 4:
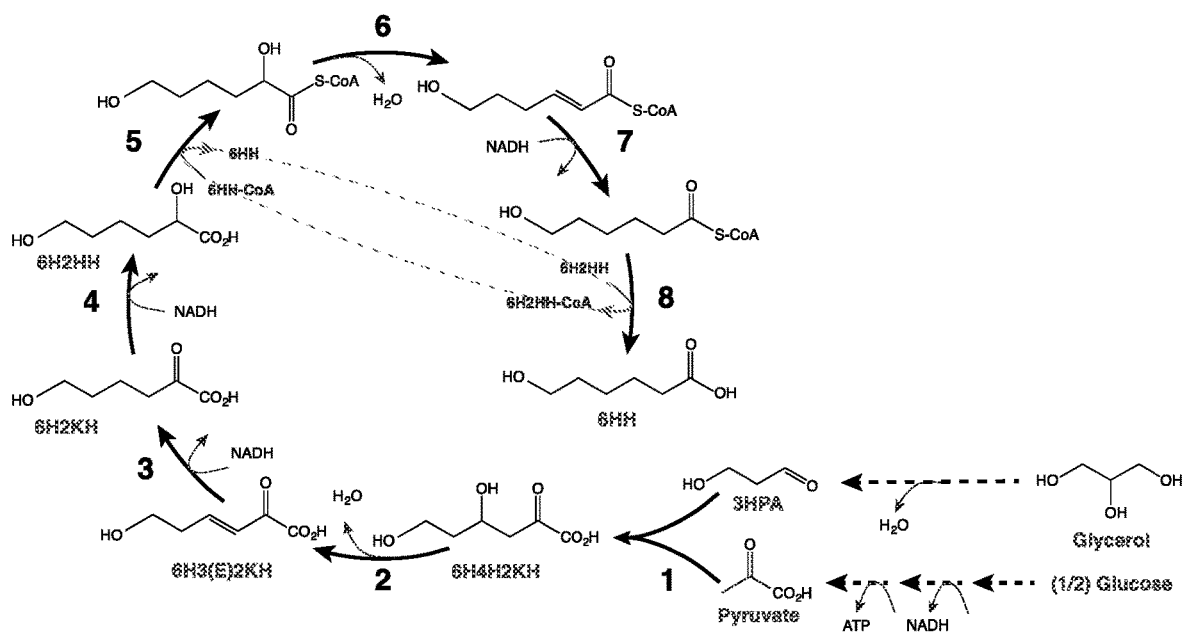
FIG. 4 shows a biosynthetic pathway for production of 6-hydroxy hexanoate via 6-hydroxy-2-keto-hexanoate (6H2KH) intermediate. As used herein 3HPA refers to 3-hydroxy-propanal; 6H4H2KH refers to 4,6-dihydroxy-2-keto-hexanoate; 6H3(E)2KH refers to 6-hydroxy-3,4-dehydro-2-keto-hexenoate; 6H2-HH refers to 2,6-dihydroxy-hexanoate; 6-HH-CoA refers to 6-hydroxy-hexanoyl-CoA; 6HH refers to 6-hydroxy hexanoate; and 6H2HH-CoA refers to 2,6-dihydroxy-hexanoyl-CoA. Either NADPH or NADH could be a cofactor. Step 5 and 8 are catalyzed by a single CoA-transferase enzyme. 6-HH-CoA is depicted as donor for Step 5 reaction and 6H2-HH as the acceptor for illustrative purposes. Other CoA-esters or carboxylic acids can serve as donors and acceptors for this enzyme in vivo.

Example 9: Preparation and Use of Microbial Organism for Production of 6-hydroxyhexanoate from 6-hydroxy-2-keto-hexanoate Intermediate In some embodiments, the present disclosure provides technologies for preparing 6HH. In some embodiments, production is carried out in one organism. In some embodiments, production is carried out in two or more organisms each expressing a different set of biosynthesis polypeptides. In some embodiments, production is carried out in a single bacteria strain. In some embodiments, production is carried out in two or more bacteria strains, each independently carrying out one or more biosynthesis reactions. In some embodiments, a culture comprises two or more or all strains for 6HH production. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L 6HH. A biosynthetic pathway for the production of 6-hydroxyhexanoate (6HH) from 6-hydroxy-2-keto-hexanoate intermediate is shown in FIG. 4. Shown below are examples incorporating the use of different enzymes for each step of this pathway to validate the production of 6HH via this pathway. Examples of genes and corresponding enzymes from which they are encoded that were used to carry out each step of the 6HH biosynthetic pathway from 6-hydroxy-2-keto-hexanoate intermediate are shown in Table 18. Each enzyme therein may be substituted with homologous enzymes that belong to the same E.C. class. Additionally, the example below highlights the confirmation of multiple enzymes for carrying out both the CoA-transfer reaction and the 2,6-dihidroxy-hexanoyl-CoA dehydration reaction.

(i) Preparation of Plasmids for 6HH Production:

The 6HH production pathway genes were cloned on two separate compatible plasmids shown below. Each plasmid had a different origin of replication and antibiotic marker, as indicated. Synthetic genes were obtained from commercial vendors, and each gene was codon optimized for expression in E. coli. Each gene was cloned under its own T7 promoter and terminator using standard molecular biology methods. Escherichia coli was used as a target organism to engineer the 6HH production. The expression strains were obtained after co-transforming all three plasmids in electro competent E. coli BL21*(DE3) ΔldhΔ, ΔadhE, ΔfrdA.

Plasmid 1 (ColE1 replicon, ampicillin marker): Gene 1, Gene 2, and Gene 3 (only examples 6 & 7)

Plasmid 3 (P15A replicon, chloramphenicol marker): Gene 4, Gene 5, Gene 6, and Gene 7.

(ii) Cell Culturing, Protein Expression, and 6HH Production Analysis:

Starter cultures were grown overnight in tubes containing 10 mL LB media with appropriate antibiotics. Cell cultures for the expression and 6HH production were carried out in 100 mL volume using glass bottles. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. Recombinant protein expression was induced at an OD600 of 0.2-0.4 with 250 μM IPTG. Post-induction expression was carried out at 30° C. under aerobic conditions for 60-90 minutes followed by 2-3 hours of anaerobic conditions. Afterwards, cells were harvested, concentrated, and re-suspended in 0.5 ml volume at OD600 of ~40 in fresh medium containing ~10 g/L glucose, 6-hydroxy-2-keto-hexanoate (5-10 g/L), and 15 g/L potassium phosphate buffer (pH 7.2). After incubation for 24 hours at room temperature, the cells were centrifuged, and supernatant was filtered and analyzed via HPLC.

(iii) HPLC analysis of HDO production: Isocratic HPLC was used to detect and quantify HDO. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of ~0.4-5 g/L of 6HH from strains of Examples 9A-9G of Table 18.

TABLE 18

Biosynthesis polypeptides for 6HH production.

| Enzyme Name | Gene Number | Example 9A Uniprot ID | Example 9B Uniprot ID | Example 9C Uniprot ID | Example 9D Uniprot ID |
|---|---|---|---|---|---|
| 6-hydroxy-2-oxohexanoate 2-reductase | Gene 1 | Q5FTU6 | Q5FTU6 | Q5FTU6 | Q5FTU6 |
| 2,6-dihydroxy-hexanoate CoA-transferase | Gene 2 and Gene 3* | A0A2X3BTQ9 | A0A2X3BTQ9 | A0A0C7GD16 | T4VW93 |
| 2,6-dihydroxy-hexanoyl-CoA 2-dehydratase -Subunit A | Gene 4 | Q5U924 | A0A2X3BK09 | A0A2X3BK09 | A0A2X3BK09 |
| 2,6-dihydroxy-hexanoyl-CoA 2-dehydratase -Subunit B | Gene 5 | Q5U925 | A0A2X3BU19 | A0A2X3BU19 | A0A2X3BU19 |
| 2,6-dihydroxy-hexanoyl-CoA 2-dehydratase -Subunit C | Gene 6 | Q5U923 | A0A1V9IXA9 | A0A1V9IXA9 | A0A1V9IXA9 |
| 2,3-dehydro-hexanoyl-CoA 2,3-reductase | Gene 7 | Q73Q47 | Q73Q47 | Q73Q47 | Q73Q47 |
| 6-hydroxyhexanoyl-CoA transferase | Gene 2 and Gene 3* | A0A2X3BTQ9 | A0A2X3BTQ9 | A0A0C7GD16 | T4VW93 |

| Enzyme Name | Example 9E Uniprot ID | Example 9F Uniprot ID | Example 9G Uniprot ID |
|---|---|---|---|
| 6-hydroxy-2-oxohexanoate 2-reductase | Q5FTU6 | Q5FTU6 | A0A1V9IP73 |
| 2,6-dihydroxy-hexanoate CoA-transferase | A0A175L1W4 | T4VW93 + A0A175L1W4* | T4VW93 + A0A175L1W4* |
| 2,6-dihydroxy-hexanoyl-CoA 2-dehydratase -Subunit A | A0A2X3BK09 | A0A2X3BK09 | A0A2X3BK09 |
| 2,6-dihydroxy-hexanoyl-CoA 2-dehydratase -Subunit B | A0A2X3BU19 | A0A2X3BU19 | A0A2X3BU19 |
| 2,6-dihydroxy-hexanoyl-CoA 2-dehydratase -Subunit C | A0A1V9IXA9 | A0A1V9IXA9 | A0A1V9IXA9 |
| 2,3-dehydro-hexanoyl-CoA 2,3-reductase | Q73Q47 | Q73Q47 | Q73Q47 |
| 6-hydroxyhexanoyl-CoA transferase | A0A175L1W4 | T4VW93 + A0A175L1W4 | T4VW93 + A0A175L1W4 |

*present only for Examples 9F and 9G

Example 10: Preparation and Use of Microbial Organism for Production of 6-hydroxy hexanoic acid (6HH) from Different Carbon Sources via 6-hydroxy-2-keto-hexanoate Intermediate In some embodiments, the present disclosure provides technologies for preparing 6HH. In some embodiments, the present disclosure provides technologies for producing 6HH using glycerol as a carbon source. In some embodiments, production is carried out in one organism. In some embodiments, production is carried out in two or more organisms each expressing a different set of biosynthesis polypeptides. In some embodiments, production is carried out in a single bacteria strain. In some embodiments, production is carried out in two or more bacteria strains, each independently carrying out one or more biosynthesis reactions. In some embodiments, a culture comprises two or more or all strains for 6HH production. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of 6HH from pyruvate and 3-hydroxy-propanal through the 6-hydroxy-2-keto-hexanoate intermediate is shown in FIG. 4. Shown below are examples incorporating the use of aldolase-hydratase based two enzyme system for production of 6HH via this pathway. A glycerol dehydratase enzyme that is vitamin B12-independent or glycerol dehydratase enzyme that is a B12-dependent enzyme can be cloned to enable production of 3-hydroxy-propionaldehyde—a 6HH pathway precursor that can be made from glycerol using this enzyme. Although both types of glycerol dehydratases were used herein, entries shown in Table 19 focus on examples that use the B12-independent glycerol dehydratase enzyme. Each enzyme therein may be substituted with homologous enzymes that belong to the same E.C. class to yield 6HH, and Examples 10B and 10C in Table 19 demonstrate this point wherein enzymes catalyzing both CoA-transfer reactions and the 2,6-dihidroxy-hexanoyl-CoA dehydration reactions have been substituted with homologous enzymes.

(i) Preparation of Plasmids & Strains for 6HH Production:

To minimize the number of 6HH production pathway genes expressed from plasmids, *E. coli* expression strain was constructed wherein certain pathway genes were integrated in the genome. Specifically, 6HH production strain BL21* (DE3) Δldh, ΔadhE, ΔfrdA containing 6HH pathway genes (Gene 12, Gene 13) at the arsB location with expression of each gene controlled by its own T7 promoter. The remaining 6HH production pathway genes were cloned on two separate plasmids shown below using techniques described in example above.

Plasmid 1 (ColE1 replicon, ampicillin marker): Gene 4, gene 3, and gene 1.

Plasmid 2 (P15A replicon, chloramphenicol marker): Gene 5, Gene 6, Gene 7, Gene 8, and Gene 2.

(ii) Cell Culturing, Protein Expression, and 6HH Production Analysis:

Starter cultures were grown overnight in tubes containing 10 mL LB media with appropriate antibiotics for each expression strain separately. Cell cultures for the expression and HDO production were carried out in 100 mL volume using glass bottles for each expression strain separately. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. for each expression strain separately. Recombinant protein expression was induced at an OD600 of 0.2-0.4 with 250 μM IPTG and was carried out separately for each expression strain. Post-induction expression was carried out at 30° C. under aerobic conditions for 30 minutes followed by 2-3 hours of anaerobic conditions for each expression strain separately. Afterwards, cells were harvested, concentrated, and re-suspended in 0.5 ml volume at OD600 of ~40 in fresh medium containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and analyzed via HPLC.

TABLE 19

Biosynthesis polypeptides for 6HH.

| Reaction Catalyzed | Enzyme Name | Enzyme ID | Gene Number | Example 10A Uniprot ID or Genbank ID | Example 10B Uniprot ID or Genbank ID | Example 10C Uniprot ID or Genbank ID |
|---|---|---|---|---|---|---|
| Pyruvate + 3-hydroxy propanal → 6-hydroxy-3,4-dehydro-2-oxohexanoate | Trans-o-hydroxybenzylidenepyruvate hydratase -aldolases | Ads-Hyd 8 | Gene 1 | A0A286PH18 | A0A286PH18 | A0A286PH18 |
| 6-hydroxy-3,4-dehydro-2-oxohexanoate → 6-hydroxy-2-oxohexanoate | Quinone oxidoreductase | Qor-1 | Gene 2 | P28304 | P28304 | P28304 |
| 6-hydroxy-2-oxohexanoate → 2,6-dihydroxy-hexanoate | 6-hydroxy-2-oxohexanoate 2-reductase | | Gene 3 | Q5FTU6 | Q5FTU6 | Q5FTU6 |
| 2,6-dihydroxy-hexanoate → 2,6-dihydroxy-hexanoyl-CoA | 2,6-dihydroxy-hexanoate CoA-transferase | | Gene 4 | T4VW93 | A0A2X3BTQ9 | T4VW93 |
| 2,6-dihydroxy-hexanoyl-CoA → 6-hydroxy-2,3-dehydro-hexanoyl-CoA | 2,6-dihydroxy-hexanoyl-CoA 2-dehydratase -Subunit A | | Gene 5 | Q5U924 | A0A2X3BK09 | A0A2X3BK09 |
| | 2,6-dihydroxy-hexanoyl-CoA 2-dehydratase -Subunit B | | Gene 6 | Q5U925 | A0A2X3BU19 | A0A2X3BU19 |
| | 2,6-dihydroxy-hexanoyl-CoA 2-dehydratase -Subunit C | | Gene 7 | Q5U923 | A0A1V9IXA9 | A0A1V9IXA9 |
| 6-hydroxy-2,3-dehydro-hexanoyl-CoA → 6-hydroxy-hexanoyl-CoA | 2,3-dehydro-hexanoyl-CoA 2,3-reductase | | Gene 8 | Q73Q47 | Q73Q47 | Q73Q47 |
| 6-hydroxy-hexanoyl-CoA → 6-hydroxy-hexanoate | 6-hydroxyhexanoyl-CoA transferase | | Gene 4 | T4VW93 | A0A2X3BTQ9 | T4VW93 |
| Glycerol dehydration | Glycerol dehydratase | | Gene 12 | Q8GEZ8 | Q8GEZ8 | Q8GEZ8 |
| | Glycerol dehydratase activator | | Gene 13 | Q8GEZ7 | Q8GEZ7 | Q8GEZ7 |

(iii) HPLC analysis of 6HH production: Isocratic HPLC was used to detect and quantify HDO. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of ~50-800 mg/L of 6HH from strains of Examples 10A-10C in Table 19. An alternative example is where B12-dependent glycerol dehydratase pduCDEGH was used (encoded as a single gene operon on a third plasmid with COLA replicon, kanamycin marker) instead of B12-independent glycerol dehydratase, wherein the rest of the enzymes of the pathway were identical to Example 10A. Such a system also led to production of ~350 mg/L of 6HH using culture conditions described for strains PeDO3 and PeDO4 containing B12-dependent enzymes in Example 5.

Figure 5:
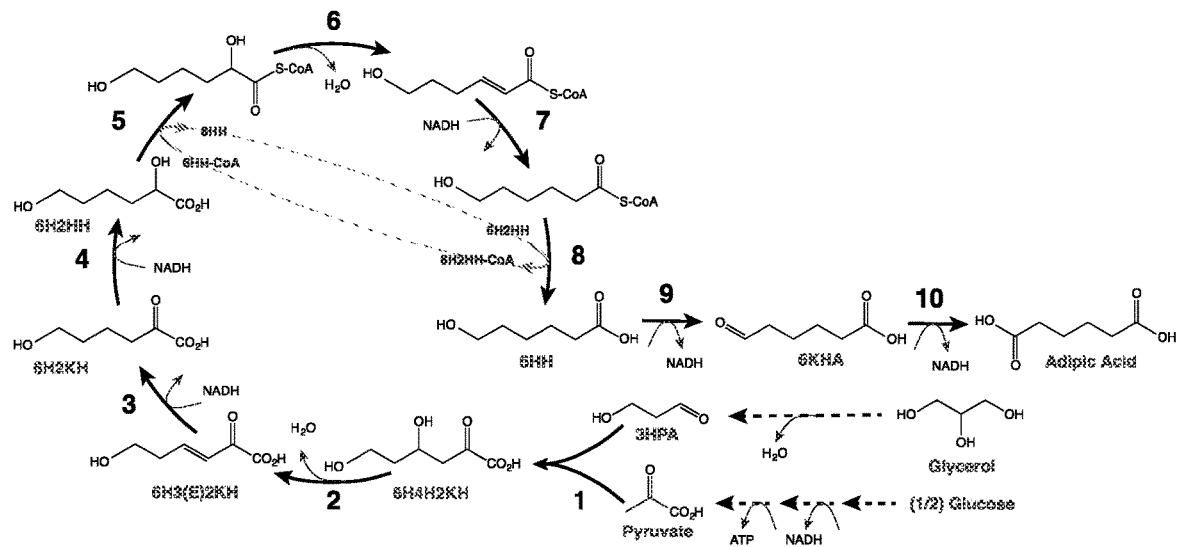
FIG. 5 shows biosynthetic pathway for production of adipic acid via 6-hydroxy-2-keto-hexanoate (6H2KH) intermediate. As used herein 3HPA refers to 3-hydroxy-propanal; 6H4H2KH refers to 4,6-dihydroxy-2-keto-hexanoate; 6H3(E)2KH refers to 6-hydroxy-3,4-dehydro-2-keto-hexenoate; 6H2-HH refers to 2,6-dihydroxy-hexanoate; 6HH-CoA refers to 6-hydroxy-hexanoyl-CoA; 6HH refers to 6-hydroxy hexanoate; 6H2-HH-CoA refers to 2,6-dihydroxy-hexanoyl-CoA; and 6KHA refers to 6-oxo-hexanoate. Either NADPH or NADH could be a cofactor. Step 5 and 8 are catalyzed by a single CoA-transferase enzyme. 6HH-CoA is depicted as donor for Step 5 reaction and 6H2-HH as the acceptor for illustrative purposes. Other CoA-esters or carboxylic acids can serve as donors and acceptors for this enzyme in vivo.

Example 11: Preparation and Use of Microbial Organism for Production of Adipic acid (AA) from 6-hydroxy-hexanoate (6HH) Intermediate In some embodiments, the present disclosure provides technologies for preparing AA. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of AA from pyruvate and 3-hydroxy-propanal through the 6-hydroxy-hexanoate intermediate is shown in FIG. 5. Shown in Table 20 are examples of enzymes that enable the conversion of 6HH to AA. It is important to note that each enzyme herein could be substituted with homologous enzymes that belong to the same E.C class to yield AA.

TABLE 20

Biosynthesis polypeptides for AA.

| Reaction Catalyzed | Enzyme Name | Gene Number | Example 11A Uniprot ID or Genbank ID | Example 11B Uniprot ID or Genbank ID |
|---|---|---|---|---|
| 6-hydroxy-hexanoate → 6-oxo-hexanoate | 6-hydroxy-hexanoate dehydrogenase | Gene 1 | Q7WVD0 | Q84H78 |
| 6-oxo-hexanoate → Adipic acid | 6-oxo-hexanoate oxidase | Gene 2 | Q9R2F4 | Q9R2F4 |

(i) Preparation of plasmids & strains for AA production from 6HH: The AA production pathway genes were cloned on a single plasmid shown below using techniques described in examples before. BL21*(DE3) Δldh, ΔadhE, ΔfrdA was used as the production strain.

Plasmid 1 (ColE1 replicon, ampicillin marker): Gene 1, and gene 2.

(ii) Cell culturing, protein expression, and AA production analysis: Starter cultures were grown overnight in tubes containing 10 mL LB media with appropriate antibiotics for each expression strain separately. Cell cultures for the expression and AA production were carried out in 100 mL volume using glass bottles for each expression strain separately. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. for each expression strain separately. Recombinant protein expression was induced at an OD600 of 0.2-0.4 with 250 μM IPTG and was carried out separately for each expression strain. Post-induction expression was carried out at 30° C. under aerobic conditions for 30-120 minutes followed by 2-3 hours of anaerobic conditions for each expression strain separately. Afterwards, cells were harvested, concentrated, and re-suspended in 0.5 ml volume at OD600 of ~40 in fresh medium containing 5-10 g/L glucose, 5 g/L 6HH, and 15 g/L potassium phosphate buffer (pH 7.2). After incubation for 3 hours at room temperature, the cells were centrifuged, and supernatant was filtered and analyzed via HPLC.

(iii) HPLC analysis of AA production: Isocratic HPLC was used to detect and quantify AA. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of 500-1500 mg/L of AA for Examples 11A and 11B of Table 20.

Example 12: Preparation and Use of Microbial Organism for Production of Adipic acid (AA) from 6-hydroxy-2-keto-hexanoate Intermediate In some embodiments, the present disclosure provides technologies for preparing AA from 6H2KH. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of AA from pyruvate and 3-hydroxy-propanal through the 6-hydroxy-2-keto-hexanoate intermediate is shown in FIG. 5. Shown below are examples incorporating the use of different enzymes for each step of this pathway to validate the production of AA via this pathway. Examples of genes and corresponding enzymes from which they are encoded that were used to carry out each step of the AA biosynthetic pathway from 6-hydroxy-2-keto-hexanoate intermediate are shown in Table 21 below. Each enzyme therein may be substituted with homologous enzymes that belong to the same E.C. class. Examples 12A and 12B in Table 21 highlight the confirmation of multiple enzymes for carrying out both CoA-transfer reaction and the 2,6-dihidroxy-hexanoyl-CoA dehydration reaction to enable successful production of AA via this pathway.

(i) Preparation of plasmids & strains for AA production from 6-hydroxy-2-keto-hexanoate: The AA production pathway genes were cloned on two separate compatible plasmids shown below. Each plasmid had a different origin of replication and antibiotic marker, as indicated. Synthetic genes were obtained from commercial vendors, and each gene was codon optimized for expression in E. coli. Each gene was cloned under its own T7 promoter and terminator using standard molecular biology methods. Escherichia coli was used as a target organism to engineer the 6HH production. The expression strains were obtained after co-transforming both plasmids in electro competent E. coli MG1655 (DE3) me 131 ΔldhA ΔadhE ΔfrdBC.

Plasmid 1 (ColE1 replicon, ampicillin marker): Gene 3, Gene 4, Gene 9, and Gene 10

Plasmid 3 (P15A replicon, chloramphenicol marker): Gene 5, Gene 6, Gene 7, and Gene 8

(ii) Cell culturing, protein expression, and AA production analysis: Same as example 11 except 10 g/L 6-hydroxy-2-keto-hexanoate was used (instead of 6HH used in example 11) as the substrate.

(iii) HPLC analysis of AA production: Isocratic HPLC was used to detect and quantify AA as described above. The results showed production of 100-800 mg/L of AA for Examples 12A-12C of Table 21.

out in two or more bacteria strains, each independently carrying out one or more biosynthesis reactions. In some embodiments, a culture comprises two or more or all strains for AA production. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. A biosynthetic pathway for the production of AA from pyruvate and 3-hydroxy-propanal through the 6-hydroxy-2-keto-hexanoate intermediate is shown in FIG. 5. Shown below are examples incorporating the use of aldolase-hydratase-based two-enzyme system for production of AA via this pathway. A glycerol dehydratase enzyme that is vitamin B12-independent or a glycerol dehydratase enzyme that is a B12-dependent enzyme can be cloned to enable production of 3-hydroxy-propionaldehyde—a 6HH pathway precursor that can be made from glycerol using this enzyme. The B12-dependent glycerol dehydratase was used herein. Examples of genes and corresponding enzymes they encode that were used to carry out each step of AA biosynthetic pathway as well as production of 3-hydroxy-propionaldehyde are shown in Table 22. Each enzyme therein may be substituted with homologous enzymes that belong to the same E.C. class.

TABLE 21

Biosynthesis polypeptides for AA.

| Reaction Catalyzed | Enzyme Name | Gene Number | Example 12A Uniprot ID or Genbank ID | Example 12B Uniprot ID or Genbank ID | Example 12C Uniprot ID or Genbank ID |
|---|---|---|---|---|---|
| 6-hydroxy-2-oxohexanoate → 2,6-dihydroxy-hexanoate | 6-hydroxy-2-oxohexanoate 2-reductase | Gene 3 | Q5FTU6 | Q5FTU6 | Q5FTU6 |
| 2,6-dihydroxy-hexanoate → 2,6-dihydroxy-hexanoyl-CoA | 2,6-dihydroxy-hexanoate CoA-transferase | Gene 4 | T4VW93 | A0A2X3BTQ9 | T4VW93 |
| 2,6-dihydroxy-hexanoyl-CoA → 6-hydroxy-2,3-dehydro-hexanoyl-CoA | 2,6-dihydroxy-hexanoyl-CoA 2-dehydratase -Subunit A | Gene 5 | Q5U924 | A0A2X3BK09 | A0A2X3BK09 |
| | 2,6-dihydroxy-hexanoyl-CoA 2-dehydratase -Subunit B | Gene 6 | Q5U925 | A0A2X3BU19 | A0A2X3BU19 |
| | 2,6-dihydroxy-hexanoyl-CoA 2-dehydratase -Subunit C | Gene 7 | Q5U923 | A0A1V9IXA9 | A0A1V9IXA9 |
| 6-hydroxy-2,3-dehydro-hexanoyl-CoA → 6-hydroxy-hexanoyl-CoA | 2,3-dehydro-hexanoyl-CoA 2,3-reductase | Gene 8 | Q73Q47 | Q73Q47 | Q73Q47 |
| 6-hydroxy-hexanoyl-CoA → 6-hydroxy-hexanoate | 6-hydroxyhexanoyl-CoA transferase | Gene 4 | T4VW93 | A0A2X3BTQ9 | T4VW93 |
| 6-hydroxy-hexanoate → 6-oxo-hexanoate | 6-hydroxyhexanoate dehydrogenase | Gene 9 | Q84H78 | Q84H78 | Q84H78 |
| 6-oxo-hexanoate → Adipic acid | 6-oxo-hexanoate oxidase | Gene 10 | Q9R2F4 | Q9R2F4 | Q9R2F4 |

Example 13: Preparation and Use of Microbial Organism for Production of Adipic acid (AA) from Different Carbon Sources via 6-hydroxy-2-keto-hexanoate Intermediate In some embodiments, the present disclosure provides technologies for preparing AA. In some embodiments, the present disclosure provides technologies for producing AA using 3HPA and pyruvate. In some embodiments, the present disclosure provides technologies for producing AA using glycerol as a carbon source. In some embodiments, production is carried out in one organism. In some embodiments, production is carried out in two or more organisms each expressing a different set of biosynthesis polypeptides. In some embodiments, production is carried out in a single bacteria strain. In some embodiments, production is carried

TABLE 22

Biosynthesis polypeptides for AA.

| Reaction Catalyzed | Enzyme Name | Enzyme ID | Gene Number | Uniprot ID or Genbank ID |
|---|---|---|---|---|
| Pyruvate + 3-hydroxy propanal → 6-hydroxy-3,4-dehydro-2-oxohexanoate | Trans-o-hydroxybenzylidenepyruvate hydratase-aldolases | Ads-Hyd 8 | Gene 1 | A0A286PH18 |
| 6-hydroxy-3,4-dehydro-2-oxohexanoate → 6-hydroxy-2-oxohexanoate | Quinone oxidoreductase | Qor 1 | Gene 2 | P28304 |
| 6-hydroxy-2-oxohexanoate → 2,6-dihydroxy-hexanoate | 6-hydroxy-2-oxohexanoate 2-reductase | | Gene 3 | Q5FTU6 |

TABLE 22-continued

Biosynthesis polypeptides for AA.

| Reaction Catalyzed | Enzyme Name | Enzyme ID | Gene Number | Uniprot ID or Genbank ID |
|---|---|---|---|---|
| 2,6-dihydroxy-hexanoate → 2,6-dihydroxy-hexanoyl-CoA | 2,6-dihydroxy-hexanoate CoA-transferase | | Gene 4 | T4VW93 |
| 2,6-dihydroxy-hexanoyl-CoA → 6-hydroxy-2,3-dehydro-hexanoyl-CoA | 2,6-dihydroxy-hexanoyl-CoA 2-dehydratase -Subunit A | | Gene 5 | Q5U924 |
| | 2,6-dihydroxy-hexanoyl-CoA 2-dehydratase -Subunit B | | Gene 6 | Q5U925 |
| | 2,6-dihydroxy-hexanoyl-CoA 2-dehydratase -Subunit C | | Gene 7 | Q5U923 |
| 6-hydroxy-2,3-dehydro-hexanoyl-CoA → 6-hydroxy-hexanoyl-CoA | 2,3-dehydro-hexanoyl-CoA 2,3-reductase | | Gene 8 | Q73Q47 |
| 6-hydroxy-hexanoyl-CoA → 6-hydroxy-hexanoate | 6-hydroxyhexanoyl-CoA transferase | | Gene 4 | T4VW93 |
| 6-hydroxy-hexanoate → 6-oxo-hexanoate | 6-hydroxyhexanoate dehydrogenase | | Gene 9 | Q84H78 |
| 6-oxo-hexanoate → Adipic acid | 6-oxo-hexanoate oxidase | | Gene 10 | Q9R2F4 |
| Glycerol dehydration | Glycerol dehydratase | | Gene 12 | Q8GEZ8 |
| | Glycerol dehydratase activator | | Gene 13 | Q8GEZ7 |

(i) Preparation of Plasmids & Strains for AA Production:

To minimize the number of AA production pathway genes expressed from plasmids, E. coli expression strain was constructed wherein certain pathway genes were integrated in the genome. Specifically, AA production strain BL21* (DE3) Δldh, ΔadhE, ΔfrdA containing pathway genes (Gene 12, Gene 13) at the arsB location with expression of each gene controlled by its own T7 promoter. Two E. coli based expression strains were constructed. Expression strain 1 was obtained after co-transforming plasmids 1, and plasmid 2 in E. coli; and Expression strain 2 was obtained after transforming plasmid 3 in E. coli.

Plasmid 1 (ColE1 replicon, ampicillin marker): Gene 4, gene 3, and gene 1.

Plasmid 2 (P15A replicon, chloramphenicol marker): Gene 5, Gene 6, Gene 7, Gene 8, and Gene 2.

Plasmid 3 (ColE1 replicon, ampicillin marker): Gene 9, gene 10, and gene 3.

(ii) Cell Culturing, Protein Expression, and AA Production Analysis:

Starter cultures were grown overnight in tubes containing 10 mL LB media with appropriate antibiotics for each expression strain separately. Cell cultures for the expression and AA production were carried out in 100 mL volume using glass bottles for each expression strain separately. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. for each expression strain separately. Recombinant protein expression was induced at an OD600 of 0.2-0.4 with 250 µM IPTG and was carried out separately for each expression strain. Post-induction expression was carried out at 30° C. under aerobic conditions for 30 minutes followed by 2-3 hours of anaerobic conditions for each expression strain separately. Afterwards, cells were harvested, concentrated, and re-suspended in 0.5 ml volume at OD600 of ~40 in fresh medium containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and analyzed via HPLC.

(iii) HPLC analysis of AA production: Isocratic HPLC was used to detect and quantify AA. The method employed a Bio-Rad Aminex HPX-87 column, 0.7 mL/min of 0.5% formic acid (or 5 mM sulfuric acid) at 35° C. Detection was carried out using an RID (refractive index detector) and UV detector, the latter of which was typically used to measure at signals at 210, 260, and 280 nm. The results showed production of 20-350 mg/L of AA.

Example 14: Multi-strain and multi-pot production of 6-hydroxyhexanoate

In some embodiments, production of a product e.g., 6HH, is carried out in one strain. In some embodiments, production is carried out in two or more strains. In some embodiments, the two or more strains together express all biosynthesis polypeptides utilized in a production. In some embodiments, a product of a biosynthesis polypeptide in one strain is a substrate of a biosynthesis polypeptide of another strain. In some embodiments, products of two or more biosynthesis polypeptides of one strain are independently substrates of two or more biosynthesis polypeptides in one or more other strains. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L of 6-hydroxyhexanoate.

Example 10 above describes the production of a 6HH in a single E. coli strain, wherein all the biosynthetic pathway enzymes necessary for converstion of pyruvate and 3-hydroxy propanal (and its production from glycerol) are all expressed simultaneously within a single E. coli strain. In some embodiments, it might be advantageous to pursue a multistrain approach, wherein the entire biosynthetic pathway is split into smaller sections called modules, wherein each module comprises a series of sequential enzymes of the biosynthetic pathway that are expressed in its own unique *E. coli* strain. For example, it was demonstrated that it was feasible to split the entire 6HH biosynthetic pathway into two modules. Specifically, described in Example 3 above is a construction of the first module, which allows for production of 6-hydroxy-2-keto-hexanoate—an intermediate of the 6HH biosynthetic pathway in a single *E. coli* strain, wherein all enzymes necessary for conversion of pyruvate and 3-hydroxy propanal (and its production from glycerol) were all expressed simultaneously within a single *E. coli* strain. Described in Example 9 above is a construction of the second module, which allows for production of 6HH from 6-hydroxy-2-keto-hexanoate in a second (separate) *E. coli* strain, wherein all enzymes necessary for conversion of 6-hydroxy-2-keto-hexanoate to 6HH are all expressed simultaneously within this single *E. coli* strain. Use of both modules leads to a complete biosynthetic pathway for production of 6HH in two separate *E. coli* strains. Such a multistrain approach can be advantageous for a number of reasons such as, but not limited to: a) constructing and testing plasmids for developing extensive biosynthetic pathways like these can result in large libraries, and conventional brute-force methods of screening for functional (or the best) genetic constructs can be inefficient and expensive; b) enzyme expression may be simplified and balanced across the pathway leading to substantially faster development cycles; c) genetic background of *E. coli* strains for each separate module may be tailored to suit redox, ATP, and other needs to maximize production for each module (since a single strain optimization may not be efficient for the entire pathway). Results summarized in Table 23 below demonstrate the successful use of this multi-strain approach for the production of 6HH either in simultaneous (i.e., one-pot) or via sequential production methodology.

1 was obtained after co-transforming plasmids 1, and plasmid 2 in *E. coli* MG1655 (DE3) rne131 ΔldhA ΔadhE ΔfrdBC ΔpoxB ΔpflB ΔackA-pta ΔyqhD, ΔadhP, ΔeutG, ΔgldA, ΔyiaY, ΔfucO; and Expression strain 2 was obtained after transforming plasmid 3 and 4 in *E. coli* MG1655 (DE3) me 131 ΔldhA ΔadhE ΔfrdBC.

Plasmid 1 (ColE1 replicon, ampicillin marker): Gene 1, gene 2, and gene 1.

Plasmid 2 (P15A replicon, chloramphenicol marker): Gene 9.

Plasmid 3 (ColE1 replicon, ampicillin marker): Gene 4.

Plasmid 4 (P15A replicon, chloramphenicol marker): Gene 5, Gene 6, Gene 7, Gene 8, and Gene 3.

(ii) Cell Culturing, Protein Expression, and 6HH Production Analysis:

Starter cultures were grown overnight in tubes containing 10 mL LB media with appropriate antibiotics for each expression strain separately. Cell cultures for the expression and 6HH production were carried out in 100 mL volume using glass bottles for each expression strain separately. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. for each expression strain separately. Recombinant protein expression was induced at an OD600 of 0.2-0.4 with 250 μM IPTG and was carried out separately for each expression strain. Post-induction expression was carried out at 30° C. under aerobic conditions for 30 minutes followed by 2-3 hours of anaerobic conditions for each expression strain separately. Afterwards, cells from both expression strains were harvested, concentrated, and re-suspended in 0.5 ml volume at OD600 of ~40. For Example 14A, equal number cells from

TABLE 23

Production of 6-hydroxyhexanoate.

|  | Example 14A | Example 14B |
| --- | --- | --- |
| Growth: | multi-pot | multi-pot |
| Production: | one-pot | sequential |
| Titer: | 350 mg/L 6HH | 1.1 g/L 6HH |

| Reaction Catalyzed | Gene Number | Uniprot ID | Host |
| --- | --- | --- | --- |
| Pyruvate + 3-hydroxy propanal → 6-hydroxy-3,4-dehydro-2-oxohexanoate | Gene 1 | A0A286PH18 | strain 1 |
| 6-hydroxy-3,4-dehydro-2-oxohexanoate → 6-hydroxy-2-oxohexanoate | Gene 2 | P28304 | strain 1 |
| 6-hydroxy-2-oxohexanoate → 2,6-dihydroxy-hexanoate | Gene 3 | Q5FTU6 | strain 2 |
| 2,6-dihydroxy-hexanoate → 2,6-dihydroxy-hexanoyl-CoA | Gene 4 | A0A2X3BTQ9 | strain 2 |
| 2,6-dihydroxy-hexanoyl-CoA → 6-hydroxy-2,3-dehydro-hexanoyl-CoA | Gene 5 | A0A2X3BK09 | strain 2 |
|  | Gene 6 | A0A2X3BU19 | strain 2 |
|  | Gene 7 | A0A1V9IXA9 | strain 2 |
| 6-hydroxy-2,3-dehydro-hexanoyl-CoA → 6-hydroxy-hexanoyl-CoA | Gene 8 | Q73Q47 | strain 2 |
| 6-hydroxy-hexanoyl-CoA → 6-hydroxy-hexanoate | Gene 4 | A0A2X3BTQ9 | strain 2 |
| Glycerol dehydratase (B12-dependent) | Gene 9 | Lre PduCDEGH* | strain 1 |

*Lre PduCDEGH is a vitamin B-12 dependent glycerol dehydratase and its corresponding activator from *Lactococcus reuteri*. It is encoded by a single gene operon encoded that is comprised of five genes as follows: pduC [Uniprot ID No. A5VMB2]; pduD [Uniprot ID No. A5VMB1]; pduE [Uniprot ID No. A5VMB0]; pduG [Uniprot ID No. A5VMA9]; and pduH [Uniprot ID No. A5VMA8]).

(i) Preparation of Plasmids & Strains for 6HH Production:

The entire 6HH biosynthetic pathway was split into two *E. coli* strains (or modules) as described above. Two *E. coli* based expression strains were constructed. Expression strain both strains were re-suspended in media containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and analyzed via HPLC. For Example 14B, cells from expression strain 1 was suspended in media containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and mixed with cells from expression strain 2. After incubation for 24 hours at room temperature, the cells were centrifuged, and supernatant was filtered and analyzed by HPLC.

(iii) HPLC analysis of 6HH production: This was carried out as mentioned before. The results showed production of 350-1100 mg/L of 6HH.

Example 15: Multi-Strain and Multi-Pot Production of 1,6-hexanediol

In some embodiments, the present disclosure provides technologies for preparing HDO. In some embodiments, the present disclosure provides technologies for producing HDO from 3HPA and pyruvate. In some embodiments, the present disclosure provides technologies for producing HDO using glycerol as a carbon source. In some embodiments, production is carried out in one organism. In some embodiments, production is carried out in two or more organisms each expressing a different set of biosynthesis polypeptides. In some embodiments, production is carried out in a single bacteria strain. In some embodiments, production is carried out in two or more bacteria strains, each independently carrying out one or more biosynthesis reactions. In some embodiments, a culture comprises two or more or all strains for HDO production. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L. Examples 8 above describe the production of HDO in a single or dual *E. coli* strain, wherein all the biosynthetic pathway enzymes necessary for conversion of pyruvate and 3-hydroxy propanal (and its production from glycerol) are all expressed simultaneously within a single *E. coli* strain or two separate *E. coli* strains. Such a multi-strain approach can be advantageous for a number of reasons mentioned in Example 14. Results summarized in Table 24 demonstrate another successful use of this multi-strain approach for the production of HDO either in simultaneous (i.e., one-pot) or via sequential production methodology.

TABLE 24

Production of 1,6-hexanediol.

| Reaction Catalyzed | Gene Number | Uniprot ID or Genbank ID | Host |
|---|---|---|---|
| | | Example 15A | Example 15B |
| Growth: | | multi-pot | multi-pot |
| Production: | | one-pot | sequential |
| Titer: | | 400 mg/L 16HDO | 800 mg/L 16HDO |
| Pyruvate + 3-hydroxy propanal → 6-hydroxy-3,4-dehydro-2-oxohexanoate | Gene 1 | A0A286PH18 | strain 1 |
| 6-hydroxy-3,4-dehydro-2-oxohexanoate → 6-hydroxy-2-oxohexanoate | Gene 2 | P28304 | strain 1 |
| 6-hydroxy-2-oxohexanoate → 2,6-dihydroxy-hexanoate | Gene 3 | Q5FTU6 | strain 2 |
| 2,6-dihydroxy-hexanoate → 2,6-dihydroxy-hexanoyl-CoA | Gene 4 | A0A2X3BTQ9 | strain 2 |
| 2,6-dihydroxy-hexanoyl-CoA → 6-hydroxy-2,3-dehydro-hexanoyl-CoA | Gene 5 | A0A2X3BK09 | strain 2 |
| | Gene 6 | A0A2X3BU19 | strain 2 |
| | Gene 7 | A0A1V9IXA9 | strain 2 |
| 6-hydroxy-2,3-dehydro-hexanoyl-CoA → 6-hydroxy-hexanoyl-CoA | Gene 8 | Q73Q47 | strain 2 |
| 6-hydroxy-hexanoyl-CoA → 6-hydroxy-hexanoate | Gene 4 | A0A2X3BTQ9 | strain 2 |
| 6-hydroxy-hexanoate → 6-hydroxy-hexanal | Gene 9 | A0R484 | strain 2 |
| | Gene 10 | P39135 | strain 2 |
| 6-hydroxy-hexanal → 1,6-hexanediol | Gene 11 | AB213459.1 | strain 2 |
| Glycerol dehydratase (B12-dependent) | Gene 12 | Lre PduCDEGH* | strain 1 |

*Lre PduCDEGH is a vitamin B-12 dependent glycerol dehydratase and its corresponding activator from *Lactococcus reuteri*. It is encoded by a single gene operon encoded that is comprised of five genes as follows: pduC [Uniprot ID No. A5VMB2]; pduD [Uniprot ID No. A5VMB1]; pduE [Uniprot ID No. A5VMB0]; pduG [Uniprot ID No. A5VMA9]; and pduH [Uniprot ID No. A5VMA8]).

(i) Preparation of Plasmids & Strains for HDO Production:

The entire HDO biosynthetic pathway was split into two *E. coli* strains (or modules) as described above. Two *E. coli* based expression strains were constructed. Expression strain 1 was obtained after co-transforming plasmids 1, and plasmid 2 in *E. coli* MG1655 (DE3) rne131 ΔldhA ΔadhE ΔfrdBC ΔpoxB ΔpflB ΔackA-pta ΔyqhD, ΔadhP, ΔeutG, ΔgldA, ΔyiaY, ΔfucO; and Expression strain 2 was obtained after transforming plasmid 3 and 4 in *E. coli* MG1655 (DE3) me 131 ΔldhA ΔadhE ΔfrdBC.

Plasmid 1 (ColE1 replicon, ampicillin marker): Gene 1, gene 2, and gene 1.

Plasmid 2 (P15A replicon, chloramphenicol marker): Gene 12.

Plasmid 3 (ColE1 replicon, ampicillin marker): Gene 3, Gene 9, Gene 4, Gene 11, and Gene 10.

Plasmid 4 (P15A replicon, chloramphenicol marker): Gene 5, Gene 6, Gene 7, Gene 8, and Gene 4.

(ii) Cell Culturing, Protein Expression, and HDO Production Analysis:

Starter cultures were grown overnight in tubes containing 10 mL LB media with appropriate antibiotics for each expression strain separately. Cell cultures for the expression and 6-HH production were carried out in 100 mL volume using glass bottles for each expression strain separately. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. for each expression strain separately. Recombinant protein expression was induced at an OD600 of 0.2-0.4 with 250 μM IPTG and was carried out separately for each expression strain. Post-induction expression was carried out at 30° C. under aerobic conditions for 30 minutes followed by 2-3 hours of anaerobic conditions for each expression strain separately. Afterwards, cells from both expression strains were harvested, concentrated, and re-suspended in 0.5 ml volume at OD600 of ~40. For Example 15A, equal number cells from both strains were re-suspended in media containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and analyzed via HPLC. For Example 15B, cells from expression strain 1 was suspended in media containing 5-20 g/L glucose, 2.5-5 g/L glycerol, and 15 g/L potassium phosphate buffer (pH 7.2). After incubation for 24 hours at room temperature, the cells were centrifuged, and supernatant was filtered and mixed with cells from expression strain 2. After incubation for 24 hours at room temperature, the cells were centrifuged, and supernatant was filtered and analyzed by HPLC.

(iii) HPLC analysis of HDO production: This was carried out as mentioned before. The results showed production of 400-800 mg/L of HDO.

Example 16: Synthesis of 3-hydroxy-propanal from glycerol

3-Hydroxy-propanal is synthesized from glycerol using glycerol dehydratases. Glycerol dehydratases can catalyze the dehydration in a coenzyme B12-dependent or coenzyme B12-independent manner in the presence of a reactivator protein. Coenzyme B12-dependent dehydratase is composed of three subunits: the large or "α" subunit, the medium or "β" subunit, and the small or "γ" subunit. These subunits assemble in an α2β2γ2 structure to form the apoenzyme. Coenzyme B12 (the active cofactor species) binds to the apoenzyme to form the catalytically active holoenzyme. Coenzyme B12 is required for catalytic activity as it is involved in the radical mechanism by which catalysis occurs. Biochemically, both coenzyme B12-dependent glycerol and coenzyme B12-dependent diol dehydratases are known to be subject to mechanism-based suicide inactivation by glycerol and other substrates (Daniel et al., *FEMS Microbiology Reviews* 22:553-566 (1999); Seifert, et al., *Eur. J. Biochem.* 268:2369-2378 (2001)). Inactivation can be overcome by relying on dehydratase reactivation factors to restore dehydratase activity (Toraya and Mori (*J. Biol. Chem.* 274:3372 (1999); and Tobimatsu et al. (*J. Bacteria* 181:4110 (1999)). Both the dehydratase reactivation and the coenzyme B12 regeneration processes require ATP. Shown below are a few examples of glycerol dehydratases, diol dehydratases and reactivating factors. One skilled in the art will recognize that glycerol dehydratases of *Citrobacter freundii, Lactococcus reuteri, Clostridium pasteurianum, Clostridium butyricum, K. pneumoniae* or their strains; diol dehydratase of *Salmonella typhimurium, Klebsiella oxytoca* or *K. pneumoniae*; and other dehydratase enzymes belonging to E.C. groups listed in Table 25 below or homologous enzymes of these sequences can also be used to carry out this step. Mutants of these enzymes (U.S. Pat. Nos. 8,445,659 & 7,410,754) can also be used herein to increase the efficiency of the process. In particular, coenzyme B12-independent-dehydratases (Raynaud, C., et al., *Proc. Natl. Acad. Sci. U.S.A.* 100, 5010-5015 (2003)) are favored for the industrial process due to the high cost of vitamin-B12.

TABLE 25

Exemplary biosynthesis polypeptides.

| Genbank ID | EC Number | Name | Organism |
| --- | --- | --- | --- |
| BAA08099.1 | 4.2.1.28 | Diol dehydrase alpha subunit | *Klebsiella oxytoca* |
| BAA08100.1 | 4.2.1.28 | Diol dehydrase beta subunit | *Klebsiella oxytoca* |
| BAA08101.1 | 4.2.1.28 | Diol dehydrase gamma subunit | *Klebsiella oxytoca* |
| ABR24274.1 | 4.2.1.30 | Glycerol dehydratase large subunit | *Klebsiella pneumoniae* |
| ABR24275.1 | 4.2.1.30 | Glycerol dehydratase medium subunit | *Klebsiella pneumoniae* |
| ABR24276.1 | 4.2.1.30 | Glycerol dehydratase small subunit | *Klebsiella pneumoniae* |
| AAM54728.1 | 4.2.1.30 | Glycerol dehydratase | *Clostridium butyricum* |
| AAM54729.1 | - | glycerol dehydratase activator | *Clostridium butyricum* |
| ACI39932.1 | 4.2.1.30 | B12-independent glycerol dehydratase | *Clostridium diolis* |
| ACI39933.1 | - | glycerol dehydratase activator | *Clostridium diolis* |
| ABQ83986.1 | 4.2.1.30 | Glyerol dehydratase (B12-dependent) large subunit | *Lactococcus reuteri* |
| ABQ83985.1 | 4.2.1.30 | Glyerol dehydratase (B12-dependent) medium subunit | *Lactococcus reuteri* |
| ABQ83984.1 | 4.2.1.30 | Glyerol dehydratase (B12-dependent) small subunit | *Lactococcus reuteri* |
| ABQ83983.1 | - | Glyerol dehydratase (B12-dependent) activator large subunit | *Lactococcus reuteri* |

TABLE 25-continued

Exemplary biosynthesis polypeptides.

| Genbank ID | EC Number | Name | Organism |
|---|---|---|---|
| ABQ83982.1 | - | Glyerol dehydratase (B12-dependent) activator small subunit | Lactococcus reuteri |

Example 17: Synthesis of Pyruvate

Conversion of Sugars to Pyruvate.

Conversion of sugars to pyruvate through glycolysis is very well known. In glycolysis, each mole of glucose gives 2 moles of ATP, 2 moles of reducing equivalents in the form of NAD(P)H and 2 moles of pyruvate.

Conversion of Glycerol to Pyruvate.

Glycerol can be converted to glycolysis intermediates both anaerobically and micro-aerobically. Anaerobically, glycerol is dehydrogenated to dihydroxyacetone which, after phosphorylation (using phosphoenol pyruvate or ATP), is converted to dihydroxyacetone phosphate a glycolytic pathway intermediate (Dharmadi, et al., *Biotechnol. Bioeng.* 94:821-829 (2006)). The respiratory pathway for glycerol conversion involves phosphorylation (by ATP) of glycerol followed by oxidation (quinone as electron acceptors) to give dihydroxyacetone phosphate that can be converted to pyruvate via glycolysis (Booth I R. Glycerol and methylglyoxal metabolism. Neidhardt F C, et al., editors. *In: Escherichia coli and Salmonella: Cellular and molecular biology* (web edition). 2005, Washington, DC, ASM Press; Durnin et al., *Biotechnol Bioeng.* 103(1):148-161 (2009)).

Example 18: Preparation and Use of Microbial Organism for Production of 2,6-dihydroxy-hexanoate from 6-hydroxy-2-keto-hexanoate Intermediate In some embodiments, the present disclosure provides technologies for producing 2,6-dihydroxy-hexanoate from 6-hydroxy-2-keto-hexanoate. Certain examples are described below.

Shown in FIG. 4 is a biosynthetic pathway for the production of 2,6-dihydroxy-hexanoate (6H2HH) from 6-hydroxy-2-keto-hexanoate intermediate. Shown below are examples incorporating the use of different 2-keto reductase enzymes for reduction of 6H2KH to 6H2HH i.e. 6-hydroxy-2-oxohexanoate 2-reductase. Examples of genes and corresponding enzymes from which they are encoded that were used to this step are shown in Table 26. Each enzyme therein may be substituted with homologous enzymes that belong to the same E.C. class.

(i) Preparation of Plasmids for 6H2HH Production:

The gene encoding 6-hydroxy-2-oxohexanoate 2-reductase was cloned on a plasmid with expression driven by T7 promoter using standard molecular biology methods. *Escherichia coli* was used as a target organism to engineer the 6H2HH production. The expression strains were obtained after co-transforming all three plasmids in electro competent *E. coli* BL21*(DE3) Δldh.

TABLE 26

Exemplary biosynthesis polypeptides.

| Name | Annotated Name | EC Number | Uniprot ID or Genbank ID of 6-hydroxy-2-oxohexanoate 2-reductases | 6H2HH Produced |
|---|---|---|---|---|
| 1 | D-2-hydroxyacid dehydrogenase | 1.1.99.6 | WP_003431407.1 | Yes |
| 2 | ketopantoate reductase | 1.1.1.169 | BAL51292.1 | Yes |
| 3 | 2-ketogluconate reductase | 1.1.1.215 | Q5FTU6 | Yes |
| 4 | D-lactate dehydrogenase | 1.1.1.28 | AKC64094.1 | Yes |
| 5 | D-2-hydroxyacid dehydrogenase | 1.1.99.6 | WP_002876862.1 | Yes |
| 6 | D-lactate dehydrogenase | 1.1.1.28 | AGP69017.1 | Yes |
| 7 | D-2-hydroxyacid dehydrogenase | 1.1.99.6 | WP_003640741.1 | Yes |
| 8 | phenyllactate dehydrogenase | 1.1.1.110 | AKC64095.1 | Yes |
| 9 | D-lactate dehydrogenase | 1.1.1.28 | AKC64094.1 | Yes |

(ii) Cell Culturing, Protein Expression, and 6H2HH Production Analysis:

Starter cultures were grown overnight in tubes containing 10 mL LB media with appropriate antibiotics. Cell cultures for the expression and 6H2HH production were carried out in 100 mL volume using glass bottles. Complex growth medium was used and supplemented with 2 g/L D-glucose, 0.5 g/L potassium phosphate buffer (pH 7.2), and other substrates/nutrients important for enzyme expression. Pre-induction growth was carried out for ~2 hours under aerobic conditions and at 30° C. Recombinant protein expression was induced at an OD600 of 0.2-0.4 with 250 µM IPTG. Post-induction expression was carried out at 30° C. under aerobic conditions for 60-90 minutes followed by 2-3 hours of anaerobic conditions. Afterwards, cells were harvested, concentrated, and re-suspended in 0.5 ml volume at OD600 of ~40 in fresh medium containing ~10 g/L glucose, 6-hydroxy-2-keto-hexanoate (5-10 g/L), and 15 g/L potassium phosphate buffer (pH 7.2). After incubation for 24 hours at room temperature, the cells were centrifuged, and supernatant was filtered and analyzed via HPLC.

(iii) HPLC analysis of 6H2HH production: Isocratic HPLC was used to detect and quantify 6H2HH. The method employed a Bio-Rad Aminex HPX-87 column, 0.7 mL/min of 0.5% formic acid (or 5 mM sulfuric acid) at 35° C. Detection was carried out using an RID (refractive index detector). The results showed production of 6H2HH from all strains of Examples 1-9 of Table 26.

Example 19: Preparation and Use of Microbial Organism for Production of 2,6-dihydroxy-hexanoate from Different Carbon Sources Via 6-hydroxy-2-keto-hexanoate Intermediate In some embodiments, the present disclosure provides technologies for producing 2,6-dihydroxy-hexanoate from various carbon sources. Certain examples are described below. In some embodiments, the present disclosure provides technologies for producing 2,6-dihydroxy-hexanoate from pyruvate and 3HPA. In some embodiments, a yield is about or at least about 10, 20, 30, 40, 50, 60, 70, 80, 90, 100, 150, 200, 250, 300, 350, 400, 450, 500, 600, 700, 800, 900, or 1000 mg/L, or is about or at least about 1.1, 1.2, 1.3, 1.4, 1.5, 1.6, 1.7, 1.8, 1.9, 2, 2.1, 2.2, 2.3, 2.4, 2.5, 2.7, 3, 3.5, 4, 4.5, 5, 6, 7, 8, 9, 10, 15, 20, 30, 40, 50, 60, 70, 80, 90, 100, 110, 120, 130, 140, 150, 160, 170, 180, 190, 200, 220, 250, or 300 g/L.

A biosynthetic pathway for the production of 6H2HH from pyruvate and 3-hydroxy-propanal through the 6-hydroxy-2-keto-hexanoate intermediate is shown in FIG. 4. Shown below are examples incorporating the use of aldolase-hydratase based two enzyme system for production of 6H2HH via this pathway. A glycerol dehydratase enzyme that is vitamin B12-independent or glycerol dehydratase enzyme that is a B12-dependent enzyme can be cloned to enable production of 3-hydroxy-propionaldehyde—a 6H2HH pathway precursor that can be made from glycerol using this enzyme. Although both types of glycerol dehydratases can be used herein, example shown herein uses the B12-dependent glycerol dehydratase enzyme. Each enzyme therein may be substituted with homologous enzymes that belong to the same E.C. class to yield 6H2HH.

(i) Preparation of plasmids & strains for 6H2HH production: MG1655(DE3) Δrne131, ΔldhA, Δ[frdB, frdC], ΔadhE, ΔpoxB, ΔpflB, Δ[ackA, pta] was used as the strain with the following plasmid comninations: Plasmid 1 (COLA replicon, kanamycin marker): Gene 1 (Glycerol dehydratase—pduCDEGH). Plasmid 2 (ColE1 replicon, ampicillin marker): Gene 2 (Ads-Hyd 8), Gene 2 (Qor-1), and Gene 3 (6-hydroxy-2-oxohexanoate 2-reductase—Q5FTU6).

(ii) Cell Culturing, Protein Expression, and 6H2HH Production Analysis:

Cell culturing (with appropriate antiobiotics), and protein expression was similar to that described in Example 1 for 3-hydroxy propanal. After incubation for 24 hours at room temperature, the cells were centrifuged, and supernatant was filtered and analyzed via HPLC.

(iii) HPLC analysis of 6H2HH production: Analysis was carried as our as mentioned in example 18. The strain was able to produce >1 g/L of 6H2HH under these conditions.

EQUIVALENTS

Unless otherwise defined, all technical and scientific terms used herein have the same meaning as commonly understood by one of ordinary skill in the art to which this present disclosure belongs. All nucleotide sequences provided herein are presented in the 5' to 3' direction.

The embodiments illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

It is to be understood that while the present technology has been described in conjunction with the above aspects, that the foregoing description and examples are intended to illustrate and not limit the scope of the present technology. Other aspects, advantages and modifications within the scope of the present technology will be apparent to those skilled in the art to which the present technology pertains.

REFERENCES

1. Eaton, R. W., & Chapman, P. J. (1992). Journal of Bacteriology, 174, 7542-7554.
2. Eaton, R. W. (2000). Applied and Environmental Microbiology, 66, 2668-2672.
3. Ferrara, S., Mapelli, E., Sello, G., & Di Gennaro, P. (2011). Biochimica et Biophysica Acta, 1814, 622-629.
4. Guido Sello, & Patrizia Di Gennar (2013). Appl Biochem Biotechnol, 170:1702-1712
5. Mueller, L. S., Hoppe, R. W., Ochsenwald, J. M., Berndt, R. T., Severin, G. B., Schwabacher, A. W. & Silvaggi, N. R. (2015). Biochemistry, 54, 3978-3988.
6. Iwabuchi, T., and Harayama, S. (1998). J. Bacteriol. 180, 945-949.
7. Siegert P, McLeish M J, Baumann M, Iding H, Kneen M M, Kenyon G L, Pohl M: *Protein Eng Des Sel* 2005, 18(7):345-357.
8. de la Plaza M, Fernandez de Palencia P, Pelaez C, Requena T. *FEMS Microbiol Lett* 2004, 238(2):367-374.
9. Gocke Dr, Graf T, Brosi H, Frindi-Wosch I, Walter L, M. *Journal of Molecular Catalysis B: Enzymatic* 2009, 61(1, Äì2):30-35.
10. Andrews F H, McLeish M J. *Bioorg Chem* 2012, 43:26-36.
11. G. M. Rodriguez, S. Atsumi, Microb. Cell Factories 11 (2012) 90.
12. D. J. Petersen, R. W. Welch, F. B. Rudolph, G. N. Bennett, J. Bacteriol. 173 (1991)1831.
13. X. Liu, Y. Dong, J. Zhang, A. Zhang, L. Wang, L. Feng, Microbiol. Read. Engl. 155 (2009) 2078.
14. A. Tani, Y. Sakai, T. Ishige, N. Kato, Appl. Environ. Microbiol. 66 (2000) 5231.
15. K. E. Breitkreuz, W. L. Allan, O. R. Van Cauwenberghe, C. Jakobs, D. Talibi, B. Andre, B. J. Shelp, J. Biol. Chem. 278(2003) 41552.
16. N. Saito, M. Robert, H. Kochi, G. Matsuo, Y. Kakazu, T. Soga, M. Tomita, J. Biol. Chem. 284 (2009) 16442.
17. R. A. Wolff, W. R. Kenealy, Protein Expr. Purif. 6 (1995)206.

| | | Certain Sequences |
|---|---|---|
| Uniprot or Genbank ID | Sequence ID Number | Sequence Information |
| D7C0E5 | SEQ ID NO: 1 | MKGYTVPLSPRGIANLAPAPPWHYAGTVVGVEFFTDPAAAAATLPEGLTPDPDSAGRGVAMFIDWQY SSTGLEYLDPARSQYREFLITLDAHCNGAPVAWCPYIYVDNDAAMARGWVQGFPKKLGAVHQTRAY SVGGPGTPVLGPGGQFGATASSAGQRIAEAKITLEQPVPDPAALMSRPVINLRHFPRLAAGQHDQPAV HELVMSVLDDTAVSDAWVGTADLAFLPAHGEELADLPVRRTGKGFHFDLAYTVTDLMTLADHSA |
| P0A144 | SEQ ID NO: 2 | MSNKIMKTSRLTAEDINGAWTIMPTPSTPDASDWRSTATVDLEETARIVEELIAAGVNGILSMGTFGEC ATLTWDEKRDYVSTIVETIRGRVPYFCGTTALNTREVIRQTRELIDIGANGTMLGVPMWVKMDLPTA VQFYRDVADAVPEAAIAIYANPEAFKFDFPRPFWAEMSKIPQVVTAKYLGIGMLDLDLRLAPNIRFLP HEDDYYAAARINPERITAFWSSGAMCGPATAIMLRDEVVRAKSTGDWAKAKAISDDMRAADSTLFPR GDFSEFSKYNIGLEKARMDAAGWLKAGPCRPPYNLVPEDYLAGAQKSGKAWAALHAKYSNELK |
| Q79EM8 | SEQ ID NO: 3 | MTSPAVTSADITGLVGIVPTPSKPGSEAPDAVDTVDLDETARMVELIVASGVDVLLTNGTFGEVATLT YEELLAFNDTVIRTVANRIPVFCGASTLNTRDTIARSLALMGLGANGLFVGRPMWLPLDDEQLVSYYA AVCDAVPAAAVVVYDNTGVFKGKISSAAYAALAEIPQIVASKHLGVLSGSDAYASDLAAVKGRFPLL PTADNWLPSLEAFPGEVPAAWSGDVACGPEPVMALRRAIAEGLWDDARAVHEDIAWATEPLFPGGDI SKFMPYSIQIDRAEFEAAGYIVPGPSRHPYGTAPAAYLEGGAEVGRRWAGIRQKYVATLAEP |
| A0A0N0AHI8 | SEQ ID NO: 4 | MKGYTYPLSPRGVANLAGKPPWHYVGDAVGVEFWTSPEAAAASLPTGLDPDPANPGHGYAVFIDWQ FNGATDDYLDPPFSQYSEFLVLLDAQWQGTPVAWCPFIWVDNDASLARGWVQGFPKKMGSIRQTRA FAIDSPAAPTVGKGGRFAAVMSAGGRRLAETTVTLDRTTDRLPALTRPLVNLRHFPRLSAGQHDNPA VHELTMSVLANLKFANTWIGTGELRFLPAPREELADLTPRRVGVGFRGSLSYTVNDLRIL |
| A0A0N1FRY3 | SEQ ID NO: 5 | MKGYTVPLSPRGVANLAPAPPWHYAGTVVGVEFFTDPAAAAALPEGLSSDPDSAGRGVAMFIDWQY YSSTDLEYLDPARSQYREFLVTLDAHYYGAPVAWCPYIYVDNDSAMARGWVQGFPKKLGAVHQTR AYSVGGQGTPVLGPGGQFGATASAAGQRIAEAKITLEQAVPDPAALMSRPVVNLRHFPRLTAGQHHK PAVHELVMSVLDGAAVSDAWAGTADLAFLPARGEELADLPIQRTGRGFHFDLAYTVTDLKTLIDHSN |
| M3DYR1 | SEQ ID NO: 6 | MLKGYTVPLSPKGEANIAPTPPWHYAGDIVGVEFFTEPAAAEATLPEGLDPDPDTSGRVVAFFVDWQF NGERDEYLDPVRSQYREFFVLVDARHQGRPVSWCPYIVDNHHALARGWIQGFPKKAGNVHQTRVF ASPGKASPTLSPGARFGASVSSDERTLAEARVTLEAPMEDPSALLSRDTINLRHFPTLEAGRYDKPAVH ELVRMDYADQQVADVWTGTSEITLFPAVGEELADLAPVRSGMGFRASMSYNVTQVEPLL |
| W7SU48 | SEQ ID NO: 7 | MLGYSLPLSANGTANVVPAPPWHYAGDVVGVEFWTTPAAAAATLPSGLTPDPTTSGHAYALFVDWQ WAGSHQEYLDPVRSQYSEFLILMDAQFQGRAVAWCPYIWVDNDAALARGWFQGFPKKLGAIRQTRA FSVPGGQASPVVGPGGQFGASLSAAGRRLAEAQITLQAPSATLPALGRPIVNLRHFPRLIAGQYDNPSVH ELTQSVLDTPVVGNNWTGTSTLNFFTAPGEELADLQPVRTGSGFRGSLSYTVTTLKMLSGPDA |
| A0A286PH18 | SEQ ID NO: 8 | MKGYTVPLSPRGIANLAPAPPWHYAGTVVGVEFFTDPAAAAATLPEGLTPDPDSAGRGVAMFIDWQY SSTGLEYLDPARSQYREFLLTLDAHYNGTPVAWCPYIYVDNDSAMARGWVQGFPKKLGAVHQTRAY SVGGPGTPVLGPGGQFGATASAAGQRIAEAKVTLEQPVPDPAALMSRPVVNLRHFPRLAAGQHDKPA VHELVMSVLDGVAVSDAWAGTADLAFLPAHGEELADLPVQRTGRGFHFDLAYTVTDLKTLIDRSN |
| Q9X9Q6 | SEQ ID NO: 9 | MARTLMKPDDVKGAWAIIPTPAKDDASDWRATKTVDLDETARVVNGLIDAGINGILSMGTLGEAAT MTHDEKLDFIKALVDAAAGRVPIFVGTTCLNTRDTIALTRQALDIGADGTMLGVPMWCAPSVDVAVQ FYKDLAEAVPEMNIAIYANPEAFKFDFPRSFWAQVAEIPQVVTAKYIGVAHLLPDLAAIRGRIKLLPIDF DYYGAARMDESIDAFWSSGAVCDPLVTTTLRDLVSQARATGDWSAARAFMGRLGPTAAPLFPNGSF KEFSTYNIALEKARMNAGGWMNAGPVRPPYHLCPEPYLEGARLSGRMWAELGKALAAEK |
| Q9WXH7 | SEQ ID NO: 10 | MAKSGLLNASDIHGVWSILPTPSKPDASDWRATNTVDLDETARAVEGLIAAGANGILSMGTLGECESL TWEEKKVFMQTIVETARGRVPVFVGTTTLNTRDTIALTRKAVDIGATGTMLGVPMWCNPCVDMAVQ YYKDVAEAVPEMNIAIYANTEAFKFDFPRAFWARVSEIRQVVAAKYIGIEFLLQDLHLTKHRMKLLPL DYQYYAAARMDDFVDAFWSSGTVCGPLVSTTLRDKVIAARRTKDWTDAHAFQGRLVKTAAPFPEDS FKTFSIYNVALEKGRIDAAGWMNAGPVRPPYNDICPASYLDSWKASGQRWAELHKQLETESSGK |
| A4XDS1 | SEQ ID NO: 11 | MARELLTAADVKGAWAIVPTPAKEGASDWRAADTVNVEEAARMIDGLIEAGVDGILSMGTLGEAAT MTLDEKLVFMKTIVDTAAGRVPVFVGTTCINTRDTIALTRKAVDIGATGTMLGVPMWCAPSVDVAV QFYRDVAEAVPDINIAIYANPEAFKFDFPRTFWGQVAEIPQVVTAKYIGVGTLLPDLAIKGRIKLLPID FDYYGAARMDDSIDAFWTSGAVCHPLVSTTLRDVVAAARASGDWSAAKAFMGRLAPTAATLFPNGS FKEFSTYNIPLEKARMTAGGWMNAGPCRPPYHLCPENYLEGARNSGRMWAELGKALEAER |
| F2J6N9 | SEQ ID NO: 12 | MTRKLLTVDDVNGCWAIMPTPSKPGASDPNAVDTVDLEETARAAEALVAAGVDGILSLGTFGEAATT TWEEKQAFMRTLVETVRGRVPVFGGTTSLNTRDTIRMTRAAREIGVDGVMLGLPMWVQPDLATAVQ FFRDVASACPDVAICAYANPEAFKFEFPRAFWAQIADIPQIVSAKYIHTAGLYADLNLTKRRIRLMPLD VDYYAAARIDPDACTAFWTSGAVCGPAPAIQLRDLVSKAKKTGDWTGAKKLTDRIGQTYRTLFPNGS FKDFSVYNIGIEKARMDAAGWMKAGPCRAPYSLVPEPYLEGARESGRQWAKLAAELATERAE |
| A0A063BFL5 | SEQ ID NO: 13 | MIHPKLRIDASGINGLWPILPTPAKPNASDWRERSTVDLDETARIVESLIDAGVDGLLSLGTYGEAHSL LWEEKKAFVGCVLETIRGRIPFFTGTTALNTREVVEQTRAMHDMGVSGTMLGVPMWCKTDLATAVQ FFRDVTEACPDTALAIYANTEAFKFEFPRPFWAEIGKMPQVACKYLGIGMLAVDLELAPNMRFLPNE QDYYAAARIDPERVTAFWSSGALCGPLPALTLRDRVARAKSSNDWTSAKEIADRMACDVGFFPKGE FSEFSKFNAPLEKARMNTAGYVNAGPCRPPYHVIPQEYLAGAERSGRAHAALNAELKQAEHSI |
| Q9ZHH6 | SEQ ID NO: 14 | MSKQRKQRLGTEDVNGAWVIMPTPAKPEASDWRATDTVDLDETARIVEALIDSGVNGILSLGTFGEC ATLTWEEKQAFIGAVVETTRGRVPFFCGTTALNTREVVRQTRAALDIGVDGTMLGVPMWSRMEVPA AVQFYRDVAEACPEAAIAVYANADAFKFEFPRAFWAQVAQIPQVVTAKYLGIGMLDLDLTLAPGIRF |

-continued

| Certain Sequences | | |
|---|---|---|
| Uniprot or Genbank ID | Sequence ID Number | Sequence Information |
| | | LPHEDDYYAAARVAPERVTAFWSSGAMCGPATAIRLRDEVAKAKQTGDWRLAKELSDAMRRADAT<br>LFPRGDFAEFSKYNIAIEKERMNAAGWLRAGPCRPPYHIAPEEYLDGARQSGRAWAELHQQYSDL |
| A0A0C1K853 | SEQ ID NO: 15 | MMSDMVKPRMTADDVNGVWVIMPTPAKPDASDWRVENTVDLDETVRIVENLLASGVNGIMSNGTF<br>GECATLTWDEKRDFIATVAETIKGRVPFFCGTTALHTREVIRQTREVMRLGADGVMLGLPMWCKME<br>TPSAIQFYRDVAEAVPDAAIAVYANPEAFKYEFPREFWAQVSEIPQVVTAKYLGIGMLDLDLRLASSIR<br>FLPHEDDYYAAARINPERMTAFWSSAAMCGPATPLKLRDAVADAKVTGKWSVAKAISDEMRKADS<br>MLFPKGDFSEFSKYNIGLEKARMDEAGWLKAGPCRPPPYHVIPEMYLEGARKSGRAWAELHAKYSAE<br>G |
| WP_034398482 | SEQ ID NO: 16 | MAKQKKSRMTAEDIHGAWVIMPTPATPDASDWRVQHTVDLEETARIVEALIAAGVNGIFSNGTFGEC<br>ATLTWEEKRDFIATVVETARGRVPPFCGTTALHTREVIRQTREAMDIGASGTMLGVPMWCKMEVPTA<br>VQFYRDVAEAVPEAAIAIYANPEAFKFDFPPRSFWAQVSNIPQVITAKYLGIGMLDLDLRLAPSIRFLPHE<br>DDYYAAARIDPERMTAFWSSGAMCGPATAIRLRDTVGAAKRSGDWTDAKAISDAMRQADSTLFPRG<br>DFSEFSKFNIGLEKARMDAAGWLKAGPCRPPYHIVPEEHLAGARKSGEAWAALHARYATLD |
| PYK12191 | SEQ ID NO: 17 | MNTAKLIGFNYPLTPKGKSTLNPPPPWYYSSDFLDVEFWAQPAAVASLLPNGLEPDPAANGHCNALF<br>YDWQFSGDNEEYLDPARYQYREFFILVDALFEGRSVSYCPYIFVDNDAALARGWTQGYPKRLGQVFQ<br>TRYYAATSKAGPALAPGSKFAGSLTAAGQLIAEAVVTLRQAVTDPSLLKQKPVINLLHVPRLAADKH<br>DKPAIHELVENVPSSVKIEQAWIGEGSLTLPVCRGEEISDLAPLRCGKGIRASMAYVVDDLKTLKDLRN |
| A0A370X7D8 | SEQ ID NO: 18 | MKSNFFVPMTPRGLSNISPPPPWHYAGDFLIIDFWARPDAVASLLPAELQPDVKAEGHAQAYFIDWQY<br>TAAHDEFLDPARYQYREFFVLVDALFQGKPVAFCPYIFVDNDAAIARGWAQGFPKRYGTILQTRLFAA<br>SGPASPKLAPGGRFGASASTAGQRIARGLVTLEKAVTDPAALGSRPTINLRHFPRLAAGQWERPAVHE<br>LVESVMDNFTVADAWMGKGELTLPECENEELSDLAPVRCGNGYRMSVSYSVTDLKTLVDHSAK |
| WP_028222253 | SEQ ID NO: 19 | MLKGYMAPLSPLGKASINPPPPWHYSGDVIGAEFWAEPEATAATLPPGLDPDPSTAGHGVVLFIDWQF<br>TAQDDEFLDPARYQYRECLFLVDAVHKGTPVMWCPYIYVDNDAALARGWAQGFPKKLASVYQTRT<br>FAAPSAAAAPVASGSRFGASLSAHGERLAEARITLRQPVADPKSLLARPTVNRRYFASLVAGLHDKPA<br>VDELVLSVTDNLSVADAWAGDAELLLFPDARGEEICAFGPVKVGGGFRFSLAYSVTDLKLLEDLTRLG<br>K |
| F2J6L6 | SEQ ID NO: 20 | MKRDMLTVDDVTGCWAIMPTPSKPNASDPSATDTVDLDETARVAEALVAAGVDGILSLGTLGECAT<br>TTWDEKQAYMRTLVETLRGRIPVFGGTTGLNTRDSIAMTRAAREIGVDGVMLGLPMWVQPDVPTAV<br>QFYRDVAAACPDVAICVYANPEAFKFEFPRAFWAQIAEIPQVVSAKYINIAALYTDLNLTRRRIRLMPL<br>DVDYYAAARVDPEACSAFWTSGAVCGPAPAIQLRDLVLEARQSGDWSKAKALTDRIGMTYRTLFPN<br>GSFKEFSVYNIGIEKARMDAAGWMTAGPVRPPYHIVPEAILEGGRESGRQWAKLAAELEREAGR |
| A0A0N0L9F6 | SEQ ID NO: 21 | MTQSYTTPLTPRGLSSIAPPPPWHYSGDFLVVEFWADPIAVANTLPAGLTVDSASPGHASAVFVDWQF<br>TGENDELLDPARYQYREFFILLDALHEGQPVSYCPYIFVDNDSALMRGLIQGFPKRLGAVHQTRTFSAP<br>SRAAAQVEPGARFAATASTAGQRIARGEVQLQHKIDDVSKLGFGARPLINLRHFPRLATGQHNDPAV<br>HELVVSVMDNPNIVDAWAGEGNLVFPQAEGEEVSDLAPTRVGAGFRASMSYTVTDLKALPNATIER |
| A0A1G9YWG7 | SEQ ID NO: 22 | MLRGFTVPKSPFGQAALTPPPPWHYAGDVVGVEFWTDPEATAATLPNGLSPDPNSNGHAVMMFLDW<br>QFTAQDDEYLEPARYQYREAFILVDAMYRDEPVMWCPYIYVDNDAALARGWTQGFPKKMGSIFQTR<br>SFAASGPAAAPVASGSRFGASLSAHGQRLAEACVTLHRPVENGLSLLSRPTVLLRYFPRLAAGYQDKP<br>AVNELAMSITDNLTVAGAWIGKGELNFPEASGEELNALAPKRIESGFRYSLSYSVSDLKILEDHGSQ |
| A0A2U1BT09 | SEQ ID NO: 23 | MSTKRTLMTANDVQGAWAIMPTSAKDGSESWRMTDSLDLDATVAAINGLIDSGVDGILTMGTYGEA<br>ATLTVDEKKRFMACLVETVAGRVPCFVGTTTLNTRDTIELTRYAADLGADGTMLGLPMWCAPTLPA<br>AVRFYRDVAEACPDMAQCIYANPEAFRFDFPPPPFWAQVADIPQVVSAKFTSVGHLIQNLEITRGKVRA<br>LPIELDYYAATRVDDDVCAFWSSGAVCGPTPTIALRDEITRAKTSGDWTKAKELTDKMWAAVTPMFP<br>AGGFREFSMYNIAIDKMRMQTAGWMRVGPTRPPYDMMPDHIRGGAVEAGKLWAELAKATVLAGA |
| A0A244DHE8 | SEQ ID NO: 24 | MSKQYAVPLSPRGLSSIAPPPPWHYSGDFLIVEFWADPAAVAATLPAGLSVDPSSPGHATALFVDWQF<br>TGQNDELLDPARYQYREFFLLVDALYEGQPVAYCPYIFVDNDSAMMRGLIQGFPKRLGAVHQTRTFA<br>APSLAAAQVAPGARFAATASTAGQRIARAEVKLTGKVDDPSTVSLAGRPIVNLRHFPRLAAGQHETPA<br>VHELVMSIMDDPRMADVWAGEGQLSLPVAEGEEISDLAPVRVGAGYRLSMSYTVTDLKTLSDGTQA<br>A |
| WP_107818191 | SEQ ID NO: 25 | MKKPLLTVDDVTGCWAIMPTPSKPNGSDINATDTVDLDETARAAEALVASGVNGILSQGTFGEAATT<br>TWEEKQAFLRTLVETVDGRVPVFGGTTSLNTRDTIRMTKAVREIGVDGVMLGPPMWCQPDVPTAVQ<br>FFRDVAEACPDTAICAYANPEAFKFDFPRAFWAQIAEIPQVVSAKYMNIAALYMDLNLTGRKIRLMPL<br>DMDYYAAARMDPEACTAFWTSGAICGPEPVIQLRDLVAEAHKTGDWGKAKALTDRIAATYRTLFPN<br>GSFKEFSVYNIGIEKARIDAAGWMTAGPCRPPYHVIPEPILDGAREAGLQWAKLVSALESEKTA |
| A0A023WZF9 | SEQ ID NO: 26 | MSNKTMKPARLTAEDIHGVWAIMPTPATPDASNWRSTNTVDLNETARIVEELIAAGVNGILSMGTFGE<br>CATLTWEEKRDYVSTIVETIRGRVPYFCGTTALNTREVIRQTREFMDMGASGTMLGVPMWVKMDLP<br>TAVQFYRDVAEAVPEAAIAIYANPEAFKFDFPRPFWAEMSKIPQVVTAKYLGIGMLDLDLKLAPNIRF<br>LPHEDDYYAAARINPERMTAFWSSGSMCGPATAIMLRDAVDQAKSSGDWIKAKAISDDMRAADSTL<br>FPRGDFSEFSKYNIGLEKARMDAAGWLTAGPCRPPYNIVPEDYIAGALKSGKAWAALHAKYSKELK |
| PYN48855 | SEQ ID NO: 27 | MLKGFNYPLTPKGKSTLNPSPPWHYSADFLDIEFWSEPSAVTAVLPAGLDPDPAANGHGHALFYDWQ<br>FAGENEEYLDPARYQYREFFLLVDALYEGQPISYCPYIFVDNDAAIARGWTQGYPKRLGQVFQTRYY |

Certain Sequences

| Uniprot or Genbank ID | Sequence ID Number | Sequence Information |
|---|---|---|
| | | AATGKAGPALAPGSKFAGSLTAGGQRLAEALVTLKEPVTDPALLKQRPIVNLLHYPQLAADKQDEPAI<br>HQLVENVPHDLKIEQAWIGDGSLTLPVCRSEELSDLAPVRCGKGIRASMAYIVDDLKTLKDLTKGFSL<br>LA |
| A0A421PAQ6 | SEQ ID NO: 28 | MLKGYTVPLSPKGEANIAPTPPWHYAGDIVGVEFFTEPSAAEATLPEGLDPDPDTSGRVVAFFVDWQF<br>NGEQDEYLDPVRSQYREFFVLVDARHQGRPVSWCPYIYVDNHHALARGWIQGFPKKAGNVHQTRVF<br>ASPGKASPTLSPGARFGATVSSDERTLAEARVTLEAPMEDPSALLARDTINLRHFPTLEVGKYDKPAV<br>HELVRMDYADQQVADVWTGTSEITLFPAVGEELADLAPVRPGMGFRASMSYNVTQVEPLG |
| WP_028217297 | SEQ ID NO: 29 | MNKPYAVPLSPRGLSSIAPPPPWHYAGDFILVEFWADPAAAAAVLPKGLSLDPASPGHATALFIDWQF<br>TGSNDEMLDPARYQYREFFVLVDALHEGKPVSFCPYIFVDNDSAMMRGLIQGFPKRYGQIHQTRTFA<br>ALSPAAAPVTAGTRFAATASAAGQRLAHAEVKLEAAVQDVSKLGIAGRPVVNQRYFPRLAAGQHDT<br>PAVNELVLSIMDNAQIADVWAGEGKLTFPFAQGEEIADLQPVRVGAGFRGSMAYSVTDLKTLVDHTK |
| WP_034507049 | SEQ ID NO: 30 | MLKGFTLPKSPFGQAALTPPPPWHYSGDVIGVEFRTDPSATAATLPNGLSPDPKSNGHAVMMFVDWQ<br>FTAQNDEYLDPARYRYREAFVLLDAVYRNAPVMWCPYVFVDNDAALARGWTQGFPKKIGSIFQTRT<br>YAAASPAAAPVAPGGRFGASLSAHGQRLAEARITLQEPVEDGLSLLSRPTVLLRYFPRLAAGYQDKPA<br>VNELTMAITDNLTVADAWIGDGELNLPEVHGEELHGLAPIAIESGFRYSLSYSVTDLKILEDHAS |
| Q47098 | SEQ ID NO: 31 | MENSFKAALKAGRPQIGLWLGLSSSYSAELLAGAGFDWLLIDGEHAPNNVQTVLTQLQAIAPYPSQPV<br>VRPSWNDPVQIKQLLDVGTQTLLVPMVQNADEAREAVRATRYPPAGIRGVGSALARASRWNRIPDYL<br>QKANDQMCVLVQIETREAMKNLPQILDVEGVDGVFIGPADLSADMGYAGNPQHPEVQAAIEQAIVQI<br>RESGKAPGILIANEQLAKRYLELGALFVAVGVDTTLLARAAEEALAARFGAQATAVKPGVY |
| P75682 | SEQ ID NO: 32 | MPQSALFTGIIPPVSTIFTADGQLDKPGTAALIDDLIKAGVDGLFFLGSGGEFSQLGAEERKAIARFAIDH<br>VDRRVPVLIGTGGTNARETIELSQHAQQAGADGIVVINPYYWKVSEANLIRYFEQVADSVTLPVMLYN<br>FPALTGQDLTPALVKTLADSRSNIIGIKDTIDSVAHLRSMIHTVKGAHPHFTVLCGYDDHLFNTLLLGG<br>DGAISASGNFAPQVSVNLLKAWRDGDVAKAAGYHQTLLQIPQMYQLDTPFVNVIKEAIVLCGRPVST<br>HVLPPASPLDEPRKAQLKTLLQQLKLC |
| P0A6L4 | SEQ ID NO: 33 | MATNLRGVMAALLTPFDQQQALDKASLRRLVQFNIQQGIDGLYVGGSTGEAFVQSLSEREQVLEIVA<br>EEAKGKIKLIAHVGCVSTAESQQLAASAKRYGFDAVSAVTPFYYPFSFEEHCDHYRAIIDSADGLPMV<br>VYNIPALSGVKLTLDQINTLVTLPGVGALKQTSGDLYQMEQIRREHPDLVLYNGYDEIFASGLLAGAD<br>GGIGSTYNIMGWRYQGIVKALKEGDIQTAQKLQTECNKVIDLLIKTGVFRGLKTVLHYMDVVSVPLC<br>RKPFGPVDEKYLPELKALAQQLMQERG |
| P23522 | SEQ ID NO: 34 | MNNDVFPNKFKAALAAKQVQIGCWSALSNPISTEVLGLAGFDWLVLDGEHAPNDISTFIPQLMALKG<br>SASAPVVRVPTNEPVIIKRLLDIGFYNFLIPPFVETKEEAELAVASTRYPPEGIRGVSVSHRANMFGTVAD<br>YFAQSNKNITILVQIESQQGVDNVDAIAATEGVDGIFVGPSDLAAALGHLGNASHPDVQKAIQHIFNRA<br>SAHGKPSGILAPVEADARRYLEWGATFVAVGSDLGVFRSATQKLADTFKK |
| P0A955 | SEQ ID NO: 35 | MKNWKTSAESILTTGPVVPVIVVKKLEHAVPMAKALVAGGVRVLEVTLRTECAVDAIRAIAKEVPEAI<br>VGAGTVLNPQQLAEVTEAGAQFAISPGLTEPLLKAATEGTIPLIPGISTVSELMLGMDYGLKEFKFFPAE<br>ANGGVKALQAIAGPFSQVRFCPTGGISPANYRDYLALKSVLCIGGSWLVPADALEAGDYDRITKLARE<br>AVEGAKL |
| Q6BF16 | SEQ ID NO: 36 | MQWQTKLPLIAILRGITPDEALAHVGAVIDAGFDAVEIPLNSPQWEQSIPAIVDAYGDKALIGAGTVLK<br>PEQVDALARMGCQLIVTPNIHSEVIRRAVGYGMTVCPGCATATEAFTALEAGAQALKIFPSSAFGPQYI<br>KALKAVLPSDIAVFAVGGVTPENLAQWIDAGCAGAGLGSDLYRAGQSVERTAQQAAAFVKAYREAV<br>Q |
| M9YI86 | SEQ ID NO: 37 | MPAPVLAATSPGAGRAIHLINPAMPAFRAAFEETLMKMPHNAFKAALQRPETQYGIWAGFASGYAAE<br>IVAGTGYDWMLIDGEHAPNSVPTILAQLQSVAPYPTQPVVRPVCGDPVLIKQLLDIGAQTLMVPMVES<br>AEQARALVRAMRYPPHGIRGVGGGLARATRWDGVPDYLNTAHEELCLIVQVESRAGVENVEAIAAV<br>EGVDAVFIGPADLSIGLGHPGDPGHPQVQELIHHAIEATRAAGKACGILAPHEEDARRYREWGCRFIA<br>VAIDISLLRQGALAGLARFRDTPASDAPSRTY |
| Q8NMD2 | SEQ ID NO: 38 | MASATFTGVIPPVMTPLHADGSVDVESLRKLVDHLINGGVDGLFALGSSGEAAFLTRAQRKLALTTIIE<br>HTAGRVPVTAGVIETTTARVIELVEDALEAGAEGLVATAPFYTRTHDVEIEEHFRKIHAAAPELPLFAY<br>NIPVSVHSNLNPVMLLTLAKDGVLAGTKDSSGNDGAIRSLIEARDDAGLTEQFKILTGSETTVDFAYLA<br>GADGVVPGLGNVDPAAYAALAKLCLDGKWAEAAALQKRINHLFHIVFVGDTSHMSGSSAGLGGFKT<br>ALAHLGIIESNAMAVPHQSLSDEETARIHAIVDEFLYTA |
| A0A1J6QD42 | SEQ ID NO: 39 | MDKNIIIGAMTALITPFKNGKVDEQSYARLIKRQIENGIDAVVPVGTTGESATLTHEEHRTCIEIAVETC<br>KETKVKVLAGAGSNATHEAVGLAKFAKEHGADGILSVAPYYNKPTQQGLYEHYKAIAQSVDIPVLLY<br>NVPGRTGCEISTDTIIKLFRDCENIYGVKEASGNIDKCVDLLAHEPRMMLISGEDAINYPILSNGGKVI<br>SVTSNLLPDMISTLTHFALDENYKEAKKINDELYNINKILFCESNPIPIKTAMYIAGLIESLEFRLPLCPPS<br>KENFAKIEEVMKKYKIKGF |
| Q8RBI5 | SEQ ID NO: 40 | MPVFKGSCVAIVTPFTENGVNFDKLGELIEWHIKEGTDAILICGTTGEASTMTDEEQKEAIKFTVEKVA<br>KRIPVIAGTGSNNTAHAIELSEYAQSVGADALLVITPYYNKTTQKGLVAHFTEIARHVDIPIIIYNVPSRT<br>SLNMLPETYLEVKKKAENVVGVKEASGDISQIAEIARIMGKSFEIYSGNDDQVIPIMSLGGLGVISVTA<br>NIIPAKIHEMTTAYLNGDIEKARDMQLELNPLNKALFIETNPIPVKTAMNLMGFGVGPLRLPLVEMSEK<br>NLEYLKSVLRQYGLLKEEN |

-continued

Certain Sequences

| Uniprot or Genbank ID | Sequence ID Number | Sequence Information |
|---|---|---|
| A3LZU9 | SEQ ID NO: 41 | MTISAALPKRGVYTPVPTFFKKDLHTIDYDSQIEHAKFLQQNGITGLVLLGSTGENSHLTRKERIELVST IHEELPDFPLMAGVAQNSVEDAIEEILQLKNAGAQHALVLPSSYFGASIKQQGIIDWYTEVADNASLPV LIYVYPGVSNNISIDPRTIKKLSAHPNIVGAKISHGDVSHHAIIGLDQEIAANQFITLTGLGQILLPVLVVG IQGTVDALCGAFPKIYVKLLENYDKGDLRAAAELQLVISRAEELVVKFGVVGIKKAIHFATGIGETYLG RAPLTQDVNDADWKSYNDYLLGIVSVESTL |
| Q4JC35 | SEQ ID NO: 42 | MEIISPIITPFDKQGKVNVDALKTHAKNLLEKGIDAIFVNGTTGLPALSKDEKRQNLNALYDVTHKLI FQVGSLNLNDVMELVKFSNEMDILGVSSHSPYYFPRLPEKFLAKYYEEIARISSHSLYIYNYPAATGYDI PPSILKSLPVKGIKDTNQDLAHSLEYKLNLPGVKVYNGSNTLIYYSLLSLDGVVASFTNFIPEVIVKQRD LIKQGKLDDALRLQELINRLADILRKYGSISAIYVLVNEFQGYDVGYPRPPIFPLTDEEALSLKREIEPLK RKIQELVH |
| O54288 | SEQ ID NO: 43 | MPEIITPIITPFTKDNRIDKEKLKIHAENLIRKGIDKLFVNGTTGLPSLSPEEKLENLKAVYDVTNKIIFQ VGGLNLDDAIRLAKLSKDFDIVGIASYAPYYYPRMSEKHLVKYFKTLCEVSPHPVYLYNYPTATGKDI DAKVAKEIGCFTGVKDTIENIIHTLDYKRLNPNMLVYSGSDMLIATVASTGLDGNVAAGSNYLPEVTV TIKKLAMERKIDEALKLQFLHDEVIEASRIFGSLSSNYVLTKYFQGYDLGYPRPPIFPLDDEEERQLIKK VEGIRAKLVELKILKE |
| F9VPG1 | SEQ ID NO: 44 | MDIVTPILTPFTKEGKIDVEKLKAHAKFLIDNGIDLLFVNGTTGLPALSKEEKLTTLKTIYDVTNKVIF QVGSLNINDVIDLVKASKDFDIVGIASYPPFYFPRLPEKFLLKYFTTIANYSPHSLYIYNYPLATGDISA KIVYQMKDLITGLKDTNQDLSHSLEYKILMPNLKVYNGSDSLVFYSLTSLDGSVTAASNYLPHVMKK MKEHITSGQVSKAIELQKLINKALDISRKYGQLSAIYYLVKEFLGYDVGYPRGPIFPLEEDEVKALLSEI QPVKKEIERAVS |
| P28304 | SEQ ID NO: 45 | MATRIEFHKHGGPEVLQAVEFTPADPAENEIQVENKAIGINFDTYIRSGLYPPPSLPSGLGTEAAGIVSK VGSGVKHIKAGDRVVYAQSALGAYSSVHNIIADKAAILPAAISFEQAAASFLKGLTVYYLLRKTYEIKP DEQFLFHAAAGGVGLIACQWAKALGAKLIGTVGTAQKAQSALKAGAWQVINYREEDLVERLKEITG GKKVRVVYDSVGRDTWERSLDCLQRRGLMVSFGNSSGAVTGVNLGILNQKGSLYVTRPSLQGYITTR EELTEASNELFSLIASGVIKVDVAEQQKYPLKDAQRAHEILESRATQGSSLLIP |
| P40783 | SEQ ID NO: 46 | MATRIEFHKHGGPEVLQTVEFTPAEPAEHEIQVENKAIGINFIDTYIRSGLYPPPSLPAGLGTEAAGVVS KVGNGVEHIRVGDRVVYAQSTLGAYSSVHNVTADKAAILPDAISFEQAAASFLKGLTVFYLLRKTYE VKPDEPFLFHAAAGGVGLIACQWAKALGAKLIGTVGSAQKAQRALDAGAWQVINYREESIVERVKEI TGGKKVRVVYDSVGKDTWEASLDCLQRRGLMVSFGNASGPVTGVNLGILNQKGSLYATRPSLQGYI TTREELTEASNELFSLIASGVIKVDVAENQRYALKDARRAHEVLESRATQGSSLLIP |
| Q0K2I0 | SEQ ID NO: 47 | MPRHGCLTIVTVAPMIAARAGHDNQETALAKAIRMYETGGPEVLRYEDAEVGDPGPGEVRIRHAAVG LNYADTYFRNGTYPVPLPGGMGVEAAGVVQAVGPGVTHVAEGDRVTYTGFINTLGAYSTERLVPAA PLIRLPEAISFETAAAMTMRGLTSAYLMRRIYPFQGGEAILLHAAAGGVGLIVSQWARLLGLTVIGTVS TEAKAEVARAHGCDHIINYSHEDVAKRVRELTDGAGVSVVFDSVGKSTFMASLDSLKRRGLMVCVG TASGTIPPFDPQLLARKGSVYLTRPALADYIADPAEKAELAAEVFGHVAAGRIRIEINQRYALQDAVQA HRDLESRKTTGSSIFVL |
| A0A1Z1SRY9 | SEQ ID NO: 48 | MAKRIQFAAHGNADVLELTSFTPAPLGDNEVQVANKAIGINYIDTYVRSGLYPVEHFPSGLGTEAAGV VIKTGAHVTSLKEGDRVVYAQSPLGAYSDTHNVPENKVARLPDNISFEQAAASFLKGLTVYYLFNETY KLRAGETFLFHAAAGGVGLIASQWAKAIGAKMIGTAGSDEKVAKAKAAGAWKVINYQTESIVERVL ALTNNQKVPVVYDSVGKATWLDSLHCLQRRGLMVSFGNASGAVTGVDLGILNKLGSLYTRPSISGY ITTREELDAASEALFTLIGRGKIDVSVPDNQKFALADAKAAHRYLESRQSQGSSLLIP |
| P43903 | SEQ ID NO: 49 | MAKRIQFAAYGGPEVLEYRDYQPAEPGPREVRVRNRAIGLNFIDTYYRSGLYPAPGLPSGLGSEGAGE VEAVGSEVTRFKVGDRVAYATGPLGAYSELHVLAEEKLVHLPDGIDFEQAAVMLKGLTTQYLLRQ TYELRGGETILFHAAAGGVGLFACQWAKALGVQLIGTVSSPEKARLARQHGAWETIDYSHENVARRV LELTDGKKCPVVYDSVGKDTWETSLDCVAPRGLLVSFGNASGPVTGVNLGILSQKGSLYVTRPTLGS YADTPEKLQAMADELFGLIERGDIRIEINQRFALAEAARAHTELAARRTTGSTVLLP |
| I7G8G0 | SEQ ID NO: 50 | MHAIEVAETGGPEVLNYIERPEPSPGPGEVLIKADAIGVNFIDTYFRSGLYPRELPFVVGTEVCGTVAAI GNDVAALKVGDRVVTANAVGAYADYCVAPADFVAYVPGVAPEAVASALLKGMTAHYLLKSTYP VQPSDTVLVHAGAGGVGLILTQWATSLGTRVITTASTPEKAELSRQAGAVEVLDYPDPDDPQPFASRV RELTGGAGVAAVYDGVGATTFDASLASLAVRGTLALFGASSGPVPPFDPQRLNAAGSVFLTRPTLAH HTRTADEFSWRAGELINAIADGSIKITVGGTYPLAEASRAHTDLQGRKTVGSIVLIP |
| Q142L2 | SEQ ID NO: 51 | MVKAIRFDKTGGPEVMKWVDVEVGEPGAGEIRVRQTAVGLNYIDVYFRTGLYPLPLPGGLGMEAAG EVTALGSGVSGLKVGDRIAYVARPPGAYAQERVLQAAQVVKVPDALTDEQAASVMLQGLTAQYLLR RTYPVKAGDTILIQAAAGGVGLLVCQWAKALGATVIGTVGSDEKAEIATAHGCDHAIVYTRENFTRR VREITNGAGVPVVYDSIGKDTFTGSLDCLAPLGMFVSFGNASGPLPPIDSSEFAGRGSLFFTRPTLFTYI AKRSDYEAMSTELFDVLVSGKVKTSINQRYALADVGRAHADLEGRRTTGSTVLLP |
| ALK19324.1 | SEQ ID NO: 52 | MPKAIRYDQPGGPDVMKWVDVEVGEPKAGEVRIRQHAVGLNYIDVYFRTGLYSQPLPGGLGMEAAG EVTAVGEGVTALKAGDRVAYVGQPPGAYAQERVMPAERLVKLPDGISYDDAASVMLQGLTAHYLL RRTYPVKAGDTILIHAAAGGVGLLVCQWAKALGATVIGTVGSDEKAALAKAHGCDHPIVYTRENPTQ RVKEITNGAGVPVVYDSIGKDTYIGSLDCLAPLGYFVSFGNASGPLPAIDSKEFSSRGSLFFTRPTLFSYI AKRADLESAAAELFDVILSGKVKTSINQRYPLAEVGRAHADLESRNTTGSTILVP |

Certain Sequences

| Uniprot or Genbank ID | Sequence ID Number | Sequence Information |
|---|---|---|
| Q5FTU6 | SEQ ID NO: 53 | MSSKPDILTIDPLVPVMKERLEKSFTLHPYTSLENLKNIAPAIRGITTGGGSGVPSEIMDALPNLEVISVN<br>GVGTDRINLDEARRRNIGVAITQNTLTDDVADMAVALMMAVMRSIVTNDAFVRAGKWPSATAPLGR<br>SLTRKKVGIAGFGHIGQAIAKRVSAFGMEVAYFNSHARPESTCHFEPDLKALATWCDVLILAVSGGPR<br>SANMIDRDTLDALGKDGFLVNIARGTVVDEAALLSALQEKRIAGAGLDVFQNEPNINPAFLSLPNTVL<br>QAHQASATVETRTTMANLVVDNLIAYFTDKTLLTPVI |
| A0A1V9IP73 | SEQ ID NO: 54 | MKILAYCVRPDEIDSFKNFSEKYGHTVDLIPDSFGPSVAHLAKGYDGISILGNDTCNREALEKIKDCGIK<br>YLATRTAGVNNIDFDAAKEFGINVANVPAYSPNSVSEFTVGLALSLTRKIPFALKRVELNNFALGGLIG<br>VELRNLTLGVIGTGRIGLKVIEGFSGFGMKKMIGYDIFENEKAKEYIEYKSLDEVYKEADIITLHAPLTD<br>DNYHMIGKESIAKMKDGVFIINAARGALIDSEALIEGLKSGKIAGAALDSYEYEQGVFHNNKMNEIMK<br>DDTLARLKSFPNVVITPHLGFYTDEAVSNMVEITLMNLQEFELKGTCKNQRVCK |
| T4VW93 | SEQ ID NO: 55 | MDNKALLKGVRVVELSSFVAAPCCAKLLGDWGAEVIKIEPLGGDGIRVMGGTFKSPCTDEENPMFEL<br>ENGNKKGISVNVKTKEGVEIIHKLLAKADIFITNVREQALSKIGLTYDQLKDEFPALIHAHILGYGENGP<br>LKDKPGFDYTAYFARGGVSQSLMEKGTSPCNTAAAFGDHYAGVSLTAGILAALYKKQMTGEGDRVT<br>VSLYHTALYGMGMMITTAQYGNKMPISRANPNSPLMTTYKCKDGKWIQLALIQYNKWLPKFCNVIN<br>RPEIMEDERFNDIKVMPLHVDEMVEIVGEAMLEKTLDEWSALLEEADLPEKVQSCEDILEDEQAWA<br>NDFLFKTKYANGNEGVLVNGPVKFKTMGIKEYTPAPRVGEHTEEVLKELGYTEEEILNMVNSQAVKL<br>DDSKELV |
| A0A0C7GD16 | SEQ ID NO: 56 | MDNRALLKGVRVVELSSFVAAPCCAKLLADWGAEVIKIEPLGGDGIRVMGGTFKSPCTDDENPMFEL<br>ENGNKKGISVNVKTKEGVEILHKLLSKSDIFVTNVREKALAKMGLTYDQLKDDFPGLIHAHILGYGEE<br>GPLKDKPGFDYTAYFARGGVSQSLMEKGTSPCNTAAGFGDHYAGISLTAGILAALYKKQITGEGDRV<br>TVSLFHTALYGMGMMITTSQYGNEMPISRTEPNSPLMTTYKCKDGKWIQLALIQYNKWLPKFCEVIN<br>RPEIMKDDRFNDIKVMPLHVDEMVKIVEKAMLEKTLDEWSDLLEEADLPEKVQSCEDIINDDQAWA<br>NDFLFKTTYENGNEGVLVNGPVKFKTMGIKEYEPAPRLGQHTEEVLKSIGYTEEEILDMVNSQAIKLD<br>DAKELV |
| A0A175L1W4 | SEQ ID NO: 57 | MTKEGLALEGVKVVELSSFVAAPSCSKLLADWGADVIKIEPIQGDNIRVVGGVYNSPARDDENPMFEL<br>ENGNKRGIAINTRSEKGKEVLGKLLKDADVFVTNVREKALQRSGLSYDQLKDKYPSLIHAHILGYGEK<br>GPLKDKPGFDYTAYFARGAVSTSLMEKGTSPANTNAGFGDHYAGMSLAAGILAALHRKTLTGKGDR<br>VTVSLYHTAIFGMGLMITTAQYGNKMPLSRRTPNNPLATTYRCKDDRWIQLALLKYDAWFPKFCKEV<br>INRPDLIEDLRFNKQSEVVKHVETFVGILEEEFIKKDLKEWADLLDKADLPYEKLQYCEDILEDEQAW<br>ANDYLFKTTYDSGNTGVLVNSPVKFSEAGMRTYKAAPKIGEDTEVVLTSLGYSKEEIEEMRKEESIK |
| A0A2X3BTQ9 | SEQ ID NO: 58 | MTKEGLALEGVKVVELSSFVAAPSCSKLLADWGADVIKIEPIQGDNIRVVGGVYNSPARDDENPMFEL<br>ENGNKRGVAINTRSEKGKEVLGKLLKDADVFVTNVREKALQRSGLSYDQLKDKYPSLIHAHILGYGE<br>KGPLKDKPGFDYTAYFARGAVSTSLMEKGTSPANTNAGFGDHYAGMSLAAGILAALHRKTLTGKGD<br>RVTVSLYHTAIFGMGLMITTAQYGNKMPLSRRTPNNPLATTYRCKDDRWIQLALLKYDAWFPKFCKE<br>VINRPDLIEDSRFNKQSEVVKHVETFVGVLEGEFIKKDLKEWADLLDKADLPYEKLQYCEDILEDEQA<br>WANDYLFKTTYDSGNTGVLVNSPVKFSEAGMRPYKAAPKIGEDTEAILTSLGYSKEEIEEMRKENAIK |
| Q5U924 | SEQ ID NO: 59 | MSEKKEARVVINDLLAEQYANAFKAKEEGRPVGWSTSVFPQELAEVFDLNVLYPENQAAGVAAKKG<br>SLELCEIAESKGYSIDLCAYARTNFGLLENGGCEALDMPAPDFLLCCNNICNQVIKWYENISRELDIPLI<br>MIDTTFNNEDEVTQSRIDYIKAQFEEAIKQLEIISGKKFDPKKFEEVMKISAENGRLWKYSMSLPADSSP<br>SPMNGFDLFTYMAVIVCARGKKETTEAFKLLIEELEDNMKTGKSSFRGEEKYRIMMEGIPCWPYIGYK<br>MKTLAKFGVNMTGSVYPHAWALQYEVNDLDGMAVAYSTMFNNVNLDRMTKYRVDSLVEGKCDG<br>AFYHMNRSCKLMSLIQYEMQRRAAEETGLPYAGFDGDQADPRAFTNAQFETRIQGLVEVMEERKKL<br>NRGEI |
| A0A2X3BK09 | SEQ ID NO: 60 | MADKKEVKKNAAKMINGILAKSYADAWKAKEEGKPVGWSTSVFPQELVETFGLDVLYPENQAAGV<br>AAKKESLSLCEAAESAGYSIDLCAYARTNFGLLEKGGSENLNMPKPDFICCCNNICNQVIKWYENIAK<br>ELDIPLIMIDTTFNNEDEVTENRIKYLRAQFEEAIKQLEKISGKKFDPKKFEEVMKISAENGKLWKYSM<br>SLPSGSFPSPMNGFDLFTYMAVIVCYRGKKETTEAFKLLISELEDNIKNKATSFRGEEKYRIMMEGIPC<br>WPYIGYKMRTLAGYGVNMTGSVYPHAWALQYEVNDLDGMAKAYSTMFNNVNLETMCKYRIDSLID<br>GNCDGAFYHMNRSCKLMSFIQYEMERKVFEETGIPYAGFDGDQADPRNFSKAQFETRLQGLVEVMEE<br>RKKGGNK |
| Q5U925 | SEQ ID NO: 61 | MYTMGLDIGSTASKGVILKNGEDIVASETISSGTGTTGPSRVLEKLYGKTGLAREDIKKVVVTGYGRM<br>NYSDADKQISELSCHARGVNFIIPETRTIIDIGGQDAKVLKLDNNGRLLNFLMNDKCAAGTGRFLDVM<br>AKIIEVDVSELGSISMNSQNEVSISSTCTVFAESEVISHLSENAKIEDIVAGIHTSVAKRVSSLVKRIGVQR<br>NVVMVGGVARNSGIVRAMAREINTEIIVPDIPQLTGALGAALYAFDEAKESQKEVKNI |
| A0A2X3BU19 | SEQ ID NO: 62 | MDNIKNILSKLEGIVKNPKKVVSDYKERTGNKVIGCFPVYTPEEIVYAADMLPIGIWGGDVEANLAKQ<br>YYPAFCCSIMQSCMEFGLKGIYEGLSAVIIPGMCDTLNCMGQNWKFAIKDIPYIALVHPQNRKLEAGV<br>EYLVEEYKHVKAKIEEIRGKEITEEEMQNSIDIYNEHRKVMRSFVDEAAKHPNTINNYQRNLVIKSGFF<br>MRKDEHTKIVKELNELLAVLPEEKYDGKKVLVTGILLDSKEMLDVFEENKLRIVADDLAQESRQFRT<br>DVPEGKNALDRLARQWSNIEGCSLAYDPKKIRGSMIAKEAKAKGIDGVVFAMMKFCDPEEYDYPIVK<br>KDIEKEDIPTTMIEVDQQNKSVEQIRTRIQTFSEIL |
| Q5U923 | SEQ ID NO: 63 | MEAILSKMKEVVENPNAAVKKYKSETGKKAIGCFPVYCPEEIIHAAGMLPVGIWGGQTELDLAKQYF<br>PAFACSIMQSCLEYGLKGAYDELSGVIIPGMCDTLICLGQNWKSAVPHIKYISLVHPQNRKLEAGVKY<br>LISEYKGVKRELEEICGYEIEEAKIHESIEVYNEHRKTMRDFVEVAYKHSNTIKPSIRSLVIKSGFFMRKE<br>EHTELVKDLIAKLNAMPEEVCSGKKVLLTGILADSKDILDILEDNNISVVADDLAQETRQFRTDVPAG |

-continued

Certain Sequences

| Uniprot or Genbank ID | Sequence ID Number | Sequence Information |
| --- | --- | --- |
| | | DDALERLARQWSNIEGCSLAYDPKKKRGSLIVDEVKKKDIDGVIFCMMKFCDPEEYDYPLVRKDIEDS<br>GIPTLYVEIDQQTQNNEQARTRIQTFAEMMSLA |
| A0A1V9IXA9 | SEQ ID NO: 64 | MYTMGLDIGSTTSKGVIIKDGEEIVASVLVPVGTGSGPLKLIKELKEKSNLTEKDIEKTVVTGYGRIQY<br>KDADKQISELSCHAKGVAFLIPGARTIIDIGGQDAKAMKLNDKGKLINFIMNDKCAAGTGRFLDVMA<br>GVLETDVSKLGEISEKSTKEVSISSTCTVFAESEVISHLSANAKKEDIVAGIHTSVVRRVSTLAMRVGIE<br>DQVVMVGGVARNKGIVKAMEKELGHDIKVPELAQLTGALGAAIYAFEETK |
| Q73Q47 | SEQ ID NO: 65 | MIVKPMVRNNICLNAHPQGCKKGVEDQIEYTKKRITAEVKAGAKAPKNVLVLGCSNGYGLASRITAA<br>FGYGAATIGVSFEKAGSETKYGTPGWYNNLAFDEAAKREGLYSVTIDGDAFSDEIKAQVIEEAKKKGI<br>KFDLIVYSLASPVRTDPDTGIMHKSVLKPFGKTFTGKTVDPFTGELKEISAEPANDEEAAATVKVMGG<br>EDWERWIKQLSKEGLLEEGCITLAYSYIGPEATQALYRKGTIGKAKEHLEATAHRLNKENPSIRAFVSV<br>NKGLVTRASAVIPVIPLYLASLFKVMKEKGNHEGCIEQITRLYAERLYRKDGTIPVDEENRIRIDDWEL<br>EEDVQKAVSALMEKVTGENAESLTDLAGYRHDFLASNGFDVEGINYEAEVERFDRI |
| A0R484 | SEQ ID NO: 66 | MTSDVHDATDGVTETALDDEQSTRRIAELYATDPEFAAAAPLPAVVDAAHKPGLRLAEILQTLFTGY<br>GDRPALGYRARELATDEGGRTVTRLLPRFDTLTYAQVWSRVQAVAAALRHNFAQPIYPGDAVATIGF<br>ASPDYLTLDLVCAYLGLVSVPLQHNAPVSRLAPILAEVEPRILTVSAEYLDLAVESVRDVNSVSQLVVF<br>DHHPEVDDHRDALARAREQLAGKGIAVTTLDAIADEGAGLPAEPIYTADHDQRLAMILYTSGSTGAP<br>KGAMYTEAMVARLWTMSFITGDPTPVINVNFMPLNHLGGRIPISTAVQNGGTSYFVPESDMSTLFEDL<br>ALVRPTELGLVPRVADMLYQHHLATVDRLVTQGADELTAEKQAGAELREQVLGGRVITGFVSTAPLA<br>AEMRAFLDITLGAHIVDGYGLTETGAVTRDGVIVRPPVIDYKLIDVPELGYFSTDKPYPRGELLVRSQT<br>LTPGYYKRPEVTASVFDRDGYYHTGDVMAETAPDHLVYVDRRNNVLKLAQGEFVAVANLEAVFSG<br>AALVRQIFVYGNSERSFLLAVVVPTPEALEQYDPAALKAALADSLQRTARDAELQSYEVPADFIVETE<br>PFSAANGLLSGVGKLLRPNLKDRYGQRLEQMYADIAATQANQLRELRRAAATQPVIDTLTQAAATIL<br>GTGSEVASDAHFTDLGGDSLSALTLSNLLSDFFGFEVPVGTIVNPATNLAQLAQHIEAQRTAGDRRPSF<br>TTVHGADATEIRASELTLDKFIDAETLRAAPGLPKVTTEPRTVLLSGANGWLGRFLTLQWLERLAPVG<br>GTLITIVRGRDDAAARARLTQAYDTDPELSRRFAELADRHLRVVAGDIGDPNLGLTPEIWHRLAAEVD<br>LVVHPAALVNHVLPYRQLFGPNVVGTAEVIKLALTERIKPVTYLSTVSVAMGIPDFEEDGDIRTVSPVR<br>PLDGGYANGYGNSKWAGEVLLREAHDLCGLPVATFRSDMILAHPRYRGQVNVPDMFTRLLLSLLITG<br>VAPRSFYIGDGERPRAHYPGLTVDFVAEAVTTLGAQQREGYVSYDVMNPHDDGISLDVFVDWLIRAG<br>HPIDRVDDYDDWVRRFETALTALPEKRRAQTVLPLLHAFRAPQAPLRGAPEPTEVFHAAVRTAKVGP<br>GDIPHLDEALIDKYIRDLREFGLI |
| A0QWI7 | SEQ ID NO: 67 | MTIETREDRFNRRIDHLFETDPQFAAAARPDEAISAAAADPELRLPAAVKQILAGYADRPALGKRAVEF<br>VTDEEGRTTAKLLPRFDTITYRQLAGRIQAVTNAWHNHPVNAGDRVAILGFTSVDYTTIDIALLELGA<br>VSVPLQTSAPVAQLQPIVAETEPKVIASSVDFLADAVALVESGPAPSRLVVFDYSHEVDDQREAFEAA<br>KGKLAGTGVVVETITDALDRGRSLADAPLYVPDEADPLTLLIYTSGSTGTPKGAMYPESKTATMWQA<br>GSKARWDETLGVMPSITLNFMPMSHVMGRGILCSTLASGGTAYFAARSDLSTFLEDLALVRPTQLNFV<br>PRIWDMLFQEYQSRLDNRRAEGSEDRAEAAVLEEVRTQLLGGRFVSALTGSAPISAEMKSWVEDLLD<br>MHLLEGYGSTEAGAVFIDGQIQRPPVIDYKLVDVPDLGYFATDRPYPRGELLVKSEQMFPGYYKRPEI<br>TAEMFDEDGYYRTGDIVAELGPDHLEYLDRRNNVLKLSQGEFVTVSKLEAVFGDSPLVRQIYVYGNS<br>ARSYLLAVVVPTEEALSRWDGDELKSRISDSLQDAARAAGLQSYEIPRDFLVETTPFTLENGLLTGIRK<br>LARPKLKAHYGERLEQLYTDLAEGQANELRELRRNGADRPVVETVSRAAVALLGASVTDLRSDAHFT<br>DLGGDSLSALSFSNLLHEIFDVDVPVGVIVSPATDLAGVAAYIEGELRGSKRPTYASVHGRDATEVRA<br>RDLAGLRKFIDAKTLSAAPGLPRSGTEIRTVLLTGATGFLGRYLALEWLERMDLVDGKVICLVRARSDD<br>EARARLDATFDTGDATLLEHYRALAADHLEVIAGDKGEADLGLDHDTWQRLADTVDLIVDPAALVN<br>HVLPYSQMFGPNALGTAELIRIALTTTIKPYVYVSTIGVGQGISPEAFVEDADIREISATRRVDDSYANG<br>YGNSKWAGEVLLREAHDWCGLPVSVFRCDMILADTTYSGQLNLPDMFTRLMLSLVATGIAPGSFYEL<br>DADGNRQRAHYDGLPVEFIAEEAISTIGSQVTDGFETFHVMNPYDDGIGLDEYVDWLIEAGYPVHRVD<br>DYATWLSRFETALRALPERQRQASLLPLLHNYQQPSPPVCGAMAPTDRFRAAVQDAKIGPDKDIPHVT<br>ADVIVKYISNLQMLGLL |
| D6Z860 | SEQ ID NO: 68 | MTQSHTQGPQASAAHSRLARRAAELLATDPQAAATLPDPEVVRQATRPGLRLAERVDAILSGYADRP<br>ALGQRSFQTVKDPITGRSSVELLPTFDTITYRELRERATAIASDLAHHPQAPAKPGDFLASIGFISVDYV<br>AIDIAGVFAGLTAVPLQTGATLATLTAITAETAPTLFAASIEHLPTAVDAVLATPSVRRLLVFDYRAGS<br>DEDREAVEAAKRKIADAGSSVLVDVLDEVIARGKSAPKAPLPPATDAGDDSLSLLIYTSGSTGTPKGA<br>MYPERNVAHFWGGVWAAAFDEDAAPPVPAINITFLPLSHVASRLSLMPTLARGGLMHFVAKSDLSTL<br>FEDLKLARPTNLFLVPRVVEMLYQHYQSELDRRGVQDGTREAEAAVKDDLRTGLLGGRILTAGFGSAP<br>LSAELAGFIESLLQIHLVDGYGSTEAGPVWRDGYLVKPPVTDYKLIDVPELGYFSTDSPHPRGELAIKT<br>QTILPGYYKRPETTAEVFDEDGFYLTGDVVAQIGPEQFAYVDRRKNVLKLSQGEFVTLAKLEAAYSSS<br>PLVRQLFVYGSSERSYLLAVIVPTPDALKKFGVGEAAKAALGESLQKIARDEGLQSYEVPRDFIIETDPF<br>TVENGLLSDARKSLRPKLKEHYGERLEAMYKELADGQANELRDIRRGVQQRPTLETVRRAAAAMLG<br>ASAAEIKPDAHFTDLGGDSLSALTFSNFLHDLFEVDVPVGVIVSAANTLGSVAEHIDAQLAGGRARPTF<br>ATVHGKGSTTIKASDLTLDKFIDEQTLEAAKHLPKPADPPRTVLLTGANGWLGRFLALEWLERLAPAG<br>GKLITIVRGKDAAQAKARLDAAYESGDPKLAGHYQDLAATTLEVLAGDFSEPRLGLDEATWNRLAD<br>EVDFISHPGALVNHVLPYNQLFGPNVAGVAEIIKLAITTRIKPVTYLSTVAVAAGVEPSALDEDGDIRT<br>VSAERSVDEGYANGYGNSKWGGEVLLREAHDRTGLPVRVFRSDMILAHQKYTGQVNATDQFTRLVQ<br>SLLATGLAPKSFYELDAQGNRQRAHYDGIPVDFTAESITTLGGDGLEGYRSYNVFNPHRDGVGLDEFV<br>DWLIEAGHPITRIDDYDQWLSRFETSLRGLPESKRQASVLPLLHAFARPGPAVDGSPFRNTVFRTDVQK<br>AKIGAEHDIPHLGKALVLKYADDIKQLGLL |
| P39135 | SEQ ID NO: 69 | MKIYGIYMDRPLSQEENERFMSFISPEKREKCRRFYHKEDAHRTLLGDVLVRSVISRQYQLDKSDIRFS<br>TQEYGKPCIPDLPDAHFNISHSGRWVICAFDSQPIGIDIEKTKPISLEIAKRFFSKTEYSDLLAKDKDEQT |

Certain Sequences

| Uniprot or Genbank ID | Sequence ID Number | Sequence Information |
| --- | --- | --- |
| | | DYFYHLWSMKESFIKQEGKGLSLPLDSFSVRLHQDGQVSIELPDSHSPCYIKTYEVDPGYKMAVCAAH<br>PDFPEDITMVSYEELL |
| AB213459.1 | SEQ ID NO: 70 | MAQYDVADRSAIVTGGGSGIGRAVALTLAASGAAVLVTDLNEEHAQAVVAEIEAAGGKAAALAGDV<br>TDPAFGEASVAGANALAPLKIAVNNAGIGGEAATVGDYSLDSWRTVIEVNLNAVFYGMQPQLKAMA<br>ANGGGAIVNMASILGSVGFANSSAYVTAKHALLGLTQNAALEYAADKVRVVAVGPGFIRTPLVEANL<br>SADALAFLEGKHALGRLGEPEEVASLVAFLASDAASFITGSYHLVDGGYTAQ |
| Q84H78 | SEQ ID NO: 71 | MRVFAVQPEDTTIHDLQVPTSPEGREVLLRVVRAGVCHTDTHLRAGGYDLGSRGMMSMKERGIEYP<br>MVLGHEVVGVVEKVGDGVESVQVGDIRLIYPWIGCGECRQCRAGHDNRCAAGKNLGVARHGGYAE<br>NILVPDEKYLVDIDGLDPSWAATLACSGLTAYSAVDKALPLEPDEPVVVFGAGGLGLTAIAILRSRGH<br>RNICAVDVAERNLALARDMGASSTVLSGTGSGADDIRGAAGGPAGAVIDFVNNGATATTAFEVLAKA<br>GIMIQVGLFGGEVTLPTALLALRMIRIEGSFVGTLVQMDLVRLAQRGELPHIPVVERSLSAAAVSQAL<br>DDLTAGGVAGRIVLTA |
| Q7WVD0 | SEQ ID NO: 72 | MHCYCVTHHGQPLEDVEKEIPQPKGTEVLLHVKAAGLCHTDLHLWEGYYDLGGGKRLSLADRGLKP<br>PLTLSHEITGQVVAVGPDAESVKVGMVSLVHPWIGCGECNYCKRGEENLCAKPQQLGIAKPGGFAEYI<br>IVPHPRYLVDIAGLDLAEAAPLACAGVTTYSALKKFGDLIQSEPVVIIGAGGLGLMALELLKAMQAKG<br>AIVVDIDDSKLEAARAAGALSVINSRSEDAAQQLIQATDGGARLILDLVGSNPTLSLALASSAARGGHIV<br>ICGLMGGEIKLSIPVIPMRPLTIQGSYVGTVEELRELVELVKETHMSAIPVKKLPISQINSAFGDLKDGN<br>VIGRIVLMHEN |
| D8GL45 | SEQ ID NO: 73 | MENFIFKNATEIIFGKDTENLVGSKVKEYSKSDKILFCYGGGSIKRSGLYDRVIKSLKENGIEFIELPGIK<br>PNPRLGPVKEGIRLCRENNIKFVLSVGGGSSADTAKAIAVGVPYKGDVWDFYTGKAEVKEALPVGVV<br>ITLPATGTESSNSSVIMNEDGWFKKGLNTVLIRPAFSIMNPELTFTLPEYQTACGACDIMAHIMERYFTN<br>VKHVDITDRLCEAALRNVINNAPIVLKDPKNYDARAEIMWTGTIAHNDVLSAGRIGDWASHKIEHELS<br>GETDIAHGAGLAIVFPAWMKYVYKHDINRFVQFAVRVWDVDLSYSSCEDIVLEGIRRMTAFFKSMGL<br>PVTLKEGSIGEDKIEEMANKCTDNGTKTVGQFVKLNKDDIVKILNLAK |
| Q04944 | SEQ ID NO: 74 | MLSFDYSIPTKVFFGKGKIDVIGEEIKKYGSRVLIVYGGGSIKRNGIYDRATAILKENNIAFYELSGVEPN<br>PRITTVKKGIEICRENNVDLVLAIGGGSAIDCSKVIAAGVYYDGDTWDMVKDPSKITKVLPIASILTLSA<br>TGSEMDQIAVISNMETNEKLGVGHDDMRPKFSVLDPTYTFTVPKNQTAAGTADIMSHTFESYFSGVEG<br>AYVQDGIAEAILRTCIKYGKIAMEKTDDYEARANLMWASSLAINGLLSLGKDRKWSCHPMEHELSAY<br>YDITHGVGLAILTPNWMEYILNDDTLHKFVSYGINVWGIDKNKDNYEIAREAIKNTREYFNSLGIPSKL<br>REVGIGKDKLELMAKQAVRNSGGTIGSLRPINAEDVLEIFKKSY |
| Q9R2F4 | SEQ ID NO: 75 | MNYPNIPLYINGEFLDHTNRDVKEVFNPVNHECIGLMACASQADLDYALESSQQAFLRWKKTSPITRS<br>EILRTFAKLAREKAAEIGRNITLDQGKPLKEAIAEVTVCAEHAEWWHAEECRRIYGRVIPPRNPNVQQLV<br>VREPLGVCLAFSPWNFPFNQAIRKISAAIAAGCTIIVKGSGDTPSAVYAIAQLFHEAGLPNGVLNVIWG<br>DSNFISDYMIKSPIIQKISFTGSTPVGKKLASQASLYMKPCTMELGGHAPVIVCDDADIDAAVEHLVGY<br>KFRNAGQVCVSPTRFYVQEGIYKEFSEKVVLRAKQIKVGCGLDASSDMGPLAQARRMHAMQQIVED<br>AVHKGSKLLLGGNKISDKGNFFEPTVLGDLCNDTQFMNDEPFGPIIGLIPFDTIDHVLEEANRLPFGLAS<br>YAFFTSSKNAHQISYGLEAGMVSINHMGLALAETPFGGIKDSGFGSEGGIETFDGYLRTKFITQLN |
| Q8GEZ8 | SEQ ID NO: 76 | MISKGFSTQTERINILKAQILNAKPCVESERAILITESFKQTEGQPAILRRALALKHILENIPITIRDQELIV<br>GSLTKEPRSSQVFPEFSNKWLQDELDRLNKRTGDAFQISEESKEKLKDVFEYWNGKTTSELATSYMTE<br>ETREAVNCDVFTVGNYYYNGVGHVSVDYGKVLRVGFNGIINEAKEQLEKNRSIDPDFIKKEKFLNSVII<br>SCEAAITYVNRYAKKAKEIADNTSDAKRKAELNEIAKICSKVSGEGAKSFYEACQLFWFIHAIINIESNG<br>HSISPARFDQYMYPYYENDKNITDKFAQELIDCIWIKLNDINKVRDEISTKHFGGYPMYQNLIVGGQNS<br>EGKDATNKVSYMALEAAVHVKLPQPSLSVRIWNKTPDEFLLRAAELTREGLGLPAYYNDEVIIPALVS<br>RGLTLEDARDYGIIGCVEPQKPGKTEGWHDSAFFNLARIVELTINSGFDKNKQIGPKTQNFEEMKSFDE<br>FMKAYKAQMEYFVKHMCCADNCIDIAHAERAPLPFLSSMVDNCIGKGKSLQDGGAEYNFSGPQGVG<br>VANIGDSLVAVKKIVFDENKITPSELKKTLNNDFKNSEEIQALLKNAPKFGNDIDEVDNLAREGALVY<br>CREVNKYTNPRGGNFQPGLYPSSINVYFGSLTGATPDGRKSGQPLADGVSPSRGCDVSGPTAACNSVS<br>KLDHFIASNGTLFNQKFHPSALKGDNGLMNLSSLIRSYFDQKGFHVQFNVIDKKILLAAQKNPEKYQD<br>LIVRVAGYSAQFISLDKSIQNDIIARTEHVM |
| Q8GEZ7 | SEQ ID NO: 77 | MSKEIKGVLFNIQKFSLHDGPGIRTIVFFKGCSMSCLWCSNPESQDIKPQVMFNKNLCTKCGRCKSQCK<br>SAAIDMNSEYRIDKSKCTECTKCVDNCLSGALVIEGRNYSVEDVIKELKKDSVQYRRSNGGITLSGGE<br>VLLQPDFAVELLKECKSYGWHTAIETAMYVNSESVKKVIPYIDLAMIDIKSMNDEIHRKFTGVSNEIIL<br>QNIKLSDELAKEIIIRIPVIEGFNADLQSIGAIAQFSKSLTNLKRIDLLPYHNYGENKYQAIGREYSLKELK<br>SPSKDKMERLKALVEIMGIPCTIGAE |
| A5VMB2 | SEQ ID NO: 78 | MKRQKRFEELEKRPIHQDTFVKEWPEEGFVAMMGPNDPKPSVKVENGKIVEMDGKKLEDFDLIDLYI<br>AKYGINIDNVEKVMNMDSTKIARMLVDPNVSRDEIIEITSALTPAKAEEIISKLDFGEMIMAVKKMRPR<br>RKPDNQCHVTNTVDNPVQIAADAADAALRGFPEQETTTAVARYAPFNAISILIGAQTGRPGVLTQCSV<br>EEATELQLGMRGFTAYAETISVYGTDRVFTGDDDTPWSKGFLASCYASRGLKMRFTSGAGSEVLMGY<br>PEGKSMLYLEARCILLTKASGVQGLQNGAVSCIEIPGAVPNGIREVLGENLLCMMCDIECASGCDQAY<br>SHSDMRRTERFIGQFIAGTDYINSGYSSTPNYDNTFAGSNTDAMDYDDMYVMERDLGQYYGIHPVKE<br>ETIIKARNKAAKALQAVFEDLGLPKITDEEVEAATYANTHDDMPKRDMVADMKAAQDMMDRGITAI<br>DIIKALYNHGFKDVAEAILNLQKQKVVGDYLQTSSIFDKDWNVTSAVNDGNDYQGPGTGYRLYEDK<br>EEWDRIKDLPFALDPEHLEL |

-continued

| Certain Sequences | | |
|---|---|---|
| Uniprot or Genbank ID | Sequence ID Number | Sequence Information |
| A5VMB1 | SEQ ID NO: 79 | MADIDENLLRKIVKEVLSETNQIDTKIDFDKSNDSTATATQEVQQPNSKAVPEKKLDWFQPVGEAKPG YSKDEVVIAVGPAFATVLDKTETGIPHKEVLRQVIAGIEEEGLKARVVKVYRSSDVAFCAVQGDHLSG SGIAIGIQSKGTTVIHQKDQDPLGNLELFPQAPVLTPETYRAIGKNAAMYAKGESPEPVPAKNDQLARI HYQAISAIMHIRETHQVVVGKPEEEIKVTFD |
| A5VMB0 | SEQ ID NO: 80 | MMSEVDDLVAKIMAQMGNSSSANSSTGTSTASTSKEMTADDYPLYQKHRDLVKTPKGHNLDDINLQ KVVNNQVDPKELRITPEALKLQGEIAANAGRPAIQKNLQRAAELTRVPDERVLEMYDALRPFRSTKQE LLNIAKELRDKYDANVCAAWFEEAADYYESRKKLKGDN |
| A5VMA9 | SEQ ID NO: 81 | MATEKVIGVDIGNSSTEVALADVSDSGQVHFINSGIAPTTGIKGTKQNLVGIRDSITQVLNKSNLTIDDI DLIRINEATPVIGDVAMETITETVVTESTMIGHNPNTPGGIGTGAGITVRLLDLLKKTDKSKNYIVVVPK DIDFEDVAKLINAYVASGYKITAAILRNDDGVLVDNRLNHKIPIVDEVAMIDKVPLNMLAAVEVAGPG QVISQLSNPYGIATLFGLTPEETKNIVPVSRALIGNRSAVVIKTPAGDVKARVIPAGKIIINGDTGKEEVG VSEGADAIMKKVSSFRHINNITGESGTNVGGMLENVRQTMADLTGKKNDEIAIQDLLAVDTQVPVEV RGGLAGEFSNESAVGIAAMVKSDHLQMEVIAKLIEKEFNTKVEIGGAEVESAIRGALTTPGTDKPIAIL DLGAGSTDASIINKENNTVAIHLAGAGDMVTMIINSELGLNDIHLAEDIKRYPLAKVENLFQIRHEDGS VQFFKDPLPSSLFAKVVVIKPDGYEPVTGNPSIEKIKLVRQSAKKRVFVTNALRALKYVSPTGNIRDPF VVIVGGSALDFEIPQLVTDELAHFNLVAGRGNVRGVEGPRNAVATGLILRYGEERRKRYEQR |
| A5VMA8 | SEQ ID NO: 82 | MNNDDSQRPSIVVGLENGITIPDSVKPLFYGIEEEQIPVSVRKININDTVERAYQSALASRLSVGIAFEGD HFIVHYKNLKENQPLFDMTINDKKQLRILGANAARLVKGIPFKEMANR |
| Q6QBS4 | SEQ ID NO: 83 | MYTVGDYLLDRLHELGIEEIFGVPGDYNLQFLDQIISREDMKWIGNANELNASYMADGYARTKKAAA FLTTFGVGELSAINGLAGSYAENLPVVEIVGSPTSKVQNDGKFVHHTLADGDFKHFMKMHEPVTAAR TLLTAENATYEIDRVLSQLLKERKPVYINLPVDVAAAKAEKPALSLEKESSTTNTTEQVILSKIEESLKN AQKPVVIAGHEVISFGLEKTVTQFVSETKLPITTLNFGKSAVDESLPSFLGIYNGKLSEISLKNFVESADF ILMLGVKLTDSSTGAFTHHLDENKMISLNIDEGIIFNKVVEDFDFRAVVSSLSELKGIEYEGQYIDKQYE EFIPSSAPLSQDRLWQAVESLTQSNETIVAEQGTSFFGASTIFLKSNSRFIGQPLWGSIGYTFPAALGSQI ADKESRHLLFIGDGSLQLTVQELGLSIREKLNPICFIINNDGYTVEREIHGPTQSYNDIPMWNYSKLPETF GATEDRVVSKIVRTENEFVSVMKEAQADVNRMYWIELVLEKEDAPKLLKKMGKLFAEQNK |
| KMK64081.1 | SEQ ID NO: 84 | MSAKRTLLTVDDVTGCWAIMPTPAKDDASDWRTEFSVDLDETARVANALVESGVDGILALGTFGEG ATLTWEEKEAYVRTVVDAVAGRVPFFAGTTSLNTRETIRQMRIVRDIGVDGVMLGIPMWVEADTATA VQFYRDVTEACPDVAICAYANPEAFKYEFGRAFWAQVSDLPQIVSAKYLNMGGLYPDLNLSKRRIRL MPLDVDYYAAARIDPDHCTAFWTSGAVCGPEPAILLRDLMEKARKSGDWAEEAKALTDRIGMTYKTL FPNGSFKEFSRYNISIEKIRMDAAGWMKAGPCRPPYHVTPEPILEGGRIAGQKWAELAESLRAGN |
| WP_070028041.1 | SEQ ID NO: 85 | MITAAEINGMYGIIPTPALPGAERLDARDTVDVDETARVVDRLIRDGVSGIIALGTTGECPALSEDDFD VVTDTVVEAVAGRVPVFVGATGAGGHGTARRLRKVAASGATGALLGLPMWQPLTTAMAVEYYAQ ASAAFPDLALMVYANARAFRYTFPVEFWQGVSSQAPTVTSAKVSRAPQLERMLEVTGKKVNFIPSDM VVHDFAARAPQTTTACWATAAGMGPEPSIALMDALRRGDSEAAGRAVAGIAWANEPLAHLFADQEI FASYNTQIEKSRIAAAGYCRPGPVRSPYHHLPEEYAAASAVCGQRWRELRERIAAGTNDQK |
| KZL92449.1 | SEQ ID NO: 86 | MIKGYSLPLTPKGTSNIVPAPPWHYVGNVLAIEYEAYAENIAAFLPEGLEFSSNQCAIYFIEWQYCSEFG EEHLDPVNSQYKETIVLVSANYKGTPVSYCPFIWVDQDLSLMRGLIQGWPKQLGETYITRPYNLPSKA ASNLEKGGKLGATLSVKGRRLVDARITVNKKTETLPNPTFAQAINLRHFPELVLGRHNQPLIHELVQL KSRDLHISPIWKGDAILNFFDHPFIELSDLKPTKVKNSYYFSAALTVDDLSQLEV |
| A0A1G9R408 | SEQ ID NO: 87 | MRAVVVRSHGGPEVLVAEELDRPEPGPGAVLVDVAAAGVNYIDTYHREGVYPIPTPFTLGLEGAGTV AALGEGVTEFAVGDRVAWASAIGSYAQQVAAPAAQLVPVSTVDLEIAAGAMLQGMTAHYLTASTH PIAEGDVALVHAAAGGMGLLLTQMIKARGGRVIGTVSTAEKEKLAREAGADEVIRYTEQDVAQRVRE LTDGVGVHVVYDGVGKDTFDASLASLRPRGLLALYGAASGAVPPFDAQRLNAGGSLFLTRPSLGHHT ATREELLWRAGEVFDAIQAGELDIAIGGRYALDSARQAHEDLQGRRTTGKLLLTTS |
| G4Q8R5 | SEQ ID NO: 88 | MKAIVMKEFGGPEVLKYVDVPDPVPEANEVLIKLAFCGVNPNETYVRTGTYNFYKPELPYTPGYDGA GVIEKVGAGVTHVKVGDRVFVAALLAKRNTGTYAQKVVCDADSVHKLPDFISFEEGASFGIPAMAAY RALFHRAHIKAGEIVMIHGAEGGVGSLAVQMAKAVGAIVIGTGTTPEGLDIVRSFGADYAIYHLKADN QDELMELTKGKGPDVIIEFLANVNLQTDLKVIAKYGRIVVVGNRGTIEINPRLAMANESTILGMALWN APANEYRESLFALRAFMQSGAVRAKVGKQLLLKDAAQAHNEIINGLAKGKMILKIE |
| ANA98723.1 | SEQ ID NO: 89 | MRAIEVPVTGGPEVLTLVEKTAPTPGPGEVLIDVDAVGVNFRDIYLRNGSYAAPLPHIPGSEVTGVVSA VGEGVENLAPGDRVASPVAAWGYAESTTAPADYTAKVPAGLSSEVAASALLQGITAHYLLTSVYPVA AGDTVLVHAGAGGMGLLLTQWASHRGVRVITTVSSAAKEKLSREAGAAEVLPYPDPTDPAEFAEKIL ELTSGEGVAVAYDGVGKSTFEASLAAVRVRGLIALYGAASGQVPPFDPQRLTAKSAVLTRPTMGHFIR TPAEFAWRADDVLDLVSRGTLKITVGASYPLEQAAQAHIDLEARKTTGSVVLVP |
| K0EUQ3 | SEQ ID NO: 90 | MRAIQVSEHGGPEVLHHVELPDPTIDADQLLVDVQATGINFIDTYIRTGRYPQDVPYVPGSEATGVVA EVGANVTEFAVGDRVAWASAPGSYAERVARVADVAKVYPLAGVAASALLQGMTAHYLLESIYT PEPGETVLVHAGAGGVGLILTQLAVARGARVITTVSSDVKEKLSREAGATEVYGDDLADEVRTLT DGVGVAAVYDGVGASTFEASLRSLRVRGMLALFGAASGPVPPFDLQRLNGAGSLFVTRPSLAFYTRD RAELLWRATDIFTAIAEGTLQIRIGATYPLAEAEQAHRDLESRKTTGSIVLLP |
| A0A061CRS8 | SEQ ID NO: 91 | MAKRIQFSQHGGSEVLEYRDYQPAAPGPREVRVANKAIGLNFIDTYFRSGLYQPPALPSSLGTEGAGV VEAIGSEVEGLKVGDRVAYATGPLGAYSELHVLPADNLVHLPDSISFEQAAAVMLKGLTVQYLLRQT |

-continued

Certain Sequences

| Uniprot or Genbank ID | Sequence ID Number | Sequence Information |
|---|---|---|
| | | YELKGGETILFHAAAGGVGSFACQWAKALGVNLIGTVSSAKKAALAKELGAWETIDYSHENVVQRV LELTDGAKCPVVYDGVGKDTWETSLDCVAPRGLLVSFGNASGAVTGVNLGILAQKGSLYVTRPTLAS YANTPQNLQAMADELFAMISSGKLQVDISNRYALKDAAAAQDALSSRQTTGSTILLP |
| Q9A212 | SEQ ID NO: 92 | MLAVQAVRTGGPEVLEVVDLPLPSPGPGQILVRHQAVGLNYIDTYHRSGLYPVKTPLVIGLEAAGVVE SVGEAVTRFKVGDRVAYNGTMGAYAQAAVVPAERAVLVPDGVSLEVAAAALLKGMTAEFLVRRCF HVKQGDWVLVHAAAGGVGQILVQWCKALGATVVATVGSTAKATIARDLGADHVIDYSHEDVAARV AELTGGRGVAVVYDGVGKDTWEASLASLARRGMLVTFGNASGPAPAFPPLALAPKSAFVTRPKLFD YIVTTEELDESAQALFAVIASGAIKIDIGQTFPLAEARAAHEALEGRRTTGATLLLP |
| A0A1I6RWW2 | SEQ ID NO: 93 | MRAIRVTSHGGPEALEVSEVEVPEPGPGQLLVDVAASGVNFIDTYQRSGVYSVPLPFTPGSEGAGEIVA VGPDVDGFAVGERVAWAMTPGSYAEKALVPARAAVKIPDGVDTRTAAAATLQGMTAHFLVTSTHEI KTGETALVHAAAGGMGLLLTQLIKSKGGNVIGTVSTDEKERLAREAGADEIIRYTEADVAAEVKDLT DGRGVDVVYDGVGKSTFEASLASLRPRGTLALFGGASGQVPPFDPQRLNGAGSLFLTRPSLAHHVLTR EELEWRAGEVFGWISSGALHIRVSGTYSLEDAARAHEDLEGRRTTGKLLILP |
| WP_ 026197277.1 | SEQ ID NO: 94 | MTNAIRVHETGGPEVLRLDEVTREAGAGQLLVRVEAAGVNFIDTYQRSGVYSVELPHALGLEGAGTV EAVGDEASDFTPGDRVAWWWAAGSYAEHTVVPVERAVRIPDDVDTKTAGALMLQGLTAHYLLRST YRVDETDTVLVHAAAGGVGLLLVQLAKSLGARVIATASTAEKRALATGAGADEVLGYEGFDTKLRE LTGGIGVSVVYDGVGKDTFDASLASIRPRGYLVLFGGSSGQVPPFDLQRLNAAGSLFVTRPSLGPYIAD RTEYEWRVGELFEAVGNGSLNVRIGGSYPLAEAANAHRDLEGRKTTGKLLLVP |
| Q5NKZ3 | SEQ ID NO: 95 | MSEAYAIIAEKAGGPEVLKKPLDLGKMKPEAGQVLLRHQAIGLNFIDIYHRSGLYKQDFPANLGCEA AGVIEWGDKVKGFKAGDRVAVFTSKPGAYATHRIVDASELVALPDDISAETAAAVLLKGMTSWML AEKCLAHAAIEGEAPKVMVLAAAGGVGSLLIPWLKYLGVTVFAHTSTEEKAAKVKANGADYVTTLP YSDLPDWVRKQNHGEGVHAVLDSVGADSWKSSIASLRKKGLWVVYGNASGPVPALSPLELSKAGSI YTSRPRLIDYVDNSVDLTTASQKLFALLRKNILKVEINQRFPLTEVAKAHQLLESRKTTGSTVLIP |
| WP_ 012333034.1 | SEQ ID NO: 96 | MPKAIRVHEYGGPEVMRYEEVDLPAPGPGQIRVRQRAVGVNFIDIYFRSGLYKAPQLPFTPGNEGTGE VVAVGEGVAGLAVGDRVAYGSAAQTYAQEAVIEARMAVKVPDGIDDATAAAMMLKGLTAQYLLR KTYRVQPGDTILFHAAAGGVGLIATQWKHLGATVIGTVGSRDKAELAKQHGCDHVILYRDEDFAA RVKEITGGKGCAVVYDGVGQATYPASLDCLRPFGMFVSFGNASGVIENFNIGLLGPKGSLYATRPTLF THVAERASLEAMADDLFGVVSGAVRIPVHSRVPLAEAAQVHRDLAGRQTTGATVLIP |
| WP_ 136898000.1 | SEQ ID NO: 97 | MAKAIRFEKTGGPEVMQWVDVEVGDPGSGEVRIKQHAVGLNYIDVYFRTGLYPMPLPGGLGMEAAG EVTAVGPDVEGLRVGDRVAYVARPPGAYAQERVLPAAALVKLPGALGYDDAASAMLQGLTAQYLL RRTYRVKAGDTILIQAAAGGVGLFVCQWAKALGATVIGTVSSDEKAELAKAHGCDYPIVYTRESFTK RVKEITGGAGVPVVVDSIGKDTFTGSLDCLAPLGLFVSFGNASGPLPPIDSSEFAGRGSLFFTRPTLFTHI AKRSDYDAMAAELFDVIVSGKVKTMIRQRFPLAEVGQAHADLEARRTTGSTILIP |
| WP_ 003431407.1 | SEQ ID NO: 98 | MKILVFGARDYEEPVIKKWSEEHKDVQVDIYPENMTEENVVKAKGYDGISIQQTNYIDNPYIYETLKD AGVKVIASRTAGVDMIHFDLVNENGLIVTNVPSYSPNAIAELAVTQAMNLLRKTPLVKKKVCEGDYR WIAELLGTEVRSITVGVIGTGKIGATSAKLFKGLGANVIAFDQYPNSDLNDILTYKDSLEDLLKEADLIT LHTPLLEGTKHMINKDTLAIMKDGAYIVNTGRGGLINTGDLIEALESGKIRAAALDTFETEGLFLNKKM NPGELTDPEINKLLSMEQVIFTHHLGFFTSTAIENIVYSSLSSAVEVIKTGTATNRVN |
| BAL51292.1 | SEQ ID NO: 99 | MRITIAGAGAMGSRFGLMLHKGGNEVTLIDGWPEHVKAIKDHGLRANYNGEELTAHLSVELQSEISS KEKTDLIILFTKAMQLDKMLQDIKPLIDEHTKVLCLLNGIGHEDTIEKYVSKNNIFIGNTMWTAGLEGP GKAKLFGDGSVELQNLISGEEETAKKLAEILSESGLNAKYSNNIHYSIYRKACVNGTMNGLCTILDTN MAGLGETKPAHDMVVTIVNEFAAVAKFENVNLDIAEVVQHVETCFDPATIGLHYPSMYQDLIKNNRL TEIDYINGAVSRKGKKYNVATPYCDFLTQLVHSKEELLKAK |
| AKC64094.1 | SEQ ID NO: 100 | MKILMYSVREHEKPAIKKWLEANPGVQIDLSDEALSEDTVCKVKDYDGIAIQQTNSIGGETVYSTLKK YGIRQIASRTAGVDMIDLKMASENNIIVTNVPAYSPNAIAELAVTHTMNLLRNIKTVNKRIAFGDYRW SADLIAREVRSITVGVVGTGKIGRTSAKLFKGLGANVIGYDAYPDKKLEENNLLTYKDSLEDLLKEAD VVTLHTPLLESTKHMINKNNLKYMKPNAFIVNTGRGGIINTEDLIEALEENKIAGAALDTFENEGLFLN KVIDPTKIPDPQLDKLLKMDQVLITHHVGFFTTTAVQNMVDTSLDSVMEVLKTNDSVNKAN |
| WP_ 002876862.1 | SEQ ID NO: 101 | MTKIAMYNVSPIEVPYIEDWAKKNDVEIKTTDQALTSATVDLAEGCSSVSLKPLGPVDEEVVYQKLSE YGVKCIGLRIVGFNTINFDWTKKYNLLVTNVPVYSPRAIAEMTVTQAMYLLRKIGEFRYRMDHDHF TWPSNLISNEIYNLTVGLIGVGHIGSAVAEIFSAMGAKVIAYDVAYNPEFEPFLTYTDFDTVLKEADIVS LHTPLLPSTENMIGEKQLKEMKKSAYLINCARGELVDTGALIKALQDGEIAGAGLDTLAGESSYFGHT GLTDSEIPEDYKTLAKMPNVVITPHSAFYTETSIRNMVQICLTDQLTIAKGGRPRSIVNL |
| AGP69017.1 | SEQ ID NO: 102 | MTKILMYTVRPDERAAIDAWVAANDIQVDTNTVEFGPDTVDLAKGYDGVVIQQHGAIPEEMVYQKL KAFGIKQLTLRITGYDIVNLDAATANGLVVTNVPAYSPRSVSELVLAQVMRLIRHLGEASAREAKDDY SWTGLEAPEIHNLTVGIIGAGKIGSAVARIFRALGATVISWDPVKRPELADTVSYVDLNTLLTTSDVVT VHTPLDGLTTHHLIDADALRKMKSTAYLINAARGPIVDTEALIKALNDHTIAGAALDTIEGEAGIFGEDR SQTLVDNQTLETLKAMPNVEISPHIGFYTDAAVKNMIDISLDDVKTILEGGKSAHQVN |
| WP_ 003640741.1 | SEQ ID NO: 103 | MKIIAYAVRDDERPFFDTWMKENPDVEVKLVPELLTEDNVDLAKGFDGADVYQQKDYTAEVLNKLA DEGVKNISLRNVGDNLDVPTVKARGLNISNVPAYSPNAIAELSVTQLMQLLRQTPLFNKKLAKQDFR WAPDIAKELNTMTVGVIGTGRIGRAAIDIFKGFGAKVIGYDVYRNAELEKEGMYVDTLDELYAQADV |

| Uniprot or Genbank ID | Sequence ID Number | Sequence Information |
|---|---|---|
| | | ITLHVPALKDNYHMLNADAFSKMKDGAYILNFARGTLIDSEDLIKALDSGKVAGAALDTYEYETKIFN KDLEGQTIDDKVFMNLFNRDNVLITPHTAFYTETAVHNMVHVSMNSNKQFIETGKADTQVKFD |
| AKC64095.1 | SEQ ID NO: 104 | MKILAYCVRPDEIDSFKNFSEKYGHTVDLIPDSFGPSVAHLAKGYDGISILGNDTCNREALEKIKDCGIK YLATRTAGVNNIDFDAAKEFGINVANVPAYSPNSVSEFTVGLALSLTRKIPFALKRVELNNFALGGLIG VELRNLTLGVIGTGRIGLKVIEGFSGFGMKKMIGYDIFENEKAKEYIEYKSLDEVYKEADIITLHAPLTD DNYHMIGKESIAKMKDGVFIINAARGALIDSEALIEGLKSGKIAGAALDSYEYEQGVFHNNKMNEIMK DDTLARLKSFPNVVITPHLGFYTDEAVSNMVEITLMNLQEFELKGTCKNQRVCK |
| AKC64094.1 | SEQ ID NO: 105 | MKILMYSVREHEKPAIKKWLEANPGVQIDLSDEALSEDTVCKVKDYDGIAIQQTNSIGGETVYSTLKK YGIRQIASRTAGVDMIDLKMASENNIIVTNVPAYSPNAIAELAVTHTMNLLRNIKTVNKRIAFGDYRW SADLIAREVRSITVGVVGTGKIGRTSAKLFKGLGANVIGYDAYPDKKLEENNLLTYKDSLEDLLKEAD VVTLHTPLLESTKHMINKNNLKYMKPNAFIVNTGRGGIINTEDLIEALEENKIAGAALDTFENEGLFLN KVIDPTKIPDPQLDKLLKMDQVLITHHVGFFTTTAVQNMVDTSLDSVMEVLKTNDSVNKAN |

The invention claimed is:

1. A method, comprising:
   contacting pyruvate and HO—CH$_2$—CH$_2$—CHO (3-hydroxy propanal) with a polypeptide having the sequence of SEQ ID NO: 24 so that HO—CH$_2$—CH$_2$—CH=CH—C(O)—COOH (6-hydroxy-2-oxo-3-hexenoic acid) or a salt thereof is produced.

2. The method of claim 1, wherein the polypeptide is in a microbe.

3. The method of claim 2, wherein the microbe is engineered to express the polypeptide.

4. The method of claim 3, wherein the microbe is *E. coli*.

5. The method of claim 2, wherein the contact is performed in a culture comprising the microbe, pyruvate, and 3-hydroxy propanal.

6. The method of claim 2, wherein (E)-6-hydroxy-2-oxo-3-hexenoic acid or a salt thereof is produced.

7. The method of claim 3, wherein the contact is performed in a culture comprising the microbe, pyruvate and 3-hydroxy propanal.

8. The method of claim 3, wherein (E)-6-hydroxy-2-oxo-3-hexenoic acid or a salt thereof is produced.

9. The method of claim 4, wherein the contact is performed in a culture comprising the microbe, pyruvate and 3-hydroxy propanal.

10. The method of claim 4, wherein (E)-6-hydroxy-2-oxo-3-hexenoic acid or a salt thereof is produced.

11. The method of claim 5, wherein (E)-6-hydroxy-2-oxo-3-hexenoic acid or a salt thereof is produced.

12. The method of claim 9, wherein (E)-6-hydroxy-2-oxo-3-hexenoic acid or a salt thereof is produced.

13. The method of claim 7, wherein (E)-6-hydroxy-2-oxo-3-hexenoic acid or a salt thereof is produced.

14. The method of claim 1, wherein (E)-6-hydroxy-2-oxo-3-hexenoic acid or a salt thereof is produced.

* * * * *

SEQUENCE LISTING

<160> NUMBER OF SEQ ID NOS: 106

<210> SEQ ID NO 1
<211> LENGTH: 265
<212> TYPE: PRT
<213> ORGANISM: Streptomyces bingchenggensis

<400> SEQUENCE: 1

```
Met Lys Gly Tyr Thr Val Pro Leu Ser Pro Arg Gly Ile Ala Asn Leu
1               5                   10                  15

Ala Pro Ala Pro Pro Trp His Tyr Ala Gly Thr Val Val Gly Val Glu
            20                  25                  30

Phe Phe Thr Asp Pro Ala Ala Ala Ala Thr Leu Pro Glu Gly Leu
        35                  40                  45

Thr Pro Asp Pro Asp Ser Ala Gly Arg Gly Val Ala Met Phe Ile Asp
    50                  55                  60

Trp Gln Tyr Ser Ser Thr Gly Leu Glu Tyr Leu Asp Pro Ala Arg Ser
65                  70                  75                  80

Gln Tyr Arg Glu Phe Leu Ile Thr Leu Asp Ala His Cys Asn Gly Ala
                85                  90                  95

Pro Val Ala Trp Cys Pro Tyr Ile Tyr Val Asp Asn Asp Ala Ala Met
            100                 105                 110

Ala Arg Gly Trp Val Gln Gly Phe Pro Lys Lys Leu Gly Ala Val His
        115                 120                 125

Gln Thr Arg Ala Tyr Ser Val Gly Gly Pro Gly Thr Pro Val Leu Gly
    130                 135                 140

Pro Gly Gly Gln Phe Gly Ala Thr Ala Ser Ser Ala Gly Gln Arg Ile
145                 150                 155                 160

Ala Glu Ala Lys Ile Thr Leu Glu Gln Pro Val Asp Pro Ala Ala
                165                 170                 175

Leu Met Ser Arg Pro Val Ile Asn Leu Arg His Phe Pro Arg Leu Ala
            180                 185                 190

Ala Gly Gln His Asp Gln Pro Ala Val His Glu Leu Met Ser Val
        195                 200                 205

Leu Asp Asp Thr Ala Val Ser Asp Ala Trp Val Gly Thr Ala Asp Leu
    210                 215                 220

Ala Phe Leu Pro Ala His Gly Glu Glu Leu Ala Asp Leu Pro Val Arg
225                 230                 235                 240
```

```
Arg Thr Gly Lys Gly Phe His Phe Asp Leu Ala Tyr Thr Val Thr Asp
                245                 250                 255

Leu Met Thr Leu Ala Asp His Ser Ala
        260                 265

<210> SEQ ID NO 2
<211> LENGTH: 334
<212> TYPE: PRT
<213> ORGANISM: Pseudomonas putida

<400> SEQUENCE: 2

Met Ser Asn Lys Ile Met Lys Thr Ser Arg Leu Thr Ala Glu Asp Ile
1               5                   10                  15

Asn Gly Ala Trp Thr Ile Met Pro Thr Pro Ser Thr Pro Asp Ala Ser
            20                  25                  30

Asp Trp Arg Ser Thr Ala Thr Val Asp Leu Glu Glu Thr Ala Arg Ile
        35                  40                  45

Val Glu Glu Leu Ile Ala Ala Gly Val Asn Gly Ile Leu Ser Met Gly
    50                  55                  60

Thr Phe Gly Glu Cys Ala Thr Leu Thr Trp Asp Glu Lys Arg Asp Tyr
65                  70                  75                  80

Val Ser Thr Ile Val Glu Thr Ile Arg Gly Arg Val Pro Tyr Phe Cys
                85                  90                  95

Gly Thr Thr Ala Leu Asn Thr Arg Glu Val Ile Arg Gln Thr Arg Glu
            100                 105                 110

Leu Ile Asp Ile Gly Ala Asn Gly Thr Met Leu Gly Val Pro Met Trp
        115                 120                 125

Val Lys Met Asp Leu Pro Thr Ala Val Gln Phe Tyr Arg Asp Val Ala
    130                 135                 140

Asp Ala Val Pro Glu Ala Ala Ile Ala Ile Tyr Ala Asn Pro Glu Ala
145                 150                 155                 160

Phe Lys Phe Asp Phe Pro Arg Pro Phe Trp Ala Glu Met Ser Lys Ile
                165                 170                 175

Pro Gln Val Val Thr Ala Lys Tyr Leu Gly Ile Gly Met Leu Asp Leu
            180                 185                 190

Asp Leu Arg Leu Ala Pro Asn Ile Arg Phe Leu Pro His Glu Asp Asp
        195                 200                 205

Tyr Tyr Ala Ala Ala Arg Ile Asn Pro Glu Arg Ile Thr Ala Phe Trp
    210                 215                 220

Ser Ser Gly Ala Met Cys Gly Pro Ala Thr Ala Ile Met Leu Arg Asp
225                 230                 235                 240

Glu Val Val Arg Ala Lys Ser Thr Gly Asp Trp Ala Lys Ala Lys Ala
                245                 250                 255

Ile Ser Asp Asp Met Arg Ala Ala Asp Ser Thr Leu Phe Pro Arg Gly
            260                 265                 270

Asp Phe Ser Glu Phe Ser Lys Tyr Asn Ile Gly Leu Glu Lys Ala Arg
        275                 280                 285

Met Asp Ala Ala Gly Trp Leu Lys Ala Gly Pro Cys Arg Pro Pro Tyr
    290                 295                 300

Asn Leu Val Pro Glu Asp Tyr Leu Ala Gly Ala Gln Lys Ser Gly Lys
305                 310                 315                 320

Ala Trp Ala Ala Leu His Ala Lys Tyr Ser Asn Glu Leu Lys
                325                 330
```

```
<210> SEQ ID NO 3
<211> LENGTH: 332
<212> TYPE: PRT
<213> ORGANISM: Nocardioides sp.

<400> SEQUENCE: 3
```

| Met | Thr | Ser | Pro | Ala | Val | Thr | Ser | Ala | Asp | Ile | Thr | Gly | Leu | Val | Gly |
|---|---|---|---|---|---|---|---|---|---|---|---|---|---|---|---|
| 1 | | | | 5 | | | | | 10 | | | | | 15 | |

| Ile | Val | Pro | Thr | Pro | Ser | Lys | Pro | Gly | Ser | Glu | Ala | Pro | Asp | Ala | Val |
|---|---|---|---|---|---|---|---|---|---|---|---|---|---|---|---|
| | | | 20 | | | | | 25 | | | | | 30 | | |

| Asp | Thr | Val | Asp | Leu | Asp | Glu | Thr | Ala | Arg | Met | Val | Glu | Leu | Ile | Val |
|---|---|---|---|---|---|---|---|---|---|---|---|---|---|---|---|
| | | | 35 | | | | | 40 | | | | | 45 | | |

| Ala | Ser | Gly | Val | Asp | Val | Leu | Leu | Thr | Asn | Gly | Thr | Phe | Gly | Glu | Val |
|---|---|---|---|---|---|---|---|---|---|---|---|---|---|---|---|
| | 50 | | | | | 55 | | | | | 60 | | | | |

| Ala | Thr | Leu | Thr | Tyr | Glu | Glu | Leu | Leu | Ala | Phe | Asn | Asp | Thr | Val | Ile |
|---|---|---|---|---|---|---|---|---|---|---|---|---|---|---|---|
| 65 | | | | | 70 | | | | | 75 | | | | | 80 |

| Arg | Thr | Val | Ala | Asn | Arg | Ile | Pro | Val | Phe | Cys | Gly | Ala | Ser | Thr | Leu |
|---|---|---|---|---|---|---|---|---|---|---|---|---|---|---|---|
| | | | | 85 | | | | | 90 | | | | | 95 | |

| Asn | Thr | Arg | Asp | Thr | Ile | Ala | Arg | Ser | Leu | Ala | Leu | Met | Gly | Leu | Gly |
|---|---|---|---|---|---|---|---|---|---|---|---|---|---|---|---|
| | | | 100 | | | | | 105 | | | | | 110 | | |

| Ala | Asn | Gly | Leu | Phe | Val | Gly | Arg | Pro | Met | Trp | Leu | Pro | Leu | Asp | Asp |
|---|---|---|---|---|---|---|---|---|---|---|---|---|---|---|---|
| | | 115 | | | | | 120 | | | | | 125 | | | |

| Glu | Gln | Leu | Val | Ser | Tyr | Tyr | Ala | Ala | Val | Cys | Asp | Ala | Val | Pro | Ala |
|---|---|---|---|---|---|---|---|---|---|---|---|---|---|---|---|
| | 130 | | | | | 135 | | | | | 140 | | | | |

| Ala | Ala | Val | Val | Tyr | Asp | Asn | Thr | Gly | Val | Phe | Lys | Gly | Lys | Ile |
|---|---|---|---|---|---|---|---|---|---|---|---|---|---|---|
| 145 | | | | | 150 | | | | | 155 | | | | 160 |

| Ser | Ser | Ala | Ala | Tyr | Ala | Ala | Leu | Ala | Glu | Ile | Pro | Gln | Ile | Val | Ala |
|---|---|---|---|---|---|---|---|---|---|---|---|---|---|---|---|
| | | | | 165 | | | | | 170 | | | | | 175 | |

| Ser | Lys | His | Leu | Gly | Val | Leu | Ser | Gly | Ser | Asp | Ala | Tyr | Ala | Ser | Asp |
|---|---|---|---|---|---|---|---|---|---|---|---|---|---|---|---|
| | | | 180 | | | | | 185 | | | | | 190 | | |

| Leu | Ala | Ala | Val | Lys | Gly | Arg | Phe | Pro | Leu | Leu | Pro | Thr | Ala | Asp | Asn |
|---|---|---|---|---|---|---|---|---|---|---|---|---|---|---|---|
| | 195 | | | | | 200 | | | | | 205 | | | | |

| Trp | Leu | Pro | Ser | Leu | Glu | Ala | Phe | Pro | Gly | Glu | Val | Pro | Ala | Ala | Trp |
|---|---|---|---|---|---|---|---|---|---|---|---|---|---|---|---|
| 210 | | | | | 215 | | | | | 220 | | | | | |

| Ser | Gly | Asp | Val | Ala | Cys | Gly | Pro | Glu | Pro | Val | Met | Ala | Leu | Arg | Arg |
|---|---|---|---|---|---|---|---|---|---|---|---|---|---|---|---|
| 225 | | | | | 230 | | | | | 235 | | | | | 240 |

| Ala | Ile | Ala | Glu | Gly | Leu | Trp | Asp | Asp | Ala | Arg | Ala | Val | His | Glu | Asp |
|---|---|---|---|---|---|---|---|---|---|---|---|---|---|---|---|
| | | | | 245 | | | | | 250 | | | | | 255 | |

| Ile | Ala | Trp | Ala | Thr | Glu | Pro | Leu | Phe | Pro | Gly | Gly | Asp | Ile | Ser | Lys |
|---|---|---|---|---|---|---|---|---|---|---|---|---|---|---|---|
| | | | 260 | | | | | 265 | | | | | 270 | | |

| Phe | Met | Pro | Tyr | Ser | Ile | Gln | Ile | Asp | Arg | Ala | Glu | Phe | Glu | Ala | Ala |
|---|---|---|---|---|---|---|---|---|---|---|---|---|---|---|---|
| | | 275 | | | | | 280 | | | | | 285 | | | |

| Gly | Tyr | Ile | Val | Pro | Gly | Pro | Ser | Arg | His | Pro | Tyr | Gly | Thr | Ala | Pro |
|---|---|---|---|---|---|---|---|---|---|---|---|---|---|---|---|
| | 290 | | | | | 295 | | | | | 300 | | | | |

| Ala | Ala | Tyr | Leu | Glu | Gly | Gly | Ala | Glu | Val | Gly | Arg | Arg | Trp | Ala | Gly |
|---|---|---|---|---|---|---|---|---|---|---|---|---|---|---|---|
| 305 | | | | | 310 | | | | | 315 | | | | | 320 |

| Ile | Arg | Gln | Lys | Tyr | Val | Ala | Thr | Leu | Ala | Glu | Pro |
|---|---|---|---|---|---|---|---|---|---|---|---|
| | | | 325 | | | | | 330 | | | |

```
<210> SEQ ID NO 4
<211> LENGTH: 259
<212> TYPE: PRT
<213> ORGANISM: Micromonospora sp.

<400> SEQUENCE: 4
```

| Met | Lys | Gly | Tyr | Thr | Tyr | Pro | Leu | Ser | Pro | Arg | Gly | Val | Ala | Asn | Leu |
|---|---|---|---|---|---|---|---|---|---|---|---|---|---|---|---|

```
            1               5                  10                 15
Ala Gly Lys Pro Pro Trp His Tyr Val Gly Asp Ala Val Gly Val Glu
                20                 25                 30
Phe Trp Thr Ser Pro Glu Ala Ala Ala Ser Leu Pro Thr Gly Leu
                35                 40                 45
Asp Pro Asp Pro Ala Asn Pro Gly His Gly Tyr Ala Val Phe Ile Asp
 50                 55                 60
Trp Gln Phe Asn Gly Ala Thr Asp Asp Tyr Leu Asp Pro Pro Phe Ser
 65                 70                 75                 80
Gln Tyr Ser Glu Phe Leu Val Leu Leu Asp Ala Gln Trp Gln Gly Thr
                85                 90                 95
Pro Val Ala Trp Cys Pro Phe Ile Trp Val Asp Asn Asp Ala Ser Leu
                100                105                110
Ala Arg Gly Trp Val Gln Gly Phe Pro Lys Lys Met Gly Ser Ile Arg
                115                120                125
Gln Thr Arg Ala Phe Ala Ile Asp Ser Pro Ala Ala Pro Thr Val Gly
                130                135                140
Lys Gly Gly Arg Phe Ala Ala Val Met Ser Ala Gly Gly Arg Arg Leu
145                 150                155                160
Ala Glu Thr Thr Val Thr Leu Asp Arg Thr Thr Asp Arg Leu Pro Ala
                165                170                175
Leu Thr Arg Pro Leu Val Asn Leu Arg His Phe Pro Arg Leu Ser Ala
                180                185                190
Gly Gln His Asp Asn Pro Ala Val His Glu Leu Thr Met Ser Val Leu
                195                200                205
Ala Asn Leu Lys Phe Ala Asn Thr Trp Ile Gly Thr Gly Glu Leu Arg
                210                215                220
Phe Leu Pro Ala Pro Arg Glu Glu Leu Ala Asp Leu Thr Pro Arg Arg
225                 230                235                240
Val Gly Val Gly Phe Arg Gly Ser Leu Ser Tyr Thr Val Asn Asp Leu
                245                250                255
Arg Ile Leu

<210> SEQ ID NO 5
<211> LENGTH: 265
<212> TYPE: PRT
<213> ORGANISM: Unknown
<220> FEATURE:
<223> OTHER INFORMATION: Description of Unknown:
      Actinobacteria bacterium sequence

<400> SEQUENCE: 5

Met Lys Gly Tyr Thr Val Pro Leu Ser Pro Arg Gly Val Ala Asn Leu
 1                  5                  10                 15
Ala Pro Ala Pro Pro Trp His Tyr Ala Gly Thr Val Val Gly Val Glu
                20                 25                 30
Phe Phe Thr Asp Pro Ala Ala Ala Ala Leu Pro Glu Gly Leu
                35                 40                 45
Ser Ser Asp Pro Asp Ser Ala Gly Arg Gly Val Ala Met Phe Ile Asp
 50                 55                 60
Trp Gln Tyr Ser Ser Thr Asp Leu Glu Tyr Leu Asp Pro Ala Arg Ser
 65                 70                 75                 80
Gln Tyr Arg Glu Phe Leu Val Thr Leu Asp Ala His Tyr Tyr Gly Ala
                85                 90                 95
Pro Val Ala Trp Cys Pro Tyr Ile Tyr Val Asp Asn Asp Ser Ala Met
```

```
            100                 105                 110
Ala Arg Gly Trp Val Gln Gly Phe Pro Lys Lys Leu Gly Ala Val His
            115                 120                 125

Gln Thr Arg Ala Tyr Ser Val Gly Gly Gln Gly Thr Pro Val Leu Gly
            130                 135                 140

Pro Gly Gly Gln Phe Gly Ala Thr Ala Ser Ala Ala Gly Gln Arg Ile
145                 150                 155                 160

Ala Glu Ala Lys Ile Thr Leu Glu Gln Ala Val Pro Asp Pro Ala Ala
                165                 170                 175

Leu Met Ser Arg Pro Val Val Asn Leu Arg His Phe Pro Arg Leu Thr
            180                 185                 190

Ala Gly Gln His His Lys Pro Ala Val His Glu Leu Val Met Ser Val
            195                 200                 205

Leu Asp Gly Ala Ala Val Ser Asp Ala Trp Ala Gly Thr Ala Asp Leu
            210                 215                 220

Ala Phe Leu Pro Ala Arg Gly Glu Leu Ala Asp Leu Pro Ile Gln
225                 230                 235                 240

Arg Thr Gly Arg Gly Phe His Phe Asp Leu Ala Tyr Thr Val Thr Asp
                245                 250                 255

Leu Lys Thr Leu Ile Asp His Ser Asn
            260                 265

<210> SEQ ID NO 6
<211> LENGTH: 262
<212> TYPE: PRT
<213> ORGANISM: Streptomyces gancidicus

<400> SEQUENCE: 6

Met Leu Lys Gly Tyr Thr Val Pro Leu Ser Pro Lys Gly Glu Ala Asn
1               5                   10                  15

Ile Ala Pro Thr Pro Pro Trp His Tyr Ala Gly Asp Ile Val Gly Val
                20                  25                  30

Glu Phe Phe Thr Glu Pro Ala Ala Ala Glu Ala Thr Leu Pro Glu Gly
            35                  40                  45

Leu Asp Pro Asp Pro Asp Thr Ser Gly Arg Val Val Ala Phe Phe Val
    50                  55                  60

Asp Trp Gln Phe Asn Gly Glu Arg Asp Glu Tyr Leu Asp Pro Val Arg
65              70                  75                  80

Ser Gln Tyr Arg Glu Phe Phe Val Leu Val Asp Ala Arg His Gln Gly
                85                  90                  95

Arg Pro Val Ser Trp Cys Pro Tyr Ile Tyr Val Asp Asn His His Ala
            100                 105                 110

Leu Ala Arg Gly Trp Ile Gln Gly Phe Pro Lys Lys Ala Gly Asn Val
            115                 120                 125

His Gln Thr Arg Val Phe Ala Ser Pro Gly Lys Ala Ser Pro Thr Leu
            130                 135                 140

Ser Pro Gly Ala Arg Phe Gly Ala Ser Val Ser Ser Asp Glu Arg Thr
145                 150                 155                 160

Leu Ala Glu Ala Arg Val Thr Leu Glu Ala Pro Met Glu Asp Pro Ser
                165                 170                 175

Ala Leu Leu Ser Arg Asp Thr Ile Asn Leu Arg His Phe Pro Thr Leu
            180                 185                 190

Glu Ala Gly Arg Tyr Asp Lys Pro Ala Val His Glu Leu Val Arg Met
            195                 200                 205
```

```
Asp Tyr Ala Asp Gln Gln Val Ala Asp Val Trp Thr Gly Thr Ser Glu
    210                 215                 220

Ile Thr Leu Phe Pro Ala Val Gly Glu Glu Leu Ala Asp Leu Ala Pro
225                 230                 235                 240

Val Arg Ser Gly Met Gly Phe Arg Ala Ser Met Ser Tyr Asn Val Thr
                245                 250                 255

Gln Val Glu Pro Leu Leu
            260
```

<210> SEQ ID NO 7
<211> LENGTH: 264
<212> TYPE: PRT
<213> ORGANISM: Kutzneria sp.

<400> SEQUENCE: 7

```
Met Leu Gly Tyr Ser Leu Pro Leu Ser Ala Asn Gly Thr Ala Asn Val
1               5                   10                  15

Val Pro Ala Pro Pro Trp His Tyr Ala Gly Asp Val Val Gly Val Glu
                20                  25                  30

Phe Trp Thr Thr Pro Ala Ala Ala Ala Thr Leu Pro Ser Gly Leu
            35                  40                  45

Thr Pro Asp Pro Thr Thr Ser Gly His Ala Tyr Ala Leu Phe Val Asp
    50                  55                  60

Trp Gln Trp Ala Gly Ser His Gln Glu Tyr Leu Asp Pro Val Arg Ser
65                  70                  75                  80

Gln Tyr Ser Glu Phe Leu Ile Leu Met Asp Ala Gln Phe Gln Gly Arg
                85                  90                  95

Ala Val Ala Trp Cys Pro Tyr Ile Trp Val Asp Asn Asp Ala Ala Leu
                100                 105                 110

Ala Arg Gly Trp Phe Gln Gly Phe Pro Lys Lys Leu Gly Ala Ile Arg
            115                 120                 125

Gln Thr Arg Ala Phe Ser Val Pro Gly Gln Ala Ser Pro Val Val Gly
    130                 135                 140

Pro Gly Gly Gln Phe Gly Ala Ser Leu Ser Ala Ala Gly Arg Arg Leu
145                 150                 155                 160

Ala Glu Ala Gln Ile Thr Leu Gln Ala Pro Ser Ala Thr Leu Pro Ala
                165                 170                 175

Leu Gly Arg Pro Ile Val Asn Leu Arg His Phe Pro Arg Leu Ile Ala
            180                 185                 190

Gly Gln Tyr Asp Asn Pro Ser Val His Glu Leu Thr Gln Ser Val Leu
    195                 200                 205

Asp Thr Pro Val Val Gly Asn Asn Trp Thr Gly Thr Ser Thr Leu Asn
    210                 215                 220

Phe Phe Thr Ala Pro Gly Glu Glu Leu Ala Asp Leu Gln Pro Val Arg
225                 230                 235                 240

Thr Gly Ser Gly Phe Arg Gly Ser Leu Ser Tyr Thr Val Thr Leu
                245                 250                 255

Lys Met Leu Ser Gly Pro Asp Ala
            260
```

<210> SEQ ID NO 8
<211> LENGTH: 265
<212> TYPE: PRT
<213> ORGANISM: Streptomyces olivochromogenes

<400> SEQUENCE: 8

Met Lys Gly Tyr Thr Val Pro Leu Ser Pro Arg Gly Ile Ala Asn Leu
1               5                   10                  15

Ala Pro Ala Pro Pro Trp His Tyr Ala Gly Thr Val Gly Val Glu
            20                  25                  30

Phe Phe Thr Asp Pro Ala Ala Ala Ala Thr Leu Pro Glu Gly Leu
            35                  40                  45

Thr Pro Asp Pro Asp Ser Ala Gly Arg Gly Val Ala Met Phe Ile Asp
50                  55                  60

Trp Gln Tyr Ser Ser Thr Gly Leu Glu Tyr Leu Asp Pro Ala Arg Ser
65                  70                  75                  80

Gln Tyr Arg Glu Phe Leu Leu Thr Leu Asp Ala His Tyr Asn Gly Thr
                85                  90                  95

Pro Val Ala Trp Cys Pro Tyr Ile Tyr Val Asp Asn Asp Ser Ala Met
            100                 105                 110

Ala Arg Gly Trp Val Gln Gly Phe Pro Lys Lys Leu Gly Ala Val His
            115                 120                 125

Gln Thr Arg Ala Tyr Ser Val Gly Gly Pro Gly Thr Pro Val Leu Gly
        130                 135                 140

Pro Gly Gly Gln Phe Gly Ala Thr Ala Ser Ala Ala Gly Gln Arg Ile
145                 150                 155                 160

Ala Glu Ala Lys Val Thr Leu Glu Gln Pro Val Pro Asp Pro Ala Ala
                165                 170                 175

Leu Met Ser Arg Pro Val Val Asn Leu Arg His Phe Pro Arg Leu Ala
            180                 185                 190

Ala Gly Gln His Asp Lys Pro Ala Val His Glu Leu Val Met Ser Val
        195                 200                 205

Leu Asp Gly Val Ala Val Ser Asp Ala Trp Ala Gly Thr Ala Asp Leu
210                 215                 220

Ala Phe Leu Pro Ala His Gly Glu Glu Leu Ala Asp Leu Pro Val Gln
225                 230                 235                 240

Arg Thr Gly Arg Gly Phe His Phe Asp Leu Ala Tyr Thr Val Thr Asp
            245                 250                 255

Leu Lys Thr Leu Ile Asp Arg Ser Asn
            260                 265

<210> SEQ ID NO 9
<211> LENGTH: 328
<212> TYPE: PRT
<213> ORGANISM: Sphingobium xenophagum

<400> SEQUENCE: 9

Met Ala Arg Thr Leu Met Lys Pro Asp Asp Val Lys Gly Ala Trp Ala
1               5                   10                  15

Ile Ile Pro Thr Pro Ala Lys Asp Ala Ser Asp Trp Arg Ala Thr
            20                  25                  30

Lys Thr Val Asp Leu Asp Glu Thr Ala Arg Val Val Asn Gly Leu Ile
            35                  40                  45

Asp Ala Gly Ile Asn Gly Ile Leu Ser Met Gly Thr Leu Gly Glu Ala
        50                  55                  60

Ala Thr Met Thr His Asp Glu Lys Leu Asp Phe Ile Lys Ala Leu Val
65                  70                  75                  80

Asp Ala Ala Ala Gly Arg Val Pro Ile Phe Val Gly Thr Thr Cys Leu
                85                  90                  95

Asn Thr Arg Asp Thr Ile Ala Leu Thr Arg Gln Ala Leu Asp Ile Gly
            100                 105                 110

```
Ala Asp Gly Thr Met Leu Gly Val Pro Met Trp Cys Ala Pro Ser Val
        115                 120                 125

Asp Val Ala Val Gln Phe Tyr Lys Asp Leu Ala Glu Ala Val Pro Glu
    130                 135                 140

Met Asn Ile Ala Ile Tyr Ala Asn Pro Glu Ala Phe Lys Phe Asp Phe
145                 150                 155                 160

Pro Arg Ser Phe Trp Ala Gln Val Ala Glu Ile Pro Gln Val Val Thr
                165                 170                 175

Ala Lys Tyr Ile Gly Val Ala His Leu Leu Pro Asp Leu Ala Ala Ile
                180                 185                 190

Arg Gly Arg Ile Lys Leu Leu Pro Ile Asp Phe Asp Tyr Tyr Gly Ala
            195                 200                 205

Ala Arg Met Asp Glu Ser Ile Asp Ala Phe Trp Ser Ser Gly Ala Val
        210                 215                 220

Cys Asp Pro Leu Val Thr Thr Thr Leu Arg Asp Leu Val Ser Gln Ala
225                 230                 235                 240

Arg Ala Thr Gly Asp Trp Ser Ala Ala Arg Ala Phe Met Gly Arg Leu
                245                 250                 255

Gly Pro Thr Ala Ala Pro Leu Phe Pro Asn Gly Ser Phe Lys Glu Phe
                260                 265                 270

Ser Thr Tyr Asn Ile Ala Leu Glu Lys Ala Arg Met Asn Ala Gly Gly
            275                 280                 285

Trp Met Asn Ala Gly Pro Val Arg Pro Pro Tyr His Leu Cys Pro Glu
        290                 295                 300

Pro Tyr Leu Glu Gly Ala Arg Leu Ser Gly Arg Met Trp Ala Glu Leu
305                 310                 315                 320

Gly Lys Ala Leu Ala Ala Glu Lys
                325

<210> SEQ ID NO 10
<211> LENGTH: 332
<212> TYPE: PRT
<213> ORGANISM: Alcaligenes faecalis

<400> SEQUENCE: 10

Met Ala Lys Ser Gly Leu Leu Asn Ala Ser Asp Ile His Gly Val Trp
1               5                   10                  15

Ser Ile Leu Pro Thr Pro Ser Lys Pro Asp Ala Ser Asp Trp Arg Ala
            20                  25                  30

Thr Asn Thr Val Asp Leu Asp Glu Thr Ala Arg Ala Val Glu Gly Leu
        35                  40                  45

Ile Ala Ala Gly Ala Asn Gly Ile Leu Ser Met Gly Thr Leu Gly Glu
    50                  55                  60

Cys Glu Ser Leu Thr Trp Glu Glu Lys Lys Val Phe Met Gln Thr Ile
65                  70                  75                  80

Val Glu Thr Ala Arg Gly Arg Val Pro Val Phe Val Gly Thr Thr Thr
                85                  90                  95

Leu Asn Thr Arg Asp Thr Ile Glu Gln Thr Arg Tyr Ala His Ser Ile
            100                 105                 110

Gly Ala Asp Gly Thr Met Leu Gly Ile Pro Met Trp Cys Asn Pro Cys
        115                 120                 125

Val Asp Met Ala Val Gln Tyr Tyr Lys Asp Val Ala Glu Ala Val Pro
    130                 135                 140

Glu Met Asn Ile Ala Ile Tyr Ala Asn Thr Glu Ala Phe Lys Phe Asp
```

```
145                 150                 155                 160

Phe Pro Arg Ala Phe Trp Ala Arg Val Ser Glu Ile Arg Gln Val Val
                165                 170                 175

Ala Ala Lys Tyr Ile Gly Ile Glu Phe Leu Leu Gln Asp Leu His Leu
                180                 185                 190

Thr Lys His Arg Met Lys Leu Leu Pro Leu Asp Tyr Gln Tyr Tyr Ala
                195                 200                 205

Ala Ala Arg Met Asp Asp Phe Val Asp Ala Phe Trp Ser Ser Gly Thr
210                 215                 220

Val Cys Gly Pro Leu Val Ser Thr Thr Leu Arg Asp Lys Val Ile Ala
225                 230                 235                 240

Ala Arg Arg Thr Lys Asp Trp Thr Asp Ala His Ala Phe Gln Gly Arg
                245                 250                 255

Leu Val Lys Thr Ala Ala Pro Phe Pro Glu Asp Ser Phe Lys Thr Phe
                260                 265                 270

Ser Ile Tyr Asn Val Ala Leu Glu Lys Gly Arg Ile Asp Ala Ala Gly
                275                 280                 285

Trp Met Asn Ala Gly Pro Val Arg Pro Pro Tyr Asn Asp Ile Cys Pro
                290                 295                 300

Ala Ser Tyr Leu Asp Ser Trp Lys Ala Ser Gly Gln Arg Trp Ala Glu
305                 310                 315                 320

Leu His Lys Gln Leu Glu Thr Glu Ser Ser Gly Lys
                325                 330

<210> SEQ ID NO 11
<211> LENGTH: 328
<212> TYPE: PRT
<213> ORGANISM: Novosphingobium aromaticivorans

<400> SEQUENCE: 11

Met Ala Arg Glu Leu Leu Thr Ala Ala Asp Val Lys Gly Ala Trp Ala
1               5                   10                  15

Ile Val Pro Thr Pro Ala Lys Glu Gly Ala Ser Asp Trp Arg Ala Ala
                20                  25                  30

Asp Thr Val Asn Val Glu Glu Ala Ala Arg Met Ile Asp Gly Leu Ile
                35                  40                  45

Glu Ala Gly Val Asp Gly Ile Leu Ser Met Gly Thr Leu Gly Glu Ala
        50                  55                  60

Ala Thr Met Thr Leu Asp Glu Lys Leu Val Phe Met Lys Thr Ile Val
65              70                  75                  80

Asp Thr Ala Ala Gly Arg Val Pro Val Phe Val Gly Thr Thr Cys Ile
                85                  90                  95

Asn Thr Arg Asp Thr Ile Ala Leu Thr Arg Lys Ala Val Asp Ile Gly
                100                 105                 110

Ala Thr Gly Thr Met Leu Gly Val Pro Met Trp Cys Ala Pro Ser Val
                115                 120                 125

Asp Val Ala Val Gln Phe Tyr Arg Asp Val Ala Glu Ala Val Pro Asp
                130                 135                 140

Ile Asn Ile Ala Ile Tyr Ala Asn Pro Glu Ala Phe Lys Phe Asp Phe
145                 150                 155                 160

Pro Arg Thr Phe Trp Gly Gln Val Ala Glu Ile Pro Gln Val Val Thr
                165                 170                 175

Ala Lys Tyr Ile Gly Val Gly Thr Leu Leu Pro Asp Leu Ala Ala Ile
                180                 185                 190
```

```
Lys Gly Arg Ile Lys Leu Leu Pro Ile Asp Phe Asp Tyr Gly Ala
            195                 200                 205
Ala Arg Met Asp Asp Ser Ile Asp Ala Phe Trp Thr Ser Gly Ala Val
210                 215                 220
Cys His Pro Leu Val Ser Thr Thr Leu Arg Asp Val Val Ala Ala Ala
225                 230                 235                 240
Arg Ala Ser Gly Asp Trp Ser Ala Ala Lys Ala Phe Met Gly Arg Leu
                245                 250                 255
Ala Pro Thr Ala Ala Thr Leu Phe Pro Asn Gly Ser Phe Lys Glu Phe
            260                 265                 270
Ser Thr Tyr Asn Ile Pro Leu Glu Lys Ala Arg Met Thr Ala Gly Gly
        275                 280                 285
Trp Met Asn Ala Gly Pro Cys Arg Pro Pro Tyr His Leu Cys Pro Glu
    290                 295                 300
Asn Tyr Leu Glu Gly Ala Arg Asn Ser Gly Arg Met Trp Ala Glu Leu
305                 310                 315                 320
Gly Lys Ala Leu Glu Ala Glu Arg
                325

<210> SEQ ID NO 12
<211> LENGTH: 331
<212> TYPE: PRT
<213> ORGANISM: Polymorphum gilvum

<400> SEQUENCE: 12

Met Thr Arg Lys Leu Leu Thr Val Asp Asp Val Asn Gly Cys Trp Ala
1               5                   10                  15
Ile Met Pro Thr Pro Ser Lys Pro Gly Ala Ser Asp Pro Asn Ala Val
                20                  25                  30
Asp Thr Val Asp Leu Glu Glu Thr Ala Arg Ala Ala Glu Ala Leu Val
            35                  40                  45
Ala Ala Gly Val Asp Gly Ile Leu Ser Leu Gly Thr Phe Gly Glu Ala
        50                  55                  60
Ala Thr Thr Thr Trp Glu Glu Lys Gln Ala Phe Met Arg Thr Leu Val
65                  70                  75                  80
Glu Thr Val Arg Gly Arg Val Pro Val Phe Gly Gly Thr Thr Ser Leu
                85                  90                  95
Asn Thr Arg Asp Thr Ile Arg Met Thr Arg Ala Ala Arg Glu Ile Gly
                100                 105                 110
Val Asp Gly Val Met Leu Gly Leu Pro Met Trp Val Gln Pro Asp Leu
            115                 120                 125
Ala Thr Ala Val Gln Phe Phe Arg Asp Val Ala Ser Ala Cys Pro Asp
        130                 135                 140
Val Ala Ile Cys Ala Tyr Ala Asn Pro Glu Ala Phe Lys Phe Glu Phe
145                 150                 155                 160
Pro Arg Ala Phe Trp Ala Gln Ile Ala Asp Ile Pro Gln Ile Val Ser
                165                 170                 175
Ala Lys Tyr Ile His Thr Ala Gly Leu Tyr Ala Asp Leu Asn Leu Thr
            180                 185                 190
Lys Arg Arg Ile Arg Leu Met Pro Leu Asp Val Asp Tyr Tyr Ala Ala
        195                 200                 205
Ala Arg Ile Asp Pro Asp Ala Cys Thr Ala Phe Trp Thr Ser Gly Ala
    210                 215                 220
Val Cys Gly Pro Ala Pro Ala Ile Gln Leu Arg Asp Leu Val Ser Lys
225                 230                 235                 240
```

```
Ala Lys Lys Thr Gly Asp Trp Thr Gly Ala Lys Lys Leu Thr Asp Arg
            245                 250                 255

Ile Gly Gln Thr Tyr Arg Thr Leu Phe Pro Asn Gly Ser Phe Lys Asp
            260                 265                 270

Phe Ser Val Tyr Asn Ile Gly Ile Glu Lys Ala Arg Met Asp Ala Ala
            275                 280                 285

Gly Trp Met Lys Ala Gly Pro Cys Arg Ala Pro Tyr Ser Leu Val Pro
            290                 295                 300

Glu Pro Tyr Leu Glu Gly Ala Arg Glu Ser Gly Arg Gln Trp Ala Lys
305                 310                 315                 320

Leu Ala Ala Glu Leu Ala Thr Glu Arg Ala Glu
                325                 330
```

<210> SEQ ID NO 13
<211> LENGTH: 333
<212> TYPE: PRT
<213> ORGANISM: Burkholderia sp.

<400> SEQUENCE: 13

```
Met Ile His Pro Lys Leu Arg Ile Asp Ala Ser Gly Ile Asn Gly Leu
1               5                   10                  15

Trp Pro Ile Leu Pro Thr Pro Ala Lys Pro Asn Ala Ser Asp Trp Arg
            20                  25                  30

Glu Arg Ser Thr Val Asp Leu Asp Glu Thr Ala Arg Ile Val Glu Ser
        35                  40                  45

Leu Ile Asp Ala Gly Val Asp Gly Leu Leu Ser Leu Gly Thr Tyr Gly
50                  55                  60

Glu Ala His Ser Leu Leu Trp Glu Glu Lys Lys Ala Phe Val Gly Cys
65                  70                  75                  80

Val Leu Glu Thr Ile Arg Gly Arg Ile Pro Phe Phe Thr Gly Thr Thr
                85                  90                  95

Ala Leu Asn Thr Arg Glu Val Val Glu Gln Thr Arg Ala Met His Asp
            100                 105                 110

Met Gly Val Ser Gly Thr Met Leu Gly Val Pro Met Trp Cys Lys Thr
        115                 120                 125

Asp Leu Ala Thr Ala Val Gln Phe Phe Arg Asp Val Thr Glu Ala Cys
130                 135                 140

Pro Asp Thr Ala Leu Ala Ile Tyr Ala Asn Thr Glu Ala Phe Lys Phe
145                 150                 155                 160

Glu Phe Pro Arg Pro Phe Trp Ala Glu Ile Gly Lys Met Pro Gln Ala
                165                 170                 175

Val Ala Cys Lys Tyr Leu Gly Ile Gly Met Leu Ala Val Asp Leu Glu
            180                 185                 190

Leu Ala Pro Asn Met Arg Phe Leu Pro Asn Glu Gln Asp Tyr Tyr Ala
        195                 200                 205

Ala Ala Arg Ile Asp Pro Glu Arg Val Thr Ala Phe Trp Ser Ser Gly
210                 215                 220

Ala Leu Cys Gly Pro Leu Pro Ala Leu Thr Leu Arg Asp Arg Val Ala
225                 230                 235                 240

Arg Ala Lys Ser Ser Asn Asp Trp Thr Ser Ala Lys Glu Ile Ala Asp
                245                 250                 255

Arg Met Arg Ala Cys Asp Val Gly Phe Phe Pro Lys Gly Glu Phe Ser
            260                 265                 270

Glu Phe Ser Lys Phe Asn Ala Pro Leu Glu Lys Ala Arg Met Asn Thr
```

```
        275                 280                 285

Ala Gly Tyr Val Asn Ala Gly Pro Cys Arg Pro Pro Tyr His Val Ile
    290                 295                 300

Pro Gln Glu Tyr Leu Ala Gly Ala Glu Arg Ser Gly Arg Ala His Ala
305                 310                 315                 320
Ala Leu Asn Ala Glu Leu Lys Gln Ala Glu His Ser Ile
                325                 330

<210> SEQ ID NO 14
<211> LENGTH: 330
<212> TYPE: PRT
<213> ORGANISM: Paraburkholderia sartisoli

<400> SEQUENCE: 14

Met Ser Lys Gln Arg Lys Gln Arg Leu Gly Thr Glu Asp Val Asn Gly
1               5                   10                  15
Ala Trp Val Ile Met Pro Thr Pro Ala Lys Pro Glu Ala Ser Asp Trp
            20                  25                  30

Arg Ala Thr Asp Thr Val Asp Leu Asp Glu Thr Ala Arg Ile Val Glu
        35                  40                  45

Ala Leu Ile Asp Ser Gly Val Asn Gly Ile Leu Ser Leu Gly Thr Phe
    50                  55                  60

Gly Glu Cys Ala Thr Leu Thr Trp Glu Glu Lys Gln Ala Phe Ile Gly
65                  70                  75                  80

Ala Val Val Glu Thr Thr Arg Gly Arg Val Pro Phe Phe Cys Gly Thr
                85                  90                  95

Thr Ala Leu Asn Thr Arg Glu Val Val Arg Gln Thr Arg Ala Ala Leu
            100                 105                 110

Asp Ile Gly Val Asp Gly Thr Met Leu Gly Val Pro Met Trp Ser Arg
        115                 120                 125

Met Glu Val Pro Ala Ala Val Gln Phe Tyr Arg Asp Val Ala Glu Ala
    130                 135                 140

Cys Pro Glu Ala Ala Ile Ala Val Tyr Ala Asn Ala Asp Ala Phe Lys
145                 150                 155                 160

Phe Glu Phe Pro Arg Ala Phe Trp Ala Gln Val Ala Gln Ile Pro Gln
                165                 170                 175

Val Val Thr Ala Lys Tyr Leu Gly Ile Gly Met Leu Asp Leu Asp Leu
            180                 185                 190

Thr Leu Ala Pro Gly Ile Arg Phe Leu Pro His Glu Asp Asp Tyr Tyr
        195                 200                 205

Ala Ala Ala Arg Val Ala Pro Glu Arg Val Thr Ala Phe Trp Ser Ser
    210                 215                 220

Gly Ala Met Cys Gly Pro Ala Thr Ala Ile Arg Leu Arg Asp Glu Val
225                 230                 235                 240

Ala Lys Ala Lys Gln Thr Gly Asp Trp Arg Leu Ala Lys Glu Leu Ser
                245                 250                 255

Asp Ala Met Arg Arg Ala Asp Ala Thr Leu Phe Pro Arg Gly Asp Phe
            260                 265                 270

Ala Glu Phe Ser Lys Tyr Asn Ile Ala Ile Glu Lys Glu Arg Met Asn
        275                 280                 285

Ala Ala Gly Trp Leu Arg Ala Gly Pro Cys Arg Pro Pro Tyr His Ile
    290                 295                 300

Ala Pro Glu Glu Tyr Leu Asp Gly Ala Arg Gln Ser Gly Arg Ala Trp
305                 310                 315                 320
```

```
Ala Glu Leu His Gln Gln Tyr Ser Asp Leu
            325                 330
```

```
<210> SEQ ID NO 15
<211> LENGTH: 332
<212> TYPE: PRT
<213> ORGANISM: Pseudomonas sp.

<400> SEQUENCE: 15
```

```
Met Met Ser Asp Met Val Lys Pro Arg Met Thr Ala Asp Asp Val Asn
1               5                   10                  15

Gly Val Trp Val Ile Met Pro Thr Pro Ala Lys Pro Asp Ala Ser Asp
                20                  25                  30

Trp Arg Val Glu Asn Thr Val Asp Leu Asp Glu Thr Val Arg Ile Val
            35                  40                  45

Glu Asn Leu Leu Ala Ser Gly Val Asn Gly Ile Met Ser Asn Gly Thr
50                  55                  60

Phe Gly Glu Cys Ala Thr Leu Thr Trp Asp Glu Lys Arg Asp Phe Ile
65                  70                  75                  80

Ala Thr Val Ala Glu Thr Ile Lys Gly Arg Val Pro Phe Phe Cys Gly
                85                  90                  95

Thr Thr Ala Leu His Thr Arg Glu Val Ile Arg Gln Thr Arg Glu Val
                100                 105                 110

Met Arg Leu Gly Ala Asp Gly Val Met Leu Gly Leu Pro Met Trp Cys
            115                 120                 125

Lys Met Glu Thr Pro Ser Ala Ile Gln Phe Tyr Arg Asp Val Ala Glu
130                 135                 140

Ala Val Pro Asp Ala Ala Ile Ala Val Tyr Ala Asn Pro Glu Ala Phe
145                 150                 155                 160

Lys Tyr Glu Phe Pro Arg Glu Phe Trp Ala Gln Val Ser Glu Ile Pro
                165                 170                 175

Gln Val Val Thr Ala Lys Tyr Leu Gly Ile Gly Met Leu Asp Leu Asp
            180                 185                 190

Leu Arg Leu Ala Ser Ser Ile Arg Phe Leu Pro His Glu Asp Asp Tyr
        195                 200                 205

Tyr Ala Ala Arg Ile Asn Pro Glu Arg Met Thr Ala Phe Trp Ser
210                 215                 220

Ser Ala Ala Met Cys Gly Pro Ala Thr Pro Leu Lys Leu Arg Asp Ala
225                 230                 235                 240

Val Ala Asp Ala Lys Val Thr Gly Lys Trp Ser Val Ala Lys Ala Ile
                245                 250                 255

Ser Asp Glu Met Arg Lys Ala Asp Ser Met Leu Phe Pro Lys Gly Asp
            260                 265                 270

Phe Ser Glu Phe Ser Lys Tyr Asn Ile Gly Leu Glu Lys Ala Arg Met
        275                 280                 285

Asp Glu Ala Gly Trp Leu Lys Ala Gly Pro Cys Arg Pro Pro Tyr His
290                 295                 300

Val Ile Pro Glu Met Tyr Leu Glu Gly Ala Arg Lys Ser Gly Arg Ala
305                 310                 315                 320

Trp Ala Glu Leu His Ala Lys Tyr Ser Ala Glu Gly
                325                 330
```

```
<210> SEQ ID NO 16
<211> LENGTH: 331
<212> TYPE: PRT
<213> ORGANISM: Comamonas thiooxydans
```

<400> SEQUENCE: 16

```
Met Ala Lys Gln Lys Lys Ser Arg Met Thr Ala Glu Asp Ile His Gly
1               5                   10                  15

Ala Trp Val Ile Met Pro Thr Pro Ala Thr Pro Asp Ala Ser Asp Trp
            20                  25                  30

Arg Val Gln His Thr Val Asp Leu Glu Glu Thr Ala Arg Ile Val Glu
        35                  40                  45

Ala Leu Ile Ala Ala Gly Val Asn Gly Ile Phe Ser Asn Gly Thr Phe
    50                  55                  60

Gly Glu Cys Ala Thr Leu Thr Trp Glu Lys Arg Asp Phe Ile Ala
65                  70                  75                  80

Thr Val Val Glu Thr Ala Arg Gly Arg Val Pro Phe Phe Cys Gly Thr
                85                  90                  95

Thr Ala Leu His Thr Arg Glu Val Ile Arg Gln Thr Arg Glu Ala Met
            100                 105                 110

Asp Ile Gly Ala Ser Gly Thr Met Leu Gly Val Pro Met Trp Cys Lys
        115                 120                 125

Met Glu Val Pro Thr Ala Val Gln Phe Tyr Arg Asp Val Ala Glu Ala
130                 135                 140

Val Pro Glu Ala Ala Ile Ala Ile Tyr Ala Asn Pro Glu Ala Phe Lys
145                 150                 155                 160

Phe Asp Phe Pro Arg Ser Phe Trp Ala Gln Val Ser Asn Ile Pro Gln
                165                 170                 175

Val Ile Thr Ala Lys Tyr Leu Gly Ile Gly Met Leu Asp Leu Asp Leu
            180                 185                 190

Arg Leu Ala Pro Ser Ile Arg Phe Leu Pro His Glu Asp Asp Tyr Tyr
        195                 200                 205

Ala Ala Ala Arg Ile Asp Pro Glu Arg Met Thr Ala Phe Trp Ser Ser
    210                 215                 220

Gly Ala Met Cys Gly Pro Ala Thr Ala Ile Arg Leu Arg Asp Thr Val
225                 230                 235                 240

Gly Ala Ala Lys Arg Ser Gly Asp Trp Thr Asp Ala Lys Ala Ile Ser
                245                 250                 255

Asp Ala Met Arg Gln Ala Asp Ser Thr Leu Phe Pro Arg Gly Asp Phe
            260                 265                 270

Ser Glu Phe Ser Lys Phe Asn Ile Gly Leu Glu Lys Ala Arg Met Asp
        275                 280                 285

Ala Ala Gly Trp Leu Lys Ala Gly Pro Cys Arg Pro Pro Tyr His Ile
    290                 295                 300

Val Pro Glu Glu His Leu Ala Gly Ala Arg Lys Ser Gly Glu Ala Trp
305                 310                 315                 320

Ala Ala Leu His Ala Arg Tyr Ala Thr Leu Asp
                325                 330
```

<210> SEQ ID NO 17
<211> LENGTH: 270
<212> TYPE: PRT
<213> ORGANISM: Unknown
<220> FEATURE:
<223> OTHER INFORMATION: Description of Unknown:
      Verrucomicrobia bacterium sequence

<400> SEQUENCE: 17

```
Met Asn Thr Ala Lys Leu Ile Gly Phe Asn Tyr Pro Leu Thr Pro Lys
1               5                   10                  15
```

Gly Lys Ser Thr Leu Asn Pro Pro Pro Trp Tyr Ser Ser Asp
                20                  25                  30

Phe Leu Asp Val Glu Phe Trp Ala Gln Pro Ala Ala Val Ala Ser Leu
            35                  40                  45

Leu Pro Asn Gly Leu Glu Pro Asp Pro Ala Ala Asn Gly His Cys Asn
50                  55                  60

Ala Leu Phe Tyr Asp Trp Gln Phe Ser Gly Asp Asn Glu Glu Tyr Leu
65                  70                  75                  80

Asp Pro Ala Arg Tyr Gln Tyr Arg Glu Phe Phe Ile Leu Val Asp Ala
                85                  90                  95

Leu Phe Glu Gly Arg Ser Val Ser Tyr Cys Pro Tyr Ile Phe Val Asp
                100                 105                 110

Asn Asp Ala Ala Leu Ala Arg Gly Trp Thr Gln Gly Tyr Pro Lys Arg
                115                 120                 125

Leu Gly Gln Val Phe Gln Thr Arg Tyr Tyr Ala Ala Thr Ser Lys Ala
            130                 135                 140

Gly Pro Ala Leu Ala Pro Gly Ser Lys Phe Ala Gly Ser Leu Thr Ala
145                 150                 155                 160

Ala Gly Gln Leu Ile Ala Glu Ala Val Val Thr Leu Arg Gln Ala Val
                165                 170                 175

Thr Asp Pro Ser Leu Leu Lys Gln Lys Pro Val Ile Asn Leu Leu His
            180                 185                 190

Val Pro Arg Leu Ala Ala Asp Lys His Asp Lys Pro Ala Ile His Glu
            195                 200                 205

Leu Val Glu Asn Val Pro Ser Ser Val Lys Ile Glu Gln Ala Trp Ile
        210                 215                 220

Gly Glu Gly Ser Leu Thr Leu Pro Val Cys Arg Gly Glu Glu Ile Ser
225                 230                 235                 240

Asp Leu Ala Pro Leu Arg Cys Gly Lys Gly Ile Arg Ala Ser Met Ala
                245                 250                 255

Tyr Val Val Asp Asp Leu Lys Thr Leu Lys Asp Leu Arg Asn
                260                 265                 270

<210> SEQ ID NO 18
<211> LENGTH: 267
<212> TYPE: PRT
<213> ORGANISM: Dyella psychrodurans

<400> SEQUENCE: 18

Met Lys Ser Asn Phe Phe Val Pro Met Thr Pro Arg Gly Leu Ser Asn
1               5                   10                  15

Ile Ser Pro Pro Pro Trp His Tyr Ala Gly Asp Phe Leu Ile Ile
                20                  25                  30

Asp Phe Trp Ala Arg Pro Asp Ala Val Ala Ser Leu Leu Pro Ala Glu
            35                  40                  45

Leu Gln Pro Asp Val Lys Ala Glu Gly His Ala Gln Ala Tyr Phe Ile
        50                  55                  60

Asp Trp Gln Tyr Thr Ala Ala His Asp Glu Phe Leu Asp Pro Ala Arg
65                  70                  75                  80

Tyr Gln Tyr Arg Glu Phe Phe Val Leu Val Asp Ala Leu Phe Gln Gly
                85                  90                  95

Lys Pro Val Ala Phe Cys Pro Tyr Ile Phe Val Asp Asn Asp Ala Ala
                100                 105                 110

Ile Ala Arg Gly Trp Ala Gln Gly Phe Pro Lys Arg Tyr Gly Thr Ile

```
                115                 120                 125
Leu Gln Thr Arg Leu Phe Ala Ala Ser Gly Pro Ala Ser Pro Lys Leu
    130                 135                 140

Ala Pro Gly Gly Arg Phe Gly Ala Ser Ala Ser Thr Ala Gly Gln Arg
145                 150                 155                 160

Ile Ala Arg Gly Leu Val Thr Leu Glu Lys Ala Val Thr Asp Pro Ala
                165                 170                 175

Ala Leu Gly Ser Arg Pro Thr Ile Asn Leu Arg His Phe Pro Arg Leu
            180                 185                 190

Ala Ala Gly Gln Trp Glu Arg Pro Ala Val His Glu Leu Val Glu Ser
        195                 200                 205

Val Met Asp Asn Phe Thr Val Ala Asp Ala Trp Met Gly Lys Gly Glu
    210                 215                 220

Leu Thr Leu Pro Glu Cys Glu Asn Glu Leu Ser Asp Leu Ala Pro
225                 230                 235                 240

Val Arg Cys Gly Asn Gly Tyr Arg Met Ser Val Ser Tyr Ser Val Thr
                245                 250                 255

Asp Leu Lys Thr Leu Val Asp His Ser Ala Lys
            260                 265

<210> SEQ ID NO 19
<211> LENGTH: 269
<212> TYPE: PRT
<213> ORGANISM: Paraburkholderia oxyphila

<400> SEQUENCE: 19

Met Leu Lys Gly Tyr Met Ala Pro Leu Ser Pro Leu Gly Lys Ala Ser
1               5                   10                  15

Ile Asn Pro Pro Pro Trp His Tyr Ser Gly Asp Val Ile Gly Ala
                20                  25                  30

Glu Phe Trp Ala Glu Pro Glu Ala Thr Ala Ala Thr Leu Pro Pro Gly
            35                  40                  45

Leu Asp Pro Asp Pro Ser Thr Ala Gly His Gly Val Val Leu Phe Ile
    50                  55                  60

Asp Trp Gln Phe Thr Ala Gln Asp Asp Glu Phe Leu Asp Pro Ala Arg
65                  70                  75                  80

Tyr Gln Tyr Arg Glu Cys Leu Phe Leu Val Asp Ala Val His Lys Gly
                85                  90                  95

Thr Pro Val Met Trp Cys Pro Tyr Ile Tyr Val Asp Asn Asp Ala Ala
                100                 105                 110

Leu Ala Arg Gly Trp Ala Gln Gly Phe Pro Lys Lys Leu Ala Ser Val
            115                 120                 125

Tyr Gln Thr Arg Thr Phe Ala Ala Pro Ser Ala Ala Ala Pro Val
    130                 135                 140

Ala Ser Gly Ser Arg Phe Gly Ala Ser Leu Ser Ala His Gly Glu Arg
145                 150                 155                 160

Leu Ala Glu Ala Arg Ile Thr Leu Arg Gln Pro Val Ala Asp Pro Lys
                165                 170                 175

Ser Leu Leu Ala Arg Pro Thr Val Asn Arg Arg Tyr Phe Ala Ser Leu
            180                 185                 190

Val Ala Gly Leu His Asp Lys Pro Ala Val Asp Glu Leu Val Leu Ser
        195                 200                 205

Val Thr Asp Asn Leu Ser Val Ala Asp Ala Trp Ala Gly Asp Ala Glu
    210                 215                 220
```

```
Leu Leu Phe Pro Asp Ala Arg Gly Glu Glu Ile Cys Ala Phe Gly Pro
225                 230                 235                 240

Val Lys Val Gly Gly Gly Phe Arg Phe Ser Leu Ala Tyr Ser Val Thr
                245                 250                 255

Asp Leu Lys Leu Leu Glu Asp Leu Thr Arg Leu Gly Lys
            260                 265
```

<210> SEQ ID NO 20
<211> LENGTH: 331
<212> TYPE: PRT
<213> ORGANISM: Polymorphum gilvum

<400> SEQUENCE: 20

```
Met Lys Arg Asp Met Leu Thr Val Asp Asp Val Thr Gly Cys Trp Ala
1               5                   10                  15

Ile Met Pro Thr Pro Ser Lys Pro Asn Ala Ser Asp Pro Ser Ala Thr
                20                  25                  30

Asp Thr Val Asp Leu Asp Glu Thr Ala Arg Val Ala Glu Ala Leu Val
            35                  40                  45

Ala Ala Gly Val Asp Gly Ile Leu Ser Leu Gly Thr Leu Gly Glu Cys
    50                  55                  60

Ala Thr Thr Thr Trp Asp Glu Lys Gln Ala Tyr Met Arg Thr Leu Val
65                  70                  75                  80

Glu Thr Leu Arg Gly Arg Ile Pro Val Phe Gly Gly Thr Thr Gly Leu
                85                  90                  95

Asn Thr Arg Asp Ser Ile Ala Met Thr Arg Ala Ala Arg Glu Ile Gly
                100                 105                 110

Val Asp Gly Val Met Leu Gly Leu Pro Met Trp Val Gln Pro Asp Val
            115                 120                 125

Pro Thr Ala Val Gln Phe Tyr Arg Asp Val Ala Ala Cys Pro Asp
    130                 135                 140

Val Ala Ile Cys Val Tyr Ala Asn Pro Glu Ala Phe Lys Phe Glu Phe
145                 150                 155                 160

Pro Arg Ala Phe Trp Ala Gln Ile Ala Glu Ile Pro Gln Val Val Ser
                165                 170                 175

Ala Lys Tyr Ile Asn Ile Ala Ala Leu Tyr Thr Asp Leu Asn Leu Thr
            180                 185                 190

Arg Arg Arg Ile Arg Leu Met Pro Leu Asp Val Asp Tyr Tyr Ala Ala
        195                 200                 205

Ala Arg Val Asp Pro Glu Ala Cys Ser Ala Phe Trp Thr Ser Gly Ala
210                 215                 220

Val Cys Gly Pro Ala Pro Ala Ile Gln Leu Arg Asp Leu Val Leu Glu
225                 230                 235                 240

Ala Arg Gln Ser Gly Asp Trp Ser Lys Ala Lys Ala Leu Thr Asp Arg
                245                 250                 255

Ile Gly Met Thr Tyr Arg Thr Leu Phe Pro Asn Gly Ser Phe Lys Glu
            260                 265                 270

Phe Ser Val Tyr Asn Ile Gly Ile Glu Lys Ala Arg Met Asp Ala Ala
        275                 280                 285

Gly Trp Met Thr Ala Gly Pro Val Arg Pro Pro Tyr His Ile Val Pro
    290                 295                 300

Glu Ala Ile Leu Glu Gly Gly Arg Glu Ser Gly Arg Gln Trp Ala Lys
305                 310                 315                 320

Leu Ala Ala Glu Leu Glu Arg Glu Ala Gly Arg
                325                 330
```

```
<210> SEQ ID NO 21
<211> LENGTH: 270
<212> TYPE: PRT
<213> ORGANISM: Pseudomonas sp.

<400> SEQUENCE: 21

Met Thr Gln Ser Tyr Thr Thr Pro Leu Thr Pro Arg Gly Leu Ser Ser
1               5                   10                  15

Ile Ala Pro Pro Pro Trp His Tyr Ser Gly Asp Phe Leu Val Val
            20                  25                  30

Glu Phe Trp Ala Asp Pro Ile Ala Val Ala Asn Thr Leu Pro Ala Gly
            35                  40                  45

Leu Thr Val Asp Ser Ala Ser Pro Gly His Ala Ser Ala Val Phe Val
        50                  55                  60

Asp Trp Gln Phe Thr Gly Glu Asn Asp Glu Leu Leu Asp Pro Ala Arg
65                  70                  75                  80

Tyr Gln Tyr Arg Glu Phe Phe Ile Leu Leu Asp Ala Leu His Glu Gly
                85                  90                  95

Gln Pro Val Ser Tyr Cys Pro Tyr Ile Phe Val Asp Asn Asp Ser Ala
            100                 105                 110

Leu Met Arg Gly Leu Ile Gln Gly Phe Pro Lys Arg Leu Gly Ala Val
            115                 120                 125

His Gln Thr Arg Thr Phe Ser Ala Pro Ser Arg Ala Ala Ala Gln Val
        130                 135                 140

Glu Pro Gly Ala Arg Phe Ala Ala Thr Ala Ser Thr Ala Gly Gln Arg
145                 150                 155                 160

Ile Ala Arg Gly Glu Val Gln Leu Gln His Lys Ile Asp Asp Val Ser
                165                 170                 175

Lys Leu Gly Phe Gly Ala Arg Pro Leu Ile Asn Leu Arg His Phe Pro
            180                 185                 190

Arg Leu Ala Thr Gly Gln His Asn Asp Pro Ala Val His Glu Leu Val
        195                 200                 205

Val Ser Val Met Asp Asn Pro Asn Ile Val Asp Ala Trp Ala Gly Glu
    210                 215                 220

Gly Asn Leu Val Phe Pro Gln Ala Glu Gly Glu Val Ser Asp Leu
225                 230                 235                 240

Ala Pro Thr Arg Val Gly Ala Gly Phe Arg Ala Ser Met Ser Tyr Thr
                245                 250                 255

Val Thr Asp Leu Lys Ala Leu Pro Asn Ala Thr Ile Glu Arg
            260                 265                 270

<210> SEQ ID NO 22
<211> LENGTH: 267
<212> TYPE: PRT
<213> ORGANISM: Afipia sp.

<400> SEQUENCE: 22

Met Leu Arg Gly Phe Thr Val Pro Lys Ser Pro Phe Gly Gln Ala Ala
1               5                   10                  15

Leu Thr Pro Pro Pro Trp His Tyr Ala Gly Asp Val Val Gly Val
            20                  25                  30

Glu Phe Trp Thr Asp Pro Glu Ala Thr Ala Ala Thr Leu Pro Asn Gly
            35                  40                  45

Leu Ser Pro Asp Pro Asn Ser Asn Gly His Ala Val Met Met Phe Leu
        50                  55                  60
```

```
Asp Trp Gln Phe Thr Ala Gln Asp Asp Glu Tyr Leu Glu Pro Ala Arg
 65                  70                  75                  80

Tyr Gln Tyr Arg Glu Ala Phe Ile Leu Val Asp Ala Met Tyr Arg Asp
                 85                  90                  95

Glu Pro Val Met Trp Cys Pro Tyr Ile Tyr Val Asp Asn Asp Ala Ala
            100                 105                 110

Leu Ala Arg Gly Trp Thr Gln Gly Phe Pro Lys Lys Met Gly Ser Ile
        115                 120                 125

Phe Gln Thr Arg Ser Phe Ala Ala Ser Gly Pro Ala Ala Ala Pro Val
    130                 135                 140

Ala Ser Gly Ser Arg Phe Gly Ala Ser Leu Ser Ala His Gly Gln Arg
145                 150                 155                 160

Leu Ala Glu Ala Cys Val Thr Leu His Arg Pro Val Glu Asn Gly Leu
                165                 170                 175

Ser Leu Leu Ser Arg Pro Thr Val Leu Leu Arg Tyr Phe Pro Arg Leu
            180                 185                 190

Ala Ala Gly Tyr Gln Asp Lys Pro Ala Val Asn Glu Leu Ala Met Ser
        195                 200                 205

Ile Thr Asp Asn Leu Thr Val Ala Gly Ala Trp Ile Gly Lys Gly Glu
    210                 215                 220

Leu Asn Phe Pro Glu Ala Ser Gly Glu Leu Asn Ala Leu Ala Pro
225                 230                 235                 240

Lys Arg Ile Glu Ser Gly Phe Arg Tyr Ser Leu Ser Tyr Ser Val Ser
                245                 250                 255

Asp Leu Lys Ile Leu Glu Asp His Gly Ser Gln
            260                 265

<210> SEQ ID NO 23
<211> LENGTH: 331
<212> TYPE: PRT
<213> ORGANISM: Pseudomonas kilonensis

<400> SEQUENCE: 23

Met Ser Thr Lys Arg Thr Leu Met Thr Ala Asn Asp Val Gln Gly Ala
 1               5                  10                  15

Trp Ala Ile Met Pro Thr Ser Ala Lys Asp Gly Ser Glu Ser Trp Arg
                20                  25                  30

Met Thr Asp Ser Leu Asp Leu Asp Ala Thr Val Ala Ala Ile Asn Gly
            35                  40                  45

Leu Ile Asp Ser Gly Val Asp Gly Ile Leu Thr Met Gly Thr Tyr Gly
        50                  55                  60

Glu Ala Ala Thr Leu Thr Val Asp Glu Lys Lys Arg Phe Met Ala Cys
 65                  70                  75                  80

Leu Val Glu Thr Val Ala Gly Arg Val Pro Cys Phe Val Gly Thr Thr
                 85                  90                  95

Thr Leu Asn Thr Arg Asp Thr Ile Glu Leu Thr Arg Tyr Ala Ala Asp
            100                 105                 110

Leu Gly Ala Asp Gly Thr Met Leu Gly Leu Pro Met Trp Cys Ala Pro
        115                 120                 125

Thr Leu Pro Ala Ala Val Arg Phe Tyr Arg Asp Val Ala Glu Ala Cys
    130                 135                 140

Pro Asp Met Ala Gln Cys Ile Tyr Ala Asn Pro Glu Ala Phe Arg Phe
145                 150                 155                 160

Asp Phe Pro Pro Pro Phe Trp Ala Gln Val Ala Asp Ile Pro Gln Val
```

```
                        165                 170                 175
Val Ser Ala Lys Phe Thr Ser Val Gly His Leu Ile Gln Asn Leu Glu
            180                 185                 190

Ile Thr Arg Gly Lys Val Arg Ala Leu Pro Ile Glu Leu Asp Tyr Tyr
        195                 200                 205

Ala Ala Thr Arg Val Asp Asp Val Cys Ala Phe Trp Ser Ser Gly
    210                 215                 220

Ala Val Cys Gly Pro Thr Pro Thr Ile Ala Leu Arg Asp Glu Ile Thr
225                 230                 235                 240

Arg Ala Lys Thr Ser Gly Asp Trp Thr Lys Ala Lys Glu Leu Thr Asp
                245                 250                 255

Lys Met Trp Ala Ala Val Thr Pro Met Phe Pro Ala Gly Gly Phe Arg
            260                 265                 270

Glu Phe Ser Met Tyr Asn Ile Ala Ile Asp Lys Met Arg Met Gln Thr
        275                 280                 285

Ala Gly Trp Met Arg Val Gly Pro Thr Arg Pro Tyr Asp Met Met
    290                 295                 300

Pro Asp His Ile Arg Gly Gly Ala Val Glu Ala Gly Lys Leu Trp Ala
305                 310                 315                 320

Glu Leu Ala Lys Ala Thr Val Leu Ala Gly Ala
                325                 330

<210> SEQ ID NO 24
<211> LENGTH: 270
<212> TYPE: PRT
<213> ORGANISM: Paraburkholderia hospita

<400> SEQUENCE: 24

Met Ser Lys Gln Tyr Ala Val Pro Leu Ser Pro Arg Gly Leu Ser Ser
1               5                   10                  15

Ile Ala Pro Pro Pro Trp His Tyr Ser Gly Asp Phe Leu Ile Val
            20                  25                  30

Glu Phe Trp Ala Asp Pro Ala Ala Val Ala Ala Thr Leu Pro Ala Gly
        35                  40                  45

Leu Ser Val Asp Pro Ser Ser Pro Gly His Ala Thr Ala Leu Phe Val
    50                  55                  60

Asp Trp Gln Phe Thr Gly Gln Asn Asp Glu Leu Leu Asp Pro Ala Arg
65                  70                  75                  80

Tyr Gln Tyr Arg Glu Phe Phe Leu Leu Val Asp Ala Leu Tyr Glu Gly
                85                  90                  95

Gln Pro Val Ala Tyr Cys Pro Tyr Ile Phe Val Asp Asn Asp Ser Ala
            100                 105                 110

Met Met Arg Gly Leu Ile Gln Gly Phe Pro Lys Arg Leu Gly Ala Val
        115                 120                 125

His Gln Thr Arg Thr Phe Ala Ala Pro Ser Leu Ala Ala Ala Gln Val
    130                 135                 140

Ala Pro Gly Ala Arg Phe Ala Ala Thr Ala Ser Thr Ala Gly Gln Arg
145                 150                 155                 160

Ile Ala Arg Ala Glu Val Lys Leu Thr Gly Lys Val Asp Asp Pro Ser
                165                 170                 175

Thr Val Ser Leu Ala Gly Arg Pro Ile Val Asn Leu Arg His Phe Pro
            180                 185                 190

Arg Leu Ala Ala Gly Gln His Glu Thr Pro Ala Val His Glu Leu Val
        195                 200                 205
```

```
Met Ser Ile Met Asp Asp Pro Arg Met Ala Asp Val Trp Ala Gly Glu
    210                 215                 220

Gly Gln Leu Ser Leu Pro Val Ala Glu Gly Glu Ile Ser Asp Leu
225                 230                 235                 240

Ala Pro Val Arg Val Gly Ala Gly Tyr Arg Leu Ser Met Ser Tyr Thr
                245                 250                 255

Val Thr Asp Leu Lys Thr Leu Ser Asp Gly Thr Gln Ala Ala
            260                 265                 270

<210> SEQ ID NO 25
<211> LENGTH: 331
<212> TYPE: PRT
<213> ORGANISM: Celeribacter persicus

<400> SEQUENCE: 25

Met Lys Lys Pro Leu Leu Thr Val Asp Asp Val Thr Gly Cys Trp Ala
1               5                   10                  15

Ile Met Pro Thr Pro Ser Lys Pro Asn Gly Ser Asp Ile Asn Ala Thr
            20                  25                  30

Asp Thr Val Asp Leu Asp Glu Thr Ala Arg Ala Ala Glu Ala Leu Val
        35                  40                  45

Ala Ser Gly Val Asn Gly Ile Leu Ser Gln Gly Thr Phe Gly Glu Ala
    50                  55                  60

Ala Thr Thr Thr Trp Glu Glu Lys Gln Ala Phe Leu Arg Thr Leu Val
65                  70                  75                  80

Glu Thr Val Asp Gly Arg Val Pro Val Phe Gly Gly Thr Thr Ser Leu
                85                  90                  95

Asn Thr Arg Asp Thr Ile Arg Met Thr Lys Ala Val Arg Glu Ile Gly
            100                 105                 110

Val Asp Gly Val Met Leu Gly Pro Pro Met Trp Cys Gln Pro Asp Val
        115                 120                 125

Pro Thr Ala Val Gln Phe Phe Arg Asp Val Ala Glu Ala Cys Pro Asp
    130                 135                 140

Thr Ala Ile Cys Ala Tyr Ala Asn Pro Glu Ala Phe Lys Phe Asp Phe
145                 150                 155                 160

Pro Arg Ala Phe Trp Ala Gln Ile Ala Glu Ile Pro Gln Val Val Ser
                165                 170                 175

Ala Lys Tyr Met Asn Ile Ala Ala Leu Tyr Met Asp Leu Asn Leu Thr
            180                 185                 190

Gly Arg Lys Ile Arg Leu Met Pro Leu Asp Met Asp Tyr Tyr Ala Ala
        195                 200                 205

Ala Arg Met Asp Pro Glu Ala Cys Thr Ala Phe Trp Thr Ser Gly Ala
    210                 215                 220

Ile Cys Gly Pro Glu Pro Val Ile Gln Leu Arg Asp Leu Val Ala Glu
225                 230                 235                 240

Ala His Lys Thr Gly Asp Trp Gly Lys Ala Lys Ala Leu Thr Asp Arg
                245                 250                 255

Ile Ala Ala Thr Tyr Arg Thr Leu Phe Pro Asn Gly Ser Phe Lys Glu
            260                 265                 270

Phe Ser Val Tyr Asn Ile Gly Ile Glu Lys Ala Arg Ile Asp Ala Ala
        275                 280                 285

Gly Trp Met Thr Ala Gly Pro Cys Arg Pro Tyr His Val Ile Pro
    290                 295                 300

Glu Pro Ile Leu Asp Gly Ala Arg Glu Ala Gly Leu Gln Trp Ala Lys
305                 310                 315                 320
```

Leu Val Ser Ala Leu Glu Ser Glu Lys Thr Ala
            325                 330

<210> SEQ ID NO 26
<211> LENGTH: 334
<212> TYPE: PRT
<213> ORGANISM: Pseudomonas stutzeri

<400> SEQUENCE: 26

Met Ser Asn Lys Thr Met Lys Pro Ala Arg Leu Thr Ala Glu Asp Ile
1               5                   10                  15

His Gly Val Trp Ala Ile Met Pro Thr Pro Ala Thr Pro Asp Ala Ser
            20                  25                  30

Asn Trp Arg Ser Thr Asn Thr Val Asp Leu Asn Glu Thr Ala Arg Ile
        35                  40                  45

Val Glu Glu Leu Ile Ala Ala Gly Val Asn Gly Ile Leu Ser Met Gly
    50                  55                  60

Thr Phe Gly Glu Cys Ala Thr Leu Thr Trp Glu Lys Arg Asp Tyr
65                  70                  75                  80

Val Ser Thr Ile Val Glu Thr Ile Arg Gly Arg Val Pro Tyr Phe Cys
                85                  90                  95

Gly Thr Thr Ala Leu Asn Thr Arg Glu Val Ile Arg Gln Thr Arg Glu
            100                 105                 110

Phe Met Asp Met Gly Ala Ser Gly Thr Met Leu Gly Val Pro Met Trp
        115                 120                 125

Val Lys Met Asp Leu Pro Thr Ala Val Gln Phe Tyr Arg Asp Val Ala
    130                 135                 140

Glu Ala Val Pro Glu Ala Ala Ile Ala Ile Tyr Ala Asn Pro Glu Ala
145                 150                 155                 160

Phe Lys Phe Asp Phe Pro Arg Pro Phe Trp Ala Glu Met Ser Lys Ile
                165                 170                 175

Pro Gln Val Val Thr Ala Lys Tyr Leu Gly Ile Gly Met Leu Asp Leu
            180                 185                 190

Asp Leu Lys Leu Ala Pro Asn Ile Arg Phe Leu Pro His Glu Asp Asp
        195                 200                 205

Tyr Tyr Ala Ala Ala Arg Ile Asn Pro Glu Arg Met Thr Ala Phe Trp
    210                 215                 220

Ser Ser Gly Ser Met Cys Gly Pro Ala Thr Ala Ile Met Leu Arg Asp
225                 230                 235                 240

Ala Val Asp Gln Ala Lys Ser Ser Gly Asp Trp Ile Lys Ala Lys Ala
                245                 250                 255

Ile Ser Asp Asp Met Arg Ala Ala Asp Ser Thr Leu Phe Pro Arg Gly
            260                 265                 270

Asp Phe Ser Glu Phe Ser Lys Tyr Asn Ile Gly Leu Glu Lys Ala Arg
        275                 280                 285

Met Asp Ala Ala Gly Trp Leu Thr Ala Gly Pro Cys Arg Pro Pro Tyr
    290                 295                 300

Asn Ile Val Pro Glu Asp Tyr Ile Ala Gly Ala Leu Lys Ser Gly Lys
305                 310                 315                 320

Ala Trp Ala Ala Leu His Ala Lys Tyr Ser Lys Glu Leu Lys
                325                 330

<210> SEQ ID NO 27
<211> LENGTH: 272
<212> TYPE: PRT

<213> ORGANISM: Unknown
<220> FEATURE:
<223> OTHER INFORMATION: Description of Unknown:
      Candidatus Rokubacteria bacterium sequence

<400> SEQUENCE: 27

```
Met Leu Lys Gly Phe Asn Tyr Pro Leu Thr Pro Lys Gly Lys Ser Thr
1               5                   10                  15

Leu Asn Pro Ser Pro Pro Trp His Tyr Ser Ala Asp Phe Leu Asp Ile
            20                  25                  30

Glu Phe Trp Ser Glu Pro Ser Ala Val Thr Ala Val Leu Pro Ala Gly
        35                  40                  45

Leu Asp Pro Asp Pro Ala Ala Asn Gly His Gly His Ala Leu Phe Tyr
50                  55                  60

Asp Trp Gln Phe Ala Gly Glu Asn Glu Glu Tyr Leu Asp Pro Ala Arg
65                  70                  75                  80

Tyr Gln Tyr Arg Glu Phe Phe Leu Leu Val Asp Ala Leu Tyr Glu Gly
                85                  90                  95

Gln Pro Ile Ser Tyr Cys Pro Tyr Ile Phe Val Asp Asn Asp Ala Ala
            100                 105                 110

Ile Ala Arg Gly Trp Thr Gln Gly Tyr Pro Lys Arg Leu Gly Gln Val
        115                 120                 125

Phe Gln Thr Arg Tyr Tyr Ala Ala Thr Gly Lys Ala Gly Pro Ala Leu
130                 135                 140

Ala Pro Gly Ser Lys Phe Ala Gly Ser Leu Thr Ala Gly Gln Arg
145                 150                 155                 160

Leu Ala Glu Ala Leu Val Thr Leu Lys Glu Pro Val Thr Asp Pro Ala
                165                 170                 175

Leu Leu Lys Gln Arg Pro Ile Val Asn Leu Leu His Tyr Pro Gln Leu
            180                 185                 190

Ala Ala Asp Lys Gln Asp Glu Pro Ala Ile His Gln Leu Val Glu Asn
        195                 200                 205

Val Pro His Asp Leu Lys Ile Glu Gln Ala Trp Ile Gly Asp Gly Ser
210                 215                 220

Leu Thr Leu Pro Val Cys Arg Ser Glu Glu Leu Ser Asp Leu Ala Pro
225                 230                 235                 240

Val Arg Cys Gly Lys Gly Ile Arg Ala Ser Met Ala Tyr Ile Val Asp
                245                 250                 255

Asp Leu Lys Thr Leu Lys Asp Leu Thr Lys Gly Phe Ser Leu Leu Ala
            260                 265                 270
```

<210> SEQ ID NO 28
<211> LENGTH: 262
<212> TYPE: PRT
<213> ORGANISM: Streptomyces sp.

<400> SEQUENCE: 28

```
Met Leu Lys Gly Tyr Thr Val Pro Leu Ser Pro Lys Gly Glu Ala Asn
1               5                   10                  15

Ile Ala Pro Thr Pro Pro Trp His Tyr Ala Gly Asp Ile Val Gly Val
            20                  25                  30

Glu Phe Phe Thr Glu Pro Ser Ala Ala Glu Ala Thr Leu Pro Glu Gly
        35                  40                  45

Leu Asp Pro Asp Pro Asp Thr Ser Gly Arg Val Val Ala Phe Phe Val
50                  55                  60

Asp Trp Gln Phe Asn Gly Glu Gln Asp Glu Tyr Leu Asp Pro Val Arg
```

```
                65                  70                  75                  80
Ser Gln Tyr Arg Glu Phe Phe Val Leu Val Asp Ala Arg His Gln Gly
                    85                  90                  95

Arg Pro Val Ser Trp Cys Pro Tyr Ile Tyr Val Asp Asn His His Ala
                100                 105                 110

Leu Ala Arg Gly Trp Ile Gln Gly Phe Pro Lys Lys Ala Gly Asn Val
                115                 120                 125

His Gln Thr Arg Val Phe Ala Ser Pro Gly Lys Ala Ser Pro Thr Leu
            130                 135                 140

Ser Pro Gly Ala Arg Phe Gly Ala Thr Val Ser Ser Asp Glu Arg Thr
145                 150                 155                 160

Leu Ala Glu Ala Arg Val Thr Leu Glu Ala Pro Met Glu Asp Pro Ser
                165                 170                 175

Ala Leu Leu Ala Arg Asp Thr Ile Asn Leu Arg His Phe Pro Thr Leu
                180                 185                 190

Glu Val Gly Lys Tyr Asp Lys Pro Ala Val His Glu Leu Val Arg Met
            195                 200                 205

Asp Tyr Ala Asp Gln Gln Val Ala Asp Val Trp Thr Gly Thr Ser Glu
210                 215                 220

Ile Thr Leu Phe Pro Ala Val Gly Glu Glu Leu Ala Asp Leu Ala Pro
225                 230                 235                 240

Val Arg Pro Gly Met Gly Phe Arg Ala Ser Met Ser Tyr Asn Val Thr
                245                 250                 255

Gln Val Glu Pro Leu Gly
            260

<210> SEQ ID NO 29
<211> LENGTH: 268
<212> TYPE: PRT
<213> ORGANISM: Paraburkholderia oxyphila

<400> SEQUENCE: 29

Met Asn Lys Pro Tyr Ala Val Pro Leu Ser Pro Arg Gly Leu Ser Ser
1               5                   10                  15

Ile Ala Pro Pro Pro Trp His Tyr Ala Gly Asp Phe Ile Leu Val
                20                  25                  30

Glu Phe Trp Ala Asp Pro Ala Ala Ala Ala Val Leu Pro Lys Gly
            35                  40                  45

Leu Ser Leu Asp Pro Ala Ser Pro Gly His Ala Thr Ala Leu Phe Ile
    50                  55                  60

Asp Trp Gln Phe Thr Gly Ser Asn Asp Glu Met Leu Asp Pro Ala Arg
65                  70                  75                  80

Tyr Gln Tyr Arg Glu Phe Phe Val Leu Val Asp Ala Leu His Glu Gly
                85                  90                  95

Lys Pro Val Ser Phe Cys Pro Tyr Ile Phe Val Asp Asn Asp Ser Ala
                100                 105                 110

Met Met Arg Gly Leu Ile Gln Gly Phe Pro Lys Arg Tyr Gly Gln Ile
            115                 120                 125

His Gln Thr Arg Thr Phe Ala Ala Leu Ser Pro Ala Ala Ala Pro Val
            130                 135                 140

Thr Ala Gly Thr Arg Phe Ala Ala Thr Ala Ser Ala Ala Gly Gln Arg
145                 150                 155                 160

Leu Ala His Ala Glu Val Lys Leu Glu Ala Ala Val Gln Asp Val Ser
                165                 170                 175
```

-continued

```
Lys Leu Gly Ile Ala Gly Arg Pro Val Val Asn Gln Arg Tyr Phe Pro
            180                 185                 190

Arg Leu Ala Ala Gly Gln His Asp Thr Pro Ala Val Asn Glu Leu Val
        195                 200                 205

Leu Ser Ile Met Asp Asn Ala Gln Ile Ala Asp Val Trp Ala Gly Glu
    210                 215                 220

Gly Lys Leu Thr Phe Pro Phe Ala Gln Gly Glu Glu Ile Ala Asp Leu
225                 230                 235                 240

Gln Pro Val Arg Val Gly Ala Gly Phe Arg Gly Ser Met Ala Tyr Ser
                245                 250                 255

Val Thr Asp Leu Lys Thr Leu Val Asp His Thr Lys
            260                 265

<210> SEQ ID NO 30
<211> LENGTH: 266
<212> TYPE: PRT
<213> ORGANISM: Agrobacterium rhizogenes

<400> SEQUENCE: 30

Met Leu Lys Gly Phe Thr Leu Pro Lys Ser Pro Phe Gly Gln Ala Ala
1               5                   10                  15

Leu Thr Pro Pro Pro Trp His Tyr Ser Gly Asp Val Ile Gly Val
            20                  25                  30

Glu Phe Arg Thr Asp Pro Ser Ala Thr Ala Ala Thr Leu Pro Asn Gly
        35                  40                  45

Leu Ser Pro Asp Pro Lys Ser Asn Gly His Ala Val Met Met Phe Val
    50                  55                  60

Asp Trp Gln Phe Thr Ala Gln Asn Asp Glu Tyr Leu Asp Pro Ala Arg
65                  70                  75                  80

Tyr Arg Tyr Arg Glu Ala Phe Val Leu Leu Asp Ala Val Tyr Arg Asn
                85                  90                  95

Ala Pro Val Met Trp Cys Pro Tyr Val Phe Val Asp Asn Asp Ala Ala
            100                 105                 110

Leu Ala Arg Gly Trp Thr Gln Gly Phe Pro Lys Lys Ile Gly Ser Ile
        115                 120                 125

Phe Gln Thr Arg Thr Tyr Ala Ala Ala Ser Pro Ala Ala Ala Pro Val
    130                 135                 140

Ala Pro Gly Gly Arg Phe Gly Ala Ser Leu Ser Ala His Gly Gln Arg
145                 150                 155                 160

Leu Ala Glu Ala Arg Ile Thr Leu Gln Glu Pro Val Glu Asp Gly Leu
                165                 170                 175

Ser Leu Leu Ser Arg Pro Thr Val Leu Leu Arg Tyr Phe Pro Arg Leu
            180                 185                 190

Ala Ala Gly Tyr Gln Asp Lys Pro Ala Val Asn Glu Leu Thr Met Ala
        195                 200                 205

Ile Thr Asp Asn Leu Thr Val Ala Asp Ala Trp Ile Gly Asp Gly Glu
    210                 215                 220

Leu Asn Leu Pro Glu Val His Gly Glu Glu Leu His Gly Leu Ala Pro
225                 230                 235                 240

Ile Ala Ile Glu Ser Gly Phe Arg Tyr Ser Leu Ser Tyr Ser Val Thr
                245                 250                 255

Asp Leu Lys Ile Leu Glu Asp His Ala Ser
            260                 265

<210> SEQ ID NO 31
```

```
<211> LENGTH: 262
<212> TYPE: PRT
<213> ORGANISM: Escherichia coli

<400> SEQUENCE: 31

Met Glu Asn Ser Phe Lys Ala Ala Leu Lys Ala Gly Arg Pro Gln Ile
1               5                   10                  15

Gly Leu Trp Leu Gly Leu Ser Ser Tyr Ser Ala Glu Leu Leu Ala
            20                  25                  30

Gly Ala Gly Phe Asp Trp Leu Leu Ile Asp Gly Glu His Ala Pro Asn
        35                  40                  45

Asn Val Gln Thr Val Leu Thr Gln Leu Gln Ala Ile Ala Pro Tyr Pro
        50                  55                  60

Ser Gln Pro Val Val Arg Pro Ser Trp Asn Asp Pro Val Gln Ile Lys
65                  70                  75                  80

Gln Leu Leu Asp Val Gly Thr Gln Thr Leu Leu Val Pro Met Val Gln
                85                  90                  95

Asn Ala Asp Glu Ala Arg Glu Ala Val Arg Ala Thr Arg Tyr Pro Pro
            100                 105                 110

Ala Gly Ile Arg Gly Val Gly Ser Ala Leu Ala Arg Ala Ser Arg Trp
        115                 120                 125

Asn Arg Ile Pro Asp Tyr Leu Gln Lys Ala Asn Asp Gln Met Cys Val
130                 135                 140

Leu Val Gln Ile Glu Thr Arg Glu Ala Met Lys Asn Leu Pro Gln Ile
145                 150                 155                 160

Leu Asp Val Glu Gly Val Asp Gly Val Phe Ile Gly Pro Ala Asp Leu
                165                 170                 175

Ser Ala Asp Met Gly Tyr Ala Gly Asn Pro Gln His Pro Glu Val Gln
            180                 185                 190

Ala Ala Ile Glu Gln Ala Ile Val Gln Ile Arg Glu Ser Gly Lys Ala
        195                 200                 205

Pro Gly Ile Leu Ile Ala Asn Glu Gln Leu Ala Lys Arg Tyr Leu Glu
    210                 215                 220

Leu Gly Ala Leu Phe Val Ala Val Gly Val Asp Thr Thr Leu Leu Ala
225                 230                 235                 240

Arg Ala Ala Glu Ala Leu Ala Ala Arg Phe Gly Ala Gln Ala Thr Ala
                245                 250                 255

Val Lys Pro Gly Val Tyr
            260

<210> SEQ ID NO 32
<211> LENGTH: 302
<212> TYPE: PRT
<213> ORGANISM: Escherichia coli

<400> SEQUENCE: 32

Met Pro Gln Ser Ala Leu Phe Thr Gly Ile Ile Pro Pro Val Ser Thr
1               5                   10                  15

Ile Phe Thr Ala Asp Gly Gln Leu Asp Lys Pro Gly Thr Ala Ala Leu
            20                  25                  30

Ile Asp Asp Leu Ile Lys Ala Gly Val Asp Gly Leu Phe Phe Leu Gly
        35                  40                  45

Ser Gly Gly Glu Phe Ser Gln Leu Gly Ala Glu Glu Arg Lys Ala Ile
    50                  55                  60

Ala Arg Phe Ala Ile Asp His Val Asp Arg Arg Val Pro Val Leu Ile
65                  70                  75                  80
```

```
Gly Thr Gly Gly Thr Asn Ala Arg Glu Thr Ile Glu Leu Ser Gln His
                85                  90                  95

Ala Gln Gln Ala Gly Ala Asp Gly Ile Val Ile Asn Pro Tyr Tyr
            100                 105                 110

Trp Lys Val Ser Glu Ala Asn Leu Ile Arg Tyr Phe Glu Gln Val Ala
            115                 120                 125

Asp Ser Val Thr Leu Pro Val Met Leu Tyr Asn Phe Pro Ala Leu Thr
        130                 135                 140

Gly Gln Asp Leu Thr Pro Ala Leu Val Lys Thr Leu Ala Asp Ser Arg
145                 150                 155                 160

Ser Asn Ile Ile Gly Ile Lys Asp Thr Ile Asp Ser Val Ala His Leu
                165                 170                 175

Arg Ser Met Ile His Thr Val Lys Gly Ala His Pro His Phe Thr Val
            180                 185                 190

Leu Cys Gly Tyr Asp Asp His Leu Phe Asn Thr Leu Leu Leu Gly Gly
            195                 200                 205

Asp Gly Ala Ile Ser Ala Ser Gly Asn Phe Ala Pro Gln Val Ser Val
        210                 215                 220

Asn Leu Leu Lys Ala Trp Arg Asp Gly Asp Val Ala Lys Ala Ala Gly
225                 230                 235                 240

Tyr His Gln Thr Leu Leu Gln Ile Pro Gln Met Tyr Gln Leu Asp Thr
                245                 250                 255

Pro Phe Val Asn Val Ile Lys Glu Ala Ile Val Leu Cys Gly Arg Pro
            260                 265                 270

Val Ser Thr His Val Leu Pro Pro Ala Ser Pro Leu Asp Glu Pro Arg
            275                 280                 285

Lys Ala Gln Leu Lys Thr Leu Leu Gln Gln Leu Lys Leu Cys
        290                 295                 300

<210> SEQ ID NO 33
<211> LENGTH: 297
<212> TYPE: PRT
<213> ORGANISM: Escherichia coli

<400> SEQUENCE: 33

Met Ala Thr Asn Leu Arg Gly Val Met Ala Ala Leu Leu Thr Pro Phe
1               5                   10                  15

Asp Gln Gln Gln Ala Leu Asp Lys Ala Ser Leu Arg Arg Leu Val Gln
            20                  25                  30

Phe Asn Ile Gln Gln Gly Ile Asp Gly Leu Tyr Val Gly Gly Ser Thr
        35                  40                  45

Gly Glu Ala Phe Val Gln Ser Leu Ser Glu Arg Glu Gln Val Leu Glu
    50                  55                  60

Ile Val Ala Glu Glu Ala Lys Gly Lys Ile Lys Leu Ile Ala His Val
65                  70                  75                  80

Gly Cys Val Ser Thr Ala Glu Ser Gln Gln Leu Ala Ala Ser Ala Lys
                85                  90                  95

Arg Tyr Gly Phe Asp Ala Val Ser Ala Val Thr Pro Phe Tyr Tyr Pro
            100                 105                 110

Phe Ser Phe Glu Glu His Cys Asp His Tyr Arg Ala Ile Ile Asp Ser
        115                 120                 125

Ala Asp Gly Leu Pro Met Val Val Tyr Asn Ile Pro Ala Leu Ser Gly
    130                 135                 140

Val Lys Leu Thr Leu Asp Gln Ile Asn Thr Leu Val Thr Leu Pro Gly
```

```
            145                 150                 155                 160

Val Gly Ala Leu Lys Gln Thr Ser Gly Asp Leu Tyr Gln Met Glu Gln
                        165                 170                 175

Ile Arg Arg Glu His Pro Asp Leu Val Leu Tyr Asn Gly Tyr Asp Glu
                        180                 185                 190

Ile Phe Ala Ser Gly Leu Leu Ala Gly Ala Asp Gly Gly Ile Gly Ser
                        195                 200                 205

Thr Tyr Asn Ile Met Gly Trp Arg Tyr Gln Gly Ile Val Lys Ala Leu
                        210                 215                 220

Lys Glu Gly Asp Ile Gln Thr Ala Gln Lys Leu Gln Thr Glu Cys Asn
    225                 230                 235                 240

Lys Val Ile Asp Leu Leu Ile Lys Thr Gly Val Phe Arg Gly Leu Lys
                        245                 250                 255

Thr Val Leu His Tyr Met Asp Val Val Ser Val Pro Leu Cys Arg Lys
                        260                 265                 270

Pro Phe Gly Pro Val Asp Glu Lys Tyr Leu Pro Glu Leu Lys Ala Leu
                        275                 280                 285

Ala Gln Gln Leu Met Gln Glu Arg Gly
                        290                 295

<210> SEQ ID NO 34
<211> LENGTH: 256
<212> TYPE: PRT
<213> ORGANISM: Escherichia coli

<400> SEQUENCE: 34

Met Asn Asn Asp Val Phe Pro Asn Lys Phe Lys Ala Ala Leu Ala Ala
    1               5                   10                  15

Lys Gln Val Gln Ile Gly Cys Trp Ser Ala Leu Ser Asn Pro Ile Ser
                        20                  25                  30

Thr Glu Val Leu Gly Leu Ala Gly Phe Asp Trp Leu Val Leu Asp Gly
                        35                  40                  45

Glu His Ala Pro Asn Asp Ile Ser Thr Phe Ile Pro Gln Leu Met Ala
    50                  55                  60

Leu Lys Gly Ser Ala Ser Ala Pro Val Val Arg Val Pro Thr Asn Glu
    65                  70                  75                  80

Pro Val Ile Ile Lys Arg Leu Leu Asp Ile Gly Phe Tyr Asn Phe Leu
                        85                  90                  95

Ile Pro Phe Val Glu Thr Lys Glu Glu Ala Glu Leu Ala Val Ala Ser
                        100                 105                 110

Thr Arg Tyr Pro Pro Glu Gly Ile Arg Gly Val Ser Val Ser His Arg
                        115                 120                 125

Ala Asn Met Phe Gly Thr Val Ala Asp Tyr Phe Ala Gln Ser Asn Lys
    130                 135                 140

Asn Ile Thr Ile Leu Val Gln Ile Glu Ser Gln Gln Gly Val Asp Asn
    145                 150                 155                 160

Val Asp Ala Ile Ala Ala Thr Glu Gly Val Asp Gly Ile Phe Val Gly
                        165                 170                 175

Pro Ser Asp Leu Ala Ala Ala Leu Gly His Leu Gly Asn Ala Ser His
                        180                 185                 190

Pro Asp Val Gln Lys Ala Ile Gln His Ile Phe Asn Arg Ala Ser Ala
                        195                 200                 205

His Gly Lys Pro Ser Gly Ile Leu Ala Pro Val Glu Ala Asp Ala Arg
                        210                 215                 220
```

```
Arg Tyr Leu Glu Trp Gly Ala Thr Phe Val Ala Val Gly Ser Asp Leu
225                 230                 235                 240

Gly Val Phe Arg Ser Ala Thr Gln Lys Leu Ala Asp Thr Phe Lys Lys
                245                 250                 255

<210> SEQ ID NO 35
<211> LENGTH: 213
<212> TYPE: PRT
<213> ORGANISM: Escherichia coli

<400> SEQUENCE: 35

Met Lys Asn Trp Lys Thr Ser Ala Glu Ser Ile Leu Thr Thr Gly Pro
1               5                   10                  15

Val Val Pro Val Ile Val Lys Lys Leu Glu His Ala Val Pro Met
            20                  25                  30

Ala Lys Ala Leu Val Ala Gly Gly Val Arg Val Leu Glu Val Thr Leu
            35                  40                  45

Arg Thr Glu Cys Ala Val Asp Ala Ile Arg Ala Ile Ala Lys Glu Val
        50                  55                  60

Pro Glu Ala Ile Val Gly Ala Gly Thr Val Leu Asn Pro Gln Gln Leu
65                  70                  75                  80

Ala Glu Val Thr Glu Ala Gly Ala Gln Phe Ala Ile Ser Pro Gly Leu
                85                  90                  95

Thr Glu Pro Leu Leu Lys Ala Ala Thr Glu Gly Thr Ile Pro Leu Ile
            100                 105                 110

Pro Gly Ile Ser Thr Val Ser Glu Leu Met Leu Gly Met Asp Tyr Gly
        115                 120                 125

Leu Lys Glu Phe Lys Phe Phe Pro Ala Glu Ala Asn Gly Gly Val Lys
130                 135                 140

Ala Leu Gln Ala Ile Ala Gly Pro Phe Ser Gln Val Arg Phe Cys Pro
145                 150                 155                 160

Thr Gly Gly Ile Ser Pro Ala Asn Tyr Arg Asp Tyr Leu Ala Leu Lys
                165                 170                 175

Ser Val Leu Cys Ile Gly Gly Ser Trp Leu Val Pro Ala Asp Ala Leu
            180                 185                 190

Glu Ala Gly Asp Tyr Asp Arg Ile Thr Lys Leu Ala Arg Glu Ala Val
        195                 200                 205

Glu Gly Ala Lys Leu
    210

<210> SEQ ID NO 36
<211> LENGTH: 205
<212> TYPE: PRT
<213> ORGANISM: Escherichia coli

<400> SEQUENCE: 36

Met Gln Trp Gln Thr Lys Leu Pro Leu Ile Ala Ile Leu Arg Gly Ile
1               5                   10                  15

Thr Pro Asp Glu Ala Leu Ala His Val Gly Ala Val Ile Asp Ala Gly
            20                  25                  30

Phe Asp Ala Val Glu Ile Pro Leu Asn Ser Pro Gln Trp Glu Gln Ser
            35                  40                  45

Ile Pro Ala Ile Val Asp Ala Tyr Gly Asp Lys Ala Leu Ile Gly Ala
        50                  55                  60

Gly Thr Val Leu Lys Pro Glu Gln Val Asp Ala Leu Ala Arg Met Gly
65                  70                  75                  80
```

```
Cys Gln Leu Ile Val Thr Pro Asn Ile His Ser Glu Val Ile Arg Arg
                85                  90                  95

Ala Val Gly Tyr Gly Met Thr Val Cys Pro Gly Cys Ala Thr Ala Thr
            100                 105                 110

Glu Ala Phe Thr Ala Leu Glu Ala Gly Ala Gln Ala Leu Lys Ile Phe
        115                 120                 125

Pro Ser Ser Ala Phe Gly Pro Gln Tyr Ile Lys Ala Leu Lys Ala Val
    130                 135                 140

Leu Pro Ser Asp Ile Ala Val Phe Ala Val Gly Val Thr Pro Glu
145                 150                 155                 160

Asn Leu Ala Gln Trp Ile Asp Ala Gly Cys Ala Gly Ala Gly Leu Gly
                165                 170                 175

Ser Asp Leu Tyr Arg Ala Gly Gln Ser Val Glu Arg Thr Ala Gln Gln
            180                 185                 190

Ala Ala Ala Phe Val Lys Ala Tyr Arg Glu Ala Val Gln
        195                 200                 205

<210> SEQ ID NO 37
<211> LENGTH: 301
<212> TYPE: PRT
<213> ORGANISM: Azotobacter vinelandii

<400> SEQUENCE: 37

Met Pro Ala Pro Val Leu Ala Ala Thr Ser Pro Gly Ala Gly Arg Ala
1               5                   10                  15

Ile His Leu Ile Asn Pro Ala Met Pro Ala Phe Arg Ala Ala Phe Glu
            20                  25                  30

Glu Thr Leu Met Lys Met Pro His Asn Ala Phe Lys Ala Ala Leu Gln
        35                  40                  45

Arg Pro Glu Thr Gln Tyr Gly Ile Trp Ala Gly Phe Ala Ser Gly Tyr
    50                  55                  60

Ala Ala Glu Ile Val Ala Gly Thr Gly Tyr Asp Trp Met Leu Ile Asp
65                  70                  75                  80

Gly Glu His Ala Pro Asn Ser Val Pro Thr Ile Leu Ala Gln Leu Gln
                85                  90                  95

Ser Val Ala Pro Tyr Pro Thr Gln Pro Val Val Arg Pro Val Cys Gly
            100                 105                 110

Asp Pro Val Leu Ile Lys Gln Leu Leu Asp Ile Gly Ala Gln Thr Leu
        115                 120                 125

Met Val Pro Met Val Glu Ser Ala Glu Gln Ala Arg Ala Leu Val Arg
    130                 135                 140

Ala Met Arg Tyr Pro Pro His Gly Ile Arg Gly Val Gly Gly Gly Leu
145                 150                 155                 160

Ala Arg Ala Thr Arg Trp Asp Gly Val Pro Asp Tyr Leu Asn Thr Ala
                165                 170                 175

His Glu Glu Leu Cys Leu Ile Val Gln Val Glu Ser Arg Ala Gly Val
            180                 185                 190

Glu Asn Val Glu Ala Ile Ala Ala Val Glu Gly Val Asp Ala Val Phe
        195                 200                 205

Ile Gly Pro Ala Asp Leu Ser Ile Gly Leu Gly His Pro Gly Asp Pro
    210                 215                 220

Gly His Pro Gln Val Gln Glu Leu Ile His His Ala Ile Glu Ala Thr
225                 230                 235                 240

Arg Ala Ala Gly Lys Ala Cys Gly Ile Leu Ala Pro His Glu Glu Asp
                245                 250                 255
```

```
Ala Arg Arg Tyr Arg Glu Trp Gly Cys Arg Phe Ile Ala Val Ala Ile
        260                 265                 270

Asp Ile Ser Leu Leu Arg Gln Gly Ala Leu Ala Gly Leu Ala Arg Phe
        275                 280                 285

Arg Asp Thr Pro Ala Ser Asp Ala Pro Ser Arg Thr Tyr
        290                 295                 300

<210> SEQ ID NO 38
<211> LENGTH: 312
<212> TYPE: PRT
<213> ORGANISM: Corynebacterium glutamicum

<400> SEQUENCE: 38

Met Ala Ser Ala Thr Phe Thr Gly Val Ile Pro Pro Val Met Thr Pro
1               5                   10                  15

Leu His Ala Asp Gly Ser Val Asp Val Glu Ser Leu Arg Lys Leu Val
            20                  25                  30

Asp His Leu Ile Asn Gly Gly Val Asp Gly Leu Phe Ala Leu Gly Ser
        35                  40                  45

Ser Gly Glu Ala Ala Phe Leu Thr Arg Ala Gln Arg Lys Leu Ala Leu
    50                  55                  60

Thr Thr Ile Ile Glu His Thr Ala Gly Arg Val Pro Val Thr Ala Gly
65                  70                  75                  80

Val Ile Glu Thr Thr Thr Ala Arg Val Ile Glu Leu Val Glu Asp Ala
                85                  90                  95

Leu Glu Ala Gly Ala Glu Gly Leu Val Ala Thr Ala Pro Phe Tyr Thr
            100                 105                 110

Arg Thr His Asp Val Glu Ile Glu Glu His Phe Arg Lys Ile His Ala
        115                 120                 125

Ala Ala Pro Glu Leu Pro Leu Phe Ala Tyr Asn Ile Pro Val Ser Val
    130                 135                 140

His Ser Asn Leu Asn Pro Val Met Leu Leu Thr Leu Ala Lys Asp Gly
145                 150                 155                 160

Val Leu Ala Gly Thr Lys Asp Ser Ser Gly Asn Asp Gly Ala Ile Arg
                165                 170                 175

Ser Leu Ile Glu Ala Arg Asp Asp Ala Gly Leu Thr Glu Gln Phe Lys
            180                 185                 190

Ile Leu Thr Gly Ser Glu Thr Thr Val Asp Phe Ala Tyr Leu Ala Gly
        195                 200                 205

Ala Asp Gly Val Val Pro Gly Leu Gly Asn Val Asp Pro Ala Ala Tyr
    210                 215                 220

Ala Ala Leu Ala Lys Leu Cys Leu Asp Gly Lys Trp Ala Glu Ala Ala
225                 230                 235                 240

Ala Leu Gln Lys Arg Ile Asn His Leu Phe His Ile Val Phe Val Gly
                245                 250                 255

Asp Thr Ser His Met Ser Gly Ser Ala Gly Leu Gly Gly Phe Lys
            260                 265                 270

Thr Ala Leu Ala His Leu Gly Ile Ile Glu Ser Asn Ala Met Ala Val
        275                 280                 285

Pro His Gln Ser Leu Ser Asp Glu Glu Thr Ala Arg Ile His Ala Ile
    290                 295                 300

Val Asp Glu Phe Leu Tyr Thr Ala
305                 310
```

-continued

```
<210> SEQ ID NO 39
<211> LENGTH: 298
<212> TYPE: PRT
<213> ORGANISM: Campylobacter jejuni

<400> SEQUENCE: 39
```

Met Asp Lys Asn Ile Ile Ile Gly Ala Met Thr Ala Leu Ile Thr Pro
1               5                   10                  15

Phe Lys Asn Gly Lys Val Asp Glu Gln Ser Tyr Ala Arg Leu Ile Lys
            20                  25                  30

Arg Gln Ile Glu Asn Gly Ile Asp Ala Val Val Pro Val Gly Thr Thr
        35                  40                  45

Gly Glu Ser Ala Thr Leu Thr His Glu Glu His Arg Thr Cys Ile Glu
    50                  55                  60

Ile Ala Val Glu Thr Cys Lys Glu Thr Lys Val Lys Val Leu Ala Gly
65                  70                  75                  80

Ala Gly Ser Asn Ala Thr His Glu Ala Val Gly Leu Ala Lys Phe Ala
                85                  90                  95

Lys Glu His Gly Ala Asp Gly Ile Leu Ser Val Ala Pro Tyr Tyr Asn
            100                 105                 110

Lys Pro Thr Gln Gln Gly Leu Tyr Glu His Tyr Lys Ala Ile Ala Gln
        115                 120                 125

Ser Val Asp Ile Pro Val Leu Leu Tyr Asn Val Pro Gly Arg Thr Gly
    130                 135                 140

Cys Glu Ile Ser Thr Asp Thr Ile Ile Lys Leu Phe Arg Asp Cys Glu
145                 150                 155                 160

Asn Ile Tyr Gly Val Lys Glu Ala Ser Gly Asn Ile Asp Lys Cys Val
                165                 170                 175

Asp Leu Leu Ala His Glu Pro Arg Met Met Leu Ile Ser Gly Glu Asp
            180                 185                 190

Ala Ile Asn Tyr Pro Ile Leu Ser Asn Gly Gly Lys Gly Val Ile Ser
        195                 200                 205

Val Thr Ser Asn Leu Leu Pro Asp Met Ile Ser Thr Leu Thr His Phe
    210                 215                 220

Ala Leu Asp Glu Asn Tyr Lys Glu Ala Lys Ile Asn Asp Glu Leu
225                 230                 235                 240

Tyr Asn Ile Asn Lys Ile Leu Phe Cys Glu Ser Asn Pro Ile Pro Ile
                245                 250                 255

Lys Thr Ala Met Tyr Ile Ala Gly Leu Ile Glu Ser Leu Glu Phe Arg
            260                 265                 270

Leu Pro Leu Cys Pro Pro Ser Lys Glu Asn Phe Ala Lys Ile Glu Glu
        275                 280                 285

Val Met Lys Lys Tyr Lys Ile Lys Gly Phe
    290                 295

```
<210> SEQ ID NO 40
<211> LENGTH: 297
<212> TYPE: PRT
<213> ORGANISM: Caldanaerobacter subterraneus

<400> SEQUENCE: 40
```

Met Pro Val Phe Lys Gly Ser Cys Val Ala Ile Val Thr Pro Phe Thr
1               5                   10                  15

Glu Asn Gly Val Asn Phe Asp Lys Leu Gly Glu Leu Ile Glu Trp His
            20                  25                  30

Ile Lys Glu Gly Thr Asp Ala Ile Leu Ile Cys Gly Thr Thr Gly Glu

```
            35                  40                  45
Ala Ser Thr Met Thr Asp Glu Glu Gln Lys Glu Ala Ile Lys Phe Thr
 50                  55                  60

Val Glu Lys Val Ala Lys Arg Ile Pro Val Ile Ala Gly Thr Gly Ser
 65                  70                  75                  80

Asn Asn Thr Ala His Ala Ile Glu Leu Ser Glu Tyr Ala Gln Ser Val
                     85                  90                  95

Gly Ala Asp Ala Leu Leu Val Ile Thr Pro Tyr Tyr Asn Lys Thr Thr
                100                 105                 110

Gln Lys Gly Leu Val Ala His Phe Thr Glu Ile Ala Arg His Val Asp
            115                 120                 125

Ile Pro Ile Ile Ile Tyr Asn Val Pro Ser Arg Thr Ser Leu Asn Met
130                 135                 140

Leu Pro Glu Thr Tyr Leu Glu Val Lys Lys Ala Glu Asn Val Val
145                 150                 155                 160

Gly Val Lys Glu Ala Ser Gly Asp Ile Ser Gln Ile Ala Glu Ile Ala
                165                 170                 175

Arg Ile Met Gly Lys Ser Phe Glu Ile Tyr Ser Gly Asn Asp Asp Gln
            180                 185                 190

Val Ile Pro Ile Met Ser Leu Gly Gly Leu Gly Val Ile Ser Val Thr
            195                 200                 205

Ala Asn Ile Ile Pro Ala Lys Ile His Glu Met Thr Thr Ala Tyr Leu
210                 215                 220

Asn Gly Asp Ile Glu Lys Ala Arg Asp Met Gln Leu Glu Leu Asn Pro
225                 230                 235                 240

Leu Asn Lys Ala Leu Phe Ile Glu Thr Asn Pro Ile Pro Val Lys Thr
                245                 250                 255

Ala Met Asn Leu Met Gly Phe Gly Val Gly Pro Leu Arg Leu Pro Leu
            260                 265                 270

Val Glu Met Ser Glu Lys Asn Leu Glu Tyr Leu Lys Ser Val Leu Arg
            275                 280                 285

Gln Tyr Gly Leu Leu Lys Glu Glu Asn
            290                 295

<210> SEQ ID NO 41
<211> LENGTH: 310
<212> TYPE: PRT
<213> ORGANISM: Scheffersomyces stipitis

<400> SEQUENCE: 41

Met Thr Ile Ser Ala Ala Leu Pro Lys Arg Gly Val Tyr Thr Pro Val
 1               5                  10                  15

Pro Thr Phe Phe Lys Lys Asp Leu His Thr Ile Asp Tyr Asp Ser Gln
                 20                  25                  30

Ile Glu His Ala Lys Phe Leu Gln Gln Asn Gly Ile Thr Gly Leu Val
             35                  40                  45

Leu Leu Gly Ser Thr Gly Glu Asn Ser His Leu Thr Arg Lys Glu Arg
         50                  55                  60

Ile Glu Leu Val Ser Thr Ile His Glu Glu Leu Pro Asp Phe Pro Leu
 65                  70                  75                  80

Met Ala Gly Val Ala Gln Asn Ser Val Glu Asp Ala Ile Glu Glu Ile
                 85                  90                  95

Leu Gln Leu Lys Asn Ala Gly Ala Gln His Ala Leu Val Leu Pro Ser
                100                 105                 110
```

```
Ser Tyr Phe Gly Ala Ser Ile Lys Gln Gln Gly Ile Asp Trp Tyr
            115                 120                 125

Thr Glu Val Ala Asp Asn Ala Ser Leu Pro Val Leu Ile Tyr Val Tyr
130                 135                 140

Pro Gly Val Ser Asn Asn Ile Ser Ile Asp Pro Arg Thr Ile Lys Lys
145                 150                 155                 160

Leu Ser Ala His Pro Asn Ile Val Gly Ala Lys Ile Ser His Gly Asp
                165                 170                 175

Val Ser His His Ala Ile Ile Gly Leu Asp Gln Glu Ile Ala Ala Asn
            180                 185                 190

Gln Phe Ile Thr Leu Thr Gly Leu Gly Gln Ile Leu Leu Pro Val Leu
        195                 200                 205

Val Val Gly Ile Gln Gly Thr Val Asp Ala Leu Cys Gly Ala Phe Pro
210                 215                 220

Lys Ile Tyr Val Lys Leu Leu Glu Asn Tyr Asp Lys Gly Asp Leu Arg
225                 230                 235                 240

Ala Ala Ala Glu Leu Gln Leu Val Ile Ser Arg Ala Glu Glu Leu Val
                245                 250                 255

Val Lys Phe Gly Val Val Gly Ile Lys Lys Ala Ile His Phe Ala Thr
            260                 265                 270

Gly Ile Gly Glu Thr Tyr Leu Gly Arg Ala Pro Leu Thr Gln Asp Val
        275                 280                 285

Asn Asp Ala Asp Trp Lys Ser Tyr Asn Asp Tyr Leu Leu Gly Ile Val
290                 295                 300

Ser Val Glu Ser Thr Leu
305                 310

<210> SEQ ID NO 42
<211> LENGTH: 288
<212> TYPE: PRT
<213> ORGANISM: Sulfolobus acidocaldarius

<400> SEQUENCE: 42

Met Glu Ile Ile Ser Pro Ile Ile Thr Pro Phe Asp Lys Gln Gly Lys
1               5                   10                  15

Val Asn Val Asp Ala Leu Lys Thr His Ala Lys Asn Leu Leu Glu Lys
                20                  25                  30

Gly Ile Asp Ala Ile Phe Val Asn Gly Thr Thr Gly Leu Gly Pro Ala
            35                  40                  45

Leu Ser Lys Asp Glu Lys Arg Gln Asn Leu Asn Ala Leu Tyr Asp Val
50                  55                  60

Thr His Lys Leu Ile Phe Gln Val Gly Ser Leu Asn Leu Asn Asp Val
65                  70                  75                  80

Met Glu Leu Val Lys Phe Ser Asn Glu Met Asp Ile Leu Gly Val Ser
                85                  90                  95

Ser His Ser Pro Tyr Tyr Phe Pro Arg Leu Pro Glu Lys Phe Leu Ala
            100                 105                 110

Lys Tyr Tyr Glu Glu Ile Ala Arg Ile Ser Ser His Ser Leu Tyr Ile
        115                 120                 125

Tyr Asn Tyr Pro Ala Ala Thr Gly Tyr Asp Ile Pro Pro Ser Ile Leu
130                 135                 140

Lys Ser Leu Pro Val Lys Gly Ile Lys Asp Thr Asn Gln Asp Leu Ala
145                 150                 155                 160

His Ser Leu Glu Tyr Lys Leu Asn Leu Pro Gly Val Lys Val Tyr Asn
                165                 170                 175
```

```
Gly Ser Asn Thr Leu Ile Tyr Tyr Ser Leu Leu Ser Leu Asp Gly Val
            180                 185                 190

Val Ala Ser Phe Thr Asn Phe Ile Pro Glu Val Ile Val Lys Gln Arg
        195                 200                 205

Asp Leu Ile Lys Gln Gly Lys Leu Asp Asp Ala Leu Arg Leu Gln Glu
    210                 215                 220

Leu Ile Asn Arg Leu Ala Asp Ile Leu Arg Lys Tyr Gly Ser Ile Ser
225                 230                 235                 240

Ala Ile Tyr Val Leu Val Asn Glu Phe Gln Gly Tyr Asp Val Gly Tyr
                245                 250                 255

Pro Arg Pro Pro Ile Phe Pro Leu Thr Asp Glu Glu Ala Leu Ser Leu
            260                 265                 270

Lys Arg Glu Ile Glu Pro Leu Lys Arg Lys Ile Gln Glu Leu Val His
        275                 280                 285

<210> SEQ ID NO 43
<211> LENGTH: 294
<212> TYPE: PRT
<213> ORGANISM: Saccharolobus solfataricus

<400> SEQUENCE: 43

Met Pro Glu Ile Ile Thr Pro Ile Ile Thr Pro Phe Thr Lys Asp Asn
1               5                   10                  15

Arg Ile Asp Lys Glu Lys Leu Lys Ile His Ala Glu Asn Leu Ile Arg
            20                  25                  30

Lys Gly Ile Asp Lys Leu Phe Val Asn Gly Thr Thr Gly Leu Gly Pro
        35                  40                  45

Ser Leu Ser Pro Glu Glu Lys Leu Glu Asn Leu Lys Ala Val Tyr Asp
    50                  55                  60

Val Thr Asn Lys Ile Ile Phe Gln Val Gly Gly Leu Asn Leu Asp Asp
65                  70                  75                  80

Ala Ile Arg Leu Ala Lys Leu Ser Lys Asp Phe Asp Ile Val Gly Ile
                85                  90                  95

Ala Ser Tyr Ala Pro Tyr Tyr Tyr Pro Arg Met Ser Glu Lys His Leu
            100                 105                 110

Val Lys Tyr Phe Lys Thr Leu Cys Glu Val Ser Pro His Pro Val Tyr
        115                 120                 125

Leu Tyr Asn Tyr Pro Thr Ala Thr Gly Lys Asp Ile Asp Ala Lys Val
    130                 135                 140

Ala Lys Glu Ile Gly Cys Phe Thr Gly Val Lys Asp Thr Ile Glu Asn
145                 150                 155                 160

Ile Ile His Thr Leu Asp Tyr Lys Arg Leu Asn Pro Asn Met Leu Val
                165                 170                 175

Tyr Ser Gly Ser Asp Met Leu Ile Ala Thr Val Ala Ser Thr Gly Leu
            180                 185                 190

Asp Gly Asn Val Ala Ala Gly Ser Asn Tyr Leu Pro Glu Val Thr Val
        195                 200                 205

Thr Ile Lys Lys Leu Ala Met Glu Arg Lys Ile Asp Glu Ala Leu Lys
    210                 215                 220

Leu Gln Phe Leu His Asp Glu Val Ile Glu Ala Ser Arg Ile Phe Gly
225                 230                 235                 240

Ser Leu Ser Ser Asn Tyr Val Leu Thr Lys Tyr Phe Gln Gly Tyr Asp
                245                 250                 255

Leu Gly Tyr Pro Arg Pro Pro Ile Phe Pro Leu Asp Asp Glu Glu Glu
```

```
                260                 265                 270
Arg Gln Leu Ile Lys Lys Val Glu Gly Ile Arg Ala Lys Leu Val Glu
            275                 280                 285

Leu Lys Ile Leu Lys Glu
            290

<210> SEQ ID NO 44
<211> LENGTH: 290
<212> TYPE: PRT
<213> ORGANISM: Sulfurisphaera tokodaii

<400> SEQUENCE: 44

Met Asp Ile Val Thr Pro Ile Leu Thr Pro Phe Thr Lys Glu Gly Lys
1               5                   10                  15

Ile Asp Val Glu Lys Leu Lys Ala His Ala Lys Phe Leu Ile Asp Asn
            20                  25                  30

Gly Ile Asp Leu Leu Phe Val Asn Gly Thr Thr Gly Leu Gly Pro Ala
        35                  40                  45

Leu Ser Lys Glu Glu Lys Leu Thr Thr Leu Lys Thr Ile Tyr Asp Val
    50                  55                  60

Thr Asn Lys Val Ile Phe Gln Val Gly Ser Leu Asn Ile Asn Asp Val
65                  70                  75                  80

Ile Asp Leu Val Lys Ala Ser Lys Asp Phe Asp Ile Val Gly Ile Ala
                85                  90                  95

Ser Tyr Pro Pro Phe Tyr Phe Pro Arg Leu Pro Glu Lys Phe Leu Leu
            100                 105                 110

Lys Tyr Phe Thr Thr Ile Ala Asn Tyr Ser Pro His Ser Leu Tyr Ile
        115                 120                 125

Tyr Asn Tyr Pro Leu Ala Thr Gly Tyr Asp Ile Ser Ala Lys Ile Val
    130                 135                 140

Tyr Gln Met Lys Asp Leu Ile Thr Gly Leu Lys Asp Thr Asn Gln Asp
145                 150                 155                 160

Leu Ser His Ser Leu Glu Tyr Lys Ile Leu Met Pro Asn Leu Lys Val
                165                 170                 175

Tyr Asn Gly Ser Asp Ser Leu Val Phe Tyr Ser Leu Thr Ser Leu Asp
            180                 185                 190

Gly Ser Val Thr Ala Ala Ser Asn Tyr Leu Pro His Val Met Lys Lys
        195                 200                 205

Met Lys Glu His Ile Thr Ser Gly Gln Val Ser Lys Ala Ile Glu Leu
    210                 215                 220

Gln Lys Leu Ile Asn Lys Ala Leu Asp Ile Ser Arg Lys Tyr Gly Gln
225                 230                 235                 240

Leu Ser Ala Ile Tyr Tyr Leu Val Lys Glu Phe Leu Gly Tyr Asp Val
                245                 250                 255

Gly Tyr Pro Arg Gly Pro Ile Phe Pro Leu Glu Glu Asp Glu Val Lys
            260                 265                 270

Ala Leu Leu Ser Glu Ile Gln Pro Val Lys Lys Glu Ile Glu Arg Ala
        275                 280                 285

Val Ser
    290

<210> SEQ ID NO 45
<211> LENGTH: 327
<212> TYPE: PRT
<213> ORGANISM: Escherichia coli
```

<400> SEQUENCE: 45

Met Ala Thr Arg Ile Glu Phe His Lys His Gly Gly Pro Glu Val Leu
1               5                   10                  15

Gln Ala Val Glu Phe Thr Pro Ala Asp Pro Ala Glu Asn Glu Ile Gln
            20                  25                  30

Val Glu Asn Lys Ala Ile Gly Ile Asn Phe Ile Asp Thr Tyr Ile Arg
        35                  40                  45

Ser Gly Leu Tyr Pro Pro Ser Leu Pro Ser Gly Leu Gly Thr Glu
    50                  55                  60

Ala Ala Gly Ile Val Ser Lys Val Gly Ser Gly Val Lys His Ile Lys
65                  70                  75                  80

Ala Gly Asp Arg Val Val Tyr Ala Gln Ser Ala Leu Gly Ala Tyr Ser
                85                  90                  95

Ser Val His Asn Ile Ile Ala Asp Lys Ala Ala Ile Leu Pro Ala Ala
            100                 105                 110

Ile Ser Phe Glu Gln Ala Ala Ser Phe Leu Lys Gly Leu Thr Val
        115                 120                 125

Tyr Tyr Leu Leu Arg Lys Thr Tyr Glu Ile Lys Pro Asp Glu Gln Phe
130                 135                 140

Leu Phe His Ala Ala Gly Gly Val Gly Leu Ile Ala Cys Gln Trp
145                 150                 155                 160

Ala Lys Ala Leu Gly Ala Lys Leu Ile Gly Thr Val Gly Thr Ala Gln
                165                 170                 175

Lys Ala Gln Ser Ala Leu Lys Ala Gly Ala Trp Gln Val Ile Asn Tyr
            180                 185                 190

Arg Glu Glu Asp Leu Val Glu Arg Leu Lys Glu Ile Thr Gly Gly Lys
        195                 200                 205

Lys Val Arg Val Val Tyr Asp Ser Val Gly Arg Asp Thr Trp Glu Arg
    210                 215                 220

Ser Leu Asp Cys Leu Gln Arg Arg Gly Leu Met Val Ser Phe Gly Asn
225                 230                 235                 240

Ser Ser Gly Ala Val Thr Gly Val Asn Leu Gly Ile Leu Asn Gln Lys
                245                 250                 255

Gly Ser Leu Tyr Val Thr Arg Pro Ser Leu Gln Gly Tyr Ile Thr Thr
            260                 265                 270

Arg Glu Glu Leu Thr Glu Ala Ser Asn Glu Leu Phe Ser Leu Ile Ala
        275                 280                 285

Ser Gly Val Ile Lys Val Asp Val Ala Glu Gln Lys Tyr Pro Leu
    290                 295                 300

Lys Asp Ala Gln Arg Ala His Glu Ile Leu Glu Ser Arg Ala Thr Gln
305                 310                 315                 320

Gly Ser Ser Leu Leu Ile Pro
                325

<210> SEQ ID NO 46
<211> LENGTH: 327
<212> TYPE: PRT
<213> ORGANISM: Salmonella enterica

<400> SEQUENCE: 46

Met Ala Thr Arg Ile Glu Phe His Lys His Gly Gly Pro Glu Val Leu
1               5                   10                  15

Gln Thr Val Glu Phe Thr Pro Ala Glu Pro Ala Glu His Glu Ile Gln
            20                  25                  30

```
Val Glu Asn Lys Ala Ile Gly Ile Asn Phe Ile Asp Thr Tyr Ile Arg
         35                  40                  45

Ser Gly Leu Tyr Pro Pro Ser Leu Pro Ala Gly Leu Gly Thr Glu
 50                  55                  60

Ala Ala Gly Val Val Ser Lys Val Gly Asn Gly Val Glu His Ile Arg
 65                  70                  75                  80

Val Gly Asp Arg Val Val Tyr Ala Gln Ser Thr Leu Gly Ala Tyr Ser
                 85                  90                  95

Ser Val His Asn Val Thr Ala Asp Lys Ala Ala Ile Leu Pro Asp Ala
             100                 105                 110

Ile Ser Phe Glu Gln Ala Ala Ser Phe Leu Lys Gly Leu Thr Val
         115                 120                 125

Phe Tyr Leu Leu Arg Lys Thr Tyr Glu Val Lys Pro Asp Glu Pro Phe
 130                 135                 140

Leu Phe His Ala Ala Gly Gly Val Gly Leu Ile Ala Cys Gln Trp
 145                 150                 155                 160

Ala Lys Ala Leu Gly Ala Lys Leu Ile Gly Thr Val Gly Ser Ala Gln
                 165                 170                 175

Lys Ala Gln Arg Ala Leu Asp Ala Gly Ala Trp Gln Val Ile Asn Tyr
             180                 185                 190

Arg Glu Glu Ser Ile Val Glu Arg Val Lys Glu Ile Thr Gly Gly Lys
         195                 200                 205

Lys Val Arg Val Val Tyr Asp Ser Val Gly Lys Asp Thr Trp Glu Ala
 210                 215                 220

Ser Leu Asp Cys Leu Gln Arg Arg Gly Leu Met Val Ser Phe Gly Asn
225                 230                 235                 240

Ala Ser Gly Pro Val Thr Gly Val Asn Leu Gly Ile Leu Asn Gln Lys
                 245                 250                 255

Gly Ser Leu Tyr Ala Thr Arg Pro Ser Leu Gln Gly Tyr Ile Thr Thr
             260                 265                 270

Arg Glu Glu Leu Thr Glu Ala Ser Asn Glu Leu Phe Ser Leu Ile Ala
         275                 280                 285

Ser Gly Val Ile Lys Val Asp Val Ala Glu Asn Gln Arg Tyr Ala Leu
 290                 295                 300

Lys Asp Ala Arg Arg Ala His Glu Val Leu Glu Ser Arg Ala Thr Gln
305                 310                 315                 320

Gly Ser Ser Leu Leu Ile Pro
                 325

<210> SEQ ID NO 47
<211> LENGTH: 354
<212> TYPE: PRT
<213> ORGANISM: Cupriavidus necator

<400> SEQUENCE: 47

Met Pro Arg His Gly Cys Leu Thr Ile Val Thr Val Ala Pro Met Ile
 1               5                  10                  15

Ala Ala Arg Ala Gly His Asp Asn Gln Glu Thr Ala Leu Ala Lys Ala
                 20                  25                  30

Ile Arg Met Tyr Glu Thr Gly Gly Pro Glu Val Leu Arg Tyr Glu Asp
             35                  40                  45

Ala Glu Val Gly Asp Pro Gly Pro Gly Glu Val Arg Ile Arg His Ala
         50                  55                  60

Ala Val Gly Leu Asn Tyr Ala Asp Thr Tyr Phe Arg Asn Gly Thr Tyr
 65                  70                  75                  80
```

```
Pro Val Pro Leu Pro Gly Gly Met Gly Val Glu Ala Ala Gly Val Val
                85                  90                  95

Gln Ala Val Gly Pro Gly Val Thr His Val Ala Glu Gly Asp Arg Val
            100                 105                 110

Thr Tyr Thr Gly Phe Ile Asn Thr Leu Gly Ala Tyr Ser Thr Glu Arg
        115                 120                 125

Leu Val Pro Ala Ala Pro Leu Ile Arg Leu Pro Glu Ala Ile Ser Phe
    130                 135                 140

Glu Thr Ala Ala Ala Met Thr Met Arg Gly Leu Thr Ser Ala Tyr Leu
145                 150                 155                 160

Met Arg Arg Ile Tyr Pro Phe Gln Gly Gly Glu Ala Ile Leu Leu His
                165                 170                 175

Ala Ala Ala Gly Gly Val Gly Leu Ile Val Ser Gln Trp Ala Arg Leu
            180                 185                 190

Leu Gly Leu Thr Val Ile Gly Thr Val Ser Thr Glu Ala Lys Ala Glu
        195                 200                 205

Val Ala Arg Ala His Gly Cys Asp His Ile Ile Asn Tyr Ser His Glu
    210                 215                 220

Asp Val Ala Lys Arg Val Arg Glu Leu Thr Asp Gly Ala Gly Val Ser
225                 230                 235                 240

Val Val Phe Asp Ser Val Gly Lys Ser Thr Phe Met Ala Ser Leu Asp
                245                 250                 255

Ser Leu Lys Arg Arg Gly Leu Met Val Cys Val Gly Thr Ala Ser Gly
            260                 265                 270

Thr Ile Pro Pro Phe Asp Pro Gln Leu Leu Ala Arg Lys Gly Ser Val
        275                 280                 285

Tyr Leu Thr Arg Pro Ala Leu Ala Asp Tyr Ile Ala Asp Pro Ala Glu
    290                 295                 300

Lys Ala Glu Leu Ala Ala Glu Val Phe Gly His Val Ala Ala Gly Arg
305                 310                 315                 320

Ile Arg Ile Glu Ile Asn Gln Arg Tyr Ala Leu Gln Asp Ala Val Gln
                325                 330                 335

Ala His Arg Asp Leu Glu Ser Arg Lys Thr Thr Gly Ser Ser Ile Phe
            340                 345                 350

Val Leu

<210> SEQ ID NO 48
<211> LENGTH: 327
<212> TYPE: PRT
<213> ORGANISM: Proteus mirabilis

<400> SEQUENCE: 48

Met Ala Lys Arg Ile Gln Phe Ala Ala His Gly Asn Ala Asp Val Leu
1               5                   10                  15

Glu Leu Thr Ser Phe Thr Pro Ala Pro Leu Gly Asp Asn Glu Val Gln
                20                  25                  30

Val Ala Asn Lys Ala Ile Gly Ile Asn Tyr Ile Asp Thr Tyr Val Arg
            35                  40                  45

Ser Gly Leu Tyr Pro Val Glu His Phe Pro Ser Gly Leu Gly Thr Glu
        50                  55                  60

Ala Ala Gly Val Val Ile Lys Thr Gly Ala His Val Thr Ser Leu Lys
65                  70                  75                  80

Glu Gly Asp Arg Val Val Tyr Ala Gln Ser Pro Leu Gly Ala Tyr Ser
                85                  90                  95
```

-continued

```
Asp Thr His Asn Val Pro Glu Asn Lys Val Ala Arg Leu Pro Asp Asn
            100                 105                 110

Ile Ser Phe Glu Gln Ala Ala Ser Phe Leu Lys Gly Leu Thr Val
    115                 120                 125

Tyr Tyr Leu Phe Asn Glu Thr Tyr Lys Leu Arg Ala Gly Glu Thr Phe
130                 135                 140

Leu Phe His Ala Ala Gly Val Gly Leu Ile Ala Ser Gln Trp
145                 150                 155                 160

Ala Lys Ala Ile Gly Ala Lys Met Ile Gly Thr Ala Gly Ser Asp Glu
                165                 170                 175

Lys Val Ala Lys Ala Lys Ala Ala Gly Ala Trp Lys Val Ile Asn Tyr
                180                 185                 190

Gln Thr Glu Ser Ile Val Glu Arg Val Leu Ala Leu Thr Asn Asn Gln
            195                 200                 205

Lys Val Pro Val Val Tyr Asp Ser Val Gly Lys Ala Thr Trp Leu Asp
            210                 215                 220

Ser Leu His Cys Leu Gln Arg Arg Gly Leu Met Val Ser Phe Gly Asn
225                 230                 235                 240

Ala Ser Gly Ala Val Thr Gly Val Asp Leu Gly Ile Leu Asn Lys Leu
                245                 250                 255

Gly Ser Leu Tyr Val Thr Arg Pro Ser Ile Ser Gly Tyr Ile Thr Thr
            260                 265                 270

Arg Glu Glu Leu Asp Ala Ala Ser Glu Ala Leu Phe Thr Leu Ile Gly
        275                 280                 285

Arg Gly Lys Ile Asp Val Ser Val Pro Asp Asn Gln Lys Phe Ala Leu
        290                 295                 300

Ala Asp Ala Lys Ala Ala His Arg Tyr Leu Glu Ser Arg Gln Ser Gln
305                 310                 315                 320

Gly Ser Ser Leu Leu Ile Pro
                325

<210> SEQ ID NO 49
<211> LENGTH: 325
<212> TYPE: PRT
<213> ORGANISM: Pseudomonas aeruginosa

<400> SEQUENCE: 49

Met Ala Lys Arg Ile Gln Phe Ala Ala Tyr Gly Gly Pro Glu Val Leu
1               5                   10                  15

Glu Tyr Arg Asp Tyr Gln Pro Ala Glu Pro Gly Pro Arg Glu Val Arg
            20                  25                  30

Val Arg Asn Arg Ala Ile Gly Leu Asn Phe Ile Asp Thr Tyr Tyr Arg
        35                  40                  45

Ser Gly Leu Tyr Pro Ala Pro Gly Leu Pro Ser Gly Leu Gly Ser Glu
    50                  55                  60

Gly Ala Gly Glu Val Glu Ala Val Gly Ser Glu Val Thr Arg Phe Lys
65                  70                  75                  80

Val Gly Asp Arg Val Ala Tyr Ala Thr Gly Pro Leu Gly Ala Tyr Ser
                85                  90                  95

Glu Leu His Val Leu Ala Glu Glu Lys Leu Val His Leu Pro Asp Gly
            100                 105                 110

Ile Asp Phe Glu Gln Ala Ala Ala Val Met Leu Lys Gly Leu Thr Thr
        115                 120                 125

Gln Tyr Leu Leu Arg Gln Thr Tyr Glu Leu Arg Gly Gly Glu Thr Ile
```

```
            130                 135                 140
Leu Phe His Ala Ala Gly Gly Val Gly Leu Phe Ala Cys Gln Trp
145                 150                 155                 160

Ala Lys Ala Leu Gly Val Gln Leu Ile Gly Thr Val Ser Ser Pro Glu
                165                 170                 175

Lys Ala Arg Leu Ala Arg Gln His Gly Ala Trp Glu Thr Ile Asp Tyr
                180                 185                 190

Ser His Glu Asn Val Ala Arg Arg Val Leu Glu Leu Thr Asp Gly Lys
            195                 200                 205

Lys Cys Pro Val Val Tyr Asp Ser Val Gly Lys Asp Thr Trp Glu Thr
        210                 215                 220

Ser Leu Asp Cys Val Ala Pro Arg Gly Leu Leu Val Ser Phe Gly Asn
225                 230                 235                 240

Ala Ser Gly Pro Val Thr Gly Val Asn Leu Gly Ile Leu Ser Gln Lys
                245                 250                 255

Gly Ser Leu Tyr Val Thr Arg Pro Thr Leu Gly Ser Tyr Ala Asp Thr
                260                 265                 270

Pro Glu Lys Leu Gln Ala Met Ala Asp Glu Leu Phe Gly Leu Ile Glu
            275                 280                 285

Arg Gly Asp Ile Arg Ile Glu Ile Asn Gln Arg Phe Ala Leu Ala Glu
        290                 295                 300

Ala Ala Arg Ala His Thr Glu Leu Ala Ala Arg Arg Thr Thr Gly Ser
305                 310                 315                 320

Thr Val Leu Leu Pro
                325

<210> SEQ ID NO 50
<211> LENGTH: 326
<212> TYPE: PRT
<213> ORGANISM: Mycolicibacterium smegmatis

<400> SEQUENCE: 50

Met His Ala Ile Glu Val Ala Glu Thr Gly Gly Pro Glu Val Leu Asn
1               5                   10                  15

Tyr Ile Glu Arg Pro Glu Pro Ser Pro Gly Pro Gly Glu Val Leu Ile
                20                  25                  30

Lys Ala Asp Ala Ile Gly Val Asn Phe Ile Asp Thr Tyr Phe Arg Ser
                35                  40                  45

Gly Leu Tyr Pro Arg Glu Leu Pro Phe Val Gly Thr Glu Val Cys
        50                  55                  60

Gly Thr Val Ala Ala Ile Gly Asn Asp Val Ala Ala Leu Lys Val Gly
65                  70                  75                  80

Asp Arg Val Val Thr Ala Asn Ala Val Gly Ala Tyr Ala Asp Tyr Cys
                85                  90                  95

Val Ala Pro Ala Asp Phe Val Ala Tyr Val Pro Asp Gly Val Ala Pro
                100                 105                 110

Glu Ala Val Ala Ser Ala Leu Leu Lys Gly Met Thr Ala His Tyr Leu
            115                 120                 125

Leu Lys Ser Thr Tyr Pro Val Gln Pro Ser Asp Thr Val Leu Val His
        130                 135                 140

Ala Gly Ala Gly Gly Val Gly Leu Ile Leu Thr Gln Trp Ala Thr Ser
145                 150                 155                 160

Leu Gly Thr Arg Val Ile Thr Thr Ala Ser Thr Pro Glu Lys Ala Glu
                165                 170                 175
```

```
Leu Ser Arg Gln Ala Gly Ala Val Glu Val Leu Asp Tyr Pro Asp Pro
            180                 185                 190

Asp Asp Pro Gln Pro Phe Ala Ser Arg Val Arg Glu Leu Thr Gly Gly
        195                 200                 205

Ala Gly Val Ala Ala Val Tyr Asp Gly Val Gly Ala Thr Thr Phe Asp
    210                 215                 220

Ala Ser Leu Ala Ser Leu Ala Val Arg Gly Thr Leu Ala Leu Phe Gly
225                 230                 235                 240

Ala Ser Ser Gly Pro Val Pro Pro Phe Asp Pro Gln Arg Leu Asn Ala
                245                 250                 255

Ala Gly Ser Val Phe Leu Thr Arg Pro Thr Leu Ala His His Thr Arg
            260                 265                 270

Thr Ala Asp Glu Phe Ser Trp Arg Ala Gly Glu Leu Ile Asn Ala Ile
        275                 280                 285

Ala Asp Gly Ser Ile Lys Ile Thr Val Gly Gly Thr Tyr Pro Leu Ala
    290                 295                 300

Glu Ala Ser Arg Ala His Thr Asp Leu Gln Gly Arg Lys Thr Val Gly
305                 310                 315                 320

Ser Ile Val Leu Ile Pro
                325

<210> SEQ ID NO 51
<211> LENGTH: 324
<212> TYPE: PRT
<213> ORGANISM: Paraburkholderia xenovorans

<400> SEQUENCE: 51

Met Val Lys Ala Ile Arg Phe Asp Lys Thr Gly Gly Pro Glu Val Met
1               5                   10                  15

Lys Trp Val Asp Val Glu Val Gly Glu Pro Gly Ala Gly Glu Ile Arg
            20                  25                  30

Val Arg Gln Thr Ala Val Gly Leu Asn Tyr Ile Asp Val Tyr Phe Arg
        35                  40                  45

Thr Gly Leu Tyr Pro Leu Pro Leu Pro Gly Gly Leu Gly Met Glu Ala
    50                  55                  60

Ala Gly Glu Val Thr Ala Leu Gly Ser Gly Val Ser Gly Leu Lys Val
65                  70                  75                  80

Gly Asp Arg Ile Ala Tyr Val Ala Arg Pro Pro Gly Ala Tyr Ala Gln
                85                  90                  95

Glu Arg Val Leu Gln Ala Ala Gln Val Val Lys Val Pro Asp Ala Leu
            100                 105                 110

Thr Asp Glu Gln Ala Ala Ser Val Met Leu Gln Gly Leu Thr Ala Gln
        115                 120                 125

Tyr Leu Leu Arg Arg Thr Tyr Pro Val Lys Ala Gly Asp Thr Ile Leu
    130                 135                 140

Ile Gln Ala Ala Gly Gly Val Gly Leu Leu Val Cys Gln Trp Ala
145                 150                 155                 160

Lys Ala Leu Gly Ala Thr Val Ile Gly Thr Val Gly Ser Asp Glu Lys
                165                 170                 175

Ala Glu Ile Ala Thr Ala His Gly Cys Asp His Ala Ile Val Tyr Thr
            180                 185                 190

Arg Glu Asn Phe Thr Arg Val Arg Glu Ile Thr Asn Gly Ala Gly
        195                 200                 205

Val Pro Val Val Tyr Asp Ser Ile Gly Lys Asp Thr Phe Thr Gly Ser
    210                 215                 220
```

```
Leu Asp Cys Leu Ala Pro Leu Gly Met Phe Val Ser Phe Gly Asn Ala
225                 230                 235                 240

Ser Gly Pro Leu Pro Pro Ile Asp Ser Ser Glu Phe Ala Gly Arg Gly
                245                 250                 255

Ser Leu Phe Phe Thr Arg Pro Thr Leu Phe Thr Tyr Ile Ala Lys Arg
            260                 265                 270

Ser Asp Tyr Glu Ala Met Ser Thr Glu Leu Phe Asp Val Leu Val Ser
            275                 280                 285

Gly Lys Val Lys Thr Ser Ile Asn Gln Arg Tyr Ala Leu Ala Asp Val
        290                 295                 300

Gly Arg Ala His Ala Asp Leu Glu Gly Arg Thr Thr Gly Ser Thr
305                 310                 315                 320

Val Leu Leu Pro

<210> SEQ ID NO 52
<211> LENGTH: 324
<212> TYPE: PRT
<213> ORGANISM: Burkholderia cepacia

<400> SEQUENCE: 52

Met Pro Lys Ala Ile Arg Tyr Asp Gln Pro Gly Gly Pro Asp Val Met
1               5                   10                  15

Lys Trp Val Asp Val Glu Val Gly Glu Pro Lys Ala Gly Glu Val Arg
            20                  25                  30

Ile Arg Gln His Ala Val Gly Leu Asn Tyr Ile Asp Val Tyr Phe Arg
        35                  40                  45

Thr Gly Leu Tyr Ser Gln Pro Leu Pro Gly Gly Leu Gly Met Glu Ala
    50                  55                  60

Ala Gly Glu Val Thr Ala Val Gly Glu Gly Val Thr Ala Leu Lys Ala
65                  70                  75                  80

Gly Asp Arg Val Ala Tyr Val Gly Gln Pro Pro Gly Ala Tyr Ala Gln
                85                  90                  95

Glu Arg Val Met Pro Ala Glu Arg Leu Val Lys Leu Pro Asp Gly Ile
            100                 105                 110

Ser Tyr Asp Asp Ala Ala Ser Val Met Leu Gln Gly Leu Thr Ala His
        115                 120                 125

Tyr Leu Leu Arg Arg Thr Tyr Pro Val Lys Ala Gly Asp Thr Ile Leu
    130                 135                 140

Ile His Ala Ala Ala Gly Gly Val Gly Leu Leu Val Cys Gln Trp Ala
145                 150                 155                 160

Lys Ala Leu Gly Ala Thr Val Ile Gly Thr Val Gly Ser Asp Glu Lys
                165                 170                 175

Ala Ala Leu Ala Lys Ala His Gly Cys Asp His Pro Ile Val Tyr Thr
            180                 185                 190

Arg Glu Asn Phe Thr Gln Arg Val Lys Glu Ile Thr Asn Gly Ala Gly
        195                 200                 205

Val Pro Val Val Tyr Asp Ser Ile Gly Lys Asp Thr Tyr Ile Gly Ser
    210                 215                 220

Leu Asp Cys Leu Ala Pro Leu Gly Tyr Phe Val Ser Phe Gly Asn Ala
225                 230                 235                 240

Ser Gly Pro Leu Pro Ala Ile Asp Ser Lys Glu Phe Ser Ser Arg Gly
                245                 250                 255

Ser Leu Phe Phe Thr Arg Pro Thr Leu Phe Ser Tyr Ile Ala Lys Arg
            260                 265                 270
```

```
Ala Asp Leu Glu Ser Ala Ala Glu Leu Phe Asp Val Ile Leu Ser
        275                 280                 285

Gly Lys Val Lys Thr Ser Ile Asn Gln Arg Tyr Pro Leu Ala Glu Val
290                 295                 300

Gly Arg Ala His Ala Asp Leu Glu Ser Arg Asn Thr Thr Gly Ser Thr
305                 310                 315                 320

Ile Leu Val Pro

<210> SEQ ID NO 53
<211> LENGTH: 310
<212> TYPE: PRT
<213> ORGANISM: Gluconobacter oxydans

<400> SEQUENCE: 53

Met Ser Ser Lys Pro Asp Ile Leu Thr Ile Asp Pro Leu Val Pro Val
1               5                   10                  15

Met Lys Glu Arg Leu Glu Lys Ser Phe Thr Leu His Pro Tyr Thr Ser
            20                  25                  30

Leu Glu Asn Leu Lys Asn Ile Ala Pro Ala Ile Arg Gly Ile Thr Thr
        35                  40                  45

Gly Gly Gly Ser Gly Val Pro Ser Glu Ile Met Asp Ala Leu Pro Asn
    50                  55                  60

Leu Glu Val Ile Ser Val Asn Gly Val Gly Thr Asp Arg Ile Asn Leu
65                  70                  75                  80

Asp Glu Ala Arg Arg Arg Asn Ile Gly Val Ala Ile Thr Gln Asn Thr
                85                  90                  95

Leu Thr Asp Asp Val Ala Asp Met Ala Val Ala Leu Met Met Ala Val
            100                 105                 110

Met Arg Ser Ile Val Thr Asn Asp Ala Phe Val Arg Ala Gly Lys Trp
        115                 120                 125

Pro Ser Ala Thr Ala Pro Leu Gly Arg Ser Leu Thr Arg Lys Lys Val
    130                 135                 140

Gly Ile Ala Gly Phe Gly His Ile Gly Gln Ala Ile Ala Lys Arg Val
145                 150                 155                 160

Ser Ala Phe Gly Met Glu Val Ala Tyr Phe Asn Ser His Ala Arg Pro
                165                 170                 175

Glu Ser Thr Cys His Phe Glu Pro Asp Leu Lys Ala Leu Ala Thr Trp
            180                 185                 190

Cys Asp Val Leu Ile Leu Ala Val Ser Gly Gly Pro Arg Ser Ala Asn
        195                 200                 205

Met Ile Asp Arg Asp Thr Leu Asp Ala Leu Gly Lys Asp Gly Phe Leu
    210                 215                 220

Val Asn Ile Ala Arg Gly Thr Val Val Asp Glu Ala Ala Leu Leu Ser
225                 230                 235                 240

Ala Leu Gln Glu Lys Arg Ile Ala Gly Ala Gly Leu Asp Val Phe Gln
                245                 250                 255

Asn Glu Pro Asn Ile Asn Pro Ala Phe Leu Ser Leu Pro Asn Thr Val
            260                 265                 270

Leu Gln Ala His Gln Ala Ser Ala Thr Val Glu Thr Arg Thr Thr Met
        275                 280                 285

Ala Asn Leu Val Val Asp Asn Leu Ile Ala Tyr Phe Thr Asp Lys Thr
    290                 295                 300

Leu Leu Thr Pro Val Ile
305                 310
```

<210> SEQ ID NO 54
<211> LENGTH: 331
<212> TYPE: PRT
<213> ORGANISM: Clostridium sporogenes

<400> SEQUENCE: 54

Met Lys Ile Leu Ala Tyr Cys Val Arg Pro Asp Glu Ile Asp Ser Phe
1               5                   10                  15

Lys Asn Phe Ser Glu Lys Tyr Gly His Thr Val Asp Leu Ile Pro Asp
            20                  25                  30

Ser Phe Gly Pro Ser Val Ala His Leu Ala Lys Gly Tyr Asp Gly Ile
        35                  40                  45

Ser Ile Leu Gly Asn Asp Thr Cys Asn Arg Glu Ala Leu Glu Lys Ile
50                  55                  60

Lys Asp Cys Gly Ile Lys Tyr Leu Ala Thr Arg Thr Ala Gly Val Asn
65                  70                  75                  80

Asn Ile Asp Phe Asp Ala Ala Lys Glu Phe Gly Ile Asn Val Ala Asn
                85                  90                  95

Val Pro Ala Tyr Ser Pro Asn Ser Val Ser Glu Phe Thr Val Gly Leu
            100                 105                 110

Ala Leu Ser Leu Thr Arg Lys Ile Pro Phe Ala Leu Lys Arg Val Glu
        115                 120                 125

Leu Asn Asn Phe Ala Leu Gly Gly Leu Ile Gly Val Glu Leu Arg Asn
130                 135                 140

Leu Thr Leu Gly Val Ile Gly Thr Gly Arg Ile Gly Leu Lys Val Ile
145                 150                 155                 160

Glu Gly Phe Ser Gly Phe Gly Met Lys Lys Met Ile Gly Tyr Asp Ile
                165                 170                 175

Phe Glu Asn Glu Lys Ala Lys Glu Tyr Ile Glu Tyr Lys Ser Leu Asp
            180                 185                 190

Glu Val Tyr Lys Glu Ala Asp Ile Ile Thr Leu His Ala Pro Leu Thr
        195                 200                 205

Asp Asp Asn Tyr His Met Ile Gly Lys Glu Ser Ile Ala Lys Met Lys
210                 215                 220

Asp Gly Val Phe Ile Ile Asn Ala Ala Arg Gly Ala Leu Ile Asp Ser
225                 230                 235                 240

Glu Ala Leu Ile Glu Gly Leu Lys Ser Gly Lys Ile Ala Gly Ala Ala
                245                 250                 255

Leu Asp Ser Tyr Glu Tyr Glu Gln Gly Val Phe His Asn Asn Lys Met
            260                 265                 270

Asn Glu Ile Met Lys Asp Asp Thr Leu Ala Arg Leu Lys Ser Phe Pro
        275                 280                 285

Asn Val Val Ile Thr Pro His Leu Gly Phe Tyr Thr Asp Glu Ala Val
290                 295                 300

Ser Asn Met Val Glu Ile Thr Leu Met Asn Leu Gln Glu Phe Glu Leu
305                 310                 315                 320

Lys Gly Thr Cys Lys Asn Gln Arg Val Cys Lys
                325                 330

<210> SEQ ID NO 55
<211> LENGTH: 410
<212> TYPE: PRT
<213> ORGANISM: Paraclostridium bifermentans

<400> SEQUENCE: 55

```
Met Asp Asn Lys Ala Leu Leu Lys Gly Val Arg Val Glu Leu Ser
1               5                   10                  15

Ser Phe Val Ala Ala Pro Cys Cys Ala Lys Leu Leu Gly Asp Trp Gly
                20                  25                  30

Ala Glu Val Ile Lys Ile Glu Pro Leu Gly Gly Asp Gly Ile Arg Val
            35                  40                  45

Met Gly Gly Thr Phe Lys Ser Pro Cys Thr Asp Glu Glu Asn Pro Met
50                      55                  60

Phe Glu Leu Glu Asn Gly Asn Lys Lys Gly Ile Ser Val Asn Val Lys
65                      70                  75                  80

Thr Lys Glu Gly Val Glu Ile Ile His Lys Leu Leu Ala Lys Ala Asp
                85                  90                  95

Ile Phe Ile Thr Asn Val Arg Glu Gln Ala Leu Ser Lys Ile Gly Leu
                100                 105                 110

Thr Tyr Asp Gln Leu Lys Asp Glu Phe Pro Ala Leu Ile His Ala His
            115                 120                 125

Ile Leu Gly Tyr Gly Glu Asn Gly Pro Leu Lys Asp Lys Pro Gly Phe
            130                 135                 140

Asp Tyr Thr Ala Tyr Phe Ala Arg Gly Val Ser Gln Ser Leu Met
145                 150                 155                 160

Glu Lys Gly Thr Ser Pro Cys Asn Thr Ala Ala Phe Gly Asp His
                165                 170                 175

Tyr Ala Gly Val Ser Leu Thr Ala Gly Ile Leu Ala Ala Leu Tyr Lys
                180                 185                 190

Lys Gln Met Thr Gly Glu Gly Asp Arg Val Thr Val Ser Leu Tyr His
            195                 200                 205

Thr Ala Leu Tyr Gly Met Gly Met Met Ile Thr Thr Ala Gln Tyr Gly
210                 215                 220

Asn Lys Met Pro Ile Ser Arg Ala Asn Pro Asn Ser Pro Leu Met Thr
225                 230                 235                 240

Thr Tyr Lys Cys Lys Asp Gly Lys Trp Ile Gln Leu Ala Leu Ile Gln
                245                 250                 255

Tyr Asn Lys Trp Leu Pro Lys Phe Cys Asn Val Ile Asn Arg Pro Glu
                260                 265                 270

Ile Met Glu Asp Glu Arg Phe Asn Asp Ile Lys Val Met Pro Leu His
                275                 280                 285

Val Asp Glu Met Val Glu Ile Val Gly Glu Ala Met Leu Glu Lys Thr
290                 295                 300

Leu Asp Glu Trp Ser Ala Leu Leu Glu Glu Ala Asp Leu Pro Phe Glu
305                 310                 315                 320

Lys Val Gln Ser Cys Glu Asp Ile Leu Glu Asp Glu Gln Ala Trp Ala
                325                 330                 335

Asn Asp Phe Leu Phe Lys Thr Lys Tyr Ala Asn Gly Asn Glu Gly Val
                340                 345                 350

Leu Val Asn Gly Pro Val Lys Phe Lys Thr Met Gly Ile Lys Glu Tyr
                355                 360                 365

Thr Pro Ala Pro Arg Val Gly Glu His Thr Glu Glu Val Leu Lys Glu
370                 375                 380

Leu Gly Tyr Thr Glu Glu Ile Leu Asn Met Val Asn Ser Gln Ala
385                 390                 395                 400

Val Lys Leu Asp Asp Ser Lys Glu Leu Val
                405                 410
```

<210> SEQ ID NO 56
<211> LENGTH: 410
<212> TYPE: PRT
<213> ORGANISM: Paeniclostridium sordellii

<400> SEQUENCE: 56

Met Asp Asn Arg Ala Leu Leu Lys Gly Val Arg Val Val Glu Leu Ser
1 5 10 15

Ser Phe Val Ala Ala Pro Cys Cys Ala Lys Leu Leu Ala Asp Trp Gly
20 25 30

Ala Glu Val Ile Lys Ile Glu Pro Leu Gly Gly Asp Gly Ile Arg Val
35 40 45

Met Gly Gly Thr Phe Lys Ser Pro Cys Thr Asp Asp Glu Asn Pro Met
50 55 60

Phe Glu Leu Glu Asn Gly Asn Lys Lys Gly Ile Ser Val Asn Val Lys
65 70 75 80

Thr Lys Glu Gly Val Glu Ile Leu His Lys Leu Leu Ser Lys Ser Asp
85 90 95

Ile Phe Val Thr Asn Val Arg Glu Lys Ala Leu Ala Lys Met Gly Leu
100 105 110

Thr Tyr Asp Gln Leu Lys Asp Asp Phe Pro Gly Leu Ile His Ala His
115 120 125

Ile Leu Gly Tyr Gly Glu Glu Gly Pro Leu Lys Asp Lys Pro Gly Phe
130 135 140

Asp Tyr Thr Ala Tyr Phe Ala Arg Gly Gly Val Ser Gln Ser Leu Met
145 150 155 160

Glu Lys Gly Thr Ser Pro Cys Asn Thr Ala Ala Gly Phe Gly Asp His
165 170 175

Tyr Ala Gly Ile Ser Leu Thr Ala Gly Ile Leu Ala Ala Leu Tyr Lys
180 185 190

Lys Gln Ile Thr Gly Glu Gly Asp Arg Val Thr Val Ser Leu Phe His
195 200 205

Thr Ala Leu Tyr Gly Met Gly Met Met Ile Thr Thr Ser Gln Tyr Gly
210 215 220

Asn Glu Met Pro Ile Ser Arg Thr Glu Pro Asn Ser Pro Leu Met Thr
225 230 235 240

Thr Tyr Lys Cys Lys Asp Gly Lys Trp Ile Gln Leu Ala Leu Ile Gln
245 250 255

Tyr Asn Lys Trp Leu Pro Lys Phe Cys Glu Val Ile Asn Arg Pro Glu
260 265 270

Ile Met Lys Asp Asp Arg Phe Asn Asp Ile Lys Val Met Pro Leu His
275 280 285

Val Asp Glu Met Val Lys Ile Val Glu Lys Ala Met Leu Glu Lys Thr
290 295 300

Leu Asp Glu Trp Ser Asp Leu Leu Glu Glu Ala Asp Leu Pro Phe Glu
305 310 315 320

Lys Val Gln Ser Cys Glu Asp Ile Ile Asn Asp Asp Gln Ala Trp Ala
325 330 335

Asn Asp Phe Leu Phe Lys Thr Thr Tyr Glu Asn Gly Asn Glu Gly Val
340 345 350

Leu Val Asn Gly Pro Val Lys Phe Lys Thr Met Gly Ile Lys Glu Tyr
355 360 365

Glu Pro Ala Pro Arg Leu Gly Gln His Thr Glu Glu Val Leu Lys Ser
370 375 380

```
Ile Gly Tyr Thr Glu Glu Ile Leu Asp Met Val Asn Ser Gln Ala
385                 390                 395                 400

Ile Lys Leu Asp Asp Ala Lys Glu Leu Val
                405                 410

<210> SEQ ID NO 57
<211> LENGTH: 404
<212> TYPE: PRT
<213> ORGANISM: Clostridium botulinum

<400> SEQUENCE: 57

Met Thr Lys Glu Gly Leu Ala Leu Glu Gly Val Lys Val Glu Leu
1               5                   10                  15

Ser Ser Phe Val Ala Ala Pro Ser Cys Ser Lys Leu Leu Ala Asp Trp
                20                  25                  30

Gly Ala Asp Val Ile Lys Ile Glu Pro Ile Gln Gly Asp Asn Ile Arg
                35                  40                  45

Val Val Gly Gly Val Tyr Asn Ser Pro Ala Arg Asp Asp Glu Asn Pro
50                  55                  60

Met Phe Glu Leu Glu Asn Gly Asn Lys Arg Gly Ile Ala Ile Asn Thr
65                  70                  75                  80

Arg Ser Glu Lys Gly Lys Glu Val Leu Gly Lys Leu Lys Asp Ala
                85                  90                  95

Asp Val Phe Val Thr Asn Val Arg Glu Lys Ala Leu Gln Arg Ser Gly
                100                 105                 110

Leu Ser Tyr Asp Gln Leu Lys Asp Lys Tyr Pro Ser Leu Ile His Ala
                115                 120                 125

His Ile Leu Gly Tyr Gly Glu Lys Gly Pro Leu Lys Asp Lys Pro Gly
                130                 135                 140

Phe Asp Tyr Thr Ala Tyr Phe Ala Arg Gly Ala Val Ser Thr Ser Leu
145                 150                 155                 160

Met Glu Lys Gly Thr Ser Pro Ala Asn Thr Asn Ala Gly Phe Gly Asp
                165                 170                 175

His Tyr Ala Gly Met Ser Leu Ala Ala Gly Ile Leu Ala Ala Leu His
                180                 185                 190

Arg Lys Thr Leu Thr Gly Lys Gly Asp Arg Val Thr Val Ser Leu Tyr
                195                 200                 205

His Thr Ala Ile Phe Gly Met Gly Leu Met Ile Thr Thr Ala Gln Tyr
                210                 215                 220

Gly Asn Lys Met Pro Leu Ser Arg Arg Thr Pro Asn Asn Pro Leu Ala
225                 230                 235                 240

Thr Thr Tyr Arg Cys Lys Asp Asp Arg Trp Ile Gln Leu Ala Leu Leu
                245                 250                 255

Lys Tyr Asp Ala Trp Phe Pro Lys Phe Cys Lys Glu Val Ile Asn Arg
                260                 265                 270

Pro Asp Leu Ile Glu Asp Leu Arg Phe Asn Lys Gln Ser Glu Val Val
                275                 280                 285

Lys His Val Glu Thr Phe Val Gly Ile Leu Glu Glu Phe Ile Lys
                290                 295                 300

Lys Asp Leu Lys Glu Trp Ala Asp Leu Leu Asp Lys Ala Asp Leu Pro
305                 310                 315                 320

Tyr Glu Lys Leu Gln Tyr Cys Glu Asp Ile Leu Glu Asp Glu Gln Ala
                325                 330                 335

Trp Ala Asn Asp Tyr Leu Phe Lys Thr Thr Tyr Asp Ser Gly Asn Thr
```

```
            340                 345                 350
Gly Val Leu Val Asn Ser Pro Val Lys Phe Ser Glu Ala Gly Met Arg
            355                 360                 365

Thr Tyr Lys Ala Ala Pro Lys Ile Gly Glu Asp Thr Glu Val Val Leu
        370                 375                 380

Thr Ser Leu Gly Tyr Ser Lys Glu Glu Ile Glu Glu Met Arg Lys Glu
385                 390                 395                 400

Glu Ser Ile Lys

<210> SEQ ID NO 58
<211> LENGTH: 404
<212> TYPE: PRT
<213> ORGANISM: Clostridium sporogenes

<400> SEQUENCE: 58

Met Thr Lys Glu Gly Leu Ala Leu Glu Gly Val Lys Val Val Glu Leu
1               5                   10                  15

Ser Ser Phe Val Ala Ala Pro Ser Cys Ser Lys Leu Leu Ala Asp Trp
            20                  25                  30

Gly Ala Asp Val Ile Lys Ile Glu Pro Ile Gln Gly Asp Asn Ile Arg
        35                  40                  45

Val Val Gly Gly Val Tyr Asn Ser Pro Ala Arg Asp Glu Asn Pro
50                  55                  60

Met Phe Glu Leu Glu Asn Gly Asn Lys Arg Gly Val Ala Ile Asn Thr
65                  70                  75                  80

Arg Ser Glu Lys Gly Lys Glu Val Leu Gly Lys Leu Leu Lys Asp Ala
            85                  90                  95

Asp Val Phe Val Thr Asn Val Arg Glu Lys Ala Leu Gln Arg Ser Gly
        100                 105                 110

Leu Ser Tyr Asp Gln Leu Lys Asp Lys Tyr Pro Ser Leu Ile His Ala
        115                 120                 125

His Ile Leu Gly Tyr Gly Glu Lys Gly Pro Leu Lys Asp Lys Pro Gly
        130                 135                 140

Phe Asp Tyr Thr Ala Tyr Phe Ala Arg Gly Ala Val Ser Thr Ser Leu
145                 150                 155                 160

Met Glu Lys Gly Thr Ser Pro Ala Asn Thr Asn Ala Gly Phe Gly Asp
            165                 170                 175

His Tyr Ala Gly Met Ser Leu Ala Ala Gly Ile Leu Ala Ala Leu His
        180                 185                 190

Arg Lys Thr Leu Thr Gly Lys Gly Asp Arg Val Thr Val Ser Leu Tyr
        195                 200                 205

His Thr Ala Ile Phe Gly Met Gly Leu Met Ile Thr Thr Ala Gln Tyr
        210                 215                 220

Gly Asn Lys Met Pro Leu Ser Arg Arg Thr Pro Asn Asn Pro Leu Ala
225                 230                 235                 240

Thr Thr Tyr Arg Cys Lys Asp Asp Arg Trp Ile Gln Leu Ala Leu Leu
            245                 250                 255

Lys Tyr Asp Ala Trp Phe Pro Lys Phe Cys Lys Glu Val Ile Asn Arg
        260                 265                 270

Pro Asp Leu Ile Glu Asp Ser Arg Phe Asn Lys Gln Ser Glu Val Val
        275                 280                 285

Lys His Val Glu Thr Phe Val Gly Val Leu Glu Gly Glu Phe Ile Lys
        290                 295                 300

Lys Asp Leu Lys Glu Trp Ala Asp Leu Leu Asp Lys Ala Asp Leu Pro
```

```
                    305                 310                 315                 320

Tyr Glu Lys Leu Gln Tyr Cys Glu Asp Ile Leu Glu Asp Gln Ala
                325                 330                 335

Trp Ala Asn Asp Tyr Leu Phe Lys Thr Thr Tyr Asp Ser Gly Asn Thr
                340                 345                 350

Gly Val Leu Val Asn Ser Pro Val Lys Phe Ser Glu Ala Gly Met Arg
                355                 360                 365

Pro Tyr Lys Ala Ala Pro Lys Ile Gly Glu Asp Thr Glu Ala Ile Leu
        370                 375                 380

Thr Ser Leu Gly Tyr Ser Lys Glu Glu Ile Glu Glu Met Arg Lys Glu
385                 390                 395                 400

Asn Ala Ile Lys

<210> SEQ ID NO 59
<211> LENGTH: 408
<212> TYPE: PRT
<213> ORGANISM: Clostridioides difficile

<400> SEQUENCE: 59

Met Ser Glu Lys Lys Glu Ala Arg Val Val Ile Asn Asp Leu Leu Ala
1               5                   10                  15

Glu Gln Tyr Ala Asn Ala Phe Lys Ala Lys Glu Glu Gly Arg Pro Val
                20                  25                  30

Gly Trp Ser Thr Ser Val Phe Pro Gln Glu Leu Ala Glu Val Phe Asp
            35                  40                  45

Leu Asn Val Leu Tyr Pro Glu Asn Gln Ala Ala Gly Val Ala Ala Lys
    50                  55                  60

Lys Gly Ser Leu Glu Leu Cys Glu Ile Ala Glu Ser Lys Gly Tyr Ser
65              70                  75                  80

Ile Asp Leu Cys Ala Tyr Ala Arg Thr Asn Phe Gly Leu Leu Glu Asn
                85                  90                  95

Gly Gly Cys Glu Ala Leu Asp Met Pro Ala Pro Asp Phe Leu Leu Cys
            100                 105                 110

Cys Asn Asn Ile Cys Asn Gln Val Ile Lys Trp Tyr Glu Asn Ile Ser
        115                 120                 125

Arg Glu Leu Asp Ile Pro Leu Ile Met Ile Asp Thr Thr Phe Asn Asn
    130                 135                 140

Glu Asp Glu Val Thr Gln Ser Arg Ile Asp Tyr Ile Lys Ala Gln Phe
145                 150                 155                 160

Glu Glu Ala Ile Lys Gln Leu Gly Ile Ile Ser Gly Lys Lys Phe Asp
                165                 170                 175

Pro Lys Lys Phe Glu Glu Val Met Lys Ile Ser Ala Glu Asn Gly Arg
            180                 185                 190

Leu Trp Lys Tyr Ser Met Ser Leu Pro Ala Asp Ser Ser Pro Ser Pro
        195                 200                 205

Met Asn Gly Phe Asp Leu Phe Thr Tyr Met Ala Val Ile Val Cys Ala
    210                 215                 220

Arg Gly Lys Lys Glu Thr Thr Glu Ala Phe Lys Leu Leu Ile Glu Glu
225                 230                 235                 240

Leu Glu Asp Asn Met Lys Thr Gly Lys Ser Ser Phe Arg Gly Glu Glu
                245                 250                 255

Lys Tyr Arg Ile Met Met Glu Gly Ile Pro Cys Trp Pro Tyr Ile Gly
            260                 265                 270

Tyr Lys Met Lys Thr Leu Ala Lys Phe Gly Val Asn Met Thr Gly Ser
```

-continued

```
        275                 280                 285

Val Tyr Pro His Ala Trp Ala Leu Gln Tyr Glu Val Asn Asp Leu Asp
    290                 295                 300

Gly Met Ala Val Ala Tyr Ser Thr Met Phe Asn Asn Val Asn Leu Asp
305                 310                 315                 320

Arg Met Thr Lys Tyr Arg Val Asp Ser Leu Val Glu Gly Lys Cys Asp
                325                 330                 335

Gly Ala Phe Tyr His Met Asn Arg Ser Cys Lys Leu Met Ser Leu Ile
            340                 345                 350

Gln Tyr Glu Met Gln Arg Arg Ala Ala Glu Glu Thr Gly Leu Pro Tyr
        355                 360                 365

Ala Gly Phe Asp Gly Asp Gln Ala Asp Pro Arg Ala Phe Thr Asn Ala
    370                 375                 380

Gln Phe Glu Thr Arg Ile Gln Gly Leu Val Glu Val Met Glu Glu Arg
385                 390                 395                 400

Lys Lys Leu Asn Arg Gly Glu Ile
                405

<210> SEQ ID NO 60
<211> LENGTH: 410
<212> TYPE: PRT
<213> ORGANISM: Clostridium sporogenes

<400> SEQUENCE: 60

Met Ala Asp Lys Lys Glu Val Lys Lys Asn Ala Ala Lys Met Ile Asn
1               5                   10                  15

Gly Ile Leu Ala Lys Ser Tyr Ala Asp Ala Trp Lys Ala Lys Glu Glu
            20                  25                  30

Gly Lys Pro Val Gly Trp Ser Thr Ser Val Phe Pro Gln Glu Leu Val
        35                  40                  45

Glu Thr Phe Gly Leu Asp Val Leu Tyr Pro Glu Asn Gln Ala Ala Gly
    50                  55                  60

Val Ala Ala Lys Lys Glu Ser Leu Ser Leu Cys Glu Ala Ala Glu Ser
65                  70                  75                  80

Ala Gly Tyr Ser Ile Asp Leu Cys Ala Tyr Ala Arg Thr Asn Phe Gly
                85                  90                  95

Leu Leu Glu Lys Gly Gly Ser Glu Asn Leu Asn Met Pro Lys Pro Asp
            100                 105                 110

Phe Ile Cys Cys Cys Asn Asn Ile Cys Asn Gln Val Ile Lys Trp Tyr
        115                 120                 125

Glu Asn Ile Ala Lys Glu Leu Asp Ile Pro Leu Ile Met Ile Asp Thr
    130                 135                 140

Thr Phe Asn Asn Glu Asp Glu Val Thr Glu Asn Arg Ile Lys Tyr Leu
145                 150                 155                 160

Arg Ala Gln Phe Glu Glu Ala Ile Lys Gln Leu Glu Lys Ile Ser Gly
                165                 170                 175

Lys Lys Phe Asp Pro Lys Lys Phe Glu Glu Val Met Lys Ile Ser Ala
            180                 185                 190

Glu Asn Gly Lys Leu Trp Lys Tyr Ser Met Ser Leu Pro Ser Gly Ser
        195                 200                 205

Phe Pro Ser Pro Met Asn Gly Phe Asp Leu Phe Thr Tyr Met Ala Val
    210                 215                 220

Ile Val Cys Tyr Arg Gly Lys Lys Glu Thr Thr Glu Ala Phe Lys Leu
225                 230                 235                 240
```

Leu Ile Ser Glu Leu Glu Asp Asn Ile Lys Asn Lys Ala Thr Ser Phe
            245                 250                 255

Arg Gly Glu Glu Lys Tyr Arg Ile Met Met Glu Gly Ile Pro Cys Trp
        260                 265                 270

Pro Tyr Ile Gly Tyr Lys Met Arg Thr Leu Ala Gly Tyr Gly Val Asn
            275                 280                 285

Met Thr Gly Ser Val Tyr Pro His Ala Trp Ala Leu Gln Tyr Glu Val
        290                 295                 300

Asn Asp Leu Asp Gly Met Ala Lys Ala Tyr Ser Thr Met Phe Asn Asn
305                 310                 315                 320

Val Asn Leu Glu Thr Met Cys Lys Tyr Arg Ile Asp Ser Leu Ile Asp
                325                 330                 335

Gly Asn Cys Asp Gly Ala Phe Tyr His Met Asn Arg Ser Cys Lys Leu
            340                 345                 350

Met Ser Phe Ile Gln Tyr Glu Met Glu Arg Lys Val Phe Glu Glu Thr
        355                 360                 365

Gly Ile Pro Tyr Ala Gly Phe Asp Gly Asp Gln Ala Asp Pro Arg Asn
    370                 375                 380

Phe Ser Lys Ala Gln Phe Glu Thr Arg Leu Gln Gly Leu Val Glu Val
385                 390                 395                 400

Met Glu Glu Arg Lys Lys Gly Gly Asn Lys
                405                 410

<210> SEQ ID NO 61
<211> LENGTH: 266
<212> TYPE: PRT
<213> ORGANISM: Clostridioides difficile

<400> SEQUENCE: 61

Met Tyr Thr Met Gly Leu Asp Ile Gly Ser Thr Ala Ser Lys Gly Val
1               5                   10                  15

Ile Leu Lys Asn Gly Glu Asp Ile Val Ala Ser Glu Thr Ile Ser Ser
            20                  25                  30

Gly Thr Gly Thr Thr Gly Pro Ser Arg Val Leu Glu Lys Leu Tyr Gly
        35                  40                  45

Lys Thr Gly Leu Ala Arg Glu Asp Ile Lys Lys Val Val Thr Gly
    50                  55                  60

Tyr Gly Arg Met Asn Tyr Ser Asp Ala Asp Lys Gln Ile Ser Glu Leu
65                  70                  75                  80

Ser Cys His Ala Arg Gly Val Asn Phe Ile Ile Pro Glu Thr Arg Thr
                85                  90                  95

Ile Ile Asp Ile Gly Gly Gln Asp Ala Lys Val Leu Lys Leu Asp Asn
            100                 105                 110

Asn Gly Arg Leu Leu Asn Phe Leu Met Asn Asp Lys Cys Ala Ala Gly
        115                 120                 125

Thr Gly Arg Phe Leu Asp Val Met Ala Lys Ile Glu Val Asp Val
    130                 135                 140

Ser Glu Leu Gly Ser Ile Ser Met Asn Ser Gln Asn Glu Val Ser Ile
145                 150                 155                 160

Ser Ser Thr Cys Thr Val Phe Ala Glu Ser Glu Val Ile Ser His Leu
                165                 170                 175

Ser Glu Asn Ala Lys Ile Glu Asp Ile Val Ala Gly Ile His Thr Ser
            180                 185                 190

Val Ala Lys Arg Val Ser Ser Leu Val Lys Arg Ile Gly Val Gln Arg
        195                 200                 205

```
Asn Val Val Met Val Gly Gly Val Ala Arg Asn Ser Gly Ile Val Arg
            210                 215                 220

Ala Met Ala Arg Glu Ile Asn Thr Glu Ile Ile Val Pro Asp Ile Pro
225                 230                 235                 240

Gln Leu Thr Gly Ala Leu Gly Ala Ala Leu Tyr Ala Phe Asp Glu Ala
            245                 250                 255

Lys Glu Ser Gln Lys Glu Val Lys Asn Ile
            260                 265

<210> SEQ ID NO 62
<211> LENGTH: 375
<212> TYPE: PRT
<213> ORGANISM: Clostridium sporogenes

<400> SEQUENCE: 62

Met Asp Asn Ile Lys Asn Ile Leu Ser Lys Leu Glu Gly Ile Val Lys
1               5                   10                  15

Asn Pro Lys Lys Val Val Ser Asp Tyr Lys Glu Arg Thr Gly Asn Lys
            20                  25                  30

Val Ile Gly Cys Phe Pro Val Tyr Thr Pro Glu Glu Ile Val Tyr Ala
        35                  40                  45

Ala Asp Met Leu Pro Ile Gly Ile Trp Gly Gly Asp Val Glu Ala Asn
50                  55                  60

Leu Ala Lys Gln Tyr Tyr Pro Ala Phe Cys Cys Ser Ile Met Gln Ser
65                  70                  75                  80

Cys Met Glu Phe Gly Leu Lys Gly Ile Tyr Glu Gly Leu Ser Ala Val
            85                  90                  95

Ile Ile Pro Gly Met Cys Asp Thr Leu Asn Cys Met Gly Gln Asn Trp
        100                 105                 110

Lys Phe Ala Ile Lys Asp Ile Pro Tyr Ile Ala Leu Val His Pro Gln
    115                 120                 125

Asn Arg Lys Leu Glu Ala Gly Val Glu Tyr Leu Val Glu Glu Tyr Lys
130                 135                 140

His Val Lys Ala Lys Ile Glu Glu Ile Arg Gly Lys Glu Ile Thr Glu
145                 150                 155                 160

Glu Glu Met Gln Asn Ser Ile Asp Ile Tyr Asn Glu His Arg Lys Val
            165                 170                 175

Met Arg Ser Phe Val Asp Glu Ala Ala Lys His Pro Asn Thr Ile Asn
        180                 185                 190

Asn Tyr Gln Arg Asn Leu Val Ile Lys Ser Gly Phe Phe Met Arg Lys
    195                 200                 205

Asp Glu His Thr Lys Ile Val Lys Glu Leu Asn Glu Leu Leu Ala Val
210                 215                 220

Leu Pro Glu Glu Lys Tyr Asp Gly Lys Lys Val Leu Val Thr Gly Ile
225                 230                 235                 240

Leu Leu Asp Ser Lys Glu Met Leu Asp Val Phe Glu Glu Asn Lys Leu
            245                 250                 255

Arg Ile Val Ala Asp Asp Leu Ala Gln Glu Ser Arg Gln Phe Arg Thr
        260                 265                 270

Asp Val Pro Glu Gly Lys Asn Ala Leu Asp Arg Leu Ala Arg Gln Trp
    275                 280                 285

Ser Asn Ile Glu Gly Cys Ser Leu Ala Tyr Asp Pro Lys Lys Ile Arg
290                 295                 300

Gly Ser Met Ile Ala Lys Glu Ala Lys Ala Lys Gly Ile Asp Gly Val
```

```
                305                 310                 315                 320
Val Phe Ala Met Met Lys Phe Cys Asp Pro Glu Glu Tyr Asp Tyr Pro
                    325                 330                 335

Ile Val Lys Lys Asp Ile Glu Lys Glu Asp Ile Pro Thr Thr Met Ile
                340                 345                 350

Glu Val Asp Gln Gln Asn Lys Ser Val Glu Gln Ile Arg Thr Arg Ile
                355                 360                 365

Gln Thr Phe Ser Glu Ile Leu
                370                 375

<210> SEQ ID NO 63
<211> LENGTH: 375
<212> TYPE: PRT
<213> ORGANISM: Clostridioides difficile

<400> SEQUENCE: 63

Met Glu Ala Ile Leu Ser Lys Met Lys Glu Val Val Glu Asn Pro Asn
1               5                   10                  15

Ala Ala Val Lys Lys Tyr Lys Ser Glu Thr Gly Lys Lys Ala Ile Gly
                20                  25                  30

Cys Phe Pro Val Tyr Cys Pro Glu Glu Ile Ile His Ala Ala Gly Met
            35                  40                  45

Leu Pro Val Gly Ile Trp Gly Gly Gln Thr Glu Leu Asp Leu Ala Lys
        50                  55                  60

Gln Tyr Phe Pro Ala Phe Ala Cys Ser Ile Met Gln Ser Cys Leu Glu
65                  70                  75                  80

Tyr Gly Leu Lys Gly Ala Tyr Asp Glu Leu Ser Gly Val Ile Ile Pro
                85                  90                  95

Gly Met Cys Asp Thr Leu Ile Cys Leu Gly Gln Asn Trp Lys Ser Ala
            100                 105                 110

Val Pro His Ile Lys Tyr Ile Ser Leu Val His Pro Gln Asn Arg Lys
        115                 120                 125

Leu Glu Ala Gly Val Lys Tyr Leu Ile Ser Glu Tyr Lys Gly Val Lys
130                 135                 140

Arg Glu Leu Glu Glu Ile Cys Gly Tyr Glu Ile Glu Glu Ala Lys Ile
145                 150                 155                 160

His Glu Ser Ile Glu Val Tyr Asn Glu His Arg Lys Thr Met Arg Asp
                165                 170                 175

Phe Val Glu Val Ala Tyr Lys His Ser Asn Thr Ile Lys Pro Ser Ile
            180                 185                 190

Arg Ser Leu Val Ile Lys Ser Gly Phe Phe Met Arg Lys Glu Glu His
        195                 200                 205

Thr Glu Leu Val Lys Asp Leu Ile Ala Lys Leu Asn Ala Met Pro Glu
210                 215                 220

Glu Val Cys Ser Gly Lys Lys Val Leu Leu Thr Gly Ile Leu Ala Asp
225                 230                 235                 240

Ser Lys Asp Ile Leu Asp Ile Leu Glu Asp Asn Asn Ile Ser Val Val
                245                 250                 255

Ala Asp Asp Leu Ala Gln Glu Thr Arg Gln Phe Arg Thr Asp Val Pro
            260                 265                 270

Ala Gly Asp Asp Ala Leu Glu Arg Leu Ala Arg Gln Trp Ser Asn Ile
        275                 280                 285

Glu Gly Cys Ser Leu Ala Tyr Asp Pro Lys Lys Lys Arg Gly Ser Leu
        290                 295                 300
```

```
Ile Val Asp Glu Val Lys Lys Asp Ile Asp Gly Val Ile Phe Cys
305                 310                 315                 320

Met Met Lys Phe Cys Asp Pro Glu Glu Tyr Asp Tyr Pro Leu Val Arg
            325                 330                 335

Lys Asp Ile Glu Asp Ser Gly Ile Pro Thr Leu Tyr Val Glu Ile Asp
        340                 345                 350

Gln Gln Thr Gln Asn Asn Glu Gln Ala Arg Thr Arg Ile Gln Thr Phe
        355                 360                 365

Ala Glu Met Met Ser Leu Ala
        370             375

<210> SEQ ID NO 64
<211> LENGTH: 257
<212> TYPE: PRT
<213> ORGANISM: Clostridium sporogenes

<400> SEQUENCE: 64

Met Tyr Thr Met Gly Leu Asp Ile Gly Ser Thr Thr Ser Lys Gly Val
1               5                   10                  15

Ile Ile Lys Asp Gly Glu Glu Ile Val Ala Ser Val Leu Val Pro Val
            20                  25                  30

Gly Thr Gly Thr Ser Gly Pro Leu Lys Leu Ile Lys Glu Leu Lys Glu
        35                  40                  45

Lys Ser Asn Leu Thr Glu Lys Asp Ile Glu Lys Thr Val Val Thr Gly
50                  55                  60

Tyr Gly Arg Ile Gln Tyr Lys Asp Ala Asp Lys Gln Ile Ser Glu Leu
65                  70                  75                  80

Ser Cys His Ala Lys Gly Val Ala Phe Leu Ile Pro Gly Ala Arg Thr
                85                  90                  95

Ile Ile Asp Ile Gly Gly Gln Asp Ala Lys Ala Met Lys Leu Asn Asp
            100                 105                 110

Lys Gly Lys Leu Ile Asn Phe Ile Met Asn Asp Lys Cys Ala Ala Gly
        115                 120                 125

Thr Gly Arg Phe Leu Asp Val Met Ala Gly Val Leu Glu Thr Asp Val
130                 135                 140

Ser Lys Leu Gly Glu Ile Ser Glu Lys Ser Thr Lys Glu Val Ser Ile
145                 150                 155                 160

Ser Ser Thr Cys Thr Val Phe Ala Glu Ser Glu Val Ile Ser His Leu
                165                 170                 175

Ser Ala Asn Ala Lys Lys Glu Asp Ile Val Ala Gly Ile His Thr Ser
            180                 185                 190

Val Val Arg Arg Val Ser Thr Leu Ala Met Arg Val Gly Ile Glu Asp
        195                 200                 205

Gln Val Val Met Val Gly Gly Val Ala Arg Asn Lys Gly Ile Val Lys
        210                 215                 220

Ala Met Glu Lys Glu Leu Gly His Asp Ile Lys Val Pro Glu Leu Ala
225                 230                 235                 240

Gln Leu Thr Gly Ala Leu Gly Ala Ala Ile Tyr Ala Phe Glu Glu Thr
                245                 250                 255

Lys

<210> SEQ ID NO 65
<211> LENGTH: 397
<212> TYPE: PRT
<213> ORGANISM: Treponema denticola
```

<400> SEQUENCE: 65

```
Met Ile Val Lys Pro Met Val Arg Asn Asn Ile Cys Leu Asn Ala His
1               5                   10                  15

Pro Gln Gly Cys Lys Lys Gly Val Glu Asp Gln Ile Glu Tyr Thr Lys
            20                  25                  30

Lys Arg Ile Thr Ala Glu Val Lys Ala Gly Ala Lys Ala Pro Lys Asn
        35                  40                  45

Val Leu Val Leu Gly Cys Ser Asn Gly Tyr Gly Leu Ala Ser Arg Ile
    50                  55                  60

Thr Ala Ala Phe Gly Tyr Gly Ala Ala Thr Ile Gly Val Ser Phe Glu
65                  70                  75                  80

Lys Ala Gly Ser Glu Thr Lys Tyr Gly Thr Pro Gly Trp Tyr Asn Asn
                85                  90                  95

Leu Ala Phe Asp Glu Ala Ala Lys Arg Glu Gly Leu Tyr Ser Val Thr
            100                 105                 110

Ile Asp Gly Asp Ala Phe Ser Asp Glu Ile Lys Ala Gln Val Ile Glu
        115                 120                 125

Glu Ala Lys Lys Lys Gly Ile Lys Phe Asp Leu Ile Val Tyr Ser Leu
130                 135                 140

Ala Ser Pro Val Arg Thr Asp Pro Asp Thr Gly Ile Met His Lys Ser
145                 150                 155                 160

Val Leu Lys Pro Phe Gly Lys Thr Phe Thr Gly Lys Thr Val Asp Pro
                165                 170                 175

Phe Thr Gly Glu Leu Lys Glu Ile Ser Ala Glu Pro Ala Asn Asp Glu
            180                 185                 190

Glu Ala Ala Ala Thr Val Lys Val Met Gly Gly Glu Asp Trp Glu Arg
        195                 200                 205

Trp Ile Lys Gln Leu Ser Lys Glu Gly Leu Leu Glu Glu Gly Cys Ile
    210                 215                 220

Thr Leu Ala Tyr Ser Tyr Ile Gly Pro Glu Ala Thr Gln Ala Leu Tyr
225                 230                 235                 240

Arg Lys Gly Thr Ile Gly Lys Ala Lys Glu His Leu Glu Ala Thr Ala
                245                 250                 255

His Arg Leu Asn Lys Glu Asn Pro Ser Ile Arg Ala Phe Val Ser Val
            260                 265                 270

Asn Lys Gly Leu Val Thr Arg Ala Ser Ala Val Ile Pro Val Ile Pro
        275                 280                 285

Leu Tyr Leu Ala Ser Leu Phe Lys Val Met Lys Glu Lys Gly Asn His
    290                 295                 300

Glu Gly Cys Ile Glu Gln Ile Thr Arg Leu Tyr Ala Glu Arg Leu Tyr
305                 310                 315                 320

Arg Lys Asp Gly Thr Ile Pro Val Asp Glu Glu Asn Arg Ile Arg Ile
                325                 330                 335

Asp Asp Trp Glu Leu Glu Glu Asp Val Gln Lys Ala Val Ser Ala Leu
            340                 345                 350

Met Glu Lys Val Thr Gly Glu Asn Ala Glu Ser Leu Thr Asp Leu Ala
        355                 360                 365

Gly Tyr Arg His Asp Phe Leu Ala Ser Asn Gly Phe Asp Val Glu Gly
    370                 375                 380

Ile Asn Tyr Glu Ala Glu Val Glu Arg Phe Asp Arg Ile
385                 390                 395
```

<210> SEQ ID NO 66

<211> LENGTH: 1173
<212> TYPE: PRT
<213> ORGANISM: Mycolicibacterium smegmatis

<400> SEQUENCE: 66

```
Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
            260                 265                 270

Ala Met Tyr Thr Glu Ala Met Val Ala Arg Leu Trp Thr Met Ser Phe
        275                 280                 285

Ile Thr Gly Asp Pro Thr Pro Val Ile Asn Val Asn Phe Met Pro Leu
290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
        355                 360                 365

Thr Gln Gly Ala Asp Glu Leu Thr Ala Glu Lys Gln Ala Gly Ala Glu
370                 375                 380

Leu Arg Glu Gln Val Leu Gly Gly Arg Val Ile Thr Gly Phe Val Ser
```

```
                385                 390                 395                 400
        Thr Ala Pro Leu Ala Ala Glu Met Arg Ala Phe Leu Asp Ile Thr Leu
                        405                 410                 415
        Gly Ala His Ile Val Asp Gly Tyr Gly Leu Thr Glu Thr Gly Ala Val
                        420                 425                 430
        Thr Arg Asp Gly Val Ile Val Arg Pro Val Ile Asp Tyr Lys Leu
                        435                 440                 445
        Ile Asp Val Pro Glu Leu Gly Tyr Phe Ser Thr Asp Lys Pro Tyr Pro
                        450                 455                 460
        Arg Gly Glu Leu Leu Val Arg Ser Gln Thr Leu Thr Pro Gly Tyr Tyr
        465                     470                 475                 480
        Lys Arg Pro Glu Val Thr Ala Ser Val Phe Asp Arg Asp Gly Tyr Tyr
                        485                 490                 495
        His Thr Gly Asp Val Met Ala Glu Thr Ala Pro Asp His Leu Val Tyr
                        500                 505                 510
        Val Asp Arg Arg Asn Asn Val Leu Lys Leu Ala Gln Gly Glu Phe Val
                        515                 520                 525
        Ala Val Ala Asn Leu Glu Ala Val Phe Ser Gly Ala Ala Leu Val Arg
                        530                 535                 540
        Gln Ile Phe Val Tyr Gly Asn Ser Glu Arg Ser Phe Leu Leu Ala Val
        545                     550                 555                 560
        Val Val Pro Thr Pro Glu Ala Leu Glu Gln Tyr Asp Pro Ala Ala Leu
                        565                 570                 575
        Lys Ala Ala Leu Ala Asp Ser Leu Gln Arg Thr Ala Arg Asp Ala Glu
                        580                 585                 590
        Leu Gln Ser Tyr Glu Val Pro Ala Asp Phe Ile Val Glu Thr Glu Pro
                        595                 600                 605
        Phe Ser Ala Ala Asn Gly Leu Leu Ser Gly Val Gly Lys Leu Leu Arg
                        610                 615                 620
        Pro Asn Leu Lys Asp Arg Tyr Gly Gln Arg Leu Glu Gln Met Tyr Ala
        625                     630                 635                 640
        Asp Ile Ala Ala Thr Gln Ala Asn Gln Leu Arg Glu Leu Arg Arg Ala
                        645                 650                 655
        Ala Ala Thr Gln Pro Val Ile Asp Thr Leu Thr Gln Ala Ala Ala Thr
                        660                 665                 670
        Ile Leu Gly Thr Gly Ser Glu Val Ala Ser Asp Ala His Phe Thr Asp
                        675                 680                 685
        Leu Gly Gly Asp Ser Leu Ser Ala Leu Thr Leu Ser Asn Leu Leu Ser
                        690                 695                 700
        Asp Phe Phe Gly Phe Glu Val Pro Val Gly Thr Ile Val Asn Pro Ala
        705                     710                 715                 720
        Thr Asn Leu Ala Gln Leu Ala Gln His Ile Glu Ala Gln Arg Thr Ala
                        725                 730                 735
        Gly Asp Arg Arg Pro Ser Phe Thr Thr Val His Gly Ala Asp Ala Thr
                        740                 745                 750
        Glu Ile Arg Ala Ser Glu Leu Thr Leu Asp Lys Phe Ile Asp Ala Glu
                        755                 760                 765
        Thr Leu Arg Ala Ala Pro Gly Leu Pro Lys Val Thr Thr Glu Pro Arg
                        770                 775                 780
        Thr Val Leu Leu Ser Gly Ala Asn Gly Trp Leu Gly Arg Phe Leu Thr
        785                     790                 795                 800
        Leu Gln Trp Leu Glu Arg Leu Ala Pro Val Gly Gly Thr Leu Ile Thr
                        805                 810                 815
```

Ile Val Arg Gly Arg Asp Asp Ala Ala Arg Ala Arg Leu Thr Gln
            820                 825                 830

Ala Tyr Asp Thr Asp Pro Glu Leu Ser Arg Arg Phe Ala Glu Leu Ala
            835                 840                 845

Asp Arg His Leu Arg Val Ala Gly Asp Ile Gly Asp Pro Asn Leu
850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
            885                 890                 895

Leu Phe Gly Pro Asn Val Val Gly Thr Ala Glu Val Ile Lys Leu Ala
            900                 905                 910

Leu Thr Glu Arg Ile Lys Pro Val Thr Tyr Leu Ser Thr Val Ser Val
            915                 920                 925

Ala Met Gly Ile Pro Asp Phe Glu Glu Asp Gly Asp Ile Arg Thr Val
930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
            965                 970                 975

Gly Leu Pro Val Ala Thr Phe Arg Ser Asp Met Ile Leu Ala His Pro
            980                 985                 990

Arg Tyr Arg Gly Gln Val Asn Val Pro Asp Met Phe Thr Arg Leu Leu
            995                 1000                1005

Leu Ser Leu Leu Ile Thr Gly Val Ala Pro Arg Ser Phe Tyr Ile
    1010                1015                1020

Gly Asp Gly Glu Arg Pro Arg Ala His Tyr Pro Gly Leu Thr Val
    1025                1030                1035

Asp Phe Val Ala Glu Ala Val Thr Thr Leu Gly Ala Gln Gln Arg
    1040                1045                1050

Glu Gly Tyr Val Ser Tyr Asp Val Met Asn Pro His Asp Asp Gly
    1055                1060                1065

Ile Ser Leu Asp Val Phe Val Asp Trp Leu Ile Arg Ala Gly His
    1070                1075                1080

Pro Ile Asp Arg Val Asp Asp Tyr Asp Asp Trp Val Arg Arg Phe
    1085                1090                1095

Glu Thr Ala Leu Thr Ala Leu Pro Glu Lys Arg Ala Gln Thr
    1100                1105                1110

Val Leu Pro Leu Leu His Ala Phe Arg Ala Pro Gln Ala Pro Leu
    1115                1120                1125

Arg Gly Ala Pro Glu Pro Thr Glu Val Phe His Ala Ala Val Arg
    1130                1135                1140

Thr Ala Lys Val Gly Pro Gly Asp Ile Pro His Leu Asp Glu Ala
    1145                1150                1155

Leu Ile Asp Lys Tyr Ile Arg Asp Leu Arg Glu Phe Gly Leu Ile
    1160                1165                1170

<210> SEQ ID NO 67
<211> LENGTH: 1168
<212> TYPE: PRT
<213> ORGANISM: Mycolicibacterium smegmatis

<400> SEQUENCE: 67

Met Thr Ile Glu Thr Arg Glu Asp Arg Phe Asn Arg Arg Ile Asp His

-continued

```
1               5                   10                  15
Leu Phe Glu Thr Asp Pro Gln Phe Ala Ala Arg Pro Asp Glu Ala
                20                  25                  30
Ile Ser Ala Ala Ala Asp Pro Glu Leu Arg Leu Pro Ala Ala Val
                35                  40                  45
Lys Gln Ile Leu Ala Gly Tyr Ala Asp Arg Pro Ala Leu Gly Lys Arg
    50                  55                  60
Ala Val Glu Phe Val Thr Asp Glu Gly Arg Thr Thr Ala Lys Leu
65                  70                  75                  80
Leu Pro Arg Phe Asp Thr Ile Thr Tyr Arg Gln Leu Ala Gly Arg Ile
                85                  90                  95
Gln Ala Val Thr Asn Ala Trp His Asn His Pro Val Asn Ala Gly Asp
                100                 105                 110
Arg Val Ala Ile Leu Gly Phe Thr Ser Val Asp Tyr Thr Thr Ile Asp
                115                 120                 125
Ile Ala Leu Leu Glu Leu Gly Ala Val Ser Val Pro Leu Gln Thr Ser
                130                 135                 140
Ala Pro Val Ala Gln Leu Gln Pro Ile Val Ala Glu Thr Glu Pro Lys
145                 150                 155                 160
Val Ile Ala Ser Ser Val Asp Phe Leu Ala Asp Ala Val Ala Leu Val
                165                 170                 175
Glu Ser Gly Pro Ala Pro Ser Arg Leu Val Val Phe Asp Tyr Ser His
                180                 185                 190
Glu Val Asp Asp Gln Arg Glu Ala Phe Glu Ala Ala Lys Gly Lys Leu
                195                 200                 205
Ala Gly Thr Gly Val Val Val Glu Thr Ile Thr Asp Ala Leu Asp Arg
210                 215                 220
Gly Arg Ser Leu Ala Asp Ala Pro Leu Tyr Val Pro Asp Glu Ala Asp
225                 230                 235                 240
Pro Leu Thr Leu Leu Ile Tyr Thr Ser Gly Ser Thr Gly Thr Pro Lys
                245                 250                 255
Gly Ala Met Tyr Pro Glu Ser Lys Thr Ala Thr Met Trp Gln Ala Gly
                260                 265                 270
Ser Lys Ala Arg Trp Asp Glu Thr Leu Gly Val Met Pro Ser Ile Thr
                275                 280                 285
Leu Asn Phe Met Pro Met Ser His Val Met Gly Arg Gly Ile Leu Cys
                290                 295                 300
Ser Thr Leu Ala Ser Gly Gly Thr Ala Tyr Phe Ala Ala Arg Ser Asp
305                 310                 315                 320
Leu Ser Thr Phe Leu Glu Asp Leu Ala Leu Val Arg Pro Thr Gln Leu
                325                 330                 335
Asn Phe Val Pro Arg Ile Trp Asp Met Leu Phe Gln Glu Tyr Gln Ser
                340                 345                 350
Arg Leu Asp Asn Arg Arg Ala Glu Gly Ser Glu Asp Arg Ala Glu Ala
                355                 360                 365
Ala Val Leu Glu Glu Val Arg Thr Gln Leu Leu Gly Gly Arg Phe Val
                370                 375                 380
Ser Ala Leu Thr Gly Ser Ala Pro Ile Ser Ala Glu Met Lys Ser Trp
385                 390                 395                 400
Val Glu Asp Leu Leu Asp Met His Leu Leu Glu Gly Tyr Gly Ser Thr
                405                 410                 415
Glu Ala Gly Ala Val Phe Ile Asp Gly Gln Ile Gln Arg Pro Pro Val
                420                 425                 430
```

-continued

```
Ile Asp Tyr Lys Leu Val Asp Val Pro Asp Leu Gly Tyr Phe Ala Thr
    435                 440                 445

Asp Arg Pro Tyr Pro Arg Gly Glu Leu Leu Val Lys Ser Glu Gln Met
450                 455                 460

Phe Pro Gly Tyr Tyr Lys Arg Pro Glu Ile Thr Ala Glu Met Phe Asp
465                 470                 475                 480

Glu Asp Gly Tyr Tyr Arg Thr Gly Asp Ile Val Ala Glu Leu Gly Pro
                485                 490                 495

Asp His Leu Glu Tyr Leu Asp Arg Arg Asn Asn Val Leu Lys Leu Ser
            500                 505                 510

Gln Gly Glu Phe Val Thr Val Ser Lys Leu Glu Ala Val Phe Gly Asp
        515                 520                 525

Ser Pro Leu Val Arg Gln Ile Tyr Val Tyr Gly Asn Ser Ala Arg Ser
530                 535                 540

Tyr Leu Leu Ala Val Val Pro Thr Glu Glu Ala Leu Ser Arg Trp
545                 550                 555                 560

Asp Gly Asp Glu Leu Lys Ser Arg Ile Ser Asp Ser Leu Gln Asp Ala
                565                 570                 575

Ala Arg Ala Ala Gly Leu Gln Ser Tyr Glu Ile Pro Arg Asp Phe Leu
            580                 585                 590

Val Glu Thr Thr Pro Phe Thr Leu Glu Asn Gly Leu Leu Thr Gly Ile
        595                 600                 605

Arg Lys Leu Ala Arg Pro Lys Leu Lys Ala His Tyr Gly Glu Arg Leu
610                 615                 620

Glu Gln Leu Tyr Thr Asp Leu Ala Glu Gly Gln Ala Asn Glu Leu Arg
625                 630                 635                 640

Glu Leu Arg Arg Asn Gly Ala Asp Arg Pro Val Val Glu Thr Val Ser
                645                 650                 655

Arg Ala Ala Val Ala Leu Leu Gly Ala Ser Val Thr Asp Leu Arg Ser
            660                 665                 670

Asp Ala His Phe Thr Asp Leu Gly Gly Asp Ser Leu Ser Ala Leu Ser
        675                 680                 685

Phe Ser Asn Leu Leu His Glu Ile Phe Asp Val Asp Val Pro Val Gly
690                 695                 700

Val Ile Val Ser Pro Ala Thr Asp Leu Ala Gly Val Ala Ala Tyr Ile
705                 710                 715                 720

Glu Gly Glu Leu Arg Gly Ser Lys Arg Pro Thr Tyr Ala Ser Val His
                725                 730                 735

Gly Arg Asp Ala Thr Glu Val Arg Ala Arg Asp Leu Ala Leu Gly Lys
            740                 745                 750

Phe Ile Asp Ala Lys Thr Leu Ser Ala Pro Gly Leu Pro Arg Ser
        755                 760                 765

Gly Thr Glu Ile Arg Thr Val Leu Leu Thr Gly Ala Thr Gly Phe Leu
770                 775                 780

Gly Arg Tyr Leu Ala Leu Glu Trp Leu Glu Arg Met Asp Leu Val Asp
785                 790                 795                 800

Gly Lys Val Ile Cys Leu Val Arg Ala Arg Ser Asp Asp Glu Ala Arg
                805                 810                 815

Ala Arg Leu Asp Ala Thr Phe Asp Thr Gly Asp Ala Thr Leu Leu Glu
            820                 825                 830

His Tyr Arg Ala Leu Ala Ala Asp His Leu Glu Val Ile Ala Gly Asp
        835                 840                 845
```

```
Lys Gly Glu Ala Asp Leu Gly Leu Asp His Asp Thr Trp Gln Arg Leu
    850                 855                 860

Ala Asp Thr Val Asp Leu Ile Val Asp Pro Ala Ala Leu Val Asn His
865                 870                 875                 880

Val Leu Pro Tyr Ser Gln Met Phe Gly Pro Asn Ala Leu Gly Thr Ala
                885                 890                 895

Glu Leu Ile Arg Ile Ala Leu Thr Thr Thr Ile Lys Pro Tyr Val Tyr
            900                 905                 910

Val Ser Thr Ile Gly Val Gly Gln Gly Ile Ser Pro Glu Ala Phe Val
        915                 920                 925

Glu Asp Ala Asp Ile Arg Glu Ile Ser Ala Thr Arg Arg Val Asp Asp
930                 935                 940

Ser Tyr Ala Asn Gly Tyr Gly Asn Ser Lys Trp Ala Gly Glu Val Leu
945                 950                 955                 960

Leu Arg Glu Ala His Asp Trp Cys Gly Leu Pro Val Ser Val Phe Arg
                965                 970                 975

Cys Asp Met Ile Leu Ala Asp Thr Thr Tyr Ser Gly Leu Asn Leu
                980                 985                 990

Pro Asp Met Phe Thr Arg Leu Met Leu Ser Leu Val Ala Thr Gly Ile
            995                 1000                1005

Ala Pro Gly Ser Phe Tyr Glu Leu Asp Ala Asp Gly Asn Arg Gln
    1010                1015                1020

Arg Ala His Tyr Asp Gly Leu Pro Val Glu Phe Ile Ala Glu Ala
    1025                1030                1035

Ile Ser Thr Ile Gly Ser Gln Val Thr Asp Gly Phe Glu Thr Phe
    1040                1045                1050

His Val Met Asn Pro Tyr Asp Gly Ile Gly Leu Asp Glu Tyr
    1055                1060                1065

Val Asp Trp Leu Ile Glu Ala Gly Tyr Pro Val His Arg Val Asp
    1070                1075                1080

Asp Tyr Ala Thr Trp Leu Ser Arg Phe Glu Thr Ala Leu Arg Ala
    1085                1090                1095

Leu Pro Glu Arg Gln Arg Gln Ala Ser Leu Leu Pro Leu Leu His
    1100                1105                1110

Asn Tyr Gln Gln Pro Ser Pro Pro Val Cys Gly Ala Met Ala Pro
    1115                1120                1125

Thr Asp Arg Phe Arg Ala Ala Val Gln Asp Ala Lys Ile Gly Pro
    1130                1135                1140

Asp Lys Asp Ile Pro His Val Thr Ala Asp Val Ile Val Lys Tyr
    1145                1150                1155

Ile Ser Asn Leu Gln Met Leu Gly Leu Leu
    1160                1165

<210> SEQ ID NO 68
<211> LENGTH: 1186
<212> TYPE: PRT
<213> ORGANISM: Segniliparus rotundus

<400> SEQUENCE: 68

Met Thr Gln Ser His Thr Gln Gly Pro Gln Ala Ser Ala Ala His Ser
1               5                   10                  15

Arg Leu Ala Arg Arg Ala Ala Glu Leu Leu Ala Thr Asp Pro Gln Ala
            20                  25                  30

Ala Ala Thr Leu Pro Asp Pro Glu Val Val Arg Gln Ala Thr Arg Pro
        35                  40                  45
```

```
Gly Leu Arg Leu Ala Glu Arg Val Asp Ala Ile Leu Ser Gly Tyr Ala
 50                  55                  60

Asp Arg Pro Ala Leu Gly Gln Arg Ser Phe Gln Thr Val Lys Asp Pro
 65                  70                  75                  80

Ile Thr Gly Arg Ser Ser Val Glu Leu Leu Pro Thr Phe Asp Thr Ile
                 85                  90                  95

Thr Tyr Arg Glu Leu Arg Glu Arg Ala Thr Ala Ile Ala Ser Asp Leu
            100                 105                 110

Ala His His Pro Gln Ala Pro Ala Lys Pro Gly Asp Phe Leu Ala Ser
        115                 120                 125

Ile Gly Phe Ile Ser Val Asp Tyr Val Ala Ile Asp Ile Ala Gly Val
    130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                165                 170                 175

Ser Ile Glu His Leu Pro Thr Ala Val Asp Ala Val Leu Ala Thr Pro
            180                 185                 190

Ser Val Arg Arg Leu Leu Val Phe Asp Tyr Arg Ala Gly Ser Asp Glu
        195                 200                 205

Asp Arg Glu Ala Val Glu Ala Ala Lys Arg Lys Ile Ala Asp Ala Gly
    210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                245                 250                 255

Ser Leu Ser Leu Leu Ile Tyr Thr Ser Gly Ser Thr Gly Thr Pro Lys
            260                 265                 270

Gly Ala Met Tyr Pro Glu Arg Asn Val Ala His Phe Trp Gly Gly Val
        275                 280                 285

Trp Ala Ala Ala Phe Asp Glu Asp Ala Ala Pro Pro Val Pro Ala Ile
    290                 295                 300

Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
                325                 330                 335

Asp Leu Ser Thr Leu Phe Glu Asp Leu Lys Leu Ala Arg Pro Thr Asn
            340                 345                 350

Leu Phe Leu Val Pro Arg Val Val Glu Met Leu Tyr Gln His Tyr Gln
        355                 360                 365

Ser Glu Leu Asp Arg Arg Gly Val Gln Asp Gly Thr Arg Glu Ala Glu
    370                 375                 380

Ala Val Lys Asp Asp Leu Arg Thr Gly Leu Leu Gly Arg Ile Leu
385                 390                 395                 400

Thr Ala Gly Phe Gly Ser Ala Pro Leu Ser Ala Glu Leu Ala Gly Phe
                405                 410                 415

Ile Glu Ser Leu Leu Gln Ile His Leu Val Asp Gly Tyr Gly Ser Thr
            420                 425                 430

Glu Ala Gly Pro Val Trp Arg Asp Gly Tyr Leu Val Lys Pro Pro Val
        435                 440                 445

Thr Asp Tyr Lys Leu Ile Asp Val Pro Glu Leu Gly Tyr Phe Ser Thr
    450                 455                 460
```

```
Asp Ser Pro His Pro Arg Gly Glu Leu Ala Ile Lys Thr Gln Thr Ile
465                 470                 475                 480

Leu Pro Gly Tyr Tyr Lys Arg Pro Glu Thr Thr Ala Glu Val Phe Asp
                485                 490                 495

Glu Asp Gly Phe Tyr Leu Thr Gly Asp Val Val Ala Gln Ile Gly Pro
            500                 505                 510

Glu Gln Phe Ala Tyr Val Asp Arg Arg Lys Asn Val Leu Lys Leu Ser
        515                 520                 525

Gln Gly Glu Phe Val Thr Leu Ala Lys Leu Glu Ala Ala Tyr Ser Ser
    530                 535                 540

Ser Pro Leu Val Arg Gln Leu Phe Val Tyr Gly Ser Ser Glu Arg Ser
545                 550                 555                 560

Tyr Leu Leu Ala Val Ile Val Pro Thr Pro Asp Ala Leu Lys Lys Phe
                565                 570                 575

Gly Val Gly Glu Ala Ala Lys Ala Ala Leu Gly Glu Ser Leu Gln Lys
            580                 585                 590

Ile Ala Arg Asp Glu Gly Leu Gln Ser Tyr Glu Val Pro Arg Asp Phe
        595                 600                 605

Ile Ile Glu Thr Asp Pro Phe Thr Val Glu Asn Gly Leu Leu Ser Asp
    610                 615                 620

Ala Arg Lys Ser Leu Arg Pro Lys Leu Lys Glu His Tyr Gly Glu Arg
625                 630                 635                 640

Leu Glu Ala Met Tyr Lys Glu Leu Ala Asp Gly Gln Ala Asn Glu Leu
                645                 650                 655

Arg Asp Ile Arg Arg Gly Val Gln Gln Arg Pro Thr Leu Glu Thr Val
            660                 665                 670

Arg Arg Ala Ala Ala Met Leu Gly Ala Ser Ala Ala Glu Ile Lys
        675                 680                 685

Pro Asp Ala His Phe Thr Asp Leu Gly Gly Asp Ser Leu Ser Ala Leu
690                 695                 700

Thr Phe Ser Asn Phe Leu His Asp Leu Phe Glu Val Asp Val Pro Val
705                 710                 715                 720

Gly Val Ile Val Ser Ala Ala Asn Thr Leu Gly Ser Val Ala Glu His
                725                 730                 735

Ile Asp Ala Gln Leu Ala Gly Gly Arg Ala Arg Pro Thr Phe Ala Thr
            740                 745                 750

Val His Gly Lys Gly Ser Thr Thr Ile Lys Ala Ser Asp Leu Thr Leu
        755                 760                 765

Asp Lys Phe Ile Asp Glu Gln Thr Leu Glu Ala Ala Lys His Leu Pro
    770                 775                 780

Lys Pro Ala Asp Pro Pro Arg Thr Val Leu Leu Thr Gly Ala Asn Gly
785                 790                 795                 800

Trp Leu Gly Arg Phe Leu Ala Leu Glu Trp Leu Glu Arg Leu Ala Pro
                805                 810                 815

Ala Gly Gly Lys Leu Ile Thr Ile Val Arg Gly Lys Asp Ala Ala Gln
            820                 825                 830

Ala Lys Ala Arg Leu Asp Ala Ala Tyr Glu Ser Gly Asp Pro Lys Leu
        835                 840                 845

Ala Gly His Tyr Gln Asp Leu Ala Ala Thr Thr Leu Glu Val Leu Ala
    850                 855                 860

Gly Asp Phe Ser Glu Pro Arg Leu Gly Leu Asp Glu Ala Thr Trp Asn
865                 870                 875                 880

Arg Leu Ala Asp Glu Val Asp Phe Ile Ser His Pro Gly Ala Leu Val
```

885                 890                 895
Asn His Val Leu Pro Tyr Asn Gln Leu Phe Gly Pro Asn Val Ala Gly
                900                 905                 910

Val Ala Glu Ile Ile Lys Leu Ala Ile Thr Thr Arg Ile Lys Pro Val
                915                 920                 925

Thr Tyr Leu Ser Thr Val Ala Val Ala Ala Gly Val Glu Pro Ser Ala
                930                 935                 940

Leu Asp Glu Asp Gly Asp Ile Arg Thr Val Ser Ala Glu Arg Ser Val
945                 950                 955                 960

Asp Glu Gly Tyr Ala Asn Gly Tyr Gly Asn Ser Lys Trp Gly Gly Glu
                965                 970                 975

Val Leu Leu Arg Glu Ala His Asp Arg Thr Gly Leu Pro Val Arg Val
                980                 985                 990

Phe Arg Ser Asp Met Ile Leu Ala His Gln Lys Tyr Thr Gly Gln Val
                995                 1000                1005

Asn Ala Thr Asp Gln Phe Thr Arg Leu Val Gln Ser Leu Leu Ala
            1010                1015                1020

Thr Gly Leu Ala Pro Lys Ser Phe Tyr Glu Leu Asp Ala Gln Gly
            1025                1030                1035

Asn Arg Gln Arg Ala His Tyr Asp Gly Ile Pro Val Asp Phe Thr
            1040                1045                1050

Ala Glu Ser Ile Thr Thr Leu Gly Gly Asp Gly Leu Glu Gly Tyr
            1055                1060                1065

Arg Ser Tyr Asn Val Phe Asn Pro His Arg Asp Gly Val Gly Leu
            1070                1075                1080

Asp Glu Phe Val Asp Trp Leu Ile Glu Ala Gly His Pro Ile Thr
            1085                1090                1095

Arg Ile Asp Asp Tyr Asp Gln Trp Leu Ser Arg Phe Glu Thr Ser
            1100                1105                1110

Leu Arg Gly Leu Pro Glu Ser Lys Arg Gln Ala Ser Val Leu Pro
            1115                1120                1125

Leu Leu His Ala Phe Ala Arg Pro Gly Pro Ala Val Asp Gly Ser
            1130                1135                1140

Pro Phe Arg Asn Thr Val Phe Arg Thr Asp Val Gln Lys Ala Lys
            1145                1150                1155

Ile Gly Ala Glu His Asp Ile Pro His Leu Gly Lys Ala Leu Val
            1160                1165                1170

Leu Lys Tyr Ala Asp Asp Ile Lys Gln Leu Gly Leu Leu
            1175                1180                1185

<210> SEQ ID NO 69
<211> LENGTH: 224
<212> TYPE: PRT
<213> ORGANISM: Bacillus subtilis

<400> SEQUENCE: 69

Met Lys Ile Tyr Gly Ile Tyr Met Asp Arg Pro Leu Ser Gln Glu Glu
1               5                   10                  15

Asn Glu Arg Phe Met Ser Phe Ile Ser Pro Glu Lys Arg Glu Lys Cys
                20                  25                  30

Arg Arg Phe Tyr His Lys Glu Asp Ala His Arg Thr Leu Leu Gly Asp
            35                  40                  45

Val Leu Val Arg Ser Val Ile Ser Arg Gln Tyr Gln Leu Asp Lys Ser
        50                  55                  60

```
Asp Ile Arg Phe Ser Thr Gln Glu Tyr Gly Lys Pro Cys Ile Pro Asp
 65                  70                  75                  80

Leu Pro Asp Ala His Phe Asn Ile Ser His Ser Gly Arg Trp Val Ile
                 85                  90                  95

Cys Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220

<210> SEQ ID NO 70
<211> LENGTH: 251
<212> TYPE: PRT
<213> ORGANISM: Leifsonia sp.

<400> SEQUENCE: 70

Met Ala Gln Tyr Asp Val Ala Asp Arg Ser Ala Ile Val Thr Gly Gly
 1               5                  10                  15

Gly Ser Gly Ile Gly Arg Ala Val Ala Leu Thr Leu Ala Ala Ser Gly
            20                  25                  30

Ala Ala Val Leu Val Thr Asp Leu Asn Glu Glu His Ala Gln Ala Val
        35                  40                  45

Val Ala Glu Ile Glu Ala Ala Gly Gly Lys Ala Ala Leu Ala Gly
 50                  55                  60

Asp Val Thr Asp Pro Ala Phe Gly Glu Ala Ser Val Ala Gly Ala Asn
 65                  70                  75                  80

Ala Leu Ala Pro Leu Lys Ile Ala Val Asn Asn Ala Gly Ile Gly Gly
                 85                  90                  95

Glu Ala Ala Thr Val Gly Asp Tyr Ser Leu Asp Ser Trp Arg Thr Val
            100                 105                 110

Ile Glu Val Asn Leu Asn Ala Val Phe Tyr Gly Met Gln Pro Gln Leu
        115                 120                 125

Lys Ala Met Ala Ala Asn Gly Gly Gly Ala Ile Val Asn Met Ala Ser
    130                 135                 140

Ile Leu Gly Ser Val Gly Phe Ala Asn Ser Ser Ala Tyr Val Thr Ala
145                 150                 155                 160

Lys His Ala Leu Leu Gly Leu Thr Gln Asn Ala Ala Leu Glu Tyr Ala
                165                 170                 175

Ala Asp Lys Val Arg Val Val Ala Val Gly Pro Gly Phe Ile Arg Thr
            180                 185                 190

Pro Leu Val Glu Ala Asn Leu Ser Ala Asp Ala Leu Ala Phe Leu Glu
        195                 200                 205

Gly Lys His Ala Leu Gly Arg Leu Gly Glu Pro Glu Glu Val Ala Ser
    210                 215                 220
```

Leu Val Ala Phe Leu Ala Ser Asp Ala Ser Phe Ile Thr Gly Ser
225                 230                 235                 240

Tyr His Leu Val Asp Gly Gly Tyr Thr Ala Gln
                245                 250

<210> SEQ ID NO 71
<211> LENGTH: 352
<212> TYPE: PRT
<213> ORGANISM: Rhodococcus sp.

<400> SEQUENCE: 71

Met Arg Val Phe Ala Val Gln Pro Glu Asp Thr Thr Ile His Asp Leu
1               5                   10                  15

Gln Val Pro Thr Pro Ser Pro Glu Gly Arg Glu Val Leu Leu Arg Val
                20                  25                  30

Val Arg Ala Gly Val Cys His Thr Asp Thr His Leu Arg Ala Gly Gly
            35                  40                  45

Tyr Asp Leu Gly Ser Arg Gly Met Met Ser Met Lys Glu Arg Gly Ile
    50                  55                  60

Glu Tyr Pro Met Val Leu Gly His Glu Val Gly Val Val Glu Lys
65                  70                  75                  80

Val Gly Asp Gly Val Glu Ser Val Gln Val Gly Asp Ile Arg Leu Ile
                85                  90                  95

Tyr Pro Trp Ile Gly Cys Gly Glu Cys Arg Gln Cys Arg Ala Gly His
            100                 105                 110

Asp Asn Arg Cys Ala Ala Gly Lys Asn Leu Gly Val Ala Arg His Gly
        115                 120                 125

Gly Tyr Ala Glu Asn Ile Leu Val Pro Asp Glu Lys Tyr Leu Val Asp
    130                 135                 140

Ile Asp Gly Leu Asp Pro Ser Trp Ala Ala Thr Leu Ala Cys Ser Gly
145                 150                 155                 160

Leu Thr Ala Tyr Ser Ala Val Asp Lys Ala Leu Pro Leu Glu Pro Asp
                165                 170                 175

Glu Pro Val Val Val Phe Gly Ala Gly Gly Leu Gly Leu Thr Ala Ile
            180                 185                 190

Ala Ile Leu Arg Ser Arg Gly His Arg Asn Ile Cys Ala Val Asp Val
        195                 200                 205

Ala Glu Arg Asn Leu Ala Leu Ala Arg Asp Met Gly Ala Ser Ser Thr
    210                 215                 220

Val Leu Ser Gly Thr Gly Ser Gly Ala Asp Asp Ile Arg Gly Ala Ala
225                 230                 235                 240

Gly Gly Pro Ala Gly Ala Val Ile Asp Phe Val Asn Asn Gly Ala Thr
                245                 250                 255

Ala Thr Thr Ala Phe Glu Val Leu Ala Lys Ala Gly Ile Met Ile Gln
            260                 265                 270

Val Gly Leu Phe Gly Gly Glu Val Thr Leu Pro Thr Ala Leu Leu Ala
        275                 280                 285

Leu Arg Met Ile Arg Ile Glu Gly Ser Phe Val Gly Thr Leu Val Gln
    290                 295                 300

Met Gln Asp Leu Val Arg Leu Ala Gln Arg Gly Glu Leu Pro His Ile
305                 310                 315                 320

Pro Val Val Glu Arg Ser Leu Ser Ala Ala Val Ser Gln Ala Leu
                325                 330                 335

Asp Asp Leu Thr Ala Gly Gly Val Ala Gly Arg Ile Val Leu Thr Ala

```
                    340              345              350

<210> SEQ ID NO 72
<211> LENGTH: 352
<212> TYPE: PRT
<213> ORGANISM: Acinetobacter sp.

<400> SEQUENCE: 72

Met His Cys Tyr Cys Val Thr His His Gly Gln Pro Leu Glu Asp Val
1               5                   10                  15

Glu Lys Glu Ile Pro Gln Pro Lys Gly Thr Glu Val Leu Leu His Val
            20                  25                  30

Lys Ala Ala Gly Leu Cys His Thr Asp Leu His Leu Trp Glu Gly Tyr
        35                  40                  45

Tyr Asp Leu Gly Gly Lys Arg Leu Ser Leu Ala Asp Arg Gly Leu
    50                  55                  60

Lys Pro Pro Leu Thr Leu Ser His Glu Ile Thr Gly Gln Val Val Ala
65                  70                  75                  80

Val Gly Pro Asp Ala Glu Ser Val Lys Val Gly Met Val Ser Leu Val
                85                  90                  95

His Pro Trp Ile Gly Cys Gly Glu Cys Asn Tyr Cys Lys Arg Gly Glu
            100                 105                 110

Glu Asn Leu Cys Ala Lys Pro Gln Gln Leu Gly Ile Ala Lys Pro Gly
        115                 120                 125

Gly Phe Ala Glu Tyr Ile Ile Val Pro His Pro Arg Tyr Leu Val Asp
    130                 135                 140

Ile Ala Gly Leu Asp Leu Ala Glu Ala Ala Pro Leu Ala Cys Ala Gly
145                 150                 155                 160

Val Thr Thr Tyr Ser Ala Leu Lys Lys Phe Gly Asp Leu Ile Gln Ser
                165                 170                 175

Glu Pro Val Val Ile Ile Gly Ala Gly Gly Leu Gly Leu Met Ala Leu
            180                 185                 190

Glu Leu Leu Lys Ala Met Gln Ala Lys Gly Ala Ile Val Val Asp Ile
        195                 200                 205

Asp Asp Ser Lys Leu Glu Ala Ala Arg Ala Ala Gly Ala Leu Ser Val
    210                 215                 220

Ile Asn Ser Arg Ser Glu Asp Ala Ala Gln Gln Leu Ile Gln Ala Thr
225                 230                 235                 240

Asp Gly Gly Ala Arg Leu Ile Leu Asp Leu Val Gly Ser Asn Pro Thr
                245                 250                 255

Leu Ser Leu Ala Leu Ala Ser Ala Ala Arg Gly His Ile Val Ile
            260                 265                 270

Cys Gly Leu Met Gly Gly Glu Ile Lys Leu Ser Ile Pro Val Ile Pro
        275                 280                 285

Met Arg Pro Leu Thr Ile Gln Gly Ser Tyr Val Gly Thr Val Glu Glu
    290                 295                 300

Leu Arg Glu Leu Val Glu Leu Val Lys Glu Thr His Met Ser Ala Ile
305                 310                 315                 320

Pro Val Lys Lys Leu Pro Ile Ser Gln Ile Asn Ser Ala Phe Gly Asp
                325                 330                 335

Leu Lys Asp Gly Asn Val Ile Gly Arg Ile Val Leu Met His Glu Asn
            340                 345                 350

<210> SEQ ID NO 73
<211> LENGTH: 391
```

```
<212> TYPE: PRT
<213> ORGANISM: Clostridium ljungdahlii

<400> SEQUENCE: 73
```

| | | | | | | | | | | | | | | |
|---|---|---|---|---|---|---|---|---|---|---|---|---|---|---|
|Met|Glu|Asn|Phe|Ile|Phe|Lys|Asn|Ala|Thr|Glu|Ile|Ile|Phe|Gly|Lys|
|1| | | |5| | | | |10| | | | |15|

Asp Thr Glu Asn Leu Val Gly Ser Lys Val Lys Glu Tyr Ser Lys Ser
                20                  25                  30

Asp Lys Ile Leu Phe Cys Tyr Gly Gly Ser Ile Lys Arg Ser Gly
         35                  40                  45

Leu Tyr Asp Arg Val Ile Lys Ser Leu Lys Glu Asn Gly Ile Glu Phe
         50                  55                  60

Ile Glu Leu Pro Gly Ile Lys Pro Asn Pro Arg Leu Gly Pro Val Lys
65                  70                  75                  80

Glu Gly Ile Arg Leu Cys Arg Glu Asn Asn Ile Lys Phe Val Leu Ser
                 85                  90                  95

Val Gly Gly Gly Ser Ser Ala Asp Thr Ala Lys Ala Ile Ala Val Gly
                100                 105                 110

Val Pro Tyr Lys Gly Asp Val Trp Asp Phe Tyr Thr Gly Lys Ala Glu
            115                 120                 125

Val Lys Glu Ala Leu Pro Val Gly Val Ile Thr Leu Pro Ala Thr
        130                 135                 140

Gly Thr Glu Ser Ser Asn Ser Ser Val Ile Met Asn Glu Asp Gly Trp
145                 150                 155                 160

Phe Lys Lys Gly Leu Asn Thr Val Leu Ile Arg Pro Ala Phe Ser Ile
                165                 170                 175

Met Asn Pro Glu Leu Thr Phe Thr Leu Pro Glu Tyr Gln Thr Ala Cys
            180                 185                 190

Gly Ala Cys Asp Ile Met Ala His Ile Met Glu Arg Tyr Phe Thr Asn
        195                 200                 205

Val Lys His Val Asp Ile Thr Asp Arg Leu Cys Glu Ala Ala Leu Arg
210                 215                 220

Asn Val Ile Asn Asn Ala Pro Ile Val Leu Lys Asp Pro Lys Asn Tyr
225                 230                 235                 240

Asp Ala Arg Ala Glu Ile Met Trp Thr Gly Thr Ile Ala His Asn Asp
                245                 250                 255

Val Leu Ser Ala Gly Arg Ile Gly Asp Trp Ala Ser His Lys Ile Glu
            260                 265                 270

His Glu Leu Ser Gly Glu Thr Asp Ile Ala His Gly Ala Gly Leu Ala
        275                 280                 285

Ile Val Phe Pro Ala Trp Met Lys Tyr Val Tyr Lys His Asp Ile Asn
290                 295                 300

Arg Phe Val Gln Phe Ala Val Arg Val Trp Asp Val Asp Leu Ser Tyr
305                 310                 315                 320

Ser Ser Cys Glu Asp Ile Val Leu Glu Gly Ile Arg Arg Met Thr Ala
                325                 330                 335

Phe Phe Lys Ser Met Gly Leu Pro Val Thr Leu Lys Glu Gly Ser Ile
            340                 345                 350

Gly Glu Asp Lys Ile Glu Glu Met Ala Asn Lys Cys Thr Asp Asn Gly
        355                 360                 365

Thr Lys Thr Val Gly Gln Phe Val Lys Leu Asn Lys Asp Asp Ile Val
    370                 375                 380

Lys Ile Leu Asn Leu Ala Lys
385                 390

<210> SEQ ID NO 74
<211> LENGTH: 389
<212> TYPE: PRT
<213> ORGANISM: Clostridium acetobutylicum

<400> SEQUENCE: 74

```
Met Leu Ser Phe Asp Tyr Ser Ile Pro Thr Lys Val Phe Gly Lys
1               5                   10                  15

Gly Lys Ile Asp Val Ile Gly Glu Glu Ile Lys Lys Tyr Gly Ser Arg
                20                  25                  30

Val Leu Ile Val Tyr Gly Gly Gly Ser Ile Lys Arg Asn Gly Ile Tyr
                35                  40                  45

Asp Arg Ala Thr Ala Ile Leu Lys Glu Asn Asn Ile Ala Phe Tyr Glu
            50                  55                  60

Leu Ser Gly Val Glu Pro Asn Pro Arg Ile Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
                100                 105                 110

Tyr Asp Gly Asp Thr Trp Asp Met Val Lys Asp Pro Ser Lys Ile Thr
            115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
            195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
                260                 265                 270

Leu Ser Ala Tyr Tyr Asp Ile Thr His Gly Val Gly Leu Ala Ile Leu
            275                 280                 285

Thr Pro Asn Trp Met Glu Tyr Ile Leu Asn Asp Asp Thr Leu His Lys
    290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
                340                 345                 350

Asp Lys Leu Glu Leu Met Ala Lys Gln Ala Val Arg Asn Ser Gly Gly
            355                 360                 365

Thr Ile Gly Ser Leu Arg Pro Ile Asn Ala Glu Asp Val Leu Glu Ile
```

```
            370                 375                 380

Phe Lys Lys Ser Tyr
385

<210> SEQ ID NO 75
<211> LENGTH: 477
<212> TYPE: PRT
<213> ORGANISM: Acinetobacter sp.

<400> SEQUENCE: 75

Met Asn Tyr Pro Asn Ile Pro Leu Tyr Ile Asn Gly Glu Phe Leu Asp
1               5                   10                  15

His Thr Asn Arg Asp Val Lys Glu Val Phe Asn Pro Val Asn His Glu
            20                  25                  30

Cys Ile Gly Leu Met Ala Cys Ala Ser Gln Ala Asp Leu Asp Tyr Ala
        35                  40                  45

Leu Glu Ser Ser Gln Gln Ala Phe Leu Arg Trp Lys Lys Thr Ser Pro
    50                  55                  60

Ile Thr Arg Ser Glu Ile Leu Arg Thr Phe Ala Lys Leu Ala Arg Glu
65                  70                  75                  80

Lys Ala Ala Glu Ile Gly Arg Asn Ile Thr Leu Asp Gln Gly Lys Pro
                85                  90                  95

Leu Lys Glu Ala Ile Ala Glu Val Thr Val Cys Ala Glu His Ala Glu
            100                 105                 110

Trp His Ala Glu Glu Cys Arg Arg Ile Tyr Gly Arg Val Ile Pro Pro
        115                 120                 125

Arg Asn Pro Asn Val Gln Gln Leu Val Val Arg Glu Pro Leu Gly Val
    130                 135                 140

Cys Leu Ala Phe Ser Pro Trp Asn Phe Pro Phe Asn Gln Ala Ile Arg
145                 150                 155                 160

Lys Ile Ser Ala Ala Ile Ala Ala Gly Cys Thr Ile Ile Val Lys Gly
                165                 170                 175

Ser Gly Asp Thr Pro Ser Ala Val Tyr Ala Ile Ala Gln Leu Phe His
            180                 185                 190

Glu Ala Gly Leu Pro Asn Gly Val Leu Asn Val Ile Trp Gly Asp Ser
        195                 200                 205

Asn Phe Ile Ser Asp Tyr Met Ile Lys Ser Pro Ile Ile Gln Lys Ile
    210                 215                 220

Ser Phe Thr Gly Ser Thr Pro Val Gly Lys Lys Leu Ala Ser Gln Ala
225                 230                 235                 240

Ser Leu Tyr Met Lys Pro Cys Thr Met Glu Leu Gly Gly His Ala Pro
                245                 250                 255

Val Ile Val Cys Asp Asp Ala Asp Ile Asp Ala Ala Val Glu His Leu
            260                 265                 270

Val Gly Tyr Lys Phe Arg Asn Ala Gly Gln Val Cys Val Ser Pro Thr
        275                 280                 285

Arg Phe Tyr Val Gln Glu Gly Ile Tyr Lys Glu Phe Ser Glu Lys Val
    290                 295                 300

Val Leu Arg Ala Lys Gln Ile Lys Val Gly Cys Gly Leu Asp Ala Ser
305                 310                 315                 320

Ser Asp Met Gly Pro Leu Ala Gln Ala Arg Arg Met His Ala Met Gln
                325                 330                 335

Gln Ile Val Glu Asp Ala Val His Lys Gly Ser Lys Leu Leu Leu Gly
            340                 345                 350
```

```
Gly Asn Lys Ile Ser Asp Lys Gly Asn Phe Phe Glu Pro Thr Val Leu
        355                 360                 365

Gly Asp Leu Cys Asn Asp Thr Gln Phe Met Asn Asp Glu Pro Phe Gly
    370                 375                 380

Pro Ile Ile Gly Leu Ile Pro Phe Asp Thr Ile Asp His Val Leu Glu
385                 390                 395                 400

Glu Ala Asn Arg Leu Pro Phe Gly Leu Ala Ser Tyr Ala Phe Thr Thr
                405                 410                 415

Ser Ser Lys Asn Ala His Gln Ile Ser Tyr Gly Leu Glu Ala Gly Met
            420                 425                 430

Val Ser Ile Asn His Met Gly Leu Ala Leu Ala Glu Thr Pro Phe Gly
        435                 440                 445

Gly Ile Lys Asp Ser Gly Phe Gly Ser Glu Gly Gly Ile Glu Thr Phe
    450                 455                 460

Asp Gly Tyr Leu Arg Thr Lys Phe Ile Thr Gln Leu Asn
465                 470                 475

<210> SEQ ID NO 76
<211> LENGTH: 787
<212> TYPE: PRT
<213> ORGANISM: Clostridium butyricum

<400> SEQUENCE: 76

Met Ile Ser Lys Gly Phe Ser Thr Gln Thr Glu Arg Ile Asn Ile Leu
1               5                   10                  15

Lys Ala Gln Ile Leu Asn Ala Lys Pro Cys Val Glu Ser Glu Arg Ala
            20                  25                  30

Ile Leu Ile Thr Glu Ser Phe Lys Gln Thr Glu Gly Gln Pro Ala Ile
        35                  40                  45

Leu Arg Arg Ala Leu Ala Leu Lys His Ile Leu Glu Asn Ile Pro Ile
    50                  55                  60

Thr Ile Arg Asp Gln Glu Leu Ile Val Gly Ser Leu Thr Lys Glu Pro
65                  70                  75                  80

Arg Ser Ser Gln Val Phe Pro Glu Phe Ser Asn Lys Trp Leu Gln Asp
                85                  90                  95

Glu Leu Asp Arg Leu Asn Lys Arg Thr Gly Asp Ala Phe Gln Ile Ser
            100                 105                 110

Glu Glu Ser Lys Glu Lys Leu Lys Asp Val Phe Glu Tyr Trp Asn Gly
        115                 120                 125

Lys Thr Thr Ser Glu Leu Ala Thr Ser Tyr Met Thr Glu Glu Thr Arg
    130                 135                 140

Glu Ala Val Asn Cys Asp Val Phe Thr Val Gly Asn Tyr Tyr Tyr Asn
145                 150                 155                 160

Gly Val Gly His Val Ser Val Asp Tyr Gly Lys Val Leu Arg Val Gly
                165                 170                 175

Phe Asn Gly Ile Ile Asn Glu Ala Lys Glu Gln Leu Glu Lys Asn Arg
            180                 185                 190

Ser Ile Asp Pro Asp Phe Ile Lys Lys Glu Lys Phe Leu Asn Ser Val
        195                 200                 205

Ile Ile Ser Cys Glu Ala Ala Ile Thr Tyr Val Asn Arg Tyr Ala Lys
    210                 215                 220

Lys Ala Lys Glu Ile Ala Asp Asn Thr Ser Asp Ala Lys Arg Lys Ala
225                 230                 235                 240

Glu Leu Asn Glu Ile Ala Lys Ile Cys Ser Lys Val Ser Gly Glu Gly
                245                 250                 255
```

-continued

```
Ala Lys Ser Phe Tyr Glu Ala Cys Gln Leu Phe Trp Phe Ile His Ala
            260                 265                 270
Ile Ile Asn Ile Glu Ser Asn Gly His Ser Ile Ser Pro Ala Arg Phe
        275                 280                 285
Asp Gln Tyr Met Tyr Pro Tyr Tyr Glu Asn Asp Lys Asn Ile Thr Asp
290                 295                 300
Lys Phe Ala Gln Glu Leu Ile Asp Cys Ile Trp Ile Lys Leu Asn Asp
305                 310                 315                 320
Ile Asn Lys Val Arg Asp Glu Ile Ser Thr Lys His Phe Gly Gly Tyr
                325                 330                 335
Pro Met Tyr Gln Asn Leu Ile Val Gly Gln Asn Ser Glu Gly Lys
            340                 345                 350
Asp Ala Thr Asn Lys Val Ser Tyr Met Ala Leu Glu Ala Val His
            355                 360                 365
Val Lys Leu Pro Gln Pro Ser Leu Ser Val Arg Ile Trp Asn Lys Thr
            370                 375                 380
Pro Asp Glu Phe Leu Leu Arg Ala Ala Glu Leu Thr Arg Glu Gly Leu
385                 390                 395                 400
Gly Leu Pro Ala Tyr Tyr Asn Asp Glu Val Ile Ile Pro Ala Leu Val
                405                 410                 415
Ser Arg Gly Leu Thr Leu Glu Asp Ala Arg Asp Tyr Gly Ile Ile Gly
            420                 425                 430
Cys Val Glu Pro Gln Lys Pro Gly Lys Thr Glu Gly Trp His Asp Ser
            435                 440                 445
Ala Phe Phe Asn Leu Ala Arg Ile Val Glu Leu Thr Ile Asn Ser Gly
            450                 455                 460
Phe Asp Lys Asn Lys Gln Ile Gly Pro Lys Thr Gln Asn Phe Glu Glu
465                 470                 475                 480
Met Lys Ser Phe Asp Glu Phe Met Lys Ala Tyr Lys Ala Gln Met Glu
                485                 490                 495
Tyr Phe Val Lys His Met Cys Cys Ala Asp Asn Cys Ile Asp Ile Ala
            500                 505                 510
His Ala Glu Arg Ala Pro Leu Pro Phe Leu Ser Ser Met Val Asp Asn
            515                 520                 525
Cys Ile Gly Lys Gly Lys Ser Leu Gln Asp Gly Gly Ala Glu Tyr Asn
530                 535                 540
Phe Ser Gly Pro Gln Gly Val Gly Val Ala Asn Ile Gly Asp Ser Leu
545                 550                 555                 560
Val Ala Val Lys Lys Ile Val Phe Asp Glu Asn Lys Ile Thr Pro Ser
                565                 570                 575
Glu Leu Lys Lys Thr Leu Asn Asn Asp Phe Lys Asn Ser Glu Glu Ile
            580                 585                 590
Gln Ala Leu Leu Lys Asn Ala Pro Lys Phe Gly Asn Asp Ile Asp Glu
            595                 600                 605
Val Asp Asn Leu Ala Arg Glu Gly Ala Leu Val Tyr Cys Arg Glu Val
610                 615                 620
Asn Lys Tyr Thr Asn Pro Arg Gly Gly Asn Phe Gln Pro Gly Leu Tyr
625                 630                 635                 640
Pro Ser Ser Ile Asn Val Tyr Phe Gly Ser Leu Thr Gly Ala Thr Pro
                645                 650                 655
Asp Gly Arg Lys Ser Gly Gln Pro Leu Ala Asp Gly Val Ser Pro Ser
            660                 665                 670
```

```
Arg Gly Cys Asp Val Ser Gly Pro Thr Ala Ala Cys Asn Ser Val Ser
            675                 680                 685

Lys Leu Asp His Phe Ile Ala Ser Asn Gly Thr Leu Phe Asn Gln Lys
    690                 695                 700

Phe His Pro Ser Ala Leu Lys Gly Asp Asn Gly Leu Met Asn Leu Ser
705                 710                 715                 720

Ser Leu Ile Arg Ser Tyr Phe Asp Gln Lys Gly Phe His Val Gln Phe
                725                 730                 735

Asn Val Ile Asp Lys Lys Ile Leu Ala Ala Gln Lys Asn Pro Glu
            740                 745                 750

Lys Tyr Gln Asp Leu Ile Val Arg Val Ala Gly Tyr Ser Ala Gln Phe
    755                 760                 765

Ile Ser Leu Asp Lys Ser Ile Gln Asn Asp Ile Ile Ala Arg Thr Glu
    770                 775                 780

His Val Met
785

<210> SEQ ID NO 77
<211> LENGTH: 304
<212> TYPE: PRT
<213> ORGANISM: Clostridium butyricum

<400> SEQUENCE: 77

Met Ser Lys Glu Ile Lys Gly Val Leu Phe Asn Ile Gln Lys Phe Ser
1               5                   10                  15

Leu His Asp Gly Pro Gly Ile Arg Thr Ile Val Phe Phe Lys Gly Cys
                20                  25                  30

Ser Met Ser Cys Leu Trp Cys Ser Asn Pro Glu Ser Gln Asp Ile Lys
            35                  40                  45

Pro Gln Val Met Phe Asn Lys Asn Leu Cys Thr Lys Cys Gly Arg Cys
    50                  55                  60

Lys Ser Gln Cys Lys Ser Ala Ala Ile Asp Met Asn Ser Glu Tyr Arg
65                  70                  75                  80

Ile Asp Lys Ser Lys Cys Thr Glu Cys Thr Lys Cys Val Asp Asn Cys
                85                  90                  95

Leu Ser Gly Ala Leu Val Ile Glu Gly Arg Asn Tyr Ser Val Glu Asp
            100                 105                 110

Val Ile Lys Glu Leu Lys Lys Asp Ser Val Gln Tyr Arg Arg Ser Asn
    115                 120                 125

Gly Gly Ile Thr Leu Ser Gly Gly Glu Val Leu Leu Gln Pro Asp Phe
130                 135                 140

Ala Val Glu Leu Leu Lys Glu Cys Lys Ser Tyr Gly Trp His Thr Ala
145                 150                 155                 160

Ile Glu Thr Ala Met Tyr Val Asn Ser Glu Ser Val Lys Lys Val Ile
                165                 170                 175

Pro Tyr Ile Asp Leu Ala Met Ile Asp Ile Lys Ser Met Asn Asp Glu
            180                 185                 190

Ile His Arg Lys Phe Thr Gly Val Ser Asn Glu Ile Ile Leu Gln Asn
    195                 200                 205

Ile Lys Leu Ser Asp Glu Leu Ala Lys Glu Ile Ile Arg Ile Pro
210                 215                 220

Val Ile Glu Gly Phe Asn Ala Asp Leu Gln Ser Ile Gly Ala Ile Ala
225                 230                 235                 240

Gln Phe Ser Lys Ser Leu Thr Asn Leu Lys Arg Ile Asp Leu Leu Pro
                245                 250                 255
```

```
Tyr His Asn Tyr Gly Glu Asn Lys Tyr Gln Ala Ile Gly Arg Glu Tyr
            260                 265                 270

Ser Leu Lys Glu Leu Lys Ser Pro Ser Lys Asp Lys Met Glu Arg Leu
        275                 280                 285

Lys Ala Leu Val Glu Ile Met Gly Ile Pro Cys Thr Ile Gly Ala Glu
    290                 295                 300

<210> SEQ ID NO 78
<211> LENGTH: 558
<212> TYPE: PRT
<213> ORGANISM: Lactobacillus reuteri

<400> SEQUENCE: 78

Met Lys Arg Gln Lys Arg Phe Glu Glu Leu Glu Lys Arg Pro Ile His
1               5                   10                  15

Gln Asp Thr Phe Val Lys Glu Trp Pro Glu Glu Gly Phe Val Ala Met
            20                  25                  30

Met Gly Pro Asn Asp Pro Lys Pro Ser Val Lys Val Glu Asn Gly Lys
        35                  40                  45

Ile Val Glu Met Asp Gly Lys Lys Leu Glu Asp Phe Asp Leu Ile Asp
    50                  55                  60

Leu Tyr Ile Ala Lys Tyr Gly Ile Asn Ile Asp Asn Val Glu Lys Val
65                  70                  75                  80

Met Asn Met Asp Ser Thr Lys Ile Ala Arg Met Leu Val Asp Pro Asn
            85                  90                  95

Val Ser Arg Asp Glu Ile Ile Gly Ile Thr Ser Ala Leu Thr Pro Ala
        100                 105                 110

Lys Ala Glu Glu Ile Ile Ser Lys Leu Asp Phe Gly Glu Met Ile Met
    115                 120                 125

Ala Val Lys Lys Met Arg Pro Arg Arg Lys Pro Asp Asn Gln Cys His
    130                 135                 140

Val Thr Asn Thr Val Asp Asn Pro Val Gln Ile Ala Ala Asp Ala Ala
145                 150                 155                 160

Asp Ala Ala Leu Arg Gly Phe Pro Glu Gln Glu Thr Thr Thr Ala Val
            165                 170                 175

Ala Arg Tyr Ala Pro Phe Asn Ala Ile Ser Ile Leu Ile Gly Ala Gln
        180                 185                 190

Thr Gly Arg Pro Gly Val Leu Thr Gln Cys Ser Val Glu Glu Ala Thr
    195                 200                 205

Glu Leu Gln Leu Gly Met Arg Gly Phe Thr Ala Tyr Ala Glu Thr Ile
    210                 215                 220

Ser Val Tyr Gly Thr Asp Arg Val Phe Thr Asp Gly Asp Thr Pro
225                 230                 235                 240

Trp Ser Lys Gly Phe Leu Ala Ser Cys Tyr Ala Ser Arg Gly Leu Lys
            245                 250                 255

Met Arg Phe Thr Ser Gly Ala Gly Ser Glu Val Leu Met Gly Tyr Pro
        260                 265                 270

Glu Gly Lys Ser Met Leu Tyr Leu Glu Ala Arg Cys Ile Leu Leu Thr
    275                 280                 285

Lys Ala Ser Gly Val Gln Gly Leu Gln Asn Gly Ala Val Ser Cys Ile
    290                 295                 300

Glu Ile Pro Gly Ala Val Pro Asn Gly Ile Arg Glu Val Leu Gly Glu
305                 310                 315                 320

Asn Leu Leu Cys Met Met Cys Asp Ile Glu Cys Ala Ser Gly Cys Asp
```

```
                    325                 330                 335
Gln Ala Tyr Ser His Ser Asp Met Arg Arg Thr Glu Arg Phe Ile Gly
                340                 345                 350

Gln Phe Ile Ala Gly Thr Asp Tyr Ile Asn Ser Gly Tyr Ser Ser Thr
            355                 360                 365

Pro Asn Tyr Asp Asn Thr Phe Ala Gly Ser Asn Thr Asp Ala Met Asp
        370                 375                 380

Tyr Asp Asp Met Tyr Val Met Glu Arg Asp Leu Gly Gln Tyr Tyr Gly
385                 390                 395                 400

Ile His Pro Val Lys Glu Glu Thr Ile Ile Lys Ala Arg Asn Lys Ala
                405                 410                 415

Ala Lys Ala Leu Gln Ala Val Phe Glu Asp Leu Gly Leu Pro Lys Ile
            420                 425                 430

Thr Asp Glu Glu Val Glu Ala Ala Thr Tyr Ala Asn Thr His Asp Asp
        435                 440                 445

Met Pro Lys Arg Asp Met Val Ala Asp Met Lys Ala Ala Gln Asp Met
    450                 455                 460

Met Asp Arg Gly Ile Thr Ala Ile Asp Ile Ile Lys Ala Leu Tyr Asn
465                 470                 475                 480

His Gly Phe Lys Asp Val Ala Glu Ala Ile Leu Asn Leu Gln Lys Gln
                485                 490                 495

Lys Val Val Gly Asp Tyr Leu Gln Thr Ser Ser Ile Phe Asp Lys Asp
            500                 505                 510

Trp Asn Val Thr Ser Ala Val Asn Asp Gly Asn Asp Tyr Gln Gly Pro
        515                 520                 525

Gly Thr Gly Tyr Arg Leu Tyr Glu Asp Lys Glu Glu Trp Asp Arg Ile
    530                 535                 540

Lys Asp Leu Pro Phe Ala Leu Asp Pro Glu His Leu Glu Leu
545                 550                 555

<210> SEQ ID NO 79
<211> LENGTH: 236
<212> TYPE: PRT
<213> ORGANISM: Lactobacillus reuteri

<400> SEQUENCE: 79

Met Ala Asp Ile Asp Glu Asn Leu Leu Arg Lys Ile Val Lys Glu Val
1               5                   10                  15

Leu Ser Glu Thr Asn Gln Ile Asp Thr Lys Ile Asp Phe Asp Lys Ser
            20                  25                  30

Asn Asp Ser Thr Ala Thr Ala Thr Gln Glu Val Gln Pro Asn Ser
        35                  40                  45

Lys Ala Val Pro Glu Lys Lys Leu Asp Trp Phe Gln Pro Val Gly Glu
    50                  55                  60

Ala Lys Pro Gly Tyr Ser Lys Asp Glu Val Ile Ala Val Gly Pro
65                  70                  75                  80

Ala Phe Ala Thr Val Leu Asp Lys Thr Glu Thr Gly Ile Pro His Lys
                85                  90                  95

Glu Val Leu Arg Gln Val Ile Ala Gly Ile Glu Glu Gly Leu Lys
            100                 105                 110

Ala Arg Val Val Lys Val Tyr Arg Ser Ser Asp Val Ala Phe Cys Ala
        115                 120                 125

Val Gln Gly Asp His Leu Ser Gly Ser Gly Ile Ala Ile Gly Ile Gln
    130                 135                 140
```

```
Ser Lys Gly Thr Thr Val Ile His Gln Lys Asp Gln Asp Pro Leu Gly
145                 150                 155                 160

Asn Leu Glu Leu Phe Pro Gln Ala Pro Val Leu Thr Pro Glu Thr Tyr
                165                 170                 175

Arg Ala Ile Gly Lys Asn Ala Ala Met Tyr Ala Lys Gly Glu Ser Pro
            180                 185                 190

Glu Pro Val Pro Ala Lys Asn Asp Gln Leu Ala Arg Ile His Tyr Gln
        195                 200                 205

Ala Ile Ser Ala Ile Met His Ile Arg Glu Thr His Gln Val Val Val
    210                 215                 220

Gly Lys Pro Glu Glu Ile Lys Val Thr Phe Asp
225                 230                 235

<210> SEQ ID NO 80
<211> LENGTH: 172
<212> TYPE: PRT
<213> ORGANISM: Lactobacillus reuteri

<400> SEQUENCE: 80

Met Met Ser Glu Val Asp Asp Leu Val Ala Lys Ile Met Ala Gln Met
1               5                   10                  15

Gly Asn Ser Ser Ala Asn Ser Ser Thr Gly Thr Ser Thr Ala Ser
            20                  25                  30

Thr Ser Lys Glu Met Thr Ala Asp Asp Tyr Pro Leu Tyr Gln Lys His
        35                  40                  45

Arg Asp Leu Val Lys Thr Pro Lys Gly His Asn Leu Asp Asp Ile Asn
    50                  55                  60

Leu Gln Lys Val Val Asn Asn Gln Val Asp Pro Lys Glu Leu Arg Ile
65                  70                  75                  80

Thr Pro Glu Ala Leu Lys Leu Gln Gly Glu Ile Ala Ala Asn Ala Gly
                85                  90                  95

Arg Pro Ala Ile Gln Lys Asn Leu Gln Arg Ala Ala Glu Leu Thr Arg
            100                 105                 110

Val Pro Asp Glu Arg Val Leu Glu Met Tyr Asp Ala Leu Arg Pro Phe
        115                 120                 125

Arg Ser Thr Lys Gln Glu Leu Leu Asn Ile Ala Lys Glu Leu Arg Asp
    130                 135                 140

Lys Tyr Asp Ala Asn Val Cys Ala Ala Trp Phe Glu Glu Ala Ala Asp
145                 150                 155                 160

Tyr Tyr Glu Ser Arg Lys Lys Leu Lys Gly Asp Asn
                165                 170

<210> SEQ ID NO 81
<211> LENGTH: 616
<212> TYPE: PRT
<213> ORGANISM: Lactobacillus reuteri

<400> SEQUENCE: 81

Met Ala Thr Glu Lys Val Ile Gly Val Asp Ile Gly Asn Ser Ser Thr
1               5                   10                  15

Glu Val Ala Leu Ala Asp Val Ser Asp Ser Gly Gln Val His Phe Ile
            20                  25                  30

Asn Ser Gly Ile Ala Pro Thr Thr Gly Ile Lys Gly Thr Lys Gln Asn
        35                  40                  45

Leu Val Gly Ile Arg Asp Ser Ile Thr Gln Val Leu Asn Lys Ser Asn
    50                  55                  60
```

```
Leu Thr Ile Asp Asp Ile Asp Leu Ile Arg Ile Asn Glu Ala Thr Pro
 65                  70                  75                  80

Val Ile Gly Asp Val Ala Met Glu Thr Ile Thr Glu Thr Val Val Thr
                 85                  90                  95

Glu Ser Thr Met Ile Gly His Asn Pro Asn Thr Pro Gly Gly Ile Gly
            100                 105                 110

Thr Gly Ala Gly Ile Thr Val Arg Leu Leu Asp Leu Leu Lys Lys Thr
            115                 120                 125

Asp Lys Ser Lys Asn Tyr Ile Val Val Pro Lys Asp Ile Asp Phe
130                 135                 140

Glu Asp Val Ala Lys Leu Ile Asn Ala Tyr Val Ala Ser Gly Tyr Lys
145                 150                 155                 160

Ile Thr Ala Ala Ile Leu Arg Asn Asp Asp Gly Val Leu Val Asp Asn
                165                 170                 175

Arg Leu Asn His Lys Ile Pro Ile Val Asp Glu Val Ala Met Ile Asp
                180                 185                 190

Lys Val Pro Leu Asn Met Leu Ala Ala Val Glu Val Ala Gly Pro Gly
                195                 200                 205

Gln Val Ile Ser Gln Leu Ser Asn Pro Tyr Gly Ile Ala Thr Leu Phe
210                 215                 220

Gly Leu Thr Pro Glu Glu Thr Lys Asn Ile Val Pro Val Ser Arg Ala
225                 230                 235                 240

Leu Ile Gly Asn Arg Ser Ala Val Val Ile Lys Thr Pro Ala Gly Asp
                245                 250                 255

Val Lys Ala Arg Val Ile Pro Ala Gly Lys Ile Ile Asn Gly Asp
                260                 265                 270

Thr Gly Lys Glu Glu Val Gly Val Ser Glu Gly Ala Asp Ala Ile Met
            275                 280                 285

Lys Lys Val Ser Ser Phe Arg His Ile Asn Asn Ile Thr Gly Glu Ser
290                 295                 300

Gly Thr Asn Val Gly Gly Met Leu Glu Asn Val Arg Gln Thr Met Ala
305                 310                 315                 320

Asp Leu Thr Gly Lys Lys Asn Asp Glu Ile Ala Ile Gln Asp Leu Leu
                325                 330                 335

Ala Val Asp Thr Gln Val Pro Val Glu Val Arg Gly Gly Leu Ala Gly
                340                 345                 350

Glu Phe Ser Asn Glu Ser Ala Val Gly Ile Ala Ala Met Val Lys Ser
            355                 360                 365

Asp His Leu Gln Met Glu Val Ile Ala Lys Leu Ile Glu Lys Glu Phe
            370                 375                 380

Asn Thr Lys Val Glu Ile Gly Gly Ala Glu Val Glu Ser Ala Ile Arg
385                 390                 395                 400

Gly Ala Leu Thr Thr Pro Gly Thr Asp Lys Pro Ile Ala Ile Leu Asp
                405                 410                 415

Leu Gly Ala Gly Ser Thr Asp Ala Ser Ile Ile Asn Lys Glu Asn Asn
                420                 425                 430

Thr Val Ala Ile His Leu Ala Gly Ala Gly Asp Met Val Thr Met Ile
            435                 440                 445

Ile Asn Ser Glu Leu Gly Leu Asn Asp Ile His Leu Ala Glu Asp Ile
            450                 455                 460

Lys Arg Tyr Pro Leu Ala Lys Val Glu Asn Leu Phe Gln Ile Arg His
465                 470                 475                 480

Glu Asp Gly Ser Val Gln Phe Phe Lys Asp Pro Leu Pro Ser Ser Leu
```

```
                    485                 490                 495
Phe Ala Lys Val Val Ile Lys Pro Asp Gly Tyr Glu Pro Val Thr
            500                 505                 510

Gly Asn Pro Ser Ile Glu Lys Ile Lys Leu Val Arg Gln Ser Ala Lys
            515                 520                 525

Lys Arg Val Phe Val Thr Asn Ala Leu Arg Ala Leu Lys Tyr Val Ser
            530                 535                 540

Pro Thr Gly Asn Ile Arg Asp Ile Pro Phe Val Val Ile Val Gly Gly
545                 550                 555                 560

Ser Ala Leu Asp Phe Glu Ile Pro Gln Leu Val Thr Asp Glu Leu Ala
                565                 570                 575

His Phe Asn Leu Val Ala Gly Arg Gly Asn Val Arg Gly Val Glu Gly
            580                 585                 590

Pro Arg Asn Ala Val Ala Thr Gly Leu Ile Leu Arg Tyr Gly Glu Glu
            595                 600                 605

Arg Arg Lys Arg Tyr Glu Gln Arg
            610                 615

<210> SEQ ID NO 82
<211> LENGTH: 119
<212> TYPE: PRT
<213> ORGANISM: Lactobacillus reuteri

<400> SEQUENCE: 82

Met Asn Asn Asp Asp Ser Gln Arg Pro Ser Ile Val Val Gly Leu Glu
1               5                   10                  15

Asn Gly Ile Thr Ile Pro Asp Ser Val Lys Pro Leu Phe Tyr Gly Ile
            20                  25                  30

Glu Glu Glu Gln Ile Pro Val Ser Val Arg Lys Ile Asn Ile Asn Asp
        35                  40                  45

Thr Val Glu Arg Ala Tyr Gln Ser Ala Leu Ala Ser Arg Leu Ser Val
    50                  55                  60

Gly Ile Ala Phe Glu Gly Asp His Phe Ile Val His Tyr Lys Asn Leu
65                  70                  75                  80

Lys Glu Asn Gln Pro Leu Phe Asp Met Thr Ile Asn Asp Lys Lys Gln
                85                  90                  95

Leu Arg Ile Leu Gly Ala Asn Ala Ala Arg Leu Val Lys Gly Ile Pro
            100                 105                 110

Phe Lys Glu Met Ala Asn Arg
        115

<210> SEQ ID NO 83
<211> LENGTH: 547
<212> TYPE: PRT
<213> ORGANISM: Lactococcus lactis

<400> SEQUENCE: 83

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
```

```
                65                  70                  75                  80
Asn Gly Leu Ala Gly Ser Tyr Ala Glu Asn Leu Pro Val Val Glu Ile
                    85                  90                  95

Val Gly Ser Pro Thr Ser Lys Val Gln Asn Asp Gly Lys Phe Val His
                100                 105                 110

His Thr Leu Ala Asp Gly Asp Phe Lys His Phe Met Lys Met His Glu
                115                 120                 125

Pro Val Thr Ala Ala Arg Thr Leu Leu Thr Ala Glu Asn Ala Thr Tyr
                130                 135                 140

Glu Ile Asp Arg Val Leu Ser Gln Leu Lys Glu Arg Lys Pro Val
145                 150                 155                 160

Tyr Ile Asn Leu Pro Val Asp Val Ala Ala Ala Lys Ala Glu Lys Pro
                    165                 170                 175

Ala Leu Ser Leu Glu Lys Glu Ser Ser Thr Thr Asn Thr Thr Glu Gln
                180                 185                 190

Val Ile Leu Ser Lys Ile Glu Glu Ser Leu Lys Asn Ala Gln Lys Pro
                195                 200                 205

Val Val Ile Ala Gly His Glu Val Ile Ser Phe Gly Leu Glu Lys Thr
                210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                    245                 250                 255

Tyr Asn Gly Lys Leu Ser Glu Ile Ser Leu Lys Asn Phe Val Glu Ser
                    260                 265                 270

Ala Asp Phe Ile Leu Met Leu Gly Val Lys Leu Thr Asp Ser Ser Thr
                    275                 280                 285

Gly Ala Phe Thr His His Leu Asp Glu Asn Lys Met Ile Ser Leu Asn
                290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                    325                 330                 335

Gly Gln Tyr Ile Asp Lys Gln Tyr Glu Glu Phe Ile Pro Ser Ser Ala
                    340                 345                 350

Pro Leu Ser Gln Asp Arg Leu Trp Gln Ala Val Glu Ser Leu Thr Gln
                355                 360                 365

Ser Asn Glu Thr Ile Val Ala Glu Gln Gly Thr Ser Phe Phe Gly Ala
                370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                    405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ser Ile Arg Glu Lys Leu Asn
                435                 440                 445

Pro Ile Cys Phe Ile Ile Asn Asn Asp Gly Tyr Thr Val Glu Arg Glu
                450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                    485                 490                 495
```

```
Lys Ile Val Arg Thr Glu Asn Glu Phe Val Ser Val Met Lys Glu Ala
                500                 505                 510

Gln Ala Asp Val Asn Arg Met Tyr Trp Ile Glu Leu Val Leu Glu Lys
            515                 520                 525

Glu Asp Ala Pro Lys Leu Leu Lys Lys Met Gly Lys Leu Phe Ala Glu
530                 535                 540

Gln Asn Lys
545

<210> SEQ ID NO 84
<211> LENGTH: 331
<212> TYPE: PRT
<213> ORGANISM: Puniceibacterium sp.

<400> SEQUENCE: 84

Met Ser Ala Lys Arg Thr Leu Leu Thr Val Asp Asp Val Thr Gly Cys
1               5                   10                  15

Trp Ala Ile Met Pro Thr Pro Ala Lys Asp Asp Ala Ser Asp Trp Arg
            20                  25                  30

Thr Glu Phe Ser Val Asp Leu Asp Glu Thr Ala Arg Val Ala Asn Ala
        35                  40                  45

Leu Val Glu Ser Gly Val Asp Gly Ile Leu Ala Leu Gly Thr Phe Gly
    50                  55                  60

Glu Gly Ala Thr Leu Thr Trp Glu Glu Lys Glu Ala Tyr Val Arg Thr
65                  70                  75                  80

Val Val Asp Ala Val Ala Gly Arg Val Pro Phe Phe Ala Gly Thr Thr
                85                  90                  95

Ser Leu Asn Thr Arg Glu Thr Ile Arg Gln Met Arg Ile Val Arg Asp
            100                 105                 110

Ile Gly Val Asp Gly Val Met Leu Gly Ile Pro Met Trp Val Glu Ala
        115                 120                 125

Asp Thr Ala Thr Ala Val Gln Phe Tyr Arg Asp Val Thr Glu Ala Cys
    130                 135                 140

Pro Asp Val Ala Ile Cys Ala Tyr Ala Asn Pro Glu Ala Phe Lys Tyr
145                 150                 155                 160

Glu Phe Gly Arg Ala Phe Trp Ala Gln Val Ser Asp Leu Pro Gln Ile
                165                 170                 175

Val Ser Ala Lys Tyr Leu Asn Met Gly Gly Leu Tyr Pro Asp Leu Asn
            180                 185                 190

Leu Ser Lys Arg Arg Ile Arg Leu Met Pro Leu Asp Val Asp Tyr Tyr
        195                 200                 205

Ala Ala Ala Arg Ile Asp Pro Asp His Cys Thr Ala Phe Trp Thr Ser
    210                 215                 220

Gly Ala Val Cys Gly Pro Glu Pro Ala Ile Leu Leu Arg Asp Leu Met
225                 230                 235                 240

Glu Lys Ala Arg Lys Ser Gly Asp Trp Ala Glu Ala Lys Ala Leu Thr
                245                 250                 255

Asp Arg Ile Gly Met Thr Tyr Lys Thr Leu Phe Pro Asn Gly Ser Phe
            260                 265                 270

Lys Glu Phe Ser Arg Tyr Asn Ile Ser Ile Glu Lys Ile Arg Met Asp
        275                 280                 285

Ala Ala Gly Trp Met Lys Ala Gly Pro Cys Arg Pro Pro Tyr His Val
    290                 295                 300

Thr Pro Glu Pro Ile Leu Glu Gly Gly Arg Ile Ala Gly Gln Lys Trp
```

```
            305                 310                 315                 320
Ala Glu Leu Ala Glu Ser Leu Arg Ala Gly Asn
                325                 330

<210> SEQ ID NO 85
<211> LENGTH: 327
<212> TYPE: PRT
<213> ORGANISM: Streptomyces sp.

<400> SEQUENCE: 85

Met Ile Thr Ala Ala Glu Ile Asn Gly Met Tyr Gly Ile Ile Pro Thr
1               5                   10                  15

Pro Ala Leu Pro Gly Ala Glu Arg Leu Asp Ala Arg Asp Thr Val Asp
            20                  25                  30

Val Asp Glu Thr Ala Arg Val Val Asp Arg Leu Ile Arg Asp Gly Val
        35                  40                  45

Ser Gly Ile Ile Ala Leu Gly Thr Thr Gly Glu Cys Pro Ala Leu Ser
    50                  55                  60

Glu Asp Asp Phe Asp Val Val Thr Asp Thr Val Val Glu Ala Val Ala
65                  70                  75                  80

Gly Arg Val Pro Val Phe Val Gly Ala Thr Gly Ala Gly Gly His Gly
                85                  90                  95

Thr Ala Arg Arg Leu Arg Lys Val Ala Ala Ser Gly Ala Thr Gly Ala
            100                 105                 110

Leu Leu Gly Leu Pro Met Trp Gln Pro Leu Thr Thr Ala Met Ala Val
        115                 120                 125

Glu Tyr Tyr Ala Gln Ala Ser Ala Ala Phe Pro Asp Leu Ala Leu Met
    130                 135                 140

Val Tyr Ala Asn Ala Arg Ala Phe Arg Tyr Thr Phe Pro Val Glu Phe
145                 150                 155                 160

Trp Gln Gly Val Ser Ser Gln Ala Pro Thr Val Thr Ser Ala Lys Val
                165                 170                 175

Ser Arg Ala Pro Gln Leu Glu Arg Met Leu Glu Val Thr Gly Lys Lys
            180                 185                 190

Val Asn Phe Ile Pro Ser Asp Met Val Val His Asp Phe Ala Ala Arg
        195                 200                 205

Ala Pro Gln Thr Thr Thr Ala Cys Trp Ala Thr Ala Ala Gly Met Gly
    210                 215                 220

Pro Glu Pro Ser Ile Ala Leu Met Asp Ala Leu Arg Arg Gly Asp Ser
225                 230                 235                 240

Glu Ala Ala Gly Arg Ala Val Ala Gly Ile Ala Trp Ala Asn Glu Pro
                245                 250                 255

Leu Ala His Leu Phe Ala Asp Gln Glu Ile Phe Ala Ser Tyr Asn Thr
            260                 265                 270

Gln Ile Glu Lys Ser Arg Ile Ala Ala Ala Gly Tyr Cys Arg Pro Gly
        275                 280                 285

Pro Val Arg Ser Pro Tyr His His Leu Pro Glu Gly Tyr Ala Ala Ala
    290                 295                 300

Ser Ala Val Cys Gly Gln Arg Trp Arg Glu Leu Arg Glu Arg Ile Ala
305                 310                 315                 320

Ala Gly Thr Asn Asp Gln Lys
                325

<210> SEQ ID NO 86
<211> LENGTH: 261
```

<212> TYPE: PRT
<213> ORGANISM: Clostridium magnum

<400> SEQUENCE: 86

Met Ile Lys Gly Tyr Ser Leu Pro Leu Thr Pro Lys Gly Thr Ser Asn
1               5                   10                  15

Ile Val Pro Ala Pro Pro Trp His Tyr Val Gly Asn Val Leu Ala Ile
            20                  25                  30

Glu Tyr Glu Ala Tyr Ala Glu Asn Ile Ala Ala Phe Leu Pro Glu Gly
        35                  40                  45

Leu Glu Phe Ser Ser Asn Gln Cys Ala Ile Tyr Phe Ile Glu Trp Gln
    50                  55                  60

Tyr Cys Ser Glu Phe Gly Glu His Leu Asp Pro Val Asn Ser Gln
65                  70                  75                  80

Tyr Lys Glu Thr Ile Val Leu Val Ser Ala Asn Tyr Lys Gly Thr Pro
                85                  90                  95

Val Ser Tyr Cys Pro Phe Ile Trp Val Asp Gln Asp Leu Ser Leu Met
            100                 105                 110

Arg Gly Leu Ile Gln Gly Trp Pro Lys Gln Leu Gly Glu Thr Tyr Ile
        115                 120                 125

Thr Arg Pro Tyr Asn Leu Pro Ser Lys Ala Ala Ser Asn Leu Glu Lys
    130                 135                 140

Gly Gly Lys Leu Gly Ala Thr Leu Ser Val Lys Gly Arg Arg Leu Val
145                 150                 155                 160

Asp Ala Arg Ile Thr Val Asn Lys Lys Thr Glu Thr Leu Pro Asn Pro
                165                 170                 175

Thr Phe Ala Gln Ala Ile Asn Leu Arg His Phe Pro Glu Leu Val Leu
            180                 185                 190

Gly Arg His Asn Gln Pro Leu Ile His Glu Leu Val Gln Leu Lys Ser
        195                 200                 205

Arg Asp Leu His Ile Ser Pro Ile Trp Lys Gly Asp Ala Ile Leu Asn
    210                 215                 220

Phe Phe Asp His Pro Phe Ile Glu Leu Ser Asp Leu Lys Pro Thr Lys
225                 230                 235                 240

Val Lys Asn Ser Tyr Tyr Phe Ser Ala Ala Leu Thr Val Asp Asp Leu
                245                 250                 255

Ser Gln Leu Glu Val
            260

<210> SEQ ID NO 87
<211> LENGTH: 323
<212> TYPE: PRT
<213> ORGANISM: Allokutzneria albata

<400> SEQUENCE: 87

Met Arg Ala Val Val Arg Ser His Gly Gly Pro Glu Val Leu Val
1               5                   10                  15

Ala Glu Glu Leu Asp Arg Pro Glu Pro Gly Ala Val Leu Val
            20                  25                  30

Asp Val Ala Ala Ala Gly Val Asn Tyr Ile Asp Thr Tyr His Arg Glu
        35                  40                  45

Gly Val Tyr Pro Ile Pro Thr Pro Phe Thr Leu Gly Leu Glu Gly Ala
    50                  55                  60

Gly Thr Val Ala Ala Leu Gly Glu Gly Val Thr Glu Phe Ala Val Gly
65                  70                  75                  80

```
Asp Arg Val Ala Trp Ala Ser Ala Ile Gly Ser Tyr Ala Gln Gln Val
                85                  90                  95

Ala Ala Pro Ala Ala Gln Leu Val Pro Val Pro Ser Thr Val Asp Leu
            100                 105                 110

Glu Ile Ala Ala Gly Ala Met Leu Gln Gly Met Thr Ala His Tyr Leu
            115                 120                 125

Thr Ala Ser Thr His Pro Ile Ala Glu Gly Asp Val Ala Leu Val His
            130                 135                 140

Ala Ala Ala Gly Gly Met Gly Leu Leu Leu Thr Gln Met Ile Lys Ala
145                 150                 155                 160

Arg Gly Gly Arg Val Ile Gly Thr Val Ser Thr Ala Glu Lys Glu Lys
                165                 170                 175

Leu Ala Arg Glu Ala Gly Ala Asp Glu Val Ile Arg Tyr Thr Glu Gln
            180                 185                 190

Asp Val Ala Gln Arg Val Arg Glu Leu Thr Asp Gly Val Gly Val His
            195                 200                 205

Val Val Tyr Asp Gly Val Gly Lys Asp Thr Phe Asp Ala Ser Leu Ala
        210                 215                 220

Ser Leu Arg Pro Arg Gly Leu Leu Ala Leu Tyr Gly Ala Ala Ser Gly
225                 230                 235                 240

Ala Val Pro Pro Phe Asp Ala Gln Arg Leu Asn Ala Gly Gly Ser Leu
                245                 250                 255

Phe Leu Thr Arg Pro Ser Leu Gly His His Thr Ala Thr Arg Glu Glu
            260                 265                 270

Leu Leu Trp Arg Ala Gly Glu Val Phe Asp Ala Ile Gln Ala Gly Glu
            275                 280                 285

Leu Asp Ile Ala Ile Gly Gly Arg Tyr Ala Leu Asp Ser Ala Arg Gln
            290                 295                 300

Ala His Glu Asp Leu Gln Gly Arg Arg Thr Thr Gly Lys Leu Leu Leu
305                 310                 315                 320

Thr Thr Ser

<210> SEQ ID NO 88
<211> LENGTH: 326
<212> TYPE: PRT
<213> ORGANISM: Acidaminococcus intestini

<400> SEQUENCE: 88

Met Lys Ala Ile Val Met Lys Glu Phe Gly Gly Pro Glu Val Leu Lys
1               5                   10                  15

Tyr Val Asp Val Pro Asp Pro Val Pro Glu Ala Asn Glu Val Leu Ile
            20                  25                  30

Lys Leu Ala Phe Cys Gly Val Asn Pro Asn Glu Thr Tyr Val Arg Thr
            35                  40                  45

Gly Thr Tyr Asn Phe Tyr Lys Pro Glu Leu Pro Tyr Thr Pro Gly Tyr
        50                  55                  60

Asp Gly Ala Gly Val Ile Glu Lys Val Gly Ala Gly Val Thr His Val
65                  70                  75                  80

Lys Val Gly Asp Arg Val Phe Val Ala Ala Leu Leu Ala Lys Arg Asn
                85                  90                  95

Thr Gly Thr Tyr Ala Gln Lys Val Val Cys Asp Ala Asp Ser Val His
            100                 105                 110

Lys Leu Pro Asp Phe Ile Ser Phe Glu Glu Gly Ala Ser Phe Gly Ile
            115                 120                 125
```

```
Pro Ala Met Ala Ala Tyr Arg Ala Leu Phe His Arg Ala His Ile Lys
        130                 135                 140

Ala Gly Glu Ile Val Met Ile His Gly Ala Glu Gly Val Gly Ser
145                 150                 155                 160

Leu Ala Val Gln Met Ala Lys Ala Val Gly Ala Ile Val Ile Gly Thr
                    165                 170                 175

Gly Thr Thr Pro Glu Gly Leu Asp Ile Val Arg Ser Phe Gly Ala Asp
                180                 185                 190

Tyr Ala Ile Tyr His Leu Lys Ala Asp Asn Gln Asp Glu Leu Met Glu
                195                 200                 205

Leu Thr Lys Gly Lys Gly Pro Asp Val Ile Ile Glu Phe Leu Ala Asn
210                 215                 220

Val Asn Leu Gln Thr Asp Leu Lys Val Ile Ala Lys Tyr Gly Arg Ile
225                 230                 235                 240

Val Val Val Gly Asn Arg Gly Thr Ile Glu Ile Asn Pro Arg Leu Ala
                245                 250                 255

Met Ala Asn Glu Ser Thr Ile Leu Gly Met Ala Leu Trp Asn Ala Pro
                260                 265                 270

Ala Asn Glu Tyr Arg Glu Ser Leu Phe Ala Leu Arg Ala Phe Met Gln
                275                 280                 285

Ser Gly Ala Val Arg Ala Lys Val Gly Lys Gln Leu Leu Lys Asp
                290                 295                 300

Ala Ala Gln Ala His Asn Glu Ile Ile Asn Gly Leu Ala Lys Gly Lys
305                 310                 315                 320

Met Ile Leu Lys Ile Glu
                325

<210> SEQ ID NO 89
<211> LENGTH: 325
<212> TYPE: PRT
<213> ORGANISM: Mycobacteroides chelonae

<400> SEQUENCE: 89

Met Arg Ala Ile Glu Val Pro Val Thr Gly Gly Pro Glu Val Leu Thr
1               5                   10                  15

Leu Val Glu Lys Thr Ala Pro Thr Pro Gly Pro Gly Glu Val Leu Ile
                20                  25                  30

Asp Val Asp Ala Val Gly Val Asn Phe Arg Asp Ile Tyr Leu Arg Asn
                35                  40                  45

Gly Ser Tyr Ala Ala Pro Leu Pro His Ile Pro Gly Ser Glu Val Thr
50                  55                  60

Gly Val Val Ser Ala Val Gly Glu Gly Val Glu Asn Leu Ala Pro Gly
65                  70                  75                  80

Asp Arg Val Ala Ser Pro Val Ala Ala Trp Gly Tyr Ala Glu Ser Thr
                85                  90                  95

Thr Ala Pro Ala Asp Tyr Thr Lys Val Pro Ala Gly Leu Ser Ser
                100                 105                 110

Glu Val Ala Ala Ser Ala Leu Leu Gln Gly Ile Thr Ala His Tyr Leu
                115                 120                 125

Leu Thr Ser Val Tyr Pro Val Ala Ala Gly Asp Thr Val Leu Val His
                130                 135                 140

Ala Gly Ala Gly Gly Met Gly Leu Leu Leu Thr Gln Trp Ala Ser His
145                 150                 155                 160

Arg Gly Val Arg Val Ile Thr Thr Val Ser Ser Ala Ala Lys Glu Lys
                165                 170                 175
```

```
Leu Ser Arg Glu Ala Gly Ala Ala Glu Val Leu Pro Tyr Pro Asp Pro
            180                 185                 190

Thr Asp Pro Ala Glu Phe Ala Glu Lys Ile Leu Glu Leu Thr Ser Gly
            195                 200                 205

Glu Gly Val Ala Val Ala Tyr Asp Gly Val Gly Lys Ser Thr Phe Glu
210                 215                 220

Ala Ser Leu Ala Ala Val Arg Val Arg Gly Leu Ile Ala Leu Tyr Gly
225                 230                 235                 240

Ala Ala Ser Gly Gln Val Pro Pro Phe Asp Pro Gln Arg Leu Thr Ala
                245                 250                 255

Lys Ser Ala Val Leu Thr Arg Pro Thr Met Gly His Phe Ile Arg Thr
            260                 265                 270

Pro Ala Glu Phe Ala Trp Arg Ala Asp Asp Val Leu Asp Leu Val Ser
        275                 280                 285

Arg Gly Thr Leu Lys Ile Thr Val Gly Ala Ser Tyr Pro Leu Glu Gln
    290                 295                 300

Ala Ala Gln Ala His Ile Asp Leu Glu Ala Arg Lys Thr Thr Gly Ser
305                 310                 315                 320

Val Val Leu Val Pro
                325

<210> SEQ ID NO 90
<211> LENGTH: 321
<212> TYPE: PRT
<213> ORGANISM: Nocardia brasiliensis

<400> SEQUENCE: 90

Met Arg Ala Ile Gln Val Ser Glu His Gly Gly Pro Glu Val Leu His
1               5                   10                  15

His Val Glu Leu Pro Asp Pro Thr Ile Asp Ala Asp Gln Leu Leu Val
            20                  25                  30

Asp Val Gln Ala Thr Gly Ile Asn Phe Ile Asp Thr Tyr Ile Arg Thr
        35                  40                  45

Gly Arg Tyr Pro Gln Asp Val Pro Tyr Val Pro Gly Ser Glu Ala Thr
    50                  55                  60

Gly Val Val Ala Glu Val Gly Ala Asn Val Thr Glu Phe Ala Val Gly
65                  70                  75                  80

Asp Arg Val Ala Trp Ala Ser Ala Pro Gly Ser Tyr Ala Glu Arg Val
                85                  90                  95

Ala Val Arg Ala Asp Val Ala Val Glu Val Pro Asp Gly Val Glu Pro
            100                 105                 110

Pro Val Ala Ala Ser Ala Leu Leu Gln Gly Met Thr Ala His Tyr Leu
        115                 120                 125

Leu Glu Ser Ile Tyr Thr Pro Glu Pro Gly Glu Thr Val Leu Val His
    130                 135                 140

Ala Gly Ala Gly Gly Val Gly Leu Ile Leu Thr Gln Leu Ala Val Ala
145                 150                 155                 160

Arg Gly Ala Arg Val Ile Thr Thr Val Ser Ser Asp Val Lys Glu Lys
                165                 170                 175

Leu Ser Arg Glu Ala Gly Ala Thr Glu Val Leu Arg Tyr Gly Asp Asp
            180                 185                 190

Leu Ala Asp Glu Val Arg Thr Leu Thr Asp Gly Val Gly Val Ala Ala
        195                 200                 205

Val Tyr Asp Gly Val Gly Ala Ser Thr Phe Glu Ala Ser Leu Arg Ser
```

```
            210                 215                 220
Leu Arg Val Arg Gly Met Leu Ala Leu Phe Gly Ala Ala Ser Gly Pro
225                 230                 235                 240

Val Pro Pro Phe Asp Leu Gln Arg Leu Asn Gly Ala Gly Ser Leu Phe
                245                 250                 255

Val Thr Arg Pro Ser Leu Ala Phe Tyr Thr Arg Asp Arg Ala Glu Leu
            260                 265                 270

Leu Trp Arg Ala Thr Asp Ile Phe Thr Ala Ile Ala Glu Gly Thr Leu
        275                 280                 285

Gln Ile Arg Ile Gly Ala Thr Tyr Pro Leu Ala Glu Ala Glu Gln Ala
    290                 295                 300

His Arg Asp Leu Glu Ser Arg Lys Thr Thr Gly Ser Ile Val Leu Leu
305                 310                 315                 320

Pro
```

<210> SEQ ID NO 91
<211> LENGTH: 325
<212> TYPE: PRT
<213> ORGANISM: Pseudomonas oleovorans

<400> SEQUENCE: 91

```
Met Ala Lys Arg Ile Gln Phe Ser Gln His Gly Gly Ser Glu Val Leu
1               5                   10                  15

Glu Tyr Arg Asp Tyr Gln Pro Ala Ala Pro Gly Pro Arg Glu Val Arg
                20                  25                  30

Val Ala Asn Lys Ala Ile Gly Leu Asn Phe Ile Asp Thr Tyr Phe Arg
            35                  40                  45

Ser Gly Leu Tyr Gln Pro Pro Ala Leu Pro Ser Ser Leu Gly Thr Glu
    50                  55                  60

Gly Ala Gly Val Val Glu Ala Ile Gly Ser Glu Val Glu Gly Leu Lys
65                  70                  75                  80

Val Gly Asp Arg Val Ala Tyr Ala Thr Gly Pro Leu Gly Ala Tyr Ser
                85                  90                  95

Glu Leu His Val Leu Pro Ala Asp Asn Leu Val His Leu Pro Asp Ser
            100                 105                 110

Ile Ser Phe Glu Gln Ala Ala Ala Val Met Leu Lys Gly Leu Thr Val
    115                 120                 125

Gln Tyr Leu Leu Arg Gln Thr Tyr Glu Leu Lys Gly Gly Glu Thr Ile
130                 135                 140

Leu Phe His Ala Ala Gly Gly Val Gly Ser Phe Ala Cys Gln Trp
145                 150                 155                 160

Ala Lys Ala Leu Gly Val Asn Leu Ile Gly Thr Val Ser Ser Ala Lys
                165                 170                 175

Lys Ala Ala Leu Ala Lys Glu Leu Gly Ala Trp Glu Thr Ile Asp Tyr
            180                 185                 190

Ser His Glu Asn Val Val Gln Arg Val Leu Glu Leu Thr Asp Gly Ala
    195                 200                 205

Lys Cys Pro Val Val Tyr Asp Gly Val Gly Lys Asp Thr Trp Glu Thr
210                 215                 220

Ser Leu Asp Cys Val Ala Pro Arg Gly Leu Leu Val Ser Phe Gly Asn
225                 230                 235                 240

Ala Ser Gly Ala Val Thr Gly Val Asn Leu Gly Ile Leu Ala Gln Lys
                245                 250                 255

Gly Ser Leu Tyr Val Thr Arg Pro Thr Leu Ala Ser Tyr Ala Asn Thr
```

```
                260                 265                 270
Pro Gln Asn Leu Gln Ala Met Ala Asp Glu Leu Phe Ala Met Ile Ser
            275                 280                 285
Ser Gly Lys Leu Gln Val Asp Ile Ser Asn Arg Tyr Ala Leu Lys Asp
        290                 295                 300
Ala Ala Ala Gln Asp Ala Leu Ser Ser Arg Gln Thr Thr Gly Ser
305                 310                 315                 320
Thr Ile Leu Leu Pro
                325

<210> SEQ ID NO 92
<211> LENGTH: 321
<212> TYPE: PRT
<213> ORGANISM: Caulobacter vibrioides

<400> SEQUENCE: 92

Met Leu Ala Val Gln Ala Val Arg Thr Gly Gly Pro Glu Val Leu Glu
1               5                   10                  15
Val Val Asp Leu Pro Leu Pro Ser Pro Gly Pro Gly Gln Ile Leu Val
                20                  25                  30
Arg His Gln Ala Val Gly Leu Asn Tyr Ile Asp Thr Tyr His Arg Ser
            35                  40                  45
Gly Leu Tyr Pro Val Lys Thr Pro Leu Val Ile Gly Leu Glu Ala Ala
        50                  55                  60
Gly Val Val Glu Ser Val Gly Glu Ala Val Thr Arg Phe Lys Val Gly
65                  70                  75                  80
Asp Arg Val Ala Tyr Asn Gly Thr Met Gly Ala Tyr Ala Gln Ala Ala
                85                  90                  95
Val Val Pro Ala Glu Arg Ala Val Leu Val Pro Asp Gly Val Ser Leu
                100                 105                 110
Glu Val Ala Ala Ala Leu Leu Lys Gly Met Thr Ala Glu Phe Leu
            115                 120                 125
Val Arg Arg Cys Phe His Val Lys Gln Gly Asp Trp Val Leu Val His
        130                 135                 140
Ala Ala Ala Gly Gly Val Gly Gln Ile Leu Val Gln Trp Cys Lys Ala
145                 150                 155                 160
Leu Gly Ala Thr Val Val Ala Thr Val Gly Ser Thr Ala Lys Ala Thr
                165                 170                 175
Ile Ala Arg Asp Leu Gly Ala Asp His Val Ile Asp Tyr Ser His Glu
            180                 185                 190
Asp Val Ala Ala Arg Val Ala Glu Leu Thr Gly Gly Arg Gly Val Ala
        195                 200                 205
Val Val Tyr Asp Gly Val Gly Lys Asp Thr Trp Glu Ala Ser Leu Ala
    210                 215                 220
Ser Leu Ala Arg Arg Gly Met Leu Val Thr Phe Gly Asn Ala Ser Gly
225                 230                 235                 240
Pro Ala Pro Ala Phe Pro Pro Leu Ala Leu Ala Pro Lys Ser Ala Phe
                245                 250                 255
Val Thr Arg Pro Lys Leu Phe Asp Tyr Ile Val Thr Thr Glu Glu Leu
            260                 265                 270
Asp Glu Ser Ala Gln Ala Leu Phe Ala Val Ile Ala Ser Gly Ala Ile
        275                 280                 285
Lys Ile Asp Ile Gly Gln Thr Phe Pro Leu Ala Glu Ala Arg Ala Ala
    290                 295                 300
```

His Glu Ala Leu Glu Gly Arg Arg Thr Thr Gly Ala Thr Leu Leu Leu
305                 310                 315                 320

Pro

<210> SEQ ID NO 93
<211> LENGTH: 322
<212> TYPE: PRT
<213> ORGANISM: Saccharopolyspora flava

<400> SEQUENCE: 93

Met Arg Ala Ile Arg Val Thr Ser His Gly Gly Pro Glu Ala Leu Glu
1               5                   10                  15

Val Ser Glu Val Glu Val Pro Glu Pro Gly Pro Gly Gln Leu Leu Val
                20                  25                  30

Asp Val Ala Ala Ser Gly Val Asn Phe Ile Asp Thr Tyr Gln Arg Ser
            35                  40                  45

Gly Val Tyr Ser Val Pro Leu Pro Phe Thr Pro Gly Ser Glu Gly Ala
        50                  55                  60

Gly Glu Ile Val Ala Val Gly Pro Asp Val Asp Gly Phe Ala Val Gly
65                  70                  75                  80

Glu Arg Val Ala Trp Ala Met Thr Pro Gly Ser Tyr Ala Glu Lys Ala
                85                  90                  95

Leu Val Pro Ala Arg Ala Ala Val Lys Ile Pro Asp Gly Val Asp Thr
            100                 105                 110

Arg Thr Ala Ala Ala Thr Leu Gln Gly Met Thr Ala His Phe Leu
        115                 120                 125

Val Thr Ser Thr His Glu Ile Lys Thr Gly Glu Thr Ala Leu Val His
130                 135                 140

Ala Ala Ala Gly Gly Met Gly Leu Leu Leu Thr Gln Leu Ile Lys Ser
145                 150                 155                 160

Lys Gly Gly Asn Val Ile Gly Thr Val Ser Thr Asp Glu Lys Glu Arg
                165                 170                 175

Leu Ala Arg Glu Ala Gly Ala Asp Glu Ile Ile Arg Tyr Thr Glu Ala
            180                 185                 190

Asp Val Ala Ala Glu Val Lys Asp Leu Thr Asp Gly Arg Gly Val Asp
        195                 200                 205

Val Val Tyr Asp Gly Val Gly Lys Ser Thr Phe Glu Ala Ser Leu Ala
210                 215                 220

Ser Leu Arg Pro Arg Gly Thr Leu Ala Leu Phe Gly Ala Ser Gly
225                 230                 235                 240

Gln Val Pro Pro Phe Asp Pro Gln Arg Leu Asn Gly Ala Gly Ser Leu
                245                 250                 255

Phe Leu Thr Arg Pro Ser Leu Ala His His Val Leu Thr Arg Glu Glu
            260                 265                 270

Leu Glu Trp Arg Ala Gly Glu Val Phe Gly Trp Ile Ser Ser Gly Ala
        275                 280                 285

Leu His Ile Arg Val Ser Gly Thr Tyr Ser Leu Glu Asp Ala Ala Arg
290                 295                 300

Ala His Glu Asp Leu Glu Gly Arg Arg Thr Thr Gly Lys Leu Leu Ile
305                 310                 315                 320

Leu Pro

<210> SEQ ID NO 94
<211> LENGTH: 320
<212> TYPE: PRT

<213> ORGANISM: Sciscionella marina

<400> SEQUENCE: 94

| | | | | | | | | | | | | | | |
|---|---|---|---|---|---|---|---|---|---|---|---|---|---|---|
| Met | Thr | Asn | Ala | Ile | Arg | Val | His | Glu | Thr | Gly | Gly | Pro | Glu | Val | Leu |
| 1 | | | | 5 | | | | | 10 | | | | | 15 | |
| Arg | Leu | Asp | Glu | Val | Thr | Arg | Glu | Ala | Gly | Ala | Gly | Gln | Leu | Leu | Val |
| | | | 20 | | | | | 25 | | | | | 30 | | |
| Arg | Val | Glu | Ala | Ala | Gly | Val | Asn | Phe | Ile | Asp | Thr | Tyr | Gln | Arg | Ser |
| | | 35 | | | | | 40 | | | | | 45 | | | |
| Gly | Val | Tyr | Ser | Val | Glu | Leu | Pro | His | Ala | Leu | Gly | Leu | Glu | Gly | Ala |
| | 50 | | | | | 55 | | | | | 60 | | | | |
| Gly | Thr | Val | Glu | Ala | Val | Gly | Asp | Glu | Ala | Ser | Asp | Phe | Thr | Pro | Gly |
| 65 | | | | | 70 | | | | | 75 | | | | | 80 |
| Asp | Arg | Val | Ala | Trp | Val | Trp | Ala | Ala | Gly | Ser | Tyr | Ala | Glu | His | Thr |
| | | | | 85 | | | | | 90 | | | | | 95 | |
| Val | Val | Pro | Val | Glu | Arg | Ala | Val | Arg | Ile | Pro | Asp | Asp | Val | Asp | Thr |
| | | | 100 | | | | | 105 | | | | | 110 | | |
| Lys | Thr | Ala | Gly | Ala | Leu | Met | Leu | Gln | Gly | Leu | Thr | Ala | His | Tyr | Leu |
| | | 115 | | | | | 120 | | | | | 125 | | | |
| Leu | Arg | Ser | Thr | Tyr | Arg | Val | Asp | Glu | Thr | Asp | Thr | Val | Leu | Val | His |
| | 130 | | | | | 135 | | | | | 140 | | | | |
| Ala | Ala | Ala | Gly | Gly | Val | Gly | Leu | Leu | Leu | Val | Gln | Leu | Ala | Lys | Ser |
| 145 | | | | | 150 | | | | | 155 | | | | | 160 |
| Leu | Gly | Ala | Arg | Val | Ile | Ala | Thr | Ala | Ser | Thr | Ala | Glu | Lys | Arg | Ala |
| | | | | 165 | | | | | 170 | | | | | 175 | |
| Leu | Ala | Thr | Gly | Ala | Gly | Ala | Asp | Glu | Val | Leu | Gly | Tyr | Glu | Gly | Phe |
| | | | 180 | | | | | 185 | | | | | 190 | | |
| Asp | Thr | Lys | Leu | Arg | Glu | Leu | Thr | Gly | Gly | Ile | Gly | Val | Ser | Val | Val |
| | | 195 | | | | | 200 | | | | | 205 | | | |
| Tyr | Asp | Gly | Val | Gly | Lys | Asp | Thr | Phe | Asp | Ala | Ser | Leu | Ala | Ser | Ile |
| 210 | | | | | 215 | | | | | 220 | | | | | |
| Arg | Pro | Arg | Gly | Tyr | Leu | Val | Leu | Phe | Gly | Gly | Ser | Ser | Gly | Gln | Val |
| 225 | | | | | 230 | | | | | 235 | | | | | 240 |
| Pro | Pro | Phe | Asp | Leu | Gln | Arg | Leu | Asn | Ala | Ala | Gly | Ser | Leu | Phe | Val |
| | | | | 245 | | | | | 250 | | | | | 255 | |
| Thr | Arg | Pro | Ser | Leu | Gly | Pro | Tyr | Ile | Ala | Asp | Arg | Thr | Glu | Tyr | Glu |
| | | | 260 | | | | | 265 | | | | | 270 | | |
| Trp | Arg | Val | Gly | Glu | Leu | Phe | Glu | Ala | Val | Gly | Asn | Gly | Ser | Leu | Asn |
| | | 275 | | | | | 280 | | | | | 285 | | | |
| Val | Arg | Ile | Gly | Gly | Ser | Tyr | Pro | Leu | Ala | Glu | Ala | Ala | Asn | Ala | His |
| | 290 | | | | | 295 | | | | | 300 | | | | |
| Arg | Asp | Leu | Glu | Gly | Arg | Lys | Thr | Thr | Gly | Lys | Leu | Leu | Leu | Val | Pro |
| 305 | | | | | 310 | | | | | 315 | | | | | 320 |

<210> SEQ ID NO 95
<211> LENGTH: 332
<212> TYPE: PRT
<213> ORGANISM: Zymomonas mobilis

<400> SEQUENCE: 95

| | | | | | | | | | | | | | | |
|---|---|---|---|---|---|---|---|---|---|---|---|---|---|---|
| Met | Ser | Glu | Ala | Tyr | Ala | Ile | Ile | Ala | Glu | Lys | Ala | Gly | Gly | Pro | Glu |
| 1 | | | | 5 | | | | | 10 | | | | | 15 | |
| Val | Leu | Val | Lys | Lys | Pro | Leu | Asp | Leu | Gly | Lys | Met | Lys | Pro | Glu | Ala |
| | | | 20 | | | | | 25 | | | | | 30 | | |
| Gly | Gln | Val | Leu | Leu | Arg | His | Gln | Ala | Ile | Gly | Leu | Asn | Phe | Ile | Asp |

```
                35                  40                  45
Ile Tyr His Arg Ser Gly Leu Tyr Lys Gln Asp Phe Pro Ala Asn Leu
 50                  55                  60

Gly Cys Glu Ala Ala Gly Val Ile Glu Val Val Gly Asp Lys Val Lys
 65                  70                  75                  80

Gly Phe Lys Ala Gly Asp Arg Val Ala Val Phe Thr Ser Lys Pro Gly
                 85                  90                  95

Ala Tyr Ala Thr His Arg Ile Val Asp Ala Ser Glu Leu Val Ala Leu
            100                 105                 110

Pro Asp Asp Ile Ser Ala Glu Thr Ala Ala Val Leu Leu Lys Gly
        115                 120                 125

Met Thr Ser Trp Met Leu Ala Glu Lys Cys Leu Ala His Ala Ala Ile
130                 135                 140

Glu Gly Glu Ala Pro Lys Val Met Val Leu Ala Ala Gly Gly Val
145                 150                 155                 160

Gly Ser Leu Leu Ile Pro Trp Leu Lys Tyr Leu Gly Val Thr Val Phe
                165                 170                 175

Ala His Thr Ser Thr Glu Glu Lys Ala Ala Lys Val Lys Ala Asn Gly
            180                 185                 190

Ala Asp Tyr Val Thr Thr Leu Pro Tyr Ser Asp Leu Pro Asp Trp Val
        195                 200                 205

Arg Lys Gln Asn His Gly Glu Gly Val His Ala Val Leu Asp Ser Val
210                 215                 220

Gly Ala Asp Ser Trp Lys Ser Ser Ile Ala Ser Leu Arg Lys Lys Gly
225                 230                 235                 240

Leu Trp Val Val Tyr Gly Asn Ala Ser Gly Pro Val Pro Ala Leu Ser
                245                 250                 255

Pro Leu Glu Leu Ser Lys Ala Gly Ser Ile Tyr Thr Ser Arg Pro Arg
            260                 265                 270

Leu Ile Asp Tyr Val Asp Asn Ser Val Asp Leu Thr Thr Ala Ser Gln
        275                 280                 285

Lys Leu Phe Ala Leu Leu Arg Lys Asn Ile Leu Lys Val Glu Ile Asn
290                 295                 300

Gln Arg Phe Pro Leu Thr Glu Val Ala Lys Ala His Gln Leu Leu Glu
305                 310                 315                 320

Ser Arg Lys Thr Thr Gly Ser Thr Val Leu Ile Pro
                325                 330

<210> SEQ ID NO 96
<211> LENGTH: 324
<212> TYPE: PRT
<213> ORGANISM: Methylobacterium sp.

<400> SEQUENCE: 96

Met Pro Lys Ala Ile Arg Val His Glu Tyr Gly Gly Pro Glu Val Met
1               5                  10                  15

Arg Tyr Glu Glu Val Asp Leu Pro Ala Pro Gly Pro Gln Ile Arg
                20                  25                  30

Val Arg Gln Arg Ala Val Gly Val Asn Phe Ile Asp Ile Tyr Phe Arg
            35                  40                  45

Ser Gly Leu Tyr Lys Ala Pro Gln Leu Pro Phe Thr Pro Gly Asn Glu
        50                  55                  60

Gly Thr Gly Glu Val Val Ala Val Gly Glu Gly Val Ala Gly Leu Ala
65                  70                  75                  80
```

```
Val Gly Asp Arg Val Ala Tyr Gly Ser Ala Ala Gln Thr Tyr Ala Gln
                85                  90                  95

Glu Ala Val Ile Glu Ala Arg Met Ala Val Lys Val Pro Asp Gly Ile
            100                 105                 110

Asp Asp Ala Thr Ala Ala Met Met Leu Lys Gly Leu Thr Ala Gln
            115                 120                 125

Tyr Leu Leu Arg Lys Thr Tyr Arg Val Gln Pro Gly Asp Thr Ile Leu
        130                 135                 140

Phe His Ala Ala Ala Gly Gly Val Gly Leu Ile Ala Thr Gln Trp Ala
145                 150                 155                 160

Lys His Leu Gly Ala Thr Val Ile Gly Thr Val Gly Ser Arg Asp Lys
                165                 170                 175

Ala Glu Leu Ala Lys Gln His Gly Cys Asp His Val Ile Leu Tyr Arg
            180                 185                 190

Asp Glu Asp Phe Ala Ala Arg Val Lys Glu Ile Thr Gly Gly Lys Gly
        195                 200                 205

Cys Ala Val Val Tyr Asp Gly Val Gly Gln Ala Thr Tyr Pro Ala Ser
    210                 215                 220

Leu Asp Cys Leu Arg Pro Phe Gly Met Phe Val Ser Phe Gly Asn Ala
225                 230                 235                 240

Ser Gly Val Ile Glu Asn Phe Asn Ile Gly Leu Leu Gly Pro Lys Gly
                245                 250                 255

Ser Leu Tyr Ala Thr Arg Pro Thr Leu Phe Thr His Val Ala Glu Arg
            260                 265                 270

Ala Ser Leu Glu Ala Met Ala Asp Asp Leu Phe Gly Val Val Gly Ser
        275                 280                 285

Gly Ala Val Arg Ile Pro Val His Ser Arg Val Pro Leu Ala Glu Ala
    290                 295                 300

Ala Gln Val His Arg Asp Leu Ala Gly Arg Gln Thr Thr Gly Ala Thr
305                 310                 315                 320

Val Leu Ile Pro

<210> SEQ ID NO 97
<211> LENGTH: 324
<212> TYPE: PRT
<213> ORGANISM: Trinickia sp.

<400> SEQUENCE: 97

Met Ala Lys Ala Ile Arg Phe Glu Lys Thr Gly Gly Pro Glu Val Met
1               5                   10                  15

Gln Trp Val Asp Val Glu Val Gly Asp Pro Gly Ser Gly Glu Val Arg
            20                  25                  30

Ile Lys Gln His Ala Val Gly Leu Asn Tyr Ile Asp Val Tyr Phe Arg
        35                  40                  45

Thr Gly Leu Tyr Pro Met Pro Leu Pro Gly Gly Leu Gly Met Glu Ala
    50                  55                  60

Ala Gly Glu Val Thr Ala Val Gly Pro Asp Val Gly Leu Arg Val
65                  70                  75                  80

Gly Asp Arg Val Ala Tyr Val Ala Arg Pro Gly Ala Tyr Ala Gln
                85                  90                  95

Glu Arg Val Leu Pro Ala Ala Ala Leu Val Lys Leu Pro Gly Ala Leu
            100                 105                 110

Gly Tyr Asp Asp Ala Ala Ser Ala Met Leu Gln Gly Leu Thr Ala Gln
        115                 120                 125
```

```
Tyr Leu Leu Arg Arg Thr Tyr Arg Val Lys Ala Gly Asp Thr Ile Leu
    130                 135                 140

Ile Gln Ala Ala Ala Gly Gly Val Gly Leu Phe Val Cys Gln Trp Ala
145                 150                 155                 160

Lys Ala Leu Gly Ala Thr Val Ile Gly Thr Val Ser Ser Asp Glu Lys
                165                 170                 175

Ala Glu Leu Ala Lys Ala His Gly Cys Asp Tyr Pro Ile Val Tyr Thr
            180                 185                 190

Arg Glu Ser Phe Thr Lys Arg Val Lys Glu Ile Thr Gly Gly Ala Gly
        195                 200                 205

Val Pro Val Val Tyr Asp Ser Ile Gly Lys Asp Thr Phe Thr Gly Ser
210                 215                 220

Leu Asp Cys Leu Ala Pro Leu Gly Leu Phe Val Ser Phe Gly Asn Ala
225                 230                 235                 240

Ser Gly Pro Leu Pro Pro Ile Asp Ser Ser Glu Phe Ala Gly Arg Gly
                245                 250                 255

Ser Leu Phe Phe Thr Arg Pro Thr Leu Phe Thr His Ile Ala Lys Arg
            260                 265                 270

Ser Asp Tyr Asp Ala Met Ala Ala Glu Leu Phe Asp Val Ile Val Ser
        275                 280                 285

Gly Lys Val Lys Thr Met Ile Arg Gln Arg Phe Pro Leu Ala Glu Val
290                 295                 300

Gly Gln Ala His Ala Asp Leu Glu Ala Arg Arg Thr Thr Gly Ser Thr
305                 310                 315                 320

Ile Leu Ile Pro

<210> SEQ ID NO 98
<211> LENGTH: 332
<212> TYPE: PRT
<213> ORGANISM: Clostridioides difficile

<400> SEQUENCE: 98

Met Lys Ile Leu Val Phe Gly Ala Arg Asp Tyr Glu Glu Pro Val Ile
1               5                   10                  15

Lys Lys Trp Ser Glu Glu His Lys Asp Val Gln Val Asp Ile Tyr Pro
            20                  25                  30

Glu Asn Met Thr Glu Glu Asn Val Val Lys Ala Lys Gly Tyr Asp Gly
        35                  40                  45

Ile Ser Ile Gln Gln Thr Asn Tyr Ile Asp Asn Pro Tyr Ile Tyr Glu
    50                  55                  60

Thr Leu Lys Asp Ala Gly Val Lys Val Ile Ala Ser Arg Thr Ala Gly
65                  70                  75                  80

Val Asp Met Ile His Phe Asp Leu Val Asn Glu Asn Gly Leu Ile Val
                85                  90                  95

Thr Asn Val Pro Ser Tyr Ser Pro Asn Ala Ile Ala Glu Leu Ala Val
            100                 105                 110

Thr Gln Ala Met Asn Leu Leu Arg Lys Thr Pro Leu Val Lys Lys Lys
        115                 120                 125

Val Cys Glu Gly Asp Tyr Arg Trp Ile Ala Glu Leu Leu Gly Thr Glu
130                 135                 140

Val Arg Ser Ile Thr Val Gly Val Ile Gly Thr Gly Lys Ile Gly Ala
145                 150                 155                 160

Thr Ser Ala Lys Leu Phe Lys Gly Leu Gly Ala Asn Val Ile Ala Phe
                165                 170                 175
```

```
Asp Gln Tyr Pro Asn Ser Asp Leu Asn Asp Ile Leu Thr Tyr Lys Asp
                180                 185                 190

Ser Leu Glu Asp Leu Leu Lys Glu Ala Asp Leu Ile Thr Leu His Thr
        195                 200                 205

Pro Leu Leu Glu Gly Thr Lys His Met Ile Asn Lys Asp Thr Leu Ala
    210                 215                 220

Ile Met Lys Asp Gly Ala Tyr Ile Val Asn Thr Gly Arg Gly Gly Leu
225                 230                 235                 240

Ile Asn Thr Gly Asp Leu Ile Glu Ala Leu Glu Ser Gly Lys Ile Arg
                245                 250                 255

Ala Ala Ala Leu Asp Thr Phe Glu Thr Glu Gly Leu Phe Leu Asn Lys
            260                 265                 270

Lys Met Asn Pro Gly Glu Leu Thr Asp Pro Glu Ile Asn Lys Leu Leu
        275                 280                 285

Ser Met Glu Gln Val Ile Phe Thr His His Leu Gly Phe Phe Thr Ser
    290                 295                 300

Thr Ala Ile Glu Asn Ile Val Tyr Ser Ser Leu Ser Ser Ala Val Glu
305                 310                 315                 320

Val Ile Lys Thr Gly Thr Ala Thr Asn Arg Val Asn
                325                 330

<210> SEQ ID NO 99
<211> LENGTH: 312
<212> TYPE: PRT
<213> ORGANISM: Lactococcus lactis

<400> SEQUENCE: 99

Met Arg Ile Thr Ile Ala Gly Ala Gly Ala Met Gly Ser Arg Phe Gly
1               5                   10                  15

Leu Met Leu His Lys Gly Gly Asn Glu Val Thr Leu Ile Asp Gly Trp
                20                  25                  30

Pro Glu His Val Lys Ala Ile Lys Asp His Gly Leu Arg Ala Asn Tyr
            35                  40                  45

Asn Gly Glu Glu Leu Thr Ala His Leu Ser Val Glu Leu Gln Ser Glu
    50                  55                  60

Ile Ser Ser Lys Glu Lys Thr Asp Leu Ile Ile Leu Phe Thr Lys Ala
65                  70                  75                  80

Met Gln Leu Asp Lys Met Leu Gln Asp Ile Lys Pro Leu Ile Asp Glu
                85                  90                  95

His Thr Lys Val Leu Cys Leu Leu Asn Gly Ile Gly His Glu Asp Thr
            100                 105                 110

Ile Glu Lys Tyr Val Ser Lys Asn Asn Ile Phe Ile Gly Asn Thr Met
        115                 120                 125

Trp Thr Ala Gly Leu Glu Gly Pro Gly Lys Ala Lys Leu Phe Gly Asp
    130                 135                 140

Gly Ser Val Glu Leu Gln Asn Leu Ile Ser Gly Glu Glu Thr Ala
145                 150                 155                 160

Lys Lys Leu Ala Glu Ile Leu Ser Glu Ser Gly Leu Asn Ala Lys Tyr
                165                 170                 175

Ser Asn Asn Ile His Tyr Ser Ile Tyr Arg Lys Ala Cys Val Asn Gly
            180                 185                 190

Thr Met Asn Gly Leu Cys Thr Ile Leu Asp Thr Asn Met Ala Gly Leu
        195                 200                 205

Gly Glu Thr Lys Pro Ala His Asp Met Val Val Thr Ile Val Asn Glu
    210                 215                 220
```

```
Phe Ala Ala Val Ala Lys Phe Glu Asn Val Asn Leu Asp Ile Ala Glu
225                 230                 235                 240

Val Val Gln His Val Glu Thr Cys Phe Asp Pro Ala Thr Ile Gly Leu
                245                 250                 255

His Tyr Pro Ser Met Tyr Gln Asp Leu Ile Lys Asn Asn Arg Leu Thr
            260                 265                 270

Glu Ile Asp Tyr Ile Asn Gly Ala Val Ser Arg Lys Gly Lys Lys Tyr
        275                 280                 285

Asn Val Ala Thr Pro Tyr Cys Asp Phe Leu Thr Gln Leu Val His Ser
    290                 295                 300

Lys Glu Glu Leu Leu Lys Ala Lys
305                 310

<210> SEQ ID NO 100
<211> LENGTH: 334
<212> TYPE: PRT
<213> ORGANISM: Clostridium sporogenes

<400> SEQUENCE: 100

Met Lys Ile Leu Met Tyr Ser Val Arg Glu His Glu Lys Pro Ala Ile
1               5                   10                  15

Lys Lys Trp Leu Glu Ala Asn Pro Gly Val Gln Ile Asp Leu Ser Asp
                20                  25                  30

Glu Ala Leu Ser Glu Asp Thr Val Cys Lys Val Lys Asp Tyr Asp Gly
            35                  40                  45

Ile Ala Ile Gln Gln Thr Asn Ser Ile Gly Gly Glu Thr Val Tyr Ser
50                  55                  60

Thr Leu Lys Lys Tyr Gly Ile Arg Gln Ile Ala Ser Arg Thr Ala Gly
65                  70                  75                  80

Val Asp Met Ile Asp Leu Lys Met Ala Ser Glu Asn Ile Ile Val
                85                  90                  95

Thr Asn Val Pro Ala Tyr Ser Pro Asn Ala Ile Ala Glu Leu Ala Val
                100                 105                 110

Thr His Thr Met Asn Leu Leu Arg Asn Ile Lys Thr Val Asn Lys Arg
            115                 120                 125

Ile Ala Phe Gly Asp Tyr Arg Trp Ser Ala Asp Leu Ile Ala Arg Glu
        130                 135                 140

Val Arg Ser Ile Thr Val Gly Val Val Gly Thr Gly Lys Ile Gly Arg
145                 150                 155                 160

Thr Ser Ala Lys Leu Phe Lys Gly Leu Gly Ala Asn Val Ile Gly Tyr
                165                 170                 175

Asp Ala Tyr Pro Asp Lys Lys Leu Glu Glu Asn Asn Leu Leu Thr Tyr
            180                 185                 190

Lys Asp Ser Leu Glu Asp Leu Leu Lys Glu Ala Asp Val Val Thr Leu
        195                 200                 205

His Thr Pro Leu Leu Glu Ser Thr Lys His Met Ile Asn Lys Asn Asn
    210                 215                 220

Leu Lys Tyr Met Lys Pro Asn Ala Phe Ile Val Asn Thr Gly Arg Gly
225                 230                 235                 240

Gly Ile Ile Asn Thr Glu Asp Leu Ile Glu Ala Leu Glu Glu Asn Lys
                245                 250                 255

Ile Ala Gly Ala Ala Leu Asp Thr Phe Glu Asn Glu Gly Leu Phe Leu
            260                 265                 270

Asn Lys Val Ile Asp Pro Thr Lys Ile Pro Asp Pro Gln Leu Asp Lys
```

```
                275                 280                 285
Leu Leu Lys Met Asp Gln Val Leu Ile Thr His His Val Gly Phe Phe
    290                 295                 300
Thr Thr Thr Ala Val Gln Asn Met Val Asp Thr Ser Leu Asp Ser Val
305                 310                 315                 320
Met Glu Val Leu Lys Thr Asn Asp Ser Val Asn Lys Ala Asn
                325                 330

<210> SEQ ID NO 101
<211> LENGTH: 333
<212> TYPE: PRT
<213> ORGANISM: Lactobacillus delbrueckii

<400> SEQUENCE: 101

Met Thr Lys Ile Ala Met Tyr Asn Val Ser Pro Ile Glu Val Pro Tyr
1               5                   10                  15
Ile Glu Asp Trp Ala Lys Lys Asn Asp Val Glu Ile Lys Thr Thr Asp
                20                  25                  30
Gln Ala Leu Thr Ser Ala Thr Val Asp Leu Ala Glu Gly Cys Ser Ser
            35                  40                  45
Val Ser Leu Lys Pro Leu Gly Pro Val Asp Glu Val Val Tyr Gln
50                  55                  60
Lys Leu Ser Glu Tyr Gly Val Lys Cys Ile Gly Leu Arg Ile Val Gly
65                  70                  75                  80
Phe Asn Thr Ile Asn Phe Asp Trp Thr Lys Lys Tyr Asn Leu Leu Val
                85                  90                  95
Thr Asn Val Pro Val Tyr Ser Pro Arg Ala Ile Ala Glu Met Thr Val
            100                 105                 110
Thr Gln Ala Met Tyr Leu Leu Arg Lys Ile Gly Glu Phe Arg Tyr Arg
        115                 120                 125
Met Asp His Asp His Asp Phe Thr Trp Pro Ser Asn Leu Ile Ser Asn
130                 135                 140
Glu Ile Tyr Asn Leu Thr Val Gly Leu Ile Gly Val Gly His Ile Gly
145                 150                 155                 160
Ser Ala Val Ala Glu Ile Phe Ser Ala Met Gly Ala Lys Val Ile Ala
                165                 170                 175
Tyr Asp Val Ala Tyr Asn Pro Glu Phe Glu Pro Phe Leu Thr Tyr Thr
            180                 185                 190
Asp Phe Asp Thr Val Leu Lys Glu Ala Asp Ile Val Ser Leu His Thr
        195                 200                 205
Pro Leu Leu Pro Ser Thr Glu Asn Met Ile Gly Glu Lys Gln Leu Lys
210                 215                 220
Glu Met Lys Lys Ser Ala Tyr Leu Ile Asn Cys Ala Arg Gly Glu Leu
225                 230                 235                 240
Val Asp Thr Gly Ala Leu Ile Lys Ala Leu Gln Asp Gly Glu Ile Ala
                245                 250                 255
Gly Ala Gly Leu Asp Thr Leu Ala Gly Glu Ser Ser Tyr Phe Gly His
            260                 265                 270
Thr Gly Leu Thr Asp Ser Glu Ile Pro Glu Asp Tyr Lys Thr Leu Ala
        275                 280                 285
Lys Met Pro Asn Val Val Ile Thr Pro His Ser Ala Phe Tyr Thr Glu
    290                 295                 300
Thr Ser Ile Arg Asn Met Val Gln Ile Cys Leu Thr Asp Gln Leu Thr
305                 310                 315                 320
```

Ile Ala Lys Gly Gly Arg Pro Arg Ser Ile Val Asn Leu
            325                 330

<210> SEQ ID NO 102
<211> LENGTH: 330
<212> TYPE: PRT
<213> ORGANISM: Lacticaseibacillus paracasei

<400> SEQUENCE: 102

Met Thr Lys Ile Leu Met Tyr Thr Val Arg Pro Asp Glu Arg Ala Ala
1               5                   10                  15

Ile Asp Ala Trp Val Ala Asn Asp Ile Gln Val Asp Thr Asn Thr
            20                  25                  30

Val Glu Phe Gly Pro Asp Thr Val Asp Leu Ala Lys Gly Tyr Asp Gly
        35                  40                  45

Val Val Ile Gln Gln His Gly Ala Ile Pro Glu Glu Met Val Tyr Gln
    50                  55                  60

Lys Leu Lys Ala Phe Gly Ile Lys Gln Leu Thr Leu Arg Ile Thr Gly
65                  70                  75                  80

Tyr Asp Ile Val Asn Leu Asp Ala Ala Thr Ala Asn Gly Leu Val Val
                85                  90                  95

Thr Asn Val Pro Ala Tyr Ser Pro Arg Ser Val Ser Glu Leu Val Leu
            100                 105                 110

Ala Gln Val Met Arg Leu Ile Arg His Leu Gly Glu Ala Ser Ala Arg
        115                 120                 125

Glu Ala Lys Asp Asp Tyr Ser Trp Thr Gly Leu Glu Ala Pro Glu Ile
    130                 135                 140

His Asn Leu Thr Val Gly Ile Ile Gly Ala Gly Lys Ile Gly Ser Ala
145                 150                 155                 160

Val Ala Arg Ile Phe Arg Ala Leu Gly Ala Thr Val Ile Val Ser Asp
                165                 170                 175

Pro Val Lys Arg Pro Glu Leu Ala Asp Thr Val Ser Tyr Val Asp Leu
            180                 185                 190

Asn Thr Leu Leu Thr Thr Ser Asp Val Val Thr Val His Thr Pro Leu
        195                 200                 205

Asp Gly Leu Thr Thr His Leu Ile Asp Ala Asp Ala Leu Arg Lys Met
    210                 215                 220

Lys Ser Thr Ala Tyr Leu Ile Asn Ala Ala Arg Gly Pro Ile Val Asp
225                 230                 235                 240

Thr Glu Ala Leu Ile Lys Ala Leu Asn Asp His Thr Ile Ala Gly Ala
                245                 250                 255

Ala Leu Asp Thr Ile Glu Gly Glu Ala Gly Ile Phe Gly Glu Asp Arg
            260                 265                 270

Ser Gln Thr Leu Val Asp Asn Gln Thr Leu Glu Thr Leu Lys Ala Met
        275                 280                 285

Pro Asn Val Glu Ile Ser Pro His Ile Gly Phe Tyr Thr Asp Ala Ala
    290                 295                 300

Val Lys Asn Met Ile Asp Ile Ser Leu Asp Asp Val Lys Thr Ile Leu
305                 310                 315                 320

Glu Gly Gly Lys Ser Ala His Gln Val Asn
                325                 330

<210> SEQ ID NO 103
<211> LENGTH: 332
<212> TYPE: PRT
<213> ORGANISM: Unknown

<220> FEATURE:
<223> OTHER INFORMATION: Description of Unknown:
      Lactobacillaceae family sequence

<400> SEQUENCE: 103

Met Lys Ile Ile Ala Tyr Ala Val Arg Asp Asp Glu Arg Pro Phe Phe
1               5                   10                  15

Asp Thr Trp Met Lys Glu Asn Pro Asp Val Glu Val Lys Leu Val Pro
            20                  25                  30

Glu Leu Leu Thr Glu Asp Asn Val Asp Leu Ala Lys Gly Phe Asp Gly
        35                  40                  45

Ala Asp Val Tyr Gln Gln Lys Asp Tyr Thr Ala Glu Val Leu Asn Lys
50                  55                  60

Leu Ala Asp Glu Gly Val Lys Asn Ile Ser Leu Arg Asn Val Gly Val
65                  70                  75                  80

Asp Asn Leu Asp Val Pro Thr Val Lys Ala Arg Gly Leu Asn Ile Ser
                85                  90                  95

Asn Val Pro Ala Tyr Ser Pro Asn Ala Ile Ala Glu Leu Ser Val Thr
            100                 105                 110

Gln Leu Met Gln Leu Leu Arg Gln Thr Pro Leu Phe Asn Lys Lys Leu
        115                 120                 125

Ala Lys Gln Asp Phe Arg Trp Ala Pro Asp Ile Ala Lys Glu Leu Asn
130                 135                 140

Thr Met Thr Val Gly Val Ile Gly Thr Gly Arg Ile Gly Arg Ala Ala
145                 150                 155                 160

Ile Asp Ile Phe Lys Gly Phe Gly Ala Lys Val Ile Gly Tyr Asp Val
                165                 170                 175

Tyr Arg Asn Ala Glu Leu Glu Lys Glu Gly Met Tyr Val Asp Thr Leu
            180                 185                 190

Asp Glu Leu Tyr Ala Gln Ala Asp Val Ile Thr Leu His Val Pro Ala
        195                 200                 205

Leu Lys Asp Asn Tyr His Met Leu Asn Ala Asp Ala Phe Ser Lys Met
210                 215                 220

Lys Asp Gly Ala Tyr Ile Leu Asn Phe Ala Arg Gly Thr Leu Ile Asp
225                 230                 235                 240

Ser Glu Asp Leu Ile Lys Ala Leu Asp Ser Gly Lys Val Ala Gly Ala
                245                 250                 255

Ala Leu Asp Thr Tyr Glu Tyr Glu Thr Lys Ile Phe Asn Lys Asp Leu
            260                 265                 270

Glu Gly Gln Thr Ile Asp Asp Lys Val Phe Met Asn Leu Phe Asn Arg
        275                 280                 285

Asp Asn Val Leu Ile Thr Pro His Thr Ala Phe Tyr Thr Glu Thr Ala
290                 295                 300

Val His Asn Met Val His Val Ser Met Asn Ser Asn Lys Gln Phe Ile
305                 310                 315                 320

Glu Thr Gly Lys Ala Asp Thr Gln Val Lys Phe Asp
                325                 330

<210> SEQ ID NO 104
<211> LENGTH: 331
<212> TYPE: PRT
<213> ORGANISM: Clostridium sporogenes

<400> SEQUENCE: 104

Met Lys Ile Leu Ala Tyr Cys Val Arg Pro Asp Glu Ile Asp Ser Phe
1               5                   10                  15

```
Lys Asn Phe Ser Glu Lys Tyr Gly His Thr Val Asp Leu Ile Pro Asp
                20                  25                  30

Ser Phe Gly Pro Ser Val Ala His Leu Ala Lys Gly Tyr Asp Gly Ile
            35                  40                  45

Ser Ile Leu Gly Asn Asp Thr Cys Asn Arg Glu Ala Leu Glu Lys Ile
 50                  55                  60

Lys Asp Cys Gly Ile Lys Tyr Leu Ala Thr Arg Thr Ala Gly Val Asn
 65                  70                  75                  80

Asn Ile Asp Phe Asp Ala Ala Lys Glu Phe Gly Ile Asn Val Ala Asn
                85                  90                  95

Val Pro Ala Tyr Ser Pro Asn Ser Val Ser Glu Phe Thr Val Gly Leu
            100                 105                 110

Ala Leu Ser Leu Thr Arg Lys Ile Pro Phe Ala Leu Lys Arg Val Glu
        115                 120                 125

Leu Asn Asn Phe Ala Leu Gly Gly Leu Ile Gly Val Glu Leu Arg Asn
130                 135                 140

Leu Thr Leu Gly Val Ile Gly Thr Gly Arg Ile Gly Leu Lys Val Ile
145                 150                 155                 160

Glu Gly Phe Ser Gly Phe Gly Met Lys Lys Met Ile Gly Tyr Asp Ile
                165                 170                 175

Phe Glu Asn Glu Lys Ala Lys Glu Tyr Ile Glu Tyr Lys Ser Leu Asp
            180                 185                 190

Glu Val Tyr Lys Glu Ala Asp Ile Ile Thr Leu His Ala Pro Leu Thr
        195                 200                 205

Asp Asp Asn Tyr His Met Ile Gly Lys Glu Ser Ile Ala Lys Met Lys
210                 215                 220

Asp Gly Val Phe Ile Ile Asn Ala Ala Arg Gly Ala Leu Ile Asp Ser
225                 230                 235                 240

Glu Ala Leu Ile Glu Gly Leu Lys Ser Gly Lys Ile Ala Gly Ala Ala
                245                 250                 255

Leu Asp Ser Tyr Glu Tyr Glu Gln Gly Val Phe His Asn Asn Lys Met
            260                 265                 270

Asn Glu Ile Met Lys Asp Asp Thr Leu Ala Arg Leu Lys Ser Phe Pro
        275                 280                 285

Asn Val Val Ile Thr Pro His Leu Gly Phe Tyr Thr Asp Glu Ala Val
290                 295                 300

Ser Asn Met Val Glu Ile Thr Leu Met Asn Leu Gln Glu Phe Glu Leu
305                 310                 315                 320

Lys Gly Thr Cys Lys Asn Gln Arg Val Cys Lys
                325                 330

<210> SEQ ID NO 105
<211> LENGTH: 334
<212> TYPE: PRT
<213> ORGANISM: Clostridium sporogenes

<400> SEQUENCE: 105

Met Lys Ile Leu Met Tyr Ser Val Arg Glu His Glu Lys Pro Ala Ile
1               5                   10                  15

Lys Lys Trp Leu Glu Ala Asn Pro Gly Val Gln Ile Asp Leu Ser Asp
                20                  25                  30

Glu Ala Leu Ser Glu Asp Thr Val Cys Lys Val Lys Asp Tyr Asp Gly
            35                  40                  45

Ile Ala Ile Gln Gln Thr Asn Ser Ile Gly Gly Glu Thr Val Tyr Ser
```

```
                50                  55                  60
Thr Leu Lys Lys Tyr Gly Ile Arg Gln Ile Ala Ser Arg Thr Ala Gly
 65                  70                  75                  80

Val Asp Met Ile Asp Leu Lys Met Ala Ser Glu Asn Asn Ile Ile Val
                 85                  90                  95

Thr Asn Val Pro Ala Tyr Ser Pro Asn Ala Ile Ala Glu Leu Ala Val
                100                 105                 110

Thr His Thr Met Asn Leu Leu Arg Asn Ile Lys Thr Val Asn Lys Arg
                115                 120                 125

Ile Ala Phe Gly Asp Tyr Arg Trp Ser Ala Asp Leu Ile Ala Arg Glu
130                 135                 140

Val Arg Ser Ile Thr Val Gly Val Val Gly Thr Gly Lys Ile Gly Arg
145                 150                 155                 160

Thr Ser Ala Lys Leu Phe Lys Gly Leu Gly Ala Asn Val Ile Gly Tyr
                165                 170                 175

Asp Ala Tyr Pro Asp Lys Lys Leu Glu Glu Asn Asn Leu Leu Thr Tyr
                180                 185                 190

Lys Asp Ser Leu Glu Asp Leu Leu Lys Glu Ala Asp Val Val Thr Leu
                195                 200                 205

His Thr Pro Leu Leu Glu Ser Thr Lys His Met Ile Asn Lys Asn Asn
                210                 215                 220

Leu Lys Tyr Met Lys Pro Asn Ala Phe Ile Val Asn Thr Gly Arg Gly
225                 230                 235                 240

Gly Ile Ile Asn Thr Glu Asp Leu Ile Glu Ala Leu Glu Glu Asn Lys
                245                 250                 255

Ile Ala Gly Ala Ala Leu Asp Thr Phe Glu Asn Glu Gly Leu Phe Leu
                260                 265                 270

Asn Lys Val Ile Asp Pro Thr Lys Ile Pro Asp Pro Gln Leu Asp Lys
                275                 280                 285

Leu Leu Lys Met Asp Gln Val Leu Ile Thr His His Val Gly Phe Phe
                290                 295                 300

Thr Thr Thr Ala Val Gln Asn Met Val Asp Thr Ser Leu Asp Ser Val
305                 310                 315                 320

Met Glu Val Leu Lys Thr Asn Asp Ser Val Asn Lys Ala Asn
                325                 330

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 106

His His His His His His
1               5
```